United States Patent [19]
Sugai et al.

[11] Patent Number: 5,736,487
[45] Date of Patent: Apr. 7, 1998

[54] ANILINE DERIVATIVES HAVING HERBICIDAL ACTIVITY, THEIR PREPARATION AND THEIR USE

[75] Inventors: Soji Sugai, Ohtsu; Hiroyuki Komai, Ohmihachiman; Noriaki Kudo, Shiga-ken; Kazuo Sato, Hikone; Toyokuni Honma; Junji Kadotani, both of Shiga-ken; Kiyoshi Koi, Moriyama; Mitsuru Ito, Shiga-ken, all of Japan

[73] Assignee: Sankyo Company, Limited, Tokyo, Japan

[21] Appl. No.: 813,174

[22] Filed: Mar. 7, 1997

[30] Foreign Application Priority Data

Mar. 11, 1996 [JP] Japan ........................... 8-052689
Sep. 13, 1996 [JP] Japan ........................... 8-243335

[51] Int. Cl.$^6$ ................. C07D 263/56; C07D 277/64; A01N 43/76; A01N 43/78
[52] U.S. Cl. ................. 504/267; 504/268; 504/270; 504/235; 504/236; 504/239; 504/247; 504/252; 504/269; 544/238; 544/333; 544/405; 544/170; 544/270.1; 544/271.1; 548/178; 548/180; 548/214; 548/217
[58] Field of Search ................. 548/178, 180, 548/217; 504/267, 268, 270

[56] References Cited

U.S. PATENT DOCUMENTS

| | | | |
|---|---|---|---|
| 4,193,787 | 3/1980 | Baker | 504/293 |
| 4,423,237 | 12/1983 | Baker | 549/362 |
| 4,500,340 | 2/1985 | Becker et al. | 504/267 |
| 4,594,425 | 6/1986 | Musser et al. | 548/217 X |
| 5,436,267 | 7/1995 | Komyoji et al. | 548/180 X |

FOREIGN PATENT DOCUMENTS 081 141  6/1983  European Pat. Off.

OTHER PUBLICATIONS

Chemical Abstracts, vol. 99, No. 23, 5 Dec. 1983, Columbus, Ohio, Abstract No. 194949d, p. 754 of JP 58 052280 A (Nissan Chemical Industries, Ltd.) 28 Mar. 1983.

Chemical Abstracts, vol. 101, No. 9, 27 Aug. 1984, Columbus, Ohio, Abstract No. 72462d, p. 618, of JP 59 027878 A (Nissan Chemical Industries, Ltd.) 14 Feb. 1984.

*Primary Examiner*—Fiona T. Powers
*Attorney, Agent, or Firm*—Frishauf, Holtz, Goodman, Langer & Chick, P.C.

[57] ABSTRACT

Compounds of formula (I):

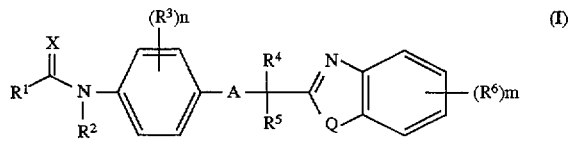

(wherein: $R^1$ is optionally substituted alkyl, cycloalkyl, optionally substituted alkoxy, or optionally substituted alkylthio; $R^2$ is hydrogen, optionally substituted alkyl, cycloalkyl, optionally substituted alkenyl, optionally substituted alkynyl or a group of formula —$YR^7$; $R^3$ is optionally substituted alkyl, cycloalkyl, optionally substituted alkoxy group, optionally substituted alkenyl, optionally substituted alkynyl, halogen, nitro or a group of formula —$COR^8$, wherein $R^8$ is hydrogen, alkyl, cycloalkyl or alkoxy; $R^4$ and $R^5$ are each hydrogen atom or alkyl; $R^6$ is optionally substituted alkyl, cycloalkyl, optionally substituted alkoxy group, optionally substituted alkenyl, optionally substituted alkynyl, halogen, nitro, or a group of formula —$COR^8$, as defined above;

A, Q and X are each oxygen or sulfur; Y is a group of formula —CO—, —COO—, —$CH_2O$—, —$CH_2S$—, —$CH_2CH_2O$—, —$CH_2CH_2S$—, —$CH_2CO$—, —$CH_2COO$—, —CH(Me)COO—, —$CH_2CH_2CO$—, —$CH_2OCO$—, $CH_2OCOO$— and —$CH_2CH_2OCO$—; $R^7$ is optionally substituted alkyl group, cycloalkyl, optionally substituted alkenyl, optionally substituted alkynyl, optionally substituted aryl, optionally substituted aralkyl, or an optionally substituted heterocycle; and m and n are each an integer from 0 to 4; and herbicidally acceptable addition salts thereof) are useful as herbicides.

163 Claims, No Drawings

ANILINE DERIVATIVES HAVING HERBICIDAL ACTIVITY, THEIR PREPARATION AND THEIR USE

BACKGROUND TO THE INVENTION

The present invention relates to a series of new aniline derivatives having an excellent selective herbicidal activity and provides methods and compositions using these compounds, as well as processes for preparing them.

The purpose of herbicides in agriculture and horticulture is to kill unwanted plants (weeds), whilst leaving unharmed plants which are wanted (crops). A herbicide is of restricted practical use if it is lethal to all plants. Accordingly, for maximum practical effect, it is desirable to target not only specific weeds, but also the desired crop, to ensure that the herbicide is lethal to the weeds and inactive against the crops.

A considerable amount of research effort has been devoted in recent years to the development of new and more potent selective herbicides. Despite this effort, there is still a particular need for a herbicide which is lethal to harmful weeds such as barnyardgrass (*Echinochloa oryzicola*), preferably at a low concentration of the herbicidally active agent, which can be applied to rice plants without harming them. Furthermore, there is a need for such a herbicide which can be applied both before and after germination of the harmful grasses with equal effectiveness.

It is believed that the closest prior art to the present invention is U.S. Pat. Nos. 4,193,787 and 4,423,237 and Japanese Unexamined Patent Publication (Kokai) No. Sho 58-52280. U.S. Pat. Nos. 4,193,787 and 4,423,23 7 disclose compounds of the following general formula (A):

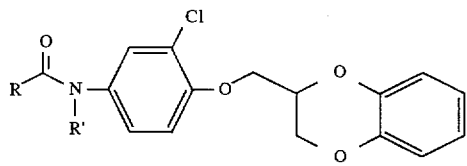

wherein R' represents a hydrogen atom, an alkylcarbonyl group, an alkoxycarbonyl group or a cycloalkylcarbonyl group and R represents an alkyl group, an alkoxy group, a cycloalkyl group and, where R' represents a hydrogen atom, a thioalkyl group, a chloroalkyl group, an alkynyl group or a substituted amino group. Japanese Unexamined Patent Publication (Kokai) No. Sho 58-52280 discloses compounds of the following general formula (B):

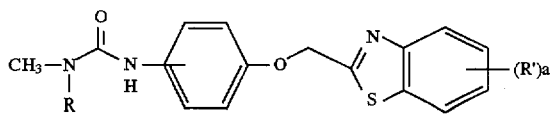

wherein R' represents an alkyl group, an alkoxy group, a haloalkoxy group or a halogen atom, a is an integer from 0 to 2, and R is a hydrogen atom, a methyl group or a methoxy group.

The compounds of general formulae (A) and (B) are both said to have herbicidal activity. However, although these compounds do not harm rice plants, they are not effective in killing harmful grasses such as barnyardgrass when applied either before or after germination of said grasses.

In accordance with the present invention, we have now discovered a series of novel aniline derivatives which show potent herbicidal activity, even at a low concentration, against harmful weeds such as barnyardgrass but which cause no damage to rice plants. Furthermore, the novel aniline derivatives can be applied to the crops both before and after germination of the weeds with equal effectiveness.

BRIEF SUMMARY OF THE INVENTION

It is therefore an object of the present invention to provide a series of aniline derivatives having potent selective herbicidal activity.

The compounds of the present invention are represented by the following general formula (I):

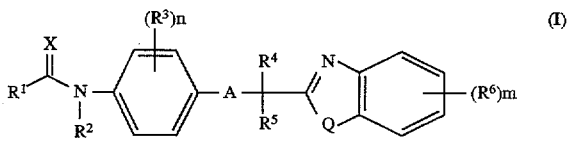

wherein:

$R^1$ represents:
 an alkyl group having from 1 to 6 carbon atoms, said alkyl group being unsubstituted or being substituted by an alkoxy group having from 1 to 6 carbon atoms or by from 1 to 4 halogen atoms;
 a cycloalkyl group having from 3 to 6 carbon atoms;
 an alkoxy group having from 1 to 6 carbon atoms, said alkoxy group being unsubstituted or being substituted by from 1 to 4 halogen atoms; or
 an alkylthio group having from 1 to 6 carbon atoms, said alkylthio group being unsubstituted or being substituted by from 1 to 4 halogen atoms;

$R^2$ represents:
 a hydrogen atom;
 an alkyl group having from 1 to 6 carbon atoms, said alkyl group being unsubstituted or being substituted by a hydroxy group or by from 1 to 4 halogen atoms;
 a cycloalkyl group having from 3 to 6 carbon atoms;
 an alkenyl group having from 2 to 6 carbon atoms, said alkenyl group being unsubstituted or being substituted by from 1 to 4 halogen atoms;
 an alkynyl group having from 2 to 6 carbon atoms, said alkynyl group being unsubstituted or being substituted by from 1 to 4 halogen atoms; or
 a group represented by the formula $-YR^7$;

$R^3$ represents:
 an alkyl group having from 1 to 6 carbon atoms, said alkyl group being unsubstituted or being substituted by an alkoxy group having from 1 to 6 carbon atoms or by from 1 to 4 halogen atoms;
 a cycloalkyl group having from 3 to 6 carbon atoms;
 an alkoxy group having from 1 to 6 carbon atoms, said alkoxy group being unsubstituted or being substituted by from 1 to 4 halogen atoms;
 an alkenyl group having from 2 to 6 carbon atoms, said alkenyl group being unsubstituted or being substituted by from 1 to 4 halogen atoms;
 an alkynyl group having from 2 to 6 carbon atoms, said alkynyl group being unsubstituted or being substituted by from 1 to 4 halogen atoms;
 a halogen atom;
 a nitro group; or
 a group of formula $-COR^8$, wherein $R^8$ represents a hydrogen atom, an alkyl group having from 1 to 6 carbon atoms, a cycloalkyl group having from 3 to 6 carbon atoms or an alkoxy group having from 1 to 6 carbon atoms;

$R^4$ and $R^5$ are the same or different and each represents a hydrogen atom or an alkyl group having from 1 to 6 carbon atoms;

$R^6$ represents:
- an alkyl group having from 1 to 6 carbon atoms, said alkyl group being unsubstituted or being substituted by an alkoxy group having from 1 to 6 carbon atoms or by from 1 to 4 halogen atoms;
- a cycloalkyl group having from 3 to 6 carbon atoms;
- an alkoxy group having from 1 to 6 carbon atoms, said alkoxy group being unsubstituted or being substituted by from 1 to 4 halogen atoms;
- an alkenyl group having from 2 to 6 carbon atoms, said alkenyl group being unsubstituted or being substituted by from 1 to 4 halogen atoms;
- an alkynyl group having from 2 to 6 carbon atoms, said alkynyl group being unsubstituted or being substituted by from 1 to 4 halogen atoms;
- a halogen atom;
- a nitro group; or
- a group of formula —$COR^8$, wherein $R^8$ represents a hydrogen atom, an alkyl group having from 1 to 6 carbon atoms, a cycloalkyl group having from 3 to 6 carbon atoms or an alkoxy group having from 1 to 6 carbon atoms;

A represents an oxygen atom or a sulfur atom;

X represents an oxygen atom or a sulfur atom;

Y represents a group selected from groups of formulae —CO—, —COO—, —$CH_2O$—, —$CH_2S$—, —$CH_2CH_2O$—, —$CH_2CH_2S$—, —$CH_2CO$—, —$CH_2COO$—, —CH(Me)COO—, —$CH_2CH_2CO$—, —$CH_2OCO$—, $CH_2OCOO$— and —$CH_2CH_2OCO$—;

$R^7$ represents:
- an alkyl group having from 1 to 6 carbon atoms, said alkyl group being unsubstituted or being substituted by an alkoxy group having from 1 to 6 carbon atoms, an alkylthio group having from 1 to 6 carbon atoms or by from 1 to 4 halogen atoms;
- a cycloalkyl group having from 3 to 6 carbon atoms;
- an alkenyl group having from 2 to 6 carbon atoms, said alkenyl group being unsubstituted or being substituted by from 1 to 4 halogen atoms;
- an alkynyl group having from 2 to 6 carbon atoms, said alkynyl group being unsubstituted or being substituted by from 1 to 4 halogen atoms;
- a carbocyclic aryl group having from 6 to 14 ring carbon atoms, said aryl group being unsubstituted or being substituted by at least one substituent selected from the group consisting of alkyl groups having from 1 to 6 carbon atoms, alkoxy groups having from 1 to 6 carbon atoms and halogen atoms;
- an aralkyl group wherein the aryl moiety is a carbocyclic aryl group having from 6 to 10 ring carbon atoms which is unsubstituted or is substituted by from 1 to 4 halogen atoms, and the alkyl moiety has from 1 to 6 carbon atoms; or
- a heterocyclic group having from 4 to 10 ring atoms including at least one ring heteroatom selected from the group consisting of oxygen atoms, sulfur atoms and nitrogen atoms, said heterocyclic group being fully unsaturated, partly unsaturated or saturated and being either unsubstituted, substituted by at least one substituent selected from alkyl groups having from 1 to 6 carbon atoms, alkoxy groups having from 1 to 6 carbon atoms and halogen atoms, or fused with a carbocyclic aryl group having from 6 to 10 ring carbon atoms;

Q represents an oxygen atom or a sulfur atom;

m represents an integer from 0 to 4 and, where m is an integer from 2 to 4, each $R^6$ may be the same or different; and n represents an integer from 0 to 4 and, where n is an integer from 2 to 4, each $R^3$ may be the same or different;

and herbicidally acceptable addition salts thereof.

The present invention also provides a herbicidal composition comprising an effective amount of a herbicidal agent in admixture with an agriculturally or horticulturally acceptable carrier or diluent, wherein the herbicidal agent is a compound of formula (I) as defined above or a herbicidally acceptable addition salt thereof.

The present invention still further provides a method of destroying weeds, either before or after germination of said weeds, by administering a herbicidal agent to a locus including said germinated or ungerminated weeds, wherein the herbicidal agent is a compound of formula (I) or a herbicidally acceptable addition salt thereof.

The present invention also provides processes for preparing the compounds of the present invention which are described in more detail below.

DETAILED DESCRIPTION OF THE INVENTION

In the compounds of the present invention, alkyl groups having from 1 to 6 carbon atoms may be straight or branched chain alkyl groups having from 1 to 6 carbon atoms, and examples include the methyl, ethyl, n-propyl, isopropyl, n-butyl, isobutyl, s-butyl, t-butyl, n-pentyl, isopentyl, 2-methylbutyl, neopentyl, 1-ethylpropyl, n-hexyl, 4-methylpentyl, 3-methylpentyl, 2-methylpentyl, 1-methylpentyl, 3,3-dimethylbutyl, 2,2-dimethylbutyl, 1,1-dimethylbutyl, 1,2-dimethylbutyl, 1,3-dimethylbutyl, 2,3-dimethylbutyl and 2-ethylbutyl groups. Of these, we prefer straight or branched alkyl groups having from 1 to 4 carbon atoms, particularly straight or branched alkyl groups having from 1 to 3 carbon atoms, examples of which include the methyl, ethyl, n-propyl and isopropyl groups. Of these, we prefer methyl groups and ethyl groups, most preferably methyl groups.

In the compounds of the present invention, cycloalkyl groups having from 3 to 6 carbon atoms include cyclopropyl, cyclobutyl, cyclopentyl and cyclohexyl groups.

In the compounds of the present invention, alkyl groups having from 1 to 6 carbon atoms substituted by an alkoxy group having from 1 to 6 carbon atoms may be straight or branched chain alkyl groups having from 1 to 6 carbon atoms substituted by a straight or branched chain alkoxy group having from 1 to 6 carbon atoms. Examples include the methoxymethyl, ethoxymethyl, n-propoxymethyl, n-butoxymethyl, s-butoxymethyl, t-butoxymethyl, n-pentyloxymethyl, n-hexyloxymethyl, methoxyethyl, ethoxyethyl, n-propoxyethyl, n-butoxyethyl, methoxy n-propyl, methoxy n-butyl, methoxy s-butyl, methoxy t-butyl, methoxy n-pentyl and methoxy n-hexyl groups. We prefer alkyl groups having from 1 to 3 carbon atoms substituted by an alkoxy group having from 1 to 3 carbon atoms, examples of which include the methoxymethyl, ethoxymethyl, n-propoxymethyl, methoxyethyl, ethoxyethyl, n-propoxyethyl and methoxy n-propyl groups, of which we particularly prefer methoxyethyl groups and ethoxymethyl groups.

In the compounds of the present invention, alkyl groups having from 1 to 6 carbon atoms substituted by an alkylthio group having from 1 to 6 carbon atoms may be straight or branched chain alkyl groups having from 1 to 6 carbon atoms substituted by a straight or branched chain alkylthio group having from 1 to 6 carbon atoms. Examples include the methylthiomethyl, ethylthiomethyl, n-propylthiomethyl, n-butylthiomethyl, t-butylthiomethyl, n-hexylthiomethyl, 1-methylthioethyl, 2-methylthioethyl, methylthio n-propyl, methylthioisopropyl and ethylthioethyl groups. We prefer alkyl groups having from 1 to 3 carbon atoms substituted by an alkylthio group having from 1 to 3 carbon atoms, and examples include the methylthiomethyl, ethylthiomethyl, n-propylthiomethyl, methylthio n-propyl and ethylthioethyl groups. Of these, we particularly prefer methylthiomethyl groups and ethylthiomethyl groups.

In the compounds of the present invention, alkyl groups having from 1 to 6 carbon atoms substituted by a hydroxy group may be straight or branched chain alkyl groups having from 1 to 6 carbon atoms substituted by a hydroxy group. Examples include the hydroxymethyl, 1-hydroxyethyl, 2-hydroxyethyl, 1-hydroxy n-propyl, 2-hydroxy n-propyl, 3-hydroxy n-propyl, 1-methyl-2-hydroxyethyl, 4-hydroxy n-butyl, 5-hydroxy n-pentyl, 6-hydroxy n-hexyl and 1-methyl-3-hydroxy n-propyl groups. We prefer alkyl groups having from 1 to 3 carbon atoms substituted by a hydroxy group, examples of which include hydroxymethyl, 1-hydroxyethyl, 2-hydroxyethyl and 3-hydroxy n-propyl groups, of which we particularly prefer hydroxymethyl groups and 2-hydroxyethyl groups.

In the compounds of the present invention, halogen atoms may be fluoride atoms, chlorine atoms, bromine atoms or iodine atoms, preferably fluorine atoms or chlorine atoms.

In the compounds of the present invention, alkyl groups having from 1 to 6 carbon atoms substituted by from 1 to 4 halogen atoms may be straight or branched chain alkyl groups having from 1 to 6 carbon atoms substituted by from 1 to 4 halogen atoms which may be the same as or different from each other. Examples include the chloromethyl, dichloromethyl, trichloromethyl, 1-chloroethyl, 2-chloroethyl, 1-chloropropyl, 3-chloropropyl, 1-chlorobutyl, 4-chlorobutyl, fluoromethyl, difluoromethyl, trifluoromethyl, 1-fluoroethyl, 2-fluoroethyl, fluorochloromethyl, bromomethyl, 1-bromoethyl and 2-bromoethyl groups. We prefer alkyl groups having from 1 to 3 carbon atoms substituted by from 1 to 4 halogen atoms which may be the same as or different from each other, and examples include the chloromethyl, dichloromethyl, trichloromethyl, 1-chloroethyl, 2-chloroethyl, 1-chloropropyl, 3-chloropropyl, fluoromethyl, difluoromethyl, trifluoromethyl, 1-fluoroethyl, 2-fluoroethyl, fluorochloromethyl, bromomethyl, 1-bromoethyl and 2-bromoethyl groups. Of these, we particularly prefer fluoromethyl groups, chloromethyl groups, trifluoromethyl groups and 2,2,2-trichloroethyl groups.

In the compounds of the present invention, alkoxy groups having from 1 to 6 carbon atoms may be straight or branched chain alkoxy groups having from 1 to 6 carbon atoms, and examples include the methoxy, ethoxy, n-propoxy, isopropoxy, n-butoxy, isobutoxy, s-butoxy, t-butoxy, n-pentoxy, isopentoxy, 2-methylbutoxy, neopentoxy, 1-ethylpropoxy, n-hexyloxy, 4-methylpentoxy, 3-methylpentoxy, 2-methylpentoxy, 1-methylpentoxy, 3,3-dimethylbutoxy, 2,2-dimethylbutoxy, 1,1-dimethylbutoxy, 1,2-dimethylbutoxy, 1,3-dimethylbutoxy, 2,3-dimethylbutoxy and 2-ethylbutoxy groups. We prefer straight or branched chain alkoxy groups having from 1 to 3 carbon atoms, more preferably methoxy groups and ethoxy groups, most preferably methoxy groups.

In the compounds of the present invention, alkoxy groups having from 1 to 6 carbon atoms substituted by from 1 to 4 halogen atoms may be straight or branched chain alkoxy groups substituted by from 1 to 4 halogen atoms which may be the same as or different from each other. Examples include the chloromethoxy, dichloromethoxy, trichloromethoxy, 1-chloroethoxy, 2-chloroethoxy, 1-chloropropoxy, fluoromethoxy, difluoromethoxy, trifluoromethoxy, 1-fluoroethoxy, 2-fluoroethoxy, fluorochloromethoxy and bromomethoxy groups. We prefer alkoxy group having from 1 to 3 carbon atoms substituted by from 1 to 4 halogen atoms, more preferably fluoromethoxy groups, chloromethoxy groups and trifluoromethoxy groups, most preferably trifluoromethoxy groups.

In the compounds of the present invention, alkylthio groups having from 1 to 6 carbon atoms may be straight or branched chain alkylthio groups having from 1 to 6 carbon atoms. Examples include the methylthio, ethylthio, n-propylthio, isopropylthio, n-butylthio, isobutylthio, s-butylthio, t-butylthio, n-pentylthio, isopentylthio, 2-methylbutylthio, neopentylthio, 1-ethylpropylthio, n-hexylthio, 4-methylpentylthio, 3-methylpentylthio, 2-methylpentylthio, 1-methylpentylthio, 3,3-dimethylbutylthio, 2,2-dimethylbutylthio, 1,1-dimethylbutylthio, 1,2-dimethylbutylthio, 1,3-dimethylbutylthio, 2,3-dimethylbutylthio and 2-ethylbutylthio groups. We prefer straight or branched chain alkylthio groups having from 1 to 3 carbon atoms, of which we particularly prefer methylthio groups and ethylthio groups.

In the compounds of the present invention, alkylthio groups having from 1 to 6 carbon atoms substituted by from 1 to 4 halogen atoms may be straight or branched chain alkylthio groups substituted by from 1 to 4 halogen atoms which may be the same as or different from each other. Examples include the chloromethylthio, dichloromethylthio, trichloromethylthio, 1-chloroethylthio, 2-chloroethylthio, 1-chloropropylthio, fluoromethylthio, difluoromethylthio, trifluoromethylthio, 1-fluoroethylthio, 2-fluoroethylthio, fluorochloromethylthio and bromomethylthio groups. We prefer fluoromethylthio groups, chloromethylthio groups and trifluoromethylthio groups, particularly trifluoromethylthio groups.

In the compounds of the present invention, alkenyl groups having from 2 to 6 carbon atoms may be straight or branched chain alkenyl groups having from 2 to 6 carbon atoms. Examples include the vinyl, 2-propenyl, 1-methyl-2-propenyl, 2-methyl-2-propenyl, 2-ethyl-2-propenyl, 2-butenyl, 1-methyl-2-butenyl, 2-methyl-2-butenyl, 1-ethyl-2-butenyl, 3-butenyl, 1-methyl-3-butenyl, 2-methyl-3-butenyl, 1-ethyl-3-butenyl, 2-pentenyl, 1-methyl-2-pentenyl, 2-methyl-2-pentenyl, 3-pentenyl, 1-methyl-3-pentenyl, 2-methyl-3-pentenyl, 4-pentenyl, 1-methyl-4-pentenyl, 2-methyl-4-pentenyl, 2-hexenyl, 3-hexenyl, 4-hexenyl and 5-hexenyl groups. We prefer straight or branched chain alkenyl groups having from 2 to 5 carbon atoms, most preferably 2-propenyl groups.

In the compounds of the present invention, alkenyl groups having from 2 to 6 carbon atoms substituted by from 1 to 4 halogen atoms may be straight or branched chain alkenyl groups having from 2 to 6 carbon atoms substituted by from 1 to 4 halogen atoms which may be the same as or different from each other. Examples include the 2-chlorovinyl, 3-chloro-2-propenyl, 2,2-dibromovinyl and 2,2-dichlorovinyl groups. We prefer alkenyl groups having from 2 to 4 carbon atoms substituted by from 1 to 3 halogen atoms which may be, the same as or different from each other, most preferably 2-chlorovinyl groups and 3-chloro-2-propenyl groups.

In the compounds of the present invention, alkynyl groups having from 2 to 6 carbon atoms may be straight or branched chain alkynyl groups having from 2 to 6 carbon atoms. Examples include the include the ethynyl, 2-propynyl, 1-methyl-2-propynyl, 2-methyl-2-propynyl, 2-ethyl-2-propynyl, 2-butynyl, 1-methyl-2-butynyl, 2-methyl-2-butynyl, 1-ethyl-2-butynyl, 3-butynyl, 1-methyl-3-butynyl, 2-methyl-3-butynyl, 1-ethyl-3-butynyl, 2-pentynyl, 1-methyl-2-pentynyl, 2-methyl-2-pentynyl, 3-pentynyl, 1-methyl-3-pentynyl, 2-methyl-3-pentynyl, 4-pentynyl, 1-methyl-4-pentynyl, 2-methyl-4-pentynyl, 2-hexynyl, 3-hexynyl, 4-hexynyl and 5-hexynyl groups. We prefer straight or branched chain alkynyl groups having from 3 to 5 carbon atoms, most preferably 2-propynyl groups.

In the compounds of the present invention, alkynyl groups having from 2 to 6 carbon atoms substituted by from 1 to 4 halogen atoms may be straight or branched chain alkynyl groups having from 2 to 6 carbon atoms substituted by from 1 to 4 halogen atoms which may be the same as or different from each other. We prefer alkynyl groups having from 3 to 5 carbon atoms substituted by 1 or 2 halogen atoms which are same as or different from each other, most preferably 1-chloro-2-propynyl groups.

In the compounds of the present invention, aryl groups may be carbocyclic aryl groups having from 6 to 14 ring carbon atoms, examples of which include phenyl and naphthyl groups, of which we particularly prefer phenyl groups.

In the compounds of the present invention, aryl groups substituted by at least one alkyl group may be carbocyclic aryl groups having from 6 to 14 ring carbon atoms substituted by at least one straight or branched chain alkyl group having from 1 to 6 carbon atoms and, where there are 2 or more alkyl substituents, these may be the same as or different from each other. We prefer carbocyclic aryl groups having from 6 to 14 carbon atoms substituted by from 1 to 3 alkyl groups having from 1 to 6 carbon atoms. Examples include the 2-methylphenyl, 3-methylphenyl, 4-methylphenyl, 2-ethylphenyl, 3-ethylphenyl, 4-ethylphenyl, 4-isopropylphenyl, 4-t-butylphenyl, 2,4-dimethylphenyl and 3,5-dimethylphenyl groups.

In the compounds of the present invention, aryl groups substituted by at least one alkoxy group may be carbocyclic aryl groups having from 6 to 14 ring carbon atoms substituted by at least one straight or branched chain alkoxy group having from 1 to 6 carbon atoms and, where there are 2 or more alkoxy substituents, these may be the same as or different from each other. We prefer carbocyclic aryl groups having from 6 to 14 carbon atoms substituted by from 1 to 3 alkoxy groups having from 1 to 6 carbon atoms. Examples include the 2-methoxyphenyl, 3-methoxyphenyl, 4-methoxyphenyl, 2-ethoxyphenyl, 3-ethoxyphenyl, 4-ethoxyphenyl, 4-isopropoxyphenyl, 4-t-butoxyphenyl, 2,4-dimethoxyphenyl and 3,5-dimethoxyphenyl groups.

In the compounds of the present invention, aryl groups substituted by at least one halogen atom may be carbocyclic aryl groups having from 6 to 14 ring carbon atoms substituted by at least one halogen atom and, where there are 2 or more halogen substituents, these may be the same as or different from each other. We prefer carbocyclic aryl groups having from 6 to 14 carbon atoms substituted by from 1 to 4 halogen atoms. Examples include the 2-chlorophenyl, 3-chlorophenyl, 4-chlorophenyl, 2-fluorophenyl, 3-fluorophenyl, 4-fluorophenyl, 2-bromophenyl, 2,4-dichlorophenyl and 2,4-difluorophenyl groups.

In the compounds of the present invention, aralkyl groups may be straight or branched chain alkyl groups having from 1 to 6 carbon atoms substituted by a carbocyclic aryl group having from 6 to 10 carbon atoms. Examples include the benzyl, α-methylbenzyl, α,α-dimethylbenzyl, phenethyl, phenylpropyl, naphthylmethyl and naphthylethyl groups, preferably benzyl groups and phenethyl groups.

In the compounds of the present invention, aralkyl groups substituted by from 1 to 4 halogen atoms may be straight or branched chain alkyl groups having from 1 to 6 carbon atoms substituted by a carbocyclic aryl group having from 6 to 10 carbon atoms in which the aryl group is substituted by from 1 to 4 halogen atoms which may be the same as or different from each other.

In the compounds of the present invention, heterocyclic groups may have from 4 to 10 ring atoms including at least one heteroatom selected from the group consisting of oxygen, sulfur and nitrogen atoms. The heterocyclic group may be unsaturated, partially saturated or completely saturated and may be unsubstituted, substituted by at least one substituent selected from the group consisting of straight or branched chain alkyl groups having from 1 to 6 carbon atoms, straight or branched chain alkoxy groups having from 1 to 6 carbon atoms and halogen atoms, or it may be fused with a carbocyclic aryl group having from 6 to 10 ring carbon atoms. Examples include the oxetanyl, azetidinyl, thietanyl, dioxanyl, furyl, thienyl, pyrrolyl, thiazolyl, isothiazolyl, oxazolyl, isoxazolyl, imidazolyl, pyrazolyl, pyranyl, pyrazinyl, pyridyl, pyridazinyl, pyrimidinyl, benzofuranyl, benzothiophenyl, benzothiazolyl, benzoxazolyl, indolyl, quinolyl, isoquinolyl, quinazolinyl, quinoxalinyl, naphthyridinyl, tetrahydrofuryl, tetrahydrothienyl, thiazolidinyl, imidazolidinyl, imidazolinyl, oxazolinyl, pyrazolidinyl, piperazinyl, tetrahydropyrimidinyl, morpholinyl, indolinyl, tetrahydroquinolyl, pyrrolidinyl, piperidinyl, 1,3-dimethyl-4-pyrazinyl, 3,5-dimethyl-4-isoxazolyl and 6-chloropyridazinyl groups.

The compounds of formula (I) of the present invention can be converted to addition salts such as sulfates, hydrochlorides, nitrates and phosphates. These addition salts are also included in the present invention as long as they are herbicidally acceptable for agricultural and horticultural use.

Hydrates of the compounds of general formula (I) of the present invention are also included in the present invention.

The compounds of the present invention may contain one or more asymmetric carbon atoms in their molecules, and may thus form optical isomers. Although these are all represented herein by a single molecular formula, the present invention includes both the individual, isolated isomers and mixtures, including racemates thereof. Where stereospecific synthesis techniques are employed or optically active compounds are employed as starting materials, individual isomers may be prepared directly; on the other hand, if a mixture of isomers is prepared, the individual isomers may be obtained by conventional resolution techniques.

Of the compounds of formula (I) of the present invention, we prefer those in which $R^1$ represents:

an alkyl group having from 1 to 6 carbon atoms, said alkyl group being unsubstituted or being substituted by an alkoxy group having from 1 to 6 carbon atoms or by from 1 to 4 halogen atoms;

a cycloalkyl group having from 3 to 6 carbon atoms; or an alkoxy group having from 1 to 6 carbon atoms, said alkoxy group being unsubstituted or being substituted by from 1 to 4 halogen atoms.

More preferably, $R^1$ represents:

an alkyl group having from 1 to 6 carbon atoms, said alkyl group being unsubstituted or being substituted by an alkoxy group having from 1 to 6 carbon atoms; or by from 1 to 4 halogen atoms; or an unsubstituted alkoxy group having from 1 to 6 carbon atoms.

Yet more preferably, $R^1$ represents:

an alkyl group having from 1 to 3 carbon atoms, said alkyl group being unsubstituted or being substituted by an alkoxy group having from 1 to 3 carbon atoms; or an unsubstituted alkoxy group having from 1 to 3 carbon atoms.

Most preferably, $R^1$ represents a methyl group or a methoxy group, particularly a methoxy group.

We also prefer compounds of formula (I) of the present invention wherein $R^2$ represents:

a hydrogen atom;

an alkyl group having from 1 to 6 carbon atoms, said alkyl group being unsubstituted or being substituted by a hydroxy group or by from 1 to 4 halogen atoms;

a cycloalkyl group having from 3 to 6 carbon atoms; or a group represented by the formula —$YR^7$.

More preferably, $R^2$ represents:

a hydrogen atom;

an alkyl group having from 1 to 6 carbon atoms, said alkyl group being unsubstituted or being substituted by a hydroxy group; or a group represented by the formula —$YR^7$.

Yet more preferably, $R^2$ represents:

a hydrogen atom;

an alkyl group having from 1 to 3 carbon atoms which is substituted by a hydroxy group; or a group represented by the formula —$YR^7$.

Most preferably, $R^2$ represents a hydrogen atom, a hydroxymethyl group or a group represented by the formula —$YR^7$ particularly a hydrogen atom.

Of those compounds of the present invention wherein $R^2$ represents a group represented by the formula —$YR^7$, we prefer:

(i) those compounds wherein Y represents a group of formula —CO—, —COO—, —$CH_2$—, —$CH_2CH_2O$—, —$CH_2CO$—, —$CH_2COO$—, —$CH_2CH_2CO$—, —$CH_2OCO$—, —$CH_2OCOO$— or —$CH_2CH_2OCO$—;

preferably those compounds wherein Y represents a group of formula —CO—, —COO—, —$CH_2$—, —$CH_2CH_2O$—, —$CH_2OCO$— or —$CH_2OCOO$—;

more preferably those compounds wherein Y represents a group of formula —CO—, —COO—, —$CH_2O$—, —$CH_2OCO$— or —$CH_2OCOO$—;

and most preferably those compounds wherein Y represents a group of formula —CO—, —COO— or —$CH_2OCO$—; and (ii) those compounds wherein $R^7$ represents an alkyl group having from 1 to 6 carbon atoms, said alkyl group being unsubstituted or being substituted by an alkoxy group having from 1 to 6 carbon atoms or by from 1 to 4 halogen atoms, a cycloalkyl group having from 3 to 6 carbon atoms, an alkenyl group having from 2 to 6 carbon atoms, said alkenyl group being unsubstituted or being substituted by from 1 to 4 halogen atoms, an alkynyl group having from 2 to 6 carbon atoms, said alkynyl group being unsubstituted or being substituted by from 1 to 4 halogen atoms, a carbocyclic aryl group having from 6 to 14 ring carbon atoms, said aryl group being unsubstituted or being substituted by from 1 to 3 alkyl groups having from 1 to 6 carbon atoms, 1 to 3 alkoxy groups having from 1 to 6 carbon atoms or by from 1 to 4 halogen atoms, an aralkyl group wherein the aryl moiety is a carbocyclic aryl group having from 6 to 14 ring carbon atoms, said aryl group being unsubstituted or being substituted by from 1 to 4 halogen atoms, and the alkyl moiety has from 1 to 6 carbon atoms, or a heterocyclic group having from 4 to 10 ring atoms including at least one ring heteroatom selected from the group consisting of oxygen atoms, sulfur atoms and nitrogen atoms, said heterocyclic group being fully unsaturated, partly unsaturated or saturated and being either unsubstituted, substituted by at least one substituent selected from alkyl groups having from 1 to 6 carbon atoms, alkoxy groups having from 1 to 6 carbon atoms and halogen atoms, or fused with a carbocyclic aryl group having from 6 to 10 ring carbon atoms;

preferably those compounds wherein $R^7$ represents an alkyl group having from 1 to 6 carbon atoms, said alkyl group being unsubstituted or being substituted by an alkoxy group having from 1 to 6 carbon atoms or by from 1 to 4 halogen atoms;

more preferably those compounds wherein $R^7$ represents an alkyl group having from 1 to 3 carbon atoms, said alkyl group being unsubstituted or being substituted by from 1 to 4 halogen atoms; and most preferably an ethyl group or a 2,2,2-trichloroethyl group.

We also prefer compounds of formula (I) of the present invention wherein $R^3$ represents:

an alkyl group having from 1 to 6 carbon atoms, said alkyl group being unsubstituted or being substituted by a alkoxy group having from 1 to 6 carbon atoms or by from 1 to 4 halogen atoms;

a cycloalkyl group having from 3 to 6 carbon atoms;

an alkoxy group having from 1 to 6 carbon atoms, said alkoxy group being unsubstituted or being substituted by from 1 to 4 halogen atoms;

a halogen atom;

a nitro group; or a group represented by the formula —$COR^8$.

More preferably, $R^3$ represents:

an alkyl group having from 1 to 6 carbon atoms, said alkyl group being unsubstituted or being substituted by an alkoxy group having from 1 to 6 carbon atoms or by from 1 to 4 halogen atoms;

an alkoxy group having from 1 to 6 carbon atoms, said alkoxy group being unsubstituted or being substituted by from 1 to 4 halogen atoms; or a halogen atom.

Yet more preferably, $R^3$ represents:

an unsubstituted alkyl group having from 1 to 3 carbon atoms;

an alkoxy group having from 1 to 3 carbon atoms; or a halogen atom.

Most preferably, $R^3$ represents a methyl group, an ethyl group, a methoxy group, an ethoxy group, a fluorine atom or a chlorine atom, particularly a methyl group.

Preferably, $R^3$ is at the 2-position of the phenyl ring in the compounds of formula (I) of the present invention.

We also prefer compounds of formula (I) of the present invention wherein $R^4$ and $R^5$ are the same or different and each represents a hydrogen atom or a methyl group. More preferably, $R^4$ represents a hydrogen atom or a methyl group and $R^5$ represents a hydrogen atom. Most preferably, $R^4$ and $R^5$ each represent a hydrogen atom.

We also prefer compounds of formula (I) of the present invention wherein $R^6$ represents:

an alkyl group having from 1 to 6 carbon atoms, said alkyl group being unsubstituted or being substituted by a alkoxy group having from 1 to 6 carbon atoms or by from 1 to 4 halogen atoms;

a cycloalkyl group having from 3 to 6 carbon atoms;

an alkoxy group having from 1 to 6 carbon atoms, said alkoxy group being unsubstituted or being substituted by from 1 to 4 halogen atoms;

a halogen atom; or a group represented by the formula $-COR^8$.

More preferably, $R^6$ represents:

an alkyl group having from 1 to 6 carbon atoms, said alkyl group being unsubstituted or being substituted by from 1 to 4 halogen atoms;

an alkoxy group having from 1 to 6 carbon atoms, said alkoxy group being unsubstituted or being substituted by from 1 to 4 halogen atoms; or a halogen atom.

Yet more preferably, p.6 represents:

an unsubstituted alkyl group having from 1 to 3 carbon atoms;

an unsubstituted alkoxy group having from 1 to 3 carbon atoms; or a halogen atom.

Most preferably, $R^6$ represents a methoxy group, a fluorine atom or a chlorine atom, particularly a fluorine atom or a chlorine atom.

Of those compounds of the present invention wherein $R^3$ and/or $R^6$ represents a group of formula $-COR^8$ we prefer those compounds wherein $R^8$ represents an alkyl group having from 1 to 3 carbon atoms or an alkoxy group having from 1 to 3 carbon atoms. More preferably, $R^8$ represents an alkoxy group having from 1 to 3 carbon atoms. Most preferably, $R^8$ represents a methoxy group.

We also prefer compounds of the present invention wherein A represents an oxygen atom, X represents an oxygen atom and Q represents a sulfur atom.

We also prefer compounds wherein m is an integer from 0 to 3; more preferably compounds wherein m is an integer of 0 or 1; and most preferably compounds wherein m is an integer of 0.

We also prefer compounds wherein n is an integer from 0 to 3; more preferably compounds wherein n is an integer of 0 to 2; yet more preferably compounds wherein n is an integer of 0 or 1; and most preferably compounds wherein n is an integer of 1.

The preferred compounds of the present invention are those compounds of formula (I) wherein:

$R^1$ represents:

an alkyl group having from 1 to 6 carbon atoms, said alkyl group being unsubstituted or being substituted by an alkoxy group having from 1 to 6 carbon atoms or by from 1 to 4 halogen atoms;

a cycloalkyl group having from 3 to 6 carbon atoms; or an alkoxy group having from 1 to 6 carbon atoms, said alkoxy group being unsubstituted or being substituted by from 1 to 4 halogen atoms;

$R^2$ represents:

a hydrogen atom;

an alkyl group having from 1 to 6 carbon atoms, said alkyl group being unsubstituted or being substituted by a hydroxy group or by from 1 to 4 halogen atoms;

a cycloalkyl group having from 3 to 6 carbon atoms; or a group represented by the formula $-YR^7$, wherein Y represents a group of formula $-CO-$, $-COO-$, $-CH_2O-$, $-CH_2CH_2O-$, $-CH_2CO-$, $-CH_2COO-$, $-CH_2CH_2CO-$, $-CH_2OCO-$, $-CH_2OCOO-$ or $-CH_2CH_2OCO-$ and $R^7$ represents an alkyl group having from 1 to 6 carbon atoms, said alkyl group being unsubstituted or being substituted by an alkoxy group having from 1 to 6 carbon atoms or by from 1 to 4 halogen atoms, a cycloalkyl group having from 3 to 6 carbon atoms, an alkenyl group having from 2 to 6 carbon atoms, said alkenyl group being unsubstituted or being substituted by from 1 to 4 halogen atoms, an alkynyl group having from 2 to 6 carbon atoms, said alkynyl group being unsubstituted or being substituted by from 1 to 4 halogen atoms, a carbocyclic aryl group having from 6 to 14 ring carbon atoms, said aryl group being unsubstituted or being substituted by from 1 to 3 alkyl groups having from 1 to 6 carbon atoms, 1 to 3 alkoxy groups having from 1 to 6 carbon atoms or by from 1 to 4 halogen atoms, an aralkyl group wherein the aryl moiety is a carbocyclic aryl group having from 6 to 14 ring carbon atoms, said aryl group being unsubstituted or being substituted by from 1 to 4 halogen atoms, and the alkyl moiety has from 1 to 6 carbon atoms, or a heterocyclic group having from 4 to 10 ring atoms including at least one ring heteroatom selected from the group consisting of oxygen atoms, sulfur atoms and nitrogen atoms, said heterocyclic group being fully unsaturated, partly unsaturated or saturated and being either unsubstituted, substituted by at least one substituent selected from alkyl groups having from 1 to 6 carbon atoms, alkoxy groups having from 1 to 6 carbon atoms and halogen atoms, or fused with a carbocyclic aryl group having from 6 to 10 ring carbon atoms;

$R^3$ represents:

an alkyl group having from 1 to 6 carbon atoms, said alkyl group being unsubstituted or being substituted by a alkoxy group having from 1 to 6 carbon atoms or by from 1 to 4 halogen atoms;

a cycloalkyl group having from 3 to 6 carbon atoms;

an alkoxy group having from 1 to 6 carbon atoms, said alkoxy group being unsubstituted or being substituted by from 1 to 4 halogen atoms;

a halogen atom;

a nitro group; or a group represented by the formula $-COR^a$, wherein $R^s$ represents an alkyl group having from 1 to 3 carbon atoms or an alkoxy group having from 1 to 3 carbon atoms;

$R^4$ and $R^s$ are the same or different and each represents a hydrogen atom or a methyl group;

$R^6$ represents:

an alkyl group having from 1 to 6 carbon atoms, said alkyl group being unsubstituted or being substituted by a alkoxy group having from 1 to 6 carbon atoms or by from 1 to 4 halogen atoms;

a cycloalkyl group having from 3 to 6 carbon atoms;

an alkoxy group having from 1 to 6 carbon atoms, said alkoxy group being unsubstituted or being substituted by from 1 to 4 halogen atoms;

a halogen atom; or a group represented by the formula $-COR^8$, wherein $R^8$ represents an alkyl group having from 1 to 3 carbon atoms or an alkoxy group having from 1 to 3 carbon atoms;

and m and n are the same or different and each represents an integer from 0 to 3.

More preferred compounds of the present invention are those compounds of formula (I) wherein:

$R^1$ represents:
an alkyl group having from 1 to 6 carbon atoms, said alkyl group being unsubstituted or being substituted by an alkoxy group having from 1 to 6 carbon atoms or by from 1 to 4 halogen atoms; or
an unsubstituted alkoxy group having from 1 to 6 carbon atoms;

$R^2$ represents:
a hydrogen atom;
an alkyl group having from 1 to 6 carbon atoms, said alkyl group being unsubstituted or being substituted by a hydroxy group; or
a group represented by the formula —$YR^7$, wherein Y represents a group of formula —CO—, —COO—, —$CH_2O$—, —$CH_2CH_2O$—, —$CH_2OCO$— or —$CH_2OCOO$— and $R^7$ represents an alkyl group having from 1 to 6 carbon atoms, said alkyl group being unsubstituted or being substituted by an alkoxy group having from 1 to 6 carbon atoms or by from 1 to 4 halogen atoms;

$R^3$ represents:
an alkyl group having from 1 to 6 carbon atoms, said alkyl group being unsubstituted or being substituted by an alkoxy group having from 1 to 6 carbon atoms or by from 1 to 4 halogen atoms;
an alkoxy group having from 1 to 6 carbon atoms, said alkoxy group being unsubstituted or being substituted by from 1 to 4 halogen atoms; or
a halogen atom;

$R^4$ and $R^5$ are the same or different and each represents a hydrogen atom or a methyl group;

$R^6$ represents:
an alkyl group having from 1 to 6 carbon atoms, said alkyl group being unsubstituted or being substituted by from 1 to 4 halogen atoms;
an alkoxy group having from 1 to 6 carbon atoms, said alkoxy group being unsubstituted or being substituted by from 1 to 4 halogen atoms; or
a halogen atom; and m represents an integer from 0 to 3 and n represents an integer from 0 to 2.

Yet more preferred compounds of the present invention are those compounds of formula (I) wherein:

$R^1$ represents:
an alkyl group having from 1 to 3 carbon atoms, said alkyl group being unsubstituted or being substituted by an alkoxy group having from 1 to 3 carbon atoms; or
an unsubstituted alkoxy group having from 1 to 3 carbon atoms;

$R^2$ represents:
a hydrogen atom;
an alkyl group having from 1 to 3 carbon atoms which is substituted by a hydroxy group; or
a group represented by the formula —$YR^7$, wherein Y represents a group of formula —CO—, —COO—, —$CH_2O$—, —$CH_2OCO$— or —$CH_2OCOO$— and $R^7$ represents an alkyl group having from 1 to 3 carbon atoms, said alkyl group being unsubstituted or being substituted by from 1 to 4 halogen atoms;

$R^3$ represents:
an unsubstituted alkyl group having from 1 to 3 carbon atoms;
an alkoxy group having from 1 to 3 carbon atoms; or
a halogen atom;

$R^4$ represents a hydrogen atom or a methyl group and $R^5$ represents a hydrogen atom;

$R^6$ represents:
an unsubstituted alkyl group having from 1 to 3 carbon atoms;
an unsubstituted alkoxy group having from 1 to 3 carbon atoms; or
a halogen atom; and m and n are the same or different and each represents an integer of 0 or 1.

Particularly preferred compounds of the present invention are those compounds of formula (I) wherein:

$R^1$ represents a methyl group or a methoxy group;

$R^2$ represents a hydrogen atom, a hydroxymethyl group or a group represented by the formula —$YR^7$ wherein Y represents a group of formula —CO—, —COO— or —$CH_2OCO$— and $R^7$ represents an ethyl group or a 2,2,2-trichloroethyl group;

$R^3$ represents a methyl group, an ethyl group, a methoxy group, an ethoxy group, a fluorine atom or a chlorine atom;

$R^4$ represents a hydrogen atom or a methyl group and $R^5$ represents a hydrogen atom;

$R^6$ represents a methoxy group, a fluorine atom or a chlorine atom;

m and n are the same or different and each represents an integer of 0 or 1;

A represents an oxygen atom;

X represents an oxygen atom; and

Q represents a sulfur atom.

Most preferred compounds of the present invention are those compounds of formula (I) wherein:

$R^1$ represents a methoxy group;

$R^2$ represents a hydrogen atom;

$R^3$ represents a methyl group;

$R^4$ and $R^5$ each represent a hydrogen atom;

m represents an integer of 0;

n represents an integer of 1;

A represents an oxygen atom;

X represents an oxygen atom; and

Q represents a sulfur atom.

Of the compounds of formula (I) of the present invention wherein n is an integer of 1, the group $R^3$ is preferably at the 2-position on the phenyl ring.

Specific examples of individual compounds of formula (I) of the present invention are shown in the following Tables 1 to 8. The present invention is not, however, limited to these compounds.

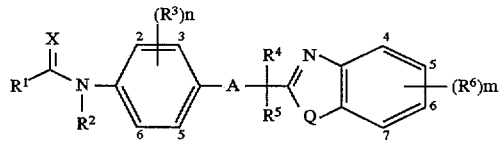

In the following tables, the following abbreviations are used:

| | |
|---|---|
| Benthi | benzo[b]thienyl |
| Bu | butyl |
| Et | ethyl |
| Furo | furoyl |
| Hex | hexyl |
| Isonico | isonicotinoyl |
| Isothi | isothiazolyl |
| Isox | isoxazolyl |
| Me | methyl |
| Nico | nicotinoyl |
| Pen | pentyl |
| Ph | phenyl |
| Pr | propyl |
| Pyra | pyrazinyl |
| Pyraz | pyrazolyl |
| Pyrd | pyridazinyl |
| Pyrim | pyrimidinyl |
| Pyrr | pyrrolyl |
| Qui | quinolyl |
| Then | thenoyl |
| THP | tetrahydropyranyl |
| Tria | triazolyl |

The presence of a hydrogen atom in the columns of Tables 1 to 8 relating to the substituents $R^3$ and $R^6$ denotes compounds wherein m and/or n is an integer of 0.

TABLE 1

| Compd. No. | $R^1$ | $R^2$ | $(R^3)_n$ | $ACR^4R^5$ | $(R^6)_m$ | X | Q |
|---|---|---|---|---|---|---|---|
| A1.1 | Me | H | H | $OCH_2$ | H | O | S |
| A1.2 | Me | H | H | $OCH_2$ | H | O | O |
| A1.3 | Me | H | H | $SCH_2$ | H | O | S |
| A1.4 | Me | H | H | $SCH_2$ | H | O | O |
| A1.5 | MeO | H | H | $OCH_2$ | H | O | S |
| A1.6 | MeO | H | H | $OCH_2$ | H | O | O |
| A1.7 | MeO | H | H | $SCH_2$ | H | O | S |
| A1.8 | MeO | H | H | $SCH_2$ | H | O | O |
| A1.9 | MeO | H | H | $OCH_2$ | H | S | S |
| A1.10 | MeO | H | H | $OCH_2$ | H | S | O |
| A1.11 | MeO | H | H | $SCH_2$ | H | S | S |
| A1.12 | MeO | H | H | $SCH_2$ | H | S | O |
| A1.13 | MeS | H | H | $OCH_2$ | H | O | S |
| A1.14 | MeS | H | H | $OCH_2$ | H | O | O |
| A1.15 | MeS | H | H | $SCH_2$ | H | O | S |
| A1.16 | MeS | H | H | $OCH_2$ | H | S | S |
| A1.17 | MeS | H | H | $OCH_2$ | H | S | O |
| A1.18 | Et | H | H | $OCH_2$ | H | O | S |
| A1.19 | Et | H | H | $SCH_2$ | H | O | S |
| A1.20 | Et | H | H | $OCH_2$ | H | O | O |
| A1.21 | EtO | H | H | $OCH_2$ | H | O | S |
| A1.22 | EtO | H | H | $OCH_2$ | H | O | O |
| A1.23 | nPr | H | H | $OCH_2$ | H | O | S |
| A1.24 | nPr | H | H | $SCH_2$ | H | O | S |
| A1.25 | nPrO | H | H | $OCH_2$ | H | O | S |
| A1.26 | iPr | H | H | $OCH_2$ | H | O | S |
| A1.27 | iPr | H | H | $SCH_2$ | H | O | S |
| A1.28 | iPrO | H | H | $OCH_2$ | H | O | S |
| A1.29 | nBu | H | H | $OCH_2$ | H | O | S |
| A1.30 | nBu | H | H | $SCH_2$ | H | O | S |
| A1.31 | nBuO | H | H | $OCH_2$ | H | O | S |
| A1.32 | tBu | H | H | $OCH_2$ | H | O | S |
| A1.33 | tBuO | H | H | $OCH_2$ | H | O | S |
| A1.34 | tBu | H | H | $OCH_2$ | H | O | O |
| A1.35 | tBuO | H | H | $OCH_2$ | H | O | O |
| A1.36 | $FCH_2$ | H | H | $OCH_2$ | H | O | S |
| A1.37 | $FCH_2$ | H | H | $OCH_2$ | H | O | O |
| A1.38 | $FCH_2$ | H | H | $SCH_2$ | H | O | S |
| A1.39 | $F_2CH$ | H | H | $OCH_2$ | H | O | S |
| A1.40 | $F_2CH$ | H | H | $OCH_2$ | H | O | O |
| A1.41 | $F_2CH$ | H | H | $SCH_2$ | H | O | S |
| A1.42 | $F_3C$ | H | H | $OCH_2$ | H | O | S |
| A1.43 | $F_3C$ | H | H | $OCH_2$ | H | O | O |
| A1.44 | $F_3C$ | H | H | $SCH_2$ | H | O | S |
| A1.45 | $ClCH_2$ | H | H | $OCH_2$ | H | O | S |
| A1.46 | $ClCH_2$ | H | H | $OCH_2$ | H | O | O |
| A1.47 | $ClCH_2$ | H | H | $SCH_2$ | H | O | S |
| A1.48 | $ClCH_2O$ | H | H | $OCH_2$ | H | O | S |
| A1.49 | $Cl_2CH$ | H | H | $OCH_2$ | H | O | S |
| A1.50 | $Cl_2CH$ | H | H | $SCH_2$ | H | O | S |
| A1.51 | $BrCH_2$ | H | H | $OCH_2$ | H | O | S |
| A1.52 | $BrCH_2$ | H | H | $SCH_2$ | H | O | S |
| A1.53 | FClCH | H | H | $OCH_2$ | H | O | S |
| A1.54 | FClCH | H | H | $SCH_2$ | H | O | S |
| A1.55 | $ClCH_2O$ | H | H | $OCH_2$ | H | O | O |
| A1.56 | $Cl_3CCH_2O$ | H | H | $OCH_2$ | H | O | S |
| A1.57 | $Cl_3CCH_2O$ | H | H | $OCH_2$ | H | O | O |
| A1.58 | $Br(CH_2)_3$ | H | H | $OCH_2$ | H | O | S |
| A1.59 | $Br(CH_2)_3$ | H | H | $SCH_2$ | H | O | S |
| A1.60 | $Br(CH_2)_4$ | H | H | $OCH_2$ | H | O | S |
| A1.61 | $Br(CH_2)_4$ | H | H | $SCH_2$ | H | O | S |
| A1.62 | $MeOCH_2$ | H | H | $OCH_2$ | H | O | S |
| A1.63 | $MeOCH_2$ | H | H | $OCH_2$ | H | O | O |
| A1.64 | $MeOCH_2$ | H | H | $SCH_2$ | H | O | S |
| A1.65 | $EtOCH_2$ | H | H | $OCH_2$ | H | O | S |
| A1.66 | $EtOCH_2$ | H | H | $OCH_2$ | H | O | O |
| A1.67 | $EtOCH_2$ | H | H | $SCH_2$ | H | O | S |
| A1.68 | $nPrOCH_2$ | H | H | $OCH_2$ | H | O | S |
| A1.69 | $nPrOCH_2$ | H | H | $SCH_2$ | H | O | S |
| A1.70 | $MeOCH_2CH_2$ | H | H | $OCH_2$ | H | O | S |
| A1.71 | $MeOCH_2CH_2$ | H | H | $OCH_2$ | H | O | O |
| A1.72 | $MeOCH_2CH_2$ | H | H | $SCH_2$ | H | O | S |
| A1.73 | $EtOCH_2CH_2$ | H | H | $OCH_2$ | H | O | S |
| A1.74 | $EtOCH_2CH_2$ | H | H | $OCH_2$ | H | O | O |
| A1.75 | $EtOCH_2CH_2$ | H | H | $SCH_2$ | H | O | S |
| A1.76 | $nPrOCH_2CH_2$ | H | H | $OCH_2$ | H | O | S |
| A1.77 | $nPrOCH_2CH_2$ | H | H | $OCH_2$ | H | O | O |

TABLE 2

| Compd. No. | $R^1$ | $R^2$ | $(R^3)_n$ | $ACR^4R^5$ | $(R^6)_m$ | X | Q |
|---|---|---|---|---|---|---|---|
| B1.1 | Me | Me | H | $OCH_2$ | H | O | S |
| B1.2 | Me | Me | H | $SCH_2$ | H | O | S |
| B1.3 | MeO | Me | H | $OCH_2$ | H | O | S |

TABLE 2-continued

| Compd. No. | R¹ | R² | (R³)ₙ | ACR⁴R⁵ | (R⁶)ₘ | X | Q |
|---|---|---|---|---|---|---|---|
| B1.4 | Me | Me | H | OCH₂ | H | O | O |
| B1.5 | MeO | Me | H | OCH₂ | H | O | O |
| B1.6 | Me | Et | H | OCH₂ | H | O | S |
| B1.7 | MeO | Et | H | OCH₂ | H | O | S |
| B1.8 | Me | Et | H | SCH₂ | H | O | S |
| B1.9 | Me | Et | H | OCH₂ | H | O | O |
| B1.10 | MeO | Et | H | OCH₂ | H | O | O |
| B1.11 | Me | iPr | H | OCH₂ | H | O | S |
| B1.12 | MeO | iPr | H | OCH₂ | H | O | S |
| B1.13 | Me | iPr | H | OCH₂ | H | O | O |
| B1.14 | MeO | iPr | H | OCH₂ | H | O | O |
| B1.15 | Et | Me | H | OCH₂ | H | O | S |
| B1.16 | Et | Et | H | OCH₂ | H | O | S |
| B1.17 | nPr | Et | H | OCH₂ | H | O | S |
| B1.18 | nBu | Et | H | OCH₂ | H | O | S |
| B1.19 | iPr | Et | H | OCH₂ | H | O | S |
| B1.20 | FCH₂ | Et | H | OCH₂ | H | O | S |
| B1.21 | F₂CH | Et | H | OCH₂ | H | O | S |
| B1.22 | F₃C | Et | H | OCH₂ | H | O | S |
| B1.23 | ClCH₂ | Et | H | OCH₂ | H | O | S |
| B1.24 | Cl₂CH | Et | H | OCH₂ | H | O | S |
| B1.25 | BrCH₂ | Et | H | OCH₂ | H | O | S |
| B1.26 | FClCH | Et | H | OCH₂ | H | O | S |
| B1.27 | MeOCH₂ | Et | H | OCH₂ | H | O | S |
| B1.28 | EtOCH₂ | Et | H | OCH₂ | H | O | S |
| B1.29 | nPrOCH₂ | Et | H | OCH₂ | H | O | S |
| B1.30 | MeOCH₂CH₂ | Et | H | OCH₂ | H | O | S |
| B1.31 | EtOCH₂CH₂ | Et | H | OCH₂ | H | O | S |
| B1.32 | Me | nPr | H | OCH₂ | H | O | S |
| B1.33 | Me | nPr | H | SCH₂ | H | O | S |
| B1.34 | Et | nPr | H | OCH₂ | H | O | S |
| B1.35 | nPr | nPr | H | OCH₂ | H | O | S |
| B1.36 | nBu | nPr | H | OCH₂ | H | O | S |
| B1.37 | iPr | nPr | H | OCH₂ | H | O | S |
| B1.38 | FCH₂ | nPr | H | OCH₂ | H | O | S |
| B1.39 | F₂CH | nPr | H | OCH₂ | H | O | S |
| B1.40 | F₃C | nPr | H | OCH₂ | H | O | S |
| B1.41 | ClCH₂ | nPr | H | OCH₂ | H | O | S |
| B1.42 | Cl₂CH | nPr | H | OCH₂ | H | O | S |
| B1.43 | BrCH₂ | nPr | H | OCH₂ | H | O | S |
| B1.44 | FClCH | nPr | H | OCH₂ | H | O | S |
| B1.45 | MeOCH₂ | nPr | H | OCH₂ | H | O | S |
| B1.46 | EtOCH₂ | nPr | H | OCH₂ | H | O | S |
| B1.47 | nPrOCH₂ | nPr | H | OCH₂ | H | O | S |
| B1.48 | MeOCH₂CH₂ | nPr | H | OCH₂ | H | O | S |
| B1.49 | EtOCH₂CH₂ | nPr | H | OCH₂ | H | O | S |
| B1.50 | Me | nBu | H | OCH₂ | H | O | S |
| B1.51 | Et | nBu | H | OCH₂ | H | O | S |
| B1.52 | nPr | nBu | H | OCH₂ | H | O | S |
| B1.53 | nBu | nBu | H | OCH₂ | H | O | S |
| B1.54 | iPr | nBu | H | OCH₂ | H | O | S |
| B1.55 | FCH₂ | nBu | H | OCH₂ | H | O | S |
| B1.56 | F₂CH | nBu | H | OCH₂ | H | O | S |
| B1.57 | F₃C | nBu | H | OCH₂ | H | O | S |
| B1.58 | ClCH₂ | nBu | H | OCH₂ | H | O | S |
| B1.59 | Cl₂CH | nBu | H | OCH₂ | H | O | S |
| B1.60 | BrCH₂ | nBu | H | OCH₂ | H | O | S |
| B1.61 | FClCH | nBu | H | OCH₂ | H | O | S |
| B1.62 | MeOCH₂ | nBu | H | OCH₂ | H | O | S |
| B1.63 | EtOCH₂ | nBu | H | OCH₂ | H | O | S |
| B1.64 | nPrOCH₂ | nBu | H | OCH₂ | H | O | S |
| B1.65 | MeOCH₂CH₂ | nBu | H | OCH₂ | H | O | S |
| B1.66 | EtOCH₂CH₂ | nBu | H | OCH₂ | H | O | S |
| B1.67 | Et | iPr | H | OCH₂ | H | O | S |
| B1.68 | nPr | iPr | H | OCH₂ | H | O | S |
| B1.69 | nBu | iPr | H | OCH₂ | H | O | S |
| B1.70 | iPr | iPr | H | OCH₂ | H | O | S |
| B1.71 | FCH₂ | iPr | H | OCH₂ | H | O | S |
| B1.72 | F₂CH | iPr | H | OCH₂ | H | O | S |
| B1.73 | F₃C | iPr | H | OCH₂ | H | O | S |
| B1.74 | ClCH₂ | iPr | H | OCH₂ | H | O | S |
| B1.75 | Cl₂CH | iPr | H | OCH₂ | H | O | S |
| B1.76 | BrCH₂ | iPr | H | OCH₂ | H | O | S |
| B1.77 | FClCH | iPr | H | OCH₂ | H | O | S |
| B1.78 | MeOCH₂ | iPr | H | OCH₂ | H | O | S |
| B1.79 | EtOCH₂ | iPr | H | OCH₂ | H | O | S |

TABLE 2-continued

| Compd. No. | R¹ | R² | (R³)ₙ | ACR⁴R⁵ | (R⁶)ₘ | X | Q |
|---|---|---|---|---|---|---|---|
| B1.80 | nPrOCH₂ | iPr | H | OCH₂ | H | O | S |
| B1.81 | MeOCH₂CH₂ | iPr | H | OCH₂ | H | O | S |
| B1.82 | EtOCH₂CH₂ | iPr | H | OCH₂ | H | O | S |
| B2.1 | F₂CH | COOMe | H | OCH₂ | H | O | S |
| B2.2 | F₃C | COOMe | H | OCH₂ | H | O | S |
| B2.3 | ClCH₂ | COOMe | H | OCH₂ | H | O | S |
| B2.4 | BrCH₂ | COOMe | H | OCH₂ | H | O | S |
| B2.5 | FClCH | COOMe | H | OCH₂ | H | O | S |
| B2.6 | EtOCH₂ | COOMe | H | OCH₂ | H | O | S |
| B2.7 | iPr | COOEt | H | OCH₂ | H | O | S |
| B2.8 | FCH₂ | COOEt | H | OCH₂ | H | O | S |
| B2.9 | F₂CH | COOEt | H | OCH₂ | H | O | S |
| B2.10 | F₃C | COOEt | H | OCH₂ | H | O | S |
| B2.11 | ClCH₂ | COOEt | H | OCH₂ | H | O | S |
| B2.12 | Cl₂CH | COOEt | H | OCH₂ | H | O | S |
| B2.13 | BrCH₂ | COOEt | H | OCH₂ | H | O | S |
| B2.14 | FClCH | COOEt | H | OCH₂ | H | O | S |
| B2.15 | MeOCH₂ | COOEt | H | OCH₂ | H | O | S |
| B2.16 | EtOCH₂ | COOEt | H | OCH₂ | H | O | S |
| B2.17 | nPrOCH₂ | COOEt | H | OCH₂ | H | O | S |
| B2.18 | MeOCH₂CH₂ | COOEt | H | OCH₂ | H | O | S |
| B2.19 | EtOCH₂CH₂ | COOEt | H | OCH₂ | H | O | S |
| B2.20 | nPr | Me | H | OCH₂ | H | O | S |
| B2.21 | iPr | Me | H | OCH₂ | H | O | S |
| B2.22 | nBu | Me | H | OCH₂ | H | O | S |
| B2.23 | tBu | Me | H | OCH₂ | H | O | S |
| B2.24 | FCH₂ | Me | H | OCH₂ | H | O | S |
| B2.25 | F₂CH | Me | H | OCH₂ | H | O | S |
| B2.26 | CF₃ | Me | H | OCH₂ | H | O | S |
| B2.27 | ClCH₂ | Me | H | OCH₂ | H | O | S |
| B2.28 | Cl₂CH | Me | H | OCH₂ | H | O | S |
| B2.29 | BrCH₂ | Me | H | OCH₂ | H | O | S |
| B2.30 | FClCH | Me | H | OCH₂ | H | O | S |
| B2.31 | MeOCH₂ | Me | H | OCH₂ | H | O | S |
| B2.32 | EtOCH₂ | Me | H | OCH₂ | H | O | S |
| B2.33 | nPrOCH₂ | Me | H | OCH₂ | H | O | S |
| B2.34 | MeOCH₂CH₂ | Me | H | OCH₂ | H | O | S |
| B2.35 | EtOCH₂CH₂ | Me | H | OCH₂ | H | O | S |
| B2.36 | Me | CH₂CH=CH₂ | H | OCH₂ | H | O | O |
| B2.37 | MeO | CH₂CH=CH₂ | H | OCH₂ | H | O | O |
| B2.38 | MeO | COMe | H | OCH₂ | H | O | S |
| B2.39 | MeO | COMe | H | SCH₂ | H | O | S |
| B2.40 | MeO | COMe | H | OCH₂ | H | O | O |
| B2.41 | MeO | COEt | H | OCH₂ | H | O | S |
| B2.42 | MeO | COEt | H | OCH₂ | H | O | O |
| B2.43 | MeO | COnPr | H | OCH₂ | H | O | S |
| B2.44 | MeO | COnPr | H | OCH₂ | H | O | O |
| B2.45 | MeO | COiPr | H | OCH₂ | H | O | S |
| B2.46 | MeO | COiPr | H | OCH₂ | H | O | O |
| B2.47 | MeO | COnBu | H | OCH₂ | H | O | S |
| B2.48 | MeO | COnBu | H | OCH₂ | H | O | O |
| B2.49 | MeO | COiBu | H | OCH₂ | H | O | S |
| B2.50 | MeO | COiBu | H | OCH₂ | H | O | O |
| B2.51 | MeO | COtBu | H | OCH₂ | H | O | S |
| B2.52 | MeO | COtBu | H | OCH₂ | H | O | O |
| B2.53 | FCH₂ | COOMe | H | OCH₂ | H | O | S |
| B2.54 | Cl₂CH | COOMe | H | OCH₂ | H | O | S |
| B2.55 | Cl₃CCH₂O | COOMe | H | OCH₂ | H | O | S |
| B2.56 | Cl₃CCH₂O | COOMe | H | OCH₂ | H | O | O |
| B2.57 | MeOCH₂ | COOMe | H | OCH₂ | H | O | S |
| B2.58 | MeOCH₂ | COOMe | H | OCH₂ | H | O | O |
| B2.59 | EtOCH₂ | COCH₂OEt | H | OCH₂ | H | O | S |
| B2.60 | MeO | COCH₂OnPr | H | OCH₂ | H | O | S |
| B2.61 | MeO | CO(CH₂)₂OMe | H | OCH₂ | H | O | S |
| B2.62 | MeO | CO(CH₂)₂OEt | H | OCH₂ | H | O | S |
| B2.63 | Me | COOEt | H | OCH₂ | H | O | S |
| B2.64 | Me | COOEt | H | SCH₂ | H | O | S |
| B2.65 | Et | COOEt | H | OCH₂ | H | O | S |
| B2.66 | nPr | COOEt | H | OCH₂ | H | O | S |
| B2.67 | nBu | COOEt | H | OCH₂ | H | O | S |

TABLE 3

| Compd. No. | $R^1$ | $R^2$ | $(R^3)_n$ | $ACR^4R^3$ | $(R^6)_m$ | X | Q |
|---|---|---|---|---|---|---|---|
| C1.1 | Me | H | 2-Me | OCH$_2$ | H | O | S |
| C1.2 | Me | H | 2-Me | OCH$_2$ | H | O | O |
| C1.3 | Me | H | 2-Me | SCH$_2$ | H | O | S |
| C1.4 | Me | H | 2-Me | SCH$_2$ | H | O | O |
| C1.5 | MeO | H | 2-Me | OCH$_2$ | H | O | S |
| C1.6 | MeO | H | 2-Me | OCH$_2$ | H | O | O |
| C1.7 | MeO | H | 2-Me | SCH$_2$ | H | O | S |
| C1.8 | MeO | H | 2-Me | SCH$_2$ | H | O | O |
| C1.9 | MeO | H | 2-Me | OCH$_2$ | H | S | S |
| C1.10 | MeO | H | 2-Me | OCH$_2$ | H | S | O |
| C1.11 | MeS | H | 2-Me | OCH$_2$ | H | O | S |
| C1.12 | MeS | H | 2-Me | OCH$_2$ | H | O | O |
| C1.13 | MeS | H | 2-Me | OCH$_2$ | H | S | S |
| C1.14 | MeS | H | 2-Me | OCH$_2$ | H | S | O |
| C1.15 | Et | H | 2-Me | OCH$_2$ | H | O | S |
| C1.16 | Et | H | 2-Me | OCH$_2$ | H | O | O |
| C1.17 | EtO | H | 2-Me | OCH$_2$ | H | O | S |
| C1.18 | EtO | H | 2-Me | OCH$_2$ | H | O | O |
| C1.19 | Cl$_3$CCH$_2$O | H | 2-Me | OCH$_2$ | H | O | S |
| C1.20 | Cl$_3$CCH$_2$O | H | 2-Me | OCH$_2$ | H | O | O |
| C1.21 | nPr | H | 2-Me | OCH$_2$ | H | O | S |
| C1.22 | iPr | H | 2-Me | OCH$_2$ | H | O | S |
| C1.23 | iPrO | H | 2-Me | OCH$_2$ | H | O | S |
| C1.24 | nPrO | H | 2-Me | OCH$_2$ | H | O | S |
| C1.25 | nPrO | H | 2-Me | OCH$_2$ | H | O | O |
| C1.26 | nBu | H | 2-Me | OCH$_2$ | H | O | S |
| C1.27 | tBu | H | 2-Me | OCH$_2$ | H | O | S |
| C1.28 | nBuO | H | 2-Me | OCH$_2$ | H | O | S |
| C1.29 | nBuO | H | 2-Me | OCH$_2$ | H | O | O |
| C1.30 | tBu | H | 2-Me | OCH$_2$ | H | O | O |
| C1.31 | tBuO | H | 2-Me | OCH$_2$ | H | O | S |
| C1.32 | tBuO | H | 2-Me | OCH$_2$ | H | O | O |
| C1.33 | iBu | H | 2-Me | OCH$_2$ | H | O | S |
| C1.34 | iBuO | H | 2-Me | OCH$_2$ | H | O | S |
| C1.35 | iBuO | H | 2-Me | OCH$_2$ | H | O | O |
| C1.36 | EtOCH$_2$ | H | 2-Me | OCH$_2$ | H | O | S |
| C1.37 | EtOCH$_2$ | H | 2-Me | OCH$_2$ | H | O | O |
| C1.38 | nPrOCH$_2$ | H | 2-Me | OCH$_2$ | H | O | S |
| C1.39 | nPrOCH$_2$ | H | 2-Me | OCH$_2$ | H | O | O |
| C1.40 | iPrOCH$_2$ | H | 2-Me | OCH$_2$ | H | O | S |
| C1.41 | iPrOCH$_2$ | H | 2-Me | OCH$_2$ | H | O | O |
| C1.42 | MeOC$_2$H$_4$ | H | 2-Me | OCH$_2$ | H | O | S |
| C1.43 | MeOC$_2$H$_4$ | H | 2-Me | OCH$_2$ | H | O | O |
| C1.44 | EtOC$_2$H$_4$ | H | 2-Me | OCH$_2$ | H | O | S |
| C1.45 | FCH$_2$ | H | 2-Me | OCH$_2$ | H | O | S |
| C1.46 | F$_2$CH | H | 2-Me | OCH$_2$ | H | O | S |
| C1.47 | F$_3$C | H | 2-Me | OCH$_2$ | H | O | S |
| C1.48 | ClCH$_2$ | H | 2-Me | OCH$_2$ | H | O | S |
| C1.49 | Cl$_2$CH | H | 2-Me | OCH$_2$ | H | O | S |
| C1.50 | BrCH$_2$ | H | 2-Me | OCH$_2$ | H | O | S |
| C1.51 | FClCH | H | 2-Me | OCH$_2$ | H | O | S |
| C1.52 | Me | H | 3-Me | OCH$_2$ | H | O | S |
| C1.53 | Me | H | 3-Me | SCH$_2$ | H | O | S |
| C1.54 | Me | H | 3-Me | OCH$_2$ | H | O | O |
| C1.55 | MeO | H | 3-Me | OCH$_2$ | H | O | S |
| C1.56 | MeO | H | 3-Me | OCH$_2$ | H | O | O |
| C1.57 | Et | H | 3-Me | OCH$_2$ | H | O | S |
| C1.58 | nPr | H | 3-Me | OCH$_2$ | H | O | S |
| C1.59 | iPr | H | 3-Me | OCH$_2$ | H | O | S |
| C1.60 | nBu | H | 3-Me | OCH$_2$ | H | O | S |
| C1.61 | FCH$_2$ | H | 3-Me | OCH$_2$ | H | O | S |
| C1.62 | F$_2$CH | H | 3-Me | OCH$_2$ | H | O | S |
| C1.63 | F$_3$C | H | 3-Me | OCH$_2$ | H | O | S |
| C1.64 | ClCH$_2$ | H | 3-Me | OCH$_2$ | H | O | S |
| C1.65 | Cl$_2$CH | H | 3-Me | OCH$_2$ | H | O | S |
| C1.66 | BrCH$_2$ | H | 3-Me | OCH$_2$ | H | O | S |
| C1.67 | FClCH | H | 3-Me | OCH$_2$ | H | O | S |
| C2.1 | Me | H | 2-Et | OCH$_2$ | H | O | S |
| C2.2 | Me | H | 2-Et | SCH$_2$ | H | O | S |
| C2.3 | Me | H | 2-Et | OCH$_2$ | H | O | O |
| C2.4 | MeO | H | 2-Et | OCH$_2$ | H | O | S |
| C2.5 | MeO | H | 2-Et | SCH$_2$ | H | O | S |
| C2.6 | MeO | H | 2-Et | OCH$_2$ | H | O | O |
| C2.7 | MeO | H | 2-Et | SCH$_2$ | H | O | O |
| C2.8 | Et | H | 2-Et | OCH$_2$ | H | O | S |
| C2.9 | nPr | H | 2-Et | OCH$_2$ | H | O | S |

TABLE 3-continued

| Compd. No. | R¹ | R² | (R³)ₙ | ACR⁴R³ | (R⁶)ₘ | X | Q |
|---|---|---|---|---|---|---|---|
| C2.10 | iPr | H | 2-Et | OCH₂ | H | O | S |
| C2.11 | nBu | H | 2-Et | OCH₂ | H | O | S |
| C2.12 | FCH₂ | H | 2-Et | OCH₂ | H | O | S |
| C2.13 | F₂CH | H | 2-Et | OCH₂ | H | O | S |
| C2.14 | F₃C | H | 2-Et | OCH₂ | H | O | S |
| C2.15 | ClCH₂ | H | 2-Et | OCH₂ | H | O | S |
| C2.16 | Cl₂CH | H | 2-Et | OCH₂ | H | O | S |
| C2.17 | BrCH₂ | H | 2-Et | OCH₂ | H | O | S |
| C2.18 | FClCH | H | 2-Et | OCH₂ | H | O | S |
| C2.19 | Me | H | 3-Et | OCH₂ | H | O | S |
| C2.20 | Me | H | 3-Et | SCH₂ | H | O | S |
| C2.21 | MeO | H | 3-Et | OCH₂ | H | O | S |
| C2.22 | MeO | H | 3-Et | OCH₂ | H | O | O |
| C2.23 | Et | H | 3-Et | OCH₂ | H | O | S |
| C2.24 | nPr | H | 3-Et | OCH₂ | H | O | S |
| C2.25 | iPr | H | 3-Et | OCH₂ | H | O | S |
| C2.26 | nBu | H | 3-Et | OCH₂ | H | O | S |
| C2.27 | FCH₂ | H | 3-Et | OCH₂ | H | O | S |
| C2.28 | F₂CH | H | 3-Et | OCH₂ | H | O | S |
| C2.29 | F₃C | H | 3-Et | OCH₂ | H | O | S |
| C2.30 | ClCH₂ | H | 3-Et | OCH₂ | H | O | S |
| C2.31 | Cl₂CH | H | 3-Et | OCH₂ | H | O | S |
| C2.32 | BrCH₂ | H | 3-Et | OCH₂ | H | O | S |
| C2.33 | FClCH | H | 3-Et | OCH₂ | H | O | S |
| C3.1 | Me | H | 2-nPr | OCH₂ | H | O | S |
| C3.2 | Me | H | 2-nPr | OCH₂ | H | O | O |
| C3.3 | MeO | H | 2-nPr | OCH₂ | H | O | S |
| C3.4 | MeO | H | 2-nPr | OCH₂ | H | O | O |
| C3.5 | Et | H | 2-nPr | OCH₂ | H | O | S |
| C3.6 | nPr | H | 2-nPr | OCH₂ | H | O | S |
| C3.7 | iPr | H | 2-nPr | OCH₂ | H | O | S |
| C3.8 | nBu | H | 2-nPr | OCH₂ | H | O | S |
| C3.9 | FCH₂ | H | 2-nPr | OCH₂ | H | O | S |
| C3.10 | F₂CH | H | 2-nPr | OCH₂ | H | O | S |
| C3.11 | F₃C | H | 2-nPr | OCH₂ | H | O | S |
| C3.12 | ClCH₂ | H | 2-nPr | OCH₂ | H | O | S |
| C3.13 | Cl₂CH | H | 2-nPr | OCH₂ | H | O | S |
| C3.14 | BrCH₂ | H | 2-nPr | OCH₂ | H | O | S |
| C3.15 | FClCH | H | 2-nPr | OCH₂ | H | O | S |
| C3.16 | Me | H | 3-nPr | OCH₂ | H | O | S |
| C3.17 | MeO | H | 3-nPr | OCH₂ | H | O | S |
| C3.18 | MeO | H | 3-nPr | OCH₂ | H | O | O |
| C3.19 | Et | H | 3-nPr | OCH₂ | H | O | S |
| C3.20 | nPr | H | 3-nPr | OCH₂ | H | O | S |
| C3.21 | iPr | H | 3-nPr | OCH₂ | H | O | S |
| C3.22 | nBu | H | 3-nPr | OCH₂ | H | O | S |
| C3.23 | FCH₂ | H | 3-nPr | OCH₂ | H | O | S |
| C3.24 | F₂CH | H | 3-nPr | OCH₂ | H | O | S |
| C3.25 | F₃C | H | 3-nPr | OCH₂ | H | O | S |
| C3.26 | ClCH₂ | H | 3-nPr | OCH₂ | H | O | S |
| C3.27 | Cl₂CH | H | 3-nPr | OCH₂ | H | O | S |
| C3.28 | BrCH₂ | H | 3-nPr | OCH₂ | H | O | S |
| C3.29 | FClCH | H | 3-nPr | OCH₂ | H | O | S |
| C3.30 | Me | H | 2-iPr | OCH₂ | H | O | S |
| C3.31 | Me | H | 2-iPr | OCH₂ | H | O | O |
| C3.32 | MeO | H | 2-iPr | OCH₂ | H | O | S |
| C3.33 | MeO | H | 2-iPr | OCH₂ | H | O | O |
| C3.34 | Et | H | 2-iPr | OCH₂ | H | O | S |
| C3.35 | Et | H | 2-iPr | OCH₂ | H | O | S |
| C3.36 | iPr | H | 2-iPr | OCH₂ | H | O | S |
| C3.37 | nBu | H | 2-iPr | OCH₂ | H | O | S |
| C3.38 | FCH₂ | H | 2-iPr | OCH₂ | H | O | S |
| C3.39 | F₂CH | H | 2-iPr | OCH₂ | H | O | S |
| C3.40 | F₃C | H | 2-iPr | OCH₂ | H | O | S |
| C3.41 | ClCH₂ | H | 2-iPr | OCH₂ | H | O | S |
| C3.42 | Cl₂CH | H | 2-iPr | OCH₂ | H | O | S |
| C3.43 | BrCH₂ | H | 2-iPr | OCH₂ | H | O | S |
| C3.44 | FClCH | H | 2-iPr | OCH₂ | H | O | S |
| C3.45 | Me | H | 3-iPr | OCH₂ | H | O | S |
| C3.46 | MeO | H | 3-iPr | OCH₂ | H | O | S |
| C3.47 | Et | H | 3-iPr | OCH₂ | H | O | S |
| C3.48 | nPr | H | 3-iPr | OCH₂ | H | O | S |
| C3.49 | iPr | H | 3-iPr | OCH₂ | H | O | S |
| C3.50 | nBu | H | 3-iPr | OCH₂ | H | O | S |
| C3.51 | FCH₂ | H | 3-iPr | OCH₂ | H | O | S |
| C3.52 | F₂CH | H | 3-iPr | OCH₂ | H | O | S |

TABLE 3-continued

| Compd. No. | R¹ | R² | (R³)ₙ | ACR⁴R³ | (R⁶)ₘ | X | Q |
|---|---|---|---|---|---|---|---|
| C3.53 | F₃C | H | 3-iPr | OCH₂ | H | O | S |
| C3.54 | ClCH₂ | H | 3-iPr | OCH₂ | H | O | S |
| C3.55 | Cl₂CH | H | 3-iPr | OCH₂ | H | O | S |
| C3.56 | BrCH₂ | H | 3-iPr | OCH₂ | H | O | S |
| C3.57 | FClCH | H | 3-iPr | OCH₂ | H | O | S |
| C4.1 | Me | H | 2-nBu | OCH₂ | H | O | S |
| C4.2 | MeO | H | 2-nBu | OCH₂ | H | O | S |
| C4.3 | MeO | H | 2-nBu | OCH₂ | H | O | O |
| C4.4 | Et | H | 2-nBu | OCH₂ | H | O | S |
| C4.5 | nPr | H | 2-nBu | OCH₂ | H | O | S |
| C4.6 | iPr | H | 2-nBu | OCH₂ | H | O | S |
| C4.7 | nBu | H | 2-nBu | OCH₂ | H | O | S |
| C4.8 | FCH₂ | H | 2-nBu | OCH₂ | H | O | S |
| C4.9 | F₃CH | H | 2-nBu | OCH₂ | H | O | S |
| C4.10 | F₃C | H | 2-nBu | OCH₂ | H | O | S |
| C4.11 | ClCH₂ | H | 2-nBu | OCH₂ | H | O | S |
| C4.12 | Cl₂CH | H | 2-nBu | OCH₂ | H | O | S |
| C4.13 | BrCH₂ | H | 2-nBu | OCH₂ | H | O | S |
| C4.14 | FClCH | H | 2-nBu | OCH₂ | H | O | S |
| C4.15 | Me | H | 2-iBu | OCH₂ | H | O | S |
| C4.16 | Et | H | 2-iBu | OCH₂ | H | O | S |
| C4.17 | nPr | H | 2-iBu | OCH₂ | H | O | S |
| C4.18 | iPr | H | 2-iBu | OCH₂ | H | O | S |
| C4.19 | nBu | H | 2-iBu | OCH₂ | H | O | S |
| C4.20 | FCH₂ | H | 2-iBu | OCH₂ | H | O | S |
| C4.21 | F₂CH | H | 2-iBu | OCH₂ | H | O | S |
| C4.22 | F₃C | H | 2-iBu | OCH₂ | H | O | S |
| C4.23 | ClCH₂ | H | 2-iBu | OCH₂ | H | O | S |
| C4.24 | Cl₂CH | H | 2-iBu | OCH₂ | H | O | S |
| C4.25 | BrCH₂ | H | 2-iBu | OCH₂ | H | O | S |
| C4.26 | FClCH | H | 2-iBu | OCH₂ | H | O | S |
| C4.27 | Me | H | 2-tBu | OCH₂ | H | O | S |
| C4.28 | Me | H | 2-tBu | OCH₂ | H | O | O |
| C4.29 | MeO | H | 2-tBu | OCH₂ | H | O | S |
| C4.30 | MeO | H | 2-tBu | OCH₂ | H | O | O |
| C4.31 | Et | H | 2-tBu | OCH₂ | H | O | S |
| C4.32 | nPr | H | 2-tBu | OCH₂ | H | O | S |
| C4.33 | iPr | H | 2-tBu | OCH₂ | H | O | S |
| C4.34 | nBu | H | 2-tBu | OCH₂ | H | O | S |
| C4.35 | FCH₂ | H | 2-tBu | OCH₂ | H | O | S |
| C4.36 | F₂CH | H | 2-tBu | OCH₂ | H | O | S |
| C4.37 | F₃C | H | 2-tBu | OCH₂ | H | O | S |
| C4.38 | ClCH₂ | H | 2-tBu | OCH₂ | H | O | S |
| C4.39 | Cl₂CH | H | 2-tBu | OCH₂ | H | O | S |
| C4.40 | BrCH₂ | H | 2-tBu | OCH₂ | H | O | S |
| C4.41 | FClCH | H | 2-tBu | OCH₂ | H | O | S |
| C4.42 | MeO | H | 3-nBu | OCH₂ | H | O | S |
| C4.43 | MeO | H | 3-nBu | OCH₂ | H | O | O |
| C4.44 | Me | H | 3-nBu | OCH₂ | H | O | S |
| C4.45 | Et | H | 3-nBu | OCH₂ | H | O | S |
| C4.46 | nPr | H | 3-nBu | OCH₂ | H | O | S |
| C4.47 | iPr | H | 3-nBu | OCH₂ | H | O | S |
| C4.48 | nBu | H | 3-nBu | OCH₂ | H | O | S |
| C4.49 | FCH₂ | H | 3-nBu | OCH₂ | H | O | S |
| C4.50 | F₂CH | H | 3-nBu | OCH₂ | H | O | S |
| C4.51 | F₃C | H | 3-nBu | OCH₂ | H | O | S |
| C4.52 | ClCH₂ | H | 3-nBu | OCH₂ | H | O | S |
| C4.53 | Cl₂CH | H | 3-nBu | OCH₂ | H | O | S |
| C4.54 | BrCH₂ | H | 3-nBu | OCH₂ | H | O | S |
| C4.55 | FClCH | H | 3-nBu | OCH₂ | H | O | S |
| C4.56 | Me | H | 3-iBu | OCH₂ | H | O | S |
| C4.57 | Et | H | 3-iBu | OCH₂ | H | O | S |
| C4.58 | nPr | H | 3-iBu | OCH₂ | H | O | S |
| C4.59 | iPr | H | 3-iBu | OCH₂ | H | O | S |
| C4.60 | nBu | H | 3-iBu | OCH₂ | H | O | S |
| C4.61 | FCH₂ | H | 3-iBu | OCH₂ | H | O | S |
| C4.62 | F₂CH | H | 3-iBu | OCH₂ | H | O | S |
| C4.63 | F₃C | H | 3-iBu | OCH₂ | H | O | S |
| C4.64 | ClCH₂ | H | 3-iBu | OCH₂ | H | O | S |
| C4.65 | Cl₂CH | H | 3-iBu | OCH₂ | H | O | S |
| C4.66 | BrCH₂ | H | 3-iBu | OCH₂ | H | O | S |
| C4.67 | FClCH | H | 3-iBu | OCH₂ | H | O | S |
| C4.68 | Me | H | 3-tBu | OCH₂ | H | O | S |
| C4.69 | MeO | H | 3-tBu | OCH₂ | H | O | S |
| C4.70 | Et | H | 3-tBu | OCH₂ | H | O | S |
| C4.71 | nPr | H | 3-tBu | OCH₂ | H | O | S |

TABLE 3-continued

| Compd. No. | R¹ | R² | (R³)ₙ | ACR⁴R³ | (R⁶)ₘ | X | Q |
|---|---|---|---|---|---|---|---|
| C4.72 | iPr | H | 3-tBu | OCH₂ | H | O | S |
| C4.73 | nBu | H | 3-tBu | OCH₂ | H | O | S |
| C4.74 | FCH₂ | H | 3-tBu | OCH₂ | H | O | S |
| C4.75 | F₂CH | H | 3-tBu | OCH₂ | H | O | S |
| C4.76 | F₃C | H | 3-tBu | OCH₂ | H | O | S |
| C4.77 | ClCH₂ | H | 3-tBu | OCH₂ | H | O | S |
| C4.78 | Cl₂CH | H | 3-tBu | OCH₂ | H | O | S |
| C4.79 | BrCH₂ | H | 3-tBu | OCH₂ | H | O | S |
| C4.80 | FClCH | H | 3-tBu | OCH₂ | H | O | S |
| C5.1 | Me | H | 2-CH₂CH=CH₂ | OCH₂ | H | O | S |
| C5.2 | MeO | H | 2-CH₂CH=CH₂ | OCH₂ | H | O | S |
| C5.3 | MeO | H | 2-CH₂CH=CH₂ | OCH₂ | H | O | O |
| C5.4 | Et | H | 2-CH₂CH=CH₂ | OCH₂ | H | O | S |
| C5.5 | nPr | H | 2-CH₂CH=CH₂ | OCH₂ | H | O | S |
| C5.6 | iPr | H | 2-CH₂CH=CH₂ | OCH₂ | H | O | S |
| C5.7 | nBu | H | 2-CH₂CH=CH₂ | OCH₂ | H | O | S |
| C5.8 | FCH₂ | H | 2-CH₂CH=CH₂ | OCH₂ | H | O | S |
| C5.9 | F₂CH | H | 2-CH₂CH=CH₂ | OCH₂ | H | O | S |
| C5.10 | F₃C | H | 2-CH₂CH=CH₂ | OCH₂ | H | O | S |
| C5.11 | ClCH₂ | H | 2-CH₂CH=CH₂ | OCH₂ | H | O | S |
| C5.12 | Cl₂CH | H | 2-CH₂CH=CH₂ | OCH₂ | H | O | S |
| C5.13 | BrCH₂ | H | 2-CH₂CH=CH₂ | OCH₂ | H | O | S |
| C5.14 | FClCH | H | 2-CH₂CH=CH₂ | OCH₂ | H | O | S |
| C5.15 | Me | H | 3-CH₂CH=CH₂ | OCH₂ | H | O | S |
| C5.16 | MeO | H | 3-CH₂CH=CH₂ | OCH₂ | H | O | S |
| C5.17 | MeO | H | 3-CH₂CH=CH₂ | OCH₂ | H | O | O |
| C5.18 | Et | H | 3-CH₂CH=CH₂ | OCH₂ | H | O | S |
| C5.19 | nPr | H | 3-CH₂CH=CH₂ | OCH₂ | H | O | S |
| C5.20 | iPr | H | 3-CH₂CH=CH₂ | OCH₂ | H | O | S |
| C5.21 | nBu | H | 3-CH₂CH=CH₂ | OCH₂ | H | O | S |
| C5.22 | FCH₂ | H | 3-CH₂CH=CH₂ | OCH₂ | H | O | S |
| C5.23 | F₂CH | H | 3-CH₂CH=CH₂ | OCH₂ | H | O | S |
| C5.24 | F₃C | H | 3-CH₂CH=CH₂ | OCH₂ | H | O | S |
| C5.25 | ClCH₂ | H | 3-CH₂CH=CH₂ | OCH₂ | H | O | S |
| C5.26 | Cl₂CH | H | 3-CH₂CH=CH₂ | OCH₂ | H | O | S |
| C5.27 | BrCH₂ | H | 3-CH₂CH=CH₂ | OCH₂ | H | O | S |
| C5.28 | FClCH | H | 3-CH₂CH=CH₂ | OCH₂ | H | O | S |
| C5.29 | Me | H | 2-CH₂C≡CH | OCH₂ | H | O | S |
| C5.30 | MeO | H | 2-CH₂C≡CH | OCH₂ | H | O | S |
| C5.31 | MeO | H | 2-CH₂C≡CH | OCH₂ | H | O | O |
| C5.32 | Et | H | 2-CH₂C≡CH | OCH₂ | H | O | S |
| C5.33 | nPr | H | 2-CH₂C≡CH | OCH₂ | H | O | S |
| C5.34 | iPr | H | 2-CH₂C≡CH | OCH₂ | H | O | S |
| C5.35 | nBu | H | 2-CH₂C≡CH | OCH₂ | H | O | S |
| C5.36 | FCH₂ | H | 2-CH₂C≡CH | OCH₂ | H | O | S |
| C5.37 | F₂CH | H | 2-CH₂C≡CH | OCH₂ | H | O | S |
| C5.38 | F₃C | H | 2-CH₂C≡CH | OCH₂ | H | O | S |
| C5.39 | ClCH₂ | H | 2-CH₂C≡CH | OCH₂ | H | O | S |
| C5.40 | Cl₂CH | H | 2-CH₂C≡CH | OCH₂ | H | O | S |
| C5.41 | BrCH₂ | H | 2-CH₂C≡CH | OCH₂ | H | O | S |
| C5.42 | FClCH | H | 2-CH₂C≡CH | OCH₂ | H | O | S |
| C5.43 | Me | H | 2-CH₂C≡CH | OCH₂ | H | O | S |
| C5.44 | MeO | H | 3-CH₂C≡CH | OCH₂ | H | O | S |
| C5.45 | Et | H | 3-CH₂C≡CH | OCH₂ | H | O | S |
| C5.46 | nPr | H | 3-CH₂C≡CH | OCH₂ | H | O | S |
| C5.47 | iPr | H | 3-CH₂C≡CH | OCH₂ | H | O | S |
| C5.48 | nBu | H | 3-CH₂C≡CH | OCH₂ | H | O | S |
| C5.49 | FCH₂ | H | 3-CH₂C≡CH | OCH₂ | H | O | S |
| C5.50 | F₂CH | H | 3-CH₂C≡CH | OCH₂ | H | O | S |
| C5.51 | F₃C | H | 3-CH₂C≡CH | OCH₂ | H | O | S |
| C5.52 | ClCH₂ | H | 3-CH₂C≡CH | OCH₂ | H | O | S |
| C5.53 | Cl₂CH | H | 3-CH₂C≡CH | OCH₂ | H | O | S |
| C5.54 | BrCH₂ | H | 3-CH₂C≡CH | OCH₂ | H | O | S |
| C5.55 | FClCH | H | 3-CH₂C≡CH | OCH₂ | H | O | S |
| C6.1 | Me | H | 2-CH₂OMe | OCH₂ | H | O | S |
| C6.2 | MeO | H | 2-CH₂OMe | OCH₂ | H | O | S |
| C6.3 | Me | H | 2-CH₂OMe | OCH₂ | H | O | O |
| C6.4 | MeO | H | 2-CH₂OMe | OCH₂ | H | O | O |
| C6.5 | Et | H | 2-CH₂OMe | OCH₂ | H | O | S |
| C6.6 | nPr | H | 2-CH₂OMe | OCH₂ | H | O | S |
| C6.7 | iPr | H | 2-CH₂OMe | OCH₂ | H | O | S |
| C6.8 | nBu | H | 2-CH₂OMe | OCH₂ | H | O | S |
| C6.9 | FCH₂ | H | 2-CH₂OMe | OCH₂ | H | O | S |
| C6.10 | F₂CH | H | 2-CH₂OMe | OCH₂ | H | O | S |
| C6.11 | F₃C | H | 2-CH₂OMe | OCH₂ | H | O | S |
| C6.12 | ClCH₂ | H | 2-CH₂OMe | OCH₂ | H | O | S |

TABLE 3-continued

| Compd. No. | R¹ | R² | (R³)ₙ | ACR⁴R³ | (R⁶)ₘ | X | Q |
|---|---|---|---|---|---|---|---|
| C6.13 | Cl₂CH | H | 2-CH₂OMe | OCH₂ | H | O | S |
| C6.14 | BrCH₂ | H | 2-CH₂OMe | OCH₂ | H | O | S |
| C6.15 | FClCH | H | 2-CH₂OMe | OCH₂ | H | O | S |
| C6.16 | Me | H | 3-CH₂OMe | OCH₂ | H | O | S |
| C6.17 | MeO | H | 3-CH₂OMe | OCH₂ | H | O | S |
| C6.18 | Et | H | 3-CH₂OMe | OCH₂ | H | O | S |
| C6.19 | nPr | H | 3-CH₂OMe | OCH₂ | H | O | S |
| C6.20 | iPr | H | 3-CH₂OMe | OCH₂ | H | O | S |
| C6.21 | nBu | H | 3-CH₂OMe | OCH₂ | H | O | S |
| C6.22 | FCH₂ | H | 3-CH₂OMe | OCH₂ | H | O | S |
| C6.23 | F₂CH | H | 3-CH₂OMe | OCH₂ | H | O | S |
| C6.24 | F₃C | H | 3-CH₂OMe | OCH₂ | H | O | S |
| C6.25 | ClCH₂ | H | 3-CH₂OMe | OCH₂ | H | O | S |
| C6.26 | Cl₂CH | H | 3-CH₂OMe | OCH₂ | H | O | S |
| C6.27 | BrCH₂ | H | 3-CH₂OMe | OCH₂ | H | O | S |
| C6.28 | FClCH | H | 3-CH₂OMe | OCH₂ | H | O | S |
| C6.29 | Me | H | 2-CH₂OEt | OCH₂ | H | O | S |
| C6.30 | Me | H | 2-CH₂OEt | OCH₂ | H | O | O |
| C6.31 | MeO | H | 2-CH₂OEt | OCH₂ | H | O | S |
| C6.32 | Et | H | 2-CH₂OEt | OCH₂ | H | O | S |
| C6.33 | nPr | H | 2-CH₂OEt | OCH₂ | H | O | S |
| C6.34 | iPr | H | 2-CH₂OEt | OCH₂ | H | O | S |
| C6.35 | nBu | H | 2-CH₂OEt | OCH₂ | H | O | S |
| C6.36 | FCH₂ | H | 2-CH₂OEt | OCH₂ | H | O | S |
| C6.37 | F₂CH | H | 2-CH₂OEt | OCH₂ | H | O | S |
| C6.38 | F₃C | H | 2-CH₂OEt | OCH₂ | H | O | S |
| C6.39 | ClCH₂ | H | 2-CH₂OEt | OCH₂ | H | O | S |
| C6.40 | Cl₂CH | H | 2-CH₂OEt | OCH₂ | H | O | S |
| C6.41 | BrCH₂ | H | 2-CH₂OEt | OCH₂ | H | O | S |
| C6.42 | FClCH | H | 2-CH₂OEt | OCH₂ | H | O | S |
| C6.43 | Me | H | 3-CH₂OEt | OCH₂ | H | O | S |
| C6.44 | Et | H | 3-CH₂OEt | OCH₂ | H | O | S |
| C6.45 | nPr | H | 3-CH₂OEt | OCH₂ | H | O | S |
| C6.46 | iPr | H | 3-CH₂OEt | OCH₂ | H | O | S |
| C6.47 | nBu | H | 3-CH₂OEt | OCH₂ | H | O | S |
| C6.48 | FCH₂ | H | 3-CH₂OEt | OCH₂ | H | O | S |
| C6.49 | F₂CH | H | 3-CH₂OEt | OCH₂ | H | O | S |
| C6.50 | F₃C | H | 3-CH₂OEt | OCH₂ | H | O | S |
| C6.51 | ClCH₂ | H | 3-CH₂OEt | OCH₂ | H | O | S |
| C6.52 | Cl₂CH | H | 3-CH₂OEt | OCH₂ | H | O | S |
| C6.53 | BrCH₂ | H | 3-CH₂OEt | OCH₂ | H | O | S |
| C6.54 | FClCH | H | 3-CH₂OEt | OCH₂ | H | O | S |
| C6.55 | Me | H | 2-CH₂CH₂OMe | OCH₂ | H | O | S |
| C6.56 | Et | H | 2-CH₂CH₂OMe | OCH₂ | H | O | S |
| C6.57 | nPr | H | 2-CH₂CH₂OMe | OCH₂ | H | O | S |
| C6.58 | iPr | H | 2-CH₂CH₂OMe | OCH₂ | H | O | S |
| C6.59 | nBu | H | 2-CH₂CH₂OMe | OCH₂ | H | O | S |
| C6.60 | FCH₂ | H | 2-CH₂CH₂OMe | OCH₂ | H | O | S |
| C6.61 | F₂CH | H | 2-CH₂CH₂OMe | OCH₂ | H | O | S |
| C6.62 | F₃C | H | 2-CH₂CH₂OMe | OCH₂ | H | O | S |
| C6.63 | ClCH₂ | H | 2-CH₂CH₂OMe | OCH₂ | H | O | S |
| C6.64 | Cl₂CH | H | 2-CH₂CH₂OMe | OCH₂ | H | O | S |
| C6.65 | BrCH₂ | H | 2-CH₂CH₂OMe | OCH₂ | H | O | S |
| C6.66 | FClCH | H | 2-CH₂CH₂OMe | OCH₂ | H | O | S |
| C6.67 | Me | H | 3-CH₂CH₂OMe | OCH₂ | H | O | S |
| C6.68 | Me | H | 3-CH₂CH₂OMe | OCH₂ | H | O | O |
| C6.69 | Et | H | 3-CH₂CH₂OMe | OCH₂ | H | O | S |
| C6.70 | nPr | H | 3-CH₂CH₂OMe | OCH₂ | H | O | S |
| C6.71 | iPr | H | 3-CH₂CH₂OMe | OCH₂ | H | O | S |
| C6.72 | nBu | H | 3-CH₂CH₂OMe | OCH₂ | H | O | S |
| C6.73 | FCH₂ | H | 3-CH₂CH₂OMe | OCH₂ | H | O | S |
| C6.74 | F₂CH | H | 3-CH₂CH₂OMe | OCH₂ | H | O | S |
| C6.75 | F₃C | H | 3-CH₂CH₂OMe | OCH₂ | H | O | S |
| C6.76 | ClCH₂ | H | 3-CH₂CH₂OMe | OCH₂ | H | O | S |
| C6.77 | Cl₂CH | H | 3-CH₂CH₂OMe | OCH₂ | H | O | S |
| C6.78 | BrCH₂ | H | 3-CH₂CH₂OMe | OCH₂ | H | O | S |
| C6.79 | FClCH | H | 3-CH₂CH₂OMe | OCH₂ | H | O | S |
| C6.80 | Me | H | 2-CH₂CH₂OEt | OCH₂ | H | O | S |
| C6.81 | Et | H | 2-CH₂CH₂OEt | OCH₂ | H | O | S |
| C6.82 | nPr | H | 2-CH₂CH₂OEt | OCH₂ | H | O | S |
| C6.83 | iPr | H | 2-CH₂CH₂OEt | OCH₂ | H | O | S |
| C6.84 | nBu | H | 2-CH₂CH₂OEt | OCH₂ | H | O | S |
| C6.85 | FCH₂ | H | 2-CH₂CH₂OEt | OCH₂ | H | O | S |
| C6.86 | F₂CH | H | 2-CH₂CH₂OEt | OCH₂ | H | O | S |
| C6.87 | F₃C | H | 2-CH₂CH₂OEt | OCH₂ | H | O | S |
| C6.88 | ClCH₂ | H | 2-CH₂CH₂OEt | OCH₂ | H | O | S |

TABLE 3-continued

| Compd. No. | R¹ | R² | (R³)ₙ | ACR⁴R³ | (R⁶)ₘ | X | Q |
|---|---|---|---|---|---|---|---|
| C6.89 | Cl₂CH | H | 2-CH₂CH₂OEt | OCH₂ | H | O | S |
| C6.90 | BrCH₂ | H | 2-CH₂CH₂OEt | OCH₂ | H | O | S |
| C6.91 | FClCH | H | 2-CH₂CH₂OEt | OCH₂ | H | O | S |
| C6.92 | Me | H | 3-CH₂CH₂OEt | OCH₂ | H | O | S |
| C6.93 | Et | H | 3-CH₂CH₂OEt | OCH₂ | H | O | S |
| C6.94 | nPr | H | 3-CH₂CH₂OEt | OCH₂ | H | O | S |
| C6.95 | iPr | H | 3-CH₂CH₂OEt | OCH₂ | H | O | S |
| C6.96 | nBu | H | 3-CH₂CH₂OEt | OCH₂ | H | O | S |
| C6.97 | FCH₂ | H | 3-CH₂CH₂OEt | OCH₂ | H | O | S |
| C6.98 | F₂CH | H | 3-CH₂CH₂OEt | OCH₂ | H | O | S |
| C6.99 | F₃C | H | 3-CH₂CH₂OEt | OCH₂ | H | O | S |
| C6.100 | ClCH₂ | H | 3-CH₂CH₂OEt | OCH₂ | H | O | S |
| C6.101 | Cl₂CH | H | 3-CH₂CH₂OEt | OCH₂ | H | O | S |
| C6.102 | BrCH₂ | H | 3-CH₂CH₂OEt | OCH₂ | H | O | S |
| C6.103 | FClCH | H | 3-CH₂CH₂OEt | OCH₂ | H | O | S |
| C7.1 | Me | H | 2-CH₂Cl | OCH₂ | H | O | S |
| C7.2 | MeO | H | 2-CH₂Cl | OCH₂ | H | O | S |
| C7.3 | Me | H | 2-CH₂Cl | SCH₂ | H | O | S |
| C7.4 | Et | H | 2-CH₂Cl | OCH₂ | H | O | S |
| C7.5 | nPr | H | 2-CH₂Cl | OCH₂ | H | O | S |
| C7.6 | iPr | H | 2-CH₂Cl | OCH₂ | H | O | S |
| C7.7 | nBu | H | 2-CH₂Cl | OCH₂ | H | O | S |
| C7.8 | FCH₂ | H | 2-CH₂Cl | OCH₂ | H | O | S |
| C7.9 | F₂CH | H | 2-CH₂Cl | OCH₂ | H | O | S |
| C7.10 | F₃C | H | 2-CH₂Cl | OCH₂ | H | O | S |
| C7.11 | ClCH₂ | H | 2-CH₂Cl | OCH₂ | H | O | S |
| C7.12 | Cl₂CH | H | 2-CH₂Cl | OCH₂ | H | O | S |
| C7.13 | BrCH₂ | H | 2-CH₂Cl | OCH₂ | H | O | S |
| C7.14 | FClCH | H | 2-CH₂Cl | OCH₂ | H | O | S |
| C7.15 | Me | H | 2-CH₂Br | OCH₂ | H | O | S |
| C7.16 | Et | H | 2-CH₂Br | OCH₂ | H | O | S |
| C7.17 | nPr | H | 2-CH₂Br | OCH₂ | H | O | S |
| C7.18 | iPr | H | 2-CH₂Br | OCH₂ | H | O | S |
| C7.19 | nBu | H | 2-CH₂Br | OCH₂ | H | O | S |
| C7.20 | FCH₂ | H | 2-CH₂Br | OCH₂ | H | O | S |
| C7.21 | F₂CH | H | 2-CH₂Br | OCH₂ | H | O | S |
| C7.22 | F₃C | H | 2-CH₂Br | OCH₂ | H | O | S |
| C7.23 | ClCH₂ | H | 2-CH₂Br | OCH₂ | H | O | S |
| C7.24 | Cl₂CH | H | 2-CH₂Br | OCH₂ | H | O | S |
| C7.25 | BrCH₂ | H | 2-CH₂Br | OCH₂ | H | O | S |
| C7.26 | FClCH | H | 2-CH₂Br | OCH₂ | H | O | S |
| C7.27 | Me | H | 3-CH₂Cl | OCH₂ | H | O | S |
| C7.28 | MeO | H | 3-CH₂Cl | OCH₂ | H | O | S |
| C7.29 | Me | H | 3-CH₂Cl | SCH₂ | H | O | S |
| C7.30 | Et | H | 3-CH₂Cl | OCH₂ | H | O | S |
| C7.31 | nPr | H | 3-CH₂Cl | OCH₂ | H | O | S |
| C7.32 | iPr | H | 3-CH₂Cl | OCH₂ | H | O | S |
| C7.33 | nBu | H | 3-CH₂Cl | OCH₂ | H | O | S |
| C7.34 | FCH₂ | H | 3-CH₂Cl | OCH₂ | H | O | S |
| C7.35 | F₂CH | H | 3-CH₂Cl | OCH₂ | H | O | S |
| C7.36 | F₃C | H | 3-CH₂Cl | OCH₂ | H | O | S |
| C7.37 | ClCH₂ | H | 3-CH₂Cl | OCH₂ | H | O | S |
| C7.38 | Cl₂CH | H | 3-CH₂Cl | OCH₂ | H | O | S |
| C7.39 | BrCH₂ | H | 3-CH₂Cl | OCH₂ | H | O | S |
| C7.40 | FClCH | H | 3-CH₂Cl | OCH₂ | H | O | S |
| C7.41 | Me | H | 3-CH₂Br | OCH₂ | H | O | S |
| C7.42 | Et | H | 3-CH₂Br | OCH₂ | H | O | S |
| C7.43 | nPr | H | 3-CH₂Br | OCH₂ | H | O | S |
| C7.44 | iPr | H | 3-CH₂Br | OCH₂ | H | O | S |
| C7.45 | nBu | H | 3-CH₂Br | OCH₂ | H | O | S |
| C7.46 | FCH₂ | H | 3-CH₂Br | OCH₂ | H | O | S |
| C7.47 | F₂CH | H | 3-CH₂Br | OCH₂ | H | O | S |
| C7.48 | F₃C | H | 3-CH₂Br | OCH₂ | H | O | S |
| C7.49 | ClCH₂ | H | 3-CH₂Br | OCH₂ | H | O | S |
| C7.50 | Cl₂CH | H | 3-CH₂Br | OCH₂ | H | O | S |
| C7.51 | BrCH₂ | H | 3-CH₂Br | OCH₂ | H | O | S |
| C7.52 | FClCH | H | 3-CH₂Br | OCH₂ | H | O | S |
| C7.53 | MeO | H | 3-CH₂F | OCH₂ | H | O | S |
| C7.54 | MeO | H | 3-CH₂F | OCH₂ | H | O | S |
| C7.55 | Me | H | 2-CHF₂ | OCH₂ | H | O | S |
| C7.56 | MeO | H | 2-CHF₂ | OCH₂ | H | O | S |
| C7.57 | Me | H | 2-CHF₂ | OCH₂ | H | O | O |
| C7.58 | MeO | H | 2-CHF₂ | OCH₂ | H | O | O |
| C8.1 | Me | H | 2-OMe | OCH₂ | H | O | S |
| C8.2 | Me | H | 2-OMe | OCH₂ | H | O | O |
| C8.3 | MeO | H | 2-OMe | OCH₂ | H | O | S |

TABLE 3-continued

| Compd. No. | R¹ | R² | (R³)ₙ | ACR⁴R³ | (R⁶)ₘ | X | Q |
|---|---|---|---|---|---|---|---|
| C8.4 | Me | H | 2-OMe | SCH₂ | H | O | S |
| C8.5 | MeO | H | 2-OMe | SCH₂ | H | O | S |
| C8.6 | MeO | H | 2-OMe | OCH₂ | H | O | O |
| C8.7 | MeO | H | 2-OMe | SCH₂ | H | O | O |
| C8.8 | Et | H | 2-OMe | OCH₂ | H | O | S |
| C8.9 | nPr | H | 2-OMe | OCH₂ | H | O | S |
| C8.10 | iPr | H | 2-OMe | OCH₂ | H | O | S |
| C8.11 | nBu | H | 2-OMe | OCH₂ | H | O | S |
| C8.12 | FCH₂ | H | 2-OMe | OCH₂ | H | O | S |
| C8.13 | F₂CH | H | 2-OMe | OCH₂ | H | O | S |
| C8.14 | F₃C | H | 2-OMe | OCH₂ | H | O | S |
| C8.15 | ClCH₂ | H | 2-OMe | OCH₂ | H | O | S |
| C8.16 | Cl₂CH | H | 2-OMe | OCH₂ | H | O | S |
| C8.17 | BrCH₂ | H | 2-OMe | OCH₂ | H | O | S |
| C8.18 | FClCH | H | 2-OMe | OCH₂ | H | O | S |
| C8.19 | Me | H | 3-OMe | OCH₂ | H | O | S |
| C8.20 | MeO | H | 3-OMe | OCH₂ | H | O | S |
| C8.21 | Me | H | 3-OMe | SCH₂ | H | O | S |
| C8.22 | Me | H | 3-OMe | OCH₂ | H | O | O |
| C8.23 | MeO | H | 3-OMe | OCH₂ | H | O | O |
| C8.24 | Et | H | 3-OMe | OCH₂ | H | O | S |
| C8.25 | nPr | H | 3-OMe | OCH₂ | H | O | S |
| C8.26 | iPr | H | 3-OMe | OCH₂ | H | O | S |
| C8.27 | nBu | H | 3-OMe | OCH₂ | H | O | S |
| C8.28 | FCH₂ | H | 3-OMe | OCH₂ | H | O | S |
| C8.29 | F₂CH | H | 3-OMe | OCH₂ | H | O | S |
| C8.30 | F₃C | H | 3-OMe | OCH₂ | H | O | S |
| C8.31 | ClCH₂ | H | 3-OMe | OCH₂ | H | O | S |
| C8.32 | Cl₂CH | H | 3-OMe | OCH₂ | H | O | S |
| C8.33 | BrCH₂ | H | 3-OMe | OCH₂ | H | O | S |
| C8.34 | FClCH | H | 3-OMe | OCH₂ | H | O | S |
| C8.35 | Me | H | 2-OEt | OCH₂ | H | O | O |
| C8.36 | Me | H | 2-OEt | SCH₂ | H | O | O |
| C8.37 | MeO | H | 2-OEt | OCH₂ | H | O | S |
| C8.38 | MeO | H | 2-OEt | OCH₂ | H | O | O |
| C8.39 | Me | H | 2-OEt | OCH₂ | H | O | S |
| C8.40 | MeO | H | 2-OEt | SCH₂ | H | O | S |
| C8.41 | Me | H | 2-OEt | SCH₂ | H | O | S |
| C8.42 | Et | H | 2-OEt | OCH₂ | H | O | S |
| C8.43 | nPr | H | 2-OEt | OCH₂ | H | O | S |
| C8.44 | iPr | H | 2-OEt | OCH₂ | H | O | S |
| C8.45 | nBu | H | 2-OEt | OCH₂ | H | O | S |
| C8.46 | FCH₂ | H | 2-OEt | OCH₂ | H | O | S |
| C8.47 | F₂CH | H | 2-OEt | OCH₂ | H | O | S |
| C8.48 | F₃C | H | 2-OEt | OCH₂ | H | O | S |
| C8.49 | ClCH₂ | H | 2-OEt | OCH₂ | H | O | S |
| C8.50 | Cl₂CH | H | 2-OEt | OCH₂ | H | O | S |
| C8.51 | BrCH₂ | H | 2-OEt | OCH₂ | H | O | S |
| C8.52 | FClCH | H | 2-OEt | OCH₂ | H | O | S |
| C8.53 | Me | H | 3-OEt | OCH₂ | H | O | S |
| C8.54 | MeO | H | 3-OEt | OCH₂ | H | O | O |
| C8.55 | MeO | H | 3-OEt | OCH₂ | H | O | S |
| C8.56 | Me | H | 3-OEt | SCH₂ | H | O | S |
| C8.57 | Et | H | 3-OEt | OCH₂ | H | O | S |
| C8.58 | nPr | H | 3-OEt | OCH₂ | H | O | S |
| C8.59 | iPr | H | 3-OEt | OCH₂ | H | O | S |
| C8.60 | nBu | H | 3-OEt | OCH₂ | H | O | S |
| C8.61 | FCH₂ | H | 3-OEt | OCH₂ | H | O | S |
| C8.62 | F₂CH | H | 3-OEt | OCH₂ | H | O | S |
| C8.63 | F₃C | H | 3-OEt | OCH₂ | H | O | S |
| C8.64 | ClCH₂ | H | 3-OEt | OCH₂ | H | O | S |
| C8.65 | Cl₂CH | H | 3-OEt | OCH₂ | H | O | S |
| C8.66 | BrCH₂ | H | 3-OEt | OCH₂ | H | O | S |
| C8.67 | FClCH | H | 3-OEt | OCH₂ | H | O | S |
| C8.68 | Me | H | 2-OiPr | OCH₂ | H | O | S |
| C8.69 | MeO | H | 2-OiPr | OCH₂ | H | O | S |
| C8.70 | Me | H | 2-OiPr | OCH₂ | H | O | O |
| C8.71 | MeO | H | 2-OiPr | OCH₂ | H | O | O |
| C8.72 | Me | H | 2-OCHF₂ | OCH₂ | H | O | S |
| C8.73 | MeO | H | 2-OCHF₂ | OCH₂ | H | O | S |
| C8.74 | Me | H | 2-OCHF₂ | OCH₂ | H | O | O |
| C8.75 | MeO | H | 2-OCHF₂ | OCH₂ | H | O | O |
| C8.76 | Me | H | 2-OCH₂CF₃ | OCH₂ | H | O | S |
| C8.77 | Me | H | 2-OCH₂CF₃ | OCH₂ | H | O | O |
| C8.78 | MeO | H | 2-OCH₂CF₃ | OCH₂ | H | O | S |
| C9.1 | Me | H | 2-F | OCH₂ | H | O | S |

TABLE 3-continued

| Compd. No. | R¹ | R² | (R³)ₙ | ACR⁴R³ | (R⁶)ₘ | X | Q |
|---|---|---|---|---|---|---|---|
| C9.2 | Me | H | 2-F | SCH₂ | H | O | S |
| C9.3 | Me | H | 2-F | OCH₂ | H | O | O |
| C9.5 | MeO | H | 2-F | SCH₂ | H | O | S |
| C9.6 | MeO | H | 2-F | OCH₂ | H | O | O |
| C9.7 | MeO | H | 2-F | SCH₂ | H | O | O |
| C9.8 | Et | H | 2-F | OCH₂ | H | O | S |
| C9.9 | nPr | H | 2-F | OCH₂ | H | O | S |
| C9.10 | iPr | H | 2-F | OCH₂ | H | O | S |
| C9.11 | nBu | H | 2-F | OCH₂ | H | O | S |
| C9.12 | FCH₂ | H | 2-F | OCH₂ | H | O | S |
| C9.13 | F₂CH | H | 2-F | OCH₂ | H | O | S |
| C9.14 | F₃C | H | 2-F | OCH₂ | H | O | S |
| C9.15 | ClCH₂ | H | 2-F | OCH₂ | H | O | S |
| C9.16 | Cl₂CH | H | 2-F | OCH₂ | H | O | S |
| C9.17 | BrCH₂ | H | 2-F | OCH₂ | H | O | S |
| C9.18 | FClCH | H | 2-F | OCH₂ | H | O | S |
| C9.20 | Me | H | 3-F | OCH₂ | H | O | S |
| C9.21 | Me | H | 3-F | SCH₂ | H | O | S |
| C9.22 | Me | H | 3-F | OCH₂ | H | O | O |
| C9.23 | MeO | H | 3-F | OCH₂ | H | O | S |
| C9.24 | MeO | H | 3-F | OCH₂ | H | O | O |
| C9.25 | Et | H | 3-F | OCH₂ | H | O | S |
| C9.26 | nPr | H | 3-F | OCH₂ | H | O | S |
| C9.27 | iPr | H | 3-F | OCH₂ | H | O | S |
| C9.28 | nBu | H | 3-F | OCH₂ | H | O | S |
| C9.29 | FCH₂ | H | 3-F | OCH₂ | H | O | S |
| C9.30 | F₂CH | H | 3-F | OCH₂ | H | O | S |
| C9.31 | F₃C | H | 3-F | OCH₂ | H | O | S |
| C9.32 | ClCH₂ | H | 3-F | OCH₂ | H | O | S |
| C9.33 | Cl₂CH | H | 3-F | OCH₂ | H | O | S |
| C9.34 | BrCH₂ | H | 3-F | OCH₂ | H | O | S |
| C9.35 | FClCH | H | 3-F | OCH₂ | H | O | S |
| C9.36 | Me | H | 2-Cl | OCH₂ | H | O | S |
| C9.37 | Me | H | 2-Cl | SCH₂ | H | O | S |
| C9.38 | Me | H | 2-Cl | OCH₂ | H | O | O |
| C9.39 | MeO | H | 2-Cl | OCH₂ | H | O | S |
| C9.40 | MeO | H | 2-Cl | OCH₂ | H | O | O |
| C9.41 | Et | H | 2-Cl | OCH₂ | H | O | S |
| C9.42 | nPr | H | 2-Cl | OCH₂ | H | O | S |
| C9.43 | iPr | H | 2-Cl | OCH₂ | H | O | S |
| C9.44 | nBu | H | 2-Cl | OCH₂ | H | O | S |
| C9.45 | F₂CH | H | 2-Cl | OCH₂ | H | O | S |
| C9.46 | F₂CH | H | 2-Cl | OCH₂ | H | O | S |
| C9.47 | F₃C | H | 2-Cl | OCH₂ | H | O | S |
| C9.48 | ClCH₂ | H | 2-Cl | OCH₂ | H | O | S |
| C9.49 | Cl₂CH | H | 2-Cl | OCH₂ | H | O | S |
| C9.50 | BrCH₂ | H | 2-Cl | OCH₂ | H | O | S |
| C9.51 | FClCH | H | 2-Cl | OCH₂ | H | O | S |
| C9.52 | Me | H | 3-Cl | OCH₂ | H | O | S |
| C9.53 | Me | H | 3-Cl | SCH₂ | H | O | S |
| C9.54 | Me | H | 3-Cl | OCH₂ | H | O | O |
| C9.55 | MeO | H | 3-Cl | OCH₂ | H | O | S |
| C9.56 | MeO | H | 3-Cl | OCH₂ | H | O | O |
| C9.57 | Et | H | 3-Cl | OCH₂ | H | O | S |
| C9.58 | nPr | H | 3-Cl | OCH₂ | H | O | S |
| C9.59 | iPr | H | 3-Cl | OCH₂ | H | O | S |
| C9.60 | nBu | H | 3-Cl | OCH₂ | H | O | S |
| C9.61 | FCH₂ | H | 3-Cl | OCH₂ | H | O | S |
| C9.62 | F₂CH | H | 3-Cl | OCH₂ | H | O | S |
| C9.63 | F₃C | H | 3-Cl | OCH₂ | H | O | S |
| C9.64 | ClCH₂ | H | 3-Cl | OCH₂ | H | O | S |
| C9.65 | Cl₂CH | H | 3-Cl | OCH₂ | H | O | S |
| C9.66 | BrCH₂ | H | 3-Cl | OCH₂ | H | O | S |
| C9.67 | FClCH | H | 3-Cl | OCH₂ | H | O | S |
| C9.68 | Me | H | 2-Br | OCH₂ | H | O | S |
| C9.69 | Et | H | 2-Br | OCH₂ | H | O | S |
| C9.70 | nPr | H | 2-Br | OCH₂ | H | O | S |
| C9.71 | iPr | H | 2-Br | OCH₂ | H | O | S |
| C9.72 | nBu | H | 2-Br | OCH₂ | H | O | S |
| C9.73 | FCH₂ | H | 2-Br | OCH₂ | H | O | S |
| C9.74 | F₂CH | H | 2-Br | OCH₂ | H | O | S |
| C9.75 | F₃C | H | 2-Br | OCH₂ | H | O | S |
| C9.76 | ClCH₂ | H | 2-Br | OCH₂ | H | O | S |
| C9.77 | Cl₂CH | H | 2-Br | OCH₂ | H | O | S |
| C9.78 | BrCH₂ | H | 2-Br | OCH₂ | H | O | S |
| C9.79 | FClCH | H | 2-Br | OCH₂ | H | O | S |

TABLE 3-continued

| Compd. No. | R¹ | R² | (R³)ₙ | ACR⁴R³ | (R⁶)ₘ | X | Q |
|---|---|---|---|---|---|---|---|
| C9.80 | Me | H | 3-Br | OCH₂ | H | O | S |
| C9.81 | Et | H | 3-Br | OCH₂ | H | O | S |
| C9.82 | nPr | H | 3-Br | OCH₂ | H | O | S |
| C9.83 | iPr | H | 3-Br | OCH₂ | H | O | S |
| C9.84 | nBu | H | 3-Br | OCH₂ | H | O | S |
| C9.85 | FCH₂ | H | 3-Br | OCH₂ | H | O | S |
| C9.86 | F₂CH | H | 3-Br | OCH₂ | H | O | S |
| C9.87 | F₃C | H | 3-Br | OCH₂ | H | O | S |
| C9.88 | ClCH₂ | H | 3-Br | OCH₂ | H | O | S |
| C9.89 | Cl₂CH | H | 3-Br | OCH₂ | H | O | S |
| C9.90 | BrCH₂ | H | 3-Br | OCH₂ | H | O | S |
| C9.91 | FClCH | H | 3-Br | OCH₂ | H | O | S |
| C9.92 | Me | H | 2-I | OCH₂ | H | O | S |
| C9.93 | Et | H | 2-I | OCH₂ | H | O | S |
| C9.94 | nPr | H | 2-I | OCH₂ | H | O | S |
| C9.95 | iPr | H | 2-I | OCH₂ | H | O | S |
| C9.96 | nBu | H | 2-I | OCH₂ | H | O | S |
| C9.97 | FCH₂ | H | 2-I | OCH₂ | H | O | S |
| C9.98 | F₂CH | H | 2-I | OCH₂ | H | O | S |
| C9.99 | F₃C | H | 2-I | OCH₂ | H | O | S |
| C9.100 | ClCH₂ | H | 2-I | OCH₂ | H | O | S |
| C9.101 | Cl₂CH | H | 2-I | OCH₂ | H | O | S |
| C9.102 | BrCH₂ | H | 2-I | OCH₂ | H | O | S |
| C9.103 | FClCH | H | 2-I | OCH₂ | H | O | S |
| C9.104 | Me | H | 2-I | OCH₂ | H | O | S |
| C9.105 | Et | H | 3-I | OCH₂ | H | O | S |
| C9.106 | nPr | H | 3-I | OCH₂ | H | O | S |
| C9.107 | iPr | H | 3-I | OCH₂ | H | O | S |
| C9.108 | nBu | H | 3-I | OCH₂ | H | O | S |
| C9.109 | FCH₂ | H | 3-I | OCH₂ | H | O | S |
| C9.110 | F₂CH | H | 3-I | OCH₂ | H | O | S |
| C9.111 | F₃C | H | 3-I | OCH₂ | H | O | S |
| C9.112 | ClCH₂ | H | 3-I | OCH₂ | H | O | S |
| C9.113 | Cl₂CH | H | 3-I | OCH₂ | H | O | S |
| C9.114 | BrCH₂ | H | 3-I | OCH₂ | H | O | S |
| C9.115 | FClCH | H | 3-I | OCH₂ | H | O | S |
| C10.1 | Me | H | 2-CF₃ | OCH₂ | H | O | S |
| C10.2 | Me | H | 2-CF₃ | SCH₂ | H | O | S |
| C10.3 | Me | H | 2-CF₃ | OCH₂ | H | O | O |
| C10.4 | MeO | H | 2-CF₃ | OCH₂ | H | O | O |
| C10.5 | MeO | H | 2-CF₃ | OCH₂ | H | O | O |
| C10.6 | Et | H | 2-CF₃ | OCH₂ | H | O | S |
| C10.7 | nPr | H | 2-CF₃ | OCH₂ | H | O | S |
| C10.8 | iPr | H | 2-CF₃ | OCH₂ | H | O | S |
| C10.9 | nBu | H | 2-CF₃ | OCH₂ | H | O | S |
| C10.10 | FCH₂ | H | 2-CF₃ | OCH₂ | H | O | S |
| C10.11 | F₂CH | H | 2-CF₃ | OCH₂ | H | O | S |
| C10.12 | F₃C | H | 2-CF₃ | OCH₂ | H | O | S |
| C10.13 | ClCH₂ | H | 2-CF₃ | OCH₂ | H | O | S |
| C10.14 | Cl₂CH | H | 2-CF₃ | OCH₂ | H | O | S |
| C10.15 | BrCH₂ | H | 2-CF₃ | OCH₂ | H | O | S |
| C10.16 | FClCH | H | 2-CF₃ | OCH₂ | H | O | S |
| C10.17 | Me | H | 3-CF₃ | OCH₂ | H | O | S |
| C10.18 | Me | H | 3-CF₃ | SCH₂ | H | O | S |
| C10.19 | Me | H | 3-CF₃ | OCH₂ | H | O | O |
| C10.20 | MeO | H | 3-CF₃ | OCH₂ | H | O | S |
| C10.21 | MeO | H | 3-CF₃ | OCH₂ | H | O | O |
| C10.22 | Et | H | 3-CF₃ | OCH₂ | H | O | S |
| C10.23 | nPr | H | 3-CF₃ | OCH₂ | H | O | S |
| C10.24 | iPr | H | 3-CF₃ | OCH₂ | H | O | S |
| C10.25 | nBu | H | 3-CF₃ | OCH₂ | H | O | S |
| C10.26 | FCH₂ | H | 3-CF₃ | OCH₂ | H | O | S |
| C10.27 | F₂CH | H | 3-CF₃ | OCH₂ | H | O | S |
| C10.28 | F₃C | H | 3-CF₃ | OCH₂ | H | O | S |
| C10.29 | ClCH₂ | H | 3-CF₃ | OCH₂ | H | O | S |
| C10.30 | Cl₂CH | H | 3-CF₃ | OCH₂ | H | O | S |
| C10.31 | BrCH₂ | H | 3-CF₃ | OCH₂ | H | O | S |
| C10.32 | FClCH | H | 3-CF₃ | OCH₂ | H | O | S |
| C10.33 | iPr | H | 3-CHO | OCH₂ | H | O | S |
| C10.34 | nBu | H | 3-CHO | OCH₂ | H | O | S |
| C10.35 | FCH₂ | H | 3-CHO | OCH₂ | H | O | S |
| C10.36 | F₂CH | H | 3-CHO | OCH₂ | H | O | S |
| C10.37 | F₃C | H | 3-CHO | OCH₂ | H | O | S |
| C10.38 | ClCH₂ | H | 3-CHO | OCH₂ | H | O | S |
| C10.39 | Cl₂CH | H | 3-CHO | OCH₂ | H | O | S |
| C10.40 | BrCH₂ | H | 3-CHO | OCH₂ | H | O | S |

TABLE 3-continued

| Compd. No. | R¹ | R² | (R³)ₙ | ACR⁴R³ | (R⁶)ₘ | X | Q |
|---|---|---|---|---|---|---|---|
| C10.41 | FClCH | H | 3-CHO | OCH₂ | H | O | S |
| C10.42 | Me | H | 2-COMe | OCH₂ | H | O | S |
| C10.43 | MeO | H | 2-COMe | OCH₂ | H | O | S |
| C10.44 | Me | H | 3-COMe | OCH₂ | H | O | S |
| C10.45 | MeO | H | 3-COMe | OCH₂ | H | O | S |
| C10.46 | Me | H | 2-NO₂ | OCH₂ | H | O | S |
| C10.47 | Me | H | 2-NO₂ | SCH₂ | H | O | S |
| C10.48 | MeO | H | 2-NO₂ | OCH₂ | H | O | S |
| C10.49 | Me | H | 2-NO₂ | OCH₂ | H | O | O |
| C10.50 | MeO | H | 2-NO₂ | OCH₂ | H | O | O |
| C10.51 | Et | H | 2-NO₂ | OCH₂ | H | O | S |
| C10.52 | nPr | H | 2-NO₂ | OCH₂ | H | O | S |
| C10.53 | iPr | H | 2-NO₂ | OCH₂ | H | O | S |
| C10.54 | nBu | H | 2-NO₂ | OCH₂ | H | O | S |
| C10.55 | FCH₂ | H | 2-NO₂ | OCH₂ | H | O | S |
| C10.56 | F₂CH | H | 2-NO₂ | OCH₂ | H | O | S |
| C10.57 | F₃C | H | 2-NO₂ | OCH₂ | H | O | S |
| C10.58 | ClCH₂ | H | 2-NO₂ | OCH₂ | H | O | S |
| C10.59 | Cl₂CH | H | 2-NO₂ | OCH₂ | H | O | S |
| C10.60 | BrCH₂ | H | 2-NO₂ | OCH₂ | H | O | S |
| C10.61 | FClCH | H | 2-NO₂ | OCH₂ | H | O | S |
| C10.62 | Me | H | 3-NO₂ | OCH₂ | H | O | S |
| C10.63 | Me | H | 3-NO₂ | SCH₂ | H | O | S |
| C10.64 | MeO | H | 3-NO₂ | OCH₂ | H | O | S |
| C10.65 | Me | H | 3-NO₂ | OCH₂ | H | O | O |
| C10.66 | MeO | H | 3-NO₂ | OCH₂ | H | O | O |
| C10.67 | Et | H | 3-NO₂ | OCH₂ | H | O | S |
| C10.68 | nPr | H | 3-NO₂ | OCH₂ | H | O | S |
| C10.69 | iPr | H | 3-NO₂ | OCH₂ | H | O | S |
| C10.70 | nBu | H | 3-NO₂ | OCH₂ | H | O | S |
| C10.71 | FCH₂ | H | 3-NO₂ | OCH₂ | H | O | S |
| C10.72 | F₂CH | H | 3-NO₂ | OCH₂ | H | O | S |
| C10.73 | F₃C | H | 3-NO₂ | OCH₂ | H | O | S |
| C10.74 | ClCH₂ | H | 3-NO₂ | OCH₂ | H | O | S |
| C10.75 | Cl₂CH | H | 3-NO₂ | OCH₂ | H | O | S |
| C10.76 | BrCH₂ | H | 3-NO₂ | OCH₂ | H | O | S |
| C10.77 | FClCH | H | 3-NO₂ | OCH₂ | H | O | S |
| C10.78 | Me | H | 2-CO₂Me | OCH₂ | H | O | S |
| C10.79 | MeO | H | 2-CO₂Me | OCH₂ | H | O | S |
| C10.80 | Me | H | 2-CO₂Me | OCH₂ | H | O | O |
| C10.81 | MeO | H | 2-CO₂Me | OCH₂ | H | O | O |
| C10.82 | Me | H | 2-CO₂Et | OCH₂ | H | O | S |
| C10.83 | MeO | H | 2-CO₂Et | OCH₂ | H | O | S |
| C10.84 | Me | H | 2-CO₂nPr | OCH₂ | H | O | S |
| C10.85 | MeO | H | 2-CO₂nPr | OCH₂ | H | O | S |
| C10.86 | Me | H | 2-CO₂iPr | OCH₂ | H | O | S |
| C10.87 | MeO | H | 2-CO₂iPr | OCH₂ | H | O | S |
| C10.88 | Me | H | 3-CO₂Me | OCH₂ | H | O | S |
| C10.89 | MeO | H | 3-CO₂Me | OCH₂ | H | O | S |
| C10.90 | Me | H | 3-CO₂Me | OCH₂ | H | O | O |
| C10.91 | MeO | H | 3-CO₂Me | OCH₂ | H | O | O |
| C10.92 | Me | H | 3-CO₂Et | OCH₂ | H | O | S |
| C10.93 | MeO | H | 3-CO₂Et | OCH₂ | H | O | S |
| C10.94 | Me | H | 3-CO₂nPr | OCH₂ | H | O | S |
| C10.95 | MeO | H | 3-CO₂nPr | OCH₂ | H | O | S |
| C10.96 | Me | H | 3-CO₂iPr | OCH₂ | H | O | S |
| C10.97 | MeO | H | 3-CO₂iPr | OCH₂ | H | O | S |
| C10.98 | Me | H | 2-CHO | OCH₂ | H | O | S |
| C10.99 | Me | H | 2-CHO | SCH₂ | H | O | S |
| C10.100 | MeO | H | 2-CHO | OCH₂ | H | O | S |
| C10.101 | MeO | H | 2-CHO | OCH₂ | H | O | O |
| C10.102 | Et | H | 2-CHO | OCH₂ | H | O | S |
| C10.103 | nPr | H | 2-CHO | OCH₂ | H | O | S |
| C10.104 | iPr | H | 2-CHO | OCH₂ | H | O | S |
| C10.105 | nBu | H | 2-CHO | OCH₂ | H | O | S |
| C10.106 | FCH₂ | H | 2-CHO | OCH₂ | H | O | S |
| C10.107 | F₂CH | H | 2-CHO | OCH₂ | H | O | S |
| C10.108 | F₃C | H | 2-CHO | OCH₂ | H | O | S |
| C10.109 | ClCH₂ | H | 2-CHO | OCH₂ | H | O | S |
| C10.110 | Cl₂CH | H | 2-CHO | OCH₂ | H | O | S |
| C10.111 | BrCH₂ | H | 2-CHO | OCH₂ | H | O | S |
| C10.112 | FClCH | H | 2-CHO | OCH₂ | H | O | S |
| C10.113 | Me | H | 2-CHO | OCH₂ | H | O | S |
| C10.114 | Me | H | 2-CHO | SCH₂ | H | O | S |
| C10.115 | MeO | H | 2-CHO | OCH₂ | H | O | S |
| C10.116 | Et | H | 2-CHO | OCH₂ | H | O | S |

TABLE 3-continued

| Compd. No. | R¹ | R² | (R³)ₙ | ACR⁴R³ | (R⁶)ₘ | X | Q |
|---|---|---|---|---|---|---|---|
| C10.117 | nPr | H | 2-CHO | OCH₂ | H | O | S |
| C11.1 | Me | H | 2,3-diMe | OCH₂ | H | O | S |
| C11.2 | Me | H | 2,3-diMe | SCH₂ | H | O | S |
| C11.3 | Me | H | 2,3-diMe | OCH₂ | H | O | O |
| C11.4 | MeO | H | 2,3-diMe | OCH₂ | H | O | S |
| C11.5 | MeO | H | 2,3-diMe | OCH₂ | H | O | O |
| C11.6 | Et | H | 2,3-diMe | OCH₂ | H | O | S |
| C11.7 | nPr | H | 2,3-diMe | OCH₂ | H | O | S |
| C11.8 | iPr | H | 2,3-diMe | OCH₂ | H | O | S |
| C11.9 | nBu | H | 2,3-diMe | OCH₂ | H | O | S |
| C11.10 | FCH₂ | H | 2,3-diMe | OCH₂ | H | O | S |
| C11.11 | F₂CH | H | 2,3-diMe | OCH₂ | H | O | S |
| C11.12 | F₃C | H | 2,3-diMe | OCH₂ | H | O | S |
| C11.13 | ClCH₂ | H | 2,3-diMe | OCH₂ | H | O | S |
| C11.14 | Cl₂CH | H | 2,3-diMe | OCH₂ | H | O | S |
| C11.15 | BrCH₂ | H | 2,3-diMe | OCH₂ | H | O | S |
| C11.16 | FClCH | H | 2,3-diMe | OCH₂ | H | O | S |
| C11.17 | Me | H | 2,5-diMe | OCH₂ | H | O | S |
| C11.18 | Me | H | 2,5-diMe | SCH₂ | H | O | S |
| C11.19 | Me | H | 2,5-diMe | OCH₂ | H | O | O |
| C11.20 | MeO | H | 2,5-diMe | OCH₂ | H | O | S |
| C11.21 | MeO | H | 2,5-diMe | OCH₂ | H | O | O |
| C11.22 | Et | H | 2,5-diMe | OCH₂ | H | O | S |
| C11.23 | nPr | H | 2,5-diMe | OCH₂ | H | O | S |
| C11.24 | iPr | H | 2,5-diMe | OCH₂ | H | O | S |
| C11.25 | nBu | H | 2,5-diMe | OCH₂ | H | O | S |
| C11.26 | FCH₂ | H | 2,5-diMe | OCH₂ | H | O | S |
| C11.27 | F₂CH | H | 2,5-diMe | OCH₂ | H | O | S |
| C11.28 | F₃C | H | 2,5-diMe | OCH₂ | H | O | S |
| C11.29 | ClCH₂ | H | 2,5-diMe | OCH₂ | H | O | S |
| C11.30 | Cl₂CH | H | 2,5-diMe | OCH₂ | H | O | S |
| C11.31 | BrCH₂ | H | 2,5-diMe | OCH₂ | H | O | S |
| C11.32 | FClCH | H | 2,5-diMe | OCH₂ | H | O | S |
| C11.33 | Me | H | 2,6-diMe | OCH₂ | H | O | S |
| C11.34 | Me | H | 2,6-diMe | SCH₂ | H | O | S |
| C11.35 | MeO | H | 2,6-diMe | OCH₂ | H | O | S |
| C11.36 | MeO | H | 2,6-diMe | OCH₂ | H | O | O |
| C11.37 | Et | H | 2,6-diMe | OCH₂ | H | O | S |
| C11.38 | nPr | H | 2,6-diMe | OCH₂ | H | O | S |
| C11.39 | iPr | H | 2,6-diMe | OCH₂ | H | O | S |
| C11.40 | nBu | H | 2,6-diMe | OCH₂ | H | O | S |
| C11.41 | FCH₂ | H | 2,6-diMe | OCH₂ | H | O | S |
| C11.42 | F₂CH | H | 2,6-diMe | OCH₂ | H | O | S |
| C11.43 | F₃C | H | 2,6-diMe | OCH₂ | H | O | S |
| C11.44 | ClCH₂ | H | 2,6-diMe | OCH₂ | H | O | S |
| C11.45 | Cl₂CH | H | 2,6-diMe | OCH₂ | H | O | S |
| C11.46 | BrCH₂ | H | 2,6-diMe | OCH₂ | H | O | S |
| C11.47 | FClCH | H | 2,6-diMe | OCH₂ | H | O | S |
| C11.48 | Me | H | 3,5-diMe | OCH₂ | H | O | S |
| C11.49 | Me | H | 3,5-diMe | SCH₂ | H | O | S |
| C11.50 | MeO | H | 3,5-diMe | OCH₂ | H | O | S |
| C11.51 | MeO | H | 3,5-diMe | OCH₂ | H | O | O |
| C11.52 | Et | H | 3,5-diMe | OCH₂ | H | O | S |
| C11.53 | nPr | H | 3,5-diMe | OCH₂ | H | O | S |
| C11.54 | iPr | H | 3,5-diMe | OCH₂ | H | O | S |
| C11.55 | nBu | H | 3,5-diMe | OCH₂ | H | O | S |
| C11.56 | FCH₂ | H | 3,5-diMe | OCH₂ | H | O | S |
| C11.57 | F₂CH | H | 3,5-diMe | OCH₂ | H | O | S |
| C11.58 | F₃C | H | 3,5-diMe | OCH₂ | H | O | S |
| C11.59 | ClCH₂ | H | 3,5-diMe | OCH₂ | H | O | S |
| C11.60 | Cl₂CH | H | 3,5-diMe | OCH₂ | H | O | S |
| C11.61 | BrCH₂ | H | 3,5-diMe | OCH₂ | H | O | S |
| C11.62 | FClCH | H | 3,5-diMe | OCH₂ | H | O | S |
| C11.63 | Me | H | 2,3,5-triMe | OCH₂ | H | O | S |
| C11.64 | MeO | H | 2,3,5-triMe | OCH₂ | H | O | S |
| C11.65 | Me | H | 2,3,5-triMe | OCH₂ | H | O | O |
| C11.66 | MeO | H | 2,3,5-triMe | OCH₂ | H | O | O |
| C11.67 | Et | H | 2,3,5-triMe | OCH₂ | H | O | S |
| C11.68 | nPr | H | 2,3,5-triMe | OCH₂ | H | O | S |
| C11.69 | iPr | H | 2,3,5-triMe | OCH₂ | H | O | S |
| C11.70 | nBu | H | 2,3,5-triMe | OCH₂ | H | O | S |
| C11.71 | FCH₂ | H | 2,3,5-triMe | OCH₂ | H | O | S |
| C11.72 | F₂CH | H | 2,3,5-triMe | OCH₂ | H | O | S |
| C11.73 | F₃C | H | 2,3,5-triMe | OCH₂ | H | O | S |
| C11.74 | ClCH₂ | H | 2,3,5-triMe | OCH₂ | H | O | S |
| C11.75 | Cl₂CH | H | 2,3,5-triMe | OCH₂ | H | O | S |

TABLE 3-continued

| Compd. No. | R¹ | R² | (R³)ₙ | ACR⁴R³ | (R⁶)ₘ | X | Q |
|---|---|---|---|---|---|---|---|
| C11.76 | BrCH₂ | H | 2,3,5-triMe | OCH₂ | H | O | S |
| C11.77 | FClCH | H | 2,3,5-triMe | OCH₂ | H | O | S |
| C11.78 | Me | H | 2,3,6-triMe | OCH₂ | H | O | S |
| C11.79 | MeO | H | 2,3,6-triMe | OCH₂ | H | O | S |
| C11.80 | Me | H | 2,3,6-triMe | OCH₂ | H | O | O |
| C11.81 | MeO | H | 2,3,6-triMe | OCH₂ | H | O | O |
| C11.82 | Et | H | 2,3,6-triMe | OCH₂ | H | O | S |
| C11.83 | Et | H | 2,3,6-triMe | OCH₂ | H | O | S |
| C11.84 | iPr | H | 2,3,6-triMe | OCH₂ | H | O | S |
| C11.85 | nBu | H | 2,3,6-triMe | OCH₂ | H | O | S |
| C11.86 | FCH₂ | H | 2,3,6-triMe | OCH₂ | H | O | S |
| C11.87 | F₂CH | H | 2,3,6-triMe | OCH₂ | H | O | S |
| C11.88 | F₃C | H | 2,3,6-triMe | OCH₂ | H | O | S |
| C11.89 | ClCH₂ | H | 2,3,6-triMe | OCH₂ | H | O | S |
| C11.90 | Cl₂CH | H | 2,3,6-triMe | OCH₂ | H | O | S |
| C11.91 | BrCH₂ | H | 2,3,6-triMe | OCH₂ | H | O | S |
| C11.92 | FClCH | H | 2,3,6-triMe | OCH₂ | H | O | S |
| C11.93 | Me | H | 2,3,5,6-tetraMe | OCH₂ | H | O | S |
| C11.94 | Et | H | 2,3,5,6-tetraMe | OCH₂ | H | O | S |
| C11.95 | nPr | H | 2,3,5,6-tetraMe | OCH₂ | H | O | S |
| C11.96 | iPr | H | 2,3,5,6-tetraMe | OCH₂ | H | O | S |
| C11.97 | nBu | H | 2,3,5,6-tetraMe | OCH₂ | H | O | S |
| C11.98 | FCH₂ | H | 2,3,5,6-tetraMe | OCH₂ | H | O | S |
| C11.99 | F₂CH | H | 2,3,5,6-tetraMe | OCH₂ | H | O | S |
| C11.100 | F₃C | H | 2,3,5,6-tetraMe | OCH₂ | H | O | S |
| C11.101 | ClCH₂ | H | 2,3,5,6-tetraMe | OCH₂ | H | O | S |
| C11.102 | Cl₂CH | H | 2,3,5,6-tetraMe | OCH₂ | H | O | S |
| C11.103 | BrCH₂ | H | 2,3,5,6-tetraMe | OCH₂ | H | O | S |
| C11.104 | FClCH | H | 2,3,5,6-tetraMe | OCH₂ | H | O | S |
| C12.1 | Me | H | 2,3-diOMe | OCH₂ | H | O | S |
| C12.2 | Me | H | 2,3-diOMe | SCH₂ | H | O | S |
| C12.3 | MeO | H | 2,3-diOMe | OCH₂ | H | O | S |
| C12.4 | Me | H | 2,3-diOMe | OCH₂ | H | O | O |
| C12.5 | MeO | H | 2,3-diOMe | OCH₂ | H | O | O |
| C12.6 | Et | H | 2,3-diOMe | OCH₂ | H | O | S |
| C12.7 | nPr | H | 2,3-diOMe | OCH₂ | H | O | S |
| C12.8 | iPr | H | 2,3-diOMe | OCH₂ | H | O | S |
| C12.9 | nBu | H | 2,3-diOMe | OCH₂ | H | O | S |
| C12.10 | FCH₂ | H | 2,3-diOMe | OCH₂ | H | O | S |
| C12.11 | F₂CH | H | 2,3-diOMe | OCH₂ | H | O | S |
| C12.12 | F₃C | H | 2,3-diOMe | OCH₂ | H | O | S |
| C12.13 | ClCH₂ | H | 2,3-diOMe | OCH₂ | H | O | S |
| C12.14 | Cl₂CH | H | 2,3-diOMe | OCH₂ | H | O | S |
| C12.15 | BrCH₂ | H | 2,3-diOMe | OCH₂ | H | O | S |
| C12.16 | FClCH | H | 2,3-diOMe | OCH₂ | H | O | S |
| C12.17 | Me | H | 2,5-diOMe | OCH₂ | H | O | S |
| C12.18 | Me | H | 2,5-diOMe | SCH₂ | H | O | S |
| C12.19 | MeO | H | 2,5-diOMe | OCH₂ | H | O | S |
| C12.20 | Et | H | 2,5-diOMe | OCH₂ | H | O | S |
| C12.21 | nPr | H | 2,5-diOMe | OCH₂ | H | O | S |
| C12.22 | iPr | H | 2,5-diOMe | OCH₂ | H | O | S |
| C12.23 | nBu | H | 2,5-diOMe | OCH₂ | H | O | S |
| C12.24 | FCH₂ | H | 2,5-diOMe | OCH₂ | H | O | S |
| C12.25 | F₂CH | H | 2,5-diOMe | OCH₂ | H | O | S |
| C12.26 | F₃C | H | 2,5-diOMe | OCH₂ | H | O | S |
| C12.27 | ClCH₂ | H | 2,5-diOMe | OCH₂ | H | O | S |
| C12.28 | Cl₂CH | H | 2,5-diOMe | OCH₂ | H | O | S |
| C12.29 | BrCH₂ | H | 2,5-diOMe | OCH₂ | H | O | S |
| C12.30 | FClCH | H | 2,5-diOMe | OCH₂ | H | O | S |
| C12.31 | Me | H | 2,6-diOMe | OCH₂ | H | O | S |
| C12.32 | Me | H | 2,6-diOMe | SCH₂ | H | O | S |
| C12.33 | MeO | H | 2,6-diOMe | OCH₂ | H | O | S |
| C12.34 | Et | H | 2,6-diOMe | OCH₂ | H | O | S |
| C12.35 | nPr | H | 2,6-diOMe | OCH₂ | H | O | S |
| C12.36 | iPr | H | 2,6-diOMe | OCH₂ | H | O | S |
| C12.37 | nBu | H | 2,6-diOMe | OCH₂ | H | O | S |
| C12.38 | FCH₂ | H | 2,6-diOMe | OCH₂ | H | O | S |
| C12.39 | F₂CH | H | 2,6-diOMe | OCH₂ | H | O | S |
| C12.40 | F₃C | H | 2,6-diOMe | OCH₂ | H | O | S |
| C12.41 | ClCH₂ | H | 2,6-diOMe | OCH₂ | H | O | S |
| C12.42 | Cl₂CH | H | 2,6-diOMe | OCH₂ | H | O | S |
| C12.43 | BrCH₂ | H | 2,6-diOMe | OCH₂ | H | O | S |
| C12.44 | FClCH | H | 2,6-diOMe | OCH₂ | H | O | S |
| C12.45 | Me | H | 3,5-diOMe | OCH₂ | H | O | S |
| C12.46 | Me | H | 3,5-diOMe | SCH₂ | H | O | S |
| C12.47 | MeO | H | 3,5-diOMe | OCH₂ | H | O | S |

TABLE 3-continued

| Compd. No. | R$^1$ | R$^2$ | (R$^3$)$_a$ | ACR$^4$R$^3$ | (R$^6$)$_m$ | X | Q |
|---|---|---|---|---|---|---|---|
| C12.48 | Et | H | 3,5-diOMe | OCH$_2$ | H | O | S |
| C12.49 | nPr | H | 3,5-diOMe | OCH$_2$ | H | O | S |
| C12.50 | iPr | H | 3,5-diOMe | OCH$_2$ | H | O | S |
| C12.51 | nBu | H | 3,5-diOMe | OCH$_2$ | H | O | S |
| C12.52 | FCH$_2$ | H | 3,5-diOMe | OCH$_2$ | H | O | S |
| C12.53 | F$_2$CH | H | 3,5-diOMe | OCH$_2$ | H | O | S |
| C12.54 | F$_3$C | H | 3,5-diOMe | OCH$_2$ | H | O | S |
| C12.55 | ClCH$_2$ | H | 3,5-diOMe | OCH$_2$ | H | O | S |
| C12.56 | Cl$_2$CH | H | 3,5-diOMe | OCH$_2$ | H | O | S |
| C12.57 | BrCH$_2$ | H | 3,5-diOMe | OCH$_2$ | H | O | S |
| C12.58 | FClCH | H | 3,5-diOMe | OCH$_2$ | H | O | S |
| C12.59 | Me | H | 2,3,5-triOMe | OCH$_2$ | H | O | S |
| C12.60 | Et | H | 2,3,5-triOMe | OCH$_2$ | H | O | S |
| C12.61 | nPr | H | 2,3,5-triOMe | OCH$_2$ | H | O | S |
| C12.62 | iPr | H | 2,3,5-triOMe | OCH$_2$ | H | O | S |
| C12.63 | nBu | H | 2,3,5-triOMe | OCH$_2$ | H | O | S |
| C12.64 | FCH$_2$ | H | 2,3,5-triOMe | OCH$_2$ | H | O | S |
| C12.65 | F$_2$CH | H | 2,3,5-triOMe | OCH$_2$ | H | O | S |
| C12.66 | F$_3$C | H | 2,3,5-triOMe | OCH$_2$ | H | O | S |
| C12.67 | ClCH$_2$ | H | 2,3,5-triOMe | OCH$_2$ | H | O | S |
| C12.68 | Cl$_2$CH | H | 2,3,5-triOMe | OCH$_2$ | H | O | S |
| C12.69 | BrCH$_2$ | H | 2,3,5-triOMe | OCH$_2$ | H | O | S |
| C12.70 | FClCH | H | 2,3,5-triOMe | OCH$_2$ | H | O | S |
| C12.71 | Me | H | 2,3,6-triOMe | OCH$_2$ | H | O | S |
| C12.72 | Et | H | 2,3,6-triOMe | OCH$_2$ | H | O | S |
| C12.73 | nPr | H | 2,3,6-triOMe | OCH$_2$ | H | O | S |
| C12.74 | iPr | H | 2,3,6-triOMe | OCH$_2$ | H | O | S |
| C12.75 | nBu | H | 2,3,6-triOMe | OCH$_2$ | H | O | S |
| C12.76 | FCH$_2$ | H | 2,3,6-triOMe | OCH$_2$ | H | O | S |
| C12.77 | F$_2$CH | H | 2,3,6-triOMe | OCH$_2$ | H | O | S |
| C12.78 | F$_3$C | H | 2,3,6-triOMe | OCH$_2$ | H | O | S |
| C12.79 | ClCH$_2$ | H | 2,3,6-triOMe | OCH$_2$ | H | O | S |
| C12.80 | Cl$_2$CH | H | 2,3,6-triOMe | OCH$_2$ | H | O | S |
| C12.81 | BrCH$_2$ | H | 2,3,6-triOMe | OCH$_2$ | H | O | S |
| C12.82 | FClCH | H | 2,3,6-triOMe | OCH$_2$ | H | O | S |
| C12.83 | Me | H | 2,3,5,6-tetraOMe | OCH$_2$ | H | O | S |
| C12.84 | Et | H | 2,3,5,6-tetraOMe | OCH$_2$ | H | O | S |
| C12.85 | nPr | H | 2,3,5,6-tetraOMe | OCH$_2$ | H | O | S |
| C12.86 | iPr | H | 2,3,5,6-tetraOMe | OCH$_2$ | H | O | S |
| C12.87 | nBu | H | 2,3,5,6-tetraOMe | OCH$_2$ | H | O | S |
| C12.88 | FCH$_2$ | H | 2,3,5,6-tetraOMe | OCH$_2$ | H | O | S |
| C12.89 | F$_2$CH | H | 2,3,5,6-tetraOMe | OCH$_2$ | H | O | S |
| C12.90 | F$_3$C | H | 2,3,5,6-tetraOMe | OCH$_2$ | H | O | S |
| C12.91 | ClCH$_2$ | H | 2,3,5,6-tetraOMe | OCH$_2$ | H | O | S |
| C12.92 | Cl$_2$CH | H | 2,3,5,6-tetraOMe | OCH$_2$ | H | O | S |
| C12.93 | BrCH$_2$ | H | 2,3,5,6-tetraOMe | OCH$_2$ | H | O | S |
| C12.94 | FClCH | H | 2,3,5,6-tetraOMe | OCH$_2$ | H | O | S |
| C13.1 | Me | H | 2,3-diF | OCH$_2$ | H | O | S |
| C13.2 | Me | H | 2,3-diF | SCH$_2$ | H | O | S |
| C13.3 | Me | H | 2,3-diF | OCH$_2$ | H | O | O |
| C13.4 | MeO | H | 2,3-diF | OCH$_2$ | H | O | S |
| C13.5 | MeO | H | 2,3-diF | OCH$_2$ | H | O | O |
| C13.6 | Et | H | 2,3-diF | OCH$_2$ | H | O | S |
| C13.7 | nPr | H | 2,3-diF | OCH$_2$ | H | O | S |
| C13.8 | iPr | H | 2,3-diF | OCH$_2$ | H | O | S |
| C13.9 | nBu | H | 2,3-diF | OCH$_2$ | H | O | S |
| C13.10 | FCH$_2$ | H | 2,3-diF | OCH$_2$ | H | O | S |
| C13.11 | F$_2$CH | H | 2,3-diF | OCH$_2$ | H | O | S |
| C13.12 | F$_3$C | H | 2,3-diF | OCH$_2$ | H | O | S |
| C13.13 | ClCH$_2$ | H | 2,3-diF | OCH$_2$ | H | O | S |
| C13.14 | Cl$_2$CH | H | 2,3-diF | OCH$_2$ | H | O | S |
| C13.15 | BrCH$_2$ | H | 2,3-diF | OCH$_2$ | H | O | S |
| C13.16 | FClCH | H | 2,3-diF | OCH$_2$ | H | O | S |
| C13.17 | Me | H | 2,5-diF | OCH$_2$ | H | O | S |
| C13.18 | Me | H | 2,5-diF | SCH$_2$ | H | O | S |
| C13.19 | MeO | H | 2,5-diF | OCH$_2$ | H | O | S |
| C13.20 | Et | H | 2,5-diF | OCH$_2$ | H | O | S |
| C13.21 | nPr | H | 2,5-diF | OCH$_2$ | H | O | S |
| C13.22 | iPr | H | 2,5-diF | OCH$_2$ | H | O | S |
| C13.23 | nBu | H | 2,5-diF | OCH$_2$ | H | O | S |
| C13.24 | FCH$_2$ | H | 2,5-diF | OCH$_2$ | H | O | S |
| C13.25 | F$_2$CH | H | 2,5-diF | OCH$_2$ | H | O | S |
| C13.26 | F$_3$C | H | 2,5-diF | OCH$_2$ | H | O | S |
| C13.27 | ClCH$_2$ | H | 2,5-diF | OCH$_2$ | H | O | S |
| C13.28 | Cl$_2$CH | H | 2,5-diF | OCH$_2$ | H | O | S |
| C13.29 | BrCH$_2$ | H | 2,5-diF | OCH$_2$ | H | O | S |

TABLE 3-continued

| Compd. No. | R¹ | R² | (R³)ₙ | ACR⁴R⁵ | (R⁶)ₘ | X | Q |
|---|---|---|---|---|---|---|---|
| C13.30 | FClCH | H | 2,5-diF | OCH₂ | H | O | S |
| C13.31 | Me | H | 2,6-diF | OCH₂ | H | O | S |
| C13.32 | Me | H | 2,6-diF | SCH₂ | H | O | S |
| C13.33 | MeO | H | 2,6-diF | OCH₂ | H | O | S |
| C13.34 | Et | H | 2,6-diF | OCH₂ | H | O | S |
| C13.35 | nPr | H | 2,6-diF | OCH₂ | H | O | S |
| C13.36 | iPr | H | 2,6-diF | OCH₂ | H | O | S |
| C13.37 | nBu | H | 2,6-diF | OCH₂ | H | O | S |
| C13.38 | FCH₂ | H | 2,6-diF | OCH₂ | H | O | S |
| C13.39 | F₂CH | H | 2,6-diF | OCH₂ | H | O | S |
| C13.40 | F₃C | H | 2,6-diF | OCH₂ | H | O | S |
| C13.41 | ClCH₂ | H | 2,6-diF | OCH₂ | H | O | S |
| C13.42 | Cl₂CH | H | 2,6-diF | OCH₂ | H | O | S |
| C13.43 | BrCH₂ | H | 2,6-diF | OCH₂ | H | O | S |
| C13.44 | FClCH | H | 2,6-diF | OCH₂ | H | O | S |
| C13.45 | Me | H | 3,5-diF | OCH₂ | H | O | S |
| C13.46 | Me | H | 3,5-diF | SCH₂ | H | O | S |
| C13.47 | MeO | H | 3,5-diF | OCH₂ | H | O | S |
| C13.48 | Et | H | 3,5-diF | OCH₂ | H | O | S |
| C13.49 | nPr | H | 3,5-diF | OCH₂ | H | O | S |
| C13.50 | iPr | H | 3,5-diF | OCH₂ | H | O | S |
| C13.51 | nBu | H | 3,5-diF | OCH₂ | H | O | S |
| C13.52 | FCH₂ | H | 3,5-diF | OCH₂ | H | O | S |
| C13.53 | F₂CH | H | 3,5-diF | OCH₂ | H | O | S |
| C13.54 | F₃C | H | 3,5-diF | OCH₂ | H | O | S |
| C13.55 | ClCH₂ | H | 3,5-diF | OCH₂ | H | O | S |
| C13.56 | Cl₂CH | H | 3,5-diF | OCH₂ | H | O | S |
| C13.57 | BrCH₂ | H | 3,5-diF | OCH₂ | H | O | S |
| C13.58 | FClCH | H | 3,5-diF | OCH₂ | H | O | S |
| C13.59 | Me | H | 2,3,5-triF | OCH₂ | H | O | S |
| C13.60 | Et | H | 2,3,5-triF | OCH₂ | H | O | S |
| C13.61 | nPr | H | 2,3,5-triF | OCH₂ | H | O | S |
| C13.62 | iPr | H | 2,3,5-triF | OCH₂ | H | O | S |
| C13.63 | nBu | H | 2,3,5-triF | OCH₂ | H | O | S |
| C13.64 | FCH₂ | H | 2,3,5-triF | OCH₂ | H | O | S |
| C13.65 | F₂CH | H | 2,3,5-triF | OCH₂ | H | O | S |
| C13.66 | F₃C | H | 2,3,5-triF | OCH₂ | H | O | S |
| C13.67 | ClCH₂ | H | 2,3,5-triF | OCH₂ | H | O | S |
| C13.68 | Cl₂CH | H | 2,3,5-triF | OCH₂ | H | O | S |
| C13.69 | BrCH₂ | H | 2,3,5-triF | OCH₂ | H | O | S |
| C13.70 | FClCH | H | 2,3,5-triF | OCH₂ | H | O | S |
| C13.71 | Me | H | 2,3,6-triF | OCH₂ | H | O | S |
| C13.72 | Et | H | 2,3,6-triF | OCH₂ | H | O | S |
| C13.73 | nPr | H | 2,3,6-triF | OCH₂ | H | O | S |
| C13.74 | iPr | H | 2,3,6-triF | OCH₂ | H | O | S |
| C13.75 | nBu | H | 2,3,6-triF | OCH₂ | H | O | S |
| C13.76 | FCH₂ | H | 2,3,6-triF | OCH₂ | H | O | S |
| C13.77 | F₂CH | H | 2,3,6-triF | OCH₂ | H | O | S |
| C13.78 | F₃C | H | 2,3,6-triF | OCH₂ | H | O | S |
| C13.79 | ClCH₂ | H | 2,3,6-triF | OCH₂ | H | O | S |
| C13.80 | Cl₂CH | H | 2,3,6-triF | OCH₂ | H | O | S |
| C13.81 | BrCH₂ | H | 2,3,6-triF | OCH₂ | H | O | S |
| C13.82 | FClCH | H | 2,3,6-triF | OCH₂ | H | O | S |
| C13.83 | Me | H | 2,3,5,6-tetraF | OCH₂ | H | O | S |
| C13.84 | Et | H | 2,3,5,6-tetraF | OCH₂ | H | O | S |
| C13.85 | nPr | H | 2,3,5,6-tetraF | OCH₂ | H | O | S |
| C13.86 | iPr | H | 2,3,5,6-tetraF | OCH₂ | H | O | S |
| C13.87 | nBu | H | 2,3,5,6-tetraF | OCH₂ | H | O | S |
| C13.88 | FCH₂ | H | 2,3,5,6-tetraF | OCH₂ | H | O | S |
| C13.89 | F₂CH | H | 2,3,5,6-tetraF | OCH₂ | H | O | S |
| C13.90 | F₃C | H | 2,3,5,6-tetraF | OCH₂ | H | O | S |
| C13.91 | ClCH₂ | H | 2,3,5,6-tetraF | OCH₂ | H | O | S |
| C13.92 | Cl₂CH | H | 2,3,5,6-tetraF | OCH₂ | H | O | S |
| C13.93 | BrCH₂ | H | 2,3,5,6-tetraF | OCH₂ | H | O | S |
| C13.94 | FClCH | H | 2,3,5,6-tetraF | OCH₂ | H | O | S |
| C14.1 | Me | H | 2,3-diCl | OCH₂ | H | O | S |
| C14.2 | Me | H | 2,3-diCl | SCH₂ | H | O | S |
| C14.3 | MeO | H | 2,3-diCl | OCH₂ | H | O | S |
| C14.4 | Et | H | 2,3-diCl | OCH₂ | H | O | S |
| C14.5 | nPr | H | 2,3-diCl | OCH₂ | H | O | S |
| C14.6 | iPr | H | 2,3-diCl | OCH₂ | H | O | S |
| C14.7 | nBu | H | 2,3-diCl | OCH₂ | H | O | S |
| C14.8 | FCH₂ | H | 2,3-diCl | OCH₂ | H | O | S |
| C14.9 | F₂CH | H | 2,3-diCl | OCH₂ | H | O | S |
| C14.10 | F₃C | H | 2,3-diCl | OCH₂ | H | O | S |
| C14.11 | ClCH₂ | H | 2,3-diCl | OCH₂ | H | O | S |

TABLE 3-continued

| Compd. No. | R$^1$ | R$^2$ | (R$^3$)$_n$ | ACR$^4$R$^3$ | (R$^6$)$_m$ | X | Q |
|---|---|---|---|---|---|---|---|
| C14.12 | Cl$_2$CH | H | 2,3-diCl | OCH$_2$ | H | O | S |
| C14.13 | BrCH$_2$ | H | 2,3-diCl | OCH$_2$ | H | O | S |
| C14.14 | FClCH | H | 2,3-diCl | OCH$_2$ | H | O | S |
| C14.15 | Me | H | 2,5-diCl | OCH$_2$ | H | O | S |
| C14.16 | Me | H | 2,5-diCl | SCH$_2$ | H | O | S |
| C14.17 | Me | H | 2,5-diCl | OCH$_2$ | H | O | O |
| C14.18 | MeO | H | 2,5-diCl | OCH$_2$ | H | O | O |
| C14.19 | MeO | H | 2,5-diCl | OCH$_2$ | H | O | S |
| C14.20 | Et | H | 2,5-diCl | OCH$_2$ | H | O | S |
| C14.21 | nPr | H | 2,5-diCl | OCH$_2$ | H | O | S |
| C14.22 | iPr | H | 2,5-diCl | OCH$_2$ | H | O | S |
| C14.23 | nBu | H | 2,5-diCl | OCH$_2$ | H | O | S |
| C14.24 | FCH$_2$ | H | 2,5-diCl | OCH$_2$ | H | O | S |
| C14.25 | F$_2$CH | H | 2,5-diCl | OCH$_2$ | H | O | S |
| C14.26 | F$_3$C | H | 2,5-diCl | OCH$_2$ | H | O | S |
| C14.27 | ClCH$_2$ | H | 2,5-diCl | OCH$_2$ | H | O | S |
| C14.28 | Cl$_2$CH | H | 2,5-diCl | OCH$_2$ | H | O | S |
| C14.29 | BrCH$_2$ | H | 2,5-diCl | OCH$_2$ | H | O | S |
| C14.30 | FClCH | H | 2,5-diCl | OCH$_2$ | H | O | S |
| C14.31 | Me | H | 2,6-diCl | OCH$_2$ | H | O | S |
| C14.32 | Me | H | 2,6-diCl | SCH$_2$ | H | O | S |
| C14.33 | MeO | H | 2,6-diCl | OCH$_2$ | H | O | S |
| C14.34 | Et | H | 2,6-diCl | OCH$_2$ | H | O | S |
| C14.35 | nPr | H | 2,6-diCl | OCH$_2$ | H | O | S |
| C14.36 | iPr | H | 2,6-diCl | OCH$_2$ | H | O | S |
| C14.37 | nBu | H | 2,6-diCl | OCH$_2$ | H | O | S |
| C14.38 | FCH$_2$ | H | 2,6-diCl | OCH$_2$ | H | O | S |
| C14.39 | F$_2$CH | H | 2,6-diCl | OCH$_2$ | H | O | S |
| C14.40 | F$_3$C | H | 2,6-diCl | OCH$_2$ | H | O | S |
| C14.41 | ClCH$_2$ | H | 2,6-diCl | OCH$_2$ | H | O | S |
| C14.42 | Cl$_2$CH | H | 2,6-diCl | OCH$_2$ | H | O | S |
| C14.43 | BrCH$_2$ | H | 2,6-diCl | OCH$_2$ | H | O | S |
| C14.44 | FClCH | H | 2,6-diCl | OCH$_2$ | H | O | S |
| C14.45 | Me | H | 3,5-diCl | OCH$_2$ | H | O | S |
| C14.46 | Me | H | 3,5-diCl | SCH$_2$ | H | O | S |
| C14.47 | Me | H | 3,5-diCl | OCH$_2$ | H | O | O |
| C14.48 | MeO | H | 3,5-diCl | OCH$_2$ | H | O | S |
| C14.49 | MeO | H | 3,5-diCl | SCH$_2$ | H | O | S |
| C14.50 | MeO | H | 3,5-diCl | OCH$_2$ | H | O | O |
| C14.51 | Et | H | 3,5-diCl | OCH$_2$ | H | O | S |
| C14.52 | nPr | H | 3,5-diCl | OCH$_2$ | H | O | S |
| C14.53 | iPr | H | 3,5-diCl | OCH$_2$ | H | O | S |
| C14.54 | nBu | H | 3,5-diCl | OCH$_2$ | H | O | S |
| C14.55 | FCH$_2$ | H | 3,5-diCl | OCH$_2$ | H | O | S |
| C14.56 | F$_2$CH | H | 3,5-diCl | OCH$_2$ | H | O | S |
| C14.57 | F$_3$C | H | 3,5-diCl | OCH$_2$ | H | O | S |
| C14.58 | ClCH$_2$ | H | 3,5-diCl | OCH$_2$ | H | O | S |
| C14.59 | Cl$_2$CH | H | 3,5-diCl | OCH$_2$ | H | O | S |
| C14.60 | BrCH$_2$ | H | 3,5-diCl | OCH$_2$ | H | O | S |
| C14.61 | FClCH | H | 3,5-diCl | OCH$_2$ | H | O | S |
| C14.62 | Me | H | 2,3,5-triCl | OCH$_2$ | H | O | S |
| C14.63 | Et | H | 2,3,5-triCl | OCH$_2$ | H | O | S |
| C14.64 | nPr | H | 2,3,5-triCl | OCH$_2$ | H | O | S |
| C14.65 | iPr | H | 2,3,5-triCl | OCH$_2$ | H | O | S |
| C14.66 | nBu | H | 2,3,5-triCl | OCH$_2$ | H | O | S |
| C14.67 | FCH$_2$ | H | 2,3,5-triCl | OCH$_2$ | H | O | S |
| C14.68 | F$_2$CH | H | 2,3,5-triCl | OCH$_2$ | H | O | S |
| C14.69 | F$_3$C | H | 2,3,5-triCl | OCH$_2$ | H | O | S |
| C14.70 | ClCH$_2$ | H | 2,3,5-triCl | OCH$_2$ | H | O | S |
| C14.71 | Cl$_2$CH | H | 2,3,5-triCl | OCH$_2$ | H | O | S |
| C14.72 | BrCH$_2$ | H | 2,3,5-triCl | OCH$_2$ | H | O | S |
| C14.73 | FClCH | H | 2,3,5-triCl | OCH$_2$ | H | O | S |
| C14.74 | Me | H | 2,3,6-triCl | OCH$_2$ | H | O | S |
| C14.75 | MeO | H | 2,3,6-triCl | OCH$_2$ | H | O | S |
| C14.76 | Et | H | 2,3,6-triCl | OCH$_2$ | H | O | S |
| C14.77 | nPr | H | 2,3,6-triCl | OCH$_2$ | H | O | S |
| C14.78 | iPr | H | 2,3,6-triCl | OCH$_2$ | H | O | S |
| C14.79 | nBu | H | 2,3,6-triCl | OCH$_2$ | H | O | S |
| C14.80 | FCH$_2$ | H | 2,3,6-triCl | OCH$_2$ | H | O | S |
| C14.81 | F$_2$CH | H | 2,3,6-triCl | OCH$_2$ | H | O | S |
| C14.82 | F$_3$C | H | 2,3,6-triCl | OCH$_2$ | H | O | S |
| C14.83 | ClCH$_2$ | H | 2,3,6-triCl | OCH$_2$ | H | O | S |
| C14.84 | Cl$_2$CH | H | 2,3,6-triCl | OCH$_2$ | H | O | S |
| C14.85 | BrCH$_2$ | H | 2,3,6-triCl | OCH$_2$ | H | O | S |
| C14.86 | FClCH | H | 2,3,6-triCl | OCH$_2$ | H | O | S |
| C14.87 | Me | H | 2,3,5,6-tetraCl | OCH$_2$ | H | O | S |

TABLE 3-continued

| Compd. No. | R¹ | R² | (R³)ₙ | ACR⁴R³ | (R⁶)ₘ | X | Q |
|---|---|---|---|---|---|---|---|
| C14.88 | Et | H | 2,3,5,6-tetraCl | OCH₂ | H | O | S |
| C14.89 | nPr | H | 2,3,5,6-tetraCl | OCH₂ | H | O | S |
| C14.90 | iPr | H | 2,3,5,6-tetraCl | OCH₂ | H | O | S |
| C14.91 | nBu | H | 2,3,5,6-tetraCl | OCH₂ | H | O | S |
| C14.92 | FCH₂ | H | 2,3,5,6-tetraCl | OCH₂ | H | O | S |
| C14.93 | F₂CH | H | 2,3,5,6-tetraCl | OCH₂ | H | O | S |
| C14.94 | F₃C | H | 2,3,5,6-tetraCl | OCH₂ | H | O | S |
| C14.95 | ClCH₂ | H | 2,3,5,6-tetraCl | OCH₂ | H | O | S |
| C14.96 | Cl₂CH | H | 2,3,5,6-tetraCl | OCH₂ | H | O | S |
| C14.97 | BrCH₂ | H | 2,3,5,6-tetraCl | OCH₂ | H | O | S |
| C14.98 | FClCH | H | 2,3,5,6-tetraCl | OCH₂ | H | O | S |
| C15.1 | Me | H | 2,3-diBr | OCH₂ | H | O | S |
| C15.2 | Et | H | 2,3-diBr | OCH₂ | H | O | S |
| C15.3 | nPr | H | 2,3-diBr | OCH₂ | H | O | S |
| C15.4 | iPr | H | 2,3-diBr | OCH₂ | H | O | S |
| C15.5 | nBu | H | 2,3-diBr | OCH₂ | H | O | S |
| C15.6 | FCH₂ | H | 2,3-diBr | OCH₂ | H | O | S |
| C15.7 | F₂CH | H | 2,3-diBr | OCH₂ | H | O | S |
| C15.8 | F₃C | H | 2,3-diBr | OCH₂ | H | O | S |
| C15.9 | ClCH₂ | H | 2,3-diBr | OCH₂ | H | O | S |
| C15.10 | Cl₂CH | H | 2,3-diBr | OCH₂ | H | O | S |
| C15.11 | BrCH₂ | H | 2,3-diBr | OCH₂ | H | O | S |
| C15.12 | FClCH | H | 2,3-diBr | OCH₂ | H | O | S |
| C15.13 | Me | H | 2,5-diBr | OCH₂ | H | O | S |
| C15.14 | Et | H | 2,5-diBr | OCH₂ | H | O | S |
| C15.15 | nPr | H | 2,5-diBr | OCH₂ | H | O | S |
| C15.16 | iPr | H | 2,5-diBr | OCH₂ | H | O | S |
| C15.17 | nBu | H | 2,5-diBr | OCH₂ | H | O | S |
| C15.18 | FCH₂ | H | 2,5-diBr | OCH₂ | H | O | S |
| C15.19 | F₂CH | H | 2,5-diBr | OCH₂ | H | O | S |
| C15.20 | F₃C | H | 2,5-diBr | OCH₂ | H | O | S |
| C15.21 | ClCH₂ | H | 2,5-diBr | OCH₂ | H | O | S |
| C15.22 | Cl₂CH | H | 2,5-diBr | OCH₂ | H | O | S |
| C15.23 | BrCH₂ | H | 2,5-diBr | OCH₂ | H | O | S |
| C15.24 | FClCH | H | 2,5-diBr | OCH₂ | H | O | S |
| C15.25 | Me | H | 2,6-diBr | OCH₂ | H | O | S |
| C15.26 | Et | H | 2,6-diBr | OCH₂ | H | O | S |
| C15.27 | nPr | H | 2,6-diBr | OCH₂ | H | O | S |
| C15.28 | iPr | H | 2,6-diBr | OCH₂ | H | O | S |
| C15.29 | nBu | H | 2,6-diBr | OCH₂ | H | O | S |
| C15.30 | FCH₂ | H | 2,6-diBr | OCH₂ | H | O | S |
| C15.31 | F₂CH | H | 2,6-diBr | OCH₂ | H | O | S |
| C15.32 | F₃C | H | 2,6-diBr | OCH₂ | H | O | S |
| C15.33 | ClCH₂ | H | 2,6-diBr | OCH₂ | H | O | S |
| C15.34 | Cl₂CH | H | 2,6-diBr | OCH₂ | H | O | S |
| C15.35 | BrCH₂ | H | 2,6-diBr | OCH₂ | H | O | S |
| C15.36 | FClCH | H | 2,6-diBr | OCH₂ | H | O | S |
| C15.37 | Me | H | 3,5-diBr | OCH₂ | H | O | S |
| C15.38 | MeO | H | 3,5-diBr | OCH₂ | H | O | S |
| C15.39 | Et | H | 3,5-diBr | OCH₂ | H | O | S |
| C15.40 | nPr | H | 3,5-diBr | OCH₂ | H | O | S |
| C15.41 | iPr | H | 3,5-diBr | OCH₂ | H | O | S |
| C15.42 | nBu | H | 3,5-diBr | OCH₂ | H | O | S |
| C15.43 | FCH₂ | H | 3,5-diBr | OCH₂ | H | O | S |
| C15.44 | F₂CH | H | 3,5-diBr | OCH₂ | H | O | S |
| C15.45 | F₃C | H | 3,5-diBr | OCH₂ | H | O | S |
| C15.46 | ClCH₂ | H | 3,5-diBr | OCH₂ | H | O | S |
| C15.47 | Cl₂CH | H | 3,5-diBr | OCH₂ | H | O | S |
| C15.48 | BrCH₂ | H | 3,5-diBr | OCH₂ | H | O | S |
| C15.49 | FClCH | H | 3,5-diBr | OCH₂ | H | O | S |
| C15.50 | Me | H | 2,3,5-triBr | OCH₂ | H | O | S |
| C15.51 | Et | H | 2,3,5-triBr | OCH₂ | H | O | S |
| C15.52 | nPr | H | 2,3,5-triBr | OCH₂ | H | O | S |
| C15.53 | iPr | H | 2,3,5-triBr | OCH₂ | H | O | S |
| C15.54 | nBu | H | 2,3,5-triBr | OCH₂ | H | O | S |
| C15.55 | FCH₂ | H | 2,3,5-triBr | OCH₂ | H | O | S |
| C15.56 | F₂CH | H | 2,3,5-triBr | OCH₂ | H | O | S |
| C15.57 | F₃C | H | 2,3,5-triBr | OCH₂ | H | O | S |
| C15.58 | ClCH₂ | H | 2,3,5-triBr | OCH₂ | H | O | S |
| C15.59 | Cl₂CH | H | 2,3,5-triBr | OCH₂ | H | O | S |
| C15.60 | BrCH₂ | H | 2,3,5-triBr | OCH₂ | H | O | S |
| C15.61 | FClCH | H | 2,3,5-triBr | OCH₂ | H | O | S |
| C15.62 | Me | H | 2,3,6-triBr | OCH₂ | H | O | S |
| C15.63 | Et | H | 2,3,6-triBr | OCH₂ | H | O | S |
| C15.64 | nPr | H | 2,3,6-triBr | OCH₂ | H | O | S |
| C15.65 | iPr | H | 2,3,6-triBr | OCH₂ | H | O | S |

TABLE 3-continued

| Compd. No. | R¹ | R² | (R³)ₙ | ACR⁴R³ | (R⁶)ₘ | X | Q |
|---|---|---|---|---|---|---|---|
| C15.66 | nBu | H | 2,3,6-triBr | OCH₂ | H | O | S |
| C15.67 | FCH₂ | H | 2,3,6-triBr | OCH₂ | H | O | S |
| C15.68 | F₂CH | H | 2,3,6-triBr | OCH₂ | H | O | S |
| C15.69 | F₃C | H | 2,3,6-triBr | OCH₂ | H | O | S |
| C15.70 | ClCH₂ | H | 2,3,6-triBr | OCH₂ | H | O | S |
| C15.71 | Cl₂CH | H | 2,3,6-triBr | OCH₂ | H | O | S |
| C15.72 | BrCH₂ | H | 2,3,6-triBr | OCH₂ | H | O | S |
| C15.73 | FClCH | H | 2,3,6-triBr | OCH₂ | H | O | S |
| C15.74 | Me | H | 2,3,5,6-tetraBr | OCH₂ | H | O | S |
| C15.75 | Et | H | 2,3,5,6-tetraBr | OCH₂ | H | O | S |
| C15.76 | nPr | H | 2,3,5,6-tetraBr | OCH₂ | H | O | S |
| C15.77 | iPr | H | 2,3,5,6-tetraBr | OCH₂ | H | O | S |
| C15.78 | nBu | H | 2,3,5,6-tetraBr | OCH₂ | H | O | S |
| C15.79 | FCH₂ | H | 2,3,5,6-tetraBr | OCH₂ | H | O | S |
| C15.80 | F₂CH | H | 2,3,5,6-tetraBr | OCH₂ | H | O | S |
| C15.81 | F₃C | H | 2,3,5,6-tetraBr | OCH₂ | H | O | S |
| C15.82 | ClCH₂ | H | 2,3,5,6-tetraBr | OCH₂ | H | O | S |
| C15.83 | Cl₂CH | H | 2,3,5,6-tetraBr | OCH₂ | H | O | S |
| C15.84 | BrCH₂ | H | 2,3,5,6-tetraBr | OCH₂ | H | O | S |
| C15.85 | FClCH | H | 2,3,5,6-tetraBr | OCH₂ | H | O | S |
| C16.1 | Me | H | 2-F,3-Me | OCH₂ | H | O | S |
| C16.2 | Me | H | 2-F,3-Me | SCH₂ | H | O | S |
| C16.3 | Et | H | 2-F,3-Me | OCH₂ | H | O | S |
| C16.4 | nPr | H | 2-F,3-Me | OCH₂ | H | O | S |
| C16.5 | nPr | H | 2-F,3-Me | OCH₂ | H | O | S |
| C16.6 | nBu | H | 2-F,3-Me | OCH₂ | H | O | S |
| C16.7 | FCH₂ | H | 2-F,3-Me | OCH₂ | H | O | S |
| C16.8 | F₂CH | H | 2-F,3-Me | OCH₂ | H | O | S |
| C16.9 | F₃C | H | 2-F,3-Me | OCH₂ | H | O | S |
| C16.10 | ClCH₂ | H | 2-F,3-Me | OCH₂ | H | O | S |
| C16.11 | Cl₂CH | H | 2-F,3-Me | OCH₂ | H | O | S |
| C16.12 | Me | H | 2-F,5-Me | OCH₂ | H | O | S |
| C16.13 | Me | H | 2-F,5-Me | SCH₂ | H | O | S |
| C16.14 | Et | H | 2-F,5-Me | OCH₂ | H | O | S |
| C16.15 | nPr | H | 2-F,5-Me | OCH₂ | H | O | S |
| C16.16 | iPr | H | 2-F,5-Me | OCH₂ | H | O | S |
| C16.17 | nBu | H | 2-F,5-Me | OCH₂ | H | O | S |
| C16.18 | FCH₂ | H | 2-F,5-Me | OCH₂ | H | O | S |
| C16.19 | F₂CH | H | 2-F,5-Me | OCH₂ | H | O | S |
| C16.20 | F₃C | H | 2-F,5-Me | OCH₂ | H | O | S |
| C16.21 | ClCH₂ | H | 2-F,5-Me | OCH₂ | H | O | S |
| C16.22 | Cl₂CH | H | 2-F,5-Me | OCH₂ | H | O | S |
| C16.23 | Me | H | 3-F,5-Me | OCH₂ | H | O | S |
| C16.24 | Me | H | 3-F,5-Me | SCH₂ | H | O | S |
| C16.25 | Et | H | 3-F,5-Me | OCH₂ | H | O | S |
| C16.26 | nPr | H | 3-F,5-Me | OCH₂ | H | O | S |
| C16.27 | iPr | H | 3-F,5-Me | OCH₂ | H | O | S |
| C16.28 | nBu | H | 3-F,5-Me | OCH₂ | H | O | S |
| C16.29 | FCH₂ | H | 3-F,5-Me | OCH₂ | H | O | S |
| C16.30 | F₂CH | H | 3-F,5-Me | OCH₂ | H | O | S |
| C16.31 | F₃C | H | 3-F,5-Me | OCH₂ | H | O | S |
| C16.32 | ClCH₂ | H | 3-F,5-Me | OCH₂ | H | O | S |
| C16.33 | Cl₂CH | H | 3-F,5-Me | OCH₂ | H | O | S |
| C16.34 | Me | H | 2-Me,3-F | OCH₂ | H | O | S |
| C16.35 | Me | H | 2-Me,3-F | SCH₂ | H | O | S |
| C16.36 | Et | H | 2-Me,3-F | OCH₂ | H | O | S |
| C16.37 | nPr | H | 2-Me,3-F | OCH₂ | H | O | S |
| C16.38 | iPr | H | 2-Me,3-F | OCH₂ | H | O | S |
| C16.39 | nBu | H | 2-Me,3-F | OCH₂ | H | O | S |
| C16.40 | FCH₂ | H | 2-Me,3-F | OCH₂ | H | O | S |
| C16.41 | F₂CH | H | 2-Me,3-F | OCH₂ | H | O | S |
| C16.42 | F₃C | H | 2-Me,3-F | OCH₂ | H | O | S |
| C16.43 | ClCH₂ | H | 2-Me,3-F | OCH₂ | H | O | S |
| C16.44 | Cl₂CH | H | 3-F,2-Me | OCH₂ | H | O | S |
| C16.45 | Me | H | 2-F,6-Me | OCH₂ | H | O | S |
| C16.46 | Me | H | 2-F,6-Me | SCH₂ | H | O | S |
| C16.47 | Et | H | 2-F,6-Me | OCH₂ | H | O | S |
| C16.48 | nPr | H | 2-F,6-Me | OCH₂ | H | O | S |
| C16.49 | iPr | H | 2-F,6-Me | OCH₂ | H | O | S |
| C16.50 | nBu | H | 2-F,6-Me | OCH₂ | H | O | S |
| C16.51 | FCH₂ | H | 2-F,6-Me | OCH₂ | H | O | S |
| C16.52 | F₂CH | H | 2-F,6-Me | OCH₂ | H | O | S |
| C16.53 | F₃C | H | 2-F,6-Me | OCH₂ | H | O | S |
| C16.54 | ClCH₂ | H | 2-F,6-Me | OCH₂ | H | O | S |
| C16.55 | Cl₂CH | H | 2-F,6-Me | OCH₂ | H | O | S |
| C16.56 | Me | H | 2-Me,5-F | OCH₂ | H | O | S |

TABLE 3-continued

| Compd. No. | $R^1$ | $R^2$ | $(R^3)_n$ | $ACR^4R^3$ | $(R^6)_m$ | X | Q |
|---|---|---|---|---|---|---|---|
| C16.57 | Me | H | 2-Me,5-F | SCH$_2$ | H | O | S |
| C16.58 | Et | H | 2-Me,5-F | OCH$_2$ | H | O | S |
| C16.59 | nPr | H | 2-Me,5-F | OCH$_2$ | H | O | S |
| C16.60 | iPr | H | 2-Me,5-F | OCH$_2$ | H | O | S |
| C16.61 | nBu | H | 2-Me,5-F | OCH$_2$ | H | O | S |
| C16.62 | FCH$_2$ | H | 2-Me,5-F | OCH$_2$ | H | O | S |
| C16.63 | F$_2$CH | H | 2-Me,5-F | OCH$_2$ | H | O | S |
| C16.64 | F$_3$C | H | 2-Me,5-F | OCH$_2$ | H | O | S |
| C16.65 | ClCH$_2$ | H | 2-Me,5-F | OCH$_2$ | H | O | S |
| C16.66 | Cl$_2$CH | H | 2-Me,5-F | OCH$_2$ | H | O | S |
| C16.67 | Me | H | 2-Cl,3-Me | OCH$_2$ | H | O | S |
| C16.68 | Me | H | 2-Cl,3-Me | SCH$_2$ | H | O | S |
| C16.69 | Et | H | 2-Cl,3-Me | OCH$_2$ | H | O | S |
| C16.70 | nPr | H | 2-Cl,3-Me | OCH$_2$ | H | O | S |
| C16.71 | iPr | H | 2-Cl,3-Me | OCH$_2$ | H | O | S |
| C16.72 | nBu | H | 2-Cl,3-Me | OCH$_2$ | H | O | S |
| C16.73 | FCH$_2$ | H | 2-Cl,3-Me | OCH$_2$ | H | O | S |
| C16.74 | F$_2$CH | H | 2-Cl,3-Me | OCH$_2$ | H | O | S |
| C16.75 | F$_3$C | H | 2-Cl,3-Me | OCH$_2$ | H | O | S |
| C16.76 | ClCH$_2$ | H | 2-Cl,3-Me | OCH$_2$ | H | O | S |
| C16.77 | Cl$_2$CH | H | 2-Cl,3-Me | OCH$_2$ | H | O | S |
| C16.78 | Me | H | 2-Cl,5-Me | OCH$_2$ | H | O | S |
| C16.79 | Me | H | 2-Cl,5-Me | SCH$_2$ | H | O | S |
| C16.80 | Et | H | 2-Cl,5-Me | OCH$_2$ | H | O | S |
| C16.81 | nPr | H | 2-Cl,5-Me | OCH$_2$ | H | O | S |
| C16.82 | iPr | H | 2-Cl,5-Me | OCH$_2$ | H | O | S |
| C16.83 | nBu | H | 2-Cl,5-Me | OCH$_2$ | H | O | S |
| C16.84 | FCH$_2$ | H | 2-Cl,5-Me | OCH$_2$ | H | O | S |
| C16.85 | F$_2$CH | H | 2-Cl,5-Me | OCH$_2$ | H | O | S |
| C16.86 | F$_3$C | H | 2-Cl,5-Me | OCH$_2$ | H | O | S |
| C16.87 | ClCH$_2$ | H | 2-Cl,5-Me | OCH$_2$ | H | O | S |
| C16.88 | Cl$_2$CH | H | 2-Cl,5-Me | OCH$_2$ | H | O | S |
| C16.89 | Me | H | 3-Cl,5-Me | OCH$_2$ | H | O | S |
| C16.90 | Me | H | 3-Cl,5-Me | SCH$_2$ | H | O | S |
| C16.91 | Et | H | 3-Cl,5-Me | OCH$_2$ | H | O | S |
| C16.92 | nPr | H | 3-Cl,5-Me | OCH$_2$ | H | O | S |
| C16.93 | iPr | H | 3-Cl,5-Me | OCH$_2$ | H | O | S |
| C16.94 | nBu | H | 3-Cl,5-Me | OCH$_2$ | H | O | S |
| C16.95 | FCH$_2$ | H | 3-Cl,5-Me | OCH$_2$ | H | O | S |
| C16.96 | F$_2$CH | H | 3-Cl,5-Me | OCH$_2$ | H | O | S |
| C16.97 | F$_3$C | H | 3-Cl,5-Me | OCH$_2$ | H | O | S |
| C16.98 | ClCH$_2$ | H | 3-Cl,5-Me | OCH$_2$ | H | O | S |
| C16.99 | Cl$_2$CH | H | 3-Cl,5-Me | OCH$_2$ | H | O | S |
| C16.100 | Me | H | 2-Me,3-Cl | OCH$_2$ | H | O | S |
| C16.101 | Me | H | 2-Me,3-Cl | SCH$_2$ | H | O | S |
| C16.102 | Et | H | 2-Me,3-Cl | OCH$_2$ | H | O | S |
| C16.103 | nPr | H | 2-Me,3-Cl | OCH$_2$ | H | O | S |
| C16.104 | iPr | H | 2-Me,3-Cl | OCH$_2$ | H | O | S |
| C16.105 | nBu | H | 2-Me,3-Cl | OCH$_2$ | H | O | S |
| C16.106 | FCH$_2$ | H | 2-Me,3-Cl | OCH$_2$ | H | O | S |
| C16.107 | F$_2$CH | H | 2-Me,3-Cl | OCH$_2$ | H | O | S |
| C16.108 | F$_3$C | H | 2-Me,3-Cl | OCH$_2$ | H | O | S |
| C16.109 | ClCH$_2$ | H | 2-Me,3-Cl | OCH$_2$ | H | O | S |
| C16.110 | Cl$_2$CH | H | 2-Me,3-Cl | OCH$_2$ | H | O | S |
| C16.111 | Me | H | 2-Cl,6-Me | OCH$_2$ | H | O | S |
| C16.112 | Me | H | 2-Cl,6-Me | SCH$_2$ | H | O | S |
| C16.113 | MeO | H | 2-Cl,6-Me | OCH$_2$ | H | O | S |
| C16.114 | MeO | H | 2-Cl,6-Me | OCH$_2$ | H | O | O |
| C16.115 | Et | H | 2-Cl,6-Me | OCH$_2$ | H | O | S |
| C16.116 | nPr | H | 2-Cl,6-Me | OCH$_2$ | H | O | S |
| C16.117 | iPr | H | 2-Cl,6-Me | OCH$_2$ | H | O | S |
| C16.118 | nBu | H | 2-Cl,6-Me | OCH$_2$ | H | O | S |
| C16.119 | FCH$_2$ | H | 2-Cl,6-Me | OCH$_2$ | H | O | S |
| C16.120 | F$_2$CH | H | 2-Cl,6-Me | OCH$_2$ | H | O | S |
| C16.121 | F$_3$C | H | 2-Cl,6-Me | OCH$_2$ | H | O | S |
| C16.122 | ClCH$_2$ | H | 2-Cl,6-Me | OCH$_2$ | H | O | S |
| C16.123 | Cl$_2$CH | H | 2-Cl,6-Me | OCH$_2$ | H | O | S |
| C16.124 | Me | H | 2-Me,5-Cl | OCH$_2$ | H | O | S |
| C16.125 | Me | H | 2-Me,5-Cl | SCH$_2$ | H | O | S |
| C16.126 | MeO | H | 2-Me,5-Cl | OCH$_2$ | H | O | S |
| C16.127 | MeO | H | 2-Me,5-Cl | OCH$_2$ | H | O | O |
| C16.128 | Et | H | 2-Me,5-Cl | OCH$_2$ | H | O | S |
| C16.129 | nPr | H | 2-Me,5-Cl | OCH$_2$ | H | O | S |
| C16.130 | iPr | H | 2-Me,5-Cl | OCH$_2$ | H | O | S |
| C16.131 | nBu | H | 2-Me,5-Cl | OCH$_2$ | H | O | S |
| C16.132 | FCH$_2$ | H | 2-Me,5-Cl | OCH$_2$ | H | O | S |

TABLE 3-continued

| Compd. No. | R¹ | R² | (R³)ₙ | ACR⁴R³ | (R⁶)ₘ | X | Q |
|---|---|---|---|---|---|---|---|
| C16.133 | F₂CH | H | 2-Me,5-Cl | OCH₂ | H | O | S |
| C16.134 | F₃C | H | 2-Me,5-Cl | OCH₂ | H | O | S |
| C16.135 | ClCH₂ | H | 2-Me,5-Cl | OCH₂ | H | O | S |
| C16.136 | Cl₂CH | H | 2-Me,5-Cl | OCH₂ | H | O | S |
| C17.1 | Me | H | 2-F,3-Cl | OCH₂ | H | O | S |
| C17.2 | Me | H | 2-F,3-Cl | SCH₂ | H | O | S |
| C17.3 | Et | H | 2-F,3-Cl | OCH₂ | H | O | S |
| C17.4 | nPr | H | 2-F,3-Cl | OCH₂ | H | O | S |
| C17.5 | iPr | H | 2-F,3-Cl | OCH₂ | H | O | S |
| C17.6 | nBu | H | 2-F,3-Cl | OCH₂ | H | O | S |
| C17.7 | FCH₂ | H | 2-F,3-Cl | OCH₂ | H | O | S |
| C17.8 | F₂CH | H | 2-F,3-Cl | OCH₂ | H | O | S |
| C17.9 | F₃C | H | 2-F,3-Cl | OCH₂ | H | O | S |
| C17.10 | ClCH₂ | H | 2-F,3-Cl | OCH₂ | H | O | S |
| C17.11 | Cl₂CH | H | 2-F,3-Cl | OCH₂ | H | O | S |
| C17.12 | Me | H | 2-F,5-Cl | OCH₂ | H | O | S |
| C17.13 | Me | H | 2-F,5-Cl | SCH₂ | H | O | S |
| C17.14 | Et | H | 2-F,5-Cl | OCH₂ | H | O | S |
| C17.15 | nPr | H | 2-F,5-Cl | OCH₂ | H | O | S |
| C17.16 | iPr | H | 2-F,5-Cl | OCH₂ | H | O | S |
| C17.18 | nBu | H | 2-F,5-Cl | OCH₂ | H | O | S |
| C17.19 | FCH₂ | H | 2-F,5-Cl | OCH₂ | H | O | S |
| C17.20 | F₂CH | H | 2-F,5-Cl | OCH₂ | H | O | S |
| C17.21 | F₃C | H | 2-F,5-Cl | OCH₂ | H | O | S |
| C17.22 | ClCH₂ | H | 2-F,5-Cl | OCH₂ | H | O | S |
| C17.23 | Cl₂CH | H | 2-F,5-Cl | OCH₂ | H | O | S |
| C17.24 | Me | H | 3-Cl,5-F | OCH₂ | H | O | S |
| C17.25 | Me | H | 3-Cl,5-F | SCH₂ | H | O | S |
| C17.26 | Et | H | 3-Cl,5-F | OCH₂ | H | O | S |
| C17.27 | nPr | H | 3-Cl,5-F | OCH₂ | H | O | S |
| C17.28 | iPr | H | 3-Cl,5-F | OCH₂ | H | O | S |
| C17.29 | nBu | H | 3-Cl,5-F | OCH₂ | H | O | S |
| C17.30 | FCH₂ | H | 3-Cl,5-F | OCH₂ | H | O | S |
| C17.31 | F₂CH | H | 3-Cl,5-F | OCH₂ | H | O | S |
| C17.32 | F₃C | H | 3-Cl,5-F | OCH₂ | H | O | S |
| C17.33 | ClCH₂ | H | 3-Cl,5-F | OCH₂ | H | O | S |
| C17.34 | Cl₂CH | H | 3-Cl,5-F | OCH₂ | H | O | S |
| C17.35 | Me | H | 2-Cl,3-F | OCH₂ | H | O | S |
| C17.36 | Me | H | 2-Cl,3-F | SCH₂ | H | O | S |
| C17.37 | Et | H | 2-Cl,3-F | OCH₂ | H | O | S |
| C17.38 | nPr | H | 2-Cl,3-F | OCH₂ | H | O | S |
| C17.39 | iPr | H | 2-Cl,3-F | OCH₂ | H | O | S |
| C17.40 | nBu | H | 2-Cl,3-F | OCH₂ | H | O | S |
| C17.41 | FCH₂ | H | 2-Cl,3-F | OCH₂ | H | O | S |
| C17.42 | F₂CH | H | 2-Cl,3-F | OCH₂ | H | O | S |
| C17.43 | F₃C | H | 2-Cl,3-F | OCH₂ | H | O | S |
| C17.44 | ClCH₂ | H | 2-Cl,3-F | OCH₂ | H | O | S |
| C17.45 | Cl₂CH | H | 2-Cl,3-F | OCH₂ | H | O | S |
| C17.46 | Me | H | 2-Cl,6-F | OCH₂ | H | O | S |
| C17.47 | Me | H | 2-Cl,6-F | SCH₂ | H | O | S |
| C17.48 | Et | H | 2-Cl,6-F | OCH₂ | H | O | S |
| C17.49 | nPr | H | 2-Cl,6-F | OCH₂ | H | O | S |
| C17.50 | iPr | H | 2-Cl,6-F | OCH₂ | H | O | S |
| C17.51 | nBu | H | 2-Cl,6-F | OCH₂ | H | O | S |
| C17.52 | FCH₂ | H | 2-Cl,6-F | OCH₂ | H | O | S |
| C17.53 | F₂CH | H | 2-Cl,6-F | OCH₂ | H | O | S |
| C17.54 | F₃C | H | 2-Cl,6-F | OCH₂ | H | O | S |
| C17.55 | ClCH₂ | H | 2-Cl,6-F | OCH₂ | H | O | S |
| C17.56 | Cl₂CH | H | 2-Cl,6-F | OCH₂ | H | O | S |
| C17.57 | Me | H | 2-Cl,5-F | OCH₂ | H | O | S |
| C17.58 | Me | H | 2-Cl,5-F | SCH₂ | H | O | S |
| C17.59 | Et | H | 2-Cl,5-F | OCH₂ | H | O | S |
| C17.60 | nPr | H | 2-Cl,5-F | OCH₂ | H | O | S |
| C17.61 | iPr | H | 2-Cl,5-F | OCH₂ | H | O | S |
| C17.62 | nBu | H | 2-Cl,5-F | OCH₂ | H | O | S |
| C17.63 | FCH₂ | H | 2-Cl,5-F | OCH₂ | H | O | S |
| C17.64 | F₂CH | H | 2-Cl,5-F | OCH₂ | H | O | S |
| C17.65 | F₃C | H | 2-Cl,5-F | OCH₂ | H | O | S |
| C17.66 | ClCH₂ | H | 2-Cl,5-F | OCH₂ | H | O | S |
| C17.67 | Cl₂CH | H | 2-Cl,5-F | OCH₂ | H | O | S |
| C17.68 | Me | H | 2-CF₃,3-Me | OCH₂ | H | O | S |
| C17.69 | Me | H | 2-CF₃,3-Me | SCH₂ | H | O | S |
| C17.70 | Et | H | 2-CF₃,3-Me | OCH₂ | H | O | S |
| C17.71 | nPr | H | 2-CF₃,3-Me | OCH₂ | H | O | S |
| C17.72 | iPr | H | 2-CF₃,3-Me | OCH₂ | H | O | S |
| C17.73 | nBu | H | 2-CF₃,3-Me | OCH₂ | H | O | S |

TABLE 3-continued

| Compd. No. | R¹ | R² | (R³)ₙ | ACR⁴R³ | (R⁶)ₘ | X | Q |
|---|---|---|---|---|---|---|---|
| C17.74 | FCH₂ | H | 2-CF₃,3-Me | OCH₂ | H | O | S |
| C17.75 | F₂CH | H | 2-CF₃,3-Me | OCH₂ | H | O | S |
| C17.76 | F₃C | H | 2-CF₃,3-Me | OCH₂ | H | O | S |
| C17.77 | ClCH₂ | H | 2-CF₃,3-Me | OCH₂ | H | O | S |
| C17.78 | Cl₂CH | H | 2-CF₃,3-Me | OCH₂ | H | O | S |
| C17.79 | Me | H | 2-CF₃,5-Me | OCH₂ | H | O | S |
| C17.80 | Me | H | 2-CF₃,5-Me | SCH₂ | H | O | S |
| C17.81 | Et | H | 2-CF₃,5-Me | OCH₂ | H | O | S |
| C17.82 | nPr | H | 2-CF₃,5-Me | OCH₂ | H | O | S |
| C17.83 | iPr | H | 2-CF₃,5-Me | OCH₂ | H | O | S |
| C17.84 | nBu | H | 2-CF₃,5-Me | OCH₂ | H | O | S |
| C17.85 | FCH₂ | H | 2-CF₃,5-Me | OCH₂ | H | O | S |
| C17.86 | F₂CH | H | 2-CF₃,5-Me | OCH₂ | H | O | S |
| C17.87 | F₃C | H | 2-CF₃,5-Me | OCH₂ | H | O | S |
| C17.88 | ClCH₂ | H | 2-CF₃,5-Me | OCH₂ | H | O | S |
| C17.89 | Cl₂CH | H | 2-CF₃,5-Me | OCH₂ | H | O | S |
| C17.90 | Me | H | 3-CF₃,5-Me | OCH₂ | H | O | S |
| C17.91 | Me | H | 3-CF₃,5-Me | SCH₂ | H | O | S |
| C17.92 | Et | H | 3-CF₃,5-Me | OCH₂ | H | O | S |
| C17.93 | nPr | H | 3-CF₃,5-Me | OCH₂ | H | O | S |
| C17.94 | iPr | H | 3-CF₃,5-Me | OCH₂ | H | O | S |
| C17.95 | nBu | H | 3-CF₃,5-Me | OCH₂ | H | O | S |
| C17.96 | FCH₂ | H | 3-CF₃,5-Me | OCH₂ | H | O | S |
| C17.97 | F₂CH | H | 3-CF₃,5-Me | OCH₂ | H | O | S |
| C17.98 | F₃C | H | 3-CF₃,5-Me | OCH₂ | H | O | S |
| C17.99 | ClCH₂ | H | 3-CF₃,5-Me | OCH₂ | H | O | S |
| C17.100 | Cl₂CH | H | 3-CF₃,5-Me | OCH₂ | H | O | S |
| C17.101 | Me | H | 2-Me,3-CF₃ | OCH₂ | H | O | S |
| C17.102 | Me | H | 2-Me,3-CF₃ | SCH₂ | H | O | S |
| C17.103 | Et | H | 2-Me,3-CF₃ | OCH₂ | H | O | S |
| C17.104 | nPr | H | 2-Me,3-CF₃ | OCH₂ | H | O | S |
| C17.105 | iPr | H | 2-Me,3-CF₃ | OCH₂ | H | O | S |
| C17.106 | nBu | H | 2-Me,3-CF₃ | OCH₂ | H | O | S |
| C17.107 | FCH₂ | H | 2-Me,3-CF₃ | OCH₂ | H | O | S |
| C17.108 | F₂CH | H | 2-Me,3-CF₃ | OCH₂ | H | O | S |
| C17.109 | F₃C | H | 2-Me,3-CF₃ | OCH₂ | H | O | S |
| C17.110 | ClCH₂ | H | 2-Me,3-CF₃ | OCH₂ | H | O | S |
| C17.111 | Cl₂CH | H | 2-Me,3-CF₃ | OCH₂ | H | O | S |
| C17.112 | Me | H | 2-CF₃,6-Me | OCH₂ | H | O | S |
| C17.113 | Me | H | 2-CF₃,6-Me | SCH₂ | H | O | S |
| C17.114 | Et | H | 2-CF₃,6-Me | OCH₂ | H | O | S |
| C17.115 | nPr | H | 2-CF₃,6-Me | OCH₂ | H | O | S |
| C17.116 | iPr | H | 2-CF₃,6-Me | OCH₂ | H | O | S |
| C17.117 | nBu | H | 2-CF₃,6-Me | OCH₂ | H | O | S |
| C17.118 | FCH₂ | H | 2-CF₃,6-Me | OCH₂ | H | O | S |
| C17.119 | F₂CH | H | 2-CF₃,6-Me | OCH₂ | H | O | S |
| C17.120 | F₃C | H | 2-CF₃,6-Me | OCH₂ | H | O | S |
| C17.121 | ClCH₂ | H | 2-CF₃,6-Me | OCH₂ | H | O | S |
| C17.122 | Cl₂CH | H | 2-CF₃,6-Me | OCH₂ | H | O | S |
| C17.123 | Me | H | 2-Me,5-CF₃ | OCH₂ | H | O | S |
| C17.124 | Me | H | 2-Me,5-CF₃ | SCH₂ | H | O | S |
| C17.125 | Et | H | 2-Me,5-CF₃ | OCH₂ | H | O | S |
| C17.126 | nPr | H | 2-Me,5-CF₃ | OCH₂ | H | O | S |
| C17.127 | iPr | H | 2-Me,5-CF₃ | OCH₂ | H | O | S |
| C17.128 | nBu | H | 2-Me,5-CF₃ | OCH₂ | H | O | S |
| C17.129 | FCH₂ | H | 2-Me,5-CF₃ | OCH₂ | H | O | S |
| C17.130 | F₂CH | H | 2-Me,5-CF₃ | OCH₂ | H | O | S |
| C17.131 | F₃C | H | 2-Me,5-CF₃ | OCH₂ | H | O | S |
| C17.132 | ClCH₂ | H | 2-Me,5-CF₃ | OCH₂ | H | O | S |
| C17.133 | Cl₂CH | H | 2-Me,5-CF₃ | OCH₂ | H | O | S |
| C18.1 | Me | H | 2-OMe,3-Me | OCH₂ | H | O | S |
| C18.2 | Me | H | 2-OMe,3-Me | SCH₂ | H | O | S |
| C18.3 | Et | H | 2-OMe,3-Me | OCH₂ | H | O | S |
| C18.4 | nPr | H | 2-OMe,3-Me | OCH₂ | H | O | S |
| C18.5 | iPr | H | 2-OMe,3-Me | OCH₂ | H | O | S |
| C18.6 | nBu | H | 2-OMe,3-Me | OCH₂ | H | O | S |
| C18.7 | FCH₂ | H | 2-OMe,3-Me | OCH₂ | H | O | S |
| C18.8 | F₂CH | H | 2-OMe,3-Me | OCH₂ | H | O | S |
| C18.9 | F₃C | H | 2-OMe,3-Me | OCH₂ | H | O | S |
| C18.10 | ClCH₂ | H | 2-OMe,3-Me | OCH₂ | H | O | S |
| C18.11 | Cl₂CH | H | 2-OMe,3-Me | OCH₂ | H | O | S |
| C18.12 | Me | H | 2-OMe,5-Me | OCH₂ | H | O | S |
| C18.13 | Me | H | 2-OMe,5-Me | SCH₂ | H | O | S |
| C18.14 | Et | H | 2-OMe,5-Me | OCH₂ | H | O | S |
| C18.15 | nPr | H | 2-OMe,5-Me | OCH₂ | H | O | S |
| C18.16 | iPr | H | 2-OMe,5-Me | OCH₂ | H | O | S |

TABLE 3-continued

| Compd. No. | R¹ | R² | (R³)ₙ | ACR⁴R³ | (R⁶)ₘ | X | Q |
|---|---|---|---|---|---|---|---|
| C18.17 | nBu | H | 2-OMe,5-Me | OCH₂ | H | O | S |
| C18.18 | FCH₂ | H | 2-OMe,5-Me | OCH₂ | H | O | S |
| C18.19 | F₂CH | H | 2-OMe,5-Me | OCH₂ | H | O | S |
| C18.20 | F₃C | H | 2-OMe,5-Me | OCH₂ | H | O | S |
| C18.21 | ClCH₂ | H | 2-OMe,5-Me | OCH₂ | H | O | S |
| C18.22 | Cl₂CH | H | 2-OMe,5-Me | OCH₂ | H | O | S |
| C18.23 | Me | H | 3-OMe,5-Me | OCH₂ | H | O | S |
| C18.24 | Me | H | 3-OMe,5-Me | SCH₂ | H | O | S |
| C18.25 | Et | H | 3-OMe,5-Me | OCH₂ | H | O | S |
| C18.26 | nPr | H | 3-OMe,5-Me | OCH₂ | H | O | S |
| C18.27 | iPr | H | 3-OMe,5-Me | OCH₂ | H | O | S |
| C18.28 | nBu | H | 3-OMe,5-Me | OCH₂ | H | O | S |
| C18.29 | FCH₂ | H | 3-OMe,5-Me | OCH₂ | H | O | S |
| C18.30 | F₂CH | H | 3-OMe,5-Me | OCH₂ | H | O | S |
| C18.31 | F₃C | H | 3-OMe,5-Me | OCH₂ | H | O | S |
| C18.32 | ClCH₂ | H | 3-OMe,5-Me | OCH₂ | H | O | S |
| C18.33 | Cl₂CH | H | 3-OMe,5-Me | OCH₂ | H | O | S |
| C18.35 | Me | H | 2-Me,3-OMe | OCH₂ | H | O | S |
| C18.36 | Me | H | 2-Me,3-OMe | SCH₂ | H | O | S |
| C18.37 | Et | H | 2-Me,3-OMe | OCH₂ | H | O | S |
| C18.38 | nPr | H | 2-Me,3-OMe | OCH₂ | H | O | S |
| C18.39 | iPr | H | 2-Me,3-OMe | OCH₂ | H | O | S |
| C18.40 | nBu | H | 2-Me,3-OMe | OCH₂ | H | O | S |
| C18.41 | FCH₂ | H | 2-Me,3-OMe | OCH₂ | H | O | S |
| C18.42 | F₂CH | H | 2-Me,3-OMe | OCH₂ | H | O | S |
| C18.43 | F₃C | H | 2-Me,3-OMe | OCH₂ | H | O | S |
| C18.44 | ClCH₂ | H | 2-Me,3-OMe | OCH₂ | H | O | S |
| C18.45 | Cl₂CH | H | 2-Me,3-OMe | OCH₂ | H | O | S |
| C18.46 | Me | H | 2-OMe,6-Me | OCH₂ | H | O | S |
| C18.47 | Me | H | 2-OMe,6-Me | SCH₂ | H | O | S |
| C18.48 | Et | H | 2-OMe,6-Me | OCH₂ | H | O | S |
| C18.49 | nPr | H | 2-OMe,6-Me | OCH₂ | H | O | S |
| C18.50 | iPr | H | 2-OMe,6-Me | OCH₂ | H | O | S |
| C18.51 | nBu | H | 2-OMe,6-Me | OCH₂ | H | O | S |
| C18.52 | FCH₂ | H | 2-OMe,6-Me | OCH₂ | H | O | S |
| C18.53 | F₂CH | H | 2-OMe,6-Me | OCH₂ | H | O | S |
| C18.54 | F₃C | H | 2-OMe,6-Me | OCH₂ | H | O | S |
| C18.55 | ClCH₂ | H | 2-OMe,6-Me | OCH₂ | H | O | S |
| C18.56 | Cl₂CH | H | 2-OMe,6-Me | OCH₂ | H | O | S |
| C18.57 | Me | H | 2-Me,5-OMe | OCH₂ | H | O | S |
| C18.58 | Me | H | 2-Me,5-OMe | SCH₂ | H | O | S |
| C18.59 | Et | H | 2-Me,5-OMe | OCH₂ | H | O | S |
| C18.60 | nPr | H | 2-Me,5-OMe | OCH₂ | H | O | S |
| C18.61 | iPr | H | 2-Me,5-OMe | OCH₂ | H | O | S |
| C18.62 | nBu | H | 2-Me,5-OMe | OCH₂ | H | O | S |
| C18.63 | FCH₂ | H | 2-Me,5-OMe | OCH₂ | H | O | S |
| C18.64 | F₂CH | H | 2-Me,5-OMe | OCH₂ | H | O | S |
| C18.65 | F₃C | H | 2-Me,5-OMe | OCH₂ | H | O | S |
| C18.66 | ClCH₃ | H | 2-Me,5-OMe | OCH₂ | H | O | S |
| C18.67 | Cl₂CH | H | 2-Me,5-OMe | OCH₂ | H | O | S |
| C18.68 | Me | H | 2-iPr,3-Me | OCH₂ | H | O | S |
| C18.69 | Et | H | 2-iPr,3-Me | OCH₂ | H | O | S |
| C18.70 | nPr | H | 2-iPr,3-Me | OCH₂ | H | O | S |
| C18.71 | iPr | H | 2-iPr,3-Me | OCH₂ | H | O | S |
| C18.72 | nBu | H | 2-iPr,3-Me | OCH₂ | H | O | S |
| C18.73 | FCH₂ | H | 2-iPr,3-Me | OCH₂ | H | O | S |
| C18.74 | F₂CH | H | 2-iPr,3-Me | OCH₂ | H | O | S |
| C18.75 | F₃C | H | 2-iPr,3-Me | OCH₂ | H | O | S |
| C18.76 | ClCH₂ | H | 2-iPr,3-Me | OCH₂ | H | O | S |
| C18.77 | Cl₂CH | H | 2-iPr,3-Me | OCH₂ | H | O | S |
| C18.78 | Me | H | 2-iPr,5-Me | OCH₂ | H | O | S |
| C18.79 | Et | H | 2-iPr,5-Me | OCH₂ | H | O | S |
| C18.80 | nPr | H | 2-iPr,5-Me | OCH₂ | H | O | S |
| C18.81 | iPr | H | 2-iPr,5-Me | OCH₂ | H | O | S |
| C18.82 | nBu | H | 2-iPr,5-Me | OCH₂ | H | O | S |
| C18.83 | FCH₂ | H | 2-iPr,5-Me | OCH₂ | H | O | S |
| C18.84 | F₂CH | H | 2-iPr,5-Me | OCH₂ | H | O | S |
| C18.85 | F₃C | H | 2-iPr,5-Me | OCH₂ | H | O | S |
| C18.86 | ClCH₂ | H | 2-iPr,5-Me | OCH₂ | H | O | S |
| C18.87 | Cl₂CH | H | 2-iPr,5-Me | OCH₂ | H | O | S |
| C18.88 | Me | H | 3-Me,5-iPr | OCH₂ | H | O | S |
| C18.89 | Et | H | 3-Me,5-iPr | OCH₂ | H | O | S |
| C18.90 | nPr | H | 3-Me,5-iPr | OCH₂ | H | O | S |
| C18.91 | iPr | H | 3-Me,5-iPr | OCH₂ | H | O | S |
| C18.92 | nBu | H | 3-Me,5-iPr | OCH₂ | H | O | S |
| C18.93 | FCH₂ | H | 3-Me,5-iPr | OCH₂ | H | O | S |

TABLE 3-continued

| Compd. No. | R¹ | R² | (R³)ₙ | ACR⁴R⁵ | (R⁶)ₘ | X | Q |
|---|---|---|---|---|---|---|---|
| C18.94 | F₂CH | H | 3-Me,5-iPr | OCH₂ | H | O | S |
| C18.95 | F₃C | H | 3-Me,5-iPr | OCH₂ | H | O | S |
| C18.96 | ClCH₂ | H | 3-Me,5-iPr | OCH₂ | H | O | S |
| C18.97 | Cl₂CH | H | 3-Me,5-iPr | OCH₂ | H | O | S |
| C18.98 | Me | H | 2-Me,3-iPr | OCH₂ | H | O | S |
| C18.99 | Et | H | 2-Me,3-iPr | OCH₂ | H | O | S |
| C18.100 | nPr | H | 2-Me,3-iPr | OCH₂ | H | O | S |
| C18.101 | iPr | H | 2-Me,3-iPr | OCH₂ | H | O | S |
| C18.102 | nBu | H | 2-Me,3-iPr | OCH₂ | H | O | S |
| C18.103 | FCH₂ | H | 2-Me,3-iPr | OCH₂ | H | O | S |
| C18.104 | F₂CH | H | 2-Me,3-iPr | OCH₂ | H | O | S |
| C18.105 | F₃C | H | 2-Me,3-iPr | OCH₂ | H | O | S |
| C18.106 | ClCH₂ | H | 2-Me,3-iPr | OCH₂ | H | O | S |
| C18.107 | Cl₂CH | H | 2-Me,3-iPr | OCH₂ | H | O | S |
| C18.108 | Me | H | 2-Me,6-iPr | OCH₂ | H | O | S |
| C18.109 | Et | H | 2-Me,6-iPr | OCH₂ | H | O | S |
| C18.110 | nPr | H | 2-Me,6-iPr | OCH₂ | H | O | S |
| C18.111 | iPr | H | 2-Me,6-iPr | OCH₂ | H | O | S |
| C18.112 | nBu | H | 2-Me,6-iPr | OCH₂ | H | O | S |
| C18.113 | FCH₂ | H | 2-Me,6-iPr | OCH₂ | H | O | S |
| C18.114 | F₂CH | H | 2-Me,6-iPr | OCH₂ | H | O | S |
| C18.115 | F₃C | H | 2-Me,6-iPr | OCH₂ | H | O | S |
| C18.116 | ClCH₂ | H | 2-Me,6-iPr | OCH₂ | H | O | S |
| C18.117 | Cl₂CH | H | 2-Me,6-iPr | OCH₂ | H | O | S |
| C18.118 | Me | H | 2-Me,5-iPr | OCH₂ | H | O | S |
| C18.119 | MeO | H | 2-Me,5-iPr | OCH₂ | H | O | S |
| C18.120 | MeO | H | 2-Me,5-iPr | OCH₂ | H | O | S |
| C18.121 | Et | H | 2-Me,5-iPr | OCH₂ | H | O | S |
| C18.122 | nPr | H | 2-Me,5-iPr | OCH₂ | H | O | S |
| C18.123 | iPr | H | 2-Me,5-iPr | OCH₂ | H | O | S |
| C18.124 | nBu | H | 2-Me,5-iPr | OCH₂ | H | O | S |
| C18.125 | FCH₂ | H | 2-Me,5-iPr | OCH₂ | H | O | S |
| C18.126 | F₂CH | H | 2-Me,5-iPr | OCH₂ | H | O | S |
| C18.127 | F₃C | H | 2-Me,5-iPr | OCH₂ | H | O | S |
| C18.128 | ClCH₂ | H | 2-Me,5-iPr | OCH₂ | H | O | S |
| C18.129 | Cl₂CH | H | 2-Me,5-iPr | OCH₂ | H | O | S |
| C18.130 | Me | H | 2-Cl,6-CO₂Me | OCH₂ | H | O | S |
| C18.131 | MeO | H | 2-Cl,6-CO₂Me | OCH₂ | H | O | S |

TABLE 4

| Compd. No. | R¹ | R² | (R³)ₙ | ACR⁴R⁵ | (R⁶)ₘ | X | Q |
|---|---|---|---|---|---|---|---|
| D1.1 | Me | Me | 2-Me | OCH₂ | H | O | S |
| D1.2 | MeO | Me | 2-Me | OCH₂ | H | O | S |
| D1.3 | Me | Me | 2-Me | OCH₂ | H | O | O |
| D1.4 | MeO | Me | 2-Me | OCH₂ | H | O | O |
| D1.5 | Me | Et | 2-Me | OCH₂ | H | O | S |
| D1.6 | MeO | Et | 2-Me | OCH₂ | H | O | S |
| D1.7 | Me | Et | 2-Me | OCH₂ | H | O | O |
| D1.8 | MeO | Et | 2-Me | OCH₂ | H | O | O |
| D1.9 | Me | iPr | 2-Me | OCH₂ | H | O | S |
| D1.10 | MeO | iPr | 2-Me | OCH₂ | H | O | S |
| D1.11 | MeO | CH₂O(1,3-Me₂-4-Pyra) | 2-Me | OCH₂ | H | O | O |
| D1.12 | MeO | iPr | 2-Me | OCH₂ | H | O | O |
| D1.13 | Me | CH₂CH=CH₂ | 2-Me | OCH₂ | H | O | S |
| D1.14 | MeO | CH₂CH=CH₂ | 2-Me | OCH₂ | H | O | S |
| D1.15 | MeO | CH₂(3,5-Me₂-4-Isox) | 2-Me | OCH₂ | H | O | O |
| D1.16 | MeO | CH₂CH=CH₂ | 2-Me | OCH₂ | H | O | O |
| D1.17 | MeO | CH₂OCO(Pyrim-2-yl) | 2-Me | OCH₂ | H | O | S |
| D1.18 | MeO | CH₂C≡CH | 2-Me | OCH₂ | H | O | S |
| D1.19 | MeO | CH₂C≡CH | 2-Me | OCH₂ | H | O | O |
| D1.20 | MeO | CH₂CH=CHCl | 2-Me | OCH₂ | H | O | S |
| D1.21 | MeO | CH₂OCO(6-Cl-Pyrd-3-yl) | 2-Me | OCH₂ | H | O | S |
| D1.22 | MeO | CH₂O(THP-2-yl) | 2-Me | OCH₂ | H | O | S |
| D1.23 | MeO | CH₂O(THP-2-yl) | 2-Me | OCH₂ | H | O | O |
| D1.24 | MeO | CH₂O(1-Me-Pyrr-2-yl) | 2-Me | OCH₂ | H | O | S |
| D1.25 | MeO | nPr | 2-Me | OCH₂ | H | O | S |
| D1.26 | Me | nPr | 2-Me | OCH₂ | H | O | O |
| D1.27 | MeO | nPr | 2-Me | OCH₂ | H | O | O |

TABLE 4-continued

| Compd. No. | R¹ | R² | (R³)ₙ | ACR⁴R⁵ | (R⁶)ₘ | X | Q |
|---|---|---|---|---|---|---|---|
| D1.28 | Me | CH₂COMe | 2-Me | OCH₂ | H | O | S |
| D1.29 | MeO | CH₂COMe | 2-Me | OCH₂ | H | O | S |
| D1.30 | MeO | CH₂OCO(Qui-3-yl) | 2-Me | OCH₂ | H | O | O |
| D1.31 | MeO | CH₂COMe | 2-Me | OCH₂ | H | O | O |
| D1.32 | MeO | CH₂COtBu | 2-Me | OCH₂ | H | O | O |
| D1.34 | Me | CH₂COtBu | 2-Me | OCH₂ | H | O | O |
| D1.35 | MeO | CH₂COtBu | 2-Me | OCH₂ | H | O | S |
| D1.36 | Me | CH₂COPh | 2-Me | OCH₂ | H | O | S |
| D1.37 | MeO | CH₂COPh | 2-Me | OCH₂ | H | O | S |
| D1.38 | Me | CH₂COPh | 2-Me | OCH₂ | H | O | O |
| D1.39 | MeO | CH₂COPh | 2-Me | OCH₂ | H | O | O |
| D1.40 | MeO | CH₂CO(4-Cl-Ph) | 2-Me | OCH₂ | H | O | S |
| D1.41 | MeO | CH₂CO(4-Cl-Ph) | 2-Me | OCH₂ | H | O | O |
| D1.42 | Me | CH₂COOEt | 2-Me | OCH₂ | H | O | S |
| D1.43 | MeO | CH₂COOEt | 2-Me | OCH₂ | H | O | S |
| D1.44 | Me | CH₂COOEt | 2-Me | OCH₂ | H | O | O |
| D1.45 | MeO | CH₂COOEt | 2-Me | OCH₂ | H | O | O |
| D1.46 | MeO | CH(Me)COOEt | 2-Me | OCH₂ | H | O | S |
| D1.47 | MeO | CH₂OH | 2-Me | OCH₂ | H | O | S |
| D1.48 | MeO | CH₂OH | 2-Me | SCH₂ | H | O | S |
| D1.49 | MeO | CH₂OH | 2-Me | OCH₂ | H | O | O |
| D1.50 | Me | CH₂OMe | 2-Me | OCH₂ | H | O | S |
| D1.51 | MeO | CH₂OMe | 2-Me | OCH₂ | H | O | S |
| D1.52 | Me | CH₂OMe | 2-Me | OCH₂ | H | O | O |
| D1.53 | MeO | CH₂OMe | 2-Me | OCH₂ | H | O | O |
| D1.54 | Me | CH₂OEt | 2-Me | OCH₂ | H | O | S |
| D1.55 | MeO | CH₂OEt | 2-Me | OCH₂ | H | O | S |
| D1.56 | MeO | CH₂OiBu | 2-Me | OCH₂ | H | O | S |
| D1.57 | MeO | CH₂OnBu | 2-Me | OCH₂ | H | O | S |
| D1.58 | MeO | CH₂OnBu | 2-Me | OCH₂ | H | O | O |
| D1.59 | MeO | CH₂OnBu | 2-Me | SCH₂ | H | O | S |
| D1.60 | MeO | CH₂OCH₂CH=CHCH₃ | 2-Me | OCH₂ | H | O | S |
| D1.61 | Me | CH₂SMe | 2-Me | OCH₂ | H | O | S |
| D1.62 | MeO | CH₂SMe | 2-Me | OCH₂ | H | O | S |
| D1.63 | Me | CH₂SMe | 2-Me | OCH₂ | H | O | O |
| D1.64 | MeO | CH₂SMe | 2-Me | OCH₂ | H | O | O |
| D1.65 | MeO | CH₂S(4-Cl-Ph) | 2-Me | OCH₂ | H | O | S |
| D1.66 | MeO | CH₂S(4-Cl-Ph) | 2-Me | OCH₂ | H | O | O |
| D1.67 | MeO | CH₂OCH₂Ph | 2-Me | OCH₂ | H | O | S |
| D1.68 | MeO | CH₂OCOMe | 2-Me | OCH₂ | H | O | S |
| D1.69 | MeO | CH₂OCOMe | 2-Me | OCH₂ | H | O | O |
| D1.70 | MeO | CH₂OCOEt | 2-Me | OCH₂ | H | O | S |
| D1.71 | MeO | CH₂OCOEt | 2-Me | OCH₂ | H | O | O |
| D1.72 | MeO | CH₂OCOnPr | 2-Me | OCH₂ | H | O | S |
| D1.73 | MeO | CH₂OCOnPr | 2-Me | OCH₂ | H | O | O |
| D1.74 | MeO | CH₂OCOiPr | 2-Me | OCH₂ | H | O | S |
| D1.75 | MeO | CH₂OCOiPr | 2-Me | OCH₂ | H | O | O |
| D1.76 | MeO | CH₂OCOnBu | 2-Me | OCH₂ | H | O | S |
| D1.77 | MeO | CH₂OCOnBu | 2-Me | OCH₂ | H | O | O |
| D1.78 | MeO | CH₂OCOtBu | 2-Me | OCH₂ | H | O | S |
| D1.79 | MeO | CH₂OCO(c-Pen) | 2-Me | OCH₂ | H | O | S |
| D1.80 | MeO | CH₂OCO(c-Hex) | 2-Me | OCH₂ | H | O | S |
| D1.81 | MeO | CH₂OCOCH₂OMe | 2-Me | OCH₂ | H | O | S |
| D1.82 | MeO | CH₂OCOCH₂OMe | 2-Me | OCH₂ | H | O | O |
| D1.83 | MeO | CH₂OCO(CH₂)₂OMe | 2-Me | OCH₂ | H | O | S |
| D1.84 | MeO | CH₂OCO(CH₂)₂OMe | 2-Me | OCH₂ | H | O | O |
| D1.85 | MeO | CH₂OCOCH₂CH₂OEt | 2-Me | OCH₂ | H | O | S |
| D1.86 | MeO | CH₂OCOCH₂CH₂OEt | 2-Me | OCH₂ | H | O | O |
| D1.87 | MeO | CH₂OCOCH₂C(Me)=CH₂ | 2-Me | OCH₂ | H | O | S |
| D1.88 | MeO | CH₂OCOCH₂Cl | 2-Me | OCH₂ | H | O | S |
| D1.89 | MeO | CH₂OCOCH₂Cl | 2-Me | OCH₂ | H | O | O |
| D1.90 | MeO | CH₂OCOPh | 2-Me | OCH₂ | H | O | S |
| D1.91 | MeO | CH₂OCOPh | 2-Me | OCH₂ | H | O | O |
| D1.92 | MeO | CH₂OCO(4-Cl-Ph) | 2-Me | OCH₂ | H | O | S |
| D1.93 | MeO | CH₂OCO(4-Me-Ph) | 2-Me | OCH₂ | H | O | S |
| D1.94 | MeO | CH₂OCO(4-MeO-Ph) | 2-Me | OCH₂ | H | O | S |
| D1.95 | MeO | CH₂OCOCH₂Ph | 2-Me | OCH₂ | H | O | S |
| D1.96 | MeO | CH₂OCOCH₂Ph | 2-Me | OCH₂ | H | O | O |
| D1.97 | MeO | CH₂O(2-Then) | 2-Me | OCH₂ | H | O | S |
| D1.98 | MeO | CH₂O(2-Then) | 2-Me | OCH₂ | H | O | O |
| D1.99 | MeO | CH₂O(2-Furo) | 2-Me | OCH₂ | H | O | S |
| D1.100 | MeO | CH₂O(Nico) | 2-Me | OCH₂ | H | O | S |
| D1.101 | MeO | CH₂O(2-Cl-Nico) | 2-Me | OCH₂ | H | O | S |
| D1.102 | MeO | CH₂OCO(Pyra) | 2-Me | OCH₂ | H | O | S |
| D1.103 | MeO | CH₂OCOOMe | 2-Me | OCH₂ | H | O | S |

TABLE 4-continued

| Compd. No. | R¹ | R² | (R³)ₙ | ACR⁴R⁵ | (R⁶)ₘ | X | Q |
|---|---|---|---|---|---|---|---|
| D1.104 | MeO | CH₂OCOOMe | 2-Me | OCH₂ | H | O | O |
| D1.105 | Me | CH₂CH₂OH | 2-Me | OCH₂ | H | O | S |
| D1.106 | MeO | CH₂CH₂OH | 2-Me | OCH₂ | H | O | S |
| D1.107 | Me | CH₂CH₂OH | 2-Me | OCH₂ | H | O | O |
| D1.108 | MeO | CH₂CH₂OH | 2-Me | OCH₂ | H | O | O |
| D1.109 | Me | CH₂CH₂OEt | 2-Me | OCH₂ | H | O | S |
| D1.110 | MeO | CH₂CH₂OEt | 2-Me | OCH₂ | H | O | S |
| D1.111 | MeO | CH₂CH₂OEt | 2-Me | OCH₂ | H | O | O |
| D1.112 | MeO | CH₂CH₂OCH=CH₂ | 2-Me | OCH₂ | H | O | S |
| D1.113 | MeO | CH₂CH₂OnPr | 2-Me | OCH₂ | H | O | S |
| D1.114 | MeO | CH₂CH₂SMe | 2-Me | OCH₂ | H | O | S |
| D1.115 | MeO | CH₂CH₂SMe | 2-Me | OCH₂ | H | O | O |
| D1.116 | MeO | CH₂CH₂SEt | 2-Me | OCH₂ | H | O | S |
| D1.117 | MeO | CH₂CH₂OPh | 2-Me | OCH₂ | H | O | S |
| D1.118 | Me | CH₂CH₂O(THP-2-yl) | 2-Me | OCH₂ | H | O | S |
| D1.119 | MeO | CH₂CH₂O(THP-2-yl) | 2-Me | OCH₂ | H | O | S |
| D1.120 | Me | CH₂CH₂O(THP-2-yl) | 2-Me | OCH₂ | H | O | O |
| D1.121 | MeO | CH₂CH₂O(THP-2-yl) | 2-Me | OCH₂ | H | O | O |
| D1.122 | Me | CH₂CH₂OCOMe | 2-Me | OCH₂ | H | O | S |
| D1.123 | MeO | CH₂CH₂OCOMe | 2-Me | OCH₂ | H | O | S |
| D1.124 | MeO | CH₂CH₂OCOMe | 2-Me | OCH₂ | H | O | O |
| D1.125 | Me | CH₂CH₂OCOEt | 2-Me | OCH₂ | H | O | S |
| D1.126 | MeO | CH₂CH₂OCOEt | 2-Me | OCH₂ | H | O | S |
| D1.127 | MeO | CH₂CH₂OCOEt | 2-Me | OCH₂ | H | O | O |
| D1.128 | Me | CH₂CH₂OCO(c-Bu) | 2-Me | OCH₂ | H | O | S |
| D1.129 | Me | CH₂CH₂OCOCH₂Cl | 2-Me | OCH₂ | H | O | S |
| D1.130 | Me | CH₂CH₂OCOCH₂OMe | 2-Me | OCH₂ | H | O | S |
| D1.131 | Me | CH₂CH₂OCOPh | 2-Me | OCH₂ | H | O | S |
| D1.132 | MeO | CH₂CH₂OCOPh | 2-Me | OCH₂ | H | O | S |
| D1.133 | Me | CH₂CH₂OCOPh | 2-Me | OCH₂ | H | O | O |
| D1.134 | MeO | CH₂CH₂OCOPh | 2-Me | OCH₂ | H | O | O |
| D1.135 | Me | CH₂CH₂O(2-Furo) | 2-Me | OCH₂ | H | O | S |
| D1.136 | Me | CH₂CH₂O(Isonico) | 2-Me | OCH₂ | H | O | S |
| D1.137 | MeO | CH₂CH₂O(Isonico) | 2-Me | OCH₂ | H | O | S |
| D1.138 | MeO | CH₂CH₂O(Nico) | 2-Me | OCH₂ | H | O | S |
| D1.139 | MeO | CH₂CH₂O(Nico) | 2-Me | OCH₂ | H | O | O |
| D2.1 | Me | COMe | 2-Me | OCH₂ | H | O | S |
| D2.2 | Me | COMe | 2-Me | OCH₂ | H | O | O |
| D2.3 | Me | COEt | 2-Me | OCH₂ | H | O | S |
| D2.4 | MeO | COEt | 2-Me | OCH₂ | H | O | S |
| D2.5 | MeO | COEt | 2-Me | OCH₂ | H | O | O |
| D2.6 | Me | COnPr | 2-Me | OCH₂ | H | O | S |
| D2.7 | MeO | COnPr | 2-Me | OCH₂ | H | O | S |
| D2.8 | Me | COnPr | 2-Me | OCH₂ | H | O | O |
| D2.9 | MeO | COnPr | 2-Me | OCH₂ | H | O | O |
| D2.10 | MeO | COiPr | 2-Me | OCH₂ | H | O | S |
| D2.11 | MeO | COnBu | 2-Me | OCH₂ | H | O | S |
| D2.12 | MeO | COnBu | 2-Me | OCH₂ | H | O | O |
| D2.13 | MeO | COiBu | 2-Me | OCH₂ | H | O | S |
| D2.14 | MeO | CO(c-Bu) | 2-Me | OCH₂ | H | O | S |
| D2.15 | MeO | CO(c-pen) | 2-Me | OCH₂ | H | O | S |
| D2.16 | Me | CO(c-Hex) | 2-Me | OCH₂ | H | O | S |
| D2.17 | MeO | CO(c-Hex) | 2-Me | OCH₂ | H | O | S |
| D2.18 | MeO | CO(c-Hex) | 2-Me | OCH₂ | H | O | O |
| D2.19 | EtO | COEt | 2-Me | OCH₂ | H | O | S |
| D2.20 | MeO | COCH₂OEt | 2-Me | OCH₂ | H | O | S |
| D2.21 | MeO | COCH=CHMe | 2-Me | OCH₂ | H | O | S |
| D2.22 | MeO | COCH=C(Me)Me | 2-Me | OCH₂ | H | O | S |
| D2.23 | EtO | COCH₂OMe | 2-Me | OCH₂ | H | O | S |
| D2.24 | EtO | COCH₂OEt | 2-Me | OCH₂ | H | O | S |
| D2.25 | Me | COCH₂OMe | 2-Me | OCH₂ | H | O | S |
| D2.26 | MeO | COCH₂OMe | 2-Me | OCH₂ | H | O | S |
| D2.27 | Me | COCH₂OMe | 2-Me | OCH₂ | H | O | O |
| D2.28 | MeO | COCH₂OMe | 2-Me | OCH₂ | H | O | O |
| D2.29 | Me | COCH₂CH₂OMe | 2-Me | OCH₂ | H | O | S |
| D2.30 | MeO | COCH₂CH₂OMe | 2-Me | OCH₂ | H | O | S |
| D2.31 | MeO | COCH₂CH₂OMe | 2-Me | OCH₂ | H | O | O |
| D2.32 | MeO | COCH₂CH₂OEt | 2-Me | OCH₂ | H | O | S |
| D2.33 | MeO | COCH₂CH₂OEt | 2-Me | OCH₂ | H | O | O |
| D2.34 | Me | COCH₂CH₂OEt | 2-Me | OCH₂ | H | O | S |
| D2.35 | Me | COCH₂CH₂OEt | 2-Me | OCH₂ | H | O | O |
| D2.36 | Me | COCH₂CH₂OnPr | 2-Me | OCH₂ | H | O | S |
| D2.37 | MeO | COCH₂CH₂OnPr | 2-Me | OCH₂ | H | O | S |
| D2.38 | Me | COCH₂CH₂OnPr | 2-Me | OCH₂ | H | O | O |
| D2.39 | MeO | COCH₂CH₂OnPr | 2-Me | OCH₂ | H | O | O |
| D2.40 | MeO | COCH(Cl)Me | 2-Me | OCH₂ | H | O | S |

TABLE 4-continued

| Compd. No. | R¹ | R² | (R³)ₙ | ACR⁴R⁵ | (R⁶)ₘ | X | Q |
|---|---|---|---|---|---|---|---|
| D2.41 | Me | COPh | 2-Me | OCH₂ | H | O | S |
| D2.42 | MeO | COPh | 2-Me | OCH₂ | H | O | S |
| D2.43 | Me | COPh | 2-Me | OCH₂ | H | O | O |
| D2.44 | MeO | COPh | 2-Me | OCH₂ | H | O | O |
| D2.45 | MeO | CO(4-tBu-Ph) | 2-Me | OCH₂ | H | O | S |
| D2.46 | MeO | CO(2-Cl-Ph) | 2-Me | OCH₂ | H | O | S |
| D2.47 | MeO | CO(3-Cl-Ph) | 2-Me | OCH₂ | H | O | S |
| D2.48 | MeO | CO(4-Cl-Ph) | 2-Me | OCH₂ | H | O | S |
| D2.49 | MeO | CO(4-Cl-Ph) | 2-Me | OCH₂ | H | O | O |
| D2.50 | MeO | CO(2,6-Cl₂-Ph) | 2-Me | OCH₂ | H | O | S |
| D2.51 | MeO | CO(3,4-Cl₂-Ph) | 2-Me | OCH₂ | H | O | S |
| D2.52 | MeO | CO(2,4-F₂-Ph) | 2-Me | OCH₂ | H | O | S |
| D2.53 | MeO | CO(2,6-F₂-Ph) | 2-Me | OCH₂ | H | O | S |
| D2.54 | MeO | CO(2-MeO-Ph) | 2-Me | OCH₂ | H | O | S |
| D2.55 | MeO | CO(2-MeO-Ph) | 2-Me | OCH₂ | H | O | O |
| D2.56 | MeO | CO(3-MeO-Ph) | 2-Me | OCH₂ | H | O | S |
| D2.57 | MeO | CO(4-MeO-Ph) | 2-Me | OCH₂ | H | O | S |
| D2.58 | MeO | CO(4-MeO-Ph) | 2-Me | OCH₂ | H | O | O |
| D2.59 | MeO | CO(3,4,5-(MeO)₃-Ph) | 2-Me | OCH₂ | H | O | S |
| D2.60 | MeO | CO(2-Me-Ph) | 2-Me | OCH₂ | H | O | S |
| D2.61 | MeO | CO(4-Me-Ph) | 2-Me | OCH₂ | H | O | S |
| D2.62 | MeO | CO(4-Me-Ph) | 2-Me | OCH₂ | H | O | O |
| D2.63 | Me | 2-Furo | 2-Me | OCH₂ | H | O | S |
| D2.64 | MeO | 2-Furo | 2-Me | OCH₂ | H | O | S |
| D2.65 | MeO | 2-Furo | 2-Me | OCH₂ | H | O | O |
| D2.66 | MeO | 2-Then | 2-Me | OCH₂ | H | O | S |
| D2.67 | Me | 2-Then | 2-Me | OCH₂ | H | O | S |
| D2.68 | MeO | Nico | 2-Me | OCH₂ | H | O | S |
| D2.69 | MeO | Nico | 2-Me | OCH₂ | H | O | O |
| D2.70 | MeO | CO(2,4-diMe-1,2,3-Tria-5-yl) | 2-Me | OCH₂ | H | O | S |
| D2.71 | MeO | CO(Isothi-4-yl) | 2-Me | OCH₂ | H | O | S |
| D2.72 | MeO | CO(3-Cl-Benthi-2-yl) | 2-Me | OCH₂ | H | O | S |
| D2.73 | MeO | COOMe | 2-Me | OCH₂ | H | O | S |
| D2.74 | MeO | COOMe | 2-Me | OCH₂ | H | O | O |
| D2.75 | MeO | COOEt | 2-Me | OCH₂ | H | O | S |
| D2.76 | MeO | COOEt | 2-Me | OCH₂ | H | O | O |
| D2.77 | MeO | COOnPr | 2-Me | OCH₂ | H | O | S |
| D2.78 | MeO | COOnPr | 2-Me | OCH₂ | H | O | O |
| D2.79 | MeO | COOiPr | 2-Me | OCH₂ | H | O | S |
| D2.80 | MeO | COOnBu | 2-Me | OCH₂ | H | O | S |
| D2.81 | MeO | COOnBu | 2-Me | OCH₂ | H | O | O |
| D2.82 | MeO | COOiBu | 2-Me | OCH₂ | H | O | S |
| D2.83 | MeO | COOCH₂CCl₃ | 2-Me | OCH₂ | H | O | S |
| D2.84 | MeO | COOCH₂CCl₃ | 2-Me | OCH₂ | H | O | O |
| D2.85 | MeO | COOPh | 2-Me | OCH₂ | H | O | S |

TABLE 5

| Compd. No. | R¹ | R² | (R³)ₙ | ACR⁴R⁵ | (R⁶)ₘ | X | Q |
|---|---|---|---|---|---|---|---|
| E1.1 | Me | H | H | OCHMe | H | O | S |
| E1.2 | Me | H | H | SCHMe | H | O | S |
| E1.3 | MeO | H | H | OCHMe | H | O | S |
| E1.4 | Me | H | H | OCHMe | H | O | O |
| E1.5 | MeO | H | H | OCHMe | H | O | O |
| E1.6 | Et | H | H | OCHMe | H | O | S |
| E1.7 | nPr | H | H | OCHMe | H | O | S |
| E1.8 | iPr | H | H | OCHMe | H | O | S |
| E1.9 | nBu | H | H | OCHMe | H | O | S |
| E1.10 | FCH₂ | H | H | OCHMe | H | O | S |
| E1.11 | F₂CH | H | H | OCHMe | H | O | S |
| E1.12 | F₃C | H | H | OCHMe | H | O | S |
| E1.13 | ClCH₂ | H | H | OCHMe | H | O | S |
| E1.14 | Cl₂CH | H | H | OCHMe | H | O | S |
| E1.15 | Me | H | 2-Me | OCHMe | H | O | S |
| E1.16 | Me | H | 2-Me | SCHMe | H | O | S |
| E1.17 | MeO | H | 2-Me | OCHMe | H | O | S |
| E1.18 | Me | H | 2-Me | OCHMe | H | O | O |
| E1.19 | MeO | H | 2-Me | OCHMe | H | O | O |
| E1.20 | Et | H | 2-Me | OCHMe | H | O | S |
| E1.21 | nPr | H | 2-Me | OCHMe | H | O | S |
| E1.22 | iPr | H | 2-Me | OCHMe | H | O | S |
| E1.23 | nBu | H | 2-Me | OCHMe | H | O | S |
| E1.24 | FCH₂ | H | 2-Me | OCHMe | H | O | S |
| E1.25 | F₂CH | H | 2-Me | OCHMe | H | O | S |
| E1.26 | F₃C | H | 2-Me | OCHMe | H | O | S |
| E1.27 | ClCH₂ | H | 2-Me | OCHMe | H | O | S |
| E1.28 | Cl₂CH | H | 2-Me | OCHMe | H | O | S |
| E1.29 | Me | H | 3-Me | OCHMe | H | O | S |
| E1.30 | Me | H | 3-Me | SCHMe | H | O | S |
| E1.31 | MeO | H | 3-Me | OCHMe | H | O | S |
| E1.32 | MeO | H | 3-Me | OCHMe | H | O | O |
| E1.33 | Et | H | 3-Me | OCHMe | H | O | S |
| E1.34 | nPr | H | 3-Me | OCHMe | H | O | S |
| E1.35 | iPr | H | 3-Me | OCHMe | H | O | S |
| E1.36 | nBu | H | 3-Me | OCHMe | H | O | S |
| E1.37 | FCH₂ | H | 3-Me | OCHMe | H | O | S |
| E1.38 | F₂CH | H | 3-Me | OCHMe | H | O | S |
| E1.39 | F₃C | H | 3-Me | OCHMe | H | O | S |
| E1.40 | ClCH₂ | H | 3-Me | OCHMe | H | O | S |

TABLE 5-continued

| Compd. No. | R¹ | R² | (R³)ₙ | ACR⁴R⁵ | (R⁶)ₘ | X | Q |
|---|---|---|---|---|---|---|---|
| E1.41 | Cl₂CH | H | 3-Me | OCHMe | H | O | S |
| E1.42 | Me | H | 2-Et | OCHMe | H | O | S |
| E1.43 | Me | R | 2-Et | SCHMe | H | O | S |
| E1.44 | MeO | H | 2-Et | OCHMe | H | O | O |
| E1.45 | Me | H | 2-Et | OCHMe | H | O | O |
| E1.46 | MeO | H | 2-Et | OCHMe | H | O | S |
| E1.47 | Et | H | 2-Et | OCHMe | H | O | S |
| E1.48 | nPr | H | 2-Et | OCHMe | H | O | S |
| E1.49 | iPr | H | 2-Et | OCHMe | H | O | S |
| E1.50 | nBu | H | 2-Et | OCHMe | H | O | S |
| E1.51 | FCH₂ | H | 2-Et | OCHMe | H | O | S |
| E1.52 | F₂CH | H | 2-Et | OCHMe | H | O | S |
| E1.53 | F₃C | H | 2-Et | OCHMe | H | O | S |
| E1.54 | ClCH₂ | H | 2-Et | OCHMe | H | O | S |
| E1.55 | Cl₂CH | H | 2-Et | OCHMe | H | O | S |
| E1.56 | Me | H | 3-Et | OCHMe | H | O | S |
| E1.57 | Me | H | 3-Et | SCHMe | H | O | S |
| E1.58 | Et | H | 3-Et | OCHMe | H | O | S |
| E1.59 | nPr | H | 3-Et | OCHMe | H | O | S |
| E1.60 | iPr | H | 3-Et | OCHMe | H | O | S |
| E1.61 | nBu | H | 3-Et | OCHMe | H | O | S |
| E1.62 | FCH₂ | H | 3-Et | OCHMe | H | O | S |
| E1.63 | F₂CH | H | 3-Et | OCHMe | H | O | S |
| E1.64 | F₃C | H | 3-Et | OCHMe | H | O | S |
| E1.65 | ClCH₂ | H | 3-Et | OCHMe | H | O | S |
| E1.66 | Cl₂CH | H | 3-Et | OCHMe | H | O | S |
| E2.1 | Me | H | 2-OMe | OCHMe | H | O | S |
| E2.2 | Me | H | 2-OMe | SCHMe | H | O | S |
| E2.3 | MeO | H | 2-OMe | OCHMe | H | O | S |
| E2.4 | Et | H | 2-OMe | OCHMe | H | O | S |
| E2.5 | nPr | H | 2-OMe | OCHMe | H | O | S |
| E2.6 | iPr | H | 2-OMe | OCHMe | H | O | S |
| E2.7 | nBu | H | 2-OMe | OCHMe | H | O | S |
| E2.8 | FCH₂ | H | 2-OMe | OCHMe | H | O | S |
| E2.9 | F₂CH | H | 2-OMe | OCHMe | H | O | S |
| E2.10 | F₃C | H | 2-OMe | OCHMe | H | O | S |
| E2.11 | ClCH₂ | H | 2-OMe | OCHMe | H | O | S |
| E2.12 | Cl₂CH | H | 2-OMe | OCHMe | H | O | S |
| E2.13 | Me | H | 3-OMe | OCHMe | H | O | S |
| E2.14 | Me | H | 3-OMe | SCHMe | H | O | S |
| E2.15 | MeO | H | 3-OMe | OCHMe | H | O | S |
| E2.16 | Et | H | 3-OMe | OCHMe | H | O | S |
| E2.17 | nPr | H | 3-OMe | OCHMe | H | O | S |
| E2.18 | iPr | H | 3-OMe | OCHMe | H | O | S |
| E2.19 | nBu | H | 3-OMe | OCHMe | H | O | S |
| E2.20 | FCH₂ | H | 3-OMe | OCHMe | H | O | S |
| E2.21 | F₂CH | H | 3-OMe | OCHMe | H | O | S |
| E2.22 | F₃C | H | 3-OMe | OCHMe | H | O | S |
| E2.23 | ClCH₂ | H | 3-OMe | OCHMe | H | O | S |
| E2.24 | Cl₂CH | H | 3-OMe | OCHMe | H | O | S |
| E2.25 | Me | H | 2,3-diMe | OCHMe | H | O | S |
| E2.26 | Me | H | 2,3-diMe | SCHMe | H | O | S |
| E2.27 | MeO | H | 2,3-diMe | OCHMe | H | O | S |
| E2.28 | Et | H | 2,3-diMe | OCHMe | H | O | S |
| E2.29 | nPr | H | 2,3-diMe | OCHMe | H | O | S |
| E2.30 | iPr | H | 2,3-diMe | OCHMe | H | O | S |
| E2.31 | nBu | H | 2,3-diMe | OCHMe | H | O | S |
| E2.32 | FCH₂ | H | 2,3-diMe | OCHMe | H | O | S |
| E2.34 | F₂CH | H | 2,3-diMe | OCHMe | H | O | S |
| E2.35 | F₃C | H | 2,3-diMe | OCHMe | H | O | S |
| E2.36 | ClCH₂ | H | 2,3-diMe | OCHMe | H | O | S |
| E2.37 | Cl₂CH | H | 2,3-diMe | OCHMe | H | O | S |
| E3.1 | Me | H | 2-F | OCHMe | H | O | S |
| E3.2 | Me | H | 2-F | SCHMe | H | O | S |
| E3.3 | MeO | H | 2-F | OCHMe | H | O | S |
| E3.4 | Me | H | 2-F | OCHMe | H | O | O |
| E3.5 | MeO | H | 2-F | OCHMe | H | O | O |
| E3.6 | Et | H | 2-F | OCHMe | H | O | S |
| E3.7 | nPr | H | 2-F | OCHMe | H | O | S |
| E3.8 | iPr | H | 2-F | OCHMe | H | O | S |
| E3.9 | nBu | H | 2-F | OCHMe | H | O | S |
| E3.10 | FCH₂ | H | 2-F | OCHMe | H | O | S |
| E3.11 | F₂CH | H | 2-F | OCHMe | H | O | S |
| E3.12 | F₃C | H | 2-F | OCHMe | H | O | S |
| E3.13 | ClCH₂ | H | 2-F | OCHMe | H | O | S |
| E3.14 | Cl₂CH | H | 2-F | OCHMe | H | O | S |
| E3.15 | Me | H | 3-F | OCHMe | H | O | S |
| E3.16 | Me | H | 3-F | SCHMe | H | O | S |
| E3.17 | Et | H | 3-F | OCHMe | H | O | S |
| E3.18 | nPr | H | 3-F | OCHMe | H | O | S |
| E3.19 | iPr | H | 3-F | OCHMe | H | O | S |
| E3.20 | nBu | H | 3-F | OCHMe | H | O | S |
| E3.21 | FCH₂ | H | 3-F | OCHMe | H | O | S |
| E3.22 | F₂CH | H | 3-F | OCHMe | H | O | S |
| E3.23 | F₃C | H | 3-F | OCHMe | H | O | S |
| E3.24 | ClCH₂ | H | 3-F | OCHMe | H | O | S |
| E3.25 | ClCH₂ | H | 3-F | OCHMe | H | O | S |
| E3.26 | Me | H | 2-Cl | OCHMe | H | O | S |
| E3.27 | Me | H | 2-Cl | SCHMe | H | O | S |
| E3.28 | MeO | H | 2-Cl | OCHMe | H | O | S |
| E3.29 | Me | H | 2-Cl | OCHMe | H | O | O |
| E3.30 | MeO | H | 2-Cl | OCHMe | H | O | O |
| E3.31 | Et | H | 2-Cl | OCHMe | H | O | S |
| E3.32 | nPr | H | 2-Cl | OCHMe | H | O | S |
| E3.33 | iPr | H | 2-Cl | OCHMe | H | O | S |
| E3.34 | nBu | H | 2-Cl | OCHMe | H | O | S |
| E3.35 | FCH₂ | H | 2-Cl | OCHMe | H | O | S |
| E3.36 | F₂CH | H | 2-Cl | OCHMe | H | O | S |
| E3.37 | F₃C | H | 2-Cl | OCHMe | H | O | S |
| E3.38 | ClCH₂ | H | 2-Cl | OCHMe | H | O | S |
| E3.39 | Cl₂CH | H | 2-Cl | OCHMe | H | O | S |
| E3.40 | Me | H | 3-Cl | OCHMe | H | O | S |
| E3.41 | Me | H | 3-Cl | SCHMe | H | O | S |
| E3.42 | Et | H | 3-Cl | OCHMe | H | O | S |
| E3.43 | nPr | H | 3-Cl | OCHMe | H | O | S |
| E3.45 | iPr | H | 3-Cl | OCHMe | H | O | S |
| E3.46 | nBu | H | 3-Cl | OCHMe | H | O | S |
| E3.47 | FCH₂ | H | 3-Cl | OCHMe | H | O | S |
| E3.48 | F₂CH | H | 3-Cl | OCHMe | H | O | S |
| E3.49 | F₃C | H | 3-Cl | OCHMe | H | O | S |
| E3.50 | ClCH₂ | H | 3-Cl | OCHMe | H | O | S |
| E3.51 | Cl₂CH | H | 3-Cl | OCHMe | H | O | S |
| E4.1 | Me | H | H | OCMe₂ | H | O | S |
| E4.2 | Me | H | H | SCMe₂ | H | O | S |
| E4.3 | MeO | H | H | OCMe₂ | H | O | S |
| E4.4 | MeO | H | H | OCMe₂ | H | O | O |
| E4.5 | Et | H | H | OCMe₂ | H | O | S |
| E4.6 | nPr | H | H | OCMe₂ | H | O | S |
| E4.7 | iPr | H | H | OCMe₂ | H | O | S |
| E4.8 | nBu | H | H | OCMe₂ | H | O | S |
| E4.9 | FCH₂ | H | H | OCMe₂ | H | O | S |
| E4.10 | F₂CH | H | H | OCMe₂ | H | O | S |
| E4.11 | F₃C | H | H | OCMe₂ | H | O | S |
| E4.12 | ClCH₂ | H | H | OCMe₂ | H | O | S |
| E4.13 | Cl₂CH | H | H | OCMe₂ | H | O | S |
| E4.14 | Me | H | 2-Me | OCMe₂ | H | O | S |
| E4.15 | Me | H | 2-Me | SCMe₂ | H | O | S |
| E4.16 | MeO | H | 2-Me | OCMe₂ | H | O | S |
| E4.17 | Me | H | 2-Me | OCMe₂ | H | O | O |
| E4.18 | MeO | H | 2-Me | OCMe₂ | H | O | O |
| E4.19 | Et | H | 2-Me | OCMe₂ | H | O | S |
| E4.20 | nPr | H | 2-Me | OCMe₂ | H | O | S |
| E4.21 | iPr | H | 2-Me | OCMe₂ | H | O | S |
| E4.22 | nBu | H | 2-Me | OCMe₂ | H | O | S |
| E4.23 | FCH₂ | H | 2-Me | OCMe₂ | H | O | S |
| E4.24 | F₂CH | H | 2-Me | OCMe₂ | H | O | S |
| E4.25 | F₃C | H | 2-Me | OCMe₂ | H | O | S |
| E4.26 | ClCH₂ | H | 2-Me | OCMe₂ | H | O | S |
| E4.27 | ClCH₂ | H | 2-Me | OCMe₂ | H | O | S |
| E4.28 | Me | H | 3-Me | OCMe₂ | H | O | S |
| E4.29 | Me | H | 3-Me | SCMe₂ | H | O | S |
| E4.30 | MeO | H | 3-Me | OCMe₂ | H | O | S |
| E4.31 | Et | H | 3-Me | OCMe₂ | H | O | S |
| E4.32 | nPr | H | 3-Me | OCMe₂ | H | O | S |
| E4.33 | iPr | H | 3-Me | OCMe₂ | H | O | S |
| E4.34 | nBu | H | 3-Me | OCMe₂ | H | O | S |
| E4.35 | FCH₂ | H | 3-Me | OCMe₂ | H | O | S |
| E4.36 | F₂CH | H | 3-Me | OCMe₂ | H | O | S |
| E4.37 | F₃C | H | 3-Me | OCMe₂ | H | O | S |
| E4.38 | ClCH₂ | H | 3-Me | OCMe₂ | H | O | S |
| E4.39 | Cl₂CH | H | 3-Me | OCMe₂ | H | O | S |
| E4.40 | Me | H | 2-Et | OCMe₂ | H | O | S |

TABLE 5-continued

| Compd. No. | R¹ | R² | (R³)ₙ | ACR⁴R⁵ | (R⁶)ₘ | X | Q |
|---|---|---|---|---|---|---|---|
| E4.41 | Me | H | 2-Et | SCMe₂ | H | O | S |
| E4.42 | Et | H | 2-Et | OCMe₂ | H | O | S |
| E4.43 | nPr | H | 2-Et | OCMe₂ | H | O | S |
| E4.44 | iPr | H | 2-Et | OCMe₂ | H | O | S |
| E4.45 | nBu | H | 2-Et | OCMe₂ | H | O | S |
| E4.46 | FCH₂ | H | 2-Et | OCMe₂ | H | O | S |
| E4.47 | F₂CH | H | 2-Et | OCMe₂ | H | O | S |
| E4.48 | F₃C | H | 2-Et | OCMe₂ | H | O | S |
| E4.49 | ClCH₂ | H | 2-Et | OCMe₂ | H | O | S |
| E4.50 | Cl₂CH | H | 2-Et | OCMe₂ | H | O | S |
| E4.51 | Me | H | 3-Et | OCMe₂ | H | O | S |
| E4.52 | Me | H | 3-Et | SCMe₂ | H | O | S |
| E4.53 | Et | H | 3-Et | OCMe₂ | H | O | S |
| E4.54 | nPr | H | 3-Et | OCMe₂ | H | O | S |
| E4.55 | iPr | H | 3-Et | OCMe₂ | H | O | S |
| E4.56 | nBu | H | 3-Et | OCMe₂ | H | O | S |
| E4.57 | FCH₂ | H | 3-Et | OCMe₂ | H | O | S |
| E4.58 | F₂CH | H | 3-Et | OCMe₂ | H | O | S |
| E4.59 | F₃C | H | 3-Et | OCMe₂ | H | O | S |
| E4.60 | ClCH₂ | H | 3-Et | OCMe₂ | H | O | S |
| E4.61 | Cl₂CH | H | 3-Et | OCMe₂ | H | O | S |
| E4.62 | Me | H | 2,3-diMe | OCMe₂ | H | O | S |
| E4.63 | Me | H | 2,3-diMe | SCMe₂ | H | O | S |
| E4.64 | Et | H | 2,3-diMe | OCMe₂ | H | O | S |
| E4.65 | nPr | H | 2,3-diMe | OCMe₂ | H | O | S |
| E4.66 | iPr | H | 2,3-diMe | OCMe₂ | H | O | S |
| E4.67 | nBu | H | 2,3-diMe | OCMe₂ | H | O | S |
| E4.68 | FCH₂ | H | 2,3-diMe | OCMe₂ | H | O | S |
| E4.69 | F₂CH | H | 2,3-diMe | OCMe₂ | H | O | S |
| E4.70 | F₃C | H | 2,3-diMe | OCMe₂ | H | O | S |
| E4.71 | ClCH₂ | H | 2,3-diMe | OCMe₂ | H | O | S |
| E4.72 | Cl₂CH | H | 2,3-diMe | OCMe₂ | H | O | S |
| E5.1 | Me | H | 2-F | OCMe₂ | H | O | S |
| E5.2 | Me | H | 2-F | SCMe₂ | H | O | S |
| E5.3 | Et | H | 2-F | OCMe₂ | H | O | S |
| E5.4 | nPr | H | 2-F | OCMe₂ | H | O | S |
| E5.5 | iPr | H | 2-F | OCMe₂ | H | O | S |
| E5.6 | nBu | H | 2-F | OCMe₂ | H | O | S |
| E5.7 | FCH₂ | H | 2-F | OCMe₂ | H | O | S |
| E5.8 | F₂CH | H | 2-F | OCMe₂ | H | O | S |
| E5.9 | F₃C | H | 2-F | OCMe₂ | H | O | S |
| E5.10 | ClCH₂ | H | 2-F | OCMe₂ | H | O | S |
| E5.11 | Cl₂CH | H | 2-F | OCMe₂ | H | O | S |
| E5.12 | Me | H | 3-F | OCMe₂ | H | O | S |
| E5.13 | Me | H | 3-F | SCMe₂ | H | O | S |
| E5.14 | Et | H | 3-F | OCMe₂ | H | O | S |
| E5.15 | nPr | H | 3-F | OCMe₂ | H | O | S |
| E5.16 | iPr | H | 3-F | OCMe₂ | H | O | S |
| E5.17 | nBu | H | 3-F | OCMe₂ | H | O | S |
| E5.18 | FCH₂ | H | 3-F | OCMe₂ | H | O | S |
| E5.19 | F₂CH | H | 3-F | OCMe₂ | H | O | S |
| E5.20 | F₃C | H | 3-F | OCMe₂ | H | O | S |
| E5.21 | ClCH₂ | H | 3-F | OCMe₂ | H | O | S |
| E5.22 | Cl₂CH | H | 3-F | OCMe₂ | H | O | S |
| E5.23 | Me | H | 2-Cl | OCMe₂ | H | O | S |
| E5.24 | Me | H | 2-Cl | SCMe₂ | H | O | S |
| E5.25 | Et | H | 2-Cl | OCMe₂ | H | O | S |
| E5.26 | nPr | H | 2-Cl | OCMe₂ | H | O | S |
| E5.27 | iPr | H | 2-Cl | OCMe₂ | H | O | S |
| E5.28 | nBu | H | 2-Cl | OCMe₂ | H | O | S |
| E5.29 | FCH₂ | H | 2-Cl | OCMe₂ | H | O | S |
| E5.30 | F₂CH | H | 2-Cl | OCMe₂ | H | O | S |
| E5.31 | F₃C | H | 2-Cl | OCMe₂ | H | O | S |
| E5.32 | ClCH₂ | H | 2-Cl | OCMe₂ | H | O | S |
| E5.33 | Cl₂CH | H | 2-Cl | OCMe₂ | H | O | S |
| E5.34 | Me | H | 3-Cl | OCMe₂ | H | O | S |
| E5.35 | Me | H | 3-Cl | SCMe₂ | H | O | S |
| E5.36 | Et | H | 3-Cl | OCMe₂ | H | O | S |
| E5.37 | nPr | H | 3-Cl | OCMe₂ | H | O | S |
| E5.38 | iPr | H | 3-Cl | OCMe₂ | H | O | S |
| E5.40 | nBu | H | 3-Cl | OCMe₂ | H | O | S |
| E5.41 | FCH₂ | H | 3-Cl | OCMe₂ | H | O | S |
| E5.42 | F₂CH | H | 3-Cl | OCMe₂ | H | O | S |
| E5.43 | F₃C | H | 3-Cl | OCMe₂ | H | O | S |
| E5.44 | ClCH₂ | H | 3-Cl | OCMe₂ | H | O | S |
| E5.45 | Cl₂CH | H | 3-Cl | OCMe₂ | H | O | S |
| E5.46 | Me | H | 2-OMe | OCMe₂ | H | O | S |
| E5.47 | Me | H | 2-OMe | SCMe₂ | H | O | S |
| E5.48 | Et | H | 2-OMe | OCMe₂ | H | O | S |
| E5.49 | nPr | H | 2-OMe | OCMe₂ | H | O | S |
| E5.50 | iPr | H | 2-OMe | OCMe₂ | H | O | S |
| E5.51 | nBu | H | 2-OMe | OCMe₂ | H | O | S |
| E5.52 | FCH₂ | H | 2-OMe | OCMe₂ | H | O | S |
| E5.53 | F₂CH | H | 2-OMe | OCMe₂ | H | O | S |
| E5.54 | F₃C | H | 2-OMe | OCMe₂ | H | O | S |
| E5.55 | ClCH₂ | H | 2-OMe | OCMe₂ | H | O | S |
| E5.56 | Cl₂CH | H | 2-OMe | OCMe₂ | H | O | S |
| E5.57 | Me | H | 3-OMe | OCMe₂ | H | O | S |
| E5.58 | Me | H | 3-OMe | SCMe₂ | H | O | S |
| E5.59 | Et | H | 3-OMe | OCMe₂ | H | O | S |
| E5.60 | nPr | H | 3-OMe | OCMe₂ | H | O | S |
| E5.61 | iPr | H | 3-OMe | OCMe₂ | H | O | S |
| E5.62 | nBu | H | 3-OMe | OCMe₂ | H | O | S |
| E5.63 | FCH₂ | H | 3-OMe | OCMe₂ | H | O | S |
| E5.64 | F₂CH | H | 3-OMe | OCMe₂ | H | O | S |
| E5.65 | F₃C | H | 3-OMe | OCMe₂ | H | O | S |
| E5.66 | ClCH₂ | H | 3-OMe | OCMe₂ | H | O | S |
| E5.67 | Cl₂CH | H | 3-OMe | OCMe₂ | H | O | S |
| E6.1 | Me | H | H | OCHEt | H | O | S |
| E6.2 | Me | H | H | SCHEt | H | O | S |
| E6.3 | MeO | H | H | OCHEt | H | O | S |
| E6.4 | Me | H | H | OCHEt | H | O | O |
| E6.5 | MeO | H | H | OCHEt | H | O | O |
| E6.6 | Et | H | H | OCHEt | H | O | S |
| E6.7 | nPr | H | H | OCHEt | H | O | S |
| F6.8 | iPr | H | H | OCHEt | H | O | S |
| E6.9 | nBu | H | H | OCHEt | H | O | S |
| E7.0 | FCH₂ | H | H | OCHEt | H | O | S |
| E7.1 | F₂CH | H | H | OCHEt | H | O | S |
| E7.2 | F₃C | H | H | OCHEt | H | O | S |
| E7.3 | ClCH₂ | H | H | OCHEt | H | O | S |
| E7.4 | Cl₂CH | H | H | OCHEt | H | O | S |
| E7.5 | Me | H | 2-Me | OCHEt | H | O | S |
| E7.6 | Me | H | 2-Me | SCHEt | H | O | S |
| E7.7 | MeO | H | 2-Me | OCHEt | H | O | S |
| E7.8 | Me | H | 2-Me | OCHEt | H | O | O |
| E7.9 | MeO | H | 2-Me | OCHEt | H | O | O |
| E7.10 | Me | Et | 2-Me | OCHEt | H | O | S |
| E7.11 | MeO | Et | 2-Me | OCHEt | H | O | S |
| E7.12 | Et | H | 2-Me | OCHEt | H | O | S |
| E7.13 | nPr | H | 2-Me | OCHEt | H | O | S |
| E7.14 | iPr | H | 2-Me | OCHEt | H | O | S |
| E7.15 | nBu | H | 2-Me | OCHEt | H | O | S |
| E7.16 | FCH₂ | H | 2-Me | OCHEt | H | O | S |
| E7.17 | F₂CH | H | 2-Me | OCHEt | H | O | S |
| E7.18 | F₃C | H | 2-Me | OCHEt | H | O | S |
| E7.19 | ClCH₂ | H | 2-Me | OCHEt | H | O | S |
| E7.20 | ClCH₂ | H | 2-Me | OCHEt | H | O | S |
| E7.21 | Me | H | 3-Me | OCHEt | H | O | S |
| E7.22 | Me | H | 3-Me | SCHEt | H | O | S |
| E7.23 | Et | H | 3-Me | OCHEt | H | O | S |
| E7.24 | nPr | H | 3-Me | OCHEt | H | O | S |
| E7.25 | iPr | H | 3-Me | OCHEt | H | O | S |
| E7.26 | nBu | H | 3-Me | OCHEt | H | O | S |
| E7.27 | FCH₂ | H | 3-Me | OCHEt | H | O | S |
| E7.28 | F₂CH | H | 3-Me | OCHEt | H | O | S |
| E7.29 | F₃C | H | 3-Me | OCHEt | H | O | S |
| E7.30 | ClCH₂ | H | 3-Me | OCHEt | H | O | S |
| E7.31 | Cl₂CH | H | 3-Me | OCHEt | H | O | S |
| E7.32 | Me | H | 2-Et | OCHEt | H | O | S |
| E7.33 | Me | H | 2-Et | SCHEt | H | O | S |
| E7.34 | Et | H | 2-Et | OCHEt | H | O | S |
| E7.35 | nPr | H | 2-Et | OCHEt | H | O | S |
| E7.36 | iPr | H | 2-Et | OCHEt | H | O | S |
| E7.37 | nBu | H | 2-Et | OCHEt | H | O | S |
| E7.38 | FCH₂ | H | 2-Et | OCHEt | H | O | S |
| E7.39 | F₂CH | H | 2-Et | OCHEt | H | O | S |
| E7.40 | F₃C | H | 2-Et | OCHEt | H | O | S |
| E7.41 | ClCH₂ | H | 2-Et | OCHEt | H | O | S |
| E7.42 | Cl₂CH | H | 2-Et | OCHEt | H | O | S |
| E7.43 | Me | H | 3-Et | OCHEt | H | O | S |
| E7.44 | Me | H | 3-Et | SCHEt | H | O | S |

TABLE 5-continued

| Compd. No. | R¹ | R² | (R³)ₙ | ACR⁴R⁵ | (R⁶)ₘ | X | Q |
|---|---|---|---|---|---|---|---|
| E7.45 | Et | H | 3-Et | OCHEt | H | O | S |
| E7.46 | nPr | H | 3-Et | OCHEt | H | O | S |
| E7.47 | iPr | H | 3-Et | OCHEt | H | O | S |
| E7.48 | nBu | H | 3-Et | OCHEt | H | O | S |
| E7.49 | FCH₂ | H | 3-Et | OCHEt | H | O | S |
| E7.50 | F₂CH | H | 3-Et | OCHEt | H | O | S |
| E7.51 | F₃C | H | 3-Et | OCHEt | H | O | S |
| E7.52 | ClCH₂ | H | 3-Et | OCHEt | H | O | S |
| E7.53 | Cl₂CH | H | 3-Et | OCHEt | H | O | S |
| E7.54 | Me | H | 2,3-diMe | OCHEt | H | O | S |
| E7.55 | Me | H | 2,3-diMe | SCHEt | H | O | S |
| E7.56 | Et | H | 2,3-diMe | OCHEt | H | O | S |
| E7.57 | nPr | H | 2,3-diMe | OCHEt | H | O | S |
| E7.58 | iPr | H | 2,3-diMe | OCHEt | H | O | S |
| E7.59 | nBu | H | 2,3-diMe | OCHEt | H | O | S |
| E7.60 | FCH₂ | H | 2,3-diMe | OCHEt | H | O | S |
| E7.61 | F₂CH | H | 2,3-diMe | OCHEt | H | O | S |
| E7.62 | F₃C | H | 2,3-diMe | OCHEt | H | O | S |
| E7.63 | ClCH₂ | H | 2,3-diMe | OCHEt | H | O | S |
| E7.64 | Cl₂CH | H | 2,3-diMe | OCHEt | H | O | S |
| E7.65 | Me | H | 2-F | OCHEt | H | O | S |
| E7.66 | Me | H | 2-F | SCHEt | H | O | S |
| E7.67 | Et | H | 2-F | OCHEt | H | O | S |
| E7.68 | nPr | H | 2-F | OCHEt | H | O | S |
| E7.69 | iPr | H | 2-F | OCHEt | H | O | S |
| E7.70 | nBu | H | 2-F | OCHEt | H | O | S |
| E7.71 | FCH₂ | H | 2-F | OCHEt | H | O | S |
| E7.72 | F₂CH | H | 2-F | OCHEt | H | O | S |
| E7.73 | F₃C | H | 2-F | OCHEt | H | O | S |
| E7.74 | ClCH₂ | H | 2-F | OCHEt | H | O | S |
| E7.75 | Cl₂CH | H | 2-F | OCHEt | H | O | S |
| E7.76 | Me | H | 3-F | OCHEt | H | O | S |
| E7.77 | Me | H | 3-F | SCHEt | H | O | S |
| E7.78 | Et | H | 3-F | OCHEt | H | O | S |
| E7.79 | nPr | H | 3-F | OCHEt | H | O | S |
| E7.80 | iPr | H | 3-F | OCHEt | H | O | S |
| E7.81 | nBu | H | 3-F | OCHEt | H | O | S |
| E7.82 | FCH₂ | H | 3-F | OCHEt | H | O | S |
| E7.83 | F₂CH | H | 3-F | OCHEt | H | O | S |
| E7.84 | F₃C | H | 3-F | OCHEt | H | O | S |
| E7.85 | ClCH₂ | H | 3-F | OCHEt | H | O | S |
| E7.86 | Cl₂CH | H | 3-F | OCHEt | H | O | S |
| E7.87 | Me | H | 2-Cl | OCHEt | H | O | S |
| E7.88 | Me | H | 2-Cl | SCHEt | H | O | S |
| E7.89 | Et | H | 2-Cl | OCHEt | H | O | S |
| E7.90 | nPr | H | 2-Cl | OCHEt | H | O | S |
| E7.91 | iPr | H | 2-Cl | OCHEt | H | O | S |
| E7.92 | nBu | H | 2-Cl | OCHEt | H | O | S |
| E7.93 | FCH₂ | H | 2-Cl | OCHEt | H | O | S |
| E7.94 | F₂CH | H | 2-Cl | OCHEt | H | O | S |
| E7.95 | F₃C | H | 2-Cl | OCHEt | H | O | S |
| E7.96 | ClCH₂ | H | 2-Cl | OCHEt | H | O | S |
| E7.97 | Cl₂CH | H | 2-Cl | OCHEt | H | O | S |
| E7.98 | Me | H | 3-Cl | OCHEt | H | O | S |
| E7.99 | Me | H | 3-Cl | SCHEt | H | O | S |
| E7.100 | Et | H | 3-Cl | OCHEt | H | O | S |
| E7.101 | nPr | H | 3-Cl | OCHEt | H | O | S |
| E7.102 | iPr | H | 3-Cl | OCHEt | H | O | S |
| E7.103 | nBu | H | 3-Cl | OCHEt | H | O | S |
| E7.104 | FCH₂ | H | 3-Cl | OCHEt | H | O | S |
| E7.105 | F₂CH | H | 3-Cl | OCHEt | H | O | S |
| E7.106 | F₃C | H | 3-Cl | OCHEt | H | O | S |
| E7.107 | ClCH₂ | H | 3-Cl | OCHEt | H | O | S |
| E7.108 | Cl₂CH | H | 3-Cl | OCHEt | H | O | S |
| E7.109 | Me | H | 2-OMe | OCHEt | H | O | S |
| E7.110 | Me | H | 2-OMe | SCHEt | H | O | S |
| E7.111 | Et | H | 2-OMe | OCHEt | H | O | S |
| E7.112 | nPr | H | 2-OMe | OCHEt | H | O | S |
| E7.113 | iPr | H | 2-OMe | OCHEt | H | O | S |
| E7.114 | nBu | H | 2-OMe | OCHEt | H | O | S |
| E7.115 | FCH₂ | H | 2-OMe | OCHEt | H | O | S |
| E7.116 | F₂CH | H | 2-OMe | OCHEt | H | O | S |
| E7.117 | F₃C | H | 2-OMe | OCHEt | H | O | S |
| E7.118 | ClCH₂ | H | 2-OMe | OCHEt | H | O | S |
| E7.119 | Cl₂CH | H | 2-OMe | OCHEt | H | O | S |
| E7.120 | Me | H | 3-OMe | OCHEt | H | O | S |
| E7.121 | Me | H | 3-OMe | SCHEt | H | O | S |
| E7.122 | Et | H | 3-OMe | OCHEt | H | O | S |
| E7.123 | nPr | H | 3-OMe | OCHEt | H | O | S |
| E7.124 | iPr | H | 3-OMe | OCHEt | H | O | S |
| E7.125 | nBu | H | 3-OMe | OCHEt | H | O | S |
| E7.126 | FCH₂ | H | 3-OMe | OCHEt | H | O | S |
| E7.127 | F₂CH | H | 3-OMe | OCHEt | H | O | S |
| E7.128 | F₃C | H | 3-OMe | OCHEt | H | O | S |
| E7.129 | ClCH₂ | H | 3-OMe | OCHEt | H | O | S |
| E7.130 | Cl₂CH | H | 3-OMe | OCHEt | H | O | S |
| E7.131 | Me | H | H | OCHiPr | H | O | S |
| E7.132 | MeO | H | H | OCHiPr | H | O | S |
| E7.133 | Me | H | H | OCHiPr | H | O | O |
| E7.134 | MeO | H | H | OCHiPr | H | O | O |
| E7.135 | Me | H | 2-Me | OCHiPr | H | O | S |
| E7.136 | MeO | H | 2-Me | OCHiPr | H | O | S |
| E7.137 | Me | H | 2-Me | OCHiPr | H | O | O |
| E7.138 | MeO | H | 2-Me | OCHiPr | H | O | O |

TABLE 6

| Compd. No. | R¹ | R² | (R³)ₙ | ACR⁴R⁵ | (R⁶)ₘ | X | Q |
|---|---|---|---|---|---|---|---|
| F1.1 | Me | H | H | OCH₂ | 4-Me | O | S |
| F1.2 | Me | H | H | SCH₂ | 4-Me | O | S |
| F1.3 | MeO | H | H | OCH₂ | 4-Me | O | S |
| F1.4 | Me | H | H | OCH₂ | 4-Me | O | O |
| F1.5 | MeO | H | H | OCH₂ | 4-Me | O | O |
| F1.6 | Et | H | H | OCH₂ | 4-Me | O | S |
| F1.7 | nPr | H | H | OCH₂ | 4-Me | O | S |
| F1.8 | iPr | H | H | OCH₂ | 4-Me | O | S |
| F1.9 | nBu | H | H | OCH₂ | 4-Me | O | S |
| F1.10 | F₃C | H | H | OCH₂ | 4-Me | O | S |
| F1.11 | Me | H | H | OCH₂ | 5-Me | O | S |
| F1.12 | Me | H | H | SCH₂ | 5-Me | O | S |
| F1.13 | MeO | H | H | OCH₂ | 5-Me | O | S |
| F1.14 | Me | H | H | OCH₂ | 5-Me | O | O |
| F1.15 | MeO | H | H | OCH₂ | 5-Me | O | O |
| F1.16 | Et | H | H | OCH₂ | 5-Me | O | S |
| F1.17 | nPr | H | H | OCH₂ | 5-Me | O | S |
| F1.18 | iPr | H | H | OCH₂ | 5-Me | O | S |
| F1.19 | nBu | H | H | OCH₂ | 5-Me | O | S |
| F1.20 | F₃C | H | H | OCH₂ | 5-Me | O | S |
| F1.21 | Me | H | H | OCH₂ | 6-Me | O | S |
| F1.22 | Me | H | H | SCH₂ | 6-Me | O | S |
| F1.23 | MeO | H | H | OCH₂ | 6-Me | O | S |
| F1.24 | Me | H | H | OCH₂ | 6-Me | O | O |
| F1.25 | MeO | H | H | OCH₂ | 6-Me | O | O |
| F1.26 | Et | H | H | OCH₂ | 6-Me | O | S |
| F1.27 | nPr | H | H | OCH₂ | 6-Me | O | S |
| F1.28 | iPr | H | H | OCH₂ | 6-Me | O | S |
| F1.29 | nBu | H | H | OCH₂ | 6-Me | O | S |
| F1.30 | F₃C | H | H | OCH₂ | 6-Me | O | S |
| F1.31 | Me | H | H | OCH₂ | 7-Me | O | S |
| F1.32 | Me | H | H | SCH₂ | 7-Me | O | S |
| F1.33 | MeO | H | H | OCH₂ | 7-Me | O | S |
| F1.34 | Me | H | H | OCH₂ | 7-Me | O | O |
| F1.35 | MeO | H | H | OCH₂ | 7-Me | O | O |
| F1.36 | Et | H | H | OCH₂ | 7-Me | O | S |
| F1.37 | nPr | H | H | OCH₂ | 7-Me | O | S |
| F1.38 | iPr | H | H | OCH₂ | 7-Me | O | S |
| F1.39 | nBu | H | H | OCH₂ | 7-Me | O | S |
| F1.40 | F₃C | H | H | OCH₂ | 7-Me | O | S |
| F1.41 | Me | H | H | OCH₂ | 4-Et | O | S |
| F1.42 | Me | H | H | SCH₂ | 4-Et | O | S |
| F1.43 | Et | H | H | OCH₂ | 4-Et | O | S |
| F1.44 | nPr | H | H | OCH₂ | 4-Et | O | S |
| F1.45 | iPr | H | H | OCH₂ | 4-Et | O | S |
| F1.46 | nBu | H | H | OCH₂ | 4-Et | O | S |
| F1.47 | F₃C | H | H | OCH₂ | 4-Et | O | S |
| F1.48 | Me | H | H | OCH₂ | 5-Et | O | S |
| F1.49 | Me | H | H | SCH₂ | 5-Et | O | S |

TABLE 6-continued

| Compd. No. | R¹ | R² | (R³)ₙ | ACR⁴R⁵ | (R⁶)ₘ | X | Q |
|---|---|---|---|---|---|---|---|
| F1.50 | Et | H | H | OCH₂ | 5-Et | O | S |
| F1.51 | nPr | H | H | OCH₂ | 5-Et | O | S |
| F1.52 | iPr | H | H | OCH₂ | 5-Et | O | S |
| F1.53 | nBu | H | H | OCH₂ | 5-Et | O | S |
| F1.54 | F₃C | H | H | OCH₂ | 5-Et | O | S |
| F1.55 | Me | H | H | OCH₂ | 6-Et | O | S |
| F1.56 | Me | H | H | SCH₂ | 6-Et | O | S |
| F1.57 | Et | H | H | OCH₂ | 6-Et | O | S |
| F1.58 | nPr | H | H | OCH₂ | 6-Et | O | S |
| F1.59 | iPr | H | H | OCH₂ | 6-Et | O | S |
| F1.60 | nBu | H | H | OCH₂ | 6-Et | O | S |
| F1.61 | F₃C | H | H | OCH₂ | 6-Et | O | S |
| F1.62 | Me | H | H | OCH₂ | 7-Et | O | S |
| F1.63 | Me | H | H | SCH₂ | 7-Et | O | S |
| F1.64 | Et | H | H | OCH₂ | 7-Et | O | S |
| F1.65 | nPr | H | H | OCH₂ | 7-Et | O | S |
| F1.66 | iPr | H | H | OCH₂ | 7-Et | O | S |
| F1.67 | nBu | H | H | OCH₂ | 7-Et | O | S |
| F1.68 | F₃C | H | H | OCH₂ | 7-Et | O | S |
| F1.69 | MeO | H | H | OCH₂ | 5-NO₂ | O | O |
| F2.1 | Me | H | H | OCH₂ | 4-CH₂CH=CH₂ | O | S |
| F2.2 | Et | H | H | OCH₂ | 4-CH₂CH=CH₂ | O | S |
| F2.3 | nPr | H | H | OCH₂ | 4-CH₂CH=CH₂ | O | S |
| F2.4 | iPr | H | H | OCH₂ | 4-CH₂CH=CH₂ | O | S |
| F2.5 | nBu | H | H | OCH₂ | 4-CH₂CH=CH₂ | O | S |
| F2.6 | F₃C | H | H | OCH₂ | 4-CH₂CH=CH₂ | O | S |
| F2.7 | Me | H | H | OCH₂ | 5-CH₂CH=CH₂ | O | S |
| F2.8 | MeO | H | H | OCH₂ | 5-CH₂CH=CH₂ | O | S |
| F2.9 | Me | H | H | OCH₂ | 5-CH₂CH=CH₂ | O | O |
| F2.10 | MeO | H | H | OCH₂ | 5-CH₂CH=CH₂ | O | O |
| F2.11 | Et | H | H | OCH₂ | 5-CH₂CH=CH₂ | O | S |
| F2.12 | nPr | H | H | OCH₂ | 5-CH₂CH=CH₂ | O | S |
| F2.13 | iPr | H | H | OCH₂ | 5-CH₂CH=CH₂ | O | S |
| F2.14 | nBu | H | H | OCH₂ | 5-CH₂CH=CH₂ | O | S |
| F2.15 | F₃C | H | H | OCH₂ | 5-CH₂CH=CH₂ | O | S |
| F2.16 | Me | H | H | OCH₂ | 6-CH₂CH=CH₂ | O | S |
| F2.17 | MeO | H | H | OCH₂ | 6-CH₂CH=CH₂ | O | S |
| F2.18 | Et | H | H | OCH₂ | 6-CH₂CH=CH₂ | O | S |
| F2.19 | nPr | H | H | OCH₂ | 6-CH₂CH=CH₂ | O | S |
| F2.20 | iPr | H | H | OCH₂ | 6-CH₂CH=CH₂ | O | S |
| F2.21 | nBu | H | H | OCH₂ | 6-CH₂CH=CH₂ | O | S |
| F2.22 | F₃C | H | H | OCH₂ | 6-CH₂CH=CH₂ | O | S |
| F2.23 | Me | H | H | OCH₂ | 7-CH₂CH=CH₂ | O | S |
| F2.24 | Et | H | H | OCH₂ | 7-CH₂CH=CH₂ | O | S |
| F2.25 | nPr | H | H | OCH₂ | 7-CH₂CH=CH₂ | O | S |
| F2.26 | iPr | H | H | OCH₂ | 7-CH₂CH=CH₂ | O | S |
| F2.27 | nBu | H | H | OCH₂ | 7-CH₂CH=CH₂ | O | S |
| F2.28 | F₃C | H | H | OCH₂ | 7-CH₂CH=CH₂ | O | S |
| F2.29 | Me | H | H | OCH₂ | 5-CH₂C≡CH | O | S |
| F2.30 | MeO | H | H | OCH₂ | 5-CH₂C≡CH | O | S |
| F2.31 | Me | H | H | OCH₂ | 5-CH₂C≡CH | O | O |
| F2.32 | MeO | H | H | OCH₂ | 5-CH₂C≡CH | O | O |
| F2.33 | Me | H | H | OCH₂ | 6-CH₂C≡CH | O | S |
| F2.34 | MeO | H | H | OCH₂ | 6-CH₂C≡CH | O | S |
| F3.1 | Me | H | H | OCH₂ | 4-OMe | O | S |
| F3.2 | Me | H | H | SCH₂ | 4-OMe | O | S |
| F3.3 | MeO | H | H | OCH₂ | 4-OMe | O | S |
| F3.4 | MeO | H | H | OCH₂ | 4-OMe | O | O |
| F3.5 | Et | H | H | OCH₂ | 4-OMe | O | S |
| F3.6 | nPr | H | H | OCH₂ | 4-OMe | O | S |
| F3.7 | iPr | H | H | OCH₂ | 4-OMe | O | S |
| F3.8 | nBu | H | H | OCH₂ | 4-OMe | O | S |
| F3.9 | F₃C | H | H | OCH₂ | 4-OMe | O | S |
| F3.10 | Me | H | H | OCH₂ | 5-OMe | O | S |
| F3.11 | Me | H | H | SCH₂ | 5-OMe | O | S |
| F3.12 | MeO | H | H | OCH₂ | 5-OMe | O | S |
| F3.13 | Me | H | H | OCH₂ | 5-OMe | O | O |
| F3.14 | MeO | H | H | OCH₂ | 5-OMe | O | O |
| F3.15 | Et | H | H | OCH₂ | 5-OMe | O | S |
| F3.16 | nPr | H | H | OCH₂ | 5-OMe | O | S |
| F3.17 | iPr | H | H | OCH₂ | 5-OMe | O | S |
| F3.18 | nBu | H | H | OCH₂ | 5-OMe | O | S |
| F3.19 | F₃C | H | H | OCH₂ | 5-OMe | O | S |
| F3.20 | Me | H | H | OCH₂ | 6-OMe | O | S |
| F3.21 | Me | H | H | SCH₂ | 6-OMe | O | S |
| F3.22 | MeO | H | H | OCH₂ | 6-OMe | O | S |
| F3.23 | MeO | H | H | OCH₂ | 6-OMe | O | O |
| F3.24 | Et | H | H | OCH₂ | 6-OMe | O | S |
| F3.25 | nPr | H | H | OCH₂ | 6-OMe | O | S |
| F3.26 | iPr | H | H | OCH₂ | 6-OMe | O | S |
| F3.27 | nBu | H | H | OCH₂ | 6-OMe | O | S |
| F3.28 | F₃C | H | H | OCH₂ | 6-OMe | O | S |
| F3.29 | Me | H | H | OCH₂ | 7-OMe | O | S |
| F3.30 | Me | H | H | SCH₂ | 7-OMe | O | S |
| F3.31 | MeO | H | H | OCH₂ | 7-OMe | O | S |
| F3.32 | MeO | H | H | OCH₂ | 7-OMe | O | O |
| F3.33 | Et | H | H | OCH₂ | 7-OMe | O | S |
| F3.34 | nPr | H | H | OCH₂ | 7-OMe | O | S |
| F3.35 | iPr | H | H | OCH₂ | 7-OMe | O | S |
| F3.36 | nBu | H | H | OCH₂ | 7-OMe | O | S |
| F3.37 | F₃C | H | H | OCH₂ | 7-OMe | O | S |
| F3.38 | Me | H | H | OCH₂ | 4-OEt | O | S |
| F3.39 | Me | H | H | SCH₂ | 4-OEt | O | S |
| F3.40 | Et | H | H | OCH₂ | 4-OEt | O | S |
| F3.41 | nPr | H | H | OCH₂ | 4-OEt | O | S |
| F3.42 | iPr | H | H | OCH₂ | 4-OEt | O | S |
| F3.43 | nBu | H | H | OCH₂ | 4-OEt | O | S |
| F3.45 | F₃C | H | H | OCH₂ | 4-OEt | O | S |
| F3.46 | Me | H | H | OCH₂ | 5-OEt | O | S |
| F3.47 | Me | H | H | SCH₂ | 5-OEt | O | S |
| F3.48 | MeO | H | H | OCH₂ | 5-OEt | O | S |
| F3.49 | Me | H | H | OCH₂ | 5-OEt | O | O |
| F3.50 | MeO | H | H | OCH₂ | 5-OEt | O | O |
| F3.51 | Et | H | H | OCH₂ | 5-OEt | O | S |
| F3.52 | nPr | H | H | OCH₂ | 5-OEt | O | S |
| F3.53 | iPr | H | H | OCH₂ | 5-OEt | O | S |
| F3.54 | nBu | H | H | OCH₂ | 5-OEt | O | S |
| F3.55 | F₃C | H | H | OCH₂ | 5-OEt | O | S |
| F3.56 | Me | H | H | OCH₂ | 6-OEt | O | S |
| F3.57 | Me | H | H | SCH₂ | 6-OEt | O | S |
| F3.58 | MeO | H | H | OCH₂ | 6-OEt | O | S |
| F3.59 | Me | H | H | OCH₂ | 6-OEt | O | O |
| F3.60 | MeO | H | H | OCH₂ | 6-OEt | O | O |
| F3.61 | Et | H | H | OCH₂ | 6-OEt | O | S |
| F3.62 | nPr | H | H | OCH₂ | 6-OEt | O | S |
| F3.63 | iPr | H | H | OCH₂ | 6-OEt | O | S |
| F3.64 | nBu | H | H | OCH₂ | 6-OEt | O | S |
| F3.65 | F₃C | H | H | OCH₂ | 6-OEt | O | S |
| F3.66 | Me | H | H | OCH₂ | 7-OEt | O | S |
| F3.67 | Me | H | H | SCH₂ | 7-OEt | O | S |
| F3.68 | Et | H | H | OCH₂ | 7-OEt | O | S |
| F3.69 | nPr | H | H | OCH₂ | 7-OEt | O | S |
| F3.70 | iPr | H | H | OCH₂ | 7-OEt | O | S |
| F3.71 | nBu | H | H | OCH₂ | 7-OEt | O | S |
| F3.72 | F₃C | H | H | OCH₂ | 7-OEt | O | S |
| F4.1 | Me | H | H | OCH₂ | 4-F | O | S |
| F4.2 | Me | H | H | SCH₂ | 4-F | O | S |
| F4.3 | MeO | H | H | OCH₂ | 4-F | O | S |
| F4.4 | Me | H | H | OCH₂ | 4-F | O | O |
| F4.5 | MeO | H | H | OCH₂ | 4-F | O | O |
| F4.6 | Et | H | H | OCH₂ | 4-F | O | S |
| F4.7 | nPr | H | H | OCH₂ | 4-F | O | S |
| F4.8 | iPr | H | H | OCH₂ | 4-F | O | S |
| F4.9 | nBu | H | H | OCH₂ | 4-F | O | S |
| F4.10 | F₃C | H | H | OCH₂ | 4-F | O | S |
| F4.11 | Me | H | H | OCH₂ | 5-F | O | S |
| F4.12 | MeO | H | H | OCH₂ | 5-F | O | S |
| F4.13 | Me | H | H | OCH₂ | 5-F | O | O |
| F4.14 | MeO | H | H | OCH₂ | 5-F | O | O |
| F4.15 | MeO | H | H | SCH₂ | 5-F | O | O |
| F4.16 | Me | H | H | SCH₂ | 5-F | O | S |
| F4.17 | MeO | H | H | SCH₂ | 5-F | O | S |
| F4.18 | Et | H | H | OCH₂ | 5-F | O | S |
| F4.19 | nPr | H | H | OCH₂ | 5-F | O | S |
| F4.20 | nBu | H | H | OCH₂ | 5-F | O | S |
| F4.21 | iPr | H | H | OCH₂ | 5-F | O | S |
| F4.22 | c-Hex | H | H | OCH₂ | 5-F | O | S |
| F4.23 | FCH₂ | H | H | OCH₂ | 5-F | O | S |
| F4.24 | FCH₂ | H | H | OCH₂ | 5-F | O | O |
| F4.25 | ClCH₂ | H | H | OCH₂ | 5-F | O | S |
| F4.26 | ClCH₂ | H | H | OCH₂ | 5-F | O | O |
| F4.27 | Cl₂CH | H | H | OCH₂ | 5-F | O | S |

TABLE 6-continued

| Compd. No. | R¹ | R² | (R³)$_n$ | ACR⁴R⁵ | (R⁶)$_m$ | X | Q |
|---|---|---|---|---|---|---|---|
| F4.28 | F₃C | H | H | OCH₂ | 5-F | O | S |
| F4.29 | F₃C | H | H | OCH₂ | 5-F | O | O |
| F4.30 | Me | H | H | OCH₂ | 6-F | O | S |
| F4.31 | MeO | H | H | OCH₂ | 6-F | O | S |
| F4.32 | Me | H | H | OCH₂ | 6-F | O | O |
| F4.33 | MeO | H | H | OCH₂ | 6-F | O | O |
| F4.34 | Me | H | H | SCH₂ | 6-F | O | S |
| F4.35 | Et | H | H | OCH₂ | 6-F | O | S |
| F4.36 | nPr | H | H | OCH₂ | 6-F | O | S |
| F4.37 | iPr | H | H | OCH₂ | 6-F | O | S |
| F4.38 | nBu | H | H | OCH₂ | 6-F | O | S |
| F4.39 | F₃C | H | H | OCH₂ | 6-F | O | S |
| F4.40 | Me | H | H | OCH₂ | 7-F | O | S |
| F4.41 | MeO | H | H | OCH₂ | 7-F | O | S |
| F4.42 | Me | H | H | OCH₂ | 7-F | O | O |
| F4.43 | MeO | H | H | OCH₂ | 7-F | O | O |
| F4.44 | Me | H | H | SCH₂ | 7-F | O | S |
| F4.45 | Et | H | H | OCH₂ | 7-F | O | S |
| F4.46 | nPr | H | H | OCH₂ | 7-F | O | S |
| F4.47 | iPr | H | H | OCH₂ | 7-F | O | S |
| F4.48 | nBu | H | H | OCH₂ | 7-F | O | S |
| F4.49 | F₃C | H | H | OCH₂ | 7-F | O | S |
| F4.50 | Me | H | H | OCH₂ | 4-Cl | O | S |
| F4.51 | Me | H | H | SCH₂ | 4-Cl | O | S |
| F4.52 | MeO | H | H | OCH₂ | 4-Cl | O | S |
| F4.53 | MeO | H | H | OCH₂ | 4-Cl | O | O |
| F4.54 | Et | H | H | OCH₂ | 4-Cl | O | S |
| F4.55 | nPr | H | H | OCH₂ | 4-Cl | O | S |
| F4.56 | iPr | H | H | OCH₂ | 4-Cl | O | S |
| F4.57 | nBu | H | H | OCH₂ | 4-Cl | O | S |
| F4.58 | F₃C | H | H | OCH₂ | 4-Cl | O | S |
| F4.59 | Me | H | H | OCH₂ | 5-Cl | O | S |
| F4.60 | Me | H | H | SCH₂ | 5-Cl | O | S |
| F4.61 | MeO | H | H | OCH₂ | 5-Cl | O | S |
| F4.62 | Me | H | H | OCH₂ | 5-Cl | O | O |
| F4.63 | MeO | H | H | OCH₂ | 5-Cl | O | O |
| F4.64 | Et | H | H | OCH₂ | 5-Cl | O | S |
| F4.65 | nPr | H | H | OCH₂ | 5-Cl | O | S |
| F4.66 | iPr | H | H | OCH₂ | 5-Cl | O | S |
| F4.67 | nBu | H | H | OCH₂ | 5-Cl | O | S |
| F4.68 | F₃C | H | H | OCH₂ | 5-Cl | O | S |
| F4.69 | Me | H | H | OCH₂ | 6-Cl | O | S |
| F4.70 | Me | H | H | SCH₂ | 6-Cl | O | S |
| F4.71 | MeO | H | H | OCH₂ | 6-Cl | O | S |
| F4.72 | Me | H | H | OCH₂ | 6-Cl | O | O |
| F4.73 | MeO | H | H | OCH₂ | 6-Cl | O | O |
| F4.74 | Et | H | H | OCH₂ | 6-Cl | O | S |
| F4.75 | nPr | H | H | OCH₂ | 6-Cl | O | S |
| F4.76 | iPr | H | H | OCH₂ | 6-Cl | O | S |
| F4.77 | nBu | H | H | OCH₂ | 6-Cl | O | S |
| F4.78 | F₃C | H | H | OCH₂ | 6-Cl | O | S |
| F4.79 | Me | H | H | OCH₂ | 7-Cl | O | S |
| F4.80 | Me | H | H | SCH₂ | 7-Cl | O | S |
| F4.81 | MeO | H | H | OCH₂ | 7-Cl | O | S |
| F4.82 | Et | H | H | OCH₂ | 7-Cl | O | S |
| F4.83 | nPr | H | H | OCH₂ | 7-Cl | O | S |
| F4.84 | iPr | H | H | OCH₂ | 7-Cl | O | S |
| F4.85 | nBu | H | H | OCH₂ | 7-Cl | O | S |
| F4.86 | F₃C | H | H | OCH₂ | 7-Cl | O | S |
| F4.87 | Me | H | H | OCH₂ | 4-Br | O | S |
| F4.88 | Me | H | H | SCH₂ | 4-Br | O | S |
| F4.89 | MeO | H | H | OCH₂ | 4-Br | O | S |
| F4.90 | Et | H | H | OCH₂ | 4-Br | O | S |
| F4.91 | nPr | H | H | OCH₂ | 4-Br | O | S |
| F4.92 | iPr | H | H | OCH₂ | 4-Br | O | S |
| F4.93 | nBu | H | H | OCH₂ | 4-Br | O | S |
| F4.94 | F₃C | H | H | OCH₂ | 4-Br | O | S |
| F4.95 | Me | H | H | OCH₂ | 5-Br | O | S |
| F4.96 | Me | H | H | SCH₂ | 5-Br | O | S |
| F4.97 | MeO | H | H | OCH₂ | 5-Br | O | S |
| F4.98 | Et | H | H | OCH₂ | 5-Br | O | S |
| F4.99 | nPr | H | H | OCH₂ | 5-Br | O | S |
| F4.100 | iPr | H | H | OCH₂ | 5-Br | O | S |
| F4.101 | nBu | H | H | OCH₂ | 5-Br | O | S |
| F4.102 | F₃C | H | H | OCH₂ | 5-Br | O | S |
| F4.103 | Me | H | H | OCH₂ | 6-Br | O | S |
| F4.104 | Me | H | H | SCH₂ | 6-Br | O | S |
| F4.105 | MeO | H | H | OCH₂ | 6-Br | O | S |
| F4.106 | Me | H | H | OCH₂ | 6-Br | O | O |
| F4.107 | MeO | H | H | OCH₂ | 6-Br | O | O |
| F4.108 | Et | H | H | OCH₂ | 6-Br | O | S |
| F4.109 | nPr | H | H | OCH₂ | 6-Br | O | S |
| F4.110 | iPr | H | H | OCH₂ | 6-Br | O | S |
| F4.111 | nBu | H | H | OCH₂ | 6-Br | O | S |
| F4.112 | F₃C | H | H | OCH₂ | 6-Br | O | S |
| F4.113 | Me | H | H | OCH₂ | 7-Br | O | S |
| F4.114 | Me | H | H | SCH₂ | 7-Br | O | S |
| F4.115 | MeO | H | H | OCH₂ | 7-Br | O | S |
| F4.116 | Et | H | H | OCH₂ | 7-Br | O | S |
| F4.117 | nPr | H | H | OCH₂ | 7-Br | O | S |
| F4.118 | iPr | H | H | OCH₂ | 7-Br | O | S |
| F4.119 | nBu | H | H | OCH₂ | 7-Br | O | S |
| F4.120 | F₃C | H | H | OCH₂ | 7-Br | O | S |
| F5.1 | Me | H | H | OCH₂ | 4-CF₃ | O | S |
| F5.2 | Me | H | H | SCH₂ | 4-CF₃ | O | S |
| F5.3 | MeO | H | H | OCH₂ | 4-CF₃ | O | S |
| F5.4 | Et | H | H | OCH₂ | 4-CF₃ | O | S |
| F5.5 | nPr | H | H | OCH₂ | 4-CF₃ | O | S |
| F5.6 | iPr | H | H | OCH₂ | 4-CF₃ | O | S |
| F5.7 | nBu | H | H | OCH₂ | 4-CF₃ | O | S |
| F5.8 | F₃C | H | H | OCH₂ | 4-CF₃ | O | S |
| F5.9 | Me | H | H | OCH₂ | 5-CF₃ | O | S |
| F5.10 | Me | H | H | SCH₂ | 5-CF₃ | O | S |
| F5.11 | MeO | H | H | OCH₂ | 5-CF₃ | O | S |
| F5.12 | Me | H | H | OCH₂ | 5-CF₃ | O | O |
| F5.13 | MeO | H | H | OCH₂ | 5-CF₃ | O | O |
| F5.14 | Et | H | H | OCH₂ | 5-CF₃ | O | S |
| F5.15 | nPr | H | H | OCH₂ | 5-CF₃ | O | S |
| F5.16 | iPr | H | H | OCH₂ | 5-CF₃ | O | S |
| F5.17 | nBu | H | H | OCH₂ | 5-CF₃ | O | S |
| F5.18 | F₃C | H | H | OCH₂ | 5-CF₃ | O | S |
| F5.19 | Me | H | H | OCH₂ | 6-CF₃ | O | S |
| F5.20 | Me | H | H | SCH₂ | 6-CF₃ | O | S |
| F5.21 | MeO | H | H | OCH₂ | 6-CF₃ | O | S |
| F5.22 | Me | H | H | OCH₂ | 6-CF₃ | O | O |
| F5.23 | MeO | H | H | OCH₂ | 6-CF₃ | O | O |
| F5.24 | Et | H | H | OCH₂ | 6-CF₃ | O | S |
| F5.25 | nPr | H | H | OCH₂ | 6-CF₃ | O | S |
| F5.26 | iPr | H | H | OCH₂ | 6-CF₃ | O | S |
| F5.27 | nBu | H | H | OCH₂ | 6-CF₃ | O | S |
| F5.28 | F₃C | H | H | OCH₂ | 6-CF₃ | O | S |
| F5.29 | Me | H | H | OCH₂ | 7-CF₃ | O | S |
| F5.30 | Me | H | H | SCH₂ | 7-CF₃ | O | S |
| F5.31 | MeO | H | H | OCH₂ | 7-CF₃ | O | S |
| F5.32 | Et | H | H | OCH₂ | 7-CF₃ | O | S |
| F5.34 | nPr | H | H | OCH₂ | 7-CF₃ | O | S |
| F5.35 | iPr | H | H | OCH₂ | 7-CF₃ | O | S |
| F5.36 | nBu | H | H | OCH₂ | 7-CF₃ | O | S |
| F5.37 | F₃C | H | H | OCH₂ | 7-CF₃ | O | S |
| F5.38 | Me | H | H | OCH₂ | 4-OCF₃ | O | S |
| F5.39 | Me | H | H | SCH₂ | 4-OCF₃ | O | S |
| F5.40 | Et | H | H | OCH₂ | 4-OCF₃ | O | S |
| F5.41 | nPr | H | H | OCH₂ | 4-OCF₃ | O | S |
| F5.42 | iPr | H | H | OCH₂ | 4-OCF₃ | O | S |
| F5.43 | nBu | H | H | OCH₂ | 4-OCF₃ | O | S |
| F5.44 | F₃C | H | H | OCH₂ | 4-OCF₃ | O | S |
| F5.45 | Me | H | H | OCH₂ | 5-OCF₃ | O | S |
| F5.46 | Me | H | H | SCH₂ | 5-OCF₃ | O | S |
| F5.47 | MeO | H | H | OCH₂ | 5-OCF₃ | O | S |
| F5.48 | Me | H | H | OCH₂ | 5-OCF₃ | O | O |
| F5.49 | MeO | H | H | OCH₂ | 5-OCF₃ | O | O |
| F5.50 | Et | H | H | OCH₂ | 5-OCF₃ | O | S |
| F5.51 | nPr | H | H | OCH₂ | 5-OCF₃ | O | S |
| F5.52 | iPr | H | H | OCH₂ | 5-OCF₃ | O | S |
| F5.53 | nBu | H | H | OCH₂ | 5-OCF₃ | O | S |
| F5.54 | F₃C | H | H | OCH₂ | 5-OCF₃ | O | S |
| F5.56 | Me | H | H | OCH₂ | 6-OCF₃ | O | S |
| F5.57 | Me | H | H | SCH₂ | 6-OCF₃ | O | S |
| F5.58 | MeO | H | H | OCH₂ | 6-OCF₃ | O | S |
| F5.59 | Et | H | H | OCH₂ | 6-OCF₃ | O | S |
| F5.60 | nPr | H | H | OCH₂ | 6-OCF₃ | O | S |
| F5.61 | iPr | H | H | OCH₂ | 6-OCF₃ | O | S |

TABLE 6-continued

| Compd. No. | R¹ | R² | (R³)ₙ | ACR⁴R⁵ | (R⁶)ₘ | X | Q |
|---|---|---|---|---|---|---|---|
| F5.62 | nBu | H | H | OCH₂ | 6-OCF₃ | O | S |
| F5.63 | F₃C | H | H | OCH₂ | 6-OCF₃ | O | S |
| F5.64 | Me | H | H | OCH₂ | 7-OCF₃ | O | S |
| F5.65 | Me | H | H | SCH₂ | 7-OCF₃ | O | S |
| F5.66 | Et | H | H | OCH₂ | 7-OCF₃ | O | S |
| F5.67 | nPr | H | H | OCH₂ | 7-OCF₃ | O | S |
| F5.68 | iPr | H | H | OCH₂ | 7-OCF₃ | O | S |
| F5.69 | nBu | H | H | OCH₂ | 7-OCF₃ | O | S |
| F5.70 | F₃C | H | H | OCH₂ | 7-OCF₃ | O | S |
| F6.1 | Me | H | H | OCH₂ | 5-CHO | O | S |
| F6.2 | MeO | H | H | OCH₂ | 5-CHO | O | S |
| F6.3 | Me | H | H | OCH₂ | 6-CHO | O | S |
| F6.4 | MeO | H | H | OCH₂ | 6-CHO | O | S |
| F6.5 | Me | H | H | OCH₂ | 5-COMe | O | S |
| F6.6 | MeO | H | H | OCH₂ | 5-COMe | O | S |
| F6.7 | Me | H | H | OCH₂ | 6-COMe | O | S |
| F6.8 | MeO | H | H | OCH₂ | 6-COMe | O | S |
| F6.9 | Me | H | H | OCH₂ | 4-COOMe | O | S |
| F6.10 | MeO | H | H | OCH₂ | 4-COOMe | O | S |
| F6.11 | Me | H | H | OCH₂ | 4-COOMe | O | O |
| F6.12 | MeO | H | H | OCH₂ | 4-COOMe | O | O |
| F6.13 | Me | H | H | OCH₂ | 5-COOMe | O | S |
| F6.14 | MeO | H | H | OCH₂ | 5-COOMe | O | S |
| F6.15 | Me | H | H | OCH₂ | 5-COOMe | O | O |
| F6.16 | MeO | H | H | OCH₂ | 5-COOMe | O | O |
| F6.17 | Me | H | H | OCH₂ | 6-COOMe | O | S |
| F6.18 | MeO | H | H | OCH₂ | 6-COOMe | O | S |
| F6.19 | Me | H | H | OCH₂ | 6-COOMe | O | O |
| F6.20 | MeO | H | H | OCH₂ | 6-COOMe | O | O |
| F6.21 | Me | H | H | OCH₂ | 7-COOMe | O | S |
| F6.22 | MeO | H | H | OCH₂ | 7-COOMe | O | S |
| F6.23 | Me | H | H | OCH₂ | 7-COOMe | O | O |
| F6.24 | MeO | H | H | OCH₂ | 7-COOMe | O | O |
| F7.1 | Me | H | H | OCH₂ | 4,5-diMe | O | S |
| F7.2 | Me | H | H | SCH₂ | 4,5-diMe | O | S |
| F7.3 | MeO | H | H | OCH₂ | 4,5-diMe | O | S |
| F7.4 | Me | H | H | OCH₂ | 4,6-diMe | O | S |
| F7.5 | Me | H | H | SCH₂ | 4,6-diMe | O | S |
| F7.6 | MeO | H | H | OCH₂ | 4,6-diMe | O | S |
| F7.7 | Me | H | H | OCH₂ | 4,6-diMe | O | O |
| F7.8 | MeO | H | H | OCH₂ | 4,6-diMe | O | O |
| F7.9 | Me | H | H | OCH₂ | 4,7-diMe | O | S |
| F7.10 | Me | H | H | SCH₂ | 4,7-diMe | O | S |
| F7.11 | Me | H | H | OCH₂ | 5,6-diMe | O | S |
| F7.12 | Me | H | H | SCH₂ | 5,6-diMe | O | S |
| F7.13 | Me | H | H | OCH₂ | 5,7-diMe | O | S |
| F7.14 | Me | H | H | SCH₂ | 5,7-diMe | O | S |
| F7.15 | MeO | H | H | OCH₂ | 5,7-diMe | O | S |
| F7.16 | Me | H | H | OCH₂ | 5,7-diMe | O | O |
| F7.17 | MeO | H | H | OCH₂ | 5,7-diMe | O | O |
| F7.18 | Me | H | H | OCH₂ | 6,7-diMe | O | S |
| F7.19 | Me | H | H | SCH₂ | 6,7-diMe | O | S |
| F7.20 | MeO | H | H | OCH₂ | 6,7-diMe | O | S |
| F7.21 | Me | H | H | OCH₂ | 4,5-diOMe | O | S |
| F7.22 | Me | H | H | SCH₂ | 4,5-diOMe | O | S |
| F7.23 | Me | H | H | OCH₂ | 4,6-diOMe | O | S |
| F7.24 | Me | H | H | SCH₂ | 4,6-diOMe | O | S |
| F7.25 | Me | H | H | OCH₂ | 4,7-diOMe | O | S |
| F7.26 | Me | H | H | SCH₂ | 4,7-diOMe | O | S |
| F7.27 | Me | H | H | OCH₂ | 5,6-diOMe | O | S |
| F7.28 | Me | H | H | SCH₂ | 5,6-diOMe | O | S |
| F7.29 | MeO | H | H | OCH₂ | 5,6-diOMe | O | S |
| F7.30 | Me | H | H | OCH₂ | 5,7-diOMe | O | S |
| F7.31 | Me | H | H | SCH₂ | 5,7-diOMe | O | S |
| F7.32 | Me | H | H | OCH₂ | 6,7-diOMe | O | S |
| F7.33 | Me | H | H | SCH₂ | 6,7-diOMe | O | S |
| F7.34 | Me | H | H | OCH₂ | 4,5-diF | O | S |
| F7.35 | Me | H | H | SCH₂ | 4,5-diF | O | S |
| F7.36 | MeO | H | H | OCH₂ | 4,5-diF | O | S |
| F7.37 | Me | H | H | OCH₂ | 4,5-diF | O | O |
| F7.38 | MeO | H | H | OCH₂ | 4,5-diF | O | O |
| F7.39 | Me | H | H | OCH₂ | 4,6-diF | O | S |
| F7.40 | Me | H | H | SCH₂ | 4,6-diF | O | S |
| F7.41 | MeO | H | H | OCH₂ | 4,6-diF | O | S |
| F7.42 | Me | H | H | OCH₂ | 4,7-diF | O | S |
| F7.43 | Me | H | H | SCH₂ | 4,7-diF | O | S |
| F7.44 | MeO | H | H | OCH₂ | 4,7-diF | O | S |
| F7.45 | Me | H | H | OCH₂ | 5,6-diF | O | S |
| F7.46 | Me | H | H | SCH₂ | 5,6-diF | O | S |
| F7.47 | MeO | H | H | OCH₂ | 5,6-diF | O | S |
| F7.48 | Me | H | H | OCH₂ | 5,6-diF | O | O |
| F7.49 | MeO | H | H | OCH₂ | 5,6-diF | O | O |
| F7.50 | Me | H | H | OCH₂ | 5,7-diF | O | S |
| F7.52 | Me | H | H | SCH₂ | 5,7-diF | O | S |
| F7.53 | MeO | H | H | OCH₂ | 5,7-diF | O | S |
| F7.54 | Me | H | H | OCH₂ | 6,7-diF | O | S |
| F7.55 | Me | H | H | SCH₂ | 6,7-diF | O | S |
| F7.56 | MeO | H | H | OCH₂ | 6,7-diF | O | O |
| F7.57 | Me | H | H | OCH₂ | 4,5-diCl | O | S |
| F7.58 | Me | H | H | SCH₂ | 4,5-diCl | O | S |
| F7.59 | Me | H | H | OCH₂ | 4,6-diCl | O | S |
| F7.60 | Me | H | H | SCH₂ | 4,6-diCl | O | S |
| F7.61 | Me | H | H | OCH₂ | 4,7-diCl | O | S |
| F7.62 | Me | H | H | SCH₂ | 4,7-diCl | O | S |
| F7.63 | Me | H | H | OCH₂ | 5,6-diCl | O | S |
| F7.64 | Me | H | H | SCH₂ | 5,6-diCl | O | S |
| F7.65 | Me | H | H | OCH₂ | 5,7-diCl | O | S |
| F7.66 | Me | H | H | SCH₂ | 5,7-diCl | O | S |
| F7.67 | MeO | H | H | OCH₂ | 5,7-diCl | O | S |
| F7.68 | Me | H | H | OCH₂ | 5,7-diCl | O | O |
| F7.69 | MeO | H | H | OCH₂ | 5,7-diCl | O | O |
| F7.70 | Me | H | H | OCH₂ | 6,7-diCl | O | S |
| F7.71 | Me | H | H | SCH₂ | 6,7-diCl | O | S |
| F7.72 | Me | H | H | OCH₂ | 4,5-diCF₃ | O | S |
| F7.73 | Me | H | H | SCH₂ | 4,5-diCF₃ | O | S |
| F7.74 | Me | H | H | OCH₂ | 4,6-diCF₃ | O | S |
| F7.75 | Me | H | H | SCH₂ | 4,6-diCF₃ | O | S |
| F7.76 | Me | H | H | OCH₂ | 4,7-diCF₃ | O | S |
| F7.77 | Me | H | H | SCH₂ | 4,7-diCF₃ | O | S |
| F7.78 | Me | H | H | OCH₂ | 5,6-diCF₃ | O | S |
| F7.79 | Me | H | H | SCH₂ | 5,6-diCF₃ | O | S |
| F7.80 | Me | H | H | OCH₂ | 5,7-diCF₃ | O | S |
| F7.81 | Me | H | H | SCH₂ | 5,7-diCF₃ | O | S |
| F7.82 | Me | H | H | OCH₂ | 6,7-diCF₃ | O | S |
| F7.83 | Me | H | H | SCH₂ | 6,7-diCF₃ | O | S |
| F7.84 | Me | H | H | OCH₂ | 4-F,5-Me | O | S |
| F7.85 | Me | H | H | SCH₂ | 4-F,5-Me | O | S |
| F7.86 | Me | H | H | OCH₂ | 4-F,6-Me | O | S |
| F7.87 | Me | H | H | SCH₂ | 4-F,6-Me | O | S |
| F7.88 | Me | H | H | OCH₂ | 4-F,7-Me | O | S |
| F7.89 | Me | H | H | SCH₂ | 4-F,7-Me | O | S |
| F7.90 | Me | H | H | OCH₂ | 4-Me,5-F | O | S |
| F7.91 | Me | H | H | SCH₂ | 4-Me,5-F | O | S |
| F7.92 | Me | H | H | OCH₂ | 5-F,6-Me | O | S |
| F7.93 | Me | H | H | SCH₂ | 5-F,6-Me | O | S |
| F7.94 | Me | H | H | OCH₂ | 5-F,7-Me | O | S |
| F7.95 | Me | H | H | SCH₂ | 5-F,7-Me | O | S |
| F7.96 | MeO | H | H | OCH₂ | 5-F,7-Me | O | S |
| F7.97 | Me | H | H | OCH₂ | 4-Me,6-F | O | S |
| F7.98 | Me | H | H | SCH₂ | 4-Me,6-F | O | S |
| F7.99 | Me | H | H | OCH₂ | 5-Me,6-F | O | S |
| F7.100 | Me | H | H | SCH₂ | 5-Me,6-F | O | S |
| F7.101 | MeO | H | H | OCH₂ | 6-F,5-Me | O | S |
| F7.102 | Me | H | H | OCH₂ | 6-F,7-Me | O | S |
| F7.103 | Me | H | H | SCH₂ | 6-F,7-Me | O | S |
| F7.104 | Me | H | H | OCH₂ | 4-Me,7-F | O | S |
| F7.105 | Me | H | H | SCH₂ | 4-Me,7-F | O | S |
| F7.106 | Me | H | H | OCH₂ | 5-Me,7-F | O | S |
| F7.107 | Me | H | H | SCH₂ | 5-Me,7-F | O | S |
| F7.108 | Me | H | H | OCH₂ | 6-Me,7-F | O | S |
| F7.109 | Me | H | H | SCH₂ | 6-Me,7-F | O | S |
| F7.110 | Me | H | H | OCH₂ | 4-Cl,5-Me | O | S |
| F7.111 | Me | H | H | SCH₂ | 4-Cl,5-Me | O | S |
| F7.112 | MeO | H | H | OCH₂ | 4-Cl,5-Me | O | S |
| F7.113 | Me | H | H | OCH₂ | 4-Cl,6-Me | O | S |
| F7.114 | Me | H | H | SCH₂ | 4-Cl,6-Me | O | S |
| F7.115 | MeO | H | H | OCH₂ | 4-Cl,6-Me | O | S |
| F7.116 | Me | H | H | OCH₂ | 4-Cl,7-Me | O | S |
| F7.117 | Me | H | H | SCH₂ | 4-Cl,7-Me | O | S |
| F7.118 | Me | H | H | OCH₂ | 4-Me,5-Cl | O | S |
| F7.119 | Me | H | H | SCH₂ | 4-Me,5-Cl | O | S |
| F7.120 | Me | H | H | OCH₂ | 5-Cl,6-Me | O | S |

TABLE 6-continued

| Compd. No. | R¹ | R² | (R³)ₙ | ACR⁴R⁵ | (R⁶)ₘ | X | Q |
|---|---|---|---|---|---|---|---|
| F7.121 | Me | H | H | SCH₂ | 5-Cl,6-Me | O | S |
| F7.122 | Me | H | H | OCH₂ | 5-Cl,7-Me | O | S |
| F7.123 | Me | H | H | SCH₂ | 5-Cl,7-Me | O | S |
| F7.124 | Me | H | H | OCH₂ | 4-Me,6-Cl | O | S |
| F7.125 | Me | H | H | SCH₂ | 4-Me,6-Cl | O | S |
| F7.126 | Me | H | H | OCH₂ | 5-Me,6-Cl | O | S |
| F7.127 | Me | H | H | SCH₂ | 5-Me,6-Cl | O | S |
| F7.128 | Me | H | H | OCH₂ | 7-Me,6-Cl | O | S |
| F7.129 | Me | H | H | SCH₂ | 7-Me,5-Cl | O | S |
| F7.130 | Me | H | H | OCH₂ | 4-Me,7-Cl | O | S |
| F7.131 | Me | H | H | SCH₂ | 4-Me,7-Cl | O | S |
| F7.132 | Me | H | H | OCH₂ | 5-Me,7-Cl | O | S |
| F7.133 | Me | H | H | SCH₂ | 5-Me,7-Cl | O | S |
| F7.134 | Me | H | H | OCH₂ | 6-Me,7-Cl | O | S |
| F7.135 | Me | H | H | SCH₂ | 6-Me,7-Cl | O | S |
| F7.136 | Me | H | H | OCH₂ | 4-Cl,5-OMe | O | S |
| F7.137 | Me | H | H | SCH₂ | 4-Cl,5-OMe | O | S |
| F7.138 | MeO | H | H | OCH₂ | 4-Cl,5-OMe | O | S |
| F7.139 | Me | H | H | OCH₂ | 4-Cl,5-OMe | O | O |
| F7.140 | MeO | H | H | OCH₂ | 4-Cl,5-OMe | O | O |
| F7.141 | Me | H | H | OCH₂ | 4-Cl,6-OMe | O | S |
| F7.142 | Me | H | H | SCH₂ | 4-Cl,6-OMe | O | S |
| F7.143 | Me | H | H | OCH₂ | 4-Cl,7-OMe | O | S |
| F7.144 | Me | H | H | SCH₂ | 4-Cl,7-OMe | O | S |
| F7.145 | Me | H | H | OCH₂ | 4-OMe,5-Cl | O | S |
| F7.146 | Me | H | H | SCH₂ | 4-OMe,5-Cl | O | S |
| F7.147 | Me | H | H | OCH₂ | 5-Cl,6-OMe | O | S |
| F7.148 | Me | H | H | SCH₂ | 5-Cl,6-OMe | O | S |
| F7.149 | MeO | H | H | OCH₂ | 5-Cl,6-OMe | O | S |
| F7.150 | MeO | H | H | OCH₂ | 5-Cl,6-OMe | O | O |
| F7.151 | Me | H | H | OCH₂ | 5-Cl,7-OMe | O | S |
| F7.152 | Me | H | H | SCH₂ | 5-Cl,7-OMe | O | S |
| F7.153 | Me | H | H | OCH₂ | 4-OMe,6-Cl | O | S |
| F7.154 | Me | H | H | SCH₂ | 4-OMe,6-Cl | O | S |
| F7.155 | Me | H | H | OCH₂ | 5-OMe,6-Cl | O | S |
| F7.156 | Me | H | H | SCH₂ | 5-OMe,6-Cl | O | S |
| F7.157 | Me | H | H | OCH₂ | 6-Cl,7-OMe | O | S |
| F7.158 | Me | H | H | SCH₂ | 6-Cl,7-OMe | O | S |
| F7.159 | Me | H | H | OCH₂ | 4-OMe,7-Cl | O | S |
| F7.160 | Me | H | H | SCH₂ | 4-OMe,7-Cl | O | S |
| F7.161 | Me | H | H | OCH₂ | 5-OMe,7-Cl | O | S |
| F7.162 | Me | H | H | SCH₂ | 5-OMe,7-Cl | O | S |
| F7.163 | Me | H | H | OCH₂ | 6-OMe,7-Cl | O | S |
| F7.164 | Me | H | H | SCH₂ | 6-OMe,7-Cl | O | S |
| F7.165 | Me | H | H | OCH₂ | 4-Cl,5-F | O | S |
| F7.166 | Me | H | H | OCH₂ | 4-Cl,6-F | O | S |
| F7.167 | Me | H | H | OCH₂ | 4-Cl,7-F | O | S |
| F7.168 | Me | H | H | OCH₂ | 4-F,5-Cl | O | S |
| F7.169 | Me | H | H | OCH₂ | 5-Cl,6-F | O | S |
| F7.170 | MeO | H | H | OCH₂ | 5-Cl,6-F | O | S |
| F7.171 | Me | H | H | OCH₂ | 5-Cl,6-F | O | O |
| F7.172 | MeO | H | H | OCH₂ | 5-Cl,6-F | O | O |
| F7.173 | Me | H | H | OCH₂ | 6-F,7-Cl | O | S |
| F7.174 | MeO | H | H | OCH₂ | 6-F,7-Cl | O | S |
| F7.175 | Me | H | H | OCH₂ | 5-Cl,7-F | O | S |
| F7.176 | Me | H | H | OCH₂ | 4-F,6-Cl | O | S |
| F7.177 | Me | H | H | OCH₂ | 5-F,6-Cl | O | S |
| F7.178 | Me | H | H | OCH₂ | 6-Cl,7-F | O | S |
| F7.179 | Me | H | H | OCH₂ | 4-F,7-Cl | O | S |
| F7.180 | Me | H | H | OCH₂ | 5-F,7-Cl | O | S |

TABLE 7

| Compd. No. | R¹ | R² | (R³)ₙ | ACR⁴R⁵ | (R⁶)ₘ | X | Q |
|---|---|---|---|---|---|---|---|
| G1.1 | Me | H | 2-Me | OCH₂ | 4-Me | O | S |
| G1.2 | Me | H | 2-Me | SCH₂ | 4-Me | O | S |
| G1.3 | MeO | H | 2-Me | OCH₂ | 4-Me | O | S |
| G1.4 | Me | H | 2-Me | OCH₂ | 4-Me | O | O |
| G1.5 | MeO | H | 2-Me | OCH₂ | 4-Me | O | O |
| G1.6 | Me | H | 2-Me | OCH₂ | 5-Me | O | S |
| G1.7 | Me | H | 2-Me | SCH₂ | 5-Me | O | S |
| G1.8 | MeO | H | 2-Me | OCH₂ | 5-Me | O | S |
| G1.9 | Me | H | 2-Me | OCH₂ | 5-Me | O | O |
| G1.10 | MeO | H | 2-Me | OCH₂ | 5-Me | O | O |
| G1.11 | Me | H | 2-Me | OCH₂ | 6-Me | O | S |
| G1.12 | Me | H | 2-Me | SCH₂ | 6-Me | O | S |
| G1.13 | MeO | H | 2-Me | OCH₂ | 6-Me | O | S |
| G1.14 | Me | H | 2-Me | OCH₂ | 6-Me | O | O |
| G1.15 | MeO | H | 2-Me | OCH₂ | 6-Me | O | O |
| G1.16 | Me | H | 2-Me | OCH₂ | 7-Me | O | S |
| G1.17 | Me | H | 2-Me | SCH₂ | 7-Me | O | S |
| G1.18 | MeO | H | 2-Me | OCH₂ | 7-Me | O | S |
| G1.19 | Me | H | 2-Me | OCH₂ | 7-Me | O | O |
| G1.20 | MeO | H | 2-Me | OCH₂ | 7-Me | O | O |
| G1.21 | Me | H | 2-Me | OCH₂ | 5-Et | O | S |
| G1.22 | Me | H | 2-Me | SCH₂ | 5-Et | O | S |
| G1.23 | MeO | H | 2-Me | OCH₂ | 5-Et | O | S |
| G1.24 | MeO | H | 2-Me | OCH₂ | 5-Et | O | O |
| G1.25 | Me | H | 2-Me | OCH₂ | 6-Et | O | S |
| G1.26 | Me | H | 2-Me | SCH₂ | 6-Et | O | S |
| G1.27 | MeO | H | 2-Me | OCH₂ | 6-Et | O | S |
| G1.28 | Me | H | 2-Me | OCH₂ | 4-OMe | O | S |
| G1.29 | Me | H | 2-Me | SCH₂ | 4-OMe | O | S |
| G1.30 | MeO | H | 2-Me | OCH₂ | 4-OMe | O | S |
| G1.31 | MeO | H | 2-Me | OCH₂ | 4-OMe | O | O |
| G1.32 | Me | H | 2-Me | OCH₂ | 5-OMe | O | S |
| G1.33 | Me | H | 2-Me | SCH₂ | 5-OMe | O | S |
| G1.34 | MeO | H | 2-Me | OCH₂ | 5-OMe | O | S |
| G1.35 | Me | H | 2-Me | OCH₂ | 5-OMe | O | O |
| G1.36 | MeO | H | 2-Me | OCH₂ | 5-OMe | O | O |
| G1.37 | Me | H | 2-Me | OCH₂ | 6-OMe | O | S |
| G1.38 | Me | H | 2-Me | SCH₂ | 6-OMe | O | S |
| G1.39 | MeO | H | 2-Me | OCH₂ | 6-OMe | O | S |
| G1.40 | Me | H | 2-Me | OCH₂ | 6-OMe | O | O |
| G1.41 | MeO | H | 2-Me | OCH₂ | 6-OMe | O | O |
| G1.42 | Me | H | 2-Me | OCH₂ | 7-OMe | O | S |
| G1.43 | Me | H | 2-Me | SCH₂ | 7-OMe | O | S |
| G1.44 | MeO | H | 2-Me | OCH₂ | 7-OMe | O | S |
| G1.45 | MeO | H | 2-Me | OCH₂ | 7-OMe | O | O |
| G1.46 | Me | H | 2-Me | OCH₂ | 5-OEt | O | S |
| G1.47 | Me | H | 2-Me | SCH₂ | 5-OEt | O | S |
| G1.48 | Me | H | 2-Me | OCH₂ | 6-OEt | O | S |
| G1.49 | Me | H | 2-Me | SCH₂ | 6-OEt | O | S |
| G1.50 | Me | H | 2-Me | OCH₂ | 4-F | O | S |
| G1.51 | Me | H | 2-Me | SCH₂ | 4-F | O | S |
| G1.52 | MeO | H | 2-Me | OCH₂ | 4-F | O | S |
| G1.53 | Me | H | 2-Me | OCH₂ | 4-F | O | O |
| G1.54 | MeO | H | 2-Me | OCH₂ | 4-F | O | O |
| G1.55 | Me | H | 2-Me | OCH₂ | 5-F | O | S |
| G1.56 | Me | H | 2-Me | SCH₂ | 5-F | O | S |
| G1.57 | MeO | H | 2-Me | OCH₂ | 5-F | O | S |
| G1.58 | Me | H | 2-Me | OCH₂ | 5-F | O | O |
| G1.59 | MeO | H | 2-Me | OCH₂ | 5-F | O | O |
| G1.60 | Me | H | 2-Me | OCH₂ | 6-F | O | S |
| G1.61 | Me | H | 2-Me | SCH₂ | 6-F | O | S |
| G1.62 | MeO | H | 2-Me | OCH₂ | 6-F | O | S |
| G1.63 | Me | H | 2-Me | OCH₂ | 6-F | O | O |
| G1.64 | MeO | H | 2-Me | OCH₂ | 6-F | O | O |
| G1.65 | Me | H | 2-Me | OCH₂ | 7-F | O | S |
| G1.66 | Me | H | 2-Me | SCH₂ | 7-F | O | S |
| G1.67 | MeO | H | 2-Me | OCH₂ | 7-F | O | S |
| G1.68 | Me | H | 2-Me | OCH₂ | 7-F | O | O |
| G1.69 | MeO | H | 2-Me | OCH₂ | 7-F | O | O |
| G1.70 | Me | H | 2-Me | OCH₂ | 4-Cl | O | S |
| G1.71 | MeO | H | 2-Me | OCH₂ | 4-Cl | O | O |
| G1.72 | Me | H | 2-Me | OCH₂ | 5-Cl | O | S |
| G1.73 | Me | H | 2-Me | SCH₂ | 5-Cl | O | S |
| G1.74 | MeO | H | 2-Me | OCH₂ | 5-Cl | O | S |
| G1.75 | MeO | H | 2-Me | SCH₂ | 5-Cl | O | S |
| G1.76 | Me | H | 2-Me | OCH₂ | 5-Cl | O | O |
| G1.77 | MeO | H | 2-Me | OCH₂ | 5-Cl | O | O |
| G1.78 | MeO | H | 2-Me | SCH₂ | 5-Cl | O | O |
| G1.79 | Me | H | 2-Me | OCH₂ | 6-Cl | O | S |
| G1.80 | Me | H | 2-Me | SCH₂ | 6-Cl | O | S |
| G1.81 | MeO | H | 2-Me | OCH₂ | 6-Cl | O | S |
| G1.82 | Me | H | 2-Me | OCH₂ | 6-Cl | O | O |
| G1.83 | MeO | H | 2-Me | OCH₂ | 6-Cl | O | O |

TABLE 7-continued

| Compd. No. | R¹ | R² | (R³)$_n$ | ACR⁴R⁵ | (R⁶)$_m$ | X | Q |
|---|---|---|---|---|---|---|---|
| G1.84 | Me | H | 2-Me | OCH$_2$ | 7-Cl | O | S |
| G1.85 | MeO | H | 2-Me | OCH$_2$ | 7-Cl | O | S |
| G1.86 | MeO | H | 2-Me | OCH$_2$ | 7-Cl | O | O |
| G1.87 | Me | H | 2-Me | OCH$_2$ | 4-CF$_3$ | O | S |
| G1.88 | Me | H | 2-Me | SCH$_2$ | 4-CF$_3$ | O | S |
| G1.89 | MeO | H | 2-Me | OCH$_2$ | 4-CF$_3$ | O | S |
| G1.90 | Me | H | 2-Me | OCH$_2$ | 4-CF$_3$ | O | O |
| G1.91 | MeO | H | 2-Me | OCH$_2$ | 4-CF$_3$ | O | O |
| G1.92 | Me | H | 2-Me | OCH$_2$ | 5-CF$_3$ | O | S |
| G1.93 | Me | H | 2-Me | SCH$_2$ | 5-CF$_3$ | O | S |
| G1.94 | MeO | H | 2-Me | OCH$_2$ | 5-CF$_3$ | O | S |
| G1.95 | Me | H | 2-Me | OCH$_2$ | 5-CF$_3$ | O | O |
| G1.96 | MeO | H | 2-Me | OCH$_2$ | 5-CF$_3$ | O | O |
| G1.97 | Me | H | 2-Me | OCH$_2$ | 6-CF$_3$ | O | S |
| G1.98 | Me | H | 2-Me | SCH$_2$ | 6-CF$_3$ | O | S |
| G1.99 | MeO | H | 2-Me | OCH$_2$ | 6-CF$_3$ | O | S |
| G1.100 | Me | H | 2-Me | OCH$_2$ | 7-CF$_3$ | O | S |
| G1.101 | Me | H | 2-Me | SCH$_2$ | 7-CF$_3$ | O | S |
| G1.102 | Me | H | 2-Me | OCH$_2$ | 5-OCF$_3$ | O | S |
| G1.103 | Me | H | 2-Me | SCH$_2$ | 5-OCF$_3$ | O | S |
| G1.104 | MeO | H | 2-Me | OCH$_2$ | 5-OCF$_3$ | O | S |
| G1.105 | MeO | H | 2-Me | OCH$_2$ | 5-OCF$_3$ | O | O |
| G1.106 | Me | H | 2-Me | OCH$_2$ | 6-OCF$_3$ | O | S |
| G1.107 | Me | H | 2-Me | SCH$_2$ | 6-OCF$_3$ | O | S |
| G1.108 | MeO | H | 2-Me | OCH$_2$ | 6-OCF$_3$ | O | S |
| G1.109 | Me | H | 2-Me | OCH$_2$ | 5-NO$_2$ | O | O |
| G1.110 | MeO | H | 2-Me | OCH$_2$ | 5-NO$_2$ | O | O |
| G1.111 | Me | H | 2-Me | OCH$_2$ | 4-COOMe | O | S |
| G1.112 | MeO | H | 2-Me | OCH$_2$ | 4-COOMe | O | S |
| G1.113 | Me | H | 2-Me | OCH$_2$ | 4-COOMe | O | O |
| G1.114 | MeO | H | 2-Me | OCH$_2$ | 4-COOMe | O | O |
| G1.115 | Me | H | 2-Me | OCH$_2$ | 5-COOMe | O | S |
| G1.116 | MeO | H | 2-Me | OCH$_2$ | 5-COOMe | O | S |
| G1.117 | Me | H | 2-Me | OCH$_2$ | 5-COOMe | O | O |
| G1.118 | MeO | H | 2-Me | OCH$_2$ | 5-COOMe | O | O |
| G1.119 | Me | H | 2-Me | OCH$_2$ | 6-COOMe | O | S |
| G1.120 | MeO | H | 2-Me | OCH$_2$ | 6-COOMe | O | S |
| G1.121 | Me | H | 2-Me | OCH$_2$ | 6-COOMe | O | O |
| G1.122 | MeO | H | 2-Me | OCH$_2$ | 6-COOMe | O | O |
| G1.123 | MeO | H | 2-Me | SCH$_2$ | 5-F | O | S |
| G1.124 | MeO | H | 2-Me | SCH$_2$ | 5-F | O | O |
| G1.125 | Me | H | 2-Me | OCH$_2$ | 7-COOMe | O | S |
| G1.126 | MeO | H | 2-Me | OCH$_2$ | 7-COOMe | O | S |
| G1.127 | Me | H | 2-Me | OCH$_2$ | 7-COOMe | O | O |
| G1.128 | MeO | H | 2-Me | OCH$_2$ | 7-COOMe | O | O |
| G2.1 | Me | H | 2-Me | OCH$_2$ | 4,5-diMe | O | S |
| G2.2 | Me | H | 2-Me | SCH$_2$ | 4,5-diMe | O | S |
| G2.3 | MeO | H | 2-Me | OCH$_2$ | 4,5-diMe | O | S |
| G2.4 | Me | H | 2-Me | OCH$_2$ | 4,6-diMe | O | S |
| G2.5 | Me | H | 2-Me | SCH$_2$ | 4,6-diMe | O | S |
| G2.6 | Me | H | 2-Me | OCH$_2$ | 4,7-diMe | O | S |
| G2.7 | Me | H | 2-Me | SCH$_2$ | 4,7-diMe | O | S |
| G2.8 | Me | H | 2-Me | OCH$_2$ | 5,6-diMe | O | S |
| G2.9 | Me | H | 2-Me | SCH$_2$ | 5,6-diMe | O | S |
| G2.10 | MeO | H | 2-Me | OCH$_2$ | 5,6-diMe | O | S |
| G2.11 | Me | H | 2-Me | OCH$_2$ | 5,7-diMe | O | S |
| G2.12 | Me | H | 2-Me | SCH$_2$ | 5,7-diMe | O | S |
| G2.13 | Me | H | 2-Me | OCH$_2$ | 5,7-diMe | O | O |
| G2.14 | MeO | H | 2-Me | OCH$_2$ | 5,7-diMe | O | O |
| G2.15 | Me | H | 2-Me | OCH$_2$ | 6,7-diMe | O | S |
| G2.16 | Me | H | 2-Me | SCH$_2$ | 6,7-diMe | O | S |
| G2.17 | Me | H | 2-Me | OCH$_2$ | 4,5-diOMe | O | S |
| G2.18 | MeO | H | 2-Me | OCH$_2$ | 4,5-diOMe | O | S |
| G2.19 | Me | H | 2-Me | OCH$_2$ | 4,5-diOMe | O | S |
| G2.20 | MeO | H | 2-Me | SCH$_2$ | 4,5-diOMe | O | S |
| G2.21 | Me | H | 2-Me | OCH$_2$ | 4,6-diOMe | O | S |
| G2.22 | Me | H | 2-Me | SCH$_2$ | 4,6-diOMe | O | S |
| G2.23 | Me | H | 2-Me | OCH$_2$ | 4,7-diOMe | O | S |
| G2.24 | Me | H | 2-Me | SCH$_2$ | 4,7-diOMe | O | S |
| G2.25 | Me | H | 2-Me | OCH$_2$ | 5,6-diOMe | O | S |
| G2.26 | Me | H | 2-Me | SCH$_2$ | 5,6-diOMe | O | S |
| G2.27 | MeO | H | 2-Me | OCH$_2$ | 5,6-diOMe | O | S |
| G2.28 | Me | H | 2-Me | OCH$_2$ | 5,6-diOMe | O | O |
| G2.29 | MeO | H | 2-Me | OCH$_2$ | 5,6-diOMe | O | O |
| G2.30 | Me | H | 2-Me | OCH$_2$ | 5,7-diOMe | O | S |
| G2.31 | Me | H | 2-Me | SCH$_2$ | 5,7-diOMe | O | S |
| G2.32 | Me | H | 2-Me | OCH$_2$ | 6,7-diOMe | O | S |
| G2.33 | Me | H | 2-Me | SCH$_2$ | 6,7-diOMe | O | S |
| G2.34 | Me | H | 2-Me | OCH$_2$ | 4,5-diF | O | S |
| G2.35 | Me | H | 2-Me | SCH$_2$ | 4,5-diF | O | S |
| G2.36 | MeO | H | 2-Me | OCH$_2$ | 4,5-diF | O | S |
| G2.37 | Me | H | 2-Me | OCH$_2$ | 4,6-diF | O | S |
| G2.38 | Me | H | 2-Me | SCH$_2$ | 4,6-diF | O | S |
| G2.39 | MeO | H | 2-Me | OCH$_2$ | 4,6-diF | O | S |
| G2.40 | Me | H | 2-Me | OCH$_2$ | 4,7-diF | O | S |
| G2.41 | Me | H | 2-Me | SCH$_2$ | 4,7-diF | O | S |
| G2.42 | Me | H | 2-Me | OCH$_2$ | 5,6-diF | O | S |
| G2.43 | Me | H | 2-Me | SCH$_2$ | 5,6-diF | O | S |
| G2.44 | MeO | H | 2-Me | OCH$_2$ | 5,6-diF | O | S |
| G2.45 | Me | H | 2-Me | OCH$_2$ | 5,7-diF | O | S |
| G2.46 | Me | H | 2-Me | SCH$_2$ | 5,7-diF | O | S |
| G2.47 | Me | H | 2-Me | OCH$_2$ | 6,7-diF | O | S |
| G2.48 | Me | H | 2-Me | SCH$_2$ | 6,7-diF | O | S |
| G2.49 | Me | H | 2-Me | OCH$_2$ | 6,7-diF | O | O |
| G2.50 | MeO | H | 2-Me | OCH$_2$ | 6,7-diF | O | O |
| G2.51 | Me | H | 2-Me | OCH$_2$ | 4,5-diCl | O | S |
| G2.52 | Me | H | 2-Me | SCH$_2$ | 4,5-diCl | O | S |
| G2.53 | Me | H | 2-Me | OCH$_2$ | 4,6-diCl | O | S |
| G2.54 | Me | H | 2-Me | SCH$_2$ | 4,6-diCl | O | S |
| G2.55 | Me | H | 2-Me | OCH$_2$ | 4,7-diCl | O | S |
| G2.56 | Me | H | 2-Me | SCH$_2$ | 4,7-diCl | O | S |
| G2.57 | Me | H | 2-Me | OCH$_2$ | 5,6-diCl | O | S |
| G2.58 | Me | H | 2-Me | SCH$_2$ | 5,6-diCl | O | S |
| G2.59 | Me | H | 2-Me | OCH$_2$ | 5,7-diCl | O | S |
| G2.60 | Me | H | 2-Me | SCH$_2$ | 5,7-diCl | O | S |
| G2.61 | Me | H | 2-Me | OCH$_2$ | 5,7-diCl | O | O |
| G2.62 | MeO | H | 2-Me | OCH$_2$ | 5,7-diCl | O | O |
| G2.63 | Me | H | 2-Me | OCH$_2$ | 6,7-diCl | O | S |
| G2.64 | Me | H | 2-Me | SCH$_2$ | 6,7-diCl | O | S |
| G2.65 | Me | H | 2-Me | OCH$_2$ | 4,5-diCF$_3$ | O | S |
| G2.67 | Me | H | 2-Me | SCH$_2$ | 4,5-diCF$_3$ | O | S |
| G2.68 | Me | H | 2-Me | OCH$_2$ | 4,6-diCF$_3$ | O | S |
| G2.69 | Me | H | 2-Me | SCH$_2$ | 4,6-diCF$_3$ | O | S |
| G2.70 | Me | H | 2-Me | OCH$_2$ | 4,7-diCF$_3$ | O | S |
| G2.71 | Me | H | 2-Me | SCH$_2$ | 4,7-diCF$_3$ | O | S |
| G2.72 | Me | H | 2-Me | OCH$_2$ | 5,6-diCF$_3$ | O | S |
| G2.73 | Me | H | 2-Me | SCH$_2$ | 5,6-diCF$_3$ | O | S |
| G2.74 | Me | H | 2-Me | OCH$_2$ | 5,7-diCF$_3$ | O | S |
| G2.75 | Me | H | 2-Me | SCH$_2$ | 5,7-diCF$_3$ | O | S |
| G2.76 | Me | H | 2-Me | OCH$_2$ | 6,7-diCF$_3$ | O | S |
| G2.77 | Me | H | 2-Me | SCH$_2$ | 6,7-diCF$_3$ | O | S |
| G2.78 | Me | H | 2-Me | OCH$_2$ | 4-F,5-Me | O | S |
| G2.79 | Me | H | 2-Me | SCH$_2$ | 4-F,5-Me | O | S |
| G2.80 | Me | H | 2-Me | OCH$_2$ | 4-F,6-Me | O | S |
| G2.81 | Me | H | 2-Me | SCH$_2$ | 4-F,6-Me | O | S |
| G2.82 | Me | H | 2-Me | OCH$_2$ | 4-F,7-Me | O | S |
| G2.83 | Me | H | 2-Me | SCH$_2$ | 4-F,7-Me | O | S |
| G2.84 | Me | H | 2-Me | OCH$_2$ | 4-Me,5-F | O | S |
| G2.85 | Me | H | 2-Me | SCH$_2$ | 4-Me,5-F | O | S |
| G2.86 | Me | H | 2-Me | OCH$_2$ | 5-F,6-Me | O | S |
| G2.87 | Me | H | 2-Me | SCH$_2$ | 5-F,6-Me | O | S |
| G2.88 | MeO | H | 2-Me | OCH$_2$ | 5-F,6-Me | O | S |
| G2.89 | Me | H | 2-Me | OCH$_2$ | 5-F,6-Me | O | O |
| G2.90 | MeO | H | 2-Me | OCH$_2$ | 5-F,6-Me | O | O |
| G2.91 | Me | H | 2-Me | OCH$_2$ | 5-F,7-Me | O | S |
| G2.92 | Me | H | 2-Me | SCH$_2$ | 5-F,7-Me | O | S |
| G2.93 | Me | H | 2-Me | OCH$_2$ | 4-Me,6-F | O | S |
| G2.94 | Me | H | 2-Me | SCH$_2$ | 4-Me,6-F | O | S |
| G2.95 | Me | H | 2-Me | OCH$_2$ | 5-Me,6-F | O | S |
| G2.96 | Me | H | 2-Me | SCH$_2$ | 5-Me,6-F | O | S |
| G2.97 | Me | H | 2-Me | OCH$_2$ | 6-F,7-Me | O | S |
| G2.98 | Me | H | 2-Me | SCH$_2$ | 6-F,7-Me | O | S |
| G2.99 | MeO | H | 2-Me | OCH$_2$ | 6-F,7-Me | O | S |
| G2.100 | Me | H | 2-Me | OCH$_2$ | 4-Me,7-F | O | S |
| G2.101 | Me | H | 2-Me | SCH$_2$ | 4-Me,7-F | O | S |
| G2.102 | Me | H | 2-Me | OCH$_2$ | 5-Me,7-F | O | S |
| G2.103 | Me | H | 2-Me | SCH$_2$ | 5-Me,7-F | O | S |
| G2.104 | Me | H | 2-Me | OCH$_2$ | 6-Me,7-F | O | S |
| G2.105 | Me | H | 2-Me | SCH$_2$ | 6-Me,7-F | O | S |
| G2.106 | Me | H | 2-Me | OCH$_2$ | 4-Cl,5-Me | O | S |
| G2.107 | Me | H | 2-Me | SCH$_2$ | 4-Cl,5-Me | O | S |
| G2.108 | MeO | H | 2-Me | OCH$_2$ | 4-Cl,5-Me | O | S |

TABLE 7-continued

| Compd. No. | R¹ | R² | (R³)ₙ | ACR⁴R⁵ | (R⁶)ₘ | X | Q |
|---|---|---|---|---|---|---|---|
| G2.109 | Me | H | 2-Me | OCH₂ | 4-Cl,6-Me | O | S |
| G2.110 | Me | H | 2-Me | SCH₂ | 4-Cl,6-Me | O | S |
| G2.111 | Me | H | 2-Me | OCH₂ | 4-Cl,7-Me | O | S |
| G2.112 | Me | H | 2-Me | SCH₂ | 4-Cl,7-Me | O | S |
| G2.113 | Me | H | 2-Me | OCH₂ | 4-Me,5-Cl | O | S |
| G2.114 | Me | H | 2-Me | SCH₂ | 4-Me,5-Cl | O | S |
| G2.115 | Me | H | 2-Me | OCH₂ | 5-Cl,6-Me | O | S |
| G2.116 | Me | H | 2-Me | SCH₂ | 5-Cl,6-Me | O | S |
| G2.117 | MeO | H | 2-Me | OCH₂ | 5-Cl,6-Me | O | S |
| G2.118 | Me | H | 2-Me | OCH₂ | 5-Cl,6-Me | O | O |
| G2.119 | MeO | H | 2-Me | OCH₂ | 5-Cl,6-Me | O | O |
| G2.120 | Me | H | 2-Me | OCH₂ | 5-Cl,7-Me | O | S |
| G2.121 | Me | H | 2-Me | SCH₂ | 5-Cl,7-Me | O | S |
| G2.122 | Me | H | 2-Me | OCH₂ | 4-Me,6-Cl | O | S |
| G2.123 | Me | H | 2-Me | SCH₂ | 4-Me,6-Cl | O | S |
| G2.124 | Me | H | 2-Me | OCH₂ | 5-Me,6-Cl | O | S |
| G2.125 | Me | H | 2-Me | SCH₂ | 5-Me,6-Cl | O | S |
| G2.126 | Me | H | 2-Me | OCH₂ | 6-Cl,7-Me | O | S |
| G2.127 | Me | H | 2-Me | SCH₂ | 6-Cl,7-Me | O | S |
| G2.128 | Me | H | 2-Me | OCH₂ | 4-Me,7-Cl | O | S |
| G2.129 | Me | H | 2-Me | SCH₂ | 4-Me,7-Cl | O | S |
| G2.130 | Me | H | 2-Me | OCH₂ | 5-Me,7-Cl | O | S |
| G2.131 | Me | H | 2-Me | SCH₂ | 5-Me,7-Cl | O | S |
| G2.132 | Me | H | 2-Me | OCH₂ | 6-Me,7-Cl | O | S |
| G2.133 | Me | H | 2-Me | SCH₂ | 6-Me,7-Cl | O | S |
| G2.134 | Me | H | 2-Me | OCH₂ | 4-Cl,6-OMe | O | S |
| G2.135 | Me | H | 2-Me | SCH₂ | 4-Cl,6-OMe | O | S |
| G2.136 | MeO | H | 2-Me | OCH₂ | 4-Cl,6-OMe | O | S |
| G2.137 | Me | H | 2-Me | OCH₂ | 5-Cl,6-OMe | O | S |
| G2.138 | Me | H | 2-Me | SCH₂ | 5-Cl,6-OMe | O | S |
| G2.139 | MeO | H | 2-Me | OCH₂ | 5-Cl,6-OMe | O | S |
| G2.140 | Me | H | 2-Me | OCH₂ | 4-Cl,5-F | O | S |
| G2.141 | Me | H | 2-Me | SCH₂ | 4-Cl,5-F | O | S |
| G2.142 | Me | H | 2-Me | OCH₂ | 4-Cl,6-F | O | S |
| G2.143 | Me | H | 2-Me | SCH₂ | 4-Cl,6-F | O | S |
| G2.144 | Me | H | 2-Me | OCH₂ | 4-Cl,7-F | O | S |
| G2.145 | Me | H | 2-Me | SCH₂ | 4-Cl,7-F | O | S |
| G2.146 | Me | H | 2-Me | OCH₂ | 4-F,5-Cl | O | S |
| G2.147 | Me | H | 2-Me | SCH₂ | 4-F,5-Cl | O | S |
| G2.148 | Me | H | 2-Me | OCH₂ | 5-Cl,6-F | O | S |
| G2.149 | Me | H | 2-Me | SCH₂ | 5-Cl,6-F | O | S |
| G2.150 | MeO | H | 2-Me | OCH₂ | 5-Cl,6-F | O | S |
| G2.151 | Me | H | 2-Me | OCH₂ | 5-Cl,6-F | O | O |
| G2.152 | MeO | H | 2-Me | OCH₂ | 5-Cl,6-F | O | O |
| G2.153 | Me | H | 2-Me | OCH₂ | 5-Cl,7-F | O | S |
| G2.154 | Me | H | 2-Me | SCH₂ | 5-Cl,7-F | O | S |
| G2.156 | Me | H | 2-Me | OCH₂ | 4-F,6-Cl | O | S |
| G2.157 | Me | H | 2-Me | SCH₂ | 4-F,6-Cl | O | S |
| G2.158 | Me | H | 2-Me | OCH₂ | 5-F,6-Cl | O | S |
| G2.159 | Me | H | 2-Me | SCH₂ | 5-F,6-Cl | O | S |
| G2.160 | Me | H | 2-Me | OCH₂ | 6-Cl,7-F | O | S |
| G2.161 | Me | H | 2-Me | SCH₂ | 6-Cl,7-F | O | S |
| G2.162 | Me | H | 2-Me | OCH₂ | 4-F,7-Cl | O | S |
| G2.163 | Me | H | 2-Me | SCH₂ | 4-F,7-Cl | O | S |
| G2.164 | Me | H | 2-Me | OCH₂ | 5-F,7-Cl | O | S |
| G2.165 | Me | H | 2-Me | SCH₂ | 5-F,7-Cl | O | S |
| G2.166 | Me | H | 2-Me | OCH₂ | 6-F,7-Cl | O | S |
| G2.167 | Me | H | 2-Me | SCH₂ | 6-F,7-Cl | O | S |
| G2.168 | MeO | H | 2-Me | OCH₂ | 6-F,7-Cl | O | S |
| G3.1 | Me | H | 3-Me | OCH₂ | 4-Me | O | S |
| G3.2 | Me | H | 3-Me | SCH₂ | 4-Me | O | S |
| G3.3 | Me | H | 3-Me | OCH₂ | 5-Me | O | S |
| G3.4 | Me | H | 3-Me | SCH₂ | 5-Me | O | S |
| G3.5 | Me | H | 3-Me | OCH₂ | 6-Me | O | S |
| G3.6 | Me | H | 3-Me | SCH₂ | 6-Me | O | S |
| G3.7 | Me | H | 3-Me | OCH₂ | 7-Me | O | S |
| G3.8 | Me | H | 3-Me | SCH₂ | 7-Me | O | S |
| G3.9 | Me | H | 3-Me | OCH₂ | 5-Et | O | S |
| G3.10 | Me | H | 3-Me | SCH₂ | 5-Et | O | S |
| G3.11 | Me | H | 3-Me | OCH₂ | 6-Et | O | S |
| G3.12 | Me | H | 3-Me | SCH₂ | 6-Et | O | S |
| G3.13 | Me | H | 3-Me | OCH₂ | 4-OMe | O | S |
| G3.14 | Me | H | 3-Me | SCH₂ | 4-OMe | O | S |
| G3.15 | Me | H | 3-Me | OCH₂ | 5-OMe | O | S |
| G3.16 | Me | H | 3-Me | SCH₂ | 5-OMe | O | S |
| G3.17 | Me | H | 3-Me | OCH₂ | 6-OMe | O | S |
| G3.18 | Me | H | 3-Me | SCH₂ | 6-OMe | O | S |
| G3.19 | Me | H | 3-Me | OCH₂ | 7-OMe | O | S |
| G3.20 | Me | H | 3-Me | SCH₂ | 7-OMe | O | S |
| G3.21 | Me | H | 3-Me | OCH₂ | 5-OEt | O | S |
| G3.22 | Me | R | 3-Me | SCH₂ | 5-OEt | O | S |
| G3.23 | Me | H | 3-Me | OCH₂ | 6-OEt | O | S |
| G3.24 | Me | H | 3-Me | SCH₂ | 6-OEt | O | S |
| G3.25 | Me | H | 3-Me | OCH₂ | 4-F | O | S |
| G3.26 | Me | H | 3-Me | SCH₂ | 4-F | O | S |
| G3.27 | Me | R | 3-Me | OCH₂ | 5-F | O | S |
| G3.28 | Me | H | 3-Me | SCH₂ | 5-F | O | S |
| G3.29 | Me | H | 3-Me | OCH₂ | 6-F | O | S |
| G3.30 | Me | H | 3-Me | SCH₂ | 6-F | O | S |
| G3.31 | Me | H | 3-Me | OCH₂ | 7-F | O | S |
| G3.32 | Me | H | 3-Me | SCH₂ | 7-F | O | S |
| G3.33 | Me | H | 3-Me | OCH₂ | 5-Cl | O | S |
| G3.34 | Me | H | 3-Me | SCH₂ | 5-Cl | O | S |
| G3.35 | Me | H | 3-Me | OCH₂ | 6-Cl | O | S |
| G3.36 | Me | H | 3-Me | SCH₂ | 6-Cl | O | S |
| G3.37 | Me | H | 3-Me | OCH₂ | 4-CF₃ | O | S |
| G3.38 | Me | H | 3-Me | SCH₂ | 4-CF₃ | O | S |
| G3.39 | Me | H | 3-Me | OCH₂ | 5-CF₃ | O. | S |
| G3.40 | Me | H | 3-Me | SCH₂ | 5-CF₃ | O | S |
| G3.41 | Me | H | 3-Me | OCH₂ | 6-CF₃ | O | S |
| G3.42 | Me | H | 3-Me | SCH₂ | 6-CF₃ | O | S |
| G3.43 | Me | H | 3-Me | OCH₂ | 7-CF₃ | O | S |
| G3.45 | Me | H | 3-Me | SCH₂ | 7-CF₃ | O | S |
| G3.46 | Me | H | 3-Me | OCH₂ | 5-OCF₃ | O | S |
| G3.47 | Me | H | 3-Me | SCH₂ | 5-OCF₃ | O | S |
| G3.48 | Me | H | 3-Me | OCH₂ | 6-OCF₃ | O | S |
| G3.49 | Me | H | 3-Me | SCH₂ | 6-OCF₃ | O | S |
| G3.50 | Me | H | 3-Me | OCH₂ | 4,5-diMe | O | S |
| G3.51 | Me | H | 3-Me | SCH₂ | 4,5-diMe | O | S |
| G3.52 | Me | H | 3-Me | OCH₂ | 4,6-diMe | O | S |
| G3.53 | Me | H | 3-Me | SCH₂ | 4,6-diMe | O | S |
| G3.54 | Me | H | 3-Me | OCH₂ | 4,7-diMe | O | S |
| G3.55 | Me | H | 3-Me | SCH₂ | 4,7-diMe | O | S |
| G3.56 | Me | H | 3-Me | OCH₂ | 5,6-diMe | O | S |
| G3.57 | Me | H | 3-Me | SCH₂ | 5,6-diMe | O | S |
| G3.58 | Me | H | 3-Me | OCH₂ | 5,7-diMe | O | S |
| G3.59 | Me | H | 3-Me | SCH₂ | 5,7-diMe | O | S |
| G3.60 | Me | H | 3-Me | OCH₂ | 6,7-diMe | O | S |
| G3.61 | Me | H | 3-Me | SCH₂ | 6,7-diMe | O | S |
| G3.62 | Me | H | 3-Me | OCH₂ | 4,5-diOMe | O | S |
| G3.63 | Me | H | 3-Me | SCH₂ | 4,5-diOMe | O | S |
| G3.64 | Me | H | 3-Me | OCH₂ | 4,6-diOMe | O | S |
| G3.65 | Me | H | 3-Me | SCH₂ | 4,6-diOMe | O | S |
| G3.66 | Me | H | 3-Me | OCH₂ | 4,7-diOMe | O | S |
| G3.67 | Me | H | 3-Me | SCH₂ | 4,7-diOMe | O | S |
| G3.68 | Me | H | 3-Me | OCH₂ | 5,6-diOMe | O | S |
| G3.69 | Me | H | 3-Me | SCH₂ | 5,6-diOMe | O | S |
| G3.70 | Me | H | 3-Me | OCH₂ | 5,7-diOMe | O | S |
| G3.71 | Me | H | 3-Me | SCH₂ | 5,7-diOMe | O | S |
| G3.72 | Me | H | 3-Me | OCH₂ | 6,7-diOMe | O | S |
| G3.73 | Me | H | 3-Me | SCH₂ | 6,7-diOMe | O | S |
| G3.74 | Me | H | 3-Me | OCH₂ | 4,5-diF | O | S |
| G3.75 | Me | H | 3-Me | SCH₂ | 4,5-diF | O | S |
| G3.76 | Me | H | 3-Me | OCH₂ | 4,6-diF | O | S |
| G3.77 | Me | H | 3-Me | SCH₂ | 4,6-diF | O | S |
| G3.78 | Me | H | 3-Me | OCH₂ | 4,7-diF | O | S |
| G3.79 | Me | H | 3-Me | SCH₂ | 4,7-diF | O | S |
| G3.80 | Me | H | 3-Me | OCH₂ | 5,6-diF | O | S |
| G3.81 | Me | H | 3-Me | SCH₂ | 5,6-diF | O | S |
| G3.82 | Me | H | 3-Me | OCH₂ | 5,7-diF | O | S |
| G3.83 | Me | H | 3-Me | SCH₂ | 5,7-diF | O | S |
| G3.84 | Me | H | 3-Me | OCH₂ | 6,7-diF | O | S |
| G3.85 | Me | H | 3-Me | SCH₂ | 6,7-diF | O | S |
| G3.86 | Me | H | 3-Me | OCH₂ | 4,5-diCl | O | S |
| G3.87 | Me | H | 3-Me | SCH₂ | 4,5-diCl | O | S |
| G3.88 | Me | H | 3-Me | OCH₂ | 4,6-diCl | O | S |
| G3.89 | Me | H | 3-Me | SCH₂ | 4,6-diCl | O | S |
| G3.90 | Me | H | 3-Me | OCH₂ | 4,7-diCl | O | S |
| G3.91 | Me | H | 3-Me | SCH₂ | 4,7-diCl | O | S |
| G3.92 | Me | H | 3-Me | OCH₂ | 5,6-diCl | O | S |
| G3.93 | Me | H | 3-Me | SCH₂ | 5,6-diCl | O | S |
| G3.94 | Me | H | 3-Me | OCH₂ | 5,7-diCl | O | S |

TABLE 7-continued

| Compd. No. | R¹ | R² | (R³)$_n$ | ACR⁴R⁵ | (R⁶)$_m$ | X | Q |
|---|---|---|---|---|---|---|---|
| G3.95 | Me | H | 3-Me | SCH$_2$ | 5,7-diCl | O | S |
| G3.96 | Me | H | 3-Me | OCH$_2$ | 6,7-diCl | O | S |
| G3.97 | Me | H | 3-Me | SCH$_2$ | 6,7-diCl | O | S |
| G3.98 | Me | H | 3-Me | OCH$_2$ | 4,5-diCF$_3$ | O | S |
| G3.99 | Me | H | 3-Me | SCH$_2$ | 4,5-diCF$_3$ | O | S |
| G3.100 | Me | H | 3-Me | OCH$_2$ | 4,6-diCF$_3$ | O | S |
| G3.101 | Me | H | 3-Me | SCH$_2$ | 4,6-diCF$_3$ | O | S |
| G3.102 | Me | H | 3-Me | OCH$_2$ | 4,7-diCF$_3$ | O | S |
| G3.103 | Me | H | 3-Me | SCH$_2$ | 4,7-diCF$_3$ | O | S |
| G3.104 | Me | H | 3-Me | OCH$_2$ | 5,6-diCF$_3$ | O | S |
| G3.105 | Me | H | 3-Me | SCH$_2$ | 5,6-diCF$_3$ | O | S |
| G3.106 | Me | H | 3-Me | OCH$_2$ | 5,7-diCF$_3$ | O | S |
| G3.107 | Me | H | 3-Me | SCH$_2$ | 5,7-diCF$_3$ | O | S |
| G3.108 | Me | H | 3-Me | OCH$_2$ | 6,7-diCF$_3$ | O | S |
| G3.109 | Me | H | 3-Me | SCH$_2$ | 6,7-diCF$_3$ | O | S |
| G4.1 | Me | H | 3-Me | OCH$_2$ | 4-F,5-Me | O | S |
| G4.2 | Me | H | 3-Me | SCH$_2$ | 4-F,5-Me | O | S |
| G4.3 | Me | H | 3-Me | OCH$_2$ | 4-F,6-Me | O | S |
| G4.4 | Me | H | 3-Me | SCH$_2$ | 4-F,6-Me | O | S |
| G4.5 | Me | H | 3-Me | OCH$_2$ | 4-F,7-Me | O | S |
| G4.6 | Me | H | 3-Me | SCH$_2$ | 4-F,7-Me | O | S |
| G4.7 | Me | H | 3-Me | OCH$_2$ | 4-Me,5-F | O | S |
| G4.8 | Me | H | 3-Me | SCH$_2$ | 4-Me,5-F | O | S |
| G4.9 | Me | H | 3-Me | OCH$_2$ | 5-F,6-Me | O | S |
| G4.10 | Me | H | 3-Me | SCH$_2$ | 5-F,6-Me | O | S |
| G4.11 | Me | H | 3-Me | OCH$_2$ | 5-F,7-Me | O | S |
| G4.12 | Me | H | 3-Me | SCH$_2$ | 5-F,7-Me | O | S |
| G4.13 | Me | H | 3-Me | OCH$_2$ | 4-Me,6-F | O | S |
| G4.14 | Me | H | 3-Me | SCH$_2$ | 4-Me,6-F | O | S |
| G4.15 | Me | H | 3-Me | OCH$_2$ | 5-Me,6-F | O | S |
| G4.16 | Me | H | 3-Me | SCH$_2$ | 5-Me,6-F | O | S |
| G4.17 | Me | H | 3-Me | OCH$_2$ | 6-F,7-Me | O | S |
| G4.18 | Me | H | 3-Me | SCH$_2$ | 6-F,7-Me | O | S |
| G4.19 | Me | H | 3-Me | OCH$_2$ | 4-Me,7-F | O | S |
| G4.20 | Me | H | 3-Me | SCH$_2$ | 4-Me,7-F | O | S |
| G4.21 | Me | H | 3-Me | OCH$_2$ | 5-Me,7-F | O | S |
| G4.22 | Me | H | 3-Me | SCH$_2$ | 5-Me,7-F | O | S |
| G4.23 | Me | H | 3-Me | OCH$_2$ | 6-Me,7-F | O | S |
| G4.24 | Me | H | 3-Me | SCH$_2$ | 6-Me,7-F | O | S |
| G4.25 | Me | H | 3-Me | OCH$_2$ | 4-Cl,5-Me | O | S |
| G4.26 | Me | H | 3-Me | SCH$_2$ | 4-Cl,5-Me | O | S |
| G4.27 | Me | H | 3-Me | OCH$_2$ | 4-Cl,6-Me | O | S |
| G4.28 | Me | H | 3-Me | SCH$_2$ | 4-Cl,6-Me | O | S |
| G4.29 | Me | H | 3-Me | OCH$_2$ | 4-Cl,7-Me | O | S |
| G4.30 | Me | H | 3-Me | SCH$_2$ | 4-Cl,7-Me | O | S |
| G4.31 | Me | H | 3-Me | OCH$_2$ | 4-Me,5-Cl | O | S |
| G4.32 | Me | H | 3-Me | SCH$_2$ | 4-Me,5-Cl | O | S |
| G4.33 | Me | H | 3-Me | OCH$_2$ | 5-Cl,6-Me | O | S |
| G4.34 | Me | H | 3-Me | SCH$_2$ | 5-Cl,6-Me | O | S |
| G4.35 | Me | H | 3-Me | OCH$_2$ | 5-Cl,7-Me | O | S |
| G4.36 | Me | H | 3-Me | SCH$_2$ | 5-Cl,7-Me | O | S |
| G4.37 | Me | H | 3-Me | OCH$_2$ | 4-Me,6-Cl | O | S |
| G4.38 | Me | H | 3-Me | SCH$_2$ | 4-Me,6-Cl | O | S |
| G4.39 | Me | H | 3-Me | OCH$_2$ | 5-Me,6-Cl | O | S |
| G4.40 | Me | H | 3-Me | SCH$_2$ | 5-Me,6-Cl | O | S |
| G4.41 | Me | H | 3-Me | OCH$_2$ | 6-Cl,7-Me | O | S |
| G4.42 | Me | H | 3-Me | SCH$_2$ | 6-Cl,7-Me | O | S |
| G4.43 | Me | H | 3-Me | OCH$_2$ | 4-Me,7-Cl | O | S |
| G4.44 | Me | H | 3-Me | SCH$_2$ | 4-Me,7-Cl | O | S |
| G4.45 | Me | H | 3-Me | OCH$_2$ | 5-Me,7-Cl | O | S |
| G4.46 | Me | H | 3-Me | SCH$_2$ | 5-Me,7-Cl | O | S |
| G4.47 | Me | H | 3-Me | OCH$_2$ | 6-Me,7-Cl | O | S |
| G4.48 | Me | H | 3-Me | SCH$_2$ | 6-Me,7-Cl | O | S |
| G4.49 | Me | H | 3-Me | OCH$_2$ | 4-Cl,5-F | O | S |
| G4.50 | Me | H | 3-Me | SCH$_2$ | 4-Cl,5-F | O | S |
| G4.51 | Me | H | 3-Me | OCH$_2$ | 4-Cl,6-F | O | S |
| G4.52 | Me | H | 3-Me | SCH$_2$ | 4-Cl,6-F | O | S |
| G4.53 | Me | H | 3-Me | OCH$_2$ | 4-Cl,7-F | O | S |
| G4.54 | Me | H | 3-Me | SCH$_2$ | 4-Cl,7-F | O | S |
| G4.55 | Me | H | 3-Me | OCH$_2$ | 4-F,5-Cl | O | S |
| G4.56 | Me | H | 3-Me | SCH$_2$ | 4-F,5-Cl | O | S |
| G4.57 | Me | H | 3-Me | OCH$_2$ | 5-Cl,6-F | O | S |
| G4.58 | Me | H | 3-Me | SCH$_2$ | 5-Cl,6-F | O | S |
| G4.59 | Me | H | 3-Me | OCH$_2$ | 5-Cl,7-F | O | S |
| G4.60 | Me | H | 3-Me | SCH$_2$ | 5-Cl,7-F | O | S |
| G4.61 | Me | H | 3-Me | OCH$_2$ | 4-F,6-Cl | O | S |
| G4.62 | Me | H | 3-Me | SCH$_2$ | 4-F,6-Cl | O | S |
| G4.63 | Me | H | 3-Me | OCH$_2$ | 5-F,6-Cl | O | S |
| G4.64 | Me | H | 3-Me | SCH$_2$ | 5-F,6-Cl | O | S |
| G4.65 | Me | H | 3-Me | OCH$_2$ | 6-Cl,7-F | O | S |
| G4.66 | Me | H | 3-Me | SCH$_2$ | 6-Cl,7-F | O | S |
| G4.67 | Me | H | 3-Me | OCH$_2$ | 4-F,7-Cl | O | S |
| G4.68 | Me | H | 3-Me | SCH$_2$ | 4-F,7-Cl | O | S |
| G4.69 | Me | H | 3-Me | OCH$_2$ | 5-F,7-Cl | O | S |
| G4.70 | Me | H | 3-Me | SCH$_2$ | 5-F,7-Cl | O | S |
| G4.71 | Me | H | 3-Me | OCH$_2$ | 6-F,7-Cl | O | S |
| G4.72 | Me | H | 3-Me | SCH$_2$ | 6-F,7-Cl | O | S |
| G5.1 | Me | H | 2-Et | OCH$_2$ | 4-Me | O | S |
| G5.2 | Me | H | 2-Et | SCH$_2$ | 4-Me | O | S |
| G5.3 | Me | H | 2-Et | OCH$_2$ | 5-Me | O | S |
| G5.4 | Me | H | 2-Et | SCH$_2$ | 5-Me | O | S |
| G5.5 | MeO | H | 2-Et | OCH$_2$ | 5-Me | O | S |
| G5.6 | Me | H | 2-Et | OCH$_2$ | 6-Me | O | S |
| G5.7 | Me | H | 2-Et | SCH$_2$ | 6-Me | O | S |
| G5.8 | MeO | H | 2-Et | OCH$_2$ | 6-Me | O | S |
| G5.9 | Me | H | 2-Et | OCH$_2$ | 7-Me | O | S |
| G5.10 | Me | H | 2-Et | SCH$_2$ | 7-Me | O | S |
| G5.11 | Me | H | 2-Et | OCH$_2$ | 5-Et | O | S |
| G5.12 | Me | H | 2-Et | SCH$_2$ | 5-Et | O | S |
| G5.13 | Me | H | 2-Et | OCH$_2$ | 6-Et | O | S |
| G5.14 | Me | H | 2-Et | SCH$_2$ | 6-Et | O | S |
| G5.15 | Me | H | 2-Et | OCH$_2$ | 4-OMe | O | S |
| G5.16 | Me | H | 2-Et | SCH$_2$ | 4-OMe | O | S |
| G5.17 | Me | H | 2-Et | OCH$_2$ | 5-OMe | O | S |
| G5.18 | Me | H | 2-Et | SCH$_2$ | 5-OMe | O | S |
| G5.19 | MeO | H | 2-Et | OCH$_2$ | 5-OMe | O | S |
| G5.20 | Me | H | 2-Et | OCH$_2$ | 6-OMe | O | S |
| G5.21 | Me | H | 2-Et | SCH$_2$ | 6-OMe | O | S |
| G5.22 | MeO | H | 2-Et | OCH$_2$ | 6-OMe | O | S |
| G5.23 | Me | H | 2-Et | OCH$_2$ | 6-OMe | O | O |
| G5.24 | MeO | H | 2-Et | OCH$_2$ | 6-OMe | O | O |
| G5.25 | Me | H | 2-Et | OCH$_2$ | 7-OMe | O | S |
| G5.26 | Me | H | 2-Et | SCH$_2$ | 7-OMe | O | S |
| G5.27 | Me | H | 2-Et | OCH$_2$ | 5-OEt | O | S |
| G5.28 | Me | H | 2-Et | SCH$_2$ | 5-OEt | O | S |
| G5.29 | Me | H | 2-Et | OCH$_2$ | 6-OEt | O | S |
| G5.30 | Me | H | 2-Et | SCH$_2$ | 6-OEt | O | S |
| G5.31 | Me | H | 2-Et | OCH$_2$ | 4-F | O | S |
| G5.32 | Me | H | 2-Et | SCH$_2$ | 4-F | O | S |
| G5.33 | Me | H | 2-Et | OCH$_2$ | 5-F | O | S |
| G5.34 | Me | H | 2-Et | SCH$_2$ | 5-F | O | S |
| G5.35 | MeO | H | 2-Et | OCH$_2$ | 5-F | O | S |
| G5.36 | Me | H | 2-Et | OCH$_2$ | 5-F | O | O |
| G5.37 | MeO | H | 2-Et | OCH$_2$ | 5-F | O | O |
| G5.38 | Me | H | 2-Et | OCH$_2$ | 6-F | O | S |
| G5.39 | Me | H | 2-Et | SCH$_2$ | 6-F | O | S |
| G5.40 | MeO | H | 2-Et | OCH$_2$ | 6-F | O | S |
| G5.41 | Me | H | 2-Et | OCH$_2$ | 6-F | O | O |
| G5.42 | MeO | H | 2-Et | OCH$_2$ | 6-F | O | O |
| G5.43 | Me | H | 2-Et | OCH$_2$ | 7-F | O | S |
| G5.44 | Me | H | 2-Et | SCH$_2$ | 7-F | O | S |
| G5.45 | Me | H | 2-Et | OCH$_2$ | 5-Cl | O | S |
| G5.46 | Me | H | 2-Et | SCH$_2$ | 5-Cl | O | S |
| G5.47 | MeO | H | 2-Et | OCH$_2$ | 5-Cl | O | S |
| G5.48 | Me | H | 2-Et | OCH$_2$ | 6-Cl | O | S |
| G5.49 | Me | H | 2-Et | SCH$_2$ | 6-Cl | O | S |
| G5.50 | Me | H | 2-Et | OCH$_2$ | 4-CF$_3$ | O | S |
| G5.51 | Me | H | 2-Et | SCH$_2$ | 4-CF$_3$ | O | S |
| G5.52 | Me | H | 2-Et | OCH$_2$ | 5-CF$_3$ | O | S |
| G5.53 | Me | H | 2-Et | SCH$_2$ | 5-CF$_3$ | O | S |
| G5.54 | MeO | H | 2-Et | OCH$_2$ | 5-CF$_3$ | O | S |
| G5.55 | Me | H | 2-Et | OCH$_2$ | 6-CF$_3$ | O | S |
| G5.56 | Me | H | 2-Et | SCH$_2$ | 6-CF$_3$ | O | S |
| G5.57 | Me | H | 2-Et | OCH$_2$ | 7-CF$_3$ | O | S |
| G5.58 | Me | H | 2-Et | SCH$_2$ | 7-CF$_3$ | O | S |
| G5.59 | Me | H | 2-Et | OCH$_2$ | 5-OCF$_3$ | O | S |
| G5.60 | Me | H | 2-Et | SCH$_2$ | 5-OCF$_3$ | O | S |
| G5.61 | Me | H | 2-Et | OCH$_2$ | 6-OCF$_3$ | O | S |
| G5.62 | Me | H | 2-Et | SCH$_2$ | 6-OCF$_3$ | O | S |
| G6.1 | Me | H | 2-Et | OCH$_2$ | 4,5-diMe | O | S |
| G6.2 | Me | H | 2-Et | SCH$_2$ | 4,5-diMe | O | S |
| G6.3 | Me | H | 2-Et | OCH$_2$ | 4,6-diMe | O | S |

TABLE 7-continued

| Compd. No. | R¹ | R² | (R³)$_n$ | ACR⁴R⁵ | (R⁶)$_m$ | X | Q |
|---|---|---|---|---|---|---|---|
| G6.4 | Me | H | 2-Et | SCH$_2$ | 4,6-diMe | O | S |
| G6.5 | Me | H | 2-Et | OCH$_2$ | 4,7-diMe | O | S |
| G6.6 | Me | H | 2-Et | SCH$_2$ | 4,7-diMe | O | S |
| G6.7 | Me | H | 2-Et | OCH$_2$ | 5,6-diMe | O | S |
| G6.8 | Me | H | 2-Et | SCH$_2$ | 5,6-diMe | O | S |
| G6.9 | Me | H | 2-Et | OCH$_2$ | 5,7-diMe | O | S |
| G6.10 | Me | H | 2-Et | SCH$_2$ | 5,7-diMe | O | S |
| G6.11 | Me | H | 2-Et | OCH$_2$ | 6,7-diMe | O | S |
| G6.12 | Me | H | 2-Et | SCH$_2$ | 6,7-diMe | O | S |
| G6.13 | Me | H | 2-Et | OCH$_2$ | 4,5-diOMe | O | S |
| G6.14 | Me | H | 2-Et | SCH$_2$ | 4,5-diOMe | O | S |
| G6.15 | Me | H | 2-Et | OCH$_2$ | 4,6-diOMe | O | S |
| G6.16 | Me | H | 2-Et | SCH$_2$ | 4,6-diOMe | O | S |
| G6.17 | Me | H | 2-Et | OCH$_2$ | 4,7-diOMe | O | S |
| G6.18 | Me | H | 2-Et | SCH$_2$ | 4,7-diOMe | O | S |
| G6.19 | Me | H | 2-Et | OCH$_2$ | 5,6-diOMe | O | S |
| G6.20 | Me | H | 2-Et | SCH$_2$ | 5,6-diOMe | O | S |
| G6.21 | Me | H | 2-Et | OCH$_2$ | 5,7-diOMe | O | S |
| G6.22 | Me | H | 2-Et | SCH$_2$ | 5,7-diOMe | O | S |
| G6.23 | Me | H | 2-Et | OCH$_2$ | 6,7-diOMe | O | S |
| G6.24 | Me | H | 2-Et | SCH$_2$ | 6,7-diOMe | O | S |
| G6.25 | Me | H | 2-Et | OCH$_2$ | 4,5-diF | O | S |
| G6.26 | Me | H | 2-Et | SCH$_2$ | 4,5-diF | O | S |
| G6.27 | Me | H | 2-Et | OCH$_2$ | 4,6-diF | O | S |
| G6.28 | Me | H | 2-Et | SCH$_2$ | 4,6-diF | O | S |
| G6.29 | Me | H | 2-Et | OCH$_2$ | 4,7-diF | O | S |
| G6.30 | Me | H | 2-Et | SCH$_2$ | 4,7-diF | O | S |
| G6.31 | Me | H | 2-Et | OCH$_2$ | 5,6-diF | O | S |
| G6.32 | Me | H | 2-Et | SCH$_2$ | 5,6-diF | O | S |
| G6.33 | MeO | H | 2-Et | OCH$_2$ | 5,6-diF | O | S |
| G6.34 | Me | H | 2-Et | OCH$_2$ | 5,7-diF | O | S |
| G6.35 | Me | H | 2-Et | SCH$_2$ | 5,7-diF | O | S |
| G6.36 | Me | H | 2-Et | OCH$_2$ | 6,7-diF | O | S |
| G6.37 | Me | H | 2-Et | SCH$_2$ | 6,7-diF | O | S |
| G6.38 | Me | H | 2-Et | OCH$_2$ | 4,5-diCl | O | S |
| G6.39 | Me | H | 2-Et | SCH$_2$ | 4,5-diCl | O | S |
| G6.40 | Me | H | 2-Et | OCH$_2$ | 4,6-diCl | O | S |
| G6.41 | Me | H | 2-Et | SCH$_2$ | 4,6-diCl | O | S |
| G6.42 | Me | H | 2-Et | OCH$_2$ | 4,7-diCl | O | S |
| G6.43 | Me | H | 2-Et | SCH$_2$ | 4,7-diCl | O | S |
| G6.44 | Me | H | 2-Et | OCH$_2$ | 5,6-diCl | O | S |
| G6.45 | Me | H | 2-Et | SCH$_2$ | 5,6-diCl | O | S |
| G6.46 | Me | H | 2-Et | OCH$_2$ | 5,7-diCl | O | S |
| G6.47 | Me | H | 2-Et | SCH$_2$ | 5,7-diCl | O | S |
| G6.48 | Me | H | 2-Et | OCH$_2$ | 6,7-diCl | O | S |
| G6.49 | Me | H | 2-Et | SCH$_2$ | 6,7-diCl | O | S |
| G6.50 | Me | H | 2-Et | OCH$_2$ | 4,5-diCF$_3$ | O | S |
| G6.51 | Me | H | 2-Et | SCH$_2$ | 4,5-diCF$_3$ | O | S |
| G6.52 | Me | H | 2-Et | OCH$_2$ | 4,6-diCF$_3$ | O | S |
| G6.53 | Me | H | 2-Et | SCH$_2$ | 4,6-diCF$_3$ | O | S |
| G6.54 | Me | H | 2-Et | OCH$_2$ | 4,7-diCF$_3$ | O | S |
| G6.55 | Me | H | 2-Et | SCH$_2$ | 4,7-diCF$_3$ | O | S |
| G6.56 | Me | H | 2-Et | OCH$_2$ | 5,6-diCF$_3$ | O | S |
| G6.57 | Me | H | 2-Et | SCH$_2$ | 5,6-diCF$_3$ | O | S |
| G6.58 | Me | H | 2-Et | OCH$_2$ | 5,7-diCF$_3$ | O | S |
| G6.59 | Me | H | 2-Et | SCH$_2$ | 5,7-diCF$_3$ | O | S |
| G6.60 | Me | H | 2-Et | OCH$_2$ | 6,7-diCF$_3$ | O | S |
| G6.61 | Me | H | 2-Et | SCH$_2$ | 6,7-diCF$_3$ | O | S |
| G6.62 | Me | H | 2-Et | OCH$_2$ | 4-F,5-Me | O | S |
| G6.63 | Me | H | 2-Et | SCH$_2$ | 4-F,5-Me | O | S |
| G6.64 | Me | H | 2-Et | OCH$_2$ | 4-F,6-Me | O | S |
| G6.65 | Me | H | 2-Et | SCH$_2$ | 4-F,6-Me | O | S |
| G6.66 | Me | H | 2-Et | OCH$_2$ | 4-F,7-Me | O | S |
| G6.67 | Me | H | 2-Et | SCH$_2$ | 4-F,7-Me | O | S |
| G6.68 | Me | H | 2-Et | OCH$_2$ | 4-Me,5-F | O | S |
| G6.69 | Me | H | 2-Et | SCH$_2$ | 4-Me,5-F | O | S |
| G6.70 | Me | H | 2-Et | OCH$_2$ | 5-F,6-Me | O | S |
| G6.71 | Me | H | 2-Et | SCH$_2$ | 5-F,6-Me | O | S |
| G6.72 | Me | H | 2-Et | OCH$_2$ | 5-F,7-Me | O | S |
| G6.73 | Me | H | 2-Et | SCH$_2$ | 5-F,7-Me | O | S |
| G6.74 | Me | H | 2-Et | OCH$_2$ | 4-Me,6-F | O | S |
| G6.75 | Me | H | 2-Et | SCH$_2$ | 4-Me,6-F | O | S |
| G6.76 | Me | H | 2-Et | OCH$_2$ | 5-Me,6-F | O | S |
| G6.77 | Me | H | 2-Et | SCH$_2$ | 5-Me,6-F | O | S |
| G6.78 | Me | H | 2-Et | OCH$_2$ | 6-F,7-Me | O | S |
| G6.79 | Me | H | 2-Et | SCH$_2$ | 6-F,7-Me | O | S |
| G6.80 | Me | H | 2-Et | OCH$_2$ | 4-Me,7-F | O | S |
| G6.81 | Me | H | 2-Et | SCH$_2$ | 4-Me,7-F | O | S |
| G6.82 | Me | H | 2-Et | OCH$_2$ | 5-Me,7-F | O | S |
| G6.83 | Me | H | 2-Et | SCH$_2$ | 5-Me,7-F | O | S |
| G6.84 | Me | H | 2-Et | OCH$_2$ | 6-Me,7-F | O | S |
| G6.85 | Me | H | 2-Et | SCH$_2$ | 6-Me,7-F | O | S |
| G6.86 | Me | H | 2-Et | OCH$_2$ | 4-Cl,5-Me | O | S |
| G6.87 | Me | H | 2-Et | SCH$_2$ | 4-Cl,5-Me | O | S |
| G6.88 | Me | H | 2-Et | OCH$_2$ | 4-Cl,6-Me | O | S |
| G6.89 | Me | H | 2-Et | SCH$_2$ | 4-Cl,6-Me | O | S |
| G6.90 | Me | H | 2-Et | OCH$_2$ | 4-Cl,7-Me | O | S |
| G6.91 | Me | H | 2-Et | SCH$_2$ | 4-Cl,7-Me | O | S |
| G6.92 | Me | H | 2-Et | OCH$_2$ | 4-Me,5-Cl | O | S |
| G6.93 | Me | H | 2-Et | SCH$_2$ | 4-Me,5-Cl | O | S |
| G6.94 | Me | H | 2-Et | OCH$_2$ | 5-Cl,6-Me | O | S |
| G6.95 | Me | H | 2-Et | SCH$_2$ | 5-Cl,6-Me | O | S |
| G6.96 | Me | H | 2-Et | OCH$_2$ | 5-Cl,7-Me | O | S |
| G6.97 | Me | H | 2-Et | SCH$_2$ | 5-Cl,7-Me | O | S |
| G6.98 | Me | H | 2-Et | OCH$_2$ | 4-Me,6-Cl | O | S |
| G6.99 | Me | H | 2-Et | SCH$_2$ | 4-Me,6-Cl | O | S |
| G6.100 | Me | H | 2-Et | OCH$_2$ | 5-Me,6-Cl | O | S |
| G6.101 | Me | H | 2-Et | SCH$_2$ | 5-Me,6-Cl | O | S |
| G6.102 | Me | H | 2-Et | OCH$_2$ | 6-Cl,7-Me | O | S |
| G6.103 | Me | H | 2-Et | SCH$_2$ | 6-Cl,7-Me | O | S |
| G6.104 | Me | H | 2-Et | OCH$_2$ | 4-Me,7-Cl | O | S |
| G6.105 | Me | H | 2-Et | SCH$_2$ | 4-Me,7-Cl | O | S |
| G6.106 | Me | H | 2-Et | OCH$_2$ | 5-Me,7-Cl | O | S |
| G6.107 | Me | H | 2-Et | SCH$_2$ | 5-Me,7-Cl | O | S |
| G6.108 | Me | H | 2-Et | OCH$_2$ | 6-Me,7-Cl | O | S |
| G6.109 | Me | H | 2-Et | SCH$_2$ | 6-Me,7-Cl | O | S |
| G6.110 | Me | H | 2-Et | OCH$_2$ | 4-Cl,5-F | O | S |
| G6.111 | Me | H | 2-Et | SCH$_2$ | 4-Cl,5-F | O | S |
| G6.112 | Me | H | 2-Et | OCH$_2$ | 4-Cl,6-F | O | S |
| G6.113 | Me | H | 2-Et | SCH$_2$ | 4-Cl,6-F | O | S |
| G6.114 | Me | H | 2-Et | OCH$_2$ | 4-Cl,7-F | O | S |
| G6.115 | Me | H | 2-Et | SCH$_2$ | 4-Cl,7-F | O | S |
| G6.116 | Me | H | 2-Et | OCH$_2$ | 4-F,5-Cl | O | S |
| G6.117 | Me | H | 2-Et | SCH$_2$ | 4-F,5-Cl | O | S |
| G6.118 | Me | H | 2-Et | OCH$_2$ | 5-Cl,6-F | O | S |
| G6.119 | Me | H | 2-Et | OCH$_2$ | 5-Cl,6-F | O | S |
| G6.120 | Me | H | 2-Et | OCH$_2$ | 5-Cl,7-F | O | S |
| G6.121 | Me | H | 2-Et | SCH$_2$ | 5-Cl,7-F | O | S |
| G6.122 | Me | H | 2-Et | OCH$_2$ | 4-F,6-Cl | O | S |
| G6.123 | Me | H | 2-Et | SCH$_2$ | 4-F,6-Cl | O | S |
| G6.124 | Me | H | 2-Et | OCH$_2$ | 5-F,6-Cl | O | S |
| G6.125 | Me | H | 2-Et | SCH$_2$ | 5-F,6-Cl | O | S |
| G6.126 | Me | H | 2-Et | OCH$_2$ | 6-Cl,7-F | O | S |
| G6.127 | Me | H | 2-Et | SCH$_2$ | 6-Cl,7-F | O | S |
| G6.128 | Me | H | 2-Et | OCH$_2$ | 4-F,7-Cl | O | S |
| G6.129 | Me | H | 2-Et | SCH$_2$ | 4-F,7-Cl | O | S |
| G6.130 | Me | H | 2-Et | OCH$_2$ | 5-F,7-Cl | O | S |
| G6.131 | Me | H | 2-Et | SCH$_2$ | 5-F,7-Cl | O | S |
| G6.132 | Me | H | 2-Et | OCH$_2$ | 6-F,7-Cl | O | S |
| G6.133 | Me | H | 2-Et | SCH$_2$ | 6-F,7-Cl | O | S |
| G7.1 | Me | H | 3-Et | OCH$_2$ | 4-Me | O | S |
| G7.2 | Me | H | 3-Et | SCH$_2$ | 4-Me | O | S |
| G7.3 | Me | H | 3-Et | OCH$_2$ | 5-Me | O | S |
| G7.4 | Me | H | 3-Et | SCH$_2$ | 5-Me | O | S |
| G7.5 | Me | H | 3-Et | OCH$_2$ | 6-Me | O | S |
| G7.6 | Me | H | 3-Et | SCH$_2$ | 6-Me | O | S |
| G7.7 | Me | H | 3-Et | OCH$_2$ | 7-Me | O | S |
| G7.8 | Me | H | 3-Et | SCH$_2$ | 7-Me | O | S |
| G7.9 | Me | H | 3-Et | OCH$_2$ | 5-Et | O | S |
| G7.10 | Me | H | 3-Et | SCH$_2$ | 5-Et | O | S |
| G7.11 | Me | H | 3-Et | OCH$_2$ | 6-Et | O | S |
| G7.12 | Me | H | 3-Et | SCH$_2$ | 6-Et | O | S |
| G7.13 | Me | H | 3-Et | OCH$_2$ | 4-OMe | O | S |
| G7.14 | Me | H | 3-Et | SCH$_2$ | 4-OMe | O | S |
| G7.15 | Me | H | 3-Et | OCH$_2$ | 5-OMe | O | S |
| G7.16 | Me | H | 3-Et | SCH$_2$ | 5-OMe | O | S |
| G7.17 | Me | H | 3-Et | OCH$_2$ | 6-OMe | O | S |
| G7.18 | Me | H | 3-Et | SCH$_2$ | 6-OMe | O | S |
| G7.19 | Me | H | 3-Et | OCH$_2$ | 7-OMe | O | S |
| G7.20 | Me | H | 3-Et | SCH$_2$ | 7-OMe | O | S |
| G7.21 | Me | H | 3-Et | OCH$_2$ | 5-OEt | O | S |
| G7.22 | Me | H | 3-Et | SCH$_2$ | 5-OEt | O | S |

TABLE 7-continued

| Compd. No. | R¹ | R² | (R³)$_n$ | ACR⁴R⁵ | (R⁶)$_m$ | X | Q |
|---|---|---|---|---|---|---|---|
| G7.23 | Me | H | 3-Et | OCH$_2$ | 6-OEt | O | S |
| G7.24 | Me | H | 3-Et | SCH$_2$ | 6-OEt | O | S |
| G7.25 | Me | H | 3-Et | OCH$_2$ | 4-F | O | S |
| G7.26 | Me | H | 3-Et | SCH$_2$ | 4-F | O | S |
| G7.27 | Me | H | 3-Et | OCH$_2$ | 5-F | O | S |
| G7.28 | Me | H | 3-Et | SCH$_2$ | 5-F | O | S |
| G7.29 | Me | H | 3-Et | OCH$_2$ | 6-F | O | S |
| G7.30 | Me | H | 3-Et | SCH$_2$ | 6-F | O | S |
| G7.31 | Me | H | 3-Et | OCH$_2$ | 7-F | O | S |
| G7.32 | Me | H | 3-Et | SCH$_2$ | 7-F | O | S |
| G7.33 | Me | H | 3-Et | OCH$_2$ | 5-Cl | O | S |
| G7.34 | Me | H | 3-Et | SCH$_2$ | 5-Cl | O | S |
| G7.35 | Me | H | 3-Et | OCH$_2$ | 6-Cl | O | S |
| G7.36 | Me | H | 3-Et | SCH$_2$ | 6-Cl | O | S |
| G7.37 | Me | H | 3-Et | OCH$_2$ | 4-CF$_3$ | O | S |
| G7.38 | Me | H | 3-Et | SCH$_2$ | 4-CF$_3$ | O | S |
| G7.39 | Me | H | 3-Et | OCH$_2$ | 5-CF$_3$ | O | S |
| G7.40 | Me | H | 3-Et | SCH$_2$ | 5-CF$_3$ | O | S |
| G7.41 | Me | H | 3-Et | OCH$_2$ | 6-CF$_3$ | O | S |
| G7.42 | Me | H | 3-Et | SCH$_2$ | 6-CF$_3$ | O | S |
| G7.43 | Me | H | 3-Et | OCH$_2$ | 7-CF$_3$ | O | S |
| G7.44 | Me | H | 3-Et | SCH$_2$ | 7-CF$_3$ | O | S |
| G7.45 | Me | H | 3-Et | OCH$_2$ | 5-OCF$_3$ | O | S |
| G7.46 | Me | H | 3-Et | SCH$_2$ | 5-OCF$_3$ | O | S |
| G7.47 | Me | H | 3-Et | OCH$_2$ | 6-OCF$_3$ | O | S |
| G7.48 | Me | H | 3-Et | SCH$_2$ | 6-OCF$_3$ | O | S |
| G7.49 | Me | H | 2-nPr | OCH$_2$ | 4-Me | O | S |
| G7.50 | Me | H | 2-nPr | SCH$_2$ | 4-Me | O | S |
| G7.51 | Me | H | 2-nPr | OCH$_2$ | 5-Me | O | S |
| G7.52 | Me | H | 2-nPr | SCH$_2$ | 5-Me | O | S |
| G7.53 | Me | H | 2-nPr | OCH$_2$ | 6-Me | O | S |
| G7.54 | Me | H | 2-nPr | SCH$_2$ | 6-Me | O | S |
| G7.55 | Me | H | 2-nPr | OCH$_2$ | 7-Me | O | S |
| G7.56 | Me | H | 2-nPr | SCH$_2$ | 7-Me | O | S |
| G7.57 | Me | H | 2-nPr | OCH$_2$ | 5-Et | O | S |
| G7.58 | Me | H | 2-nPr | SCH$_2$ | 5-Et | O | S |
| G7.59 | Me | H | 2-nPr | OCH$_2$ | 6-Et | O | S |
| G7.60 | Me | H | 2-nPr | SCH$_2$ | 6-Et | O | S |
| G7.61 | Me | H | 2-nPr | OCH$_2$ | 4-OMe | O | S |
| G7.62 | Me | H | 2-nPr | SCH$_2$ | 4-OMe | O | S |
| G7.63 | Me | H | 2-nPr | OCH$_2$ | 5-OMe | O | S |
| G7.64 | Me | H | 2-nPr | SCH$_2$ | 5-OMe | O | S |
| G7.65 | Me | H | 2-nPr | OCH$_2$ | 6-OMe | O | S |
| G7.66 | Me | H | 2-nPr | SCH$_2$ | 6-OMe | O | S |
| G7.67 | Me | H | 2-nPr | OCH$_2$ | 7-OMe | O | S |
| G7.68 | Me | H | 2-nPr | SCH$_2$ | 7-OMe | O | S |
| G7.69 | Me | H | 2-nPr | OCH$_2$ | 5-OEt | O | S |
| G7.70 | Me | H | 2-nPr | SCH$_2$ | 5-OEt | O | S |
| G7.71 | Me | H | 2-nPr | OCH$_2$ | 6-OEt | O | S |
| G7.72 | Me | H | 2-nPr | SCH$_2$ | 6-OEt | O | S |
| G7.73 | Me | H | 2-nPr | OCH$_2$ | 4-F | O | S |
| G7.74 | Me | H | 2-nPr | SCH$_2$ | 4-F | O | S |
| G7.75 | Me | H | 2-nPr | OCH$_2$ | 5-F | O | S |
| G7.76 | Me | H | 2-nPr | SCH$_2$ | 5-F | O | S |
| G7.77 | Me | H | 2-nPr | OCH$_2$ | 6-F | O | S |
| G7.78 | Me | H | 2-nPr | SCH$_2$ | 6-F | O | S |
| G7.79 | Me | H | 2-nPr | OCH$_2$ | 7-F | O | S |
| G7.80 | Me | H | 2-nPr | SCH$_2$ | 7-F | O | S |
| G7.81 | Me | H | 2-nPr | OCH$_2$ | 5-Cl | O | S |
| G7.82 | Me | H | 2-nPr | SCH$_2$ | 5-Cl | O | S |
| G7.83 | Me | H | 2-nPr | OCH$_2$ | 6-Cl | O | S |
| G7.84 | Me | H | 2-nPr | SCH$_2$ | 6-Cl | O | S |
| G7.85 | Me | H | 2-nPr | OCH$_2$ | 4-CF$_3$ | O | S |
| G7.86 | Me | H | 2-nPr | SCH$_2$ | 4-CF$_3$ | O | S |
| G7.87 | Me | H | 2-nPr | OCH$_2$ | 5-CF$_3$ | O | S |
| G7.88 | Me | H | 2-nPr | SCH$_2$ | 5-CF$_3$ | O | S |
| G7.89 | Me | H | 2-nPr | OCH$_2$ | 6-CF$_3$ | O | S |
| G7.90 | Me | H | 2-nPr | SCH$_2$ | 6-CF$_3$ | O | S |
| G7.91 | Me | H | 2-nPr | OCH$_2$ | 7-CF$_3$ | O | S |
| G7.92 | Me | H | 2-nPr | SCH$_2$ | 7-CF$_3$ | O | S |
| G7.93 | Me | H | 2-nPr | OCH$_2$ | 5-OCF$_3$ | O | S |
| G7.94 | Me | H | 2-nPr | SCH$_2$ | 5-OCF$_3$ | O | S |
| G7.95 | Me | H | 2-nPr | OCH$_2$ | 6-OCF$_3$ | O | S |
| G7.96 | Me | H | 2-nPr | SCH$_2$ | 6-OCF$_3$ | O | S |
| G7.97 | Me | H | 3-nPr | OCH$_2$ | 4-Me | O | S |
| G7.98 | Me | H | 3-nPr | SCH$_2$ | 4-Me | O | S |
| G7.99 | Me | H | 3-nPr | OCH$_2$ | 5-Me | O | S |
| G7.100 | Me | H | 3-nPr | SCH$_2$ | 5-Me | O | S |
| G7.101 | Me | H | 3-nPr | OCH$_2$ | 6-Me | O | S |
| G7.102 | Me | H | 3-nPr | SCH$_2$ | 6-Me | O | S |
| G7.103 | Me | H | 3-nPr | OCH$_2$ | 7-Me | O | S |
| G7.104 | Me | H | 3-nPr | SCH$_2$ | 7-Me | O | S |
| G7.105 | Me | H | 3-nPr | OCH$_2$ | 5-Et | O | S |
| G7.106 | Me | H | 3-nPr | SCH$_2$ | 5-Et | O | S |
| G7.107 | Me | H | 3-nPr | OCH$_2$ | 6-Et | O | S |
| G7.108 | Me | H | 3-nPr | SCH$_2$ | 6-Et | O | S |
| G7.109 | Me | H | 3-nPr | OCH$_2$ | 4-OMe | O | S |
| G7.110 | Me | H | 3-nPr | SCH$_2$ | 4-OMe | O | S |
| G7.111 | Me | H | 3-nPr | OCH$_2$ | 5-OMe | O | S |
| G7.112 | Me | H | 3-nPr | SCH$_2$ | 5-OMe | O | S |
| G7.113 | Me | H | 3-nPr | OCH$_2$ | 6-OMe | O | S |
| G7.114 | Me | H | 3-nPr | SCH$_2$ | 6-OMe | O | S |
| G7.115 | Me | H | 3-nPr | OCH$_2$ | 7-OMe | O | S |
| G7.116 | Me | H | 3-nPr | SCH$_2$ | 7-OMe | O | S |
| G7.117 | Me | H | 3-nPr | OCH$_2$ | 5-OEt | O | S |
| G7.118 | Me | H | 3-nPr | SCH$_2$ | 5-OEt | O | S |
| G7.119 | Me | H | 3-nPr | OCH$_2$ | 6-OEt | O | S |
| G7.120 | Me | H | 3-nPr | SCH$_2$ | 6-OEt | O | S |
| G7.121 | Me | H | 3-nPr | OCH$_2$ | 4-F | O | S |
| G7.122 | Me | H | 3-nPr | SCH$_2$ | 4-F | O | S |
| G7.123 | Me | H | 3-nPr | OCH$_2$ | 5-F | O | S |
| G7.124 | Me | H | 3-nPr | SCH$_2$ | 5-F | O | S |
| G7.125 | Me | H | 3-nPr | OCH$_2$ | 6-F | O | S |
| G7.126 | Me | H | 3-nPr | SCH$_2$ | 6-F | O | S |
| G7.127 | Me | H | 3-nPr | OCH$_2$ | 7-F | O | S |
| G7.128 | Me | H | 3-nPr | SCH$_2$ | 7-F | O | S |
| G7.129 | Me | H | 3-nPr | OCH$_2$ | 5-Cl | O | S |
| G7.130 | Me | H | 3-nPr | SCH$_2$ | 5-Cl | O | S |
| G7.131 | Me | H | 3-nPr | OCH$_2$ | 6-Cl | O | S |
| G7.132 | Me | H | 3-nPr | SCH$_2$ | 6-Cl | O | S |
| G7.133 | Me | H | 3-nPr | OCH$_2$ | 4-CF$_3$ | O | S |
| G7.134 | Me | H | 3-nPr | SCH$_2$ | 4-CF$_3$ | O | S |
| G7.135 | Me | H | 3-nPr | OCH$_2$ | 5-CF$_3$ | O | S |
| G7.136 | Me | H | 3-nPr | SCH$_2$ | 5-CF$_3$ | O | S |
| G7.137 | Me | H | 3-nPr | OCH$_2$ | 6-CF$_3$ | O | S |
| G7.138 | Me | H | 3-nPr | SCH$_2$ | 6-CF$_3$ | O | S |
| G7.139 | Me | H | 3-nPr | OCH$_2$ | 7-CF$_3$ | O | S |
| G7.140 | Me | H | 3-nPr | SCH$_2$ | 7-CF$_3$ | O | S |
| G7.141 | Me | H | 3-nPr | OCH$_2$ | 5-OCF$_3$ | O | S |
| G7.142 | Me | H | 3-nPr | SCH$_2$ | 5-OCF$_3$ | O | S |
| G7.143 | Me | H | 3-nPr | OCH$_2$ | 6-OCF$_3$ | O | S |
| G7.144 | Me | H | 3-nPr | SCH$_2$ | 6-OCF$_3$ | O | S |
| G8.1 | Me | H | 2-OMe | OCH$_2$ | 4-Me | O | S |
| G8.2 | Me | H | 2-OMe | SCH$_2$ | 4-Me | O | S |
| G8.3 | Me | H | 2-OMe | OCH$_2$ | 5-Me | O | S |
| G8.4 | Me | H | 2-OMe | SCH$_2$ | 5-Me | O | S |
| G8.5 | MeO | H | 2-OMe | OCH$_2$ | 5-Me | O | S |
| G8.6 | Me | H | 2-OMe | OCH$_2$ | 6-Me | O | S |
| G8.7 | Me | H | 2-OMe | SCH$_2$ | 6-Me | O | S |
| G8.8 | MeO | H | 2-OMe | SCH$_2$ | 6-Me | O | S |
| G8.9 | Me | H | 2-OMe | OCH$_2$ | 7-Me | O | S |
| G8.10 | Me | H | 2-OMe | SCH$_2$ | 7-Me | O | S |
| G8.11 | Me | H | 2-OMe | OCH$_2$ | 5-Et | O | S |
| G8.12 | Me | H | 2-OMe | SCH$_2$ | 5-Et | O | S |
| G8.13 | Me | H | 2-OMe | OCH$_2$ | 6-Et | O | S |
| G8.14 | Me | H | 2-OMe | SCH$_2$ | 6-Et | O | S |
| G8.15 | Me | H | 2-OMe | OCH$_2$ | 4-OMe | O | S |
| G8.16 | Me | H | 2-OMe | SCH$_2$ | 4-OMe | O | S |
| G8.17 | Me | H | 2-OMe | OCH$_2$ | 5-OMe | O | S |
| G8.18 | Me | H | 2-OMe | SCH$_2$ | 5-OMe | O | S |
| G8.19 | Me | H | 2-OMe | OCH$_2$ | 6-OMe | O | S |
| G8.20 | Me | H | 2-OMe | SCH$_2$ | 6-OMe | O | S |
| G8.21 | Me | H | 2-OMe | OCH$_2$ | 7-OMe | O | S |
| G8.22 | Me | H | 2-OMe | SCH$_2$ | 7-OMe | O | S |
| G8.23 | Me | H | 2-OMe | OCH$_2$ | 5-OEt | O | S |
| G8.24 | Me | H | 2-OMe | SCH$_2$ | 5-OEt | O | S |
| G8.25 | Me | H | 2-OMe | OCH$_2$ | 6-OEt | O | S |
| G8.26 | Me | H | 2-OMe | SCH$_2$ | 6-OEt | O | S |
| G8.27 | Me | H | 2-OMe | OCH$_2$ | 4-F | O | S |
| G8.28 | Me | H | 2-OMe | SCH$_2$ | 4-F | O | S |
| G8.29 | MeO | H | 2-OMe | OCH$_2$ | 4-F | O | S |
| G8.30 | MeO | H | 2-OMe | OCH$_2$ | 4-F | O | O |

TABLE 7-continued

| Compd. No. | R¹ | R² | (R³)ₙ | ACR⁴R⁵ | (R⁶)ₘ | X | Q |
|---|---|---|---|---|---|---|---|
| G8.31 | Me | H | 2-OMe | OCH₂ | 5-F | O | S |
| G8.32 | Me | H | 2-OMe | SCH₂ | 5-F | O | S |
| G8.33 | MeO | H | 2-OMe | OCH₂ | 5-F | O | S |
| G8.34 | Me | H | 2-OMe | OCH₂ | 5-F | O | O |
| G8.35 | MeO | H | 2-OMe | OCH₂ | 5-F | O | O |
| G8.36 | EtO | H | 2-OMe | OCH₂ | 5-F | O | S |
| G8.37 | EtO | H | 2-OMe | OCH₂ | 5-F | O | O |
| G8.38 | Me | H | 2-OMe | OCH₂ | 6-F | O | S |
| G8.39 | Me | H | 2-OMe | SCH₂ | 6-F | O | S |
| G8.40 | MeO | H | 2-OMe | OCH₂ | 6-F | O | S |
| G8.41 | MeO | H | 2-OMe | OCH₂ | 6-F | O | O |
| G8.42 | Me | H | 2-OMe | OCH₂ | 7-F | O | S |
| G8.43 | Me | H | 2-OMe | SCH₂ | 7-F | O | S |
| G8.44 | MeO | H | 2-OMe | OCH₂ | 7-F | O | S |
| G8.45 | MeO | H | 2-OMe | OCH₂ | 7-F | O | O |
| G8.46 | Me | H | 2-OMe | OCH₂ | 5-Cl | O | S |
| G8.47 | Me | H | 2-OMe | SCH₂ | 5-Cl | O | S |
| G8.48 | Me | H | 2-OMe | OCH₂ | 6-Cl | O | S |
| G8.49 | Me | H | 2-OMe | SCH₂ | 6-Cl | O | S |
| G8.50 | Me | H | 2-OMe | OCH₂ | 4-CF₃ | O | S |
| G8.51 | Me | H | 2-OMe | SCH₂ | 4-CF₃ | O | S |
| G8.52 | Me | H | 2-OMe | OCH₂ | 5-CF₃ | O | S |
| G8.53 | Me | H | 2-OMe | SCH₂ | 5-CF₃ | O | S |
| G8.54 | Me | H | 2-OMe | OCH₂ | 6-CF₃ | O | S |
| G8.55 | Me | H | 2-OMe | SCH₂ | 6-CF₃ | O | S |
| G8.56 | Me | H | 2-OMe | OCH₂ | 7-CF₃ | O | S |
| G8.57 | Me | H | 2-OMe | SCH₂ | 7-CF₃ | O | S |
| G8.58 | Me | H | 2-OMe | OCH₂ | 5-OCF₃ | O | S |
| G8.59 | Me | H | 2-OMe | SCH₂ | 5-OCF₃ | O | S |
| G8.60 | Me | H | 2-OMe | OCH₂ | 6-OCF₃ | O | S |
| G8.61 | Me | H | 2-OMe | SCH₂ | 6-OCF₃ | O | S |
| G8.62 | Me | H | 2-OMe | OCH₂ | 4,5-diMe | O | S |
| G9.1 | Me | H | 2-OMe | SCH₂ | 4,5-diMe | O | S |
| G9.2 | Me | H | 2-OMe | OCH₂ | 4,6-diMe | O | S |
| G9.3 | Me | H | 2-OMe | SCH₂ | 4,6-diMe | O | S |
| G9.4 | Me | H | 2-OMe | OCH₂ | 4,7-diMe | O | S |
| G9.5 | Me | H | 2-OMe | SCH₂ | 4,7-diMe | O | S |
| G9.6 | Me | H | 2-OMe | OCH₂ | 5,6-diMe | O | S |
| G9.7 | Me | H | 2-OMe | SCH₂ | 5,6-diMe | O | S |
| G9.8 | Me | H | 2-OMe | OCH₂ | 5,7-diMe | O | S |
| G9.9 | Me | H | 2-OMe | SCH₂ | 5,7-diMe | O | S |
| G9.10 | Me | H | 2-OMe | OCH₂ | 6,7-diMe | O | S |
| G9.11 | Me | H | 2-OMe | SCH₂ | 6,7-diMe | O | S |
| G9.12 | Me | H | 2-OMe | OCH₂ | 4,5-diMe | O | S |
| G9.13 | Me | H | 2-OMe | SCH₂ | 4,5-diMe | O | S |
| G9.14 | Me | H | 2-OMe | OCH₂ | 4,6-diOMe | O | S |
| G9.15 | Me | H | 2-OMe | SCH₂ | 4,6-diOMe | O | S |
| G9.16 | Me | H | 2-OMe | OCH₂ | 4,7-diOMe | O | S |
| G9.17 | Me | H | 2-OMe | SCH₂ | 4,7-diOMe | O | S |
| G9.18 | Me | H | 2-OMe | OCH₂ | 5,6-diOMe | O | S |
| G9.19 | Me | H | 2-OMe | SCH₂ | 5,6-diOMe | O | S |
| G9.20 | Me | H | 2-OMe | OCH₂ | 5,7-diOMe | O | S |
| G9.21 | Me | H | 2-OMe | SCH₂ | 5,7-diOMe | O | S |
| G9.22 | Me | H | 2-OMe | OCH₂ | 6,7-diOMe | O | S |
| G9.23 | Me | H | 2-OMe | SCH₂ | 6,7-diOMe | O | S |
| G9.24 | Me | H | 2-OMe | OCH₂ | 4,5-diF | O | S |
| G9.25 | Me | H | 2-OMe | SCH₂ | 4,5-diF | O | S |
| G9.26 | Me | H | 2-OMe | OCH₂ | 4,6-diF | O | S |
| G9.27 | Me | H | 2-OMe | SCH₂ | 4,6-diF | O | S |
| G9.28 | Me | H | 2-OMe | OCH₂ | 4,7-diF | O | S |
| G9.29 | Me | H | 2-OMe | SCH₂ | 4,7-diF | O | S |
| G9.30 | Me | H | 2-OMe | OCH₂ | 5,6-diF | O | S |
| G9.31 | Me | H | 2-OMe | SCH₂ | 5,6-diF | O | S |
| G9.32 | Me | H | 2-OMe | OCH₂ | 5,7-diF | O | S |
| G9.33 | Me | H | 2-OMe | SCH₂ | 5,7-diF | O | S |
| G9.34 | Me | H | 2-OMe | OCH₂ | 6,7-diF | O | S |
| G9.35 | Me | H | 2-OMe | SCH₂ | 6,7-diF | O | S |
| G9.36 | Me | H | 2-OMe | OCH₂ | 4,5-Cl | O | S |
| G9.37 | Me | H | 2-OMe | SCH₂ | 4,5-Cl | O | S |
| G9.38 | Me | H | 2-OMe | OCH₂ | 4,6-Cl | O | S |
| G9.39 | Me | H | 2-OMe | SCH₂ | 4,6-Cl | O | S |
| G9.40 | Me | H | 2-OMe | OCH₂ | 4,7-Cl | O | S |
| G9.41 | Me | H | 2-OMe | SCH₂ | 4,7-Cl | O | S |
| G9.42 | Me | H | 2-OMe | OCH₂ | 5,6-Cl | O | S |
| G9.43 | Me | H | 2-OMe | SCH₂ | 5,6-Cl | O | S |
| G9.44 | Me | H | 2-OMe | OCH₂ | 5,7-Cl | O | S |
| G9.45 | Me | H | 2-OMe | SCH₂ | 5,7-Cl | O | S |
| G9.46 | Me | H | 2-OMe | OCH₂ | 6,7-Cl | O | S |
| G9.47 | Me | H | 2-OMe | SCH₂ | 6,7-Cl | O | S |
| G9.48 | Me | H | 2-OMe | OCH₂ | 4,5-diCF₃ | O | S |
| G9.49 | Me | H | 2-OMe | SCH₂ | 4,5-diCF₃ | O | S |
| G9.50 | Me | H | 2-OMe | OCH₂ | 4,6-diCF₃ | O | S |
| G9.51 | Me | H | 2-OMe | SCH₂ | 4,6-diCF₃ | O | S |
| G9.52 | Me | H | 2-OMe | OCH₂ | 4,7-diCF₃ | O | S |
| G9.53 | Me | H | 2-OMe | SCH₂ | 4,7-diCF₃ | O | S |
| G9.54 | Me | H | 2-OMe | OCH₂ | 5,6-diCF₃ | O | S |
| G9.55 | Me | H | 2-OMe | SCH₂ | 5,6-diCF₃ | O | S |
| G9.56 | Me | H | 2-OMe | OCH₂ | 5,7-diCF₃ | O | S |
| G9.57 | Me | H | 2-OMe | SCH₂ | 5,7-diCF₃ | O | S |
| G9.58 | Me | H | 2-OMe | OCH₂ | 6,7-diCF₃ | O | S |
| G9.59 | Me | H | 2-OMe | SCH₂ | 6,7-diCF₃ | O | S |
| G9.60 | Me | H | 2-OMe | OCH₂ | 4-F,5-Me | O | S |
| G9.61 | Me | H | 2-OMe | SCH₂ | 4-F,5-Me | O | S |
| G9.62 | Me | H | 2-OMe | OCH₂ | 4-F,6-Me | O | S |
| G9.63 | Me | H | 2-OMe | SCH₂ | 4-F,6-Me | O | S |
| G9.64 | Me | H | 2-OMe | OCH₂ | 4-F,7-Me | O | S |
| G9.65 | Me | H | 2-OMe | SCH₂ | 4-F,7-Me | O | S |
| G9.66 | Me | H | 2-OMe | OCH₂ | 4-Me,5-F | O | S |
| G9.67 | Me | H | 2-OMe | SCH₂ | 4-Me,5-F | O | S |
| G9.68 | Me | H | 2-OMe | OCH₂ | 5-F,6-Me | O | S |
| G9.69 | Me | H | 2-OMe | SCH₂ | 5-F,6-Me | O | S |
| G9.70 | Me | H | 2-OMe | OCH₂ | 5-F,7-Me | O | S |
| G9.71 | Me | H | 2-OMe | SCH₂ | 5-F,7-Me | O | S |
| G9.72 | Me | H | 2-OMe | OCH₂ | 4-Me,6-F | O | S |
| G9.73 | Me | H | 2-OMe | SCH₂ | 4-Me,6-F | O | S |
| G9.74 | Me | H | 2-OMe | OCH₂ | 5-Me,6-F | O | S |
| G9.75 | Me | H | 2-OMe | SCH₂ | 5-Me,6-F | O | S |
| G9.76 | Me | H | 2-OMe | OCH₂ | 6-F,7-Me | O | S |
| G9.77 | Me | H | 2-OMe | SCH₂ | 6-F,7-Me | O | S |
| G9.78 | Me | H | 2-OMe | OCH₂ | 4-Me,7-F | O | S |
| G9.79 | Me | H | 2-OMe | SCH₂ | 4-Me,7-F | O | S |
| G9.80 | Me | H | 2-OMe | OCH₂ | 5-Me,7-F | O | S |
| G9.81 | Me | H | 2-OMe | SCH₂ | 5-Me,7-F | O | S |
| G9.82 | Me | H | 2-OMe | OCH₂ | 6-Me,7-F | O | S |
| G9.83 | Me | H | 2-OMe | SCH₂ | 6-Me,7-F | O | S |
| G9.84 | Me | H | 2-OMe | OCH₂ | 4-Cl,5-Me | O | S |
| G9.85 | Me | H | 2-OMe | SCH₂ | 4-Cl,5-Me | O | S |
| G9.86 | Me | H | 2-OMe | OCH₂ | 4-Cl,6-Me | O | S |
| G9.87 | Me | H | 2-OMe | SCH₂ | 4-Cl,6-Me | O | S |
| G9.88 | Me | H | 2-OMe | OCH₂ | 4-Cl,7-Me | O | S |
| G9.89 | Me | H | 2-OMe | SCH₂ | 4-Cl,7-Me | O | S |
| G9.90 | Me | H | 2-OMe | OCH₂ | 4-Me,5-Cl | O | S |
| G9.91 | Me | H | 2-OMe | SCH₂ | 4-Me,5-Cl | O | S |
| G9.92 | Me | H | 2-OMe | OCH₂ | 5-Cl,6-Me | O | S |
| G9.93 | Me | H | 2-OMe | SCH₂ | 5-Cl,6-Me | O | S |
| G9.94 | Me | H | 2-OMe | OCH₂ | 5-Cl,7-Me | O | S |
| G9.95 | Me | H | 2-OMe | SCH₂ | 5-Cl,7-Me | O | S |
| G9.96 | Me | H | 2-OMe | OCH₂ | 4-Me,6-Cl | O | S |
| G9.97 | Me | H | 2-OMe | SCH₂ | 4-Me,6-Cl | O | S |
| G9.98 | Me | H | 2-OMe | OCH₂ | 5-Me,6-Cl | O | S |
| G9.99 | Me | H | 2-OMe | SCH₂ | 5-Me,6-Cl | O | S |
| G9.100 | Me | H | 2-OMe | OCH₂ | 6-Cl,7-Me | O | S |
| G9.101 | Me | H | 2-OMe | SCH₂ | 6-Cl,7-Me | O | S |
| G9.102 | Me | H | 2-OMe | OCH₂ | 4-Me,7-Cl | O | S |
| G9.103 | Me | H | 2-OMe | SCH₂ | 4-Me,7-Cl | O | S |
| G9.104 | Me | H | 2-OMe | OCH₂ | 5-Me,7-Cl | O | S |
| G9.105 | Me | H | 2-OMe | SCH₂ | 5-Me,7-Cl | O | S |
| G9.106 | Me | H | 2-OMe | OCH₂ | 6-Me,7-Cl | O | S |
| G9.107 | Me | H | 2-OMe | SCH₂ | 6-Me,7-Cl | O | S |
| G9.108 | Me | H | 2-OMe | OCH₂ | 4-Cl,5-F | O | S |
| G9.109 | Me | H | 2-OMe | SCH₂ | 4-Cl,5-F | O | S |
| G9.110 | Me | H | 2-OMe | OCH₂ | 4-Cl,6-F | O | S |
| G9.111 | Me | H | 2-OMe | SCH₂ | 4-Cl,6-F | O | S |
| G9.112 | Me | H | 2-OMe | OCH₂ | 4-Cl,7-F | O | S |
| G9.113 | Me | H | 2-OMe | SCH₂ | 4-Cl,7-F | O | S |
| G9.114 | Me | H | 2-OMe | OCH₂ | 4-F,5-Cl | O | S |
| G9.115 | Me | H | 2-OMe | SCH₂ | 4-F,5-Cl | O | S |
| G9.116 | Me | H | 2-OMe | OCH₂ | 5-Cl,6-F | O | S |
| G9.117 | Me | H | 2-OMe | SCH₂ | 5-Cl,6-F | O | S |
| G9.118 | Me | H | 2-OMe | OCH₂ | 5-Cl,7-F | O | S |
| G9.119 | Me | H | 2-OMe | SCH₂ | 5-Cl,7-F | O | S |
| G9.120 | Me | H | 2-OMe | OCH₂ | 4-F,6-Cl | O | S |

TABLE 7-continued

| Compd. No. | R¹ | R² | (R³)ₙ | ACR⁴R⁵ | (R⁶)ₘ | X | Q |
|---|---|---|---|---|---|---|---|
| G9.121 | Me | H | 2-OMe | SCH₂ | 4-F,6-Cl | O | S |
| G9.122 | Me | H | 2-OMe | OCH₂ | 5-F,6-Cl | O | S |
| G9.123 | Me | H | 2-OMe | SCH₂ | 5-F,6-Cl | O | S |
| G9.124 | Me | H | 2-OMe | OCH₂ | 7-F,6-Cl | O | S |
| G9.125 | Me | H | 2-OMe | SCH₂ | 7-F,6-Cl | O | S |
| G9.126 | Me | H | 2-OMe | OCH₂ | 4-F,7-Cl | O | S |
| G9.127 | Me | H | 2-OMe | SCH₂ | 4-F,7-Cl | O | S |
| G9.128 | Me | H | 2-OMe | OCH₂ | 5-F,7-Cl | O | S |
| G9.129 | Me | H | 2-OMe | SCH₂ | 5-F,7-Cl | O | S |
| G9.130 | Me | H | 2-OMe | OCH₂ | 6-F,7-Cl | O | S |
| G9.131 | Me | H | 2-OMe | SCH₂ | 6-F,7-Cl | O | S |
| G10.1 | Me | H | 3-OMe | OCH₂ | 4-Me | O | S |
| G10.2 | Me | H | 3-OMe | SCH₂ | 4-Me | O | S |
| G10.3 | Me | H | 3-OMe | OCH₂ | 5-Me | O | S |
| G10.4 | Me | H | 3-OMe | SCH₂ | 5-Me | O | S |
| G10.5 | Me | H | 3-OMe | OCH₂ | 6-Me | O | S |
| G10.6 | Me | H | 3-OMe | SCH₂ | 6-Me | O | S |
| G10.7 | Me | H | 3-OMe | OCH₂ | 7-Me | O | S |
| G10.8 | Me | H | 3-OMe | SCH₂ | 7-Me | O | S |
| G10.9 | Me | H | 3-OMe | OCH₂ | 5-Et | O | S |
| G10.10 | Me | H | 3-OMe | SCH₂ | 5-Et | O | S |
| G10.11 | Me | H | 3-OMe | OCH₂ | 6-Et | O | S |
| G10.12 | Me | H | 3-OMe | SCH₂ | 6-Et | O | S |
| G10.13 | Me | H | 3-OMe | OCH₂ | 4-OMe | O | S |
| G10.14 | Me | H | 3-OMe | SCH₂ | 4-OMe | O | S |
| G10.15 | Me | H | 3-OMe | OCH₂ | 5-OMe | O | S |
| G10.16 | Me | H | 3-OMe | SCH₂ | 5-OMe | O | S |
| G10.17 | Me | H | 3-OMe | OCH₂ | 6-OMe | O | S |
| G10.18 | Me | H | 3-OMe | SCH₂ | 6-OMe | O | S |
| G10.19 | Me | H | 3-OMe | OCH₂ | 7-OMe | O | S |
| G10.20 | Me | H | 3-OMe | SCH₂ | 7-OMe | O | S |
| G10.21 | Me | H | 3-OMe | OCH₂ | 5-OEt | O | S |
| G10.22 | Me | H | 3-OMe | SCH₂ | 5-OEt | O | S |
| G10.23 | Me | H | 3-OMe | OCH₂ | 6-OEt | O | S |
| G10.24 | Me | H | 3-OMe | SCH₂ | 6-OEt | O | S |
| G10.25 | Me | H | 3-OMe | OCH₂ | 4-F | O | S |
| G10.26 | Me | H | 3-OMe | SCH₂ | 4-F | O | S |
| G10.27 | Me | H | 3-OMe | OCH₂ | 5-F | O | S |
| G10.28 | Me | H | 3-OMe | SCH₂ | 5-F | O | S |
| G10.29 | MeO | H | 3-OMe | OCH₂ | 5-F | O | S |
| G10.30 | Me | H | 3-OMe | SCH₂ | 6-F | O | S |
| G10.31 | Me | H | 3-OMe | OCH₂ | 6-F | O | S |
| G10.32 | MeO | H | 3-OMe | OCH₂ | 6-F | O | S |
| G10.33 | Me | H | 3-OMe | OCH₂ | 7-F | O | S |
| G10.34 | Me | H | 3-OMe | SCH₂ | 7-F | O | S |
| G10.35 | Me | H | 3-OMe | OCH₂ | 5-Cl | O | S |
| G10.36 | Me | H | 3-OMe | SCH₂ | 5-Cl | O | S |
| G10.37 | Me | H | 3-OMe | OCH₂ | 6-Cl | O | S |
| G10.38 | Me | H | 3-OMe | SCH₂ | 6-Cl | O | S |
| G10.39 | Me | H | 3-OMe | OCH₂ | 4-CF₃ | O | S |
| G10.40 | Me | H | 3-OMe | SCH₂ | 4-CF₃ | O | S |
| G10.41 | Me | H | 3-OMe | OCH₂ | 5-CF₃ | O | S |
| G10.42 | Me | H | 3-OMe | SCH₂ | 5-CF₃ | O | S |
| G10.43 | Me | H | 3-OMe | OCH₂ | 6-CF₃ | O | S |
| G10.44 | Me | H | 3-OMe | SCH₂ | 6-CF₃ | O | S |
| G10.45 | Me | H | 3-OMe | OCH₂ | 7-CF₃ | O | S |
| G10.46 | Me | H | 3-OMe | SCH₂ | 7-CF₃ | O | S |
| G10.47 | Me | H | 3-OMe | OCH₂ | 5-OCF₃ | O | S |
| G10.48 | Me | H | 3-OMe | SCH₂ | 5-OCF₃ | O | S |
| G10.49 | Me | H | 3-OMe | OCH₂ | 6-OCF₃ | O | S |
| G10.50 | Me | H | 3-OMe | SCH₂ | 6-OCF₃ | O | S |
| G10.51 | Me | H | 2-OEt | OCH₂ | 5-F | O | S |
| G10.52 | Me | H | 2-OEt | SCH₂ | 5-F | O | S |
| G10.53 | Me | H | 2-OEt | OCH₂ | 5-F | O | O |
| G10.54 | MeO | H | 2-OEt | OCH₂ | 5-F | O | S |
| G10.55 | MeO | H | 2-OEt | SCH₂ | 5-F | O | S |
| G10.56 | MeO | H | 2-OEt | OCH₂ | 5-F | O | O |
| G10.57 | Me | H | 2-CHF₂ | OCH₂ | 5-F | O | S |
| G10.58 | MeO | H | 2-CHF₂ | OCH₂ | 5-F | O | S |
| G10.59 | Me | H | 2-CHF₂ | OCH₂ | 5-F | O | O |
| G10.60 | MeO | H | 2-CHF₂ | OCH₂ | 5-F | O | O |
| G10.61 | Me | H | 2-OCHF₂ | OCH₂ | 5-F | O | S |
| G10.62 | MeO | H | 2-OCHF₂ | OCH₂ | 5-F | O | S |
| G10.63 | Me | H | 2-OCH₂CF₃ | OCH₂ | 5-F | O | S |
| G10.65 | MeO | H | 2-OCH₂CF₃ | OCH₂ | 5-F | O | S |
| G10.65 | Me | H | 2-OCH₂CF₃ | OCH₂ | 5-F | O | O |
| G10.66 | MeO | H | 2-OCH₂CF₃ | OCH₂ | 5-F | O | O |
| G11.1 | Me | H | 2-CH₂OMe | OCH₂ | 4-Me | O | S |
| G11.2 | Me | H | 2-CH₂OMe | SCH₂ | 4-Me | O | S |
| G11.3 | Me | H | 2-CH₂OMe | OCH₂ | 5-Me | O | S |
| G11.4 | Me | H | 2-CH₂OMe | SCH₂ | 5-Me | O | S |
| G11.5 | Me | H | 2-CH₂OMe | OCH₂ | 6-Me | O | S |
| G11.6 | Me | H | 2-CH₂OMe | SCH₂ | 6-Me | O | S |
| G11.7 | Me | H | 2-CH₂OMe | OCH₂ | 7-Me | O | S |
| G11.8 | Me | H | 2-CH₂OMe | SCH₂ | 7-Me | O | S |
| G11.9 | Me | H | 2-CH₂OMe | OCH₂ | 5-Et | O | S |
| G11.10 | Me | H | 2-CH₂OMe | SCH₂ | 5-Et | O | S |
| G11.11 | Me | H | 2-CH₂OMe | OCH₂ | 6-Et | O | S |
| G11.12 | Me | H | 2-CH₂OMe | SCH₂ | 6-Et | O | S |
| G11.13 | Me | H | 2-CH₂OMe | OCH₂ | 4-OMe | O | S |
| G11.14 | Me | H | 2-CH₂OMe | SCH₂ | 4-OMe | O | S |
| G11.15 | Me | H | 2-CH₂OMe | OCH₂ | 5-OMe | O | S |
| G11.16 | Me | H | 2-CH₂OMe | SCH₂ | 5-OMe | O | S |
| G11.17 | Me | H | 2-CH₂OMe | OCH₂ | 6-OMe | O | S |
| G11.18 | Me | H | 2-CH₂OMe | SCH₂ | 6-OMe | O | S |
| G11.19 | Me | H | 2-CH₂OMe | OCH₂ | 7-OMe | O | S |
| G11.20 | Me | H | 2-CH₂OMe | SCH₂ | 7-OMe | O | S |
| G11.21 | Me | H | 2-CH₂OMe | OCH₂ | 5-OEt | O | S |
| G11.22 | Me | H | 2-CH₂OMe | SCH₂ | 5-OEt | O | S |
| G11.23 | Me | H | 2-CH₂OMe | OCH₂ | 6-OEt | O | S |
| G11.24 | Me | H | 2-CH₂OMe | SCH₂ | 6-OEt | O | S |
| G11.25 | Me | H | 2-CH₂OMe | OCH₂ | 4-F | O | S |
| G11.26 | Me | H | 2-CH₂OMe | SCH₂ | 4-F | O | S |
| G11.27 | Me | H | 2-CH₂OMe | OCH₂ | 5-F | O | S |
| G11.28 | Me | H | 2-CH₂OMe | SCH₂ | 5-F | O | S |
| G11.29 | Me | H | 2-CH₂OMe | OCH₂ | 6-F | O | S |
| G11.30 | Me | H | 2-CH₂OMe | SCH₂ | 6-F | O | S |
| G11.31 | Me | H | 2-CH₂OMe | OCH₂ | 7-F | O | S |
| G11.32 | Me | H | 2-CH₂OMe | SCH₂ | 7-F | O | S |
| G11.33 | Me | H | 2-CH₂OMe | OCH₂ | 5-Cl | O | S |
| G11.34 | Me | H | 2-CH₂OMe | SCH₂ | 5-Cl | O | S |
| G11.35 | Me | H | 2-CH₂OMe | OCH₂ | 6-Cl | O | S |
| G11.36 | Me | H | 2-CH₂OMe | SCH₂ | 6-Cl | O | S |
| G11.37 | Me | H | 2-CH₂OMe | OCH₂ | 4-CF₃ | O | S |
| G11.38 | Me | H | 2-CH₂OMe | SCH₂ | 4-CF₃ | O | S |
| G11.39 | Me | H | 2-CH₂OMe | OCH₂ | 5-CF₃ | O | S |
| G11.40 | Me | H | 2-CH₂OMe | SCH₂ | 5-CF₃ | O | S |
| G11.41 | Me | H | 2-CH₂OMe | OCH₂ | 6-CF₃ | O | S |
| G11.42 | Me | H | 2-CH₂OMe | SCH₂ | 6-CF₃ | O | S |
| G11.43 | Me | H | 2-CH₂OMe | OCH₂ | 7-CF₃ | O | S |
| G11.44 | Me | H | 2-CH₂OMe | SCH₂ | 7-CF₃ | O | S |
| G11.45 | Me | H | 2-CH₂OMe | OCH₂ | 5-OCF₃ | O | S |
| G11.46 | Me | H | 2-CH₂OMe | SCH₂ | 5-OCF₃ | O | S |
| G11.47 | Me | H | 2-CH₂OMe | OCH₂ | 6-OCF₃ | O | S |
| G11.48 | Me | H | 2-CH₂OMe | SCH₂ | 6-OCF₃ | O | S |
| G11.49 | Me | H | 3-CH₂OMe | OCH₂ | 4-Me | O | S |
| G11.50 | Me | H | 3-CH₂OMe | SCH₂ | 4-Me | O | S |
| G11.51 | Me | H | 3-CH₂OMe | OCH₂ | 5-Me | O | S |
| G11.52 | Me | H | 3-CH₂OMe | SCH₂ | 5-Me | O | S |
| G11.53 | Me | H | 3-CH₂OMe | OCH₂ | 6-Me | O | S |
| G11.54 | Me | H | 3-CH₂OMe | SCH₂ | 6-Me | O | S |
| G11.55 | Me | H | 3-CH₂OMe | OCH₂ | 7-Me | O | S |
| G11.56 | Me | H | 3-CH₂OMe | SCH₂ | 7-Me | O | S |
| G11.57 | Me | H | 3-CH₂OMe | OCH₂ | 5-Et | O | S |
| G11.58 | Me | H | 3-CH₂OMe | SCH₂ | 5-Et | O | S |
| G11.59 | Me | H | 3-CH₂OMe | OCH₂ | 6-Et | O | S |
| G11.60 | Me | H | 3-CH₂OMe | SCH₂ | 6-Et | O | S |
| G11.61 | Me | H | 3-CH₂OMe | OCH₂ | 4-OMe | O | S |
| G11.62 | Me | H | 3-CH₂OMe | SCH₂ | 4-OMe | O | S |
| G11.63 | Me | H | 3-CH₂OMe | OCH₂ | 5-OMe | O | S |
| G11.64 | Me | H | 3-CH₂OMe | SCH₂ | 5-OMe | O | S |
| G11.65 | Me | H | 3-CH₂OMe | OCH₂ | 6-OMe | O | S |
| G11.66 | Me | H | 3-CH₂OMe | SCH₂ | 6-OMe | O | S |
| G11.67 | Me | H | 3-CH₂OMe | OCH₂ | 7-OMe | O | S |
| G11.68 | Me | H | 3-CH₂OMe | SCH₂ | 7-OMe | O | S |
| G11.69 | Me | H | 3-CH₂OMe | OCH₂ | 5-OEt | O | S |
| G11.70 | Me | H | 3-CH₂OMe | SCH₂ | 5-OEt | O | S |
| G11.71 | Me | H | 3-CH₂OMe | OCH₂ | 6-OEt | O | S |
| G11.72 | Me | H | 3-CH₂OMe | SCH₂ | 6-OEt | O | S |
| G11.73 | Me | H | 3-CH₂OMe | OCH₂ | 4-F | O | S |
| G11.74 | Me | H | 3-CH₂OMe | SCH₂ | 4-F | O | S |
| G11.75 | Me | H | 3-CH₂OMe | OCH₂ | 5-F | O | S |

TABLE 7-continued

| Compd. No. | R¹ | R² | (R³)ₙ | ACR⁴R⁵ | (R⁶)ₘ | X | Q |
|---|---|---|---|---|---|---|---|
| G11.76 | Me | H | 3-CH₂OMe | SCH₂ | 5-F | O | S |
| G11.77 | Me | H | 3-CH₂OMe | OCH₂ | 6-F | O | S |
| G11.78 | Me | H | 3-CH₂OMe | SCH₂ | 6-F | O | S |
| G11.79 | Me | H | 3-CH₂OMe | OCH₂ | 7-F | O | S |
| G11.80 | Me | H | 3-CH₂OMe | SCH₂ | 7-F | O | S |
| G11.81 | Me | H | 3-CH₂OMe | OCH₂ | 5-Cl | O | S |
| G11.82 | Me | H | 3-CH₂OMe | SCH₂ | 5-Cl | O | S |
| G11.83 | Me | H | 3-CH₂OMe | OCH₂ | 6-Cl | O | S |
| G11.84 | Me | H | 3-CH₂OMe | SCH₂ | 6-Cl | O | S |
| G11.85 | Me | H | 3-CH₂OMe | OCH₂ | 4-CF₃ | O | S |
| G11.86 | Me | H | 3-CH₂OMe | SCH₂ | 4-CF₃ | O | S |
| G11.87 | Me | H | 3-CH₂OMe | OCH₂ | 5-CF₃ | O | S |
| G11.88 | Me | H | 3-CH₂OMe | SCH₂ | 5-CF₃ | O | S |
| G11.89 | Me | H | 3-CH₂OMe | OCH₂ | 6-CF₃ | O | S |
| G11.90 | Me | H | 3-CH₂OMe | SCH₂ | 6-CF₃ | O | S |
| G11.91 | Me | H | 3-CH₂OMe | OCH₂ | 7-CF₃ | O | S |
| G11.92 | Me | H | 3-CH₂OMe | SCH₂ | 7-CF₃ | O | S |
| G11.93 | Me | H | 3-CH₂OMe | OCH₂ | 6-OCF₃ | O | S |
| G11.94 | Me | H | 3-CH₂OMe | SCH₂ | 6-OCF₃ | O | S |
| G11.95 | Me | H | 3-CH₂OMe | OCH₂ | 7-OCF₃ | O | S |
| G11.96 | Me | H | 3-CH₂OMe | SCH₂ | 7-OCF₃ | O | S |
| G12.1 | Me | H | 2-CH₂OEt | OCH₂ | 4-Me | O | S |
| G12.2 | Me | H | 2-CH₂OEt | SCH₂ | 4-Me | O | S |
| G12.3 | Me | H | 2-CH₂OEt | OCH₂ | 5-Me | O | S |
| G12.4 | Me | H | 2-CH₂OEt | SCH₂ | 5-Me | O | S |
| G12.5 | Me | H | 2-CH₂OEt | OCH₂ | 6-Me | O | S |
| G12.6 | Me | H | 2-CH₂OEt | SCH₂ | 6-Me | O | S |
| G12.7 | Me | H | 2-CH₂OEt | OCH₂ | 7-Me | O | S |
| G12.8 | Me | H | 2-CH₂OEt | SCH₂ | 7-Me | O | S |
| G12.9 | Me | H | 2-CH₂OEt | OCH₂ | 5-Et | O | S |
| G12.10 | Me | H | 2-CH₂OEt | SCH₂ | 5-Et | O | S |
| G12.11 | Me | H | 2-CH₂OEt | OCH₂ | 6-Et | O | S |
| G12.12 | Me | H | 2-CH₂OEt | SCH₂ | 6-Et | O | S |
| G12.13 | Me | H | 2-CH₂OEt | OCH₂ | 4-OMe | O | S |
| G12.14 | Me | H | 2-CH₂OEt | SCH₂ | 4-OMe | O | S |
| G12.15 | Me | H | 2-CH₂OEt | OCH₂ | 5-OMe | O | S |
| G12.16 | Me | H | 2-CH₂OEt | SCH₂ | 5-OMe | O | S |
| G12.17 | Me | H | 2-CH₂OEt | OCH₂ | 6-OMe | O | S |
| G12.18 | Me | H | 2-CH₂OEt | SCH₂ | 6-OMe | O | S |
| G12.19 | Me | H | 2-CH₂OEt | OCH₂ | 7-OMe | O | S |
| G12.20 | Me | H | 2-CH₂OEt | SCH₂ | 7-OMe | O | S |
| G12.21 | Me | H | 2-CH₂OEt | OCH₂ | 5-OEt | O | S |
| G12.22 | Me | H | 2-CH₂OEt | SCH₂ | 5-OEt | O | S |
| G12.23 | Me | H | 2-CH₂OEt | OCH₂ | 6-OEt | O | S |
| G12.24 | Me | H | 2-CH₂OEt | SCH₂ | 6-OEt | O | S |
| G12.25 | Me | H | 2-CH₂OEt | OCH₂ | 4-F | O | S |
| G12.26 | Me | H | 2-CH₂OEt | SCH₂ | 4-F | O | S |
| G12.27 | Me | H | 2-CH₂OEt | OCH₂ | 5-F | O | S |
| G12.28 | Me | H | 2-CH₂OEt | SCH₂ | 5-F | O | S |
| G12.29 | Me | H | 2-CH₂OEt | OCH₂ | 6-F | O | S |
| G12.30 | Me | H | 2-CH₂OEt | SCH₂ | 6-F | O | S |
| G12.31 | Me | H | 2-CH₂OEt | OCH₂ | 7-F | O | S |
| G12.32 | Me | H | 2-CH₂OEt | SCH₂ | 7-F | O | S |
| G12.33 | Me | H | 2-CH₂OEt | OCH₂ | 5-Cl | O | S |
| G12.34 | Me | H | 2-CH₂OEt | SCH₂ | 5-Cl | O | S |
| G12.35 | Me | H | 2-CH₂OEt | OCH₂ | 6-Cl | O | S |
| G12.36 | Me | H | 2-CH₂OEt | SCH₂ | 6-Cl | O | S |
| G12.37 | Me | H | 2-CH₂OEt | OCH₂ | 4-CF₃ | O | S |
| G12.38 | Me | H | 2-CH₂OEt | SCH₂ | 4-CF₃ | O | S |
| G12.39 | Me | H | 2-CH₂OEt | OCH₂ | 5-CF₃ | O | S |
| G12.40 | Me | H | 2-CH₂OEt | SCH₂ | 5-CF₃ | O | S |
| G12.41 | Me | H | 2-CH₂OEt | OCH₂ | 6-CF₃ | O | S |
| G12.42 | Me | H | 2-CH₂OEt | SCH₂ | 6-CF₃ | O | S |
| G12.43 | Me | H | 2-CH₂OEt | OCH₂ | 7-CF₃ | O | S |
| G12.44 | Me | H | 2-CH₂OEt | SCH₂ | 7-CF₃ | O | S |
| G12.45 | Me | H | 2-CH₂OEt | OCH₂ | 5-OCF₃ | O | S |
| G12.46 | Me | H | 2-CH₂OEt | SCH₂ | 5-OCF₃ | O | S |
| G12.47 | Me | H | 2-CH₂OEt | OCH₂ | 6-OCF₃ | O | S |
| G12.48 | Me | H | 2-CH₂OEt | SCH₂ | 6-OCF₃ | O | S |
| G12.49 | Me | H | 3-CH₂OEt | OCH₂ | 4-Me | O | S |
| G12.50 | Me | H | 3-CH₂OEt | SCH₂ | 4-Me | O | S |
| G12.51 | Me | H | 3-CH₂OEt | OCH₂ | 5-Me | O | S |
| G12.52 | Me | H | 3-CH₂OEt | SCH₂ | 5-Me | O | S |
| G12.53 | Me | H | 3-CH₂OEt | OCH₂ | 6-Me | O | S |
| G12.54 | Me | H | 3-CH₂OEt | SCH₂ | 6-Me | O | S |
| G12.55 | Me | H | 3-CH₂OEt | OCH₂ | 7-Me | O | S |

TABLE 7-continued

| Compd. No. | R¹ | R² | (R³)ₙ | ACR⁴R⁵ | (R⁶)ₘ | X | Q |
|---|---|---|---|---|---|---|---|
| G12.56 | Me | H | 3-CH₂OEt | SCH₂ | 7-Me | O | S |
| G12.57 | Me | H | 3-CH₂OEt | OCH₂ | 5-Et | O | S |
| G12.58 | Me | H | 3-CH₂OEt | SCH₂ | 5-Et | O | S |
| G12.59 | Me | H | 3-CH₂OEt | OCH₂ | 6-Et | O | S |
| G12.60 | Me | H | 3-CH₂OEt | SCH₂ | 6-Et | O | S |
| G12.61 | Me | H | 3-CH₂OEt | OCH₂ | 4-OMe | O | S |
| G12.62 | Me | H | 3-CH₂OEt | SCH₂ | 4-OMe | O | S |
| G12.63 | Me | H | 3-CH₂OEt | OCH₂ | 5-OMe | O | S |
| G12.64 | Me | H | 3-CH₂OEt | SCH₂ | 5-OMe | O | S |
| G12.65 | Me | H | 3-CH₂OEt | OCH₂ | 6-OMe | O | S |
| G12.66 | Me | H | 3-CH₂OEt | SCH₂ | 6-OMe | O | S |
| G12.67 | Me | H | 3-CH₂OEt | OCH₂ | 7-OMe | O | S |
| G12.68 | Me | H | 3-CH₂OEt | SCH₂ | 7-OMe | O | S |
| G12.69 | Me | H | 3-CH₂OEt | OCH₂ | 5-OEt | O | S |
| G12.70 | Me | H | 3-CH₂OEt | SCH₂ | 5-OEt | O | S |
| G12.71 | Me | H | 3-CH₂OEt | OCH₂ | 6-OEt | O | S |
| G12.72 | Me | H | 3-CH₂OEt | SCH₂ | 6-OEt | O | S |
| G12.73 | Me | H | 3-CH₂OEt | OCH₂ | 4-F | O | S |
| G12.74 | Me | H | 3-CH₂OEt | SCH₂ | 4-F | O | S |
| G12.75 | Me | H | 3-CH₂OEt | OCH₂ | 5-F | O | S |
| G12.76 | Me | H | 3-CH₂OEt | SCH₂ | 5-F | O | S |
| G12.77 | Me | H | 3-CH₂OEt | OCH₂ | 6-F | O | S |
| G12.78 | Me | H | 3-CH₂OEt | SCH₂ | 6-F | O | S |
| G12.79 | Me | H | 3-CH₂OEt | OCH₂ | 7-F | O | S |
| G12.80 | Me | H | 3-CH₂OEt | SCH₂ | 7-F | O | S |
| G12.81 | Me | H | 3-CH₂OEt | OCH₂ | 5-Cl | O | S |
| G12.82 | Me | H | 3-CH₂OEt | SCH₂ | 5-Cl | O | S |
| G12.83 | Me | H | 3-CH₂OEt | OCH₂ | 6-Cl | O | S |
| G12.84 | Me | H | 3-CH₂OEt | SCH₂ | 6-Cl | O | S |
| G12.85 | Me | H | 3-CH₂OEt | OCH₂ | 4-CF₃ | O | S |
| G12.86 | Me | H | 3-CH₂OEt | SCH₂ | 4-CF₃ | O | S |
| G12.87 | Me | H | 3-CH₂OEt | OCH₂ | 5-CF₃ | O | S |
| G12.88 | Me | H | 3-CH₂OEt | SCH₂ | 5-CF₃ | O | S |
| G12.89 | Me | H | 3-CH₂OEt | OCH₂ | 6-CF₃ | O | S |
| G12.90 | Me | H | 3-CH₂OEt | SCH₂ | 6-CF₃ | O | S |
| G12.91 | Me | H | 3-CH₂OEt | OCH₂ | 7-CF₃ | O | S |
| G12.92 | Me | H | 3-CH₂OEt | SCH₂ | 7-CF₃ | O | S |
| G12.93 | Me | H | 3-CH₂OEt | OCH₂ | 6-OCF₃ | O | S |
| G12.94 | Me | H | 3-CH₂OEt | SCH₂ | 6-OCF₃ | O | S |
| G12.95 | Me | H | 3-CH₂OEt | OCH₂ | 7-OCF₃ | O | S |
| G12.96 | Me | H | 3-CH₂OEt | SCH₂ | 7-OCF₃ | O | S |

TABLE 8

| Compd. No. | R¹ | R² | (R³)ₙ | ACR⁴R⁵ | (R⁶)ₘ | X | Q |
|---|---|---|---|---|---|---|---|
| H1.1 | Me | H | 2-CH₂Cl | OCH₂ | 4-Me | O | S |
| H1.2 | Me | H | 2-CH₂Cl | SCH₂ | 4-Me | O | S |
| H1.3 | Me | H | 2-CH₂Cl | OCH₃ | 5-Me | O | S |
| H1.4 | Me | H | 2-CH₂Cl | SCH₂ | 5-Me | O | S |
| H1.5 | Me | H | 2-CH₂Cl | OCH₂ | 6-Me | O | S |
| H1.6 | Me | H | 2-CH₂Cl | SCH₂ | 6-Me | O | S |
| H1.7 | Me | H | 2-CH₂Cl | OCH₂ | 7-Me | O | S |
| H1.8 | Me | H | 2-CH₂Cl | SCH₂ | 7-Me | O | S |
| H1.9 | Me | H | 2-CH₂Cl | OCH₂ | 5-Et | O | S |
| H1.10 | Me | H | 2-CH₂Cl | SCH₂ | 5-Et | O | S |
| H1.11 | Me | H | 2-CH₂Cl | OCH₂ | 6-Et | O | S |
| H1.12 | Me | H | 2-CH₂Cl | SCH₂ | 6-Et | O | S |
| H1.13 | Me | H | 2-CH₂Cl | OCH₂ | 4-OMe | O | S |
| H1.14 | Me | H | 2-CH₂Cl | SCH₂ | 4-OMe | O | S |
| H1.15 | Me | H | 2-CH₂Cl | OCH₂ | 5-OMe | O | S |
| H1.16 | Me | H | 2-CH₂Cl | SCH₂ | 5-OMe | O | S |
| H1.17 | Me | H | 2-CH₂Cl | OCH₂ | 6-OMe | O | S |
| H1.18 | Me | H | 2-CH₂Cl | SCH₂ | 6-OMe | O | S |
| H1.19 | Me | H | 2-CH₂Cl | OCH₂ | 7-OMe | O | S |
| H1.20 | Me | H | 2-CH₂Cl | SCH₂ | 7-OMe | O | S |
| H1.21 | Me | H | 2-CH₂Cl | OCH₂ | 5-OEt | O | S |
| H1.22 | Me | H | 2-CH₂Cl | SCH₂ | 5-OEt | O | S |
| H1.23 | Me | H | 2-CH₂Cl | OCH₂ | 6-OEt | O | S |
| H1.24 | Me | H | 2-CH₂Cl | SCH₂ | 6-OEt | O | S |
| H1.25 | Me | H | 2-CH₂Cl | OCH₂ | 4-F | O | S |
| H1.26 | Me | H | 2-CH₂Cl | SCH₂ | 4-F | O | S |

TABLE 8-continued

| Compd. No. | R¹ | R² | (R³)ₙ | ACR⁴R⁵ | (R⁶)ₘ | X | Q |
|---|---|---|---|---|---|---|---|
| H1.27 | Me | H | 2-CH₂Cl | OCH₂ | 5-F | O | S |
| H1.28 | Me | H | 2-CH₂Cl | SCH₂ | 5-F | O | S |
| H1.29 | Me | H | 2-CH₂Cl | OCH₂ | 6-F | O | S |
| H1.30 | Me | H | 2-CH₂Cl | SCH₂ | 6-F | O | S |
| H1.31 | Me | H | 2-CH₂Cl | OCH₂ | 7-F | O | S |
| H1.32 | Me | H | 2-CH₂Cl | SCH₂ | 7-F | O | S |
| H1.33 | Me | H | 2-CH₂Cl | OCH₂ | 5-Cl | O | S |
| H1.34 | Me | H | 2-CH₂Cl | SCH₂ | 5-Cl | O | S |
| H1.35 | Me | H | 2-CH₂Cl | OCH₂ | 6-Cl | O | S |
| H1.36 | Me | H | 2-CH₂Cl | SCH₂ | 6-Cl | O | S |
| H1.37 | Me | H | 2-CH₂Cl | OCH₂ | 4-CF₃ | O | S |
| H1.38 | Me | H | 2-CH₂Cl | SCH₂ | 4-CF₃ | O | S |
| H1.39 | Me | H | 2-CH₂Cl | OCH₂ | 5-CF₃ | O | S |
| H1.40 | Me | H | 2-CH₂Cl | SCH₂ | 5-CF₃ | O | S |
| H1.41 | Me | H | 2-CH₂Cl | OCH₂ | 6-CF₃ | O | S |
| H1.42 | Me | H | 2-CH₂Cl | SCH₂ | 6-CF₃ | O | S |
| H1.43 | Me | H | 2-CH₂Cl | OCH₂ | 7-CF₃ | O | S |
| H1.44 | Me | H | 2-CH₂Cl | SCH₂ | 7-CF₃ | O | S |
| H1.45 | Me | H | 2-CH₂Cl | OCH₂ | 5-OCF₃ | O | S |
| H1.46 | Me | H | 2-CH₂Cl | SCH₂ | 5-OCF₃ | O | S |
| H1.47 | Me | H | 2-CH₂Cl | OCH₂ | 6-OCF₃ | O | S |
| H1.48 | Me | H | 2-CH₂Cl | SCH₂ | 6-OCF₃ | O | S |
| H1.49 | Me | H | 3-CH₂Cl | OCH₂ | 4-Me | O | S |
| H1.50 | Me | H | 3-CH₂Cl | SCH₂ | 4-Me | O | S |
| H1.51 | Me | H | 3-CH₂Cl | OCH₂ | 5-Me | O | S |
| H1.52 | Me | H | 3-CH₂Cl | SCH₂ | 5-Me | O | S |
| H1.53 | Me | H | 3-CH₂Cl | OCH₂ | 6-Me | O | S |
| H1.54 | Me | H | 3-CH₂Cl | SCH₂ | 6-Me | O | S |
| H1.55 | Me | H | 3-CH₂Cl | OCH₂ | 7-Me | O | S |
| H1.56 | Me | H | 3-CH₂Cl | SCH₂ | 7-Me | O | S |
| H1.57 | Me | H | 3-CH₂Cl | OCH₂ | 5-Et | O | S |
| H1.58 | Me | H | 3-CH₂Cl | SCH₂ | 5-Et | O | S |
| H1.59 | Me | H | 3-CH₂Cl | OCH₂ | 6-Et | O | S |
| H1.60 | Me | H | 3-CH₂Cl | SCH₂ | 6-Et | O | S |
| H1.61 | Me | H | 3-CH₂Cl | OCH₂ | 4-OMe | O | S |
| H1.62 | Me | H | 3-CH₂Cl | SCH₂ | 4-OMe | O | S |
| H1.63 | Me | H | 3-CH₂Cl | OCH₂ | 5-OMe | O | S |
| H1.64 | Me | H | 3-CH₂Cl | SCH₂ | 5-OMe | O | S |
| H1.65 | Me | H | 3-CH₂Cl | OCH₂ | 6-OMe | O | S |
| H1.66 | Me | H | 3-CH₂Cl | SCH₂ | 6-OMe | O | S |
| H1.67 | Me | H | 3-CH₂Cl | OCH₂ | 7-OMe | O | S |
| H1.68 | Me | H | 3-CH₂Cl | SCH₂ | 7-OMe | O | S |
| H1.69 | Me | H | 3-CH₂Cl | OCH₂ | 5-OEt | O | S |
| H1.70 | Me | H | 3-CH₂Cl | SCH₂ | 5-OEt | O | S |
| H1.71 | Me | H | 3-CH₂Cl | OCH₂ | 6-OEt | O | S |
| H1.72 | Me | H | 3-CH₂Cl | SCH₂ | 6-OEt | O | S |
| H1.73 | Me | H | 3-CH₂Cl | OCH₂ | 4-F | O | S |
| H1.74 | Me | H | 3-CH₂Cl | SCH₂ | 4-F | O | S |
| H1.75 | Me | H | 3-CH₂Cl | OCH₂ | 5-F | O | S |
| H1.76 | Me | H | 3-CH₂Cl | SCH₂ | 5-F | O | S |
| H1.77 | Me | H | 3-CH₂Cl | OCH₂ | 6-F | O | S |
| H1.78 | Me | H | 3-CH₂Cl | SCH₂ | 6-F | O | S |
| H1.79 | Me | H | 3-CH₂Cl | OCH₂ | 7-F | O | S |
| H1.80 | Me | H | 3-CH₂Cl | SCH₂ | 7-F | O | S |
| H1.81 | Me | H | 3-CH₂Cl | OCH₂ | 5-Cl | O | S |
| H1.83 | Me | H | 3-CH₂Cl | SCH₂ | 5-Cl | O | S |
| H1.84 | Me | H | 3-CH₂Cl | OCH₂ | 6-Cl | O | S |
| H1.85 | Me | H | 3-CH₂Cl | SCH₂ | 6-Cl | O | S |
| H1.86 | Me | H | 3-CH₂Cl | OCH₂ | 4-CF₃ | O | S |
| H1.87 | Me | H | 3-CH₂Cl | SCH₂ | 4-CF₃ | O | S |
| H1.88 | Me | H | 3-CH₂Cl | OCH₂ | 5-CF₃ | O | S |
| H1.89 | Me | H | 3-CH₂Cl | SCH₂ | 5-CF₃ | O | S |
| H1.90 | Me | H | 3-CH₂Cl | OCH₂ | 6-CF₃ | O | S |
| H1.91 | Me | H | 3-CH₂Cl | OCH₂ | 6-CF₃ | O | S |
| H1.92 | Me | H | 3-CH₂Cl | OCH₂ | 7-CF₃ | O | S |
| H1.93 | Me | H | 3-CH₂Cl | SCH₂ | 7-CF₃ | O | S |
| H1.94 | Me | H | 3-CH₂Cl | OCH₂ | 5-OCF₃ | O | S |
| H1.95 | Me | H | 3-CH₂Cl | SCH₂ | 5-OCF₃ | O | S |
| H1.96 | Me | H | 3-CH₂Cl | OCH₂ | 6-OCF₃ | O | S |
| H1.97 | Me | H | 3-CH₂Cl | SCH₂ | 6-OCF₃ | O | S |
| H2.1 | Me | H | 2-CH₂Br | OCH₂ | 4-Me | O | S |
| H2.2 | Me | H | 2-CH₂Br | SCH₂ | 4-Me | O | S |
| H2.3 | Me | H | 2-CH₂Br | OCH₂ | 5-Me | O | S |
| H2.4 | Me | H | 2-CH₂Br | SCH₂ | 5-Me | O | S |
| H2.5 | Me | H | 2-CH₂Br | OCH₂ | 6-Me | O | S |
| H2.6 | Me | H | 2-CH₂Br | SCH₂ | 6-Me | O | S |
| H2.7 | Me | H | 2-CH₂Br | OCH₂ | 7-Me | O | S |
| H2.8 | Me | H | 2-CH₂Br | SCH₂ | 7-Me | O | S |
| H2.9 | Me | H | 2-CH₂Br | OCH₂ | 5-Et | O | S |
| H2.10 | Me | H | 2-CH₂Br | SCH₂ | 5-Et | O | S |
| H2.11 | Me | H | 2-CH₂Br | OCH₂ | 6-Et | O | S |
| H2.12 | Me | H | 2-CH₂Br | SCH₂ | 6-Et | O | S |
| H2.13 | Me | H | 2-CH₂Br | OCH₂ | 4-OMe | O | S |
| H2.14 | Me | H | 2-CH₂Br | SCH₂ | 4-OMe | O | S |
| H2.15 | Me | H | 2-CH₂Br | OCH₂ | 5-OMe | O | S |
| H2.16 | Me | H | 2-CH₂Br | SCH₂ | 5-OMe | O | S |
| H2.17 | Me | H | 2-CH₂Br | OCH₂ | 6-OMe | O | S |
| H2.18 | Me | H | 2-CH₂Br | SCH₂ | 6-OMe | O | S |
| H2.19 | Me | H | 2-CH₂Br | OCH₂ | 7-OMe | O | S |
| H2.20 | Me | H | 2-CH₂Br | SCH₂ | 7-OMe | O | S |
| H2.21 | Me | H | 2-CH₂Br | OCH₂ | 5-OEt | O | S |
| H2.22 | Me | H | 2-CH₂Br | SCH₂ | 5-OEt | O | S |
| H2.23 | Me | H | 2-CH₂Br | OCH₂ | 6-OEt | O | S |
| H2.24 | Me | H | 2-CH₂Br | SCH₂ | 6-OEt | O | S |
| H2.25 | Me | H | 2-CH₂Br | OCH₂ | 4-F | O | S |
| H2.26 | Me | H | 2-CH₂Br | SCH₂ | 4-F | O | S |
| H2.27 | Me | H | 2-CH₂Br | OCH₂ | 5-F | O | S |
| H2.28 | Me | H | 2-CH₂Br | SCH₂ | 5-F | O | S |
| H2.29 | Me | H | 2-CH₂Br | OCH₂ | 6-F | O | S |
| H2.30 | Me | H | 2-CH₂Br | SCH₂ | 6-F | O | S |
| H2.31 | Me | H | 2-CH₂Br | OCH₂ | 7-F | O | S |
| H2.32 | Me | H | 2-CH₂Br | SCH₂ | 7-F | O | S |
| H2.33 | Me | H | 2-CH₂Br | OCH₂ | 5-Cl | O | S |
| H2.34 | Me | H | 2-CH₂Br | SCH₂ | 5-Cl | O | S |
| H2.35 | Me | H | 2-CH₂Br | OCH₂ | 6-Cl | O | S |
| H2.36 | Me | H | 2-CH₂Br | SCH₂ | 6-Cl | O | S |
| H2.37 | Me | H | 2-CH₂Br | OCH₂ | 4-CF₃ | O | S |
| H2.38 | Me | H | 2-CH₂Br | SCH₂ | 4-CF₃ | O | S |
| H2.39 | Me | H | 2-CH₂Br | OCH₂ | 5-CF₃ | O | S |
| H2.40 | Me | H | 2-CH₂Br | SCH₂ | 5-CF₃ | O | S |
| H2.41 | Me | H | 2-CH₂Br | OCH₂ | 6-CF₃ | O | S |
| H2.42 | Me | H | 2-CH₂Br | SCH₂ | 6-CF₃ | O | S |
| H2.43 | Me | H | 2-CH₂Br | OCH₂ | 7-CF₃ | O | S |
| H2.44 | Me | H | 2-CH₂Br | SCH₂ | 7-CF₃ | O | S |
| H2.45 | Me | H | 2-CH₂Br | OCH₂ | 5-OCF₃ | O | S |
| H2.46 | Me | H | 2-CH₂Br | SCH₂ | 5-OCF₃ | O | S |
| H2.47 | Me | H | 2-CH₂Br | OCH₂ | 6-OCF₃ | O | S |
| H2.48 | Me | H | 2-CH₂Br | SCH₂ | 6-OCF₃ | O | S |
| H2.49 | Me | H | 3-CH₂Br | OCH₂ | 4-Me | O | S |
| H2.50 | Me | H | 3-CH₂Br | SCH₂ | 4-Me | O | S |
| H2.51 | Me | H | 3-CH₂Br | OCH₂ | 5-Me | O | S |
| H2.52 | Me | H | 3-CH₂Br | SCH₂ | 5-Me | O | S |
| H2.53 | Me | H | 3-CH₂Br | OCH₂ | 6-Me | O | S |
| H2.54 | Me | H | 3-CH₂Br | SCH₂ | 6-Me | O | S |
| H2.55 | Me | H | 3-CH₂Br | OCH₂ | 7-Me | O | S |
| H2.56 | Me | H | 3-CH₂Br | SCH₂ | 7-Me | O | S |
| H2.57 | Me | H | 3-CH₂Br | OCH₂ | 5-Et | O | S |
| H2.58 | Me | H | 3-CH₂Br | OCH₂ | 5-Et | O | S |
| H2.59 | Me | H | 3-CH₂Br | OCH₂ | 6-Et | O | S |
| H2.60 | Me | H | 3-CH₂Br | SCH₂ | 6-Et | O | S |
| H2.61 | Me | H | 3-CH₂Br | OCH₂ | 4-OMe | O | S |
| H2.62 | Me | H | 3-CH₂Br | OCH₂ | 4-OMe | O | S |
| H2.63 | Me | H | 3-CH₂Br | OCH₂ | 5-OMe | O | S |
| H2.64 | Me | H | 3-CH₂Br | SCH₂ | 5-OMe | O | S |
| H2.65 | Me | H | 3-CH₂Br | OCH₂ | 6-OMe | O | S |
| H2.66 | Me | H | 3-CH₂Br | SCH₂ | 6-OMe | O | S |
| H2.67 | Me | H | 3-CH₂Br | OCH₂ | 7-OMe | O | S |
| H2.68 | Me | H | 3-CH₂Br | SCH₂ | 7-OMe | O | S |
| H2.70 | Me | H | 3-CH₂Br | OCH₂ | 5-OEt | O | S |
| H2.71 | Me | H | 3-CH₂Br | SCH₂ | 5-OEt | O | S |
| H2.72 | Me | H | 3-CH₂Br | OCH₂ | 6-OEt | O | S |
| H2.73 | Me | H | 3-CH₂Br | SCH₂ | 6-OEt | O | S |
| H2.74 | Me | H | 3-CH₂Br | OCH₂ | 4-F | O | S |
| H2.75 | Me | H | 3-CH₂Br | OCH₂ | 4-F | O | S |
| H2.76 | Me | H | 3-CH₂Br | OCH₂ | 5-F | O | S |
| H2.77 | Me | H | 3-CH₂Br | SCH₂ | 5-F | O | S |
| H2.78 | Me | H | 3-CH₂Br | OCH₂ | 6-F | O | S |
| H2.79 | Me | H | 3-CH₂Br | SCH₂ | 6-F | O | S |
| H2.80 | Me | H | 3-CH₂Br | OCH₂ | 7-F | O | S |
| H2.81 | Me | H | 3-CH₂Br | SCH₂ | 7-F | O | S |
| H2.82 | Me | H | 3-CH₂Br | OCH₂ | 5-Cl | O | S |
| H2.83 | Me | H | 3-CH₂Br | SCH₂ | 5-Cl | O | S |

TABLE 8-continued

| Compd. No. | R¹ | R² | (R³)ₙ | ACR⁴R⁵ | (R⁶)ₘ | X | Q |
|---|---|---|---|---|---|---|---|
| H2.84 | Me | H | 3-CH₂Br | OCH₂ | 6-Cl | O | S |
| H2.85 | Me | H | 3-CH₂Br | SCH₂ | 6-Cl | O | S |
| H2.86 | Me | H | 3-CH₂Br | OCH₂ | 4-CF₃ | O | S |
| H2.87 | Me | H | 3-CH₂Br | SCH₂ | 4-CF₃ | O | S |
| H2.88 | Me | H | 3-CH₂Br | OCH₂ | 5-CF₃ | O | S |
| H2.89 | Me | H | 3-CH₂Br | SCH₂ | 5-CF₃ | O | S |
| H2.90 | Me | H | 3-CH₂Br | OCH₂ | 6-CF₃ | O | S |
| H2.91 | Me | H | 3-CH₂Br | SCH₂ | 6-CF₃ | O | S |
| H2.92 | Me | H | 3-CH₂Br | OCH₂ | 7-CF₃ | O | S |
| H2.93 | Me | H | 3-CH₂Br | SCH₂ | 7-CF₃ | O | S |
| H2.94 | Me | H | 3-CH₂Br | OCH₂ | 5-OCF₃ | O | S |
| H2.95 | Me | H | 3-CH₂Br | SCH₂ | 5-OCF₃ | O | S |
| H2.96 | Me | H | 3-CH₂Br | OCH₂ | 6-OCF₃ | O | S |
| H2.97 | Me | H | 3-CH₂Br | SCH₂ | 6-OCF₃ | O | S |
| H3.1 | Me | H | 2-F | OCH₂ | 4-Me | O | S |
| H3.2 | Me | H | 2-F | SCH₂ | 4-Me | O | S |
| H3.3 | MeO | H | 2-F | OCH₂ | 4-Me | O | S |
| H3.4 | Me | H | 2-F | OCH₂ | 5-Me | O | S |
| H3.5 | Me | H | 2-F | SCH₂ | 5-Me | O | S |
| H3.6 | MeO | H | 2-F | OCH₃ | 5-Me | O | S |
| H3.7 | MeO | H | 2-F | OCH₂ | 5-Me | O | O |
| H3.8 | Me | H | 2-F | OCH₂ | 6-Me | O | S |
| H3.9 | Me | H | 2-F | SCH₂ | 6-Me | O | S |
| H3.10 | MeO | H | 2-F | OCH₂ | 6-Me | O | S |
| H3.11 | MeO | H | 2-F | OCH₂ | 6-Me | O | O |
| H3.12 | Me | H | 2-F | OCH₂ | 7-Me | O | S |
| H3.13 | Me | H | 2-F | SCH₂ | 7-Me | O | S |
| H3.14 | MeO | H | 2-F | OCH₂ | 7-Me | O | S |
| H3.15 | Me | H | 2-F | OCH₂ | 5-Et | O | S |
| H3.16 | Me | H | 2-F | SCH₂ | 5-Et | O | S |
| H3.17 | MeO | H | 2-F | OCH₂ | 5-Et | O | S |
| H3.18 | MeO | H | 2-F | SCH₂ | 5-Et | O | S |
| H3.19 | Me | H | 2-F | OCH₂ | 6-Et | O | S |
| H3.20 | Me | H | 2-F | SCH₂ | 6-Et | O | S |
| H3.21 | MeO | H | 2-F | OCH₂ | 6-Et | O | S |
| H3.22 | MeO | H | 2-F | SCH₂ | 6-Et | O | S |
| H3.23 | Me | H | 2-F | OCH₂ | 4-F | O | S |
| H3.24 | Me | H | 2-F | SCH₂ | 4-F | O | S |
| H3.25 | MeO | H | 2-F | OCH₂ | 4-F | O | S |
| H3.26 | Me | H | 2-F | OCH₂ | 5-F | O | S |
| H3.27 | Me | H | 2-F | SCH₂ | 5-F | O | S |
| H3.28 | MeO | H | 2-F | OCH₂ | 5-F | O | S |
| H3.29 | MeO | H | 2-F | SCH₂ | 5-F | O | S |
| H3.30 | MeO | H | 2-F | OCH₂ | 5-F | O | O |
| H3.31 | MeO | H | 2-F | SCH₂ | 5-F | O | O |
| H3.32 | Me | H | 2-F | OCH₂ | 6-F | O | S |
| H3.33 | Me | H | 2-F | SCH₂ | 6-F | O | S |
| H3.34 | MeO | H | 2-F | OCH₂ | 6-F | O | S |
| H3.35 | MeO | H | 2-F | OCH₂ | 6-F | O | O |
| H3.36 | Me | H | 2-F | OCH₂ | 7-F | O | S |
| H3.37 | Me | H | 2-F | SCH₂ | 7-F | O | S |
| H3.38 | MeO | H | 2-F | OCH₂ | 7-F | O | S |
| H3.39 | MeO | H | 2-F | OCH₂ | 7-F | O | O |
| H3.40 | Me | H | 2-F | OCH₂ | 5-Cl | O | S |
| H3.41 | Me | H | 2-F | SCH₂ | 5-Cl | O | S |
| H3.42 | Me | H | 2-F | OCH₂ | 6-Cl | O | S |
| H3.43 | Me | H | 2-F | SCH₂ | 6-Cl | O | S |
| H3.44 | Me | H | 2-F | OCH₂ | 4-OMe | O | S |
| H3.45 | Me | H | 2-F | SCH₂ | 4-OMe | O | S |
| H3.46 | Me | H | 2-F | OCH₂ | 5-OMe | O | S |
| H3.47 | Me | H | 2-F | SCH₂ | 5-OMe | O | S |
| H3.48 | MeO | H | 2-F | OCH₂ | 5-OMe | O | S |
| H3.49 | Me | H | 2-F | OCH₂ | 6-OMe | O | S |
| H3.50 | Me | H | 2-F | SCH₂ | 6-OMe | O | S |
| H3.51 | MeO | H | 2-F | OCH₂ | 6-OMe | O | S |
| H3.52 | Me | H | 2-F | OCH₂ | 6-OMe | O | O |
| H3.53 | MeO | H | 2-F | OCH₂ | 6-OMe | O | O |
| H3.54 | Me | H | 2-F | OCH₂ | 7-OMe | O | S |
| H3.55 | Me | H | 2-F | SCH₂ | 7-OMe | O | S |
| H3.56 | Me | H | 2-F | OCH₂ | 5-OEt | O | S |
| H3.57 | Me | H | 2-F | SCH₂ | 5-OEt | O | S |
| H3.58 | Me | H | 2-F | OCH₂ | 6-OEt | O | S |
| H3.59 | Me | H | 2-F | SCH₂ | 6-OEt | O | S |
| H3.60 | Me | H | 2-F | OCH₂ | 4-CF₃ | O | S |
| H3.61 | Me | H | 2-F | SCH₂ | 4-CF₃ | O | S |
| H3.62 | Me | H | 2-F | OCH₂ | 5-CF₃ | O | S |
| H3.63 | Me | H | 2-F | SCH₂ | 5-CF₃ | O | S |
| H3.64 | MeO | H | 2-F | OCH₂ | 5-CF₃ | O | S |
| H3.65 | Me | H | 2-F | OCH₂ | 6-CF₃ | O | S |
| H3.66 | Me | H | 2-F | SCH₂ | 6-CF₃ | O | S |
| H3.67 | Me | H | 2-F | OCH₂ | 7-CF₃ | O | S |
| H3.68 | Me | H | 2-F | SCH₂ | 7-CF₃ | O | S |
| H3.69 | Me | H | 2-F | OCH₂ | 5-OCF₃ | O | S |
| H3.70 | Me | H | 2-F | SCH₂ | 5-OCF₃ | O | S |
| H3.71 | Me | H | 2-F | OCH₂ | 6-OCF₃ | O | S |
| H3.72 | Me | H | 2-F | SCH₂ | 6-OCF₃ | O | S |
| H3.73 | Me | H | 3-F | OCH₂ | 4-Me | O | S |
| H3.74 | Me | H | 3-F | SCH₂ | 4-Me | O | S |
| H3.75 | Me | H | 3-F | OCH₂ | 5-Me | O | S |
| H3.76 | Me | H | 3-F | SCH₂ | 5-Me | O | S |
| H3.77 | Me | H | 3-F | OCH₂ | 6-Me | O | S |
| H3.78 | Me | H | 3-F | SCH₂ | 6-Me | O | S |
| H3.79 | Me | H | 3-F | OCH₂ | 7-Me | O | S |
| H3.80 | Me | H | 3-F | SCH₂ | 7-Me | O | S |
| H3.81 | Me | H | 3-F | OCH₂ | 5-Et | O | S |
| H3.82 | Me | H | 3-F | SCH₂ | 5-Et | O | S |
| H3.83 | Me | H | 3-F | OCH₂ | 6-Et | O | S |
| H3.84 | Me | H | 3-F | SCH₂ | 6-Et | O | S |
| H3.85 | Me | H | 3-F | OCH₂ | 4-OMe | O | S |
| H3.86 | Me | H | 3-F | SCH₂ | 4-OMe | O | S |
| H3.87 | Me | H | 3-F | OCH₂ | 5-OMe | O | S |
| H3.88 | Me | H | 3-F | SCH₂ | 5-OMe | O | S |
| H3.89 | Me | H | 3-F | OCH₂ | 6-OMe | O | S |
| H3.90 | Me | H | 3-F | SCH₂ | 6-OMe | O | S |
| H3.91 | Me | H | 3-F | OCH₂ | 7-OMe | O | S |
| H3.92 | Me | H | 3-F | SCH₂ | 7-OMe | O | S |
| H3.93 | Me | H | 3-F | OCH₂ | 5-OEt | O | S |
| H3.94 | Me | H | 3-F | SCH₂ | 5-OEt | O | S |
| H3.95 | Me | H | 3-F | OCH₂ | 6-OEt | O | S |
| H3.96 | Me | H | 3-F | SCH₂ | 6-OEt | O | S |
| H3.97 | Me | H | 3-F | OCH₂ | 4-F | O | S |
| H3.98 | Me | H | 3-F | SCH₂ | 4-F | O | S |
| H3.99 | Me | H | 3-F | OCH₂ | 5-F | O | S |
| H3.100 | Me | H | 3-F | SCH₂ | 5-F | O | S |
| H3.101 | Me | H | 3-F | OCH₂ | 6-F | O | S |
| H3.102 | Me | H | 3-F | SCH₂ | 6-F | O | S |
| H3.103 | Me | H | 3-F | OCH₂ | 7-F | O | S |
| H3.104 | Me | H | 3-F | SCH₂ | 7-F | O | S |
| H3.105 | Me | H | 3-F | OCH₂ | 5-Cl | O | S |
| H3.106 | Me | H | 3-F | SCH₂ | 5-Cl | O | S |
| H3.107 | Me | H | 3-F | OCH₂ | 6-Cl | O | S |
| H3.108 | Me | H | 3-F | SCH₂ | 6-Cl | O | S |
| H3.109 | Me | H | 3-F | OCH₂ | 4-CF₃ | O | S |
| H3.110 | Me | H | 3-F | SCH₂ | 4-CF₃ | O | S |
| H3.111 | Me | H | 3-F | OCH₂ | 5-CF₃ | O | S |
| H3.112 | Me | H | 3-F | SCH₂ | 5-CF₃ | O | S |
| H3.113 | Me | H | 3-F | OCH₂ | 6-CF₃ | O | S |
| H3.114 | Me | H | 3-F | SCH₂ | 6-CF₃ | O | S |
| H3.115 | Me | H | 3-F | OCH₂ | 7-CF₃ | O | S |
| H3.116 | Me | H | 3-F | SCH₂ | 7-CF₃ | O | S |
| H3.117 | Me | H | 3-F | OCH₂ | 5-OCF₃ | O | S |
| H3.118 | Me | H | 3-F | SCH₂ | 5-OCF₃ | O | S |
| H3.119 | Me | H | 3-F | OCH₂ | 6-OCF₃ | O | S |
| H3.120 | Me | H | 3-F | SCH₂ | 6-OCF₃ | O | S |
| H4.1 | Me | H | 2-Cl | OCH₂ | 4-Me | O | S |
| H4.2 | Me | H | 2-Cl | SCH₂ | 4-Me | O | S |
| H4.3 | Me | H | 2-Cl | OCH₂ | 5-Me | O | S |
| H4.4 | Me | H | 2-Cl | SCH₂ | 5-Me | O | S |
| H4.5 | MeO | H | 2-Cl | OCH₂ | 5-Me | O | S |
| H4.6 | Me | H | 2-Cl | OCH₂ | 5-Me | O | O |
| H4.7 | MeO | H | 2-Cl | OCH₂ | 5-Me | O | O |
| H4.8 | Me | H | 2-Cl | OCH₂ | 6-Me | O | S |
| H4.9 | Me | H | 2-Cl | SCH₂ | 6-Me | O | S |
| H4.10 | MeO | H | 2-Cl | OCH₂ | 6-Me | O | S |
| H4.11 | Me | H | 2-Cl | OCH₂ | 7-Me | O | S |
| H4.12 | Me | H | 2-Cl | SCH₂ | 7-Me | O | S |
| H4.13 | Me | H | 2-Cl | OCH₂ | 5-Et | O | S |
| H4.14 | Me | H | 2-Cl | SCH₂ | 5-Et | O | S |
| H4.15 | Me | H | 2-Cl | OCH₂ | 6-Et | O | S |
| H4.16 | Me | H | 2-Cl | SCH₂ | 6-Et | O | S |
| H4.17 | Me | H | 2-Cl | OCH₂ | 4-OMe | O | S |
| H4.18 | Me | H | 2-Cl | SCH₂ | 4-OMe | O | S |

TABLE 8-continued

| Compd. No. | R¹ | R² | (R³)$_n$ | ACR⁴R⁵ | (R⁶)$_m$ | X | Q |
|---|---|---|---|---|---|---|---|
| H4.19 | Me | H | 2-Cl | OCH$_2$ | 5-OMe | O | S |
| H4.20 | Me | H | 2-Cl | SCH$_2$ | 5-OMe | O | S |
| H4.21 | MeO | H | 2-Cl | OCH$_2$ | 5-OMe | O | S |
| H4.22 | Me | H | 2-Cl | OCH$_2$ | 6-OMe | O | S |
| H4.23 | Me | H | 2-Cl | SCH$_2$ | 6-OMe | O | S |
| H4.24 | MeO | H | 2-Cl | OCH$_2$ | 6-OMe | O | S |
| H4.25 | Me | H | 2-Cl | OCH$_2$ | 6-OMe | O | O |
| H4.26 | MeO | H | 2-Cl | OCH$_2$ | 6-OMe | O | O |
| H4.27 | Me | H | 2-Cl | OCH$_2$ | 7-OMe | O | S |
| H4.28 | Me | H | 2-Cl | SCH$_2$ | 7-OMe | O | S |
| H4.29 | Me | H | 2-Cl | OCH$_2$ | 5-OEt | O | S |
| H4.30 | Me | H | 2-Cl | SCH$_2$ | 5-OEt | O | S |
| H4.31 | Me | H | 2-Cl | OCH$_2$ | 6-OEt | O | S |
| H4.32 | Me | H | 2-Cl | SCH$_2$ | 6-OEt | O | S |
| H4.33 | Me | H | 2-Cl | OCH$_2$ | 4-F | O | S |
| H4.34 | Me | H | 2-Cl | SCH$_2$ | 4-F | O | S |
| H4.35 | Me | H | 2-Cl | OCH$_2$ | 5-F | O | S |
| H4.36 | Me | H | 2-Cl | SCH$_2$ | 5-F | O | S |
| H4.37 | MeO | H | 2-Cl | OCH$_2$ | 5-F | O | S |
| H4.38 | Me | H | 2-Cl | OCH$_2$ | 6-F | O | S |
| H4.39 | Me | H | 2-Cl | SCH$_2$ | 6-F | O | S |
| H4.40 | MeO | H | 2-Cl | OCH$_2$ | 6-F | O | S |
| H4.41 | Me | H | 2-Cl | OCH$_2$ | 7-F | O | S |
| H4.42 | Me | H | 2-Cl | SCH$_2$ | 7-F | O | S |
| H4.43 | Me | H | 2-Cl | OCH$_2$ | 5-Cl | O | S |
| H4.44 | Me | H | 2-Cl | SCH$_2$ | 5-Cl | O | S |
| H4.45 | MeO | H | 2-Cl | OCH$_2$ | 5-Cl | O | S |
| H4.46 | Me | H | 2-Cl | OCH$_2$ | 6-Cl | O | S |
| H4.47 | Me | H | 2-Cl | SCH$_2$ | 6-Cl | O | S |
| H4.48 | Me | H | 2-Cl | OCH$_2$ | 4-CF$_3$ | O | S |
| H4.49 | Me | H | 2-Cl | SCH$_2$ | 4-CF$_3$ | O | S |
| H4.50 | Me | H | 2-Cl | OCH$_2$ | 5-CF$_3$ | O | S |
| H4.51 | Me | H | 2-Cl | SCH$_2$ | 5-CF$_3$ | O | S |
| H4.52 | MeO | H | 2-Cl | OCH$_2$ | 5-CF$_3$ | O | S |
| H4.53 | Me | H | 2-Cl | OCH$_2$ | 6-CF$_3$ | O | S |
| H4.54 | Me | H | 2-Cl | SCH$_2$ | 6-CF$_3$ | O | S |
| H4.55 | Me | H | 2-Cl | OCH$_2$ | 7-CF$_3$ | O | S |
| H4.56 | Me | H | 2-Cl | SCH$_2$ | 7-CF$_3$ | O | S |
| H4.57 | Me | H | 2-Cl | OCH$_2$ | 5-OCF$_3$ | O | S |
| H4.58 | Me | H | 2-Cl | SCH$_2$ | 5-OCF$_3$ | O | S |
| H4.59 | Me | H | 2-Cl | OCH$_2$ | 6-OCF$_3$ | O | S |
| H4.60 | Me | H | 2-Cl | SCH$_2$ | 6-OCF$_3$ | O | S |
| H4.61 | Me | H | 2-Cl | OCH$_2$ | 4,5-diMe | O | S |
| H4.62 | Me | H | 2-Cl | SCH$_2$ | 4,5-diMe | O | S |
| H4.63 | Me | H | 2-Cl | OCH$_2$ | 4,6-diMe | O | S |
| H4.64 | Me | H | 2-Cl | SCH$_2$ | 4,6-diMe | O | S |
| H4.65 | Me | H | 2-Cl | OCH$_2$ | 4,7-diMe | O | S |
| H4.66 | Me | H | 2-Cl | SCH$_2$ | 4,7-diMe | O | S |
| H4.67 | Me | H | 2-Cl | OCH$_2$ | 5,6-diMe | O | S |
| H4.68 | Me | H | 2-Cl | SCH$_2$ | 5,6-diMe | O | S |
| H4.69 | Me | H | 2-Cl | OCH$_2$ | 5,7-diMe | O | S |
| H4.70 | Me | H | 2-Cl | SCH$_2$ | 5-7-diMe | O | S |
| H4.71 | Me | H | 2-Cl | OCH$_2$ | 6,7-diMe | O | S |
| H4.72 | Me | H | 2-Cl | SCH$_2$ | 6,7-diMe | O | S |
| H4.73 | Me | H | 2-Cl | OCH$_2$ | 4,5-diOMe | O | S |
| H4.74 | Me | H | 2-Cl | SCH$_2$ | 4,5-diOMe | O | S |
| H4.75 | Me | H | 2-Cl | OCH$_2$ | 4,6-diOMe | O | S |
| H4.76 | Me | H | 2-Cl | SCH$_2$ | 4,6-diOMe | O | S |
| H4.77 | Me | H | 2-Cl | OCH$_2$ | 4,7-diOMe | O | S |
| H4.78 | Me | H | 2-Cl | SCH$_2$ | 4,7-diOMe | O | S |
| H4.79 | Me | H | 2-Cl | OCH$_2$ | 5,6-diOMe | O | S |
| H4.80 | Me | H | 2-Cl | SCH$_2$ | 5,6-diOMe | O | S |
| H4.81 | Me | H | 2-Cl | OCH$_2$ | 5,7-diOMe | O | S |
| H4.82 | Me | H | 2-Cl | SCH$_2$ | 5,7-diOMe | O | S |
| H4.83 | Me | H | 2-Cl | OCH$_2$ | 6,7-diOMe | O | S |
| H4.84 | Me | H | 2-Cl | SCH$_2$ | 6,7-diOMe | O | S |
| H4.85 | Me | H | 2-Cl | OCH$_2$ | 4,5-diF | O | S |
| H4.86 | Me | H | 2-Cl | SCH$_2$ | 4,5-diF | O | S |
| H4.87 | Me | H | 2-Cl | OCH$_2$ | 4,6-diF | O | S |
| H4.88 | Me | H | 2-Cl | SCH$_2$ | 4,6-diF | O | S |
| H4.89 | Me | H | 2-Cl | OCH$_2$ | 4,7-diF | O | S |
| H4.90 | Me | H | 2-Cl | SCH$_2$ | 4,7-diF | O | S |
| H4.91 | Me | H | 2-Cl | OCH$_2$ | 5,6-diF | O | S |
| H4.92 | Me | H | 2-Cl | SCH$_2$ | 5,6-diF | O | S |
| H4.93 | MeO | H | 2-Cl | OCH$_2$ | 5,6-diF | O | S |
| H4.94 | Me | H | 2-Cl | OCH$_2$ | 5,7-diF | O | S |
| H4.95 | Me | H | 2-Cl | SCH$_2$ | 5,7-diF | O | S |
| H4.96 | Me | H | 2-Cl | OCH$_2$ | 6,7-diF | O | S |
| H4.97 | Me | H | 2-Cl | SCH$_2$ | 6,7-diF | O | S |
| H4.98 | Me | H | 2-Cl | OCH$_2$ | 4,5-diCl | O | S |
| H4.99 | Me | H | 2-Cl | SCH$_2$ | 4,5-diCl | O | S |
| H4.100 | Me | H | 2-Cl | OCH$_2$ | 4,6-diCl | O | S |
| H4.101 | Me | H | 2-Cl | SCH$_2$ | 4,6-diCl | O | S |
| H4.102 | Me | H | 2-Cl | OCH$_2$ | 4,7-diCl | O | S |
| H4.103 | Me | H | 2-Cl | SCH$_2$ | 4,7-diCl | O | S |
| H4.104 | Me | H | 2-Cl | OCH$_2$ | 5,6-diCl | O | S |
| H4.105 | Me | H | 2-Cl | SCH$_2$ | 5,6-diCl | O | S |
| H4.106 | Me | H | 2-Cl | OCH$_2$ | 5,7-diCl | O | S |
| H4.107 | Me | H | 2-Cl | SCH$_2$ | 5,7-diCl | O | S |
| H4.108 | Me | H | 2-Cl | OCH$_2$ | 6,7-diCl | O | S |
| H4.109 | Me | H | 2-Cl | SCH$_2$ | 6,7-diCl | O | S |
| H5.1 | Me | H | 2-Cl | OCH$_2$ | 4,5-diCF$_3$ | O | S |
| H5.2 | Me | H | 2-Cl | SCH$_2$ | 4,5-diCF$_3$ | O | S |
| H5.3 | Me | H | 2-Cl | OCH$_2$ | 4,6-diCF$_3$ | O | S |
| H5.4 | Me | H | 2-Cl | SCH$_2$ | 4,6-diCF$_3$ | O | S |
| H5.5 | Me | H | 2-Cl | OCH$_2$ | 4,7-diCF$_3$ | O | S |
| H5.6 | Me | H | 2-Cl | SCH$_2$ | 4,7-diCF$_3$ | O | S |
| H5.7 | Me | H | 2-Cl | OCH$_2$ | 5,6-diCF$_3$ | O | S |
| H5.8 | Me | H | 2-Cl | SCH$_2$ | 5,6-diCF$_3$ | O | S |
| H5.9 | Me | H | 2-Cl | OCH$_2$ | 5,7-diCF$_3$ | O | S |
| H5.10 | Me | H | 2-Cl | SCH$_2$ | 5,7-diCF$_3$ | O | S |
| H5.11 | Me | H | 2-Cl | OCH$_2$ | 6,7-diCF$_3$ | O | S |
| H5.12 | Me | H | 2-Cl | SCH$_2$ | 6,7-diCF$_3$ | O | S |
| H5.13 | Me | H | 2-Cl | OCH$_2$ | 4-F,5-Me | O | S |
| H5.14 | Me | H | 2-Cl | SCH$_2$ | 4-F,5-Me | O | S |
| H5.15 | Me | H | 2-Cl | OCH$_2$ | 4-F,6-Me | O | S |
| H5.16 | Me | H | 2-Cl | SCH$_2$ | 4-F,6-Me | O | S |
| H5.17 | Me | H | 2-Cl | OCH$_2$ | 4-F,7-Me | O | S |
| H5.18 | Me | H | 2-Cl | SCH$_2$ | 4-F,7-Me | O | S |
| H5.19 | Me | H | 2-Cl | OCH$_2$ | 4-Me,5-F | O | S |
| H5.20 | Me | H | 2-Cl | SCH$_2$ | 4-Me,5-F | O | S |
| H5.21 | Me | H | 2-Cl | OCH$_2$ | 5-F,6-Me | O | S |
| H5.22 | Me | H | 2-Cl | SCH$_2$ | 5-F,6-Me | O | S |
| H5.23 | Me | H | 2-Cl | OCH$_2$ | 5-F,7-Me | O | S |
| H5.24 | Me | H | 2-Cl | SCH$_2$ | 5-F,7-Me | O | S |
| H5.25 | Me | H | 2-Cl | OCH$_2$ | 4-Me,6-F | O | S |
| H5.26 | Me | H | 2-Cl | SCH$_2$ | 4-Me,6-F | O | S |
| H5.27 | Me | H | 2-Cl | OCH$_2$ | 5-Me,6-F | O | S |
| H5.28 | Me | H | 2-Cl | SCH$_2$ | 5-Me,6-F | O | S |
| H5.29 | Me | H | 2-Cl | OCH$_2$ | 6-F,7-Me | O | S |
| H5.30 | Me | H | 2-Cl | SCH$_2$ | 6-F,7-Me | O | S |
| H5.31 | Me | H | 2-Cl | OCH$_2$ | 4-Me,7-F | O | S |
| H5.32 | Me | H | 2-Cl | SCH$_2$ | 4-Me,7-F | O | S |
| H5.34 | Me | H | 2-Cl | OCH$_2$ | 5-Me,7-F | O | S |
| H5.35 | Me | H | 2-Cl | SCH$_2$ | 5-Me,7-F | O | S |
| H5.36 | Me | H | 2-Cl | OCH$_2$ | 6-Me,7-F | O | S |
| H5.37 | Me | H | 2-Cl | SCH$_2$ | 6-Me,7-F | O | S |
| H5.38 | Me | H | 2-Cl | OCH$_2$ | 4-Cl,5-Me | O | S |
| H5.39 | Me | H | 2-Cl | SCH$_2$ | 4-Cl,5-Me | O | S |
| H5.40 | Me | H | 2-Cl | OCH$_2$ | 4-Cl,6-Me | O | S |
| H5.41 | Me | H | 2-Cl | SCH$_2$ | 4-Cl,6-Me | O | S |
| H5.42 | Me | H | 2-Cl | OCH$_2$ | 4-Cl,7-Me | O | S |
| H5.43 | Me | H | 2-Cl | SCH$_2$ | 4-Cl,7-Me | O | S |
| H5.44 | Me | H | 2-Cl | OCH$_2$ | 4-Me,5-Cl | O | S |
| H5.45 | Me | H | 2-Cl | SCH$_2$ | 4-Me,5-Cl | O | S |
| H5.46 | Me | H | 2-Cl | OCH$_2$ | 5-Cl,6-Me | O | S |
| H5.47 | Me | H | 2-Cl | SCH$_2$ | 5-Cl,6-Me | O | S |
| H5.48 | Me | H | 2-Cl | OCH$_2$ | 5-Cl,7-Me | O | S |
| H5.49 | Me | H | 2-Cl | SCH$_2$ | 5-Cl,7-Me | O | S |
| H5.50 | Me | H | 2-Cl | OCH$_2$ | 4-Me,6-Cl | O | S |
| H5.51 | Me | H | 2-Cl | SCH$_2$ | 4-Me,6-Cl | O | S |
| H5.52 | Me | H | 2-Cl | OCH$_2$ | 5-Me,6-Cl | O | S |
| H5.53 | Me | H | 2-Cl | SCH$_2$ | 5-Me,6-Cl | O | S |
| H5.54 | Me | H | 2-Cl | OCH$_2$ | 6-Cl,7-Me | O | S |
| H5.56 | Me | H | 2-Cl | SCH$_2$ | 6-Cl,7-Me | O | S |
| H5.57 | Me | H | 2-Cl | OCH$_2$ | 4-Me,7-Cl | O | S |
| H5.58 | Me | H | 2-Cl | SCH$_2$ | 4-Me,7-Cl | O | S |
| H5.59 | Me | H | 2-Cl | OCH$_2$ | 5-Me,7-Cl | O | S |
| H5.60 | Me | H | 2-Cl | SCH$_2$ | 5-Me,7-Cl | O | S |
| H5.61 | Me | H | 2-Cl | OCH$_2$ | 6-Me,7-Cl | O | S |
| H5.62 | Me | H | 2-Cl | SCH$_2$ | 6-Me,7-Cl | O | S |
| H5.63 | Me | H | 2-Cl | OCH$_2$ | 4-Cl,5-F | O | S |

TABLE 8-continued

| Compd. No. | R¹ | R² | (R³)ₙ | ACR⁴R⁵ | (R⁶)ₘ | X | Q |
|---|---|---|---|---|---|---|---|
| H5.64 | Me | H | 2-Cl | SCH₂ | 4-Cl,5-F | O | S |
| H5.65 | Me | H | 2-Cl | OCH₂ | 4-Cl,6-F | O | S |
| H5.66 | Me | H | 2-Cl | SCH₂ | 4-Cl,6-F | O | S |
| H5.67 | Me | H | 2-Cl | OCH₂ | 4-Cl,7-F | O | S |
| H5.68 | Me | H | 2-Cl | SCH₂ | 4-Cl,7-F | O | S |
| H5.69 | Me | H | 2-Cl | OCH₂ | 4-F,5-Cl | O | S |
| H5.70 | Me | H | 2-Cl | SCH₂ | 4-F,5-Cl | O | S |
| H5.71 | Me | H | 2-Cl | OCH₂ | 5-Cl,6-F | O | S |
| H5.72 | Me | H | 2-Cl | SCH₂ | 5-Cl,6-F | O | S |
| H5.73 | Me | H | 2-Cl | OCH₂ | 5-Cl,7-F | O | S |
| H5.74 | Me | H | 2-Cl | SCH₂ | 5-Cl,7-F | O | S |
| H5.75 | Me | H | 2-Cl | OCH₂ | 4-F,6-Cl | O | S |
| H5.76 | Me | H | 2-Cl | SCH₂ | 4-F,6-Cl | O | S |
| H5.77 | Me | H | 2-Cl | OCH₂ | 5-F,6-Cl | O | S |
| H5.78 | Me | H | 2-Cl | SCH₂ | 5-F,6-Cl | O | S |
| H5.79 | Me | H | 2-Cl | OCH₂ | 6-Cl,7-F | O | S |
| H5.80 | Me | H | 2-Cl | SCH₂ | 6-Cl,7-F | O | S |
| H5.81 | Me | H | 2-Cl | OCH₂ | 4-F,7-Cl | O | S |
| H5.82 | Me | H | 2-Cl | SCH₂ | 4-F,7-Cl | O | S |
| H5.83 | Me | H | 2-Cl | OCH₂ | 5-F,7-Cl | O | S |
| H5.84 | Me | H | 2-Cl | SCH₂ | 5-F,7-Cl | O | S |
| H5.85 | Me | H | 2-Cl | OCH₂ | 6-F,7-Cl | O | S |
| H5.86 | Me | H | 2-Cl | SCH₂ | 6-F,7-Cl | O | S |
| H6.1 | Me | H | 3-Cl | OCH₂ | 4-Me | O | S |
| H6.2 | Me | H | 3-Cl | SCH₂ | 4-Me | O | S |
| H6.3 | Me | H | 3-Cl | OCH₂ | 5-Me | O | S |
| H6.4 | Me | H | 3-Cl | SCH₂ | 5-Me | O | S |
| H6.5 | Me | H | 3-Cl | OCH₂ | 6-Me | O | S |
| H6.6 | Me | H | 3-Cl | SCH₂ | 6-Me | O | S |
| H6.7 | Me | H | 3-Cl | OCH₂ | 7-Me | O | S |
| H6.8 | Me | H | 3-Cl | SCH₂ | 7-Me | O | S |
| H6.9 | Me | H | 3-Cl | OCH₂ | 5-Et | O | S |
| H6.10 | Me | H | 3-Cl | SCH₂ | 5-Et | O | S |
| H6.11 | Me | H | 3-Cl | OCH₂ | 6-Et | O | S |
| H6.12 | Me | H | 3-Cl | SCH₂ | 6-Et | O | S |
| H6.13 | Me | H | 3-Cl | OCH₂ | 4-OMe | O | S |
| H6.14 | Me | H | 3-Cl | SCH₂ | 4-OMe | O | S |
| H6.15 | Me | H | 3-Cl | OCH₂ | 5-OMe | O | S |
| H6.16 | Me | H | 3-Cl | SCH₂ | 5-OMe | O | S |
| H6.17 | Me | H | 3-Cl | OCH₂ | 6-OMe | O | S |
| H6.18 | Me | H | 3-Cl | SCH₂ | 6-OMe | O | S |
| H6.19 | Me | H | 3-Cl | OCH₂ | 7-OMe | O | S |
| H6.20 | Me | H | 3-Cl | SCH₂ | 7-OMe | O | S |
| H6.21 | Me | H | 3-Cl | OCH₂ | 5-OEt | O | S |
| H6.22 | Me | H | 3-Cl | SCH₂ | 5-OEt | O | S |
| H6.23 | Me | H | 3-Cl | OCH₂ | 6-OEt | O | S |
| H6.24 | Me | H | 3-Cl | SCH₂ | 6-OEt | O | S |
| H6.25 | Me | H | 3-Cl | OCH₂ | 4-F | O | S |
| H6.26 | Me | H | 3-Cl | SCH₂ | 4-F | O | S |
| H6.27 | Me | H | 3-Cl | OCH₂ | 5-F | O | S |
| H6.28 | Me | H | 3-Cl | SCH₂ | 5-F | O | S |
| H6.29 | Me | H | 3-Cl | OCH₂ | 6-F | O | S |
| H6.30 | Me | H | 3-Cl | SCH₂ | 6-F | O | S |
| H6.31 | Me | H | 3-Cl | OCH₂ | 7-F | O | S |
| H6.32 | Me | H | 3-Cl | SCH₂ | 7-F | O | S |
| H6.33 | Me | H | 3-Cl | OCH₂ | 5-Cl | O | S |
| H6.34 | Me | H | 3-Cl | SCH₂ | 5-Cl | O | S |
| H6.35 | Me | H | 3-Cl | OCH₂ | 6-Cl | O | S |
| H6.36 | Me | H | 3-Cl | SCH₂ | 6-Cl | O | S |
| H6.37 | Me | H | 3-Cl | OCH₂ | 4-CF₃ | O | S |
| H6.38 | Me | H | 3-Cl | SCH₂ | 4-CF₃ | O | S |
| H6.39 | Me | H | 3-Cl | OCH₂ | 5-CF₃ | O | S |
| H6.40 | Me | H | 3-Cl | SCH₂ | 5-CF₃ | O | S |
| H6.41 | Me | H | 3-Cl | OCH₂ | 6-CF₃ | O | S |
| H6.42 | Me | H | 3-Cl | SCH₂ | 6-CF₃ | O | S |
| H6.43 | Me | H | 3-Cl | OCH₂ | 7-CF₃ | O | S |
| H6.44 | Me | H | 3-Cl | SCH₂ | 7-CF₃ | O | S |
| H6.45 | Me | H | 3-Cl | OCH₂ | 5-OCF₃ | O | S |
| H6.46 | Me | H | 3-Cl | SCH₂ | 5-OCF₃ | O | S |
| H6.47 | Me | H | 3-Cl | OCH₂ | 6-OCF₃ | O | S |
| H6.48 | Me | H | 3-Cl | SCH₂ | 6-OCF₃ | O | S |
| H7.1 | Me | H | 2,3-diMe | OCH₂ | 4-Me | O | S |
| H7.2 | Me | H | 2,3-diMe | SCH₂ | 4-Me | O | S |
| H7.3 | MeO | H | 2,3-diMe | OCH₂ | 4-Me | O | S |
| H7.4 | Me | H | 2,3-diMe | OCH₂ | 5-Me | O | S |
| H7.5 | Me | H | 2,3-diMe | SCH₂ | 5-Me | O | S |
| H7.6 | MeO | H | 2,3-diMe | OCH₂ | 5-Me | O | S |
| H7.7 | Me | H | 2,3-diMe | OCH₂ | 5-Me | O | O |
| H7.8 | MeO | H | 2,3-diMe | OCH₂ | 5-Me | O | O |
| H7.9 | Me | H | 2,3-diMe | OCH₂ | 6-Me | O | S |
| H7.10 | Me | H | 2,3-diMe | SCH₂ | 6-Me | O | S |
| H7.11 | Me | H | 2,3-diMe | OCH₂ | 6-Me | O | S |
| H7.12 | Me | H | 2,3-diMe | OCH₂ | 7-Me | O | S |
| H7.13 | Me | H | 2,3-diMe | SCH₂ | 7-Me | O | S |
| H7.14 | MeO | H | 2,3-diMe | OCH₂ | 7-Me | O | S |
| H7.15 | Me | H | 2,3-diMe | OCH₂ | 4-OMe | O | S |
| H7.16 | Me | H | 2,3-diMe | SCH₂ | 4-OMe | O | S |
| H7.17 | MeO | H | 2,3-diMe | OCH₂ | 4-OMe | O | S |
| H7.18 | Me | H | 2,3-diMe | OCH₂ | 5-OMe | O | S |
| H7.19 | Me | H | 2,3-diMe | SCH₂ | 5-OMe | O | S |
| H7.20 | MeO | H | 2,3-diMe | OCH₂ | 5-OMe | O | S |
| H7.21 | Me | H | 2,3-diMe | OCH₂ | 6-OMe | O | S |
| H7.22 | Me | H | 2,3-diMe | SCH₂ | 6-OMe | O | S |
| H7.23 | MeO | H | 2,3-diMe | OCH₂ | 6-OMe | O | S |
| H7.24 | Me | H | 2,3-diMe | OCH₂ | 6-OMe | O | O |
| H7.25 | MeO | H | 2,3-diMe | OCH₂ | 6-OMe | O | O |
| H7.26 | Me | H | 2,3-diMe | OCH₂ | 7-OMe | O | S |
| H7.27 | Me | H | 2,3-diMe | SCH₂ | 7-OMe | O | S |
| H7.28 | MeO | H | 2,3-diMe | OCH₂ | 7-Me | O | S |
| H7.29 | Me | H | 2,3-diMe | OCH₂ | 5-OEt | O | S |
| H7.30 | Me | H | 2,3-diMe | SCH₂ | 5-OEt | O | S |
| H7.31 | Me | H | 2,3-diMe | OCH₂ | 6-OEt | O | S |
| H7.32 | Me | H | 2,3-diMe | SCH₂ | 6-OEt | O | S |
| H7.33 | Me | H | 2,3-diMe | OCH₂ | 4-F | O | S |
| H7.34 | Me | H | 2,3-diMe | SCH₂ | 4-F | O | S |
| H7.35 | MeO | H | 2,3-diMe | OCH₂ | 4-F | O | S |
| H7.36 | Me | H | 2,3-diMe | OCH₂ | 5-F | O | S |
| H7.37 | Me | H | 2,3-diMe | SCH₂ | 5-F | O | S |
| H7.38 | MeO | H | 2,3-diMe | OCH₂ | 5-F | O | S |
| H7.39 | Me | H | 2,3-diMe | OCH₂ | 5-F | O | O |
| H7.40 | MeO | H | 2,3-diMe | OCH₂ | 5-F | O | O |
| H7.41 | Me | H | 2,3-diMe | OCH₂ | 6-F | O | S |
| H7.42 | Me | H | 2,3-diMe | SCH₂ | 6-F | O | S |
| H7.43 | MeO | H | 2,3-diMe | OCH₂ | 6-F | O | S |
| H7.44 | Me | H | 2,3-diMe | OCH₂ | 6-F | O | O |
| H7.45 | MeO | H | 2,3-diMe | OCH₂ | 6-F | O | O |
| H7.46 | Me | H | 2,3-diMe | OCH₂ | 7-F | O | S |
| H7.47 | Me | H | 2,3-diMe | SCH₂ | 7-F | O | S |
| H7.48 | MeO | H | 2,3-diMe | OCH₂ | 7-F | O | S |
| H7.49 | Me | H | 2,3-diMe | OCH₂ | 5-Cl | O | S |
| H7.50 | Me | H | 2,3-diMe | SCH₂ | 5-Cl | O | S |
| H7.51 | MeO | H | 2,3-diMe | OCH₂ | 5-Cl | O | S |
| H7.52 | Me | H | 2,3-diMe | OCH₂ | 6-Cl | O | S |
| H7.53 | Me | H | 2,3-diMe | SCH₂ | 6-Cl | O | S |
| H7.54 | MeO | H | 2,3-diMe | OCH₂ | 6-Cl | O | S |
| H7.55 | Me | H | 2,3-diMe | OCH₂ | 5-Et | O | S |
| H7.56 | Me | H | 2,3-diMe | SCH₂ | 5-Et | O | S |
| H7.57 | MeO | H | 2,3-diMe | OCH₂ | 5-Et | O | S |
| H7.58 | Me | H | 2,3-diMe | OCH₂ | 6-Et | O | S |
| H7.59 | Me | H | 2,3-diMe | SCH₂ | 6-Et | O | S |
| H7.60 | MeO | H | 2,3-diMe | OCH₂ | 6-Et | O | S |
| H7.61 | Me | H | 2,3-diMe | OCH₂ | 4-CF₃ | O | S |
| H7.62 | Me | H | 2,3-diMe | SCH₂ | 4-CF₃ | O | S |
| H7.63 | Me | H | 2,3-diMe | OCH₂ | 5-CF₃ | O | S |
| H7.64 | Me | H | 2,3-diMe | SCH₂ | 5-CF₃ | O | S |
| H7.65 | MeO | H | 2,3-diMe | OCH₂ | 5-CF₃ | O | S |
| H7.66 | Me | H | 2,3-diMe | OCH₂ | 6-CF₃ | O | S |
| H7.67 | Me | H | 2,3-diMe | SCH₂ | 6-CF₃ | O | S |
| H7.68 | MeO | H | 2,3-diMe | OCH₂ | 6-CF₃ | O | S |
| H7.69 | Me | H | 2,3-diMe | OCH₂ | 7-CF₃ | O | S |
| H7.70 | Me | H | 2,3-diMe | SCH₂ | 7-CF₃ | O | S |
| H7.71 | Me | H | 2,3-diMe | OCH₂ | 5-OCF₃ | O | S |
| H7.72 | Me | H | 2,3-diMe | SCH₂ | 5-OCF₃ | O | S |
| H7.73 | Me | H | 2,3-diMe | OCH₂ | 6-OCF₃ | O | S |
| H7.74 | Me | H | 2,3-diMe | SCH₂ | 6-OCF₃ | O | S |
| H7.75 | Me | H | 2,3-diMe | OCH₂ | 4,5-diMe | O | S |
| H7.76 | Me | H | 2,3-diMe | SCH₂ | 4,5-diMe | O | S |
| H7.77 | MeO | H | 2,3-diMe | OCH₂ | 4,5-diMe | O | S |
| H7.78 | Me | H | 2,3-diMe | OCH₂ | 4,6-diMe | O | S |
| H7.79 | Me | H | 2,3-diMe | SCH₂ | 4,6-diMe | O | S |
| H7.80 | Me | H | 2,3-diMe | OCH₂ | 4,7-diMe | O | S |
| H7.81 | Me | H | 2,3-diMe | SCH₂ | 4,7-diMe | O | S |

TABLE 8-continued

| Compd. No. | R¹ | R² | (R³)ₙ | ACR⁴R⁵ | (R⁶)ₘ | X | Q |
|---|---|---|---|---|---|---|---|
| H7.82 | Me | H | 2,3-diMe | OCH₂ | 5,6-diMe | O | S |
| H7.83 | Me | H | 2,3-diMe | SCH₂ | 5,6-diMe | O | S |
| H7.84 | Me | H | 2,3-diMe | OCH₂ | 5,7-diMe | O | S |
| H7.85 | Me | H | 2,3-diMe | SCH₂ | 5,7-diMe | O | S |
| H7.86 | Me | H | 2,3-diMe | OCH₂ | 6,7-diMe | O | S |
| H7.87 | Me | H | 2,3-diMe | SCH₂ | 6,7-diMe | O | S |
| H7.88 | Me | H | 2,3-diMe | OCH₂ | 4,5-diMe | O | S |
| H7.89 | Me | H | 2,3-diMe | SCH₂ | 4,5-diMe | O | S |
| H7.90 | Me | H | 2,3-diMe | OCH₂ | 4,6-diOMe | O | S |
| H7.91 | Me | H | 2,3-diMe | SCH₂ | 4,6-diOMe | O | S |
| H7.92 | Me | H | 2,3-diMe | OCH₂ | 4,7-diOMe | O | S |
| H7.93 | Me | H | 2,3-diMe | SCH₂ | 4,7-diOMe | O | S |
| H7.94 | Me | H | 2,3-diMe | OCH₂ | 5,6-diOMe | O | S |
| H7.95 | Me | H | 2,3-diMe | SCH₂ | 5,6-diOMe | O | S |
| H7.96 | Me | H | 2,3-diMe | OCH₂ | 5,7-diOMe | O | S |
| H7.97 | Me | H | 2,3-diMe | SCH₂ | 5,7-diOMe | O | S |
| H7.98 | Me | H | 2,3-diMe | OCH₂ | 6,7-diOMe | O | S |
| H7.99 | Me | H | 2,3-diMe | SCH₂ | 6,7-diOMe | O | S |
| H7.100 | Me | H | 2,3-diMe | OCH₂ | 4,5-diF | O | S |
| H7.101 | Me | H | 2,3-diMe | SCH₂ | 4,5-diF | O | S |
| H7.102 | Me | H | 2,3-diMe | OCH₂ | 4,6-diF | O | S |
| H7.103 | Me | H | 2,3-diMe | SCH₂ | 4,6-diF | O | S |
| H7.104 | Me | H | 2,3-diMe | OCH₂ | 4,7-diF | O | S |
| H7.105 | Me | H | 2,3-diMe | SCH₂ | 4,7-diF | O | S |
| H7.106 | Me | H | 2,3-diMe | OCH₂ | 5,6-diF | O | S |
| H7.107 | Me | H | 2,3-diMe | SCH₂ | 5,6-diF | O | S |
| H7.108 | MeO | H | 2,3-diMe | OCH₂ | 5,6-diF | O | S |
| H7.109 | Me | H | 2,3-diMe | OCH₂ | 5,7-diF | O | S |
| H7.110 | Me | H | 2,3-diMe | SCH₂ | 5,7-diF | O | S |
| H7.111 | Me | H | 2,3-diMe | OCH₂ | 6,7-diF | O | S |
| H7.112 | Me | H | 2,3-diMe | SCH₂ | 6,7-diF | O | S |
| H8.1 | Me | H | 2,3-diMe | OCH₂ | 4,5-diCl | O | S |
| H8.2 | Me | H | 2,3-diMe | SCH₂ | 4,5-diCl | O | S |
| H8.3 | Me | H | 2,3-diMe | OCH₂ | 4,6-diCl | O | S |
| H8.4 | Me | H | 2,3-diMe | SCH₂ | 4,6-diCl | O | S |
| H8.5 | Me | H | 2,3-diMe | OCH₂ | 4,7-diCl | O | S |
| H8.6 | Me | H | 2,3-diMe | SCH₂ | 4,7-diCl | O | S |
| H8.7 | Me | H | 2,3-diMe | OCH₂ | 5,6-diCl | O | S |
| H8.8 | Me | H | 2,3-diMe | SCH₂ | 5,6-diCl | O | S |
| H8.9 | MeO | H | 2,3-diMe | OCH₂ | 5,6-diCl | O | S |
| H8.10 | Me | H | 2,3-diMe | OCH₂ | 5,7-diCl | O | S |
| H8.11 | Me | H | 2,3-diMe | SCH₂ | 5,7-diCl | O | S |
| H8.12 | Me | H | 2,3-diMe | OCH₂ | 6,7-diCl | O | S |
| H8.13 | Me | H | 2,3-diMe | SCH₂ | 6,7-diCl | O | S |
| H8.14 | Me | H | 2,3-diMe | OCH₂ | 4,5-diCF₃ | O | S |
| H8.15 | Me | H | 2,3-diMe | SCH₂ | 4,5-diCF₃ | O | S |
| H8.16 | Me | H | 2,3-diMe | OCH₂ | 4,6-diCF₃ | O | S |
| H8.17 | Me | H | 2,3-diMe | SCH₂ | 4,6-diCF₃ | O | S |
| H8.18 | Me | H | 2,3-diMe | OCH₂ | 4,7-diCF₃ | O | S |
| H8.19 | Me | H | 2,3-diMe | SCH₂ | 4,7-diCF₃ | O | S |
| H8.20 | Me | H | 2,3-diMe | OCH₂ | 5,6-diCF₃ | O | S |
| H8.21 | Me | H | 2,3-diMe | SCH₂ | 5,6-diCF₃ | O | S |
| H8.22 | Me | H | 2,3-diMe | OCH₂ | 5,7-diCF₃ | O | S |
| H8.23 | Me | H | 2,3-diMe | SCH₂ | 5,7-diCF₃ | O | S |
| H8.24 | Me | H | 2,3-diMe | OCH₂ | 6,7-diCF₃ | O | S |
| H8.25 | Me | H | 2,3-diMe | SCH₂ | 6,7-diCF₃ | O | S |
| H8.26 | Me | H | 2,3-diMe | OCH₂ | 4-F,5-Me | O | S |
| H8.27 | Me | H | 2,3-diMe | SCH₂ | 4-F,5-Me | O | S |
| H8.28 | Me | H | 2,3-diMe | OCH₂ | 4-F,6-Me | O | S |
| H8.29 | Me | H | 2,3-diMe | SCH₂ | 4-F,6-Me | O | S |
| H8.30 | MeO | H | 2,3-diMe | OCH₂ | 4-F,6-Me | O | S |
| H8.31 | Me | H | 2,3-diMe | OCH₂ | 4-F,7-Me | O | S |
| H8.32 | Me | H | 2,3-diMe | SCH₂ | 4-F,7-Me | O | S |
| H8.33 | Me | H | 2,3-diMe | OCH₂ | 4-Me,5-F | O | S |
| H8.34 | Me | H | 2,3-diMe | SCH₂ | 4-Me,5-F | O | S |
| H8.35 | Me | H | 2,3-diMe | OCH₂ | 5-F,6-Me | O | S |
| H8.36 | Me | H | 2,3-diMe | SCH₂ | 5-F,6-Me | O | S |
| H8.37 | Me | H | 2,3-diMe | OCH₂ | 5-F,7-Me | O | S |
| H8.38 | Me | H | 2,3-diMe | SCH₂ | 5-F,7-Me | O | S |
| H8.39 | Me | H | 2,3-diMe | OCH₂ | 4-Me,6-F | O | S |
| H8.40 | Me | H | 2,3-diMe | SCH₂ | 4-Me,6-F | O | S |
| H8.41 | Me | H | 2,3-diMe | OCH₂ | 5-Me,6-F | O | S |
| H8.42 | Me | H | 2,3-diMe | SCH₂ | 5-Me,6-F | O | S |
| H8.43 | Me | H | 2,3-diMe | OCH₂ | 6-F,7-Me | O | S |
| H8.44 | Me | H | 2,3-diMe | SCH₂ | 6-F,7-Me | O | S |
| H8.45 | Me | H | 2,3-diMe | OCH₂ | 4-Me,7-F | O | S |
| H8.46 | Me | H | 2,3-diMe | SCH₂ | 4-Me,7-F | O | S |
| H8.47 | Me | H | 2,3-diMe | OCH₂ | 5-Me,7-F | O | S |
| H8.48 | Me | H | 2,3-diMe | SCH₂ | 5-Me,7-F | O | S |
| H8.49 | Me | H | 2,3-diMe | OCH₂ | 6-Me,7-F | O | S |
| H8.50 | Me | H | 2,3-diMe | SCH₂ | 6-Me,7-F | O | S |
| H8.51 | Me | H | 2,3-diMe | OCH₂ | 4-Cl,5-Me | O | S |
| H8.52 | Me | H | 2,3-diMe | SCH₂ | 4-Cl,5-Me | O | S |
| H8.53 | Me | H | 2,3-diMe | OCH₂ | 4-Cl,6-Me | O | S |
| H8.54 | Me | H | 2,3-diMe | SCH₂ | 4-Cl,6-Me | O | S |
| H8.55 | MeO | H | 2,3-diMe | OCH₂ | 4-Cl,6-Me | O | S |
| H8.56 | Me | H | 2,3-diMe | OCH₂ | 4-Cl,7-Me | O | S |
| H8.57 | Me | H | 2,3-diMe | SCH₂ | 4-Cl,7-Me | O | S |
| H8.58 | Me | H | 2,3-diMe | OCH₂ | 4-Me,5-Cl | O | S |
| H8.59 | Me | H | 2,3-diMe | SCH₂ | 4-Me,5-Cl | O | S |
| H8.60 | Me | H | 2,3-diMe | OCH₂ | 5-Cl,6-Me | O | S |
| H8.61 | Me | H | 2,3-diMe | SCH₂ | 5-Cl,6-Me | O | S |
| H8.62 | Me | H | 2,3-diMe | OCH₂ | 5-Cl,7-Me | O | S |
| H8.63 | Me | H | 2,3-diMe | SCH₂ | 5-Cl,7-Me | O | S |
| H8.64 | Me | H | 2,3-diMe | OCH₂ | 4-Me,6-Cl | O | S |
| H8.65 | Me | H | 2,3-diMe | SCH₂ | 4-Me,6-Cl | O | S |
| H8.66 | Me | H | 2,3-diMe | OCH₂ | 5-Me,6-Cl | O | S |
| H8.67 | Me | H | 2,3-diMe | SCH₂ | 5-Me,6-Cl | O | S |
| H8.68 | Me | H | 2,3-diMe | OCH₂ | 6-Cl,7-Me | O | S |
| H8.69 | Me | H | 2,3-diMe | SCH₂ | 6-Cl,7-Me | O | S |
| H8.70 | Me | H | 2,3-diMe | OCH₂ | 4-Me,7-Cl | O | S |
| H8.71 | Me | H | 2,3-diMe | SCH₂ | 4-Me,7-Cl | O | S |
| H8.72 | Me | H | 2,3-diMe | OCH₂ | 5-Me,7-Cl | O | S |
| H8.73 | Me | H | 2,3-diMe | SCH₂ | 5-Me,7-Cl | O | S |
| H8.74 | Me | H | 2,3-diMe | OCH₂ | 6-Me,7-Cl | O | S |
| H8.75 | Me | H | 2,3-diMe | SCH₂ | 6-Me,7-Cl | O | S |
| H8.76 | Me | H | 2,3-diMe | OCH₂ | 4-Cl,5-F | O | S |
| H8.77 | Me | H | 2,3-diMe | SCH₂ | 4-Cl,5-F | O | S |
| H8.78 | MeO | H | 2,3-diMe | OCH₂ | 4-Cl,5-F | O | S |
| H8.79 | Me | H | 2,3-diMe | OCH₂ | 4-Cl,6-F | O | S |
| H8.80 | Me | H | 2,3-diMe | SCH₂ | 4-Cl,6-F | O | S |
| H8.81 | Me | H | 2,3-diMe | OCH₂ | 4-Cl,7-F | O | S |
| H8.82 | Me | H | 2,3-diMe | SCH₂ | 4-Cl,7-F | O | S |
| H8.83 | Me | H | 2,3-diMe | OCH₂ | 4-F,5-Cl | O | S |
| H8.84 | Me | H | 2,3-diMe | SCH₂ | 4-F,5-Cl | O | S |
| H8.85 | Me | H | 2,3-diMe | OCH₂ | 5-Cl,6-F | O | S |
| H8.86 | Me | H | 2,3-diMe | SCH₂ | 5-Cl,6-F | O | S |
| H8.87 | Me | H | 2,3-diMe | OCH₂ | 5-Cl,7-F | O | S |
| H8.88 | Me | H | 2,3-diMe | SCH₂ | 5-Cl,7-F | O | S |
| H8.89 | Me | H | 2,3-diMe | OCH₂ | 4-F,6-Cl | O | S |
| H8.90 | Me | H | 2,3-diMe | SCH₂ | 4-F,6-Cl | O | S |
| H8.91 | Me | H | 2,3-diMe | OCH₂ | 5-F,6-Cl | O | S |
| H8.92 | Me | H | 2,3-diMe | SCH₂ | 5-F,6-Cl | O | S |
| H8.93 | Me | H | 2,3-diMe | OCH₂ | 6-Cl,7-F | O | S |
| H8.94 | Me | H | 2,3-diMe | SCH₂ | 6-Cl,7-F | O | S |
| H8.95 | Me | H | 2,3-diMe | OCH₂ | 4-F,7-Cl | O | S |
| H8.96 | Me | H | 2,3-diMe | SCH₂ | 4-F,7-Cl | O | S |
| H8.97 | Me | H | 2,3-diMe | OCH₂ | 5-F,7-Cl | O | S |
| H8.98 | Me | H | 2,3-diMe | SCH₂ | 5-F,7-Cl | O | S |
| H8.99 | Me | H | 2,3-diMe | OCH₂ | 6-F,7-Cl | O | S |
| H8.100 | Me | H | 2,3-diMe | SCH₂ | 6-F-7-Cl | O | S |
| H8.101 | MeO | H | 2,5-diMe | OCH₂ | 5-F | O | S |
| H8.102 | MeO | H | 2,5-diMe | OCH₂ | 5-F | O | O |
| H8.103 | MeO | H | 2,6-diMe | OCH₂ | 5-F | O | S |
| H8.104 | MeO | H | 2,6-diMe | OCH₂ | 5-F | O | O |
| H8.105 | MeO | H | 3,5-diMe | OCH₂ | 5-F | O | S |
| H8.106 | MeO | H | 3,5-diMe | OCH₂ | 5-F | O | O |
| H9.1 | Me | H | 2,3-diF | OCH₂ | 4-Me | O | S |
| H9.2 | Me | H | 2,3-diF | SCH₂ | 4-Me | O | S |
| H9.3 | Me | H | 2,3-diF | OCH₂ | 5-Me | O | S |
| H9.4 | Me | H | 2,3-diF | SCH₂ | 5-Me | O | S |
| H9.5 | Me | H | 2,3-diF | OCH₂ | 6-Me | O | S |
| H9.6 | Me | H | 2,3-diF | SCH₂ | 6-Me | O | S |
| H9.7 | Me | H | 2,3-diF | OCH₂ | 7-Me | O | S |
| H9.8 | Me | H | 2,3-diF | SCH₂ | 7-Me | O | S |
| H9.10 | Me | H | 2,3-diF | OCH₂ | 5-Et | O | S |
| H9.11 | Me | H | 2,3-diF | SCH₂ | 5-Et | O | S |
| H9.12 | Me | H | 2,3-diF | OCH₂ | 6-Et | O | S |
| H9.13 | Me | H | 2,3-diF | SCH₂ | 6-Et | O | S |
| H9.14 | Me | H | 2,3-diF | OCH₂ | 4-OMe | O | S |
| H9.15 | Me | H | 2,3-diF | SCH₂ | 4-OMe | O | S |
| H9.16 | Me | H | 2,3-diF | OCH₂ | 5-OMe | O | S |

TABLE 8-continued

| Compd. No. | R¹ | R² | (R³)ₙ | ACR⁴R⁵ | (R⁶)ₘ | X | Q |
|---|---|---|---|---|---|---|---|
| H9.17 | Me | H | 2,3-diF | SCH₂ | 5-OMe | O | S |
| H9.18 | Me | H | 2,3-diF | OCH₂ | 6-OMe | O | S |
| H9.19 | Me | H | 2,3-diF | SCH₂ | 6-OMe | O | S |
| H9.20 | Me | H | 2,3-diF | OCH₂ | 7-OMe | O | S |
| H9.21 | Me | H | 2,3-diF | SCH₂ | 7-OMe | O | S |
| H9.22 | Me | H | 2,3-diF | OCH₂ | 5-OEt | O | S |
| H9.23 | Me | H | 2,3-diF | SCH₂ | 5-OEt | O | S |
| H9.24 | Me | H | 2,3-diF | OCH₂ | 6-OEt | O | S |
| H9.25 | Me | H | 2,3-diF | SCH₂ | 6-OEt | O | S |
| H9.26 | Me | H | 2,3-diF | OCH₂ | 4-F | O | S |
| H9.27 | Me | H | 2,3-diF | SCH₂ | 4-F | O | S |
| H9.28 | Me | H | 2,3-diF | OCH₂ | 5-F | O | S |
| H9.29 | Me | H | 2,3-diF | SCH₂ | 5-F | O | S |
| H9.30 | Me | H | 2,3-diF | OCH₂ | 6-F | O | S |
| H9.31 | Me | H | 2,3-diF | SCH₂ | 6-F | O | S |
| H9.32 | Me | H | 2,3-diF | OCH₂ | 7-F | O | S |
| H9.34 | Me | H | 2,3-diF | SCH₂ | 7-F | O | S |
| H9.35 | Me | H | 2,3-diF | OCH₂ | 5-Cl | O | S |
| H9.36 | Me | H | 2,3-diF | SCH₂ | 5-Cl | O | S |
| H9.37 | Me | H | 2,3-diF | OCH₂ | 6-Cl | O | S |
| H9.38 | Me | H | 2,3-diF | SCH₂ | 6-Cl | O | S |
| H9.39 | Me | H | 2,3-diF | OCH₂ | 4-CF₃ | O | S |
| H9.40 | Me | H | 2,3-diF | SCH₂ | 4-CF₃ | O | S |
| H9.41 | Me | H | 2,3-diF | OCH₂ | 5-CF₃ | O | S |
| H9.42 | Me | H | 2,3-diF | SCH₂ | 5-CF₃ | O | S |
| H9.43 | Me | H | 2,3-diF | OCH₂ | 6-CF₃ | O | S |
| H9.44 | Me | H | 2,3-diF | SCH₂ | 6-CF₃ | O | S |
| H9.45 | Me | H | 2,3-diF | OCH₂ | 7-CF₃ | O | S |
| H9.46 | Me | H | 2,3-diF | SCH₂ | 7-CF₃ | O | S |
| H9.47 | Me | H | 2,3-diF | OCH₂ | 5-OCF₃ | O | S |
| H9.48 | Me | H | 2,3-diF | SCH₂ | 5-OCF₃ | O | S |
| H9.49 | Me | H | 2,3-diF | OCH₂ | 6-OCF₃ | O | S |
| H9.50 | Me | H | 2,3-diF | SCH₂ | 6-OCF₃ | O | S |
| H9.51 | Me | H | 2,3-diF | OCH₂ | 4,5-diMe | O | S |
| H9.52 | Me | H | 2,3-diF | SCH₂ | 4,5-diMe | O | S |
| H9.53 | Me | H | 2,3-diF | OCH₂ | 4,6-diMe | O | S |
| H9.54 | Me | H | 2,3-diF | SCH₂ | 4,6-diMe | O | S |
| H9.55 | Me | H | 2,3-diF | OCH₂ | 4,7-diMe | O | S |
| H9.56 | Me | H | 2,3-diF | SCH₂ | 4,7-diMe | O | S |
| H9.57 | Me | H | 2,3-diF | OCH₂ | 5,6-diMe | O | S |
| H9.58 | Me | H | 2,3-diF | SCH₂ | 5,6-diMe | O | S |
| H9.60 | Me | H | 2,3-diF | OCH₂ | 5,7-diMe | O | S |
| H9.61 | Me | H | 2,3-diF | SCH₂ | 5,7-diMe | O | S |
| H9.62 | Me | H | 2,3-diF | OCH₂ | 6,7-diMe | O | S |
| H9.63 | Me | H | 2,3-diF | SCH₂ | 6,7-diMe | O | S |
| H9.64 | Me | H | 2,3-diF | OCH₂ | 4,5-diOMe | O | S |
| H9.65 | Me | H | 2,3-diF | SCH₂ | 4,5-diOMe | O | S |
| H9.66 | Me | H | 2,3-diF | OCH₂ | 4,6-diOMe | O | S |
| H9.67 | Me | H | 2,3-diF | SCH₂ | 4,6-diOMe | O | S |
| H9.68 | Me | H | 2,3-diF | OCH₂ | 4,7-diOMe | O | S |
| H9.69 | Me | H | 2,3-diF | SCH₂ | 4,7-diOMe | O | S |
| H9.70 | Me | H | 2,3-diF | OCH₂ | 5,6-diOMe | O | S |
| H9.71 | Me | H | 2,3-diF | SCH₂ | 5,6-diOMe | O | S |
| H9.72 | Me | H | 2,3-diF | OCH₂ | 5,7-diOMe | O | S |
| H9.73 | Me | H | 2,3-diF | SCH₂ | 5,7-diOMe | O | S |
| H9.74 | Me | H | 2,3-diF | OCH₂ | 6,7-diOMe | O | S |
| H9.75 | Me | H | 2,3-diF | SCH₂ | 6,7-diOMe | O | S |
| H9.76 | Me | H | 2,3-diF | OCH₂ | 4,5-diF | O | S |
| H9.77 | Me | H | 2,3-diF | SCH₂ | 4,5-diF | O | S |
| H9.78 | Me | H | 2,3-diF | OCH₂ | 4,6-diF | O | S |
| H9.79 | Me | H | 2,3-diF | SCH₂ | 4,6-diF | O | S |
| H9.80 | Me | H | 2,3-diF | OCH₂ | 4,7-diF | O | S |
| H9.81 | Me | H | 2,3-diF | SCH₂ | 4,7-diF | O | S |
| H9.82 | Me | H | 2,3-diF | OCH₂ | 5,6-diF | O | S |
| H9.83 | Me | H | 2,3-diF | SCH₂ | 5,6-diF | O | S |
| H9.84 | Me | H | 2,3-diF | OCH₂ | 5,7-diF | O | S |
| H9.85 | Me | H | 2,3-diF | SCH₂ | 5,7-diF | O | S |
| H9.86 | Me | H | 2,3-diF | OCH₂ | 6,7-diF | O | S |
| H9.87 | Me | H | 2,3-diF | SCH₂ | 6,7-diF | O | S |
| H9.88 | Me | H | 2,3-diF | OCH₂ | 4,5-diCl | O | S |
| H9.89 | Me | H | 2,3-diF | SCH₂ | 4,5-diCl | O | S |
| H9.90 | Me | H | 2,3-diF | OCH₂ | 4,6-diCl | O | S |
| H9.91 | Me | H | 2,3-diF | SCH₂ | 4,6-diCl | O | S |
| H9.92 | Me | H | 2,3-diF | OCH₂ | 4,7-diCl | O | S |
| H9.93 | Me | H | 2,3-diF | SCH₂ | 4,7-diCl | O | S |
| H9.94 | Me | H | 2,3-diF | OCH₂ | 5,6-diCl | O | S |
| H9.95 | Me | H | 2,3-diF | SCH₂ | 5,6-diCl | O | S |
| H9.96 | Me | H | 2,3-diF | OCH₂ | 5,7-diCl | O | S |
| H9.97 | Me | H | 2,3-diF | SCH₂ | 5,7-diCl | O | S |
| H9.98 | Me | H | 2,3-diF | OCH₂ | 6,7-diCl | O | S |
| H9.99 | Me | H | 2,3-diF | SCH₂ | 6,7-diCl | O | S |
| H9.100 | Me | H | 2,3-diF | OCH₂ | 4,5-diCF₃ | O | S |
| H9.101 | Me | H | 2,3-diF | SCH₂ | 4,5-diCF₃ | O | S |
| H9.102 | Me | H | 2,3-diF | OCH₂ | 4,6-diCF₃ | O | S |
| H9.103 | Me | H | 2,3-diF | SCH₂ | 4,6-diCF₃ | O | S |
| H9.104 | Me | H | 2,3-diF | OCH₂ | 4,7-diCF₃ | O | S |
| H9.105 | Me | H | 2,3-diF | SCH₂ | 4,7-diCF₃ | O | S |
| H9.106 | Me | H | 2,3-diF | OCH₂ | 5,6-diCF₃ | O | S |
| H9.107 | Me | H | 2,3-diF | SCH₂ | 5,6-diCF₃ | O | S |
| H9.108 | Me | H | 2,3-diF | OCH₂ | 5,7-diCF₃ | O | S |
| H9.109 | Me | H | 2,3-diF | SCH₂ | 5,7-diCF₃ | O | S |
| H9.110 | Me | H | 2,3-diF | OCH₂ | 6,7-diCF₃ | O | S |
| H9.111 | Me | H | 2,3-diF | SCH₂ | 6,7-diCF₃ | O | S |
| H10.1 | Me | H | 2,3-diF | OCH₂ | 4-F,5-Me | O | S |
| H10.2 | Me | H | 2,3-diF | SCH₂ | 4-F,5-Me | O | S |
| H10.3 | Me | H | 2,3-diF | OCH₂ | 4-F,6-Me | O | S |
| H10.4 | Me | H | 2,3-diF | SCH₂ | 4-F,6-Me | O | S |
| H10.5 | Me | H | 2,3-diF | OCH₂ | 4-F,7-Me | O | S |
| H10.6 | Me | H | 2,3-diF | SCH₂ | 4-F,7-Me | O | S |
| H10.7 | Me | H | 2,3-diF | OCH₂ | 4-Me,5-F | O | S |
| H10.8 | Me | H | 2,3-diF | SCH₂ | 4-Me,5-F | O | S |
| H10.9 | Me | H | 2,3-diF | OCH₂ | 5-F,6-Me | O | S |
| H10.10 | Me | H | 2,3-diF | SCH₂ | 5-F,6-Me | O | S |
| H10.11 | Me | H | 2,3-diF | OCH₂ | 5-F,7-Me | O | S |
| H10.12 | Me | H | 2,3-diF | SCH₂ | 5-F,7-Me | O | S |
| H10.13 | Me | H | 2,3-diF | OCH₂ | 4-Me,6-F | O | S |
| H10.14 | Me | H | 2,3-diF | SCH₂ | 4-Me,6-F | O | S |
| H10.15 | Me | H | 2,3-diF | OCH₂ | 5-Me,6-F | O | S |
| H10.16 | Me | H | 2,3-diF | SCH₂ | 5-Me,6-F | O | S |
| H10.17 | Me | H | 2,3-diF | OCH₂ | 6-F,7-Me | O | S |
| H10.18 | Me | H | 2,3-diF | SCH₂ | 6-F,7-Me | O | S |
| H10.19 | Me | H | 2,3-diF | OCH₂ | 4-Me,7-F | O | S |
| H10.20 | Me | H | 2,3-diF | SCH₂ | 4-Me,7-F | O | S |
| H10.21 | Me | H | 2,3-diF | OCH₂ | 5-Me,7-F | O | S |
| H10.22 | Me | H | 2,3-diF | SCH₂ | 5-Me,7-F | O | S |
| H10.23 | Me | H | 2,3-diF | OCH₂ | 6-Me,7-F | O | S |
| H10.24 | Me | H | 2,3-diF | SCH₂ | 6-Me,7-F | O | S |
| H10.25 | Me | H | 2,3-diF | OCH₂ | 4-Cl,5-Me | O | S |
| H10.26 | Me | H | 2,3-diF | SCH₂ | 4-Cl,5-Me | O | S |
| H10.27 | Me | H | 2,3-diF | OCH₂ | 4-Cl,6-Me | O | S |
| H10.28 | Me | H | 2,3-diF | SCH₂ | 4-Cl,6-Me | O | S |
| H10.29 | Me | H | 2,3-diF | OCH₂ | 4-Cl,7-Me | O | S |
| H10.30 | Me | H | 2,3-diF | SCH₂ | 4-Cl,7-Me | O | S |
| H10.31 | Me | H | 2,3-diF | OCH₂ | 4-Me,5-Cl | O | S |
| H10.32 | Me | H | 2,3-diF | SCH₂ | 4-Me,5-Cl | O | S |
| H10.33 | Me | H | 2,3-diF | OCH₂ | 5-Cl,6-Me | O | S |
| H10.34 | Me | H | 2,3-diF | SCH₂ | 5-Cl,6-Me | O | S |
| H10.35 | Me | H | 2,3-diF | OCH₂ | 5-Cl,7-Me | O | S |
| H10.36 | Me | H | 2,3-diF | SCH₂ | 5-Cl,7-Me | O | S |
| H10.37 | Me | H | 2,3-diF | OCH₂ | 4-Me,6-Cl | O | S |
| H10.38 | Me | H | 2,3-diF | SCH₂ | 4-Me,6-Cl | O | S |
| H10.39 | Me | H | 2,3-diF | OCH₂ | 6-Cl,5-Me | O | S |
| H10.40 | Me | H | 2,3-diF | SCH₂ | 6-Cl,5-Me | O | S |
| H10.41 | Me | H | 2,3-diF | OCH₂ | 6-Cl,7-Me | O | S |
| H10.42 | Me | H | 2,3-diF | SCH₂ | 6-Cl,7-Me | O | S |
| H10.43 | Me | H | 2,3-diF | OCH₂ | 4-Me,7-Cl | O | S |
| H10.44 | Me | H | 2,3-diF | SCH₂ | 4-Me,7-Cl | O | S |
| H10.45 | Me | H | 2,3-diF | OCH₂ | 5-Me,7-Cl | O | S |
| H10.46 | Me | H | 2,3-diF | SCH₂ | 5-Me,7-Cl | O | S |
| H10.47 | Me | H | 2,3-diF | OCH₂ | 6-Me,7-Cl | O | S |
| H10.48 | Me | H | 2,3-diF | SCH₂ | 6-Me,7-Cl | O | S |
| H10.49 | Me | H | 2,3-diF | OCH₂ | 4-Cl,5-F | O | S |
| H10.50 | Me | H | 2,3-diF | SCH₂ | 4-Cl,5-F | O | S |
| H10.51 | Me | H | 2,3-diF | OCH₂ | 4-Cl,6-F | O | S |
| H10.52 | Me | H | 2,3-diF | SCH₂ | 4-Cl,6-F | O | S |
| H10.53 | Me | H | 2,3-diF | OCH₂ | 4-Cl,7-F | O | S |
| H10.54 | Me | H | 2,3-diF | SCH₂ | 4-Cl,7-F | O | S |
| H10.55 | Me | H | 2,3-diF | OCH₂ | 4-F,5-Cl | O | S |
| H10.56 | Me | H | 2,3-diF | SCH₂ | 4-F,5-Cl | O | S |
| H10.57 | Me | H | 2,3-diF | OCH₂ | 5-Cl,6-F | O | S |
| H10.58 | Me | H | 2,3-diF | SCH₂ | 5-Cl,6-F | O | S |
| H10.59 | Me | H | 2,3-diF | OCH₂ | 5-Cl,7-F | O | S |

TABLE 8-continued

| Compd. No. | R¹ | R² | (R³)ₙ | ACR⁴R⁵ | (R⁶)ₘ | X | Q |
|---|---|---|---|---|---|---|---|
| H10.60 | Me | H | 2,3-diF | SCH₂ | 5-Cl,7-F | O | S |
| H10.61 | Me | H | 2,3-diF | OCH₂ | 4-F,6-Cl | O | S |
| H10.62 | Me | H | 2,3-diF | SCH₂ | 4-F,6-Cl | O | S |
| H10.63 | Me | H | 2,3-diF | OCH₂ | 5-F,6-Cl | O | S |
| H10.64 | Me | H | 2,3-diF | SCH₂ | 5-F,6-Cl | O | S |
| H10.65 | Me | H | 2,3-diF | OCH₂ | 7-F,6-Cl | O | S |
| H10.66 | Me | H | 2,3-diF | SCH₂ | 7-F,6-Cl | O | S |
| H10.67 | Me | H | 2,3-diF | OCH₂ | 4-F,7-Cl | O | S |
| H10.68 | Me | H | 2,3-diF | SCH₂ | 4-F,7-Cl | O | S |
| H10.69 | Me | H | 2,3-diF | OCH₂ | 5-F,7-Cl | O | S |
| H10.70 | Me | H | 2,3-diF | SCH₂ | 5-F,7-Cl | O | S |
| H10.71 | Me | H | 2,3-diF | OCH₂ | 6-F,7-Cl | O | S |
| H10.72 | Me | H | 2,3-diF | SCH₂ | 6-F,7-Cl | O | S |
| H11.1 | Me | H | 2,3-diOMe | OCH₂ | 4-Me | O | S |
| H11.2 | Me | H | 2,3-diOMe | SCH₂ | 4-Me | O | S |
| H11.3 | Me | H | 2,3-diOMe | OCH₂ | 5-Me | O | S |
| H11.4 | Me | H | 2,3-diOMe | SCH₂ | 5-Me | O | S |
| H11.5 | Me | H | 2,3-diOMe | OCH₂ | 6-Me | O | S |
| H11.6 | Me | H | 2,3-diOMe | SCH₂ | 6-Me | O | S |
| H11.7 | Me | H | 2,3-diOMe | OCH₂ | 7-Me | O | S |
| H11.8 | Me | H | 2,3-diOMe | SCH₂ | 7-Me | O | S |
| H11.9 | Me | H | 2,3-diOMe | OCH₂ | 5-Et | O | S |
| H11.10 | Me | H | 2,3-diOMe | SCH₂ | 5-Et | O | S |
| H11.11 | Me | H | 2,3-diOMe | OCH₂ | 6-Et | O | S |
| H11.12 | Me | H | 2,3-diOMe | SCH₂ | 6-Et | O | S |
| H11.13 | Me | H | 2,3-diOMe | OCH₂ | 4-OMe | O | S |
| H11.14 | Me | H | 2,3-diOMe | SCH₂ | 4-OMe | O | S |
| H11.15 | Me | H | 2,3-diOMe | OCH₂ | 5-OMe | O | S |
| H11.16 | Me | H | 2,3-diOMe | SCH₂ | 5-OMe | O | S |
| H11.17 | Me | H | 2,3-diOMe | OCH₂ | 6-OMe | O | S |
| H11.18 | Me | H | 2,3-diOMe | SCH₂ | 6-OMe | O | S |
| H11.19 | Me | H | 2,3-diOMe | OCH₂ | 7-OMe | O | S |
| H11.20 | Me | H | 2,3-diOMe | SCH₂ | 7-OMe | O | S |
| H11.21 | Me | H | 2,3-diOMe | OCH₂ | 5-OEt | O | S |
| H11.22 | Me | H | 2,3-diOMe | SCH₂ | 5-OEt | O | S |
| H11.23 | Me | H | 2,3-diOMe | OCH₂ | 6-OEt | O | S |
| H11.24 | Me | H | 2,3-diOMe | SCH₂ | 6-OEt | O | S |
| H11.25 | Me | H | 2,3-diOMe | OCH₂ | 4-F | O | S |
| H11.26 | Me | H | 2,3-diOMe | SCH₂ | 4-F | O | S |
| H11.27 | Me | H | 2,3-diOMe | OCH₂ | 5-F | O | S |
| H11.28 | Me | H | 2,3-diOMe | SCH₂ | 5-F | O | S |
| H11.29 | Me | H | 2,3-diOMe | OCH₂ | 6-F | O | S |
| H11.30 | Me | H | 2,3-diOMe | SCH₂ | 6-F | O | S |
| H11.31 | Me | H | 2,3-diOMe | OCH₂ | 7-F | O | S |
| H11.32 | Me | H | 2,3-diOMe | SCH₂ | 7-F | O | S |
| H11.33 | Me | H | 2,3-diOMe | OCH₂ | 5-Cl | O | S |
| H11.34 | Me | H | 2,3-diOMe | SCH₂ | 5-Cl | O | S |
| H11.35 | Me | H | 2,3-diOMe | OCH₂ | 6-Cl | O | S |
| H11.36 | Me | H | 2,3-diOMe | SCH₂ | 6-Cl | O | S |
| H11.37 | Me | H | 2,3-diOMe | OCH₂ | 4-CF₃ | O | S |
| H11.38 | Me | H | 2,3-diOMe | SCH₂ | 4-CF₃ | O | S |
| H11.39 | Me | H | 2,3-diOMe | OCH₃ | 5-CF₃ | O | S |
| H11.40 | Me | H | 2,3-diOMe | SCH₃ | 5-CF₃ | O | S |
| H11.41 | Me | H | 2,3-diOMe | OCH₃ | 6-CF₃ | O | S |
| H11.42 | Me | H | 2,3-diOMe | SCH₃ | 6-CF₃ | O | S |
| H11.43 | Me | H | 2,3-diOMe | OCH₃ | 7-CF₃ | O | S |
| H11.44 | Me | H | 2,3-diOMe | SCH₃ | 7-CF₃ | O | S |
| H11.45 | Me | H | 2,3-diOMe | OCH₃ | 5-OCF₃ | O | S |
| H11.46 | Me | H | 2,3-diOMe | SCH₃ | 5-OCF₃ | O | S |
| H11.47 | Me | H | 2,3-diOMe | OCH₃ | 6-OCF₃ | O | S |
| H11.48 | Me | H | 2,3-diOMe | SCH₃ | 6-OCF₃ | O | S |
| H11.49 | Me | H | 2,3-diCl | OCH₃ | 5-F | O | S |
| H11.50 | Me | H | 2,5-diCl | OCH₃ | 5-F | O | S |
| H11.51 | Me | H | 2,6-diCl | OCH₂ | 5-F | O | S |
| H11.52 | MeO | H | 3,5-diCl | OCH₂ | 5-F | O | S |

Of the compounds listed above, preferred compounds are Compounds No. A1.1, A1.2, A1.3, A1.5, A1.6, A1.7, A1.8, A1.9, A1.13, A1.16, A1.18, A1.21, A1.25, A1.28, A1.31, A1.32, A1.45, A1.56, A1.58, A1.60, A1.62, A1.65, A1.70, B1.1, B1.3, B1.5, B1.10, B2.37, B2.63, C1.1, C1.2, C1.3, C1.5, C1.6, C1.11, C1.13, C1.17, C1.19, C1.23, C1.24, C1.27, C1.28, C1.36, C1.42, C1.44, C1.52, C1.55, C2.1, C2.4, C2.19, C3.30, C3.32, C4.27, C4.29, C6.1, C6.29, C7.55, C8.1, C8.2, C8.3, C8.6, C8.19, C8.20, C8.22, C8.23, C8.39, C8.72, C8.76, C9.1, C9.3, C9.4, C9.6, C9.20, C9.22, C9.23, C9.24, C9.36, C9.38, C9.39, C9.40, C9.52, C9.54, C9.55, C9.56, C10.1, C10.3, C10.4, C10.5, C10.17, C10.20, C10.42, C10.44, C10.46, C10.48, C10.49, C10.50, C10.62, C10.64, C10.65, C10.66, C10.78, C10.82, C10.84, C10.86, C10.88, C10.92, C10.94, C10.96, C10.98, C11.1, C11.4, C11.17, C11.20, C11.33, C11.48, C11.63, C11.64, C11.78, C11.79, C12.45, C12.47, C14.15, C14.18, C14.31, C14.45, C14.74, C15.37, C16.113, C16.126, C18.118, C18.119, C18.130, D1.1, D1.2, D1.4, D1.5, D1.8, D1.10, D1.13, D1.14, D1.16, D1.18, D1.35, D1.37, D1.40, D1.43, D1.46, D1.47, D1.49, D1.50, D1.51, D1.55, D1.56, D1.57, D1.60, D1.62, D1.65, D1.67, D1.68, D1.69, D1.70, D1.71, D1.72, D1.74, D1.76, D1.78, D1.79, D1.80, D1.81, D1.82, D1.83, D1.85, D1.87, D1.88, D1.90, D1.91, D1.92, D1.93, D1.94, D1.95, D1.97, D1.98, D1.99, D1.100, D 1.101, D1.102, D1.103, D 1.104, D1.105, D1.106, D1.109, D1.110, D1.112, D 1.113, D1.114, D1.116, D1.117, D1.118, D1.119, D1.122, D1.123, D1.125, D1.126, D1.128, D1.129, D1.130, D1.131, D1.132, D1.135, D1.136, D2.1, D2.4, D2.5, D2.6, D2.7, D2.9, D2.10, D2.11, D2.13, D2.14, D2.15, D2.17, D2.19, D2.20, D2.21, D2.22, D2.23, D2.25, D2.26, D2.28, D2.29, D2.30, D2.32, D2.40, D2.41, D2.42, D2.44, D2.45, D2.46, D2.47, D2.48, D2.50, D2.52, D2.53, D2.54, D2.55, D2.56, D2.57, D2.60, D2.61, D2.63, D2.65, D2.66, D2.67, D2.68, D2.72, D2.73, D2.74, D2.75, D2.76, D2.77, D2.78, D2.79, D2.80, D2.81, D2.82, D2.83, D2.84, D2.85, E1.1, E1.3, E1.15, E1.17, E4.1, EG.1, E7.5, E7.10, E7.131, E7.135, F1.1, F1.3, F1.5, F1.11, F1.15, F1.21, F1.25, F1.31, F1.33, F1.69, F3.1, F3.3, F3.10, F3.14, F3.20, F3.21, F3.22, F3.29, F3.31, F3.56, F4.1, F4.11, F4.12, F4.14, F4.16, F4.19, F4.20, F4.22, F4.23, F4.25, F4.27, F4.28, F4.30, F4.33, F4.40, F4.41, F4.43, F4.59, F4.61, F4.63, F4.69, F4.71, F4.79, F4.81, F4.103, F5.3, F5.9, F5.13, F6.11, F6.12, F6.15, F6.16, F6.19, F6.20, F6.23, F6.24, F7.17, F7.34, F7.39, F7.45, F7.56, F7.69, F7.92, F7.99, F7.120, F7.136, F7.147, F7.169, F7.173, G1.3, G1.4, G1.5, G1.6, G1.8, G1.9, G1.10, G1.11, G1.13, G1.14, G1.15, G1.19, G1.20, G1.30, G1.32, G1.34, G1.35, G1.36, G1.37, G1.39, G1.44, G1.50, G1.52, G1.55, G1.57, G1.58, G1.59, G1.60, G1.62, G1.63, G1.64, G1.67, G1.68, G1.69, G1.72, G1.74, G1.76, G1.77, G1.81, G1.85, G1.87, G1.89, G1.92, G1.94, G1.95, G1.96, G1.97, G1.99, G1.109, G1.113, G1.114, G1.117, G1.118, G1.121, G1.122, G1.127, G1.128, G2.13, G2.14, G2.42, G2.49, G2.50, G2.61, G2.62, G2.86, G2.97, G2.115, G2.137, G2.148, G2.166, G5.3, G5.6, G5.17, G5.20, G5.33, G5.38, G5.45, G5.52, G6.31, G8.31, G8.33, G8.36, G8.38, G10.51, G10.57, G10.61, G10.63, H4.3, H4.8, H4.19, H4.22, H4.35, H4.38, H4.43, H4.50, H4.91, H7.4, H7.9, H7.18, H7.21, H7.36, H7.41, H7.49, H7.63 and H7.106.

More preferred compounds are Compounds No. A1.1, A1.2, A1.5, A1.6, A1.7, A1.9, A1.18, A1.21, A1.25, A1.28, A1.62, A1.65, A1.70, B1.1, B1.3, B1.5, B1.10, B2.63, C1.1, C1.2, C1.5, C1.6, C1.17, C1.23, C1.24, C1.36, C1.42, C1.44, C1.52, C1.55, C2.1, C2.4, C2.19, C3.30, C3.32, C8.1, C8.2, C8.3, C8.6, C8.19, C8.20, C8.22, C8.23, C8.39, C9.1, C9.3, C9.4, C9.6, C9.20, C9.22, C9.23, C9.24, C9.36, C9.38, C9.39, C9.40, C9.52, C9.54, C9.55, C9.56, C11.1, D1.1, D1.2, D1.4, D1.5, D1.8, D1.10, D1.47, D1.49, D1.50, D1.51, D1.55, D1.66, D1.68, D1.70, D1.71, D1.72, D1.74, D1.103, D1.105, D1.106, D2.1, D2.4, D2.5, D2.6, D2.7, D2.9, D2.10, D2.11, D2.19, D2.20, D2.26, D2.28, D2.30, 12)2.40, D2.65, D2.73, D2.74, D2.75, D2.76, D2.77, D2.78, D2.79, D2.84, E1.1, E1.15, F1.1, F1.3, F1.5, F1.11, F1.15, F1.21, F1.25, F1.31, F1.33, F3.1, F3.3, F3.10, F3.14, F3.20, F3.22, F3.29, F3.31, F3.56, F4.1, F4.11, F4.12, F4.14, F4.19, F4.20, F4.22, F4.23, F4.25, F4.27, F4.28, F4.30, F4.33, F4.40, F4.41, F4.43, F4.59, F4.61, F4.63, F4.69, F4.71, F4.79, F4.81, F4.103, F5.13, F6.24, F7.34, F7.39, F7.45, F7.56, G1.3, G1.4, G1.5, G1.6, G1.8, G1.9, G1.10, G1.11, G1.13, G1.14, G1.15, G1.19, G1.20, G1.30, G1.32, G1.34, G1.35, G1.36, G1.37, G1.39, G1.44, G1.50, G1.52, G1.55, G1.57, G1.58, G1.59, G1.60, G1.62, G1.63, G1.64, G1.67, G1.68, G1.69, G1.72, G1.74, G1.76, G1.77, G1.81, G1.85, G1.92, G2.5, G2.42, G5.3, G5.6, G5.17, G5.33, G5.38, G5.45, G6.31, G8.31, G8.33, G8.36, G8.38, G10.51, H4.3, H4.8, H4.19, H4.22, H4.35, H4.38, H4.43, H4.91 and H7.36.

Still more preferred compounds are Compounds No. C1.1, C1.2, C1.5, C1.6, D1.47, D1.70, D2.4, D2.5, D2.75, D2.76, D2.84, G1.32, G1.34, G1.35, G1.36, G1.37, G1.39, G1.50, G1.52, G1.55, G1.57, G1.58, G1.59, G1.60, G1.62, G1.63, G1.64, G1.72, G1.74, G1.76, G1.77 and G1.81.

The most preferred compounds are Compounds No.:

C1.1. N-[4-(benzothiazol-2-ylmethoxy)-2-methylphenyl] acetamide;

C1.2. N-[4-(benzoxazol-2-ylmethoxy)-2-methylphenyl] acetamide;

C1.5. methyl N-[4-(benzothiazol-2-ylmethoxy)-2-methylphenyl]carbamate;

C1.6. methyl N-[4-(benzoxazol-2-ylmethoxy)-2-methylphenyl]carbamate;

D1.47. methyl N-[4-(benzothiazol-2-ylmethoxy)-2-methylphenyl]-N-hydroxymethylcarbamate;

D1.70. methyl N-[4-(benzothiazol-2-ylmethoxy)-2-methylphenyl]-N-propionyloxymethylcarbamate;

D2.4. N-[4-(benzothiazol-2-ylmethoxy)-2-methylphenyl]-N-methoxycarbonylpropionamide;

G1.39. methyl N-[4-(6-methoxybenzothiazol-2-ylmethoxy)-2-methylphenyl]carbamate;

G1.57. methyl N-[4-(5-fluorobenzothiazol-2-ylmethoxy)-2-methylphenyl]carbamate; and G1.62. methyl N-[4-(6-fluorobenzothiazol-2-ylmethoxy)-2-methylphenyl]carbamate.

The compounds of the present invention can be prepared by a variety of methods well known in the art for compounds of this type. For example, in general terms, the compounds may be prepared according to he following steps:

(i) reacting a compound of general formula (II)

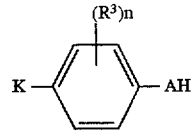

wherein $R^3$, A and n are as defined above and K represents a group of formula $N(R^2)C(=X)R^1$ wherein $R^1$, X and $R^2$ are as defined above, a nitro group or an amino group, with a group of formula (III):

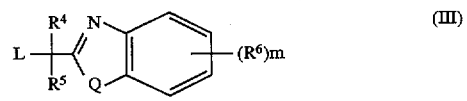

wherein $R^4$, $R^5$, $R^6$, Q and m are as defined above and L is a leaving group, to give a compound of formula (Ia), (VIa) or (VIIa):

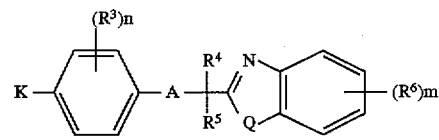

(Ia): K = N(R²)C(=X)R¹
(VIa): K = NO₂
(VIIa): K = NH₂ wherein $R^3$, A, $R^4$, $R^5$, $R^6$, Q, m and n are as defined above and K is as shown;

(ii) where the compound produced in step (i) above is a compound of formula (VIa), wherein K represents a nitro group, reacting said compound with a reducing agent to give a compound of formula (VIIa) wherein K is an amino group;

(iii) where the compound is a compound of formula (VIIa) produced in step (i) or (ii) above, reacting said compound with a group of formula $R^1C(=X)L^2$ wherein $R^1$ and X are as defined above and $L^2$ represents a leaving group, to give a compound of formula (Ia')

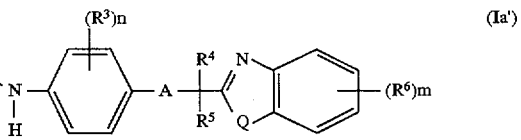

wherein $R^1$, X, $R^3$, A, $R^4$, $R^5$, $R^6$, Q, m and n are as defined above;

(iv) optionally, reacting said compound of formula (Ia) or (Ia') with a compound of formula $R^{2a}L^3$, wherein $R^{2a}$ represents any of the groups represented by $R^2$ other than a hydrogen atom and $L^3$ represents a leaving group, to give a compound of formula (Ib')

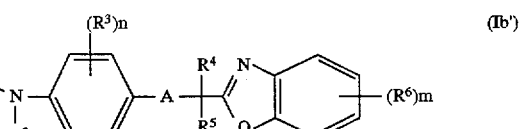

wherein $R^1$, $R^{2a}$, X, $R^3$, A, $R^4$, $R^5$, $R^6$, Q, m and n are as defined above; and (v) optionally reacting said compound of formula (Ib') with a suitable reagent to give a compound of formula (Ic')

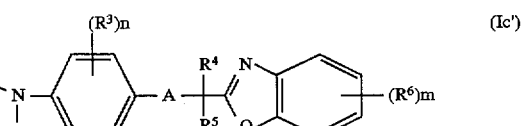

in which the group of Formula $R^{2a}$ in the compound of formula (Ib') is converted to a group of formula $R^{2c}$, wherein $R^{2c}$ is a different group falling within the definition of the group $R^2$. The compound of formula (Ia), (Ia'), (Ib') or (Ic') may, if desired, be salified to give the addition salt thereof.

More specifically, the compounds of formula (I) of the present invention may be prepared as illustrated in the following Reaction Scheme A:

Reaction Scheme A

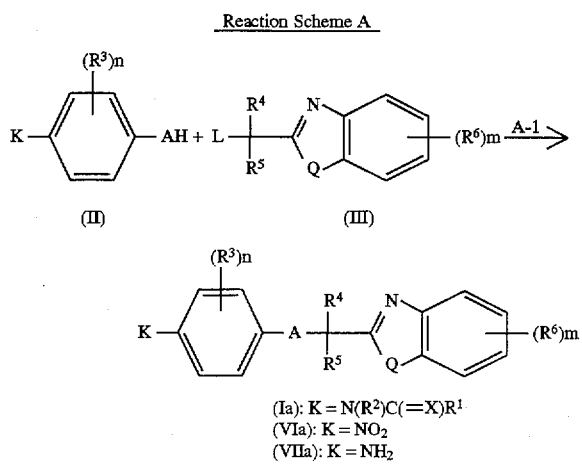

(Ia): K = N(R²)C(=X)R¹
(VIa): K = NO₂
(VIIa): K = NH₂

In the above formulae, $R^1$, $R^2$, $R^3$, $R^4$, $R^5$, $R^6$, A, X, Q, m and n are as defined above and K is as shown. L represents a group of formula $Z^1$, wherein $Z^1$ represents a chlorine atom, a bromine atom or an iodine atom, or a group of formula $OR^9$, wherein $R^9$ represents an alkylsulfonyl group (e.g. a methanesulfonyl group), an arylsulfonyl group (e.g. a p-toluenesulfonyl group) or a dialkylphosphinyl group (e.g. a dimethylphosphinyl or diethylphosphinyl group).

Step A-1

Depending upon the nature of the group K in the starting compound of formula (II), Step A-1 can give:
(i) a compound of formula (I) of the present invention in the case that K represents a group represented by N(R²)C(=X)R¹; or
(ii) compounds of formulae (VIa) or (VIIa) in the case that K represents a nitro group or an amino group respectively, which are starting materials for use in the preparation of the compounds of formula (I) of the present invention.

The reaction of Step A-1 involves the condensation of a phenolic derivative or a thiophenolic derivative of formula (II), which can be prepared according to Reaction Scheme B below, with a benzothiazole compound or a benzoxazole compound of formula (III), which can be prepared according to Reaction Schemes C and D below.

The present step is carried out in the presence of a solvent and, if necessary, in the presence of a base.

Where a base is employed, the precise nature of the base is not critical. Examples of suitable bases include alkali metal hydroxides such as sodium hydroxide and potassium hydroxide; alkali metal carbonates such as sodium carbonate, potassium carbonate and caesium carbonate; metal alkoxides such as sodium methoxide, sodium ethoxide and potassium t-butoxide; alkali metal hydrides such as sodium hydride and potassium hydride; aliphatic tertiary amines such as triethylamine, tri-n-butylamine and diisopropylethylamine; aliphatic cyclic tertiary amines such as 1,4-diazabicyclo[2.2.2]octane (DABCO) and 1,8-diazabicyclo[5.4.0]undec-7-ene (DBU); pyridines such as pyridine, collidine and 4-(N,N-dimethylamino)pyridine; and organic metal bases such as n-butyl lithium, s-butyl lithium, lithium diisopropylamide, sodium bis(trimethylsilyl)amide and lithium bis(trimethylsilyl)amide.

There is no particular restriction on the nature of the solvent employed provided that it has no adverse effect on the reaction or on the reagents involved and that it dissolves the starting materials, at least to some extent. Examples of preferred solvents include water; alcohols such as methanol, ethanol and t-butanol; ketones such as acetone and methyl isobutyl ketone; nitriles such as acetonitrile; esters such as ethyl acetate; halogenated hydrocarbons such as methylene chloride, chloroform and dichloroethane; ethers such as diethyl ether, tetrahydrofuran and dioxane; aromatic hydrocarbons such as toluene; amides such as dimethylformamide and dimethylacetamide; sulfoxides such as dimethyl sulfoxide; and mixed solvents thereof.

The reaction can take place over a wide range of temperatures, and the precise reaction temperature is not critical to the invention. In general, we find it convenient to carry out the reaction at a temperature of from −90° C. to 200° C., preferably 0° C. to 100° C.

The reaction time may vary widely, depending on many factors, notably the reaction temperature, the nature of the starting compounds, the nature of the reaction reagents and the nature of the solvents used. In general, we find it convenient to carry out the reaction for a time of from 5 minutes to 24 hours, preferably from 15 minutes to 6 hours.

Reaction Scheme B

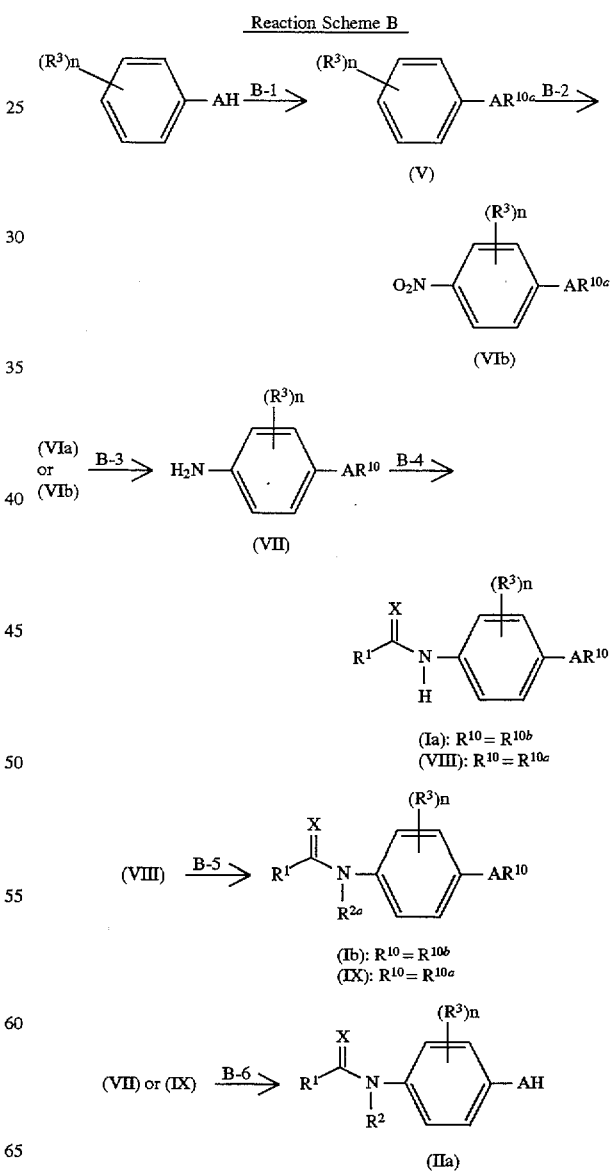

(Ia): $R^{10} = R^{10b}$
(VIII): $R^{10} = R^{10a}$ (Ib): $R^{10} = R^{10b}$
(IX): $R^{10} = R^{10a}$

-continued
Reaction Scheme B

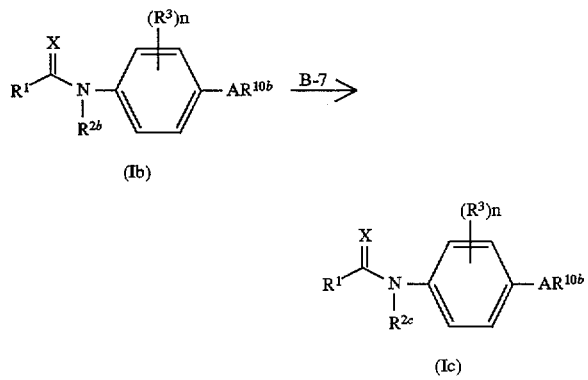

In the above formulae:

$R^{10}$ represents a group of formula $R^{10a}$ or a group of formula $R^{10b}$, wherein $R^{10a}$ represents a hydroxy protecting group or a mercapto protecting group and $R^{10b}$ represents a group of formula (IIIa)

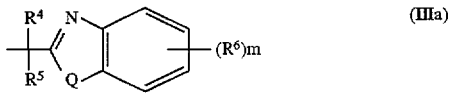

wherein $R^4$, $R^5$, $R^6$, Q and m are as defined above;
$R^1$, $R^2$, $R^3$, $R^4$, $R^5$, $R^6$, A, Q, X, m and n are as defined above;

$R^{2a}$ represents an alkyl group having from 1 to 6 carbon atoms, said alkyl group being unsubstituted or being substituted by a hydroxy group or by from 1 to 4 halogen atoms, a cycloalkyl group having from 3 to 6 carbon atoms, an alkenyl group having from 2 to 6 carbon atoms, said alkenyl group being unsubstituted or being substituted by from 1 to 4 halogen atoms, an alkynyl group having from 2 to 6 carbon atoms, said alkynyl group being unsubstituted or being substituted by from 1 to 4 halogen atoms, or by a group represented by the formula —$YR^7$, as defined above;

$R^{2b}$ represents a group chosen from the groups of formula $CH_2OH$, $CH_2CH_2OH$, $CH_2OR^7$, $CH_2CH_2OR^7$; and $R^{2c}$ represents a group chosen from the groups of formula $CH_2OH$, $CH_2CH_2OH$, $CH_2OR^7$, $CH_2CH_2OR^7$, $CH_2OCOR^7$ and $CH_2CH_2OCOR^7$.

The nature of the hydroxy protecting group and the mercapto protecting group is not particularly critical, provided that said protecting groups can be removed under appropriate conditions to give the hydroxy group or mercapto group without harming the rest of the molecule and that said protecting groups do not react with any of the reagents employed in the steps of the reaction scheme before the protecting groups are removed. Preferred examples of suitable hydroxy and mercapto protecting groups include acyl groups such as acetyl and propionyl groups; and alkoxycarbonyl groups such as methoxycarbonyl groups and ethoxycarbonyl groups.

Step B-1

The object of Step B-1 is the protection of the hydroxyl group or the mercapto group in the phenolic derivative or the thiophenolic derivative of formula (IV) with a protecting group of formula $R^{10a}$ to give a protected compound of formula (V).

The present step is carried out by reacting the compound of formula (IV) in a solvent in the presence of a base with a compound represented by the general formula $R^{10a}L^1$ (wherein $R^{10a}$ is as defined above and $L^1$ represents a leaving group which is usually a nucleophilic residue, preferred examples of which include chlorine atoms, bromine atoms, iodine atoms, sulfonyloxy groups such as methanesulfonyloxy and p-toluenesulfonyloxy groups, sulfinyloxy groups such as methylsulfinyloxy and ethylsulfinyloxy groups, and phosphinyloxy groups such as dimethylphosphinyloxy groups and diethylphosphinyloxy groups).

The nature of the base employed is not particularly critical, provided that it has the basicity necessary to eliminate the proton of the hydroxy group on the phenoli c ring or the mercapto group on the thiophenolic ring. Preferred examples include alkali metal hydroxides such as sodium hydroxide and potassium hydroxide; alkali metal carbonates such as sodium carbonate and potassium carbonate; metal alkoxides such as sodium methoxide, sodium ethoxide and potassium t-butoxide; alkali metal hydrides such as sodium hydride and potassium hydride; aliphatic tertiary amines such as triethylamine, tri-n-butylamine and diisopropylethylamine; aliphatic cyclic tertiary amines such as 1,4-diazabicyclo[2.2.2]octane (DABCO) and 1,8-diazabicyclo[5.4.0]undec-7-ene (DBU); and pyridines such as pyridine, collidine and 4-(N,N-dimethylamino)pyridine.

There is no particular restriction on the nature of the solvent employed provided that it has no adverse effect on the reaction or on the reagents involved and that it dissolves the starting materials, at least to some extent. Examples of preferred solvents include water; alcohols such as methanol, ethanol and t-butanol; ketones such as acetone and methyl isobutyl ketone; nitriles such as acetonitrile; esters such as ethyl acetate; halogenated hydrocarbons such as methylene chloride, chloroform and dichloroethane; ethers such as diethyl ether, tetrahydrofuran and dioxane; aromatic hydrocarbons such as toluene; amides such as dimethylformamide and dimethylacetamide; and sulfoxides such as dimethyl sulfoxide.

The reaction can take place over a wide range of temperatures, and the, precise reaction temperature is not critical to the invention. In general, we find it convenient to carry out the reaction at a temperature of from −70° C. to 200° C., preferably −10° C. to 80° C.

The reaction time may vary widely, depending on many factors, notably the reaction temperature, the nature of the starting compounds, the nature of the reaction reagents and the nature of the solvents used. In general, we find it convenient to carry out the reaction for a time of from 5 minutes to 24 hours, preferably from 30 minutes to 5 hours.

Step B-2

The object of Step B-2 is the nitration of a compound of formula (V), prepared as described in Step B-1 above, to give a compound of formula (VIb) in which a nitro group has been introduced para to the hydroxy group or the mercapto group.

The present reaction can be carried out using well known methods for the nitration of an aromatic ring. Examples of such methods include nitration using a mixed acid of concentrated sulfuric acid and concentrated nitric acid and nitration using potassium nitrate.

The present step may be carried out in the presence or absence of a solvent. Where a solvent is employed, there is no particular restriction on the nature of the solvent provided that it has no adverse effect on the reaction or on the reagents involved and that it dissolves the starting materials, at least to some extent. Examples of preferred solvents include acetic acid and halogenated hydrocarbons such as dichloromethane, chloroform and 1,2-dichloroethane.

The reaction can take place over a wide range of temperatures, and the precise reaction temperature is not critical to the invention. In general, we find it convenient to carry out the reaction at a temperature of from −90° C. to 200° C., preferably −50° C. to 80° C.

The reaction time may vary widely, depending on many factors, notably the reaction temperature, the nature of the starting compounds, the nature of the reaction reagents and the nature of the solvents used. In general, we find it convenient to carry out the reaction for a time of from 5 minutes to 24 hours, preferably from 30 minutes to 6 hours.

Step B-3

The object of Step B-3 depends on the nature of the starting material used and is either:

(i) the production of a 4-aminophenol or 4-aminothiophenol derivative of formula (VII), wherein $R^{10}$ represents a protecting group of formula $R^{10a}$ as defined above, by reducing the nitro group of the compound (VIb) prepared according to Step B-2; or (ii) the production of a compound of formula (VII) wherein $R^{10}$ represents a group of formula $R^{10b}$ as defined above [i.e. a compound of formula (VIIa)] by reducing the nitro group in the compound of formula (via), prepared according to Step A-1 above.

The present step can be carried out using known methods for reducing a nitro group to an amino group. Examples include hydrogenation in the presence of palladium-on-charcoal catalyst; treatment of the starting compound with stannous chloride in the presence of concentrated hydrochloric acid; and treatment of the starting compound with zinc chloride in acetic acid.

The present step may be carried out in the presence or absence of a solvent.. Where a solvent is employed, there is no particular restriction on the nature of the solvent provided that it has no adverse effect on the reaction or on the reagents involved and that it dissolves the starting materials, at least to some extent. Examples of preferred solvents include water, alcohols such as methanol, ethanol and t-butanol; esters such as ethyl acetate; ethers such as diethyl ether, tetrahydrofuran and dioxane; aromatic hydrocarbons such as toluene; organic acids such as acetic acid and formic acid; amides such as dimethylformamide and dimethylacetoamide; and sulfoxides such as dimethyl sulfoxide.

The reaction can take place over a wide range of temperatures, and the precise reaction temperature is not critical to the invention. In general, we find it convenient to carry out the reaction at a temperature of from −90° C. to 200° C., preferably 0° C. to 100° C.

The reaction time may vary widely, depending on many factors, notably the reaction temperature, the nature of the starting compounds, the nature of the reaction reagents and the nature of the solvents used. In general, we find it convenient to carry out the reaction for a time of from 5 minutes to 24 hours, preferably from 30 minutes to 12 hours.

Step B-4

The object of Step B-3 depends on the nature of the starting material used and is either:

(i) the production of an amide or carbamate of formula (Ia') by the reaction of a compound of formula (VIIa), in the presence or absence of a solvent and, if necessary, in the presence of a base, with a compound represented by the general formula $R^1C(=X)L^2$ (wherein $R^1$ and X are as defined above, and $L^2$ represents a leaving group which is usually a nucleophilic residue, preferred examples of which include chlorine atoms, bromine atoms, iodine atoms, sulfonyloxy groups such as methanesulfonyloxy and p-toluenesulfonyloxy groups, sulfinyloxy groups such as methylsulfinyloxy and ethylsulfinyloxy groups, and phosphinyloxy groups such as dimethylphosphinyloxy groups and diethylphosphinyloxy groups); or (ii) the production of an amide or carbamate of formula (VIII) by the reaction of a compound of formula (VII), wherein $R^{10}$ represents a protecting group of formula $R^{10a}$ as defined above, in the presence or absence of a solvent and, if necessary in the presence of a base, with a compound represented by the general formula: $R^1C(=X)L^2$ (wherein $R^1$, X and $L^2$ are as defined above).

Where a base is employed, the nature of the base employed is not particularly critical. Preferred examples include alkali metal hydroxides such as sodium hydroxide and potassium hydroxide; alkali metal carbonates such as sodium carbonate and potassium carbonate; metal alkoxides such as sodium methoxide, sodium ethoxide and potassium t-butoxide; alkali metal hydrides such as sodium hydride and potassium hydride; aliphatic tertiary amines such as triethylamine, tri-n-butylamine and diisopropylethylamine; tertiary anilines such as N,N-dimethylaniline and N,N-diethylaniline; aliphatic cyclic tertiary amines such as 1,4-diazabicyclo[2.2.2]octane (DABCO) and 1,8-diazabicyclo [5.4.0]undec-7-ene (DBU); pyridines such as pyridine, collidine and 4-(N,N-dimethylamino)pyridine; and organic metal bases such as n-butyl lithium, s-butyl lithium, lithium diisopropylamide, sodium bis(trimethylsilyl)amide and lithium bis(trimethylsilyl)amide.

Where a solvent is employed, there is no particular restriction on the nature of the solvent provided that it has no adverse effect on the reaction or on the reagents involved and that it dissolves the starting materials, at least to some extent. Examples of preferred solvents include water; alcohols such as methanol, ethanol and t-butanol; ketones such as acetone and methyl isobutyl ketone; nitriles such as acetonitrile; esters such as ethyl acetate; halogenated hydrocarbons such as methylene chloride, chloroform and dichloroethane; ethers such as diethyl ether, tetrahydrofuran and dioxane; aromatic hydrocarbons such as toluene and mixed solvents thereof.

The reaction can take place over a wide range of temperatures, and the precise reaction temperature is not critical to the invention. In general, we find it convenient to carry out the reaction at a temperature of from −90° C. to 200° C., preferably −10° C. to 100° C.

The reaction time may vary widely, depending on many factors, notably the reaction temperature, the nature of the starting compounds, the nature of the reaction reagents and the nature of the solvents used. In general, we find it convenient to carry out the reaction for a time of from 5 minutes to 24 hours, preferably from 15 minutes to 6 hours.

In the present step, optionally an isocyanate or an isothiocyanate can be produced as an intermediate by reacting the compound of formula (VII) or (VIIa) with a compound represented by the formula $C(=X)Cl_2$ (wherein X is as defined above) in the presence or absence of a solvent and, if necessary, in the presence of a base, where the target compound of formula (Ia') or (VIII) is one wherein $R^1$ represents a group of formula $R^{1a}$ (wherein $R^{1a}$ represents an alkoxy group having from 1 to 6 carbon atoms, which is unsubstituted or is substituted by 1 to 4 halogen atoms, or an alkylthio group having from 1 to 6 carbon, which is unsubstituted or is substituted by 1 to 4 halogen atoms). The intermediate thus produced is reacted with a compound of formula $R^{1a}Z^2$ (wherein $R^{1a}$ is as defined above and $Z^2$ represents a hydrogen atom or an alkali metal such as sodium and potassium), in the presence or absence of a solvent and, if necessary, in the presence of a base to give a compound of formula (Ia') or (VIII).

Where a base is employed in this optional step, the nature of the base employed is not particularly critical. Preferred examples include alkali metal hydroxides such as sodium hydroxide and potassium hydroxide; alkali metal carbonates such as sodium carbonate, potassium carbonate and caesium carbonate; metal alkoxides such as sodium methoxide, sodium ethoxide and potassium t-butoxide; alkali metal hydrides such as sodium hydride and potassium hydride; aliphatic tertiary amines such as triethylamine, tri-n-butylamine and diisopropylethylamine; aliphatic cyclic tertiary amines such as 1,4-diazabicyclo[2.2.2]octane (DABCO) and 1,8-diazabicyclo[5.4.0]undec-7-ene (DBU); pyridines such as pyridine, collidine and 4-(N,N-dimethylamino)pyridine; and organic metal bases such as n-butyl lithium, s-butyl lithium, lithium diisopropylamide, sodium bis(trimethylsilyl)amide and lithium bis(trimethylsilyl)amide.

Where a solvent is employed, there is no particular restriction on the nature of the solvent provided that it has no adverse effect on the reaction or on the reagents involved and that it dissolves the starting materials, at least to some extent. Examples of preferred solvents include alcohols such as methanol, ethanol and t-butanol; ketones such as acetone and methyl isobutyl ketone; esters such as ethyl acetate; halogenated hydrocarbons such as methylene chloride, chloroform and dichloroethane; ethers such as diethyl ether, tetrahydrofuran and dioxane; aromatic hydrocarbons such as toluene; amides such as dimethylformamide and dimethylacetamide; sulfoxides such as dimethyl sulfoxide; and mixed solvents thereof.

The reaction can take place over a wide range of temperatures, and the precise reaction temperature is not critical to the invention. In general, we find it convenient to carry out the reaction at a temperature of from −90° C. to 200° C., preferably −10° C. to 100° C.

The reaction time may vary widely, depending on many factors, notably the reaction temperature, the nature of the starting compounds, the nature of the reaction reagents and the nature of the solvents used. In general, we find it convenient to carry out the reaction for a time of from 3 minutes to 24 hours, preferably from 5 minutes to 6 hours.

As a further option, when the target compound is a compound of formula (Ia') or (VIII) wherein X represents a sulfur atom and $R^1$ represents an alkylthio group having from 1 to 6 carbon atoms, said alkylthio group being unsubstituted or being substituted by 1 to 4 halogen atoms, the present step may also be carried out by reacting a compound of formula (VIIa) or (VII) with carbon disulfide to give a dithiocarbamate intermediate, which is then reacted with a compound of formula $R^{1b}Z^3$ (wherein $R^{1b}$ represents an alkylthio group having from 1 to 6 carbon atoms, said alkylthio group being unsubstituted or being substituted by 1 to 4 halogen atoms, and $Z^3$ represents a chlorine atom, a bromine atom or an iodine atom) in the presence or absence of a solvent and in the presence of a base.

The nature of the base employed is not particularly critical. Preferred examples include alkali metal hydroxides such as sodium hydroxide and potassium hydroxide; alkali metal carbonates such as sodium carbonate, potassium carbonate and caesium carbonate; metal alkoxides such as sodium methoxide, sodium ethoxide and potassium t-butoxide; alkali metal hydrides such as sodium hydride and potassium hydride; aliphatic tertiary amines such as triethylamine, tri-n-butylamine and diisopropylethylamine; aliphatic cyclic tertiary amines such as 1,4-diazabicyclo[2.2.2]octane (DABCO) and 1,8-diazabicyclo[5.4.0]undec-7-ene (DBU); pyridines such as pyridine, collidine and 4-(N,N-dimethylamino)pyridine; and organic metal bases such as n-butyl lithium, s-butyl lithium, lithium diisopropylamide, sodium bis(trimethylsilyl)amide and lithium bis(trimethylsilyl)amide.

Where a solvent is employed, there is no particular restriction on the nature of the solvent provided that it has no adverse effect on the reaction or on the reagents involved and that it dissolves the starting materials, at least to some extent. Examples of preferred solvents include water; alcohols such as methanol, ethanol and t-butanol; ketones such as acetone and methyl isobutyl ketone; nitriles such as acetonitrile; esters such as ethyl acetate; halogenated hydrocarbons such as methylene chloride, chloroform and dichloroethane; ethers such as diethyl ether, tetrahydrofuran and dioxane; aromatic hydrocarbons such as toluene; amides such as dimethylformamide and dimethylacetamide; sulfoxides such as dimethyl sulfoxide; and mixed solvents thereof.

The reaction can take place over a wide range of temperatures, and the precise reaction temperature is not critical to the invention. In general, we find it convenient to carry out the reaction at a temperature of from −90° C. to 200° C., preferably −10° C. to 100° C.

The reaction time may vary widely, depending on many factors, notably the reaction temperature, the nature of the starting compounds, the nature of the reaction reagents and the nature of the solvents used. In general, we find it convenient to carry out the reaction for a time of from 5 minutes to 24 hours, preferably from 10 minutes to 6 hours.

Step B-5

The object of Step B-5 is the introduction of the substituent $R^{2a}$, wherein $R^{2a}$ is as defined above, at the nitrogen atom of the amide group or the carbamate group of the compound of formula (Ia') or (VIII) to give a compound of formula (Ib) or (IX) respectively.

The present step may be carried out by reacting the compound (Ia') or (VIII) with a compound of general formula $R^{2a}L^3$ (wherein $R^{2a}$ is as defined above and $L^3$ represents a leaving group which is usually a nucleophilic residue, preferred examples of which include chlorine atoms, bromine atoms, iodine atoms, sulfonyloxy groups such as methanesulfonyloxy and p-toluenesulfonyloxy groups, sulfinyloxy groups such as methylsulfinyloxy and ethylsulfinyloxy groups, and phosphinyloxy groups such as dimethylphosphinyloxy groups and diethylphosphinyloxy groups), in a solvent in the presence of a base.

The nature of the base employed is not particularly critical. Preferred examples include alkali metal hydroxides such as sodium hydroxide and potassium hydroxide; alkali metal carbonates such as sodium carbonate and potassium carbonate; metal alkoxides such as sodium methoxide, sodium ethoxide and potassium t-butoxide; alkali metal hydrides such as sodium hydride and potassium hydride; aliphatic tertiary amines such as triethylamine, tri-n-butylamine and diisopropylethylamine; aliphatic cyclic tertiary amines such as 1,4-diazabicyclo[2.2.2]octane (DABCO) and 1,8-diazabicyclo[5.4.0]undec-7-ene (DBU); and pyridines such as pyridine, collidine and 4-(N,N-dimethylamino)pyridine.

There is no particular restriction on the nature of the solvent employed provided that it has no adverse effect on the reaction or on the reagents involved and that it dissolves the starting materials, at least to some extent. Examples of preferred solvents include water; alcohols such as methanol, ethanol and t-butanol; ketones such as acetone and methyl isobutyl ketone; nitriles such as acetonitrile; esters such as ethyl acetate; halogenated hydrocarbons such as methylene chloride, chloroform and dichloroethane; ethers such as diethyl ether, tetrahydrofuran and dioxane; aromatic hydrocarbons such as toluene; amides such as dimethylformamide and dimethylacetamide; and sulfoxides such as dimethyl sulfoxide.

The reaction can take place over a wide range of temperatures, and the precise reaction temperature is not critical to the invention. In general, we find it convenient to carry out the reaction at a temperature of from −70° C. to 200° C., preferably −10° C. to 80° C.

The reaction time may vary widely, depending on many factors, notably the reaction temperature, the nature of the starting compounds, the nature of the reaction reagents and the nature of the solvents used. In general, we find it convenient to carry out the reaction for a time of from 5 minutes to 24 hours, preferably from 30 minutes to 5 hours. Where $R^{2a}$ represents a $CH_2OH$ group, the present step is performed by reacting the compound of formula (Ia') or (VIII) with formaldehyde in the presence or absence of a solvent, if necessary in the presence of a base.

Where a base is used for this step for the production of compounds of formula (Ib) or (IX) wherein $R^{2a}$ represents a $CH_2OH$ group, the nature of the base employed is not particularly critical. Preferred examples include alkali metal hydroxides such as sodium hydroxide and potassium hydroxide, alkali metal carbonates such as sodium carbonate, potassium carbonate and caesium carbonate; metal alkoxides such as sodium methoxide, sodium ethoxide and potassium t-butoxide; alkali metal hydrides such as sodium hydride and potassium hydride; aliphatic tertiary amines such as triethylamine, tri-n-butylamine and diisopropylethylamine; aliphatic cyclic tertiary amines such as 1,4-diazabicyclo[2.2.2]octane (DABCO) and 1,8-diazabicyclo[5.4.0]undec-7-ene (DBU); pyridines such as pyridine, collidine and 4-(N,N-dimethylamino)pyridine; and organic metal bases such as n-butyl lithium, s-butyl lithium, lithium diisopropylamide, sodium bis(trimethylsilyl)amide and lithium bis(trimethylsilyl)amide.

There is no particular restriction on the nature of the solvent employed provided that it has no adverse effect on the reaction or on the reagents involved and that it dissolves the starting materials, at least to some extent. Examples of preferred solvents include water; alcohols such as methanol, ethanol and t-butanol; ketones such as acetone and methyl isobutyl ketone; nitriles such as acetonitrile; esters such as ethyl acetate; halogenated hydrocarbons such as methylene chloride, chloroform and dichloroethane; ethers such as diethyl ether, tetrahydrofuran and dioxane; aromatic hydrocarbons such as toluene; amides such as dimethylformamide and dimethylacetamide; sulfoxides such as dimethyl sulfoxide; and mixed solvents thereof.

The reaction can take place over a wide range of temperatures, and the precise reaction temperature is not critical to the invention. In general, we find it convenient to carry out the reaction at a temperature of from −90° C. to 200° C., preferably 0° C. to 50° C.

The reaction time may vary widely, depending on many factors, notably the reaction temperature, the nature of the starting compounds, the nature of the reaction reagents and the nature of the solvents used. In general, we find it convenient to carry out the reaction for a time of from 5 minutes to 24 hours, preferably from 10 minutes to 12 hours.

Preferably, this step should be performed with ultrasonic irradiation of the reaction mixture.

Step B-6

The object of Step B-6 is the production of a phenolic derivative or a thiophenolic derivative of formula (IIa), which is a starting material in Step A-1 above, by removing the protecting group $R^{10a}$ from the compound of formula (VIII) prepared according to Step B-4 or from the compound of formula (IX) prepared according to Step B-5.

The present step may be carried out using any of the standard techniques for the removal of protecting groups, and the technique employed will obviously depend on the nature of the protecting group. A typical example involves the hydrolysis of the compounds (VIII) and (IX), wherein the protecting group $R^{10a}$ is an acyl group or an alkoxycarbonyl group, in the presence of an alkali to give a compound of formula (IIa).

The nature of the alkali employed is not particularly critical. Preferred examples include alkali metal hydroxides such as sodium hydroxide and potassium hydroxide; alkali metal carbonates such as sodium carbonate, potassium carbonate and caesium carbonate; and alkali metal hydrogen carbonates such as sodium hydrogencarbonate.

There is no particular restriction on the nature of the solvent employed provided that it has no adverse effect on the reaction or on the reagents involved and that it dissolves the starting materials, at least to some extent. Examples of preferred solvents include water; alcohols such as methanol, ethanol and t-butanol; ethers such as diethyl ether, tetrahydrofuran and dioxane; aromatic hydrocarbons such as toluene; and mixed solvents thereof.

The reaction can take place over a wide range of temperatures, and the precise reaction temperature is not critical to the invention. In general, we find it convenient to carry out the reaction at a temperature of from −90° C. to 200° C., preferably −50° C. to 100° C.

The reaction time may vary widely, depending on many factors, notably the reaction temperature, the nature of the starting compounds, the nature of the reaction reagents and the nature of the solvents used. In general, we find it convenient to carry out the reaction for a time of from 5 minutes to 24 hours, preferably from 30 minutes to 12 hours.

Step B-7

The object of Step B-7 is to convert, using appropriate reagents, compounds of formula (Ib) containing groups of formula $R^{2b}$, as defined above, to compounds of formula (Ic) in which the group of formula $R^{2b}$ has been converted to a group of formula $R^{2c}$ as defined above.

The actual reagents and reaction conditions used will depend upon the nature of the conversion to be performed.

Where the compound of formula (Ib) is one in which $R^{2b}$ is a $CH_2OH$ group or a $CH_2CH_2OH$ group, this can be converted to a compound of formula (Ic) in which the group $R^{2c}$ is a group of formula $CH_2OCOR^7$, a group of formula $CH_2CH_2OCOR^7$, a group of formula $CH2OR^7$ or a group of formula $CH2CH2OR^7$, wherein $R^7$ is as defined above.

The conversion of a compound of formula (Ib) in which $R^{2b}$ is a $CH_2OH$ group or a $CH_2CH_2OH$ group to a compound of formula (Ic) in which the group $R^{2c}$ is a group of formula $CH_2OCOR^7$ or a group of formula $CH_2CH_2OCOR^7$, is a simple esterification which may be performed using standard esterification techniques. The reaction conditions employed are essentially identical to those used in Step B-4 above.

The conversion of a compound of formula (Ib) in which $R^{2b}$ is a $CH_2OH$ group or a $CH_2CH_2OH$ group to a compound of formula (Ic) in which the group $R^{2c}$ is a group of formula $CH_2OR^7$ or a group of formula $CH_2CH_2OR^7$ is a simple etherification reaction and can be performed using standard etherification techniques, such as reaction of the compound of formula (Ib) with an excess amount of a compound of formula $R^7OH$ in the presence of an acidic reagent.

The acidic reagent employed is not particularly critical. Preferred examples include inorganic acid such as hydrochloric acid and sulfuric acid; Lewis acid such as titanium (IV) chloride, boron trifluoride diethyl ether and zinc chloride; and organic acid such as trifluoroacetic acid, trifluoromethanesulfonic acid, p-toluenesulfonic acid. Particularly preferred are inorganic acids such as hydrochloric acid.

There is no particular restriction on the nature of the solvent employed provided that it has no adverse effect on the reaction or on the reagents involved and that it dissolves the starting materials, at least to some extent. Examples of preferred solvents include water; nitriles such as acetonitrile; esters such as ethyl acetate; halogenated hydrocarbons such as methylene chloride, chloroform and dichloroethane; ethers such as diethyl ether, tetrahydrofuran and dioxane; aromatic hydrocarbons such as toluene; and mixed solvents thereof.

The reaction can take place over a wide range of temperatures, and the precise reaction temperature is not critical to the invention. In general, we find it convenient to carry out the reaction at a temperature of from −10° C. to 100° C., preferably 0° C. to 40° C.

The reaction time may vary widely, depending on many factors, notably the reaction temperature, the nature of the starting compounds, the nature of the reaction reagents and the nature of the solvents used. In general, we find it convenient to carry out the reaction for a time of from 5 minutes to 24 hours, preferably from 10 minutes to 6 hours.

Where the compound of formula (Ib) is one in which the group $R^{2b}$ is a protected alcohol such as a CH$_2$O (tetrahydropyran-2-yl) group or a CH$_2$CH$_2$O (tetrahydropyran-2-yl) group, this may be converted to a compound of formula (Ic) wherein $R^{2c}$ is an unprotected alcohol such as a CH2OH group or a CH2CH2OH group. This reaction is a simple deprotection reaction and may be performed using standard techniques for the deprotection of a protected alcohol. Typically, the deprotection is conducted in the presence of acidic or basic reagents, and is preferably conducted in the presence of an acidic reagent. The nature of the acidic reagent employed is not particularly critical, but preferred examples include inorganic acids such as hydrochloric acid and sulfuric acid; Lewis acids such as titanium (IV) chloride, boron trifluoride diethyl ether and zinc chloride; and organic acids such as trifluoroacetic acid, trifluoromethanesulfonic acid, p-toluenesulfonic acid. The most preferred acidic reagent for this step is an organic acid such as p-toluenesulfonic acid.

There is no particular restriction on the nature of the solvent employed provided that it has no adverse effect on the reaction or on the reagents involved and that it dissolves the starting materials, at least to some extent. Examples of preferred solvents include water; alcohols such as methanol, ethanol and t-butanol; ketones such as acetone and methyl isobutyl ketone; nitriles such as acetonitrile; esters such as ethyl acetate; halogenated hydrocarbons such as methylene chloride, chloroform and dichloroethane; ethers such as diethyl ether, tetrahydrofuran and dioxane; aromatic hydrocarbons such as toluene; amides such as dimethylformamide and dimethylacetamide; sulfoxides such as dimethyl sulfoxide; and mixed solvents thereof.

The reaction can take place over a wide range of temperatures, and the precise reaction temperature is not critical to the invention. In general, we find it convenient to carry out the reaction at a temperature of from −10° C. to 100° C., preferably 0° C. to 40° C.

The reaction time may vary widely, depending on many factors, notably the reaction temperature, the nature of the starting compounds, the nature of the reaction reagents and the nature of the solvents used. In general, we find it convenient to carry out the reaction for a time of from 5 minutes to 24 hours, preferably from 10 minutes to 6 hours.

In Reaction Scheme B, the protection of-AH group is shown in Step B-1 and the deprotection of —AR$^{10a}$ group is shown in Step B-6, because such a combination of protection and deprotection procedures is considered to be the most common and convenient method for preparing the compounds of formula (IIa). However, the protection and deprotection of —AH group can be carried out after any of the steps of Reaction Scheme B, provided that this does not cause a problem in any of the remaining steps of the reaction mechanism such as the introduction of a nitro group into the benzene ring shown in Step B-2, reduction of the nitro group to an amino group shown in Step B-3, acylation or carbamation of the amino group shown in Step B-4 and introduction of a substituent on the nitrogen atom of the amide group or the carbamate group shown in Step B-5. In some cases, no protection of the hydroxy group or the mercapto group is needed at all. The method of the present invention for preparing compounds of formula (IIa) includes all of these alternative methods.

By way of example, among the compounds represented by the formula (VIII) as a starting material in Step B-6, there are compounds in which $R^{10}$ is a group of formula C(=X) $R^1$, wherein $R^1$ and X are as defined above. This group can be introduced at the —AH group at the same time as introducing the same group at the —NH$_2$ group of the corresponding 4-aminophenol compound or 4-aminothiophenol compound. This reaction can be carried out according to the general procedure of step B-4 above. However, in this step the compound of formula $R^1C(=X)L^2$ (wherein $R^1$, X and $L^2$ are as defined above) should be added in an amount of not less than 2 equivalents relative to the staging material.

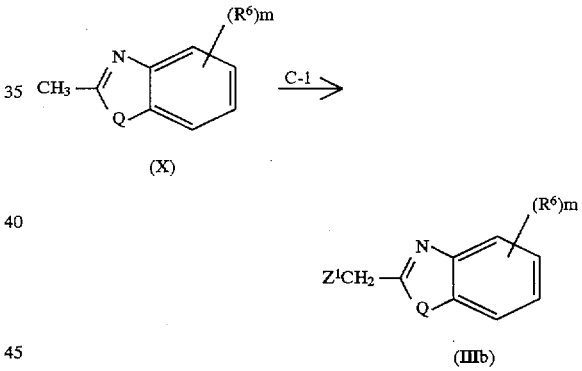

In the above formulae, $R^6$, Q and m are as defined above and $Z^1$ represents a chlorine atom, a bromine atom or an iodine atom.

Step C-1

The object of Step C-1 is the preparation of a compound of formula (IIIb), in which the 2-position of the benzothiazole or benzoxazole group is substituted by a halomethyl group, by halogenating the compound of formula (X) in which the 2-position of the benzothiazole or benzoxazole is substituted by a methyl group. The compound of formula (IIIb) may be used as a starting material in Step A-1 above.

The present step is carried out by reacting the compound of formula (X), in the presence or absence of a solvent and optionally in the presence of a radical initiating agent, with a halogenating agent.

The halogenating agent employed is not particularly critical, but preferred examples include chlorine, bromine, N-chlorosuccinimide, N-bromosuccinimide, N-iodosuccinimide and the like.

If used, the precise nature of the radical initiating agent employed is not particularly critical, but suitable examples include dibenzoyl peroxide (BPO), azobisisobutyronitrile (AIBN) and the like.

There is no particular restriction on the nature of the solvent employed provided that it has no adverse effect on the reaction or on the reagents involved and that it dissolves the starting materials, at least to some extent. Examples of preferred solvents include water; halogenated hydrocarbons such as carbon tetrachloride, methylene chloride, chloroform and dichloroethane; acetic acid; and dimethylformamide (DMF).

The reaction can take place over a wide range of temperatures, and the precise reaction temperature is not critical to the invention. In general, we find it convenient to carry out the reaction at a temperature of from −90° C. to 200° C., preferably −10° C. to 100° C.

The reaction time may vary widely, depending on many factors, notably the reaction temperature, the nature of the starting compounds, the nature of the reaction reagents and the nature of the solvents used. In general, we find it convenient to carry out the reaction for a time of from 30 minutes to 100 hours, preferably from 1 hour to 50 hours.

The 2-methyl compound of formula (X), which is a starting material in the present step, may be prepared according to the method described in J. Org. Chem. 39 (22) 3277 (1974), J. Org. Chem. 43 (11) 2296 (1978) and J. Chem. Soc. Perkin Trans 2 1582 (1972).

The desired compound (IIIa) of the present step may also be prepared according to the method described in Synthetic Communications 19 (16) 2921 (1989), J. Med. Chem. 35 (3) 457 (1992), J. Med. Chem. 35 (21) 3792 (1992) and Synthesis 102 (1979).

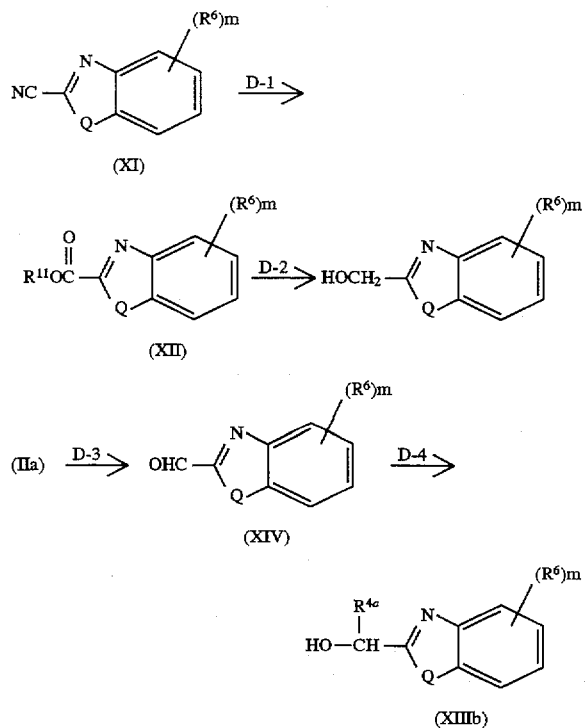

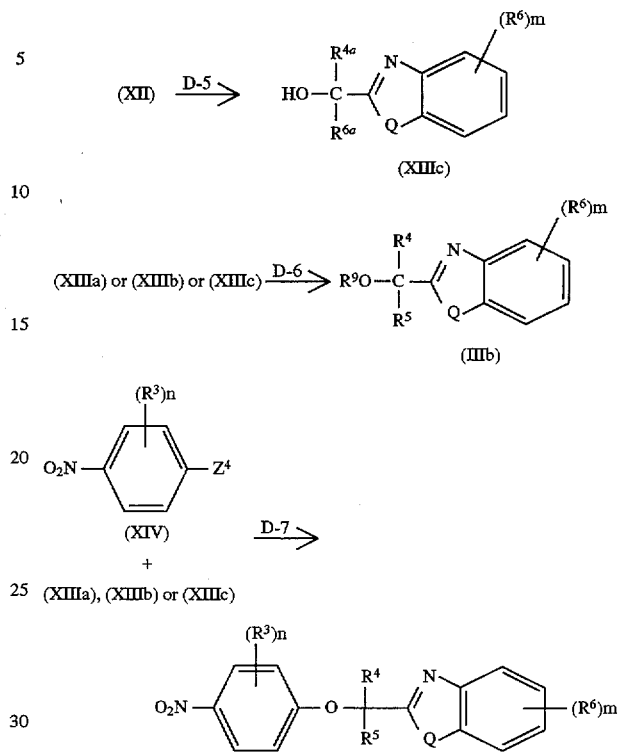

In the above formulae, $R^4$, $R^5$, $R^6$, Q, m and $R^9$ are as defined above. $R^{11}$ represents an alkyl group having from 1 to 6 carbon atoms and each of $R^{4a}$ and $R^{5a}$ may be the same or different and each represents an alkyl group having from 1 to 6 carbon atoms.

Step D-1

The object of Step D-1 is the preparation of the compound of formula (XII) which has an alkoxycarbonyl group at the 2-position of the benzothiazole ring or the benzoxazole ring. This is achieved by hydrolyzing the compound of formula (XI), which has a cyano group at the 2-position of the benzothiazole ring or the benzoxazole ring, in the presence of an alcohol of general formula $R^{11}OH$, wherein $R^{11}$ is as defined above (examples of such an alcohol include methanol and ethanol).

The present step can be carried out by hydrolyzing the compound (XI) in the presence of the alcohol of formula $R^{11}OH$ and an acid.

The precise nature of the acid employed is not particularly critical, but suitable examples include inorganic acids such as hydrochloric acid and sulfuric acid; and organic acids such as p-toluenesulfonic acid.

There is no particular restriction on the nature of the solvent employed, provided that it has no adverse effect on the reaction or on the reagents involved and that it dissolves the staging materials, at least to some extent. Examples of preferred solvents include alcohols such as methanol and ethanol.

The reaction can take place over a wide range of temperatures, and the precise reaction temperature is not critical to the invention. In general, we find it convenient to carry out the reaction at a temperature of from −90° C. to 200° C., preferably 0° C. to 100° C.

The reaction time may vary widely, depending on many factors, notably the reaction temperature, the nature of the starting compounds, the nature of the reaction reagents and the nature of the solvents used. In general, we find it convenient to carry out the reaction for a time of from 1 minute to 12 hours, preferably from 2 minutes to 6 hours.

The 2-cyanobenzothiazole compound or 2-cyanobenzoxazole compound of formula (XI), which is a starting material in the present step, may be prepared according to the method described in J. Heterocyclic Chem. 29 639 (1992).

The desired compound of formula (XII) of the present step may also be prepared according to the method described in Synthetic Communication 14 (10) 947 (1984) and Tetrahedron Letters (9) 645 (1973).

Step D-2

The object of Step D-2 is the preparation of a compound of formula (XIIIa) in which the 2-position of the benzothiazole ring or the benzoxazole ring is substituted by a hydroxymethyl group. This is achieved by reduction of the alkoxycarbonyl group at the 2-position of the benzothiazole ring or the benzoxazole ring of the compound of formula (XII) prepared according to Step D-1 above.

The present step can be carried out according using known methods for reducing esters to primary alcohols, and typically employs a reducing agent such as sodium borohydride and lithium borohydride.

There is no particular restriction on the nature of the solvent employed provided that it has no adverse effect on the reaction or on the reagents involved and that it dissolves the starting materials, at least to some extent. Examples of preferred solvents include alcohols such as methanol and ethanol.

The reaction can take place over a wide range of temperatures, and the precise reaction temperature is not critical to the invention. In general, we find it convenient to carry out the reaction at a temperature of from −90° C. to 200° C., preferably −20° C. to 80° C.

The reaction time may vary widely, depending on many factors, notably the reaction temperature, the nature of the starting compounds, the nature of the reaction reagents and the nature of the solvents used. In general, we find it convenient to carry out the reaction for a time of from 5 minutes to 24 hours, preferably from 10 minutes to 12 hours.

The desired compound of formula (IIa) of the present step can also be prepared according to the method described in Helvetica Chimica Acta 55 1782 (1972).

Step D-3

The object of Step D-3 is the preparation of a 2-formylbenzothiazole compound or a 2-formylbenzoxazole compound of general formula (XIV) by oxidizing the hydroxymethyl group at the 2-position of the benzothiazole compound or benzoxazole compound of general formula (XIIIa), prepared according to Step D-2, to a formyl group.

The present step can be carried out using standard methods for the oxidation of a hydroxymethyl group to a formyl group, examples of which include Swern oxidation and Jones oxidation.

The target compound of formula (XIV) of the present step can also be prepared according to the method described in Liebigs. Ann. Chem. 542 (1980).

Step D-4

The object of Step D-4 is the preparation of a compound of general formula (XIIIb) by reacting the 2-formylbenzothiazole compound or the 2-formylbenzoxazole compound of general formula (XIV), prepared according to Step D-3 above, with a Grignard reagent of general formula $R^{4a}MgZ^1$ (wherein $R^{4a}$ is as defined above and $Z^1$ represents a chlorine atom, a bromine atom or an iodine atom).

The present step can be carried out according to standard methods for performing a Grignard reaction.

There is no particular restriction on the nature of the solvent employed provided that it has no adverse effect on the reaction or on the reagents involved and that it dissolves the starting materials, at least to some extent. Examples of preferred solvents include ethers such as diethyl ether, tetrahydrofuran and dioxane.

The reaction can take place over a wide range of temperatures, and the precise reaction temperature is not critical to the invention. In general, we find it convenient to carry out the reaction at a temperature of from −1 00° C. to 100° C., preferably −40° C. to 50° C.

The reaction time may vary widely, depending on many factors, notably the reaction temperature, the nature of the starting compounds, the nature of the reaction reagents and the nature of the solvents used. In general, we find it convenient to carry out the reaction for a time of from 5 minutes to 24 hours, preferably from 10 minutes to 12 hours.

Step D-5

The object of Step D-5 is the preparation of the compound of general formula (XIIIc) by reacting the compound of general formula (XII) having an alkoxycarbonyl group at the 2-position on the benzoxazole ring or the benzothiazole ring, prepared according to Step D-1, with a Grignard reagent of general formula $R^{4a}MgX$ and $R^{5a}MgX$ (wherein X, $R^{4a}$ and $R^{5a}$ are as defined above).

The present step can be carried out using the general procedure and reaction conditions of Step D-4 above. However, in the present step, it is desirable to add 2 equivalents or more of the Grignard reagent relative to the starting materials in the case where $R^{4a}$ and $R^{5a}$ are the same. It is also desirable to add two kinds of the Grignard reagent in an amount of 1 equivalent or more, respectively, relative to the starting materials in the case where $R^{4a}$ and $R^{5a}$ are different.

Step D-6

The object of Step D-6 is the preparation of a compound of general formula (IIIb), in which the methylene group at the 2-position of the benzoxazole ring or the benzothiazole ring is substituted by a group formula $—OR^9$, as defined above. This is achieved either (i) by reacting a compound of formula (XIIIa), (XIIIb) or (XIIIc), prepared according to Step D-2, Step D-4 and Step D-5 respectively, with a compound of general formula $R^9L^4$ (wherein $R^9$ is as defined above and $L^4$ represents a leaving group which is usually a nucleophilic residue, preferred examples of which include chlorine atoms, bromine atoms, iodine atoms, sulfonyloxy groups such as methanesulfonyloxy and p-toluenesulfonyloxy groups, sulfinyloxy groups such as methylsulfinyloxy and ethylsulfinyloxy groups, and phosphinyloxy groups such as dimethylphosphinyloxy groups and diethylphosphinyloxy groups); or (ii) by sulfonation or phosphination of the hydroxyl group of the compounds (XIIIa), (XIIIb) and (XIIIc).

The present step is carried out in the presence of a solvent and, if necessary, in the presence of a base.

Where a base is employed, the precise nature of the base employed is not particularly critical. Suitable examples include alkali metal hydroxides such as sodium hydroxide and potassium hydroxide; alkali metal carbonates such as sodium carbonate and potassium carbonate; metal alkoxides such as sodium methoxide, sodium ethoxide and potassium t-butoxide; alkali metal hydrides such as sodium hydride and potassium hydride; aliphatic tertiary amines such as triethylamine, tri-n-butylamine and diisopropylethylamine; tertiary anilines such as N,N-dimethylaniline and N,N- diethylaniline; aliphatic cyclic tertiary amines such as 1,4-diazabicyclo[2.2.2]octane (DABCO)and 1,8-diazabicyclo[5.4.0]undec-7-ene (DBU); pyridines such as pyridine, collidine and 4-(N,N-dimethylamino)pyridine; and organic metal bases such as n-butyl lithium, s-butyl lithium, lithium diisopropylamide, sodium bis(trimethylsilyl)amide and lithium bis(trimethylsilyl)amide.

There is no particular restriction on the nature of the solvent employed provided that it has no adverse effect on the reaction or on the reagents involved and that it dissolves the starting materials, at least to some extent. Examples of preferred solvents include water; ketones such as acetone and methyl isobutyl ketone; nitriles such as acetonitrile; esters such as ethyl acetate; halogenated hydrocarbons such as methylene chloride, chloroform and dichloroethane; ethers such as diethyl ether, tetrahydrofuran and dioxane; aromatic hydrocarbons such as toluene; and mixed solvents thereof.

The reaction can take place over a wide range of temperatures, and the precise reaction temperature is not critical to the invention. In general, we find it convenient to carry out the reaction at a temperature of from $-90°$ C. to $200°$ C., preferably $-20°$ C. to $100°$ C.

The reaction time may vary widely, depending on many factors, notably the reaction temperature, the nature of the starting compounds, the nature of the reaction reagents and the nature of the solvents used. In general, we find it convenient to carry out the reaction for a time of from 5 minutes to 24 hours, preferably from 15 minutes to 6 hours.

Step D-7

The object of Step D-7 is the preparation of a compound of general formula (VIa), in which A is an oxygen atom and $R^3$, $R^4$, $R^5$, $R^6$, m and n are as defined above, by the reaction of a compound of formula (XIIIa), (XIIIb) or (XIIIc), prepared according to Step D-2, Step D-4 and Step D-5 respectively, with a compound of general formula (XIV) in which $R^3$ and n are as defined above and $Z^4$ is a fluorine atom, a chlorine atom or a bromine atom. This step is carried out using the same general procedure and reaction conditions as Step D-6 above.

In the reaction Schemes A and B, the condensation reaction of the compound of formula (II) with the compound of formula (III) is stated to be carried out after introduction of a nitro group into the benzene ring as shown in Step B-2, reduction of the nitro group to an amino group as shown in Step B-3, carbamation or amidation of the amino group as shown in Step B-4 and introduction of the substituents on the nitrogen atom of the carbamate group or amide group as shown in Steps B-5 and B-6. However, the condensation reaction of the compound of formula (II) with the compound of formula (III) can take place before any of the steps noted above provided that this does not interfere with any of the later steps. That is, the above-mentioned steps can be simplified as: nitration→reduction→carbamation or amidation→introduction of substituents into the carbamate or amide group→condensation with (III). The above-mentioned steps can also be carried out in the following order: nitration→reduction→condensation with (III) →carbamation or amidation→introduction of substituents into the carbamate group or amide group. Alternatively, the above-mentioned steps can also be carried out in the following order: nitration→condensation with (III) →reduction→carbamation or amidation→introduction of the substituents into the amide group or the carbamate group. Finally, the above-mentioned steps can also be carried out in the following order: condensation with (III) →nitration→reduction→carbamation or amidation→introduction of substituents into the carbamate or amide group. The method of preparing the compounds of formula (I) of the present invention includes all of these methods.

After completion of each reaction in reaction Schemes A to D above, the target compound from each of the steps can be collected from the reaction mixture according to conventional techniques. An example of one such technique comprises: neutralising appropriately the reaction mixture; if insoluble materials exist, filtering them off; adding a water-immiscible solvent; separating the organic phase and washing it with water; and finally distilling off the organic solvent. The product thus obtained can be further purified, if necessary, by conventional means, for example, recrystallization, reprecipitation or the various chromatography techniques, notably column chromatography or preparative thin layer chromatography.

For use as a herbicide, the compounds of formula (I) of the present invention may be used in the form of any preparation commonly used for this purpose, for example, as dusts, coarse dusts, as granules, as fine granules, as wettable powders, as flowable agents, as emulsions and as liquid formulations and the like, by mixing said compounds of formula (I) with a carrier and, if necessary with other adjuvants (e.g. surface active agents). The carrier with which the compounds of the invention may be mixed may be a synthethic or natural inorganic or organic substance, and is incorporated into a herbicide in order to assist the active compound to reach the target plant or in order to facilitate storage, transportation or handling of the active compound.

Examples of suitable solid carriers include: clays, such as those of the kaolinite group, the montmorillonite group or the attapulgite group; inorganic substances, such as talc, mica, pyrophylite, pumice, vermiculite, gypsum, dolomite, diatomaceous earth, magnesium lime, phosphor lime, zeolite, silicic anhydride, synthetic calcium silicate, kaolin, bentonite or calcium carbonate; vegetable organic substances, such as soybean powder, tobacco powder, walnut powder, wheat powder, wood flour, starch or crystal cellulose; synthetic or natural high molecular compounds, such as coumarone resin, petroleum resin, alkyd resin, poly(vinyl chloride), poly(alkylene glycol), ketone resin, ester gum, copal gum or dammar gum, waxes, such as carnauba wax, paraffin wax or beeswax; and urea.

Examples of suitable liquid carriers include: paraffin type or naphthene type hydrocarbons, such as kerosene, mineral oil, spindle oil or white oil; aromatic hydrocarbons, such as benzene, toluene, xylene, ethylbenzene, cumene or methylnaphthalene; chlorinated hydrocarbons, such as carbon tetrachloride, chloroform, trichloroethylene, monochlorobenzene or chlorotoluene; ethers, such as dioxane or tetrahydrofuran; ketones, such as acetone, methyl ethyl ketone, diisobutyl ketone, cyclohexanone, acetophenone or isophorone; esters, such as ethyl acetate, amyl acetate, ethylene glycol acetate, diethylene glycol acetate, dibutyl maleate or diethyl succinate; alcohols, such as methanol, n-hexanol, ethylene glycol, diethylene glycol, cyctohexanol or benzyl alcohol; ether alcohols, such as ethylene glycol ethyl ether, ethylene glycol phenyl ether, diethylene glycol ethyl ether or diethylene glycol butyl ether; polar solvents, such as dimethylformamide or dimethyl sulfoxide; and water.

In order to facilitate emulsification, dispersion, moisturizing, diffusion, spreading, bonding and control of disintegration, to stabilize the active compound, to improve mobility and corrosion prevention, and to accelerate absorption in the plant, the compounds of the present invention may be used in admixture with one or more surface active agents, which may be either ionic or non-ionic.

Examples of suitable non-ionic surface active agents include: fatty acid sucrose esters; addition polymers of ethylene oxide with higher alcohols, such as lauryl alcohol, stearyl alcohol or oleyl alcohol; addition polymers of ethylene oxide with alkylphenols such as isooctylphenol or nonylphenol; addition polymers of ethylene oxide with alkylnaphthols such as butylnaphthol or octylnaphthol; addition polymers of ethylene oxide with higher fatty acids such as palmitic acid, stearic acid or oleic acid; addition polymers of ethylene oxide with mono- or dialkylphosphoric acids such as stearylphosphoric acid or dilaurylphosphoric acid; addition polymers of ethylene oxide with higher aliphatic amines such as dodecylamine or stearic acid amide; higher fatty acid esters of a polyhydric alcohol, such as sorbitan and addition polymers of ethylene oxide with such higher fatty acid esters of a polyhydric alcohol; and addition polymers of ethylene oxide with propylene oxide.

Examples of suitable anionic surface active agents include: alkylsulfuric acid ester salts such as sodium laurylsulfate or an amine salt of oleyl sulfate; fatty acid salts such as sodium sulfosuccinic acid dioctyl ester, sodium oleate or sodium stearate; and alkylarylsulfonates such as sodium isopropylnaphthalenesulfonate, sodium methylenebisnaphthalenesulfonate, sodium ligninsulfonate and sodium dodecylbenzenesulfonate.

Examples of suitable cationic surface active agent include: higher aliphatic amines, quaternary ammonium salts and alkyl pyridinium salts.

Further, in order to improve the property of the preparations and enhance the biological effect thereof, the herbicides of the present invention may optionally contain a high-molecular weight compound, such as gelatin, gum arabic, casein, albumin, hide glue, sodium alginate, poly (vinyl alcohol), carboxymethyl cellulose, methyl cellulose or hydroxymethyl cellulose; thixotropic agents, such as sodium polyphosphate or bentonite; or other adjuvants.

These carriers and adjuvants can be used singly or in combination depending upon the purpose of the preparation and the method of application.

The amount of the active compound in the preparation may vary over a wide range, and there is no particular restriction on its concentration. However, the preferred concentration of the preparation will depend primarily on the nature of the preparation, as well as upon the intended manner of use and the nature of the weeds to be killed. If desired, the preparation may be supplied in a concentrated form intended to be diluted by the user.

Dusts usually contain 2 to 10 wt. % of the active compound, the remainder being a solid carrier.

Wettable powders usually contain 10 to 80 wt.% of the active compound and the remainder is a solid carrier and a dispersing or moistening agent and, if necessary, a protective colloidal agent, a thixotropic agent, an antifoaming agent or the like.

Granules usually contain 0.1 to 10 wt. % of the active compound, the remainder, for the most part, being a solid carrier. The active compound may be homogeneously mixed with the solid carrier, or adhered on or adsorbed by the solid carrier. The particle diameter is preferably in the range of from about 0.2 to 1.5 mm.

Emulsions usually contain 1 to 50 wt. % of the active compound and about from 5 to 20 wt. % of an emulsion. The remainder is a liquid carrier and, if necessary, a corrosion preventing agent.

When the compounds of the present invention, formulated into the various forms described above, they may be used for soil treatment, for example in a paddy field, before or after germination of harmful grasses to be treated. The active compound may be used in an amount of 1 g to 1000 g of the active compound per 10 ares, preferably 10 g to 300 g per 10 ares, of the paddy field for the soil treatment to kill the harmful grasses effectively.

The herbicides of the present invention may be used in admixture with other herbicides in order to increase the herbicidal spectrum, and a synergistic effect may be expected in some cases.

The herbicides of the present invention can, of course, be used in admixture with other active agents such as a plant growth regulator, a fungicide, an insecticide, an acaricide, a nematocide or a fertilizer.

The compounds of the present invention show a potent, selective herbicidal activity. They are particularly effective in the treatment of harmful grasses in paddy fields, but it is also believed that they may be usefully employed as herbicides in the treatment of upland fields, orchards, pastures, tuff, forests and non-agricultural lands.

The compounds of the present invention can be used to control various weeds which present problems in field crop cultivations, usually by means of foliar application or soil treatment.

In particular, the compounds of the present invention exhibit potent herbicidal activity against various weeds which present problems in paddy fields such as gramineous weeds, e.g. barnyardgrass (*Echinochloa oryzicola*); broad-leaved weeds, e.g. monochoria (*Monochoria viginalis*), false pimpernel (*Lindernia pyxidaria* L. ), toothcup (*Rotala indica*) and waterwort (*Elatine triandra* Schk.); and cyperaceous weeds, e.g. smallflower umbrellaplant (*Cyperus difformis* L.), Japanese bulrush (*Scirpus juncoides* Roxb. var. horatrui Ohwi), slender spikerush (*Eleocharis acicularis* L.) and flat sedge (*Cyperus serotinus* Rottb.); and cause no significant injury to the paddy rice plants.

In particular, gramineous weeds such as barnyardgrass (*Echinochloa oryzicola*), Beauv. var. formosensis Ohwi (*Echinochloa crus-galli*) and cockspurgrass (*Echinochloa crus-galli*), which flourish in paddy fields and are difficult to treat using conventional herbicides, can be controlled effectively by applying the compounds of the invention into water when the soil is subjected to irrigation treatment. This treatment is effective both before and after germination of the weeds. The compounds of the present invention show great selectivity, so that the transplanted paddy rice plants are not damaged by them, making the compounds of the present invention particularly advantageous.

It is believed that the compounds of the present invention may also be usefully applied in orchards, mulberry fields and non-agricultural lands as well as in upland fields and paddy fields.

The compounds of the present invention can generally be applied, in the standard agricultural chemical formulations of the type discussed above, by means of soil treatment, foliar application or irrigation treatment before germination of weeds or within about one month after their germination. The soil treatment includes soil surface application, soil incorporation, etc. The foliar application includes application over the plants and directed application for treating the weeds only, so as to prevent the chemical from adhering to field crops. The irrigation treatment includes spraying of granules or flowables and application of the formulations onto the surface of irrigation water.

The particular advantages of the compounds of the present invention as herbicides is illustrated by way of the following tests.

Biological Activity
Pre-Emergence Application to a Paddy field

Soil taken from a paddy field was placed in a pot having a surface area of 100 cm$^2$. Seeds broken from dormancy of barnyardgrass were mixed in the outer layer of the soil at a depth of 1 cm. Paddy rice seedlings at the two-leaf stage were then transplanted to each of the same pots, watered, and then allowed to grow in a greenhouse. After three days, a predetermined amount of a test compound in the form of wettable powder (prepared according to the procedure of Formulation Example 1 below) was applied to water to be employed for irrigation treatment of the soil. After 21 days, investigation was carried out in accordance with the evaluation criteria shown below. The results are shown in Table 9 below.

In Table 9 below, "Barn" means Barnyardgrass (*Echinochloa oryzicola*) and "Rice" means Paddy-field rice (*Oryza sativa*).

TABLE 9

Evaluation criteria
0: Growth inhibitory rate 0 to 10%
1: Growth inhibitory rate 11 to 30%
2: Growth inhibitory rate 31 to 50%
3: Growth inhibitory rate 51 to 70%
4: Growth inhibitory rate 71 to 90%
5: Growth inhibitory rate 91 to 100%

| Compound No. | Amount of Chemical (g/a) | Treatment before germination of grass in paddy field Barn | Rice | Compound No. | Amount of Chemical (g/a) | Treatment before germination of grass in paddy field Barn | Rice |
|---|---|---|---|---|---|---|---|
| A1.1 | 20 | 5 | 0 | A1.5 | 20 | 5 | 0 |
| A1.6 | 20 | 5 | 0 | A1.7 | 20 | 5 | 0 |
| A1.9 | 20 | 5 | 0 | A1.13 | 20 | 5 | 0 |
| A1.16 | 20 | 5 | 0 | A1.18 | 20 | 5 | 0 |
| A1.45 | 20 | 4 | 0 | A1.62 | 20 | 4 | 0 |
| A1.65 | 20 | 5 | 0 | A1.70 | 20 | 5 | 0 |
| B1.1 | 20 | 5 | 0 | B1.3 | 20 | 5 | 0 |
| B1.5 | 20 | 5 | 0 | B1.10 | 20 | 5 | 0 |
| B2.37 | 20 | 5 | 0 | B2.63 | 20 | 5 | 0 |
| C1.1 | 20 | 5 | 0 | C1.2 | 20 | 5 | 0 |
| C1.3 | 20 | 5 | 0 | C1.5 | 20 | 5 | 0 |
| C1.6 | 20 | 5 | 0 | C1.11 | 20 | 5 | 0 |
| C1.13 | 20 | 5 | 0 | C1.36 | 20 | 5 | 0 |
| C1.17 | 20 | 5 | 0 | C1.42 | 20 | 5 | 0 |
| C1.52 | 20 | 5 | 0 | C1.55 | 20 | 5 | 0 |
| C2.1 | 20 | 5 | 0 | C2.4 | 20 | 5 | 0 |
| C2.19 | 20 | 4 | 0 | C3.30 | 20 | 4 | 0 |
| C3.32 | 20 | 5 | 0 | C4.27 | 20 | 4 | 0 |
| C6.1 | 20 | 5 | 0 | C7.55 | 20 | 5 | 0 |
| C8.1 | 20 | 5 | 0 | C8.2 | 20 | 5 | 0 |
| C8.3 | 20 | 5 | 0 | C8.6 | 20 | 5 | 0 |
| C8.19 | 20 | 5 | 0 | C8.20 | 20 | 5 | 0 |
| C8.72 | 20 | 5 | 0 | C9.1 | 20 | 5 | 0 |
| C9.3 | 20 | 5 | 0 | C9.4 | 20 | 5 | 0 |
| C9.6 | 20 | 5 | 0 | C9.20 | 20 | 5 | 0 |
| C9.22 | 20 | 5 | 0 | C9.23 | 20 | 5 | 0 |
| C9.24 | 20 | 5 | 0 | C9.36 | 20 | 5 | 0 |
| C9.38 | 20 | 5 | 0 | C9.39 | 20 | 5 | 0 |
| C9.40 | 20 | 5 | 0 | C9.52 | 20 | 5 | 0 |
| C9.54 | 20 | 5 | 0 | C9.55 | 20 | 5 | 0 |
| C9.56 | 20 | 5 | 0 | C10.1 | 20 | 5 | 0 |
| C10.3 | 20 | 5 | 0 | C10.4 | 20 | 5 | 0 |
| C10.5 | 20 | 5 | 0 | C10.46 | 20 | 4 | 0 |
| C10.48 | 20 | 5 | 0 | C10.49 | 20 | 5 | 0 |
| C10.50 | 20 | 5 | 0 | C11.1 | 20 | 5 | 0 |
| C11.4 | 20 | 5 | 0 | C11.33 | 20 | 5 | 0 |
| C11.63 | 20 | 5 | 0 | D1.1 | 20 | 4 | 0 |
| D1.2 | 20 | 5 | 0 | D1.4 | 20 | 5 | 0 |
| D1.5 | 20 | 5 | 0 | D1.8 | 20 | 5 | 0 |
| D1.10 | 20 | 5 | 0 | D1.14 | 20 | 5 | 0 |
| D1.18 | 20 | 5 | 0 | D1.43 | 20 | 5 | 0 |
| D1.47 | 20 | 5 | 0 | D1.50 | 20 | 4 | 0 |
| D1.51 | 20 | 5 | 0 | D1.55 | 20 | 5 | 0 |
| D1.56 | 20 | 5 | 0 | D1.57 | 20 | 5 | 0 |
| D1.60 | 20 | 5 | 0 | D1.62 | 20 | 5 | 0 |
| D1.67 | 20 | 5 | 0 | D1.68 | 20 | 5 | 0 |
| D1.70 | 20 | 5 | 0 | D1.72 | 20 | 5 | 0 |
| D1.76 | 20 | 5 | 0 | D1.78 | 20 | 5 | 0 |
| D1.79 | 20 | 5 | 0 | D1.80 | 20 | 5 | 0 |
| D1.81 | 20 | 5 | 0 | D1.83 | 20 | 5 | 0 |
| D1.87 | 20 | 5 | 0 | D1.88 | 20 | 5 | 0 |
| D1.90 | 20 | 5 | 0 | D1.93 | 20 | 5 | 0 |

TABLE 9-continued

Evaluation criteria
0: Growth inhibitory rate 0 to 10%
1: Growth inhibitory rate 11 to 30%
2: Growth inhibitory rate 31 to 50%
3: Growth inhibitory rate 51 to 70%
4: Growth inhibitory rate 71 to 90%
5: Growth inhibitory rate 91 to 100%

| Compound No. | Amount of Chemical (g/a) | Treatment before germination of grass in paddy field Barn | Rice | Compound No. | Amount of Chemical (g/a) | Treatment before germination of grass in paddy field Barn | Rice |
|---|---|---|---|---|---|---|---|
| D1.94 | 20 | 5 | 0 | D1.97 | 20 | 5 | 0 |
| D1.99 | 20 | 5 | 0 | D1.100 | 20 | 5 | 0 |
| D1.101 | 20 | 5 | 0 | D1.102 | 20 | 5 | 0 |
| D1.103 | 20 | 5 | 0 | D1.106 | 20 | 5 | 0 |
| D1.110 | 20 | 5 | 0 | D1.112 | 20 | 5 | 0 |
| D1.119 | 20 | 5 | 0 | D1.123 | 20 | 5 | 0 |
| D2.1 | 20 | 5 | 0 | D2.4 | 20 | 5 | 0 |
| D2.5 | 20 | 5 | 0 | D2.6 | 20 | 5 | 0 |
| D2.7 | 20 | 5 | 0 | D2.9 | 20 | 5 | 0 |
| D2.10 | 20 | 5 | 0 | D2.11 | 20 | 5 | 0 |
| D2.13 | 20 | 5 | 0 | D2.14 | 20 | 5 | 0 |
| D2.15 | 20 | 5 | 0 | D2.17 | 20 | 5 | 0 |
| D2.20 | 20 | 5 | 0 | D2.21 | 20 | 5 | 0 |
| D2.22 | 20 | 5 | 0 | D2.25 | 20 | 5 | 0 |
| D2.26 | 20 | 5 | 0 | D2.30 | 20 | 5 | 0 |
| D2.40 | 20 | 5 | 0 | D2.41 | 20 | 5 | 0 |
| D2.42 | 20 | 5 | 0 | D2.44 | 20 | 5 | 0 |
| D2.47 | 20 | 5 | 0 | D2.48 | 20 | 5 | 0 |
| D2.52 | 20 | 5 | 0 | D2.54 | 20 | 5 | 0 |
| D2.55 | 20 | 5 | 0 | D2.56 | 20 | 5 | 0 |
| D2.57 | 20 | 5 | 0 | D2.60 | 20 | 5 | 0 |
| D2.61 | 20 | 5 | 0 | D2.66 | 20 | 5 | 0 |
| D2.68 | 20 | 5 | 0 | D2.73 | 20 | 5 | 0 |
| D2.74 | 20 | 5 | 0 | D2.75 | 20 | 5 | 0 |
| D2.76 | 20 | 5 | 0 | D2.77 | 20 | 5 | 0 |
| D2.78 | 20 | 5 | 0 | D2.79 | 20 | 5 | 0 |
| D2.80 | 20 | 5 | 0 | D2.81 | 20 | 5 | 0 |
| D2.82 | 20 | 5 | 0 | D2.83 | 20 | 5 | 0 |
| D2.84 | 20 | 5 | 0 | D2.85 | 20 | 5 | 0 |
| E1.1 | 20 | 5 | 0 | E1.3 | 20 | 5 | 0 |
| E1.15 | 20 | 5 | 0 | E1.17 | 20 | 5 | 0 |
| E6.1 | 20 | 5 | 0 | E7.5 | 20 | 5 | 0 |
| E7.131 | 20 | 5 | 0 | E7.135 | 20 | 5 | 0 |
| F1.1 | 20 | 5 | 0 | F1.3 | 20 | 5 | 0 |
| F1.5 | 20 | 5 | 0 | F1.11 | 20 | 5 | 0 |
| F1.15 | 20 | 5 | 0 | F1.21 | 20 | 5 | 0 |
| F1.25 | 20 | 5 | 0 | F1.31 | 20 | 5 | 0 |
| F1.69 | 20 | 5 | 0 | F3.1 | 20 | 5 | 0 |
| F3.3 | 20 | 5 | 0 | F3.10 | 20 | 5 | 0 |
| F3.14 | 20 | 5 | 0 | F3.20 | 20 | 5 | 0 |
| F3.21 | 20 | 4 | 0 | F3.22 | 20 | 5 | 0 |
| F3.29 | 20 | 4 | 0 | F3.56 | 20 | 5 | 0 |
| F4.1 | 20 | 5 | 0 | F4.11 | 20 | 5 | 0 |
| F4.12 | 20 | 5 | 0 | F4.14 | 20 | 5 | 0 |
| F4.16 | 20 | 5 | 0 | F4.19 | 20 | 5 | 0 |
| F4.20 | 20 | 5 | 0 | F4.23 | 20 | 5 | 0 |
| F4.25 | 20 | 5 | 0 | F4.28 | 20 | 5 | 0 |
| F4.30 | 20 | 5 | 0 | F4.33 | 20 | 5 | 0 |
| F4.40 | 20 | 5 | 0 | F4.41 | 20 | 5 | 0 |
| F4.43 | 20 | 5 | 0 | F4.59 | 20 | 5 | 0 |
| F4.61 | 20 | 5 | 0 | F4.63 | 20 | 5 | 0 |
| F4.69 | 20 | 5 | 0 | F4.71 | 20 | 5 | 0 |
| F4.79 | 20 | 5 | 0 | F4.103 | 20 | 5 | 0 |
| F5.9 | 20 | 5 | 0 | F5.13 | 20 | 5 | 0 |
| F7.34 | 20 | 5 | 0 | F7.39 | 20 | 5 | 0 |
| F7.45 | 20 | 5 | 0 | F7.56 | 20 | 5 | 0 |
| F7.92 | 20 | 5 | 0 | F7.99 | 20 | 5 | 0 |
| F7.136 | 20 | 5 | 0 | F7.169 | 20 | 5 | 0 |
| F7.173 | 20 | 5 | 0 | G1.3 | 20 | 5 | 0 |
| G1.4 | 20 | 5 | 0 | G1.5 | 20 | 5 | 0 |
| G1.6 | 20 | 5 | 0 | G1.8 | 20 | 5 | 0 |
| G1.9 | 20 | 5 | 0 | G1.10 | 20 | 5 | 0 |
| G1.11 | 20 | 5 | 0 | G1.13 | 20 | 5 | 0 |
| G1.14 | 20 | 5 | 0 | G1.15 | 20 | 5 | 0 |

TABLE 9-continued

Evaluation criteria
0: Growth inhibitory rate 0 to 10%
1: Growth inhibitory rate 11 to 30%
2: Growth inhibitory rate 31 to 50%
3: Growth inhibitory rate 51 to 70%
4: Growth inhibitory rate 71 to 90%
5: Growth inhibitory rate 91 to 100%

| Compound No. | Amount of Chemical (g/a) | Treatment before germination of grass in paddy field | | Compound No. | Amount of Chemical (g/a) | Treatment before germination of grass in paddy field | |
|---|---|---|---|---|---|---|---|
| | | Barn | Rice | | | Barn | Rice |
| G1.19 | 20 | 5 | 0 | G1.20 | 20 | 5 | 0 |
| G1.30 | 20 | 5 | 0 | G1.32 | 20 | 5 | 0 |
| G1.34 | 20 | 5 | 0 | G1.35 | 20 | 5 | 0 |
| G1.36 | 20 | 5 | 0 | G1.37 | 20 | 5 | 0 |
| G1.39 | 20 | 5 | 0 | G1.44 | 20 | 5 | 0 |
| G1.50 | 20 | 5 | 0 | G1.52 | 20 | 5 | 0 |
| G1.55 | 20 | 5 | 0 | G1.57 | 20 | 5 | 0 |
| G1.58 | 20 | 5 | 0 | G1.59 | 20 | 5 | 0 |
| G1.60 | 20 | 5 | 0 | G1.62 | 20 | 5 | 0 |
| G1.63 | 20 | 5 | 0 | G1.64 | 20 | 5 | 0 |
| G1.67 | 20 | 5 | 0 | G1.69 | 20 | 5 | 0 |
| G1.72 | 20 | 5 | 0 | G1.74 | 20 | 5 | 0 |
| G1.76 | 20 | 5 | 0 | G1.77 | 20 | 5 | 0 |
| G1.81 | 20 | 5 | 0 | G1.85 | 20 | 5 | 0 |
| G1.87 | 20 | 5 | 0 | G1.92 | 20 | 5 | 0 |
| G1.94 | 20 | 5 | 0 | G1.95 | 20 | 5 | 0 |
| G1.96 | 20 | 5 | 0 | G1.97 | 20 | 4 | 0 |
| G1.99 | 20 | 5 | 0 | G1.109 | 20 | 5 | 0 |
| G2.42 | 20 | 5 | 0 | G2.49 | 20 | 5 | 0 |
| G2.50 | 20 | 5 | 0 | G2.61 | 20 | 5 | 0 |
| G2.86 | 20 | 5 | 0 | G2.97 | 20 | 5 | 0 |
| G2.148 | 20 | 5 | 0 | G2.166 | 20 | 5 | 0 |
| G5.3 | 20 | 5 | 0 | G5.6 | 20 | 5 | 0 |
| G5.17 | 20 | 5 | 0 | G5.20 | 20 | 5 | 0 |
| G5.33 | 20 | 5 | 0 | G5.38 | 20 | 5 | 0 |
| G5.45 | 20 | 5 | 0 | G5.52 | 20 | 5 | 0 |
| G6.31 | 20 | 5 | 0 | G8.31 | 20 | 5 | 0 |
| G8.33 | 20 | 5 | 0 | G8.38 | 20 | 5 | 0 |
| G10.51 | 20 | 5 | 0 | G10.57 | 20 | 5 | 0 |
| G10.61 | 20 | 5 | 0 | H4.3 | 20 | 5 | 0 |
| H4.8 | 20 | 5 | 0 | H4.19 | 20 | 5 | 0 |
| H4.22 | 20 | 5 | 0 | H4.35 | 20 | 5 | 0 |
| H4.38 | 20 | 5 | 0 | H4.43 | 20 | 5 | 0 |
| H4.50 | 20 | 5 | 0 | H4.91 | 20 | 5 | 0 |
| H7.4 | 20 | 5 | 0 | H7.18 | 20 | 5 | 0 |
| H7.36 | 20 | 5 | 0 | H7.41 | 20 | 5 | 0 |
| H7.49 | 20 | 5 | 0 | H7.106 | 20 | 5 | 0 |
| Comp. A | 20 | 1 | 0 | Comp. B | 20 | 4 | 0 |

Test Example 2

Treatment of Barnyardgrass at the 2.5-Leaf Stage

Following the procedure of Test Example 1, seeds of barnyardgrass were sown and paddy-rice plants at the 2-leaf stage were planted in the same pot. After the barnyardgrass had grown to the 2.5-leaf stage, a predetermined amount of the test compound in the form of wettable powder (prepared according to Formulation Example 1 below) was applied to water to be employed for irrigation treatment of the soil, in the manner of Test Example 1. After 21 days, investigation of the plants was carried out. Results are shown in Table 10 (the evaluation criteria are the same as those in Test Example 1).

TABLE 10

| Compound No. | Amount of chemical (g/a) | Treatment of 2.5-leaf stage of Barnyardgrass | |
|---|---|---|---|
| | | Barnyardgrass (Echinochloa oryzicola) | Paddy-field rice (Oryza sativa) |
| A1.1 | 10 | 5 | 0 |
| | 5 | 5 | 0 |
| A1.5 | 10 | 5 | 0 |
| | 5 | 5 | 0 |
| A1.6 | 10 | 5 | 0 |
| | 5 | 5 | 0 |
| A1.9 | 10 | 5 | 0 |
| | 5 | 4 | 0 |
| C1.1 | 10 | 5 | 0 |
| | 5 | 5 | 0 |
| C1.5 | 10 | 5 | 0 |
| | 5 | 5 | 0 |
| C1.6 | 10 | 5 | 0 |
| | 5 | 5 | 0 |

TABLE 10-continued

| | Amount of | Treatment of 2.5-leaf stage of Barnyardgrass | |
|---|---|---|---|
| Compound No. | chemical (g/a) | Barnyardgrass (Echinochloa oryzicola) | Paddy-field rice (Oryza sativa) |
| C2.1 | 10 | 5 | 0 |
|  | 5 | 4 | 0 |
| C8.1 | 10 | 5 | 0 |
|  | 5 | 4 | 0 |
| C9.3 | 10 | 5 | 0 |
|  | 5 | 5 | 0 |
| C9.4 | 10 | 5 | 0 |
|  | 5 | 5 | 0 |
| C9.6 | 10 | 5 | 0 |
|  | 5 | 4 | 0 |
| C9.23 | 10 | 5 | 0 |
|  | 5 | 4 | 0 |
| C9.39 | 10 | 5 | 0 |
|  | 5 | 5 | 0 |
| C9.40 | 10 | 5 | 0 |
|  | 5 | 5 | 0 |
| C9.55 | 10 | 5 | 0 |
|  | 5 | 4 | 0 |
| C9.56 | 10 | 4 | 0 |
|  | 5 | 4 | 0 |
| C11.1 | 10 | 5 | 0 |
|  | 5 | 4 | 0 |
| D1.47 | 10 | 5 | 0 |
|  | 5 | 5 | 0 |
| D1.68 | 10 | 5 | 0 |
|  | 5 | 5 | 0 |
| D1.70 | 10 | 5 | 0 |
|  | 5 | 5 | 0 |
| D1.72 | 10 | 5 | 0 |
|  | 5 | 5 | 0 |
| D1.76 | 10 | 5 | 0 |
|  | 5 | 5 | 0 |
| D1.81 | 10 | 5 | 0 |
|  | 5 | 5 | 0 |
| D1.90 | 10 | 5 | 0 |
|  | 5 | 4 | 0 |
| D2.11 | 10 | 5 | 0 |
|  | 5 | 4 | 0 |
| D2.20 | 10 | 5 | 0 |
|  | 5 | 5 | 0 |
| D2.26 | 10 | 5 | 0 |
|  | 5 | 5 | 0 |
| D2.40 | 10 | 5 | 0 |
|  | 5 | 5 | 0 |
| E1.18 | 10 | 5 | 0 |
|  | 5 | 4 | 0 |
| F1.1 | 10 | 5 | 0 |
|  | 5 | 5 | 0 |
| F1.21 | 10 | 5 | 0 |
|  | 5 | 4 | 0 |
| F3.20 | 10 | 5 | 0 |
|  | 5 | 5 | 0 |
| F3.22 | 10 | 5 | 0 |
|  | 5 | 5 | 0 |
| F4.11 | 10 | 5 | 0 |
|  | 5 | 4 | 0 |
| F4.12 | 10 | 5 | 0 |
|  | 5 | 5 | 0 |
| F4.14 | 10 | 5 | 0 |
|  | 5 | 5 | 0 |
| F4.30 | 10 | 5 | 0 |
|  | 5 | 5 | 0 |
| F4.33 | 10 | 5 | 0 |
|  | 5 | 5 | 0 |
| F4.43 | 10 | 5 | 0 |
|  | 5 | 4 | 0 |
| F4.63 | 10 | 5 | 0 |
|  | 5 | 4 | 0 |
| F7.56 | 10 | 5 | 0 |
|  | 5 | 5 | 0 |
| G1.3 | 10 | 5 | 0 |
|  | 5 | 5 | 0 |
| G1.6 | 10 | 5 | 0 |
|  | 5 | 4 | 0 |
| G1.8 | 10 | 5 | 0 |
|  | 5 | 5 | 0 |
| G1.34 | 10 | 5 | 0 |
|  | 5 | 5 | 0 |
| G1.39 | 10 | 5 | 0 |
|  | 5 | 5 | 0 |
| G1.50 | 10 | 5 | 0 |
|  | 5 | 5 | 0 |
| G1.52 | 10 | 5 | 0 |
|  | 5 | 5 | 0 |
| G1.55 | 10 | 5 | 0 |
|  | 5 | 5 | 0 |
| G1.57 | 10 | 5 | 0 |
|  | 5 | 5 | 0 |
| G1.59 | 10 | 5 | 0 |
|  | 5 | 5 | 0 |
| G1.60 | 10 | 5 | 0 |
|  | 5 | 5 | 0 |
| G1.62 | 10 | 5 | 0 |
|  | 5 | 5 | 0 |
| G1.63 | 10 | 5 | 0 |
|  | 5 | 5 | 0 |
| G1.64 | 10 | 5 | 0 |
|  | 5 | 5 | 0 |
| G1.69 | 10 | 5 | 0 |
|  | 5 | 5 | 0 |
| G2.5 | 10 | 5 | 0 |
|  | 5 | 4 | 0 |
| G2.42 | 10 | 5 | 0 |
|  | 5 | 5 | 0 |
| G5.33 | 10 | 5 | 0 |
|  | 5 | 5 | 0 |
| G5.38 | 10 | 5 | 0 |
|  | 5 | 5 | 0 |
| G6.31 | 10 | 5 | 0 |
|  | 5 | 5 | 0 |
| H4.91 | 10 | 5 | 0 |
|  | 5 | 4 | 0 |
| Comparative Compound A | 10 | 0 | 0 |
| Comparative Compound A | 5 | 0 | 0 |
| Comparative Compound B | 10 | 2 | 0 |
| Comparative Compound B | 5 | 1 | 0 |

In Tables 9 and 10 above, "g/a" stands for "grammes/are". The comparative compound A in the above tables is Compound No. 1 disclosed in U.S. Pat. No. 4,423,237; and the comparative compound B is Compound No. 3 disclosed in Japanese Unexamined Patent Publication (Kokai) No. 58-52280. They are represented by the following formulae, respectively:

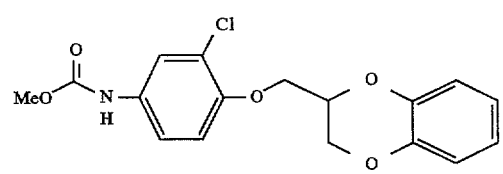

Comparative Compound A

145
-continued

Comparative Compound B

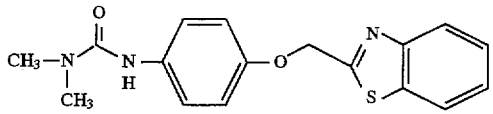

The invention is further illustrated by the following non-limiting Examples, which demonstrate the preparation of compounds of the present invention as well as of certain of the starting materials used in the preparation of compounds of the present invention, as well as by the subsequent non-limiting Formulation Examples showing the preparation of certain herbicidal formulations of the present invention.

EXAMPLE 1

N-[4-(Benzothiazol-2-ylmethoxy)phenyl]acetamide (Compound No. A1.1)

(Step A-1)

0.24 g of sodium hydride (as a 60% w/w dispersion in mineral oil) were added to a solution of 133.9 mg of 4-acetamidophenol in 2.7 ml of dimethylformamide, followed by the addition of a solution of 205.6 mg of 2-bromomethylbenzothiazole in 2 ml of dimethylformamide. The resulting mixture was stirred at room temperature for 7 hours, after which the reaction mixture was diluted with ethyl acetate, washed with water, tried over sodium sulfate and the solvent removed by evaporation under reduced pressure. The resulting residue was purified by column chromatography through silica gel, using a 1:2 by volume mixture of hexane and ethyl acetate as the eluent, to give 221.1 mg (yield 84%) of the title compound as a solid having a melting point of 168 to 170° C.

Nuclear Magnetic Resonance Spectrum (200 MHz, CDCl$_3$). δ ppm: 8.03 (1H, doublet, J=7.4 Hz); 7.90 (1H, doublet, J=6.9 Hz); 7.55–7.35 (2H, multiplet); 7.42 (2H, doublet, J=9.0 Hz); 7.07 (1H, broad singlet); 7.00 (2H, doublet, J=9.0 Hz); 5.47 (2H, singlet); 2.16 (3H, singlet).

EXAMPLE 2

N-[4-(Benzothiazol-2-ylmethoxy)phenyl] propionamide (Compound No. A1.18)

2(a) 4-(Benzothiazol-2-ylmethoxy)aniline
(Step A-1)

4.56 g of 2-bromomethylbenzothiazole and 3.25 g of cesium carbonate were added to a solution of 2.17 g of 4-aminophenol in 70 ml of acetone, and the resulting mixture was stirred at room temperature for 8.5 hours, after which a further 3.25 g of cesium carbonate were added and the reaction mixture was stirred at room temperature for a further 4 hours. The reaction mixture was then filtered and the filtrate was concentrated by evaporation under reduced pressure. The resulting crude crystalline solid was purified by column chromatography through silica gel using a mixture of hexane and ethyl acetate as the eluent, initially using a gradient of the two solvents starting with a 1:1 by volume mixture and changing to a final 3:2 by volume mixture to give 2.67 g (yield 52%) of the title compound as a solid having a melting point of 87° to 89° C.

Nuclear Magnetic Resonance Spectrum (200 MHz, CDCl$_3$+CD$_3$OD), δ ppm: 8.00 (1H, doublet, J=7.5 Hz); 7.92 (1H, doublet, J=8.0 Hz); 7.56–7.38 (3H, multiplet); 6.89 (2H, broad doublet, J=9.0 Hz); 6.70 (2H, broad doublet, J=9.0 Hz); 5.41 (2H, singlet).

146

2(b) N-[4-(Benzothiazol-2-ylmethoxy)phenyl] propionamide
(Step B-4)

0.09 ml of triethylamine and 0.06 ml of propionyl chloride were added to a solution of 149.1 mg of 4-(benzothiazol-2-ylmethoxy)aniline [prepared as described in step (a) above] in 6 ml of methylene chloride cooled in an ice-water bath, and the resulting mixture was stirred at the same temperature for 3 hours. At the end of this time, water was added to the reaction mixture and the resulting mixture was extracted with methylene chloride. The extract was washed with water, dried over anhydrous sodium sulfate and the solvent was then removed under reduced pressure. The resulting residue was purified by column chromatography through silica gel using a 1:2 by volume mixture of hexane and ethyl acetate to give 165.5 mg of the title compound (yield 91%) as a solid having a melting point of 182° C.

Nuclear Magnetic Resonance Spectrum (200 MHz, CDCl$_3$). δ ppm: 8.03 (1H, doublet, J=7.7 Hz); 7.90 (1H, doublet, J=7.7 Hz); 7.55–7.36 (2H, multiplet); 7.44 (2H, doublet, J=8.8 Hz); 7.00 (3H, broad doublet, J=8.9 Hz); 5.47 (2H, singlet); 2.37 (2H, quartet, J=7.6 Hz); 1.24 (3H, triplet, J=7.5 Hz).

EXAMPLE 3

N-[4-(Benzothiazol-2-ylmethoxy)phenyl] chloroacetamide (Compound No. A1.45)

3(a) O-(Benzothiazol-2-ylmethyl)-4-nitrophenol
(Step A-1)

855.5 mg of sodium hydride (as a 60% w/w dispersion in mineral oil) were added to a solution of 2.83 g of 4-nitrophenol in 30 ml of dimethylformamide cooled in an ice-water bath. The resulting mixture was stirred at the same temperature for 5 minutes, after which a solution of 4.88 g of 2-bromomethylbenzothiazole in 25 ml of dimethylformamide was added thereto. The temperature of the resulting mixture was elevated to room temperature, and the mixture was then stirred at this temperature for 4 hours. At the end of this time the reaction mixture was cooled in an ice-water bath and 100 ml of water was added to said reaction mixture resulting in the precipitation of a crystalline solid which was filtered off, washed with water and then further washed with hexane. The resulting crude crystalline solid was purified by column chromatography through silica gel using a 10:1 by volume mixture of hexane and ethyl acetate, to give 4.99 g (yield 86%) of the title compound having a melting point of 189° to 191° C.

Nuclear Magnetic Resonance Spectrum (200 MHz, CDCl$_3$). δ ppm: 8.24 (2H, broad doublet, J=9.3 Hz);
8.06 doublet, J=7.7 Hz); 7.92 (1H, doublet, J=7.3 Hz); 7.58–7.40 (2H, multiplet); 7.14 (2H, broad doublet, J=9.3 Hz); 5.59 (2H, singlet).

3(b) 4-(Benzothiazol-2-ylmethoxy)aniline
(Step B-3)

15 ml of concentrated hydrochloric acid were carefully added to 4.99 g of O-(benzothiazol-2-ylmethyl)-4-nitrophenol [prepared as described in step (a) above] suspended in 100 ml of ethanol, with ice cooling, after which 8.26 g of stannous chloride were added in small portions to the resulting mixture at the same temperature. The temperature of the reaction mixture was then elevated to room temperature and the mixture stirred for 30 minutes at this temperature, before elevating the temperature further to 50° C. and stirring at this new temperature for a further 1.5 hours. At the end of this time 15 ml of concentrated hydrochloric acid and 8.26 g of stannous chloride were added to the reaction mixture and the resulting mixture was then stirred at 50° C. for 4 hours. The reaction mixture was then allowed to cool to room temperature, after which a saturated aqueous sodium hydroxide solution was added to the reaction mixture to adjust it to pH 10 and the resulting mixture was extracted with ethyl acetate. The resulting extract was washed with water, dried over anhydrous sodium sulfate and the solvent was removed by evaporation under reduced pressure to give a crude crystalline solid which was washed with a 10:1 by volume mixture of hexane and ethyl acetate to give 1.92 g (yield 43%) of the title compound as a solid having a melting point of 87° to 90° C.

Nuclear Magnetic Resonance Spectrum (200 MHz, CDCl$_3$), δ ppm: 8.02 (1H, doublet, J=7.9 Hz); 7.90(1H, doublet, J=7.6 Hz); 7.53–7.35 (2H, multiplet); 6.88 (2H, broad doublet, J=8.8 Hz); 6.65 (2H, broad doublet, J=8.8 Hz); 5.41 (2H, singlet); 3.65–3.20 (2H, broad).

3(c) N-[4-(Benzothiazol-2-ylmethoxy)phenyl]chloroacetamide (Step B-4)

0.24 ml of triethylamine and 0.17 ml of chloroacetyl chloride were added to a solution of 300 mg of 4-(benzothiazol-2-ylmethoxy)aniline [prepared as described in step (b) above] in 6 ml of methylene chloride cooled in an ice-water bath, and the resulting mixture was stirred for 1 hour. After this time, a saturated aqueous ammonium chloride solution was added to the reaction mixture and the resulting mixture was extracted with methylene chloride. The resulting extract was washed with water, dried over anhydrous sodium sulfate and the solvent was then removed by evaporation under reduced pressure. The resulting residue was recrystallized from a mixed solvent of methylene chloride and hexane to obtain 259.4 mg (yield 65.5%) of the title compound as a solid having a melting point of 196° to 197° C.

Nuclear Magnetic Resonance Spectrum (200 MHz, CDCl$_3$), δ ppm: 8.17–8.10 (1H, broad singlet); 8.06 (1H, multiplet); 7.94–7.90 (1H, multiplet); 7.59–7.44 (4H, multiplet); 7.07–7.03 (2H, multiplet); 5.55 (2H, singlet); 4.19 (2H, singlet).

EXAMPLE 4

N-[4-(Benzothiazol-2-ylmethoxy)-2-fluorophenyl]acetamide (Compound No. C9.1)

4(a) Methyl 3-fluorophenyl carbonate (Step B-1)

4.00 g of 3-fluorophenol were added to a solution of 2.00 g of sodium hydroxide in 18 ml of water, the resulting mixture was cooled in an ice-water bath and then 3.7 ml of methyl chlorocarbonate was added thereto. The resulting mixture was stirred for 20 minutes, the temperature of the mixture was elevated to room temperature and the mixture was then stirred for a further 2 hours. After this time, ethyl acetate was added to the reaction mixture, the organic layer was washed first with water and then an aqueous sodium chloride solution and then it was dried over anhydrous magnesium sulfate. The solvent was removed by evaporation under reduced pressure to give 5.85 g of a crude crystalline solid containing the title compound.

4(b) Methyl 3-fluoro-4-nitrophenyl carbonate (Step B-2)

3.6 ml of concentrated sulfuric acid were added to 5.85 g of the crude crystalline solid prepared as described in step(a) with cooling in an ice-water bath and the mixture was stirred. A mixed acid of 3.0 ml of concentrated nitric acid and 3.0 ml of concentrated sulfuric acid was then carefully added dropwise to the resulting mixture. The reaction mixture was then stirred for 1 hour at the same temperature, at the end of which the reaction mixture was carefully added to ice-water to give a crystalline solid which was filtered off. The crystalline solid was washed with water and then dried in vacuo to give 7.58 g of a crude crystalline solid containing the title compound.

4(c) 3-Fluoro-4-nitrophenol 36 ml of a 3N aqueous sodium hydroxide solution were added to a solution of 7.58 g of the crude crystalline solid prepared as described in step (b) above in 120 ml of methanol which was cooled in an ice-water bath. The temperature of the resulting mixture was elevated to room temperature and the mixture was then stirred for 1.5 hours. At the end of this time, concentrated hydrochloric acid was added until the reaction mixture was adjusted to pH 1. The solvent was then removed by evaporation under reduced pressure, ethyl acetate was added to the resulting mixture and the resulting solution was washed with water and then dried over magnesium sulfate. The solvent was removed by evaporation under reduced pressure and the resulting residue was purified by column chromatography through silica gel using a mixture of hexane and ethyl acetate acetate as the eluent, using a gradient of the solvents changing from a 20:1 by volume mixture of the two to a 10:1 by volume mixture and finally to a 1:1 by volume mixture to give 1.21 g (yield 22%) of the title compound as a yellow solid.

Nuclear Magnetic Resonance Spectrum (200 MHz, CDCl$_3$), δ ppm: 8.07 (1H, triplet, J=8.9 Hz); 7.32 (1H, broad singlet); 6.75 (2H, doublet, J=11.2 Hz).

4(d) N-(2-Fluoro-4-hydroxyphenyl)acetamide (Steps B-3 & B-4)

373.3 mg of iron powder were added to a solution of 300 mg of 3-fluoro-4-nitrophenol [prepared as described in step (c) above] in 6 ml of glacial acetic acid. The resulting mixture was stirred under reflux for 6 hours, after which it was allowed to cool to room temperature. Ice-water was then added to the reaction mixture and the solvent was removed by evaporation under reduced pressure. Ethyl acetate was added to the residue and the resulting solution was washed with water and then dried over sodium sulfate. The solvent was removed by evaporation under reduced pressure and the resulting residue was purified by column chromatography through silica gel using a mixture of hexane and ethyl acetate as the eluent, initially using a 2:1 by volume mixture of the two solvents and then changing to a 1:1 by volume mixture, to give 206.8 mg (yield 64%) of the title compound as a brown solid.

Nuclear Magnetic Resonance Spectrum (200 MHz, CDCl$_3$), δ ppm: 7.92 (1H, triplet, J=8.5 Hz); 7.12 (1H, broad singlet); 6.66–6.52 (2H, multiplet); 5.64 (1H, broad singlet).

4(e) N-[(4-Benzothiazol-2-ylmethoxy)-2-fluorophenyl]acetamide (Step A-1)

53.8 mg of sodium hydride (as a 60% w/w dispersion in mineral oil) were added to a solution of 206.8 mg of N-(2-fluoro-4-hydroxyphenyl)acetamide [prepared as described in step (d) above] in 5 ml of dimethylformamide with cooling in an ice-water bath and the mixture was then stirred for 5 minutes. 305.7 mg of 2-bromomethylbenzothiazole were then added to the reaction mixture, the temperature of the mixture was elevated to room temperature and the mixture was then stirred for a further 2.5 hours. At the end of this time, saturated aqueous ammonium chloride solution was added to the reaction mixture and the resulting mixture was extracted with ethyl acetate. The resulting extract was washed with a saturated aqueous sodium chloride solution and then dried over anhydrous sodium sulfate. The solvent was then removed by evaporation under reduced pressure and the resulting residue was recrystallized from a mixed solvent of methylene chloride and hexane to give 287.2 mg (yield 74.4%) of the title compound as a solid having a melting point of 167° to 169° C.

Nuclear Magnetic Resonance Spectrum (200 MHz, CDCl$_3$), δ ppm: 8.19–7.88 (3H, multiplet); 7.51–7.41 (2H, multiplet); 7.15 ( 1 H, broad singlet); 6.86–6.80 (2H, multiplet); 5.46 (2H, singlet); 2.19 (3H, singlet).

EXAMPLE 5

N-[4-(6-(Fluorobenzothiazol-2-ylmethoxy)phenyl] acetamide (Compound No. F4.30)

5(a) Methyl (6-fluorobenzothiazol-2-yl)formate
(Step D-1)

Hydrogen chloride gas was introduced over 3 minutes into a flask containing a solution of 137.2 mg of 2-cyano-6-fluorobenzothiazole in 2.7 ml of methanol with stirring, the reaction mixture being cooled in an ice-water bath. The reaction mixture was stirred at the same temperature for 2 minutes, and then water was added thereto. The resulting mixture was extracted with ethyl acetate to give an extract which was washed first with water and then an aqueous sodium chloride solution and then dried over sodium sulfate. The solvent was then removed by evaporation under reduced pressure and the resulting residue was purified by column chromatography through silica gel using a 5:1 by volume mixture of hexane and ethyl acetate as the eluent, to give 106.8 mg (yield 68%) of the title compound as a pale yellow crystalline solid.

Nuclear Magnetic Resonance Spectrum (200 MHz, CDCl$_3$), δ ppm: 8.21 ( 1 H, doublet of doublets, J=9.1 & 4.9 Hz); 7.66 (1H, doublet of doublets, J=8.1 & 2.5 Hz); 7.34 (1H, triplet of doublets, J$_f$=8.9 Hz, J$_d$=2.6 Hz); 4.09 (3H, singlet).

5(b) 6-Fluoro-2-hydroxymethylbenzothiazole
(Step D-2)

16.5 mg of lithium borohydride were added to a solution of 106.1 mg of methyl (6-fluorobenzothiazol-2-yl)formate [prepared as described in step (a) above] in 2.1 ml of methanol cooled in an ice-water bath, and the resulting mixture was stirred at the same temperature for 10 minutes. At the end of this time a further 10 mg of lithium borohydride were added to the reaction mixture which was then stirred at the same temperature for a further 10 minutes. Water was then added to the reaction mixture and the resulting mixture was extracted with ethyl acetate. The resulting extract was washed consecutively with water and an aqueous sodium chloride solution and then dried over sodium sulfate. The solvent was then removed by evaporation under reduced pressure to give 93.1 mg of the title compound as a crude white crystalline solid.

5(c) 6-Fluoro-2-methanesulfonyloxymethylbenzothiazole
(Step D-6)

0.08 ml of triethylamine and 0.05 ml of methanesulfonyl chloride were added to a solution of 93.1 mg of 6-fluoro-2-hydroxymethylbenzothiazole [prepared as described in step (b) above] in 1.8 mi of methylene chloride cooled in an ice-water bath. The temperature of the resulting mixture was elevated to room temperature and the mixture was stirred for 1 hour. At the end of this time, water was added to the reaction mixture and the resulting mixture was extracted with methylene chloride. The resulting extract was washed consecutively with water and an aqueous sodium chloride solution and then dried over anhydrous sodium sulfate. The solvent was removed by evaporation under reduced pressure and the resulting residue was purified by column chromatography through silica gel using a 1:1 by volume mixture of hexane and ethyl acetate as the eluent, to give 125.3 mg (yield 94%) of the title compound as a solid having a melting point of 68° to 72° C.

Nuclear Magnetic Resonance Spectrum (200 MHz, CDCl$_3$), δ ppm: 8.01 (1H, doublet of doublets, J=8.9 & 4.8 Hz); 7.61 (1H, doublet of doublets, J=8.1 & 2.5 Hz); 7.23 (1H, triplet of doublets, J$_f$=8.9Hz, J$_d$=2.5Hz); 5.58 (2H, singlet); 3.15(3H, singlet).

5(d) N-[4-(6-Fluorobenzothiazol-2-ylmethoxy)phenyl] acetamide
(Step A-1)

18.8 mg of sodium hydride (as a 60% w/w dispersion in mineral oil) were added to a solution of 64.6 mg of 4-acetamidophenol in 1.3 ml of dimethylformamide cooled in an ice-water bath, and the resulting mixture stirred at the same temperature for 3 minutes. A solution of 122.8 mg of 6-fluoro-2-methanesulfonyloxymethylbenzothiazole [prepared as described in step (c) above] in 0.4 ml of dimethylformamide was then added to the reaction mixture. The temperature of the resulting mixture was then elevated to room temperature and the mixture was stirred for 3 hours. At the end of this time, a saturated aqueous ammonium chloride solution was added to the reaction mixture and the resulting mixture was extracted with ethyl acetate. The resulting extract was washed consecutively with water and an aqueous sodium chloride solution and then dried over sodium sulfate. The solvent was removed by evaporation under reduced pressure, and the resulting residue was purified by column chromatography through silica gel using a 1:2 by volume mixture of hexane and ethyl acetate as the eluent, to give 38.3 mg (yield 28%) of the title compound as a solid having a melting point of 204° to 205° C.

Nuclear Magnetic Resonance Spectrum (200 MHz, CDCl$_3$), δ ppm: 7.97 (1H, doublet of doublets, J=8.8 & 4.8 Hz); 7.57 (1H, doublet of doublets, J=8.0 & 2.5 Hz); 7.43 (2H, doublet, J=8.8 Hz); 7.31–7.18 (1H, multiplet); 7.08 (1H, broad singlet); 7.00 (2H, doublet, J=9.0 Hz); 5.44 (2H, singlet); 2.16 (3H, singlet).

EXAMPLE 6

N-[4-(6-Methoxybenzothiazol-2-ylmethoxy)phenyl] acetamide (Compound No. F3.20)

6(a) 2-Bromomethyl-6-methoxybenzothiazole
(Step C-1)

17.4 mg of dibenzoyl peroxide were added to a solution of 0.8 ml of 2-methyl-6-methoxybenzothiazole and 1.05 g of N-bromosuccinimide in 20 ml of carbon tetrachloride at room temperature and the resulting mixture was stirred under reflux for 5 hours. At the end of this time, the mixture was allowed to cool to room temperature and then extracted with methylene chloride. The resulting extract was washed consecutively with a saturated aqueous sodium sulfite solution, water and an aqueous sodium chloride solution and then dried over sodium sulfate. The solvent was then removed by evaporation under reduced pressure and the resulting residue was purified by column chromatography through silica gel using an 8:1 by volume mixture of hexane and ethyl acetate, to give 649.3 mg (yield 47%) of the title compound as a solid having a melting point of 78° to 81° C.

Nuclear Magnetic Resonance Spectrum (200 MHz, CDCl$_3$), δ ppm: 7.91 (1H, doublet, J=9.0 Hz); 7.32 (1H, doublet, J=2.5 Hz); 7.10 (1H, doublet of doublets, J=9.0 & 2.5 Hz); 4.80 (2H, singlet); 3.89 (3H, singlet).

6(b) N-[4-(6-Methoxybenzothiazol-2-ylmethoxy)phenyl] acetamide
(Step A-1)

57.6 mg of sodium hydride (as a 60% w/w dispersion in mineral oil) were added to a solution of 197.8 mg of 4-acetamidophenol in 4 ml of dimethylformamide cooled in an ice-water bath and the resulting mixture was stirred at this temperature for 5 minutes. A solution of 371.5 mg of 2-bromomethyl-6-methoxybenzothiazole [prepared as described in step (a) above] in 1 ml of dimethylformamide was added to the reaction mixture, the temperature of the mixture was elevated to room temperature and the mixture was stirred for 2 hours. At the end of this time, a saturated aqueous ammonium chloride solution was added to the reaction mixture and the mixture was extracted with ethyl acetate. The resulting extract was washed consecutively with water and an aqueous sodium chloride solution and them dried over anhydrous sodium sulfate. The solvent was then removed by evaporation under reduced pressure and the resulting residue was purified by column chromatography through silica gel using a 1:2 by volume mixture of hexane and ethyl acetate to give 399.1 mg (yield 93%) of the title compound as a solid having a melting point of 145°–147° C.

Nuclear Magnetic Resonance Spectrum (200 MHz, $CDCl_3$), δ ppm: 7.90 (1H, doublet, J=9.0 Hz); 7.41 (2H, doublet, J=9.1 Hz); 7.33 (1H, doublet, J=2.5 Hz); 7.16 (1H, broad singlet); 7.11 (1H, doublet of doublets, J=8.9 & 2.5 Hz); 6.77 (2H, doublet, J=9.1 Hz); 5.41 (2H, singlet); 3.88 (3H, singlet); 2.15 (3H, singlet).

EXAMPLE 7

N-{4-[1-(benzothiazol-2-yl)ethoxy]phenyl}acetamide (Compound No. E 1.1)

7(a) 2-Formylbenzothiazole
(Step D-3)

5.47 g of manganese dioxide were added at room temperature to a solution of 2.26 g of 2-hydroxymethylbenzothiazole in 20 ml of acetone. The resulting mixture was stirred under reflux for 5 hours, at the end of which time the temperature of the mixture was cooled to room temperature and the mixture was left to stand for 14 hours. A further 3.06 g of manganese dioxide were then added and the resulting mixture was stirred under reflux for 6 hours. At the end of this time, the reaction mixture was cooled to room temperature and then filtered. The resulting filtrate was concentrated by evaporation under reduced pressure, petroleum ether was added to the thus obtained crude crystalline solid and the mixture was filtered. The filtrate was then concentrated to about half its volume causing precipitation of a crystalline solid which was filtered off and dried in vacuo to give 432.6 mg (yield 19.3%) of the title compound as a solid having a melting point of 69° to 70° C.

Nuclear Magnetic Resonance Spectrum (200 MHz, $CDCl_3$), δ ppm: 10.18 (1H, singlet); 8.28–8.23 (1H, multiplet); 8.05–8.00 (1H, multiplet); 7.68–7.54 (2H, m).

7(b) 2-(1-Hydroxyethyl)benzothiazole
(Step D-4)

5.0 ml of methylmagnesium bromide were added dropwise to a solution of 0.61 g of 2-formylbenzothiazole [prepared as described in step (a) above] which was cooled in an acetone-dry ice bath. The reaction vessel was transferred to an ice-water bath and the reaction mixture was stirred for 3.5 hours. At the end of this time, a saturated aqueous ammonium chloride solution was added to the reaction mixture and the resulting mixture was extracted with ethyl acetate. The resulting extract was washed with a saturated aqueous sodium chloride solution and then dried over anhydrous sodium sulfate. The solvent was then removed by evaporation under reduced pressure and the resulting residue was purified by column chromatography through silica gel using a 4:1 by volume mixture of hexane and ethyl acetate as the eluent, to give 0.44 g (yield 66%) of the title compound as a solid having a melting point of 59° to 60° C.

Nuclear Magnetic Resonance Spectrum (200 MHz, $CDCl_3$), δ ppm: 7.97 (1H, doublet, J=8.3 Hz); 7.87 (1H, doublet of doublets, J=8.2 & 1.3 Hz); 7.47 (1H, triplet of doublets, $J_t$=7.7 Hz, $J_d$=1.5 Hz); 7.37 (1H, triplet of doublets, $J_t$=7.5 Hz, $J_d$=1.4 Hz); 5.26 (1H, quartet of doublets, $J_q$=14.1 Hz, $J_d$=4.8 Hz); 3.7–3.5 (1H, broad singlet); 1.71 (1H, doublet, J=6.6 Hz).

7(c) 2-(1-Methanesulfonyloxyethyl)benzothiazole
(Step D-6)

0.33 ml of triethylamine were added to a solution of 384.4 mg of 2-(1-hydroxyethyl)-benzothiazole [prepared as described in step (b) above] in 4 ml of methylene chloride cooled in an ice-water bath, and then 0.18 ml of methanesulfonyl chloride were added thereto. The temperature of the resulting mixture was elevated to room temperature, and the mixture was then stirred for 2 hours. At the end of this time, a saturated aqueous sodium chloride solution was added to the reaction mixture and the resulting mixture was then extracted with methylene chloride. The resulting extract was washed with water and dried over anhydrous sodium sulfate. The solvent was then removed by evaporation under reduced pressure to given 519.4 mg (yield 94.3%) of the title compound as an oil.

Nuclear Magnetic Resonance Spectrum (200 MHz, $CDCl_3$), δ ppm: 8.05 (1H, doublet of doublets, J=7.5 & 1.3 Hz); 7.92 (1H, doublet of doublets, J=7.7 & 2.0 Hz); 7.51 (1H, triplet of doublets, $J_t$=7.2 Hz, $J_d$=1.4 Hz); 7.44 (1H, triplet of doublets, $J_t$=7.7 Hz, $J_d$=1.5 Hz); 6.10 (1H, quartet, J=6.6 Hz); 3.07 (3H, singlet); 1.93 (3H, doublet, J=6.6 Hz).

7(d) N-{4-[1-benzothiazol-2-yl)ethoxy]phenyl}acetamide
(Step A-1)

84 mg of 4-acetamidophenol and 22 mg of sodium hydride (as a 60% w/w dispersion in mineral oil) were added to a solution of 143.3 mg of 2-(1-methanesulfonyloxyethyl)-benzothiazole [prepared as described in step (c) above] in 2.3 ml of dimethylformamide cooled in an ice-water bath. The temperature of the resulting mixture was; elevated to room temperature and the mixture then stirred for 2.5 hours. At the end of this time, water was added to the reaction mixture and the resulting mixture was extracted with ethyl acetate. The resulting extract was washed with a saturated aqueous sodium chloride solution and dried over anhydrous sodium sulfate. The solvent was removed by evaporation under reduced pressure, and the resulting residue was purified by preparative thin layer chromatography using ethyl acetate as the eluent to give 70.4 mg (yield 40.5%) of the title compound as an oil.

Nuclear Magnetic Resonance Spectrum (200 MHz, $CDCl_3$), δ ppm: 8.01 (1H, doublet, J=7.3 Hz); 7.86 (1H, doublet of doublets, J=7.2 & 1.3 Hz); 7.49 (1H, triplet of doublets, $J_t$=7.6 Hz, $J_d$=1.4 Hz); 7.42–7.34 (1H, multiplet); 7.35 (2H, doublet, J=9.0 Hz); 7.05 (1H, broad singlet); 6.96 (2H, doublet, J=9.0 Hz); 5.70 (1H, quartet, J=6.5 Hz); 2.13 (3H, singlet); 1.83 (3H, doublet, J=6.5 Hz).

EXAMPLE 8

N-{4-[1-(Benzothiazol-2-yl)-1-methylethoxy]phenyl}acetamide (Compound No. E 4.1)

8(a) 2-(1-Hydroxy-1-methylethyl)benzothiazole
(Step D-5)

5.0 ml of a solution of 3M methylmagnesium bromide in tetrahydrofuran were added dropwise to a solution of 304.4 mg of ethyl (benzothiazol-2-yl)carboxylate in 6.1 ml of diethyl ether cooled in an acetone-dry ice bath. The resulting mixture was stirred at the same temperature for 30 minutes, and then the temperature of the mixture was elevated to room temperature, and the mixture stirred for a further 2 hours. At the end of this time, 1N hydrochloric acid was added to the reaction mixture and the resulting mixture was extracted with diethyl ether. The resulting extract was washed consecutively with water and a saturated aqueous sodium chloride solution and then dried over anhydrous sodium sulfate. The solvent was then removed by evaporation under reduced pressure and the resulting residue was purified by column chromatography through silica gel using a 6:1 by volume mixture of hexane and ethyl acetate as the eluent, to give 197.1 mg (yield 70%) of the title compound as a white crystalline solid.

Nuclear Magnetic Resonance Spectrum (200 MHz, $CDCl_3$), δ ppm: 7.99 (1H, broad doublet, J=8.8 Hz); 7.89 (1H, broad doublet, J=7.7 Hz); 7.52–7.30 (2H, multiplet); 3.06 (1H, singlet); 1.76 (6H, singlet).

8(b) O-[1-(Benzothiazol-2-yl)-1-methylethyl]-4-nitrophenol
(Step D-7)

108.9 mg of potassium t-butoxide and 134.1 mg of 4-chloronitrobenzene were added to a solution of 156.6 mg of 2-(1-hydroxy-1-methylethyl)benzothiazole [prepared as described in step (a) above] in 3.1 ml of dimethylformamide at room temperature. The resulting mixture was stirred at room temperature for 3 hours, and then it was stirred at 60° C. for a further 4 hours. The temperature of the reaction mixture was then raised to 90° C. and the mixture stirred at this temperature for a further 5 hours, after which it was cooled to room temperature. A saturated aqueous ammonium chloride solution was then added to the reaction mixture and the mixture was extracted with ethyl acetate. The resulting extract was washed consecutively with water and a saturated aqueous sodium chloride solution and then dried over anhydrous sodium sulfate. The solvent was then removed by evaporation under reduced pressure and the resulting residue was purified by column chromatography through silica gel using a 10:1 by volume mixture of hexane and ethyl acetate as the eluent, to give 197.1 mg (yield 70%) of the title compound as an oil.

Nuclear Magnetic Resonance Spectrum (200 MHz, $CDCl_3$), δ ppm: 8.06 (3H, broad doublet, J=9.4 Hz); 7.87 (1H, doublet, J=7.4 Hz); 7.58–7.38 (2H, multiplet); 6.87 (2H, doublet, J=9.2 Hz); 1.99 (6H, singlet).

8(c) O-[1-(Benzothiazol-2-yl)-1-methylethyl]-4-aminophenol
(Step B-3)

Hydrogenation of a solution of 55.2 mg of O-[1-(benzothiazol-2-yl)-1-methylethyl]-4-nitrophenol [prepared as described in step (b) above] in 1.1 ml of methanol was carried out in the presence of a 5% palladium-charcoal catalyst. After 4.5 hours, the reaction vessel was blown through with nitrogen gas to give a nitrogen gas atmosphere. The mixture was then filtered and the solvent was removed from the resulting filtrate by evaporation under reduced pressure to give 45.3 mg of the crude product as an oil.

8(d) N-{4-[1-(Benzothiazol-2-yl)-1-methylethoxy]phenyl}acetamide
(Step B-4)

0.025 ml of triethylamine and 0.013 ml of acetyl chloride were added to a solution of 45.3 mg of the crude product [prepared as described in step (c) above] in 4 ml of methylene chloride with cooling in an ice-water bath. The temperature of the resulting mixture was then elevated to room temperature and the mixture was stirred for 2 hours. At the end of this time water was added to the reaction mixture and the resulting mixture was extracted with methylene chloride. The resulting extract was washed consecutively with water and saturated aqueous sodium chloride solution and then dried over anhydrous sodium sulfate. The solvent was then removed by evaporation under reduced pressure and the resulting residue was purified by column chromatography through silica gel using a 1:2 by volume mixture of hexane and ethyl acetate as the eluent, to give 48.0 mg (yield 84%) of the title compound as a solid having a melting point of 149° to 150° C.

Nuclear Magnetic Resonance Spectrum (200 MHz, $CDCl_3$), δ ppm: 8.03 (1H, broad doublet, J=8.6 Hz); 7.90 (1H, broad doublet, J=7.6 Hz); 7.53–7.28 (4H, multiplet); 7.05 (1H, broad singlet); 6.85 (2H, doublet, J=8.9 Hz); 2.14 (3H, singlet); 1.84 (6H, singlet).

EXAMPLE 9

N-[4-(5-Fluorobenzothiazol-2-ylmethoxy)phenyl]butyramide (Compound No. F4.19)
9(a) O-(5-Fluorobenzothiazol-2-ylmethyl)-4-nitrophenol
(Step A-1)

452.9 mg of sodium hydride (as a 60% w/w dispersion in mineral oil) were added to a solution of 1.5 g of 4-nitrophenol in 30 ml of dimethylformamide cooled in an ice-water bath. The resulting mixture was stirred at this temperature for 5 minutes, after which a solution of 2.79 g of 2-bromomethyl-5-fluorobenzothiazole in 5 ml of dimethylformamide was added thereto. The temperature of the resulting mixture was elevated to room temperature and the mixture was then stirred for 3 hours. At the end of this time, a saturated aqueous ammonium chloride solution was added to the reaction mixture and the resulting mixture was extracted with ethyl acetate. The resulting extract was washed consecutively with water and a saturated aqueous sodium chloride solution and then dried over anhydrous sodium sulfate. The solvent was removed by evaporation under reduced pressure and the resulting residue was washed with a mixed solvent of methylene chloride and hexane to give 2.33 g of the title compound as a crude crystalline solid.

9(b) 4-(5-Fluorobenzothiazol-2-ylmethoxy)aniline
(Step B-3)

1.5 ml of concentrated hydrochloric acid were carefully added to a solution of 2.33 g of O-(5-fluorobenzothiazol-2-ylmethyl)-4-nitrophenol [prepared as described in step (a) above] in 47 ml of ethanol with stirring at room temperature and then 3.63 g of stannous chloride were added in small portions to the resulting mixture. The reaction mixture was then stirred at room temperature for 30 minutes, at the end of which time 3 ml of concentrated hydrochloric acid were added and the mixture was stirred for a further 1.5 hours at room temperature. The reaction mixture was then heated to 50° C. and stirred at this temperature for 4 hours. The reaction mixture was then cooled in an ice-water bath and 10% aqueous sodium hydroxide solution was added to said solution to adjust the pH to 10. The resulting mixture was then extracted with ethyl acetate and the resulting extract was washed consecutively with water and a saturated aqueous sodium chloride solution and then dried over anhydrous sodium sulfate. The solvent was then removed under reduced pressure and the resulting residue was recrystallized from a mixed solvent of methylene chloride and hexane to give 1.54 g (yield 73%) of the title compound as a solid having a melting point of 125° to 128° C.

Nuclear Magnetic Resonance Spectrum (200 MHz, $CDCl_3$), δ ppm: 7.84 (1H, doublet of doublets, J=9.0 & 4.7

Hz); 7.72 (1H, doublet of doublets, J=9.5 & 2.5 Hz); 7.23–7.12 (1H, multiplet); 6.87 (2H, broad doublet, J=8.8 Hz); 6.65 (2H, broad doublet, J=8.9 Hz); 5.39 (2H, singlet); 3.48 (2H, broad singlet).

9(c) N-[4-(5-Fluorobenzothiazol-2-ylmethoxy)phenyl] butyramide
(Step B-4)

0.09 ml of triethylamine and 0.07 ml of butyryl chloride were added to a solution of 150.8 mg of 4-(5-fluorobenzothiazol-2-ylmethoxy)aniline [prepared as described in step (b) above] in 3 ml of methylene chloride cooled in an ice-water bath. The temperature of the resulting mixture was then elevated to room temperature and the mixture was stirred for 1 hour. At the end of this time, water was added to the reaction mixture and the resulting mixture was extracted with methylene chloride. The resulting extract was washed consecutively with water and a saturated aqueous sodium chloride solution and then dried over anhydrous sodium sulfate. The solvent was then removed by evaporation under reduced pressure and the resulting residue was recrystallized from a mixed solvent of methylene chloride and hexane to give 104.5 mg (yield 55%) of the title compound as a solid having a melting point of 201° to 202° C.

Nuclear Magnetic Resonance Spectrum (200 MHz, CDCl$_3$). δ ppm: 7.82 (1H, doublet of doublets, J=8.8 & 5.1 Hz); 7.70 (1H, doublet of doublets, J=9.5 & 2.5 Hz); 7.45 (2H, doublet, J=9.0 Hz); 7.18(1H, triplet of doublets, J$_f$=8.9 Hz, J$_d$=2.5 Hz); 7.02 (1H, broad singlet); 6.99 (2H, doublet, J=9.2 Hz); 5.45 (2H, singlet); 2.32 (2H, triplet, J=7.5 Hz); 1.76 (2H, sextet, J=7.3 Hz); 1.01 (2H, triplet, J=7.4 Hz).

EXAMPLE 10

N-[4-(Benzothiazol-2-ylmethoxy)phenyl]-N-methylacetamide (Compound No. B1.1)
(Step B-5)

15.1 mg of sodium hydride (as a 60% w/w dispersion in mineral oil) were added to a solution of 102.0 mg of N-(benzothiazol-2-ylmethoxy)acetamide (prepared as described in Example 1) in 2 ml of dimethylformamide cooled in an ice-water bath. The resulting mixture was stirred for 5 minutes, after which 0.023 ml of methyl iodide were added, the temperature of the resulting mixture was elevated to room temperature and the mixture was then stirred for 1.5 hours. At the end of this time, a saturated aqueous ammonium chloride solution was added to the reaction mixture and the resulting mixture was extracted with ethyl acetate. The resulting extract was washed consecutively with water and a saturated aqueous sodium chloride solution and then dried over anhydrous sodium sulfate. The solvent was then removed by evaporation under reduced pressure and the resulting residue was purified by column chromatography through silica gel using a 1:1 by volume mixture of hexane and ethyl acetate to give 106.8 mg (yield 100%) of the title compound as a solid having a melting point of 119° to 120° C.

Nuclear Magnetic Resonance Spectrum (200 MHz, CDCl$_3$). δ ppm: 8.05 (1H, broad doublet, J=7.7 Hz); 7.92 (1H, broad doublet, J=8.3 Hz); 7.65–7.38 (2H, multiplet); 7.15 (2H, doublet, J=9.0 Hz); 7.05 (2H, doublet, J=9.0 Hz); 5.51 (2H, singlet); 3.22 (3H, singlet); 1.85 (3H, singlet).

EXAMPLE 11

Methyl N-[4-(benzothiazol-2-ylmethoxy)phenyl] carbamate (Compound No. A1.5)
(Step B-4)

0.14 ml of triethylamine and 0.08 ml of methyl chloroformate were added to a solution of 250 mg of 4-(benzothiazol-2-ylmethoxy)aniline [prepared as described in Example 3(b)] in 5 ml of methylene chloride cooled in an ice-water bath and the resulting mixture was stirred at the same temperature for 50 minutes. The temperature of the reaction mixture was then elevated to room temperature and the mixture was stirred for a further 30 minutes. At the end of this time water was added to the reaction mixture and the resulting mixture was extracted with methylene chloride. The resulting extract was; washed with water and then dried over anhydrous sodium sulfate. The solvent was then removed by evaporation under reduced pressure to give a residue which was purified by column chromatography through silica gel using a 3:1 by volume mixture of hexane and ethyl acetate to give 243.1 mg (yield 79%) of the title compound as a solid having a melting point of 142°–144° C.

Nuclear Magnetic Resonance Spectrum (200 MHz, CDCl$_3$). δ ppm: 8.03 (1H, doublet of doublets, J=8.8 & 1.5 Hz); 7.90 (1H, doublet of doublets, J=6.9 & 1.0 Hz); 7.54–7.36 (2H, multiplet); 7.15 (4H, multiplet); 6.48 (1H, broad singlet); 5.46 (2H, singlet); 3.76 (3H, singlet).

EXAMPLE 12

Ethyl N-(4-[benzothiazol-2-ylmethoxy)phenyl] carbamate (Compound No. A1.21)
(Step B-4)

0.14 ml of triethylamine and 0.08 ml of ethyl chloroformate were added to a solution of 250 mg of 4-(benzothiazol-2-ylmethoxy)aniline [prepared as described in Example 3(b) above] in 5 ml of methylene chloride cooled in an ice-water bath, and the resulting mixture was then stirred for 1.5 hours. At the end of this time, water was added to the reaction mixture and the resulting mixture was extracted with methylene chloride. The resulting extract was washed with water and dried over anhydrous sodium sulfate. The solvent was then removed by evaporation under reduced pressure and the resulting residue was purified by column chromatography through silica gel using a 3:1 by volume mixture of hexane and ethyl acetate to give 284.8 mg (yield 88%) of the title compound as a solid having a melting point of 149°–150° C.

Nuclear Magnetic Resonance Spectrum (200 MHz, CDCl$_3$). δ ppm: 8.03 (1H, doublet, J=5.9 Hz); 7.90 (1H, doublet of doublets, J=7.6 & 0.9 Hz); 7.54–7.36 (2H, multiplet); 7.15 (4H, multiplet); 6.47 (1H, broad singlet); 5.50 (2H, singlet); 4.21 (2H, quartet, J=7.2 Hz); 1.30 (3H, triplet, J=7.0 Hz).

EXAMPLE 13

Methyl N-[4-(benzothiazol-2-ylmethoxy)phenyl]-N-methylcarbamate (Compound No. B1.3)
(Step B-5)

0.27 ml of methyl iodide were added to a solution of 138.6 mg of methyl N-[4-(benzothiazol-2-ylmethoxy)phenyl] carbamate (prepared as described in Example 11) in 5 ml of dimethylformamide cooled in an ice-water bath and then 19.4 mg of sodium hydride (as a 60% w/w dispersion in mineral oil) were added to the resulting mixture. The reaction mixture was stirred at the same temperature for 10 minutes, the temperature of the mixture was then elevated to room temperature and the mixture was stirred for a further 30 minutes. At the end of this time, water was added to the reaction mixture and the resulting mixture was extracted with ethyl acetate. The resulting extract was washed consecutively with water and a saturated aqueous sodium chloride solution and was then dried over anhydrous sodium sulfate. The solvent was then removed by evaporation under reduced pressure to give a crude crystalline solid which was purified by column chromatography through silica gel using a 2:1 by volume mixture of hexane and ethyl acetate to give 126.7 mg (yield 87%) of the title compound as a solid having a melting point of 85°–87° C.

Nuclear Magnetic Resonance Spectrum (200 MHz, $CDCl_3$), δ ppm: 8.04 (1H, doublet of doublets, J=8.7 & 1.2 Hz); 7.91 (1H, doublet of doublets, J=6.8 & 0.9 Hz); 7.56–7.41 (2H, multiplet); 7.17 (2H, doublet, J=9.0 Hz); 7.06–6.99 (2H, multiplet); 5.48 (2H, singlet); 3.69 (3H, singlet); 3.26 (3H, singlet).

EXAMPLE 14

Methyl N-[4-(benzothiazol-2-ylmethoxy)-2-methylphenyl]dithiocarbamate (Compound No. C1.13)

(Step B-4)

0.13 ml of carbon disulfide were added to a stirred solution of 500 mg of 4-(benzothiazol-2-yl)methoxy-2-methylaniline [prepared as described in Example 21(b) below] and 114.5 mg of potassium hydroxide in 6 ml of dimethylformamide and 6 ml of water with cooling in an ice-water bath, and the resulting mixture was stirred for 10 minutes. The temperature of the mixture was then elevated to room temperature and the mixture was stirred for a further 30 minutes at this temperature. The reaction mixture was again cooled in an ice-water bath and 0.15 ml of methyl iodide were added thereto and the resulting mixture stirred at this temperature for 10 minutes. The temperature of the reaction mixture was then elevated to room temperature and the mixture was stirred at this temperature for 2.5 hours. At the end of this time, water was added to the reaction mixture and the resulting mixture was extracted with ethyl acetate. The resulting extract was washed with water and then dried over anhydrous sodium sulfate. The solvent was removed by evaporation under reduced pressure to give a crude crystalline solid which was purified by column chromatography through silica gel using a 3:1 by volume mixture of hexane and ethyl acetate to give 458.2 mg (yield 68%) of the title compound as a solid having a melting point of 133°–135° C.

Nuclear Magnetic Resonance Spectrum (200 MHz, $CDCl_3$), δ ppm: 8.70–8.60 (1H, broad multiplet); 8.04 (1H, doublet, J=8.1 Hz); 7.91 (1H, doublet of doublets, J=11.1 & 7.3 Hz); 7.56–7.38 (2H, multiplet); 7.24 (1H, doublet, J=9.9 Hz); 6.97–6.88 (2H, multiplet); 5.49 (2H, singlet); 2.62 (3H, singlet); 2.28 (3H, singlet).

EXAMPLE 15

Methyl N-[4-(6-fluorobenzothiazol-2-ylmethoxy)-2-methylphenyl]carbamate (Compound No. G1.62)

15(a) Methyl N-(4-hydroxy-2-methylphenyl)carbamate
(Step B-4)

12.0 g of potassium carbonate were added to a solution of 100 g of 4-amino-3-methylphenol in 400 ml of acetone cooled in an ice-water bath, followed by the addition of 80 ml of methyl chloroformate at the same temperature. The resulting mixture was stirred at the same temperature for 3 hours, at the end of which time the reaction mixture was filtered. The resulting filtrate was concentrated under reduced pressure to give 151 g (yield 100%) of the title compound as an amorphous powder.

Nuclear Magnetic Resonance Spectrum (200 MHz, $CDCl_3$), δ ppm: 7.22 (1H, broad singlet); 6.61–6.52 (2H, multiplet); 6.26 (2H, broad singlet); 3.76 (3H, singlet); 2.17 (3H, singlet).

15(b) Methyl N-[4-(6-fluorobenzothiazol-2-ylmethoxy)-2-methylphenyl]carbamate
(Step A-1)

15.2 mg of sodium hydride (as a 60% w/w dispersion in mineral oil) were added to a solution of 62.6 mg of methyl N-(4-hydroxy-2-methylphenyl)carbamate [prepared as described in step (a) above] in 4 ml of dimethylformamide with cooling in an ice-water bath. The resulting mixture was stirred at the same temperature for 10 minutes, and then 100.0 mg of 6-fluoro-2-methanesulfonyloxymethylbenzothiazole [prepared as described in Example 5(c)] were added to the reaction mixture. The temperature of the resulting mixture was elevated to room temperature and the mixture was stirred for 3 hours. At the end of this time a saturated aqueous ammonium chloride solution was added to the reaction mixture and the resulting mixture was extracted with ethyl acetate. The resulting extract was washed with water and then dried over anhydrous sodium sulfate. The solvent was then removed by evaporation under reduced pressure to give a crude crystalline product which was purified by column chromatography through silica gel using a 3:1 by volume mixture of hexane and ethyl acetate as the eluent, to give a crystalline solid which was washed with diethyl ether and then dried in vacuo to give 41.4 mg (yield 35%) of the title compound as a solid having a melting point of 149°–151° C.

Nuclear Magnetic Resonance Spectrum (200 MHz, $CDCl_3$), δ ppm: 8.00–7.93 (1H, multiplet); 7.66–7.54 (2H, multiplet); 7.38–7.31 (1H, broad multiplet); 6.89–6.86 (2H, multiplet); 6.22–6.20 (1H, broad multiplet); 5.43 (2H, singlet); 3.76 (3H, singlet); 2.24 (3H, singlet).

EXAMPLE 16

Methyl N-[4-(Benzothiazol-2-ylmethoxy)phenyl]thiocarbamate (Compound No. A1.9)

(Step B-4)

20.8 ml of sodium hydrogencarbonate and 0.05 ml of thiophosgen were added to a solution of 50.2 mg of 4-(benzothiazol-2-ylmethoxy)aniline [prepared as described in Example 3 (b)] in 2 ml of methylene chloride and the resulting mixture was stirred at room temperature for 2 hours. 8 ml of methylene chloride were then added to the reaction mixture and the resulting mixture was washed with water and the organic fraction then dried over anhydrous sodium sulfate. The solvent was removed by evaporation under reduced pressure and the resulting residue was then dissolved in 3 ml of tetrahydrofuran and 0.01 ml of methanol. 13.2 mg of sodium hydride (as a 60% w/w dispersion in mineral oil) were added to the resulting mixture which was then stirred at room temperature for 30 minutes. At the end of this time, 5 mg of sodium methoxide were added to the reaction mixture which was then stirred for 30 minutes. A saturated aqueous sodium chloride solution was then added to the reaction mixture and the resulting mixture was extracted with ethyl acetate. The resulting extract was washed with a saturated aqueous sodium chloride solution and then dried over anhydrous sodium sulfate. The solvent was removed by evaporation under reduced pressure and the resulting residue was recrystallized from a mixed solvent of ethyl acetate and hexane to give 49.7 mg (yield 76%) of the title compound as a solid having a melting point of 160°–162° C.

Nuclear Magnetic Resonance Spectrum (200 MHz, $DMSO-d_6$) δ: 11.02 (1H, broad singlet); 8.16–8.02 (2H, multiplet); 7.60–7.44 (3H, multiplet); 7.30–7.24 (1H, multiplet); 7.14–7.07 (2H, multiplet); 5.61 (2H, singlet); 3.96 (3H, broad singlet).

EXAMPLE 17

Methyl N-[4-(benzothiazol-2-ylmethoxy)-3-chlorophenyl]carbamate (Compound No. C9.55)

17(a) Methyl N-(3-chloro-4-hydroxyphenyl)carbamate (Step B-4)

5 ml of water and 2.5 ml of 10% aqueous sodium hydroxide solution were carefully added to 1.70 g of 4-amino-2-chlorophenol cooled in an ice-water bath and 2 ml of methyl chloroformate were added dropwise to the resulting mixture. The reaction mixture was then stirred for 3 hours at room temperature, at the end of which it was acidified with 4 ml of 2N hydrochloric acid, and the resulting mixture was extracted with methylene; chloride. The resulting extract was washed with water and then dried over anhydrous sodium sulfate. The solvent was then removed by evaporation under reduced pressure to give a crude crystalline solid which was purified by column chromatography through silica gel using a 2:1 by volume mixture of hexane and ethyl acetate as the eluent to give 2.08 g (yield 87%) of the title compound as a pale brown crystalline solid.

17(b) Methyl N-[4-(benzothiazol-2-ylmethoxy)-3-chlorophenyl]carbamate (Step A-1)

44.4 mg of sodium hydride (as a 60% w/w dispersion in mineral oil) were added to a solution of 203.6 mg of methyl N-(3-chloro-4-hydroxyphenyl)carbamate [prepared as described in step (a) above] in 4 ml of dimethylformamide cooled in an ice-water bath. The resulting mixture was stirred at the same temperature for 3 minutes, and then 241.9 mg of 2-bromomethylbenzothiazole were added. The temperature of the reaction mixture was then elevated to room temperature and the mixture was stirred for 1.5 hours. At the end of this time, a saturated aqueous ammonium chloride solution was added to the reaction mixture and the resulting mixture was extracted with ethyl acetate. The resulting extract was washed consecutively with water and a saturated aqueous sodium chloride solution and then dried over anhydrous sodium sulfate. The solvent was removed by evaporation under reduced pressure to give a crude crystalline solid which was purified by column chromatography through silica gel using a 2:1 by volume mixture of hexane and ethyl acetate as the eluent, to give 286.9 mg (yield 81%) of the title compound as a solid having a melting point of 133°–135° C.

Nuclear Magnetic Resonance Spectrum (200 MHz, $CDCl_3$), δ ppm: 8.03 (1H, broad doublet, J=7.0 Hz); 7.92 (1H, broad doublet, J=7.6 Hz); 7.58–7.37 (3H, multiplet); 7.18 (1H, doublet of doublets, J=8.8 & 2.7 Hz); 7.00 (1H, doublet, J=8.9 Hz); 6.53 (1H, broad singlet); 5.51 (2H, singlet); 3.77 (3H, singlet).

EXAMPLE 18

Methyl N-[4-(benzothiazol-2-ylmethoxy)-2-methylphenyl]-N-(2-hydroxyethyl)carbamate (Compound No. D1.106)

(Step B-7)

Methyl N-[4-(benzothiazol-2-ylmethoxy)-2-methylphenyl]-N-[2-(2-tetrahydropyranyloxy)ethyl]carbamate (Compound No. D1.119) was first prepared from methyl N-[4-(benzothiazol-2-ylmethoxy)-2-methylphenyl]carbamate (Compound No. C1.5, prepared as described in Example 21 below) and 2-(2-tetrahydropyranyloxy)ethyl bromide according to the general procedure of Example 13 above. A catalytic amount (approximately 10 mg) of p-toluenesulfonic acid monohydrate was added to a solution of 658.1 mg of the thus prepared methyl N-[4-(benzothiazol-2-ylmethoxy)-2-methylphenyl]-N-[2-(2-tetrahydropyranyloxy)ethyl]carbamate in 6.6 ml of methanol at room temperature. The resulting mixture was stirred for 2 hours at room temperature, and water was then added to the reaction mixture. The resulting mixture was extracted with ethyl acetate and the organic layer was washed consecutively with water and a saturated aqueous sodium chloride solution and then dried over anhydrous sodium sulfate. The solvent was then removed by evaporation under reduced pressure to give a residue which was purified by column chromatography through silica gel using a 1:2 by volume mixture of hexane and ethyl acetate as the eluent, to give 702.5 mg (yield 94.1%) of the title compound as a solid having a melting point of 109°–110° C.

Nuclear Magnetic Resonance Spectrum (200 MHz, $CDCl_3$), δ ppm: 8.04 (1H, doublet, J=8.2 Hz); 7.92 (1H, doublet, J=7.9 Hz); 7.57–7.37 (2H, multiplet); 7.19–6.80 (3H, multiplet); 5.47 (2H, singlet); 4.02–3.42 (4H, multiplet); 3.66 (3H, singlet); 2.70–2.60 (1H, multiplet); 2.21 (3H, singlet).

EXAMPLE 19

Methyl N-[4-(benzothiazol-2-ylmethoxy)-2-methylphenyl]-N-hydroxymethylcarbamate (Compound No. D1.47)

(Step B-5)

A mixture of 130 ml of acetone and 0.5 ml of water was added to a mixture of 10.01 g of methyl N-[4-(benzothiazol-2-ylmethoxy)-2-methylphenyl]carbamate (prepared as described in Example 21(c) below) and 5.0 g of paraformaldehyde at room temperature. 0.30 g of potassium carbonate were added to the resulting mixture and the mixture was then stirred for 12 hours at 30° C. while subjected to ultrasonic irradiation. At the end of this time the reaction mixture was filtered and the solvent was removed from the filtrate by evaporation under reduced pressure to give a residue which was purified by column chromatography through silica gel, using a gradient of dichloromethane and acetone as the eluent, gradually changing from a 9:1 by volume mixture of dichloromethane and acetone to a final 4:1 by volume mixture, to give 8.02 g (yield 73.4%) of the title compound as a solid having a melting point of 121°–123° C.

Nuclear Magnetic Resonance Spectrum (200 MHz, $CDCl_3$), δ ppm: 8.06–7.88 (2H, multiplet); 7.55–7.37 (2H, multiplet); 7.14 (1H, doublet, J=8.4 Hz); 6.93 (1H, doublet, J=3.0 Hz); 6.86 (1H, doublet of doublets, J=8.4 & 3.0 Hz); 5.47 (2H, singlet); 5.20–5.11 (1H, multiplet); 4.84–4.75 (1H, multiplet); 3.90–3.62 (3H, multiplet); 3.51–3.43 (1H, multiplet); 2.22 (3H, singlet).

EXAMPLE 20

Methyl N-[4-(benzothiazol-2-ylmethoxy)-2-methylphenyl]-N-butoxymethylcarbamate (Compound No. D1.57)

(Step B-7)

49.8 mg of methyl N-hydroxymethyl-N-[4-(benzothiazol-2-ylmethoxy)-2-methylphenyl]carbamate [prepared as described in Example 19] were dissolved in 2 ml of butanol at room temperature, and the pH of the resulting solution was adjusted with concentrated sulfuric acid to pH 3. A catalytic amount of hydroquinone (2 mg) was added to the resulting mixture at room temperature and the mixture was then stirred for 1 hour at 85° C. The reaction mixture was then cooled to room temperature, diluted with aqueous sodium hydrogen sulfate and then extracted with ethyl acetate. The resulting extract was washed with a saturated aqueous sodium chloride solution and then dried over anhydrous sodium sulfate. The solvent was removed by evaporation under reduced pressure to give a residue which was purified by column chromatography through silica gel using a 2:1 by volume mixture of hexane and ethyl acetate as the eluent, to give 702.5 mg (yield 94.1%) of the title compound as an oil.

Nuclear Magnetic Resonance Spectrum (200 MHz, CDCl$_3$), δ ppm: 8.07–7.89 (2H, multiplet); 7.55–7.37 (2H, multiplet); 7.09 (1H, doublet, J=8.4 Hz); 6.92 (1H, doublet, J=3.0 Hz); 6.86 (1H, doublet of doublets, J=8.4 & 2.8 Hz); 5.46 (2H, singlet); 4.96 (2H, AB quartet, J=10.4Hz, Δv=106.1 Hz); 3.82–3.50 (5H, multiplet); 2.18 (3H, singlet); 1.60–1.27 (4H, multiplet); 0.91 (3H, triplet, J=7.2 Hz).

EXAMPLE 21

Methyl N-[4-(benzothiazol-2-ylmethoxy)-2-methylphenyl]carbamate (Compound No. C1.5)

21(a) O-(Benzothiazol-2-ylmethyl)-3-methyl-4-nitrophenol
(Step A-1)

23.0 g of sodium hydride (as a 60% w/w dispersion in mineral oil) were added to a solution of 80.0 g of 3-methyl-4-nitrophenol in 700 ml of dimethylformamide cooled in an ice-water bath. The resulting mixture was stirred at the same temperature for 20 minutes, at the end of which time a solution of 95.9 g of 2-chloromethylbenzothiazole in 50 ml of dimethylformamide was added to the reaction mixture. The temperature of the resulting mixture was elevated to 80° C. and the mixture was then stirred for 2 hours. At the end of this time, the reaction mixture was poured into ice-water and the precipitated crystalline solid was washed with water. The crude crystalline solid thus obtained was recrystallised from toluene to give 98.8 g (yield 63%) of the title compound as a solid having a melting point of 145° to 147° C.

Nuclear Magnetic Resonance Spectrum (200 MHz, CDCl$_3$), δ ppm: 8.08 (1H, doublet, J=9.8 Hz); 8.05 (1H, doublet of doublets, J=8.9 & 1.5 Hz); 7.91 (1H, doublet of doublets, J=7.7 & 1.5 Hz); 7.57–7.39 (2H, multiplet); 6.99–6.93 (2H, multiplet); 5.56 (2H, singlet); 2.63 (3H, singlet).

21(b) 4-(Benzothiazol-2-ylmethoxy)-2-methylaniline
(Step B-3)

1.0 g of platinum oxide were added to a solution of 35.0 g of O-(benzothiazol-2-ylmethyl)-3-methyl-4-nitrophenol [prepared as described in step (a) above] in 500 ml of tetrahydrofuran at room temperature and the mixture was vigorously stirred under a hydrogen atmosphere for 2 hours. At the end of this time, the reaction mixture was filtered through Celite™ and the resulting filtrate was concentrated by evaporation under reduced pressure to give a crude residue which was washed with diisopropyl ether to give 32.1 g (yield 100%) of the title compound as a solid having a melting point of 110° to 111° C.

Nuclear Magnetic Resonance Spectrum (200 MHz, CDCl$_3$), δ ppm: 8.01 (1H, doublet, J=8.1 Hz); 7.87 (1H, doublet of doublets, J=7.7 & 1.5 Hz); 7.52–7.33 (2H, multiplet); 6.81–6.71 (2H, multiplet); 6.59 (1H, doublet, J=8.4 Hz); 5.39 (2H, singlet); 3.40 (2H, broad singlet); 2.14 (3H, singlet).

21(c) Methyl N-[4-(benzothiazol-2-ylmethoxy)-2-methylphenyl]carbamate
(Step B-4)

82.5 ml of pyridine and 18.9 ml of methyl chloroformate were added to a solution of 55.0 g of 4-(benzothiazol-2-ylmethoxy)-2-methylaniline [prepared as described in step (b) above] in 400 ml of dimethylformamide cooled in an ice-water bath and the resulting mixture was stirred at the same temperature for 2 hours. At the end of this time, the reaction mixture was poured into water resulting in the precipitation of a crystalline solid which was washed with water and then further washed with diethyl ether to give a crude crystalline solid. This was recrystallised from a 4:1 by volume mixture of tetrachloromethane and acetone to give 36.2 g (yield 54%) of the title compound as a solid having a melting point of 147° to 149° C.

Nuclear Magnetic Resonance Spectrum (200 MHz, CDCl$_3$), δ ppm: 8.03 (1H, doublet, J=7.3 Hz); 7.90 (1H, doublet of doublets, J=6.8 & 0.8 Hz); 7.55–7.36 (3H, multiplet); 6.91–6.86 (2H, multiplet); 6.21 (2H, broad singlet); 5.46 (2H, singlet); 3.76 (3H, singlet); 2.24 (3H, singlet).

EXAMPLE 22

Methyl N-[4-(benzothiazol-2-ylmethoxy)-2-methylphenyl]carbamate (Compound No. C1.5)
(Step A-1)

A solution of 3.6 g of potassium hydroxide in 10 ml of water was added to a solution of 10.0 g of methyl N-(4-hydroxy-2-methylphenyl)carbamate [prepared as described in Example 15(a) above] in 30 ml of dimethylformamide and 6 ml of water cooled in an ice-water bath. The resulting mixture was stirred at the same temperature for 20 minutes, and then a solution of 10.0 g of 2-chloromethylbenzothiazole in 25 ml of dimethylformamide was added to the reaction mixture. The temperature of the resulting mixture was elevated to room temperature and the mixture was stirred for 1 hour, at the end of which time the temperature was elevated further to 60° C. and the reaction mixture stirred for a further 2 hours. The reaction mixture was then poured into water to give a crystalline precipitate which was washed with water and further washed with diethyl ether and then recrystallised from ethyl acetate to give 10.5 g (yield 59%) of the title compound as a crystalline solid having a melting point of 147° to 149° C. The proton nuclear magnetic resonance spectrum was identical to that for the title compound of Example 21.

EXAMPLE 23

N-[4-(Benzothiazol-2-ylmethylthio)phenyl]acetamide (Compound No. A1.3)
(Step A-1)

79.7 mg of sodium hydride (as a 60% w/w dispersion in mineral oil) were added to a solution of 303.1 mg of 4-acetamidothiophenol in 6 ml of dimethylformamide at room temperature, followed by the addition of a solution of 454.8 mg of 2-bromomethyl-benzothiazole in 1 ml of dimethylformamide. The resulting mixture was stirred at room temperature for 2 hours, after which the reaction mixture was diluted with ethyl acetate, washed with water and then dried over anhydrous sodium sulfate. The solvent was then removed by evaporation under reduced pressure and the resulting residue was purified by column chromatography through silica gel using a 1:2 by volume mixture of hexane and ethyl acetate as the eluent, to give 462.7 mg (yield 81%) of the title compound as a solid having a melting point of 147° to 149° C.

Nuclear Magnetic Resonance Spectrum (200 MHz, CDCl$_3$), δ ppm: 7.94 (1H, broad doublet, J=7.8 Hz); 7.83 (1H, broad doublet, J=6.7 Hz); 7.50–7.30 (6H, multiplet); 7.14 (1H, broad singlet); 4.47 (2H, singlet); 2.15 (3H, singlet).

EXAMPLE 24

Methyl N-[4-(benzothiazol-2-ylmethylthio)phenyl]carbamate (Compound No. A1.7)

24(a) Methyl N-(4-mercaptophenyl)carbamate
(Step B-4)

17.4 ml of a 10% aqueous sodium hydroxide solution were carefully added to 2.40 g of 4-aminothiophenol at room temperature and 3.27 ml of methyl chloroformate were added dropwise to the resulting mixture. The reaction mixture was then stirred at room temperature for 2 hours, at the end of which time the reaction mixture was acidified with 1.5 ml of 4N hydrochloric acid, and the resulting mixture was extracted with methylene: chloride. The resulting extract was washed with water and then dried over anhydrous sodium sulfate. The solvent was then removed by evaporation under reduced pressure to give a crude crystalline solid. 4 ml of methanol and 10 ml of a 2M solution of sodium methoxide in methanol were added to the crude crystalline solid at room temperature. The resulting mixture was then stirred at room temperature for 1.5 hours, at the end of which time the reaction mixture was acidified with 2 ml of 4N hydrochloric acid, and the resulting mixture was extracted with methylene chloride. The resulting extract was washed with water and then dried over anhydrous sodium sulfate. The solvent was then removed by evaporation under reduced pressure to give a crude crystalline residue which was recrystallised from a mixed solvent of methylene chloride and hexane to give 1.135 g (yield 32%) of the title compound as a solid having a melting point of 94° to 96° C.

Nuclear Magnetic Resonance Spectrum (200 MHz, $CDCl_3$), δ ppm: 7.27 (4H, singlet); 6.54 (1H, broad singlet); 3.77 (3H, singlet); 1.57 (1H, singlet).

24(b) Methyl N-[4-(benzothiazol-2-ylmethylthio)phenyl] carbamate (Step A-1)

100.5 mg of sodium hydride (as a 60% w/w dispersion in mineral oil) were added to a solution of 418.5 mg of methyl N-(4-mercaptophenyl)carbamate [prepared as described in step (a) above] in 8.4 ml of dimethylformamide cooled in an ice-water bath. The resulting mixture was stirred at the same temperature for 10 minutes, and then 573.1 mg of 2-bromomethylbenzothiazole were added. The temperature of the reaction mixture was then elevated to room temperature and the mixture was stirred for 3.5 hours. At the end of this time, a saturated aqueous ammonium chloride solution was added to the reaction mixture and the resulting mixture was extracted with ethyl acetate. The resulting extract was washed consecutively with water and a saturated aqueous sodium chloride solution and then dried over anhydrous sodium sulfate. The solvent was then removed by evaporation under reduced pressure to give a crude crystalline solid which was purified by column chromatography through silica gel using a 4:1 by volume mixture of hexane and ethyl acetate as the eluent, to give 462.7 mg (yield 81%) of the title compound as a solid having a melting point of 139° to 141° C.

Nuclear Magnetic Resonance Spectrum (200 MHz, $CDCl_3$), δ ppm: 7.94 (1H, broad doublet, J=7.6 Hz); 7.83 (1H, broad doublet, J=6.5 Hz); 7.49–7.26 (6H, multiplet); 6.56 (1H, broad singlet); 4.45 (2H, singlet); 3.76 (3H, singlet).

EXAMPLE 25

N-[4-(Benzothiazol-2-ylmethoxy)phenyl]-N-ethoxycarbonylacetamide (Compound No. B2.63)

(Step B-5)

28 mg of sodium hydride (as a 60% w/w dispersion in mineral oil) were added to a solution of 187 mg of N-[4-(benzothiazol-2-ylmethoxy)phenyl]acetamide (prepared as described in Example 1 above) in 4 ml of dimethylformamide cooled in an ice-water bath. The resulting mixture was stirred for 5 minutes at the same temperature, after which 0.066 ml of ethyl chloroformate were added, the temperature of the resulting mixture was elevated to room temperature and the mixture was stirred for 5 hours. At the end of this time, the reaction mixture was added to a saturated aqueous ammonium chloride solution and the resulting mixture was extracted with ethyl acetate. The resulting extract was washed consecutively with water and a saturated aqueous sodium chloride solution and then dried over anhydrous sodium sulfate. The solvent was then removed by evaporation under reduced pressure to give a crude crystalline solid which was purified by column chromatography through silica gel using a 1:1 by volume mixture of hexane and ethyl acetate as the eluent, to give 25.6 mg (yield 81%) of the title compound as a solid having a melting point of 155° to 160° C.

Nuclear Magnetic Resonance Spectrum (200 MHz, $CDCl_3$), δ ppm: 8.04 doublet, J=6.3 Hz); 7.72 (1H, doublet, J=6.9 Hz); 7.55–7.26 (4H, multiplet); 7.06 (2H, singlet); 5.50 (2H, singlet); 4.18 (2H, quartet, J=6.6 Hz); 2.60 (3H, singlet); 1.18 (3H, triplet, J=6.7 Hz).

EXAMPLE 26

Methyl N-[4-(benzothiazol-2-ylmethoxy)-2-methylphenyl]-N-(3,3-dimethyl-2-oxobutyl) carbamate (Compound No. D1.35)

(Step B-5)

18 mg of sodium hydride (as a 60% w/w dispersion in mineral oil) were added to a solution of 100 mg of methyl N-[4-(benzothiazol-2-ylmethoxy)-2-methylphenyl] carbamate (prepared as described in Example 22 above) in 3 ml of dimethylformamide cooled in an ice-water bath. The resulting mixture was stirred for 30 minutes at the same temperature, after which 0.062 ml of 2-bromo-3,3-dimethyl-2-butanone were added, the temperature of the resulting mixture was elevated to room temperature and the mixture was stirred for 1 hour. At the end of this time, water was added to the reaction mixture and the resulting mixture was extracted with ethyl acetate. The resulting extract was washed consecutively with water and a saturated aqueous sodium chloride solution and then dried over anhydrous sodium sulfate. The solvent was then removed by evaporation under reduced pressure to give a crude crystalline solid which was purified by preparative thin layer chromatography using a 1:1 by volume mixture of hexane and ethyl acetate to give 92 mg (yield 71%) of the title compound as an oil.

Nuclear Magnetic Resonance Spectrum (200 MHz, $CDCl_3$), δ ppm: 8.02 (1H, doublet, J=7.6 Hz); 7.90 (1H, doublet, J=7.7 Hz); 7.38–7.54 (2H, multiplet); 7.31 (1H, triplet, J=9.3 Hz); 6.79–6.94 (2H, multiplet); 5.46 (2H, singlet); 3.64 (3H, singlet); 2.24 (3H, singlet); 1.18 (9H, singlet).

EXAMPLE 27

Methyl N-[4-(benzothiazol-2-ylmethoxy)-2-methylphenyl]-N-propionyloxymethylcarbamate (Compound No. D1.70)

(Step B-7)

0.1 ml of pyridine and 0.1 ml of propionyl chloride were added to a solution of 121 mg of methyl N-[4-(benzothiazol-2-ylmethoxy)-2-methylphenyl]-N-hydroxymethylcarbamate (prepared as described in Example 19 above) in 2 ml of methylene chloride cooled in an ice-water bath and the resulting mixture was stirred at the same temperature for 10 minutes. At the end of this time, water was added to the reaction mixture and the resulting mixture was extracted with methylene chloride. The resulting extract was washed with water and then dried over anhydrous sodium sulfate. The solvent was then removed by evaporation under reduced pressure to give a crude residue which was purified by column chromatography through silica gel using a 5:1 by volume mixture of hexane and ethyl acetate to give 133 mg (yield 94%) of the title compound as an oil.

Nuclear Magnetic Resonance Spectrum (200 MHz, CDCl$_3$), δ ppm: 8.06–7.89 (2H, multiplet); 7.55–7.37 (2H, multiplet); 7.09 (1H, doublet, J=8.0 Hz); 6.93 (1H, doublet, J=2.8 Hz); 6.86 (1H, doublet of doublets, J=8.6 & 2.8 Hz); 5.56 (2H, AB quartet, J=10.2 Hz, Δv=62.2 Hz); 5.47 (2H, singlet); 3.81–3.65 (3H, multiplet); 2.34 (2H, quartet, J=7.6 Hz); 2.20 (3H, singlet); 1.11 (3H, triplet, J=7.6 Hz).

EXAMPLE 28

Methyl N-[4-(benzoxazol-2-ylmethoxy)-2-methylphenyl]carbamate (Compound No. C1.6)

28(a) 2-Bromomethylbenzoxazole
(Step C-1)

509.8 mg of dibenzoyl peroxide were added to a solution of 56 ml of 2-methylbenzoxazole and 18.73 g of N-bromosuccinimide in 20 ml of carbon tetrachloride at room temperature and the resulting mixture was stirred under reflux for 6 hours. At the end of this time, the reaction mixture was filtered and the resulting filtrate was concentrated by evaporation under reduced pressure to give a crude crystalline solid. This was dissolved in ethyl acetate and then washed consecutively with a saturated aqueous sodium sulfite solution, water and a saturated aqueous sodium chloride solution and then dried over anhydrous sodium sulfate. The solvent was then removed by evaporation under reduced pressure to give a crude residue which was purified by column chromatography through silica gel using a 10:1 by volume mixture of hexane and ethyl acetate to give 3.34 g (yield 37%) of the title compound as an oil.

Nuclear Magnetic Resonance Spectrum (200 MHz, CDCl$_3$), δ ppm: 7.79–7.68 (2H, multiplet); 7.58–7.50 (2H, multiplet); 7.46–7.30 (4H, multiplet); 4.60 (2H, singlet).

28(b) Methyl N-[4-(benzoxazol-2-ylmethoxy)-2-methylphenyl]carbamate
(Step A-1)

52.8 mg of sodium hydride (as a 60% w/w dispersion in mineral oil) were added to a solution of 200 mg of methyl N-(4-hydroxy-2-methylphenyl)carbamate [prepared as described in Example 15(a) above] in 5 ml of dimethylformamide cooled in an ice-water bath. The resulting mixture was stirred at the same temperature for 5 minutes, and then 305.4 mg of 2-bromomethylbenzoxazole [prepared as described in step (a) above] were added. The temperature of the resulting mixture was elevated to room temperature and the mixture was stirred for 20 minutes. At the end of this time, the temperature of the reaction mixture was elevated to 50° C. and the mixture was stirred for a further 1 hour. A saturated aqueous ammonium chloride solution was then added to the reaction mixture and the resulting mixture was extracted with ethyl acetate. The resulting extract was washed consecutively with water and a saturated aqueous sodium chloride solution and then dried over anhydrous sodium sulfate. The solvent was then removed by evaporation under reduced pressure to give a crude crystalline solid which was purified by column chromatography through silica gel using a 2:1 by volume mixture of hexane and ethyl acetate as the eluent, to give 320.4 mg (yield 85.5%) of the title compound as a solid having a melting point of 159° to 162° C.

Nuclear Magnetic Resonance Spectrum (200 MHz, CDCl$_3$), δ ppm: 7.78–7.73 (1H, multiplet); 7.61–7.51 (1H, multiplet); 7.41–7.32 (3H, multiplet); 6.93–6.88 (2H, multiplet); 6.22 (1H, broad singlet); 5.30 (2H, singlet); 3.76 (3H, singlet); 2.24 (3H, singlet).

EXAMPLE 29

N-[4-(Benzothiazol-2-ylmethoxy)-2-methylphenyl] acetamide (Compound No. C1.1)

29(a) 2-Bromomethylbenzothiazole
(Step C-1)

476 mg of dibenzoyl peroxide were added to a solution of 5.87 g of 2-methylbenzothiazole and 15.4 g of N-bromosuccinimide in 60 ml of carbon tetrachloride at room temperature and the resulting mixture was stirred under reflux for 9 hours. At the end of this time, the reaction mixture was filtered and the resulting filtrate was concentrated by evaporation under reduced pressure to give a crude crystalline solid which was purified by column chromatography through silica gel using a 10:1 by volume mixture of hexane and ethyl acetate to give 6.10 g (yield 68%) of the title compound as a solid having a metling point of 43° to 45° C.

Nuclear Magnetic Resonance Spectrum (200 MHz, CDCl$_3$), δ ppm: 8.03 (1H, doublet, J=7.6 Hz); 7.89 (1H, doublet of doublets, J=6.8 & 1.1 Hz); 7.56–7.39 (2H, multiplet); 4.82 (2H, singlet).

29(b) N-[4-(Benzothiazol-2-ylmethoxy)-2-methylphenyl] acetamide
(Step A-1)

23.3 mg of sodium hydride (as a 60% w/w dispersion in mineral oil) were added to a solution of 97.7 mg of 4-acetamido-2-methylphenol in 3 ml of dimethylformamide cooled in an ice-water bath. The resulting mixture was stirred at the same temperature for 3 minutes, and then 132.2 mg of 2-bromomethylbenzothiazole [prepared as described in step (a) above] were added. The temperature of the resulting mixture was elevated to room temperature and the mixture was stirred for 3 hours. At the end of this time, a saturated aqueous ammonium chloride solution was added to the reaction mixture and the resulting mixture was extracted with ethyl acetate. The resulting extract was washed consecutively with water and a saturated aqueous sodium chloride solution and then dried over anhydrous sodium sulfate. The solvent was then removed by evaporation under reduced pressure and the resulting residue was recrystallised from a mixed solvent of methylene chloride and hexane to give 85.7 mg (yield 82%) of the title compound as a solid having a melting point of 179° to 182° C.

Nuclear Magnetic Resonance Spectrum (200 MHz, CDCl$_3$), δ ppm: 8.05–7.85 (2H, multiplet); 7.55–7.28 (3H, multiplet); 5.46 (2H, singlet); 2.24 (3H, singlet); 2.19 (3H, singlet).

EXAMPLE 30

N-[4-(Benzoxazol-2-ylmethoxy)-2-methylphenyl] acetamide (Compound No. C1.2)
(Step A-1)

53.2 mg of sodium hydride (as a 60% w/w dispersion in mineral oil) were added to a solution of 200.0 mg of 4-acetamido-3-methylphenol in 10 ml of dimethylformamide cooled in an ice-water bath. The resulting mixture was stirred at the same temperature for 5 minutes, and then 307.9 mg of 2-bromomethylbenzoxazole [prepared as described in Example 28(a) above] were added. The temperature of the resulting mixture was elevated to room temperature and the mixture was stirred for 30 minutes. At the end of this time, the temperature of the reaction mixture was elevated to 50° C. and the mixture was stirred for a further 1.5 hours. At the end of this time, a saturated aqueous ammonium chloride solution was added to the reaction mixture and the resulting mixture was extracted with ethyl acetate. The resulting extract was washed consecutively with water and a saturated aqueous sodium chloride solution and then dried over anhydrous sodium sulfate. The solvent was then removed by evaporation under reduced pressure to give a crude crystalline solid which was purified by column chromatography through silica gel using a 3:1 by volume mixture of ethyl acetate and hexane as the eluent, to give 218.5 mg (yield 61%) of the title compound as a solid having a melting point of 160° C.

Nuclear Magnetic Resonance Spectrum, (200 MHz, CDCl$_3$) δ ppm: 7.78–7.74 (1H, multiplet); 7.58–7.51 (2H, multiplet); 7.39–7.34 (1H, multiplet); 6.92–6.84 (3H, multiplet); 5.30 (2H, singlet); 2.24 (3H, singlet); 2.18 (3H, singlet).

EXAMPLE 31

N-[4-(Benzothiazol-2-ylmethoxy)-2-methylphenyl]-N-methoxycarbonyl-2-chloropropionamide (Compound No. D2.40)

(Step B-5)

18 mg of sodium hydride (as a 60% w/w dispersion in mineral oil) were added to a solution of 100 mg of methyl N-[4-(benzothiazol-2-ylmethoxy)-2-methylphenyl]carbamate (prepared as described in Example 22 above) in 4 ml of dimethylformamide cooled in an ice-water bath. The resulting mixture was stirred for 15 minutes at the same temperature, after which 0.059 mi of 2-chloropropionyl chloride were added. The temperature of the resulting mixture was elevated to room temperature and the mixture was stirred for 3 hours. At the end of this time, water was added to the reaction mixture and the resulting mixture was extracted with ethyl acetate. The resulting extract was washed consecutively with water and a saturated aqueous sodium chloride solution and then dried over anhydrous sodium sulfate. The solvent was then removed by evaporation under reduced pressure. The resulting.; residue was purified by preparative thin layer chromatography using a 1:1 by volume mixture of hexane and ethyl acetate to give 70 mg (yield 54%) of the title compound as an oil.

Nuclear Magnetic Resonance Spectrum (200 MHz, CDCl$_3$), δ ppm: 8.04 (1H, doublet, J=7.3 Hz); 7.92(1H, doublet, J=7.5 Hz); 7.34–7.56 (2H, multiplet); 6.84–7.07 (3H, multiplet); 5.73 (1H, doublet of quartets, J$_d$=1.4 Hz, J$_q$=6.7 Hz); 5.48 (2H, singlet); 3.75 (3H, singlet); 2.16 (singlet) and 2.10 (singlet) (3H); 1.74 (doublet, J=6.7 Hz) and 1.73 (doublet, J=6.7 Hz) (3H).

EXAMPLE 32

Methyl N-[4-(6-methoxybenzothiazol-2-ylmethoxy)-2-methylphenyl]carbamate (Compound No. G1.39)

(Step A-1)

23 mg of sodium hydride (as a 60% w/w dispersion in mineral oil) were added to a solution of 82 mg of methyl N-(4-hydroxy-2-methylphenyl)carbamate [prepared as described in Example 15(a) above] in 5 ml of dimethylformamide cooled in an ice-water bath. The resulting mixture was stirred at the same temperature for 15 minutes, and then 150 mg of 2-bromomethyl-6-methoxybenzothiazole [prepared as described in Example 6(a) above] were added. The temperature of the resulting mixture was elevated to room temperature and the mixture was stirred for 6 hours. At the end of this time, a saturated aqueous ammonium chloride solution was added to the reaction mixture and the resulting mixture was extracted with ethyl acetate. The resulting extract was washed with water and then dried over anhydrous sodium sulfate. The solvent was then removed by evaporation under reduced pressure and the resulting residue was purified by column chromatography through silica gel using a 2:1 by volume mixture of hexane and ethyl acetate as the eluent, to give 110 mg (yield 68%) of the title compound as a solid having a melting point of 123° to 125° C.

Nuclear Magnetic Resonance Spectrum (200 MHz, CDCl$_3$), δ ppm: 7.90 (1H, doublet, J=8.9 Hz); 7.52 (1H, broad singlet); 7.33 (1H, doublet, J=2.5 Hz); 7.09 (1H, doublet of doublets, J=8.9 & 2.5 Hz); 6.90–6.86 (2H, multiplet); 6.20–6.19 (1H, broad multiplet); 5.41 (2H, singlet); 3.88 (3H, singlet); 3.76 (3H, singlet); 2.23 (3H, singlet).

EXAMPLE 33

Methyl N-[4-(5-fluorobenzothiazol-2-ylmethoxy)-2-methylphenyl]carbamate (Compound No. G1.57)

33(a) 2-Bromomethyl-5-fluorobenzothiazole (Step C-1)

127 mg of dibenzoyl peroxide were added to a solution of 8.79 g of 2-methyl-5-fluorobenzothiazole and 20.6 g of N-bromosuccinimide in 88 ml of carbon tetrachloride at room temperature and the resulting mixture was stirred under reflux for 6 hours. At the end of this time, the reaction mixture was filtered and the resulting filtrate was concentrated by evaporation under reduced pressure to give a crude crystalline solid which was purified by column chromatography through silica gel using a 10:1 by volume mixture of hexane and ethyl acetate to give 850 mg (yield 7%) of the title compound as a solid.

Nuclear Magnetic Resonance Spectrum (200 MHz, CDCl$_3$), δ ppm: 7.81 (1H, doublet of doublets, J=8.9 & 5.1 Hz); 7.70 (1H, doublet of doublets, J=9.3 & 2.4 Hz); 7.26–7.16 (1H, multiplet); 4.80 (2H, singlet).

33(b) Methyl N-[4-(5-fluorobenzothiazol-2-ylmethoxy)-2-methylphenyl]carbamate (Step A-1)

54.6 mg of sodium hydride (as a 60% w/w dispersion in mineral oil) were added to a solution of 204.9 mg of methyl N-(4-hydroxy-2-methylphenyl)carbamate [prepared as described in Example 15(a) above] in 5 ml of dimethylformamide cooled in an ice-water bath. The resulting mixture was stirred at the same temperature for 5 minutes, and then 366.2 mg of 2-bromomethyl-5-fluorobenzothiazole [prepared as described in step (a) above] were added. The temperature of the resulting mixture was elevated to room temperature and the mixture was stirred for 1.5 hours. At the end of this time, a saturated aqueous ammonium chloride solution was added to the reaction mixture and the resulting mixture was extracted with ethyl acetate. The resulting extract was washed consecutively with water and a saturated aqueous sodium chloride solution and then dried over anhydrous sodium sulfate. The solvent was then removed by evaporation under reduced pressure to give a crude crystalline solid which was purified by column chromatography through silica gel using a 3:1 by volume mixture of hexane and ethyl acetate as the eluent to give 263.3 mg (yield 65%) of the title compound as a solid having a melting point of 165° to 168° C.

Nuclear Magnetic Resonance Spectrum (200 MHz, CDCl$_3$), δ ppm: 7.82 (1H, doublet of doublets, J=8.8 & 5.1

Hz); 7.70 (1H, doublet of doublets, J=9.4 & 2.4 Hz); 7.60–7.50 (1H, broad singlet); 7.18 (1H, triplet of doublets, J=8.8 & 2.4 Hz); 6.90–6.84 (2H, multiplet); 6.22 (1H, broad singlet); 5.43 (2H, singlet); 3.76 (3H, singlet).

EXAMPLES 34 TO 455

Using the general synthetic procedures of Examples 1 to 33 above, the compounds of the following Examples 34 to 455 were produced. The compounds of Examples 34 to 86 were produced according to the procedure detailed in Example 1. The compounds of Examples 87 to 90 were produced according to the procedure detailed in Example 2. The compounds of Examples 91 to 112 were produced according to the procedure detailed in Example 3. The compounds of Examples 113 to 147 were produced according to the procedure detailed in Example 4. The compounds of Examples 148 to 198 were produced according to the procedure detailed in Example 5. The compounds of Examples 199 to 221 were produced according to the procedure detailed in Example 6. The compounds of Examples 222 to 255 and the compound of Example 455 were produced according to the procedure detailed in Example 10. The compounds of Examples 256 to 267 were produced according to the procedure detailed in Example 11. The compounds of Examples 268 to 279 were produced according to the procedure detailed in Example 12. The compounds of Examples 280 to 331 were produced according to the procedure detailed in Example 13. The compounds of Examples 332 to 363 were produced according to the procedure detailed in Example 15. The compounds of Examples 364 and 365 were produced according to the procedure detailed in Example 16. The compounds of Examples 366 to 405 were produced according to the procedure detailed in Example 17. The compound of Example 406 was produced according to the procedure detailed in Example 18. The compound of Example 407 was produced according to the procedure detailed in Example 19. The compounds of Examples 408 to 452 were produced according to the procedure detailed in Example 20. The compounds of Examples 453 and 454 were produced according to the procedure detailed in Example 26.

EXAMPLE 34

N-[4-(Benzoxazol-2-ylmethoxy)phenyl]acetamide (Compound No. A1.2)

Melting Point: 146° to 148° C. Nuclear Magnetic Resonance Spectrum (200 MHz, CDCl$_3$), δ ppm: 7.79–7.73 (1H, multiplet); 7.59–7.48 (1H, multiplet); 7.48–7.25 (4H, multiplet); 7.19–6.95 (3H, multiplet); 5.31 (2H, singlet); 2.16 (3H, singlet).

EXAMPLE 35

S-Methyl N-[4-(benzothiazol-2-ylmethoxy)phenyl] thiocarbamate (Compound No. A1.13)

Melting Point: 162° to 164° C. Nuclear Magnetic Resonance Spectrum (200 MHz, CDCl$_3$), δ ppm: 8.03 (1H, doublet of doublets, J=8.7 & 1.0 Hz); 7.93–7.88 (1H, multiplet); 7.51–7.33 (4H, multiplet); 7.03–6.96 (3H, multiplet); 5.47 (2H, singlet); 2.41 (3H, singlet).

EXAMPLE 36

N-[4-(Benzothiazol-2-ylmethoxy)-3-methoxyphenyl] acetamide (Compound No. C8.19)

Melting Point: 108° to 113° C. Nuclear Magnetic Resonance Spectrum (270 MHz, CDCl$_3$), δ ppm: 8.01 (1H, doublet, J=7.7 Hz); 7.89 (1H, doublet, J=7.7 Hz); 7.52–7.32 (2H, multiplet); 6.92 (1H, doublet, J=8.6 Hz); 6.74 (1H, doublet of doublets, J=2.5 & 8.6 Hz); 5.50 (2H, singlet); 3.89 (3H, singlet); 2.14 (3H, singlet).

EXAMPLE 37

N-[4-(Benzothiazol-2-ylmethoxy)-2-trifluoromethylphenyl]acetamide (Compound No. C10.1)

Melting Point: 178° C. Nuclear Magnetic Resonance Spectrum (200 MHz, CDCl$_3$+CD$_3$OD), δ ppm: 7.97 (1H, doublet of doublets, J=8.7 & 1.3 Hz); 7.86 (1H, doublet of doublets, J=7.9 & 1.3 Hz); 7.69 (1H, doublet, J=9.2 Hz); 7.51–7.14 (4H, multiplet); 5.44 (2H, singlet); 2.12 (3H, singlet).

EXAMPLE 38

N-[4-(Benzothiazol-2-ylmethoxy)-2-nitrophenyl] acetamide (Compound No. C10.46)

Melting Point: 191° to 193° C. Nuclear Magnetic Resonance Spectrum (200 MHz, CDCl$_3$), δ ppm: 10.09 (1H, broad singlet); 8.70 (1H, doublet, J=9.3 Hz); 8.08–8.04 (1H, multiplet); 7.94–7.86 (2H, multiplet); 7.57–7.35 (3H, multiplet); 5.53 (2H, singlet); 2.27 (3H, singlet).

EXAMPLE 39

N-[4-(Benzothiazol-2-ylmethoxy)-3-nitrophenyl] acetamide (Compound No. C10.62)

Melting Point: 188° to 190° C. Nuclear Magnetic Resonance Spectrum (270 MHz, CDCl$_3$), δ ppm: 9.22 (1H, broad singlet); 8.15 (1H, doublet, J=2.7 Hz); 8.03 (1H, doublet, J=9.0 Hz); 7.94 (1H, doublet, J=9.0 Hz); 7.93 (1H, doublet of doublets, J=2.7 & 9.0 Hz); 7.57–7.37 (2H, multiplet); 7.14 (1H, doublet, J=9.0 Hz); 5.59 (2H, singlet); 2.15 (3H, singlet).

EXAMPLE 40

N-[4-(Benzothiazol-2-ylmethoxy)-2-ethoxycarbonylphenyl]acetamide (Compound No. C10.82)

Melting Point: 140° C. Nuclear Magnetic Resonance Spectrum (200 MHz, CDCl$_3$), δ ppm: 10.84 (1H, broad singlet); 8.65 (1H, doublet, J=9.3 Hz); 8.02 (1H, doublet of doublets, J=8.5 & 1.0 Hz); 7.89 (1H, doublet of doublets, J=7.9 & 1.9 Hz); 7.68 (1H, doublet, J=3.1 Hz); 7.54–7.36 (2H, multiplet); 7.24 (2H, doublet of doublets, J=9.3 & 3.1 Hz); 5.48 (2H, singlet); 4.36 (2H, quartet, J=7.1 Hz); 2.20 (3H, singlet); 1.40 (3H, triplet, J=7.1 Hz).

EXAMPLE 41

N-[4-(Benzothiazol-2-ylmethoxy)-2-propoxycarbonylphenyl]acetamide (Compound No. C 10.84)

Melting Point: 127° to 128° C. Nuclear Magnetic Resonance Spectrum (200 MHz, CDCl$_3$), δ ppm: 10.86 (1H, broad singlet); 8.66 (1H, doublet, J=9.2 Hz); 8.03 (1H, doublet, J=7.8 Hz); 7.90 (1H, doublet of doublets, J=7.3 & 1.4 Hz); 7.68 (1H, doublet, J=3.1 Hz); 7.55–7.40 (2H, multiplet); 7.25 (1H, doublet of doublets, J=9.2 & 3.1 Hz); 5.49 (2H, singlet); 4.27 (2H, triplet, J=6.6 Hz); 2.21 (3H, singlet); 1.79 (2H, sextet, J=7.1 Hz); 1.02 (3H, triplet, J=7.4 Hz).

EXAMPLE 42

N-[4-(Benzothiazol-2-ylmethoxy)-2-isopropoxycarbonylphenyl]acetamide (Compound No. C10.86)

Melting Point: 127° to 128° C. Nuclear Magnetic Resonance Spectrum (200 MHz, CDCl$_3$), δ ppm: 10.89 (1H, broad singlet); 8.65 (1H, doublet, J=9.3 Hz); 8.03 (1H, doublet, J=7.1 Hz); 7.90 (1H, doublet of doublets, J=7.2 & 1.1 Hz); 7.67 (1H, doublet, J=3.1 Hz); 7.54–7.40 (2H, multiplet); 7.24(1H, doublet of doublets, J=9.3 & 3.1 Hz); 5.48 (2H, singlet); 5.22 (1H, heptet, J=6.3 Hz); 2.20 (3H, singlet); 1.38(6H, doublet, J=6.3 Hz).

EXAMPLE 43

N-[4-(Benzothiazol-2-ylmethoxy)-3-methoxycarbonylphenyl]acetamide (Compound No. C10.88)

Melting Point: 167° to 168° C. Nuclear Magnetic Resonance Spectrum (200 MHz, CDCl$_3$), δ ppm: 8.02 (1H, doublet, J=8.5 Hz); 7.94–7.75 (3H, multiplet); 7.55–7.37 (2H, multiplet); 7.06 (1H, doublet, J=8.9 Hz); 5.53 (2H, singlet); 3.96 (3H, singlet); 2.17 (3H, singlet).

EXAMPLE 44

N-[4-(Benzothiazol-2-ylmethoxy)-3-ethoxycarbonylphenyl]acetamide (Compound No. C 10.92)

Melting Point: 164° to 165° C. Nuclear Magnetic Resonance Spectrum (200 MHz, CDCl$_3$), δ ppm: 7.96–7.72 (4H, multiplet); 7.45–7.35 (3H, multiplet); 7.00 (1H, doublet, J=9.0 Hz); 5.45 (2H, singlet); 4.35 (2H, quartet, J=7.0 Hz); 2.06 (3H, singlet); 1.33 (3H, triplet, J=7.0 Hz).

EXAMPLE 45

N-[4-(Benzothiazol-2-ylmethoxy)-3-propoxycarbonylphenyl]acetamide (Compound No. C10.94)

Melting Point: 129° C. Nuclear Magnetic Resonance Spectrum (200 MHz, CDCl$_3$), δ ppm: 8.00 (1H, doublet, J=8.2 Hz); 7.91–7.70 (4H, multiplet); 7.52–7.34 (2H, multiplet); 7.00 (1H, doublet, J=9.0 Hz); 5.49 (2H, singlet); 4.28 (2H, triplet, J=6.7 Hz); 2.13 (3H, singlet); 1.76 (2H, sextet, J=7.1 Hz); 0.97 (3H, triplet, J=7.4 Hz).

EXAMPLE 46

N-[4-(Benzothiazol-2-ylmethoxy)-3-isopropoxycarbonylphenyl]acetamide (Compound No. C10.96)

Melting Point: 153.5° to 155° C. Nuclear Magnetic Resonance Spectrum (200 MHz, CDCl$_3$), δ ppm: 8.03 (1H, doublet of doublets, J=8.1 & 1.5 Hz); 7.92 (1H, doublet of doublets, J=7.7 & 1.0 Hz); 7.82–7.77 (2H, multiplet); 7.55–7.37 (2H, multiplet); 7.18 (1H, broad singlet); 7.06 (1H, doublet, J=9.9 Hz); 5.53 (2H, singlet); 5.30 (1H, heptet, J=6.3 Hz); 2.17 (3H, singlet); 1.38 (6H, doublet, J=6.3 Hz).

EXAMPLE 47

N-[4-(Benzothiazol-2-ylmethoxy)-2-formylphenyl] acetamide (Compound No. C10.98)

Melting Point: 174° to 176° C. Nuclear Magnetic Resonance Spectrum (200 MHz, CDCl$_3$), δ ppm: 0.89 (1H, singlet); 9.87 (1H, singlet); 8.71 (1H, doublet, J=10.3 Hz); 8.04 (1H, doublet of doublets, J=8.2 & 1.3 Hz); 7.91 (1H, doublet of doublets, J=7.6 & 1.5 Hz); 7.56–7.31 (4H, multiplet); 5.54 (2H, singlet); 2.23 (3H, singlet).

EXAMPLE 48

N-{4-[1-(Benzothiazol-2-yl)ethoxy]-2-methylphenyl}acetamide (Compound No. E1.15)

Melting Point: 57° to 60° C. Nuclear Magnetic Resonance Spectrum (200 MHz, CDCl$_3$), δ ppm: 8.00 (1H, doublet, J=7.7 Hz); 7.85 (1H, doublet, J=7.7 Hz); 7.30–7.51 (2H, multiplet); 7.05 (1H, broad singlet); 6.76–6.92 (2H, multiplet); 5.68 (1H, quartet, J=6.5 Hz); 2.15 (3H, singlet); 2.11 (3H, singlet); 1.81 (3H, singlet).

EXAMPLE 49

N-{4-[1-(Benzothiazol-2-yl)propoxy]phenyl}acetamide (Compound No. E6.1)

Oil

Nuclear Magnetic Resonance Spectrum (200 MHz, CDCl$_3$), δ ppm: 8.01 (1H, doublet, J=8.2 Hz); 7.85 (1H, doublet, J=7.7 Hz); 7.25–7.52 (4H, multiplet); 6.94 (2H, doublet, J=9.1 Hz); 5.46 (1H, triplet, J=6.2 Hz); 2.10–2.24 (2H, multiplet); 2.10 (3H, singlet); 1.11 (3H, triplet, J=7.4 Hz).

EXAMPLE 50

N-{4-[1-(Benzothiazol-2-yl)propoxy]-2-methylphenyl}acetamide (Compound No. E7.5)

Gum

Nuclear Magnetic Resonance Spectrum (200 MHz, CDCl$_3$), δ ppm: 8.02 (1H, doublet, J=8.1 Hz); 7.86 (1H, doublet, J=7.9 Hz); 7.31–7.51 (3H, multiplet); 6.78–6.99 (3H, multiplet); 5.47 (1H, triplet, J=5.8 Hz); 2.10–2.23 (2H, multiplet); 2.16(3H, singlet); 2.13(3H, singlet); 1.10 (3H, triplet, J=7.3 Hz).

EXAMPLE 51

N-{4-[1-(Benzothiazol-2-yl)-2-methylpropoxy]phenyl}acetamide (Compound No. E7.131)

Oil

Nuclear Magnetic Resonance Spectrum (200 MHz, CDCl$_3$), δ ppm: 8.02 (1H, doublet, J=8.1 Hz); 7.85 (1H, doublet, J=7.6 Hz); 7.28–7.51 (4H, multiplet); 6.91 (2H, doublet, J=9.0 Hz); 5.24 (1H, doublet, J=6.4 Hz); 2.39 (1H, heptet, J=6.7 Hz); 2.08 (3H, singlet); 1.16 (3H, doublet, J=6.7 Hz); 1.04 (3H, doublet, J=6.7 Hz).

EXAMPLE 52

N-{4-[1-(Benzothiazol-2-yl)-2-methylpropoxy]-2-methylphenyl}acetamide (Compound No. E7.135)

Oil

Nuclear Magnetic Resonance Spectrum (200 MHz, CDCl$_3$) δ ppm: 8.02 (1H, doublet, J=8.4 Hz); 7.85 (1H, doublet, J=7.5 Hz); 7.31–7.55 (3H, multiplet); 6.78–6.90 (3H, multiplet); 5.26 (1H, doublet, J=6.3 Hz); 2.39 (1H, heptet, J=6.8 Hz); 2.16 (3H, singlet); 2.14 (3H, singlet); 1.16 (3H, doublet, J=6.8 Hz); 1.04(3H, doublet, J=6.8 Hz).

EXAMPLE 53

N-[4-(4-Methylbenzothiazol-2-ylmethoxy)phenyl] acetamide (Compound No. F1.1)

Melting Point: 154° to 156° C. Nuclear Magnetic Resonance Spectrum (200 MHz, CDCl$_3$), δ ppm: 7.72 (1H, triplet, J=4.7 Hz); 7.45–7.40 (2H, multiplet); 7.29 (2H, doublet, J=5.29 Hz), 7.05–6.98 (3H, multiplet); 5.48 (2H, singlet); 2.76 (3H, singlet); 2.16 (3H, singlet).

EXAMPLE 54

N-[4-(6-Methylbenzothiazol-2-ylmethoxy)phenyl]acetamide(Compound No. F1.21)

Melting Point: 201° to 202° C. Nuclear Magnetic Resonance Spectrum (200 MHz, CDCl$_3$), δ ppm: 7.90 (1H, doublet, J=8.3 Hz); 7.68 (1H, singlet); 7.43–7.39 (2H, multiplet); 7.34–7.28 (1H, multiplet); 7.10 (1H, broad singlet); 7.01–6.97 (2H, multiplet); 5.44 (2H, singlet); 2.49 (3H, singlet); 2.15 (3H, singlet).

EXAMPLE 55

N-[4-(4-Methoxybenzothiazol-2-ylmethoxy)phenyl]acetamide (Compound No. F3.1)

Melting Point: 147° to 148° C. Nuclear Magnetic Resonance Spectrum (200 MHz, CDCl$_3$), δ ppm: 7.49–7.31 (4H, multiplet); 7.07–6.90 (4H, multiplet); 5.49 (2H, singlet); 4.67 (3H, singlet); 2.15 (3H, singlet).

EXAMPLE 56

N-[4-(5-Methoxybenzothiazol-2-ylmethoxy)phenyl]acetamide (Compound No. F3.10)

Melting Point: 217° to 219° C. Nuclear Magnetic Resonance Spectrum (200 MHz, CDCl$_3$), δ ppm: 7.73 (1H, doublet, J=8.8 Hz); 7.51 (1H, doublet, J=2.2 Hz); 7.44–7.40 (2H, multiplet); 7.08–6.97 (4H, multiplet); 5.44 (2H, singlet); 3.90 (3H, singlet); 2.15 (3H, singlet).

EXAMPLE 57

N-[4-(7-Fluorobenzothiazol-2-ylmethoxy)phenyl]acetamide (Compound No. F4.40)

Melting Point: 149° to 152° C. Nuclear Magnetic Resonance Spectrum (200 MHz, CDCl$_3$), δ ppm: 7.83 (1H, doublet, J=8.1 Hz); 7.48–7.41 (3H, multiplet); 7.17–7.08 (2H, multiplet); 7.02–6.97 (2H, multiplet); 5.46 (2H, singlet); 2.16 (3H, singlet).

EXAMPLE 58

N-[4-(4-Methoxycarbonylbenzoxazol-2-ylmethoxy)phenyl]acetamide (Compound No. F6.11)

Melting Point: 158° to 160° C. Nuclear Magnetic Resonance Spectrum (200 MHz, CDCl$_3$), δ ppm: 8.05 (1H, doublet, J=7.9 Hz); 7.79 (1H, doublet of doublets, J=1.0 & 8.1 Hz); 7.31–7.49 (4H, multiplet); 6.98 (2H, doublet, J=8.9 Hz); 5.36 (2H, singlet); 4.03 (3H, singlet); 2.14 (3H, singlet).

EXAMPLE 59

Methyl N-[4-(4-methoxycarbonylbenzoxazol-2-ylmethoxy)phenyl]carbamate (Compound No. F6.12)
Gum
Nuclear Magnetic Resonance Spectrum (200 MHz, CDCl$_3$), δ ppm: 8.04 (1H, doublet, J=7.8 Hz); 7.76 (1H, doublet, J=8.2 Hz); 7.44 (1H, triplet, J=8.0 Hz); 7.23–7.37 (3H, multiplet); 7.00 (2H, doublet, J=8.9 Hz); 6.61 (1H, broad singlet); 5.36 (2H, singlet); 4.03 (3H, singlet); 3.75 (3H, singlet).

EXAMPLE 60

N-[4-(5-Methoxycarbonylbenzoxazol-2-ylmethoxy)phenyl]acetamide (Compound No. F6.15)

Melting Point: 165° to 168° C. Nuclear Magnetic Resonance Spectrum (200 MHz, CDCl$_3$), δ ppm: 8.45 (1H, singlet); 8.14 (1H, doublet of doublets, J=1.7 & 8.5 Hz); 7.60 (1H, doublet, J=8.5 Hz); 7.43 (2H, doublet, J=9.0 Hz); 7.13 (1H, broad singlet); 7.02 (2H, doublet, J=9.0 Hz); 5.32 (2H, singlet); 3.96 (3H, singlet); 2.16 (3H, singlet).

EXAMPLE 6 1

Methyl N-[4-(5-methoxycarbonylbenzoxazol-2-ylmethoxy)phenyl]carbamate (Compound No. F6.16)

Melting Point: 163° to 167° C. Nuclear Magnetic Resonance Spectrum (200 MHz, CDCl$_3$), δ ppm: 8.45 (1H, doublet, J=1.6 Hz); 8.13 (1H, doublet of doublets, J=1.6 & 8.6 Hz); 7.59 (1H, doublet, J=8.6 Hz); 7.31 (2H, doublet, J=9.0 Hz); 7.02 (2H, doublet, J=9.0 Hz); 6.51 (1H, broad singlet); 5.31 (2H, singlet); 3.96 (3H, singlet); 3.76 (3H, singlet).

EXAMPLE 62

N-[4-(6-Methoxycarbonylbenzoxazol-2-ylmethoxy)phenyl]acetamide (Compound No. F6.19)

Melting Point: 155° to 158° C. Nuclear Magnetic Resonance Spectrum (200 MHz, CDCl$_3$), δ ppm: 8.24 (1H, doublet, J=1.6 Hz); 8.09 (1H, doublet of doublets, J=1.6 & 8.4 Hz); 7.78 (1H, doublet, J=8.4 Hz); 7.43 (2H, doublet, J=9.3 Hz); 7.01 (2H, doublet, J=9.3 Hz); 5.32 (2H, singlet); 3.96 (3H, singlet); 2.05 (3H, singlet).

EXAMPLE 63

Methyl N-[4-(6-methoxycarbonylbenzoxazol-2-ylmethoxy)phenyl]carbamate (Compound No. F6.20)

Melting Point: approximately 230° C. Nuclear Magnetic Resonance Spectrum (200 MHz, CDCl$_3$), δ ppm: 8.25 (1H, doublet, J=0.8 Hz); 8.09 (1H, doublet of doublets, J=0.8 & 8.4 Hz); 7.78 (1H, doublet, J=8.4 Hz); 7.32 (2H, doublet, J=9.2 Hz); 7.01 (2H, doublet, J=9.2 Hz); 6.50 (1H, broad singlet); 5.33 (2H, singlet); 3.97 (3H, singlet); 3.76 (3H, singlet).

EXAMPLE 64

N-[4-(7-Methoxycarbonylbenzoxazol-2-ylmethoxy)phenyl]acetamide (Compound No. F6.23)

Melting Point: 102° to 105° C. Nuclear Magnetic Resonance Spectrum (200 MHz, CDCl$_3$), δ ppm: 8.02 (1H, doublet, J=7.8 Hz); 7.95 (1H, doublet, J=7.8 Hz); 7.46–7.39 (4H, multiplet); 7.01 (2H, doublet, J=8.8 Hz); 5.34 (2H, singlet); 4.01 (3H, singlet); 2.14 (3H, singlet).

EXAMPLE 65

Methyl N-[4-(7-methoxycarbonylbenzoxazol-2-ylmethoxy)phenyl]carbamate (Compound No. F6.24)

Melting Point: 142° to 146° C. Nuclear Magnetic Resonance Spectrum (200 MHz, CDCl$_3$+CD$_3$OD), δ ppm: 7.96

(1H, doublet of doublets, J=7.8 & 1.1 Hz); 7.88 (1H, doublet of doublets, J=8.0 & 1.1 Hz); 7.42–7.25 (3H, multiplet); 6.95 (2H, doublet, J=9.1 Hz); 5.28 (2H, singlet); 3.95 (3H, singlet); 3.67 (3H, singlet).

EXAMPLE 66

N-[2-Methyl-4-(4-methylbenzoxazol-2-ylmethoxy) phenyl]acetamide (Compound No. G1.4)

Melting Point: 160° to 161° C. Nuclear Magnetic Resonance Spectrum (200 MHz, CDCl$_3$), δ ppm: 7.56–7.51 (1H, multiplet); 7.40–7.36 (1H, multiplet); 7.29–7.22 (1H, multiplet); 7.17–7.13 (1 H, multiplet); 6.92–6.82 (3H, multiplet); 5.29 (2H, singlet); 2.63 (3H, singlet); 2.24 (3H, singlet); 2.18 (3H, doublet, J=2.5 Hz).

EXAMPLE 67

N-[2-Methyl-4-(5-methylbenzoxazol-2-ylmethoxy) phenyl]acetamide (Compound No. G1.9)

Melting Point: 177° to 180° C. Nuclear Magnetic Resonance Spectrum (200 MHz, CDCl$_3$), δ ppm: 7.55–7.51 (2H, multiplet); 7.42 (1H, doublet, J=7.9 Hz); 7.19–7.15 ( 1H, multiplet); 6.91–6.87 (3H, multiplet); 5.27 (2H, singlet); 2.47 (3H, singlet); 2.23 (3H, singlet); 2.18 (3H, singlet).

EXAMPLE 68

N-[2-Methyl-4-(6-methylbenzoxazol-2-ylmethoxy) phenyl]acetamide (Compound No. G1.14)

Melting Point: 185° to 188° C. Nuclear Magnetic Resonance Spectrum (200 MHz, CDCl$_3$), δ ppm: 7.61 (1H, doublet, J=8.2 Hz); 7.55–7.50 (1H, multiplet); 7.35 (1H, singlet); 7.19–7.14 (1H, multiplet); 6.91–6.82 (3H, multiplet); 5.30 (2H, singlet); 2.49 (3H, singlet); 2.23 (3H, singlet); 2.18 (3H, singlet).

EXAMPLE 69

N-[2-Methyl-4-(7-methylbenzoxazol-2-ylmethoxy) phenyl]acetamide (Compound No. G1.19)

Melting Point: 170° to 173° C. Nuclear Magnetic Resonance Spectrum (200 MHz, CDCl$_3$), δ ppm: 7.60–7.51 (2H, multiplet); 7.29–7.14 (2H, multiplet); 6.95–6.89 (2H, multiplet); 6.85–6.59 (1H, broad multiplet); 5.29 (2H, singlet); 2.54 (3H, singlet); 2.19 (3H, singlet).

EXAMPLE 70

N-[4-(5-Fluorobenzoxazol-2-ylmethoxy)-2-methylphenyl]acetamide (Compound No. G1.58)

Melting Point: 183° to 185° C. Nuclear Magnetic Resonance Spectrum (200 MHz, CDCl$_3$), δ ppm: 7.53–7.46 (3H, multiplet); 7.15–7.05 (1H, multiplet); 6.91–6.89 (3H, multiplet); 5.28 (2H, singlet); 2.24 (3H, singlet); 2.19 (3H, singlet).

EXAMPLE 71

N-[4-(6-Fluorobenzoxazol-2-ylmethoxy)-2-methylphenyl]acetamide (Compound No. G1.63)

Melting Point: 178° to 179° C. Nuclear Magnetic Resonance Spectrum (200 MHz, CDCl$_3$), δ ppm: 7.72–7.65 (1H, multiplet); 7.57–7.52 (1H, multiplet); 7.31–7.24 (1H, multiplet); 6.91–6.81 (3H, multiplet); 5.27 (2H, singlet); 2.24 (3H, singlet); 2.19 (3H, singlet).

EXAMPLE 72

N-[4-(7-Fluorobenzoxazol-2-ylmethoxy)-2-methylphenyl]acetamide (Compound No. G1.68)

Melting Point: 173° to 175° C. Nuclear Magnetic Resonance Spectrum (200 MHz, CDCl$_3$), δ ppm: 7.55 (2H, doublet, J=7.1 Hz); 7.33–7.25 (1H, multiplet); 7.13 (1H, doublet, J=9.2 Hz); 6.92–6.82 (3H, multiplet); 5.31 (2H, singlet); 2.24 (3H, singlet); 2.19 (3H, singlet).

EXAMPLE 73

N-[4-(5-Chlorobenzoxazol-2-ylmethoxy)-2-methylphenyl]acetamide (Compound No. G1.76)

Melting Point: 207° to 209° C. Nuclear Magnetic Resonance Spectrum (200 MHz, CDCl$_3$), δ ppm: 7.74 (1H, doublet, J=1.9 Hz); 7.56–7.46 (2H, multiplet); 7.35 (1H, doublet of doublets, J=8.8 & 1.8 Hz); 6.90–6.81 (3H, multiplet); 5.28 (2H, singlet); 2.24 (3H, singlet); 2.19 (3H, singlet).

EXAMPLE 74

N-[2-Methyl-4-(5-trifluoromethylbenzoxazol-2-ylmethoxy)phenyl]acetamide (Compound No. G1.95)

Melting Point: 216° to 218° C. Nuclear Magnetic Resonance Spectrum (200 MHz, CDCl$_3$), δ ppm: 8.05 (1H, singlet); 7.67 (2H, doublet, J=1.2 Hz); 7.58–7.53 (1H, multiplet); 6.91–6.81 (3H, multiplet); 5.33 (2H, multiplet); 2.25 (3H, singlet); 2.19 (3H, singlet).

EXAMPLE 75

N-[2-Methyl-4-(5-nitrobenzoxazol-2-ylmethoxy) phenyl]acetamide (Compound No. G1.109)

Melting Point: 212° to 216° C. Nuclear Magnetic Resonance Spectrum (200 MHz, CDCl$_3$), δ ppm: 8.65 (1H, doublet, J=2.5 Hz); 8.39–8.33 (1H, multiplet); 7.68 (1H, doublet, J=8.8 Hz); 7.58–7.53 (1H, multiplet); 6.95–6.81 (3H, multiplet); 5.34 (2H, singlet); 2.24 (3H, singlet); 2.19 (3H, singlet).

EXAMPLE 76

N-[4-(4-Methoxycarbonylbenzoxazol-2-ylmethoxy)-2-methylphenyl]acetamide (Compound No. G1.113)

Gum

Nuclear Magnetic Resonance Spectrum (200 MHz, CDCl$_3$), δ ppm: 8.05 (1H, doublet, J=7.7 Hz); 7.76 (1H, doublet of doublets, J=1.0 & 8.2 Hz); 7.47 (2H, quartet, J=8.0 Hz); 6.81–6.95 (3H, multiplet); 5.36 (2H, singlet); 4.04 (3H, singlet); 2.23 (3H, singlet); 2.18 (3H, singlet).

EXAMPLE 77

Methyl N-[4-(4-methoxycarbonylbenzoxazol-2-ylmethoxy)-2-methylphenyl]carbamate (Compound No. G1.114)

Oil

Nuclear Magnetic Resonance Spectrum (200 MHz, CDCl$_3$), δ ppm: 8.05 (1H, doublet of doublets, J=1.0 & 7.7 Hz); 7.77 (1H, doublet of doublets, J=1.0 & 8.3 Hz); 7.52 (1H, broad singlet); 7.45 (1H, triplet, J=7.8 Hz); 6.86–6.94 (2H, multiplet); 6.21 (1H, broad singlet); 5.37 (2H, singlet); 4.04 (3H, singlet); 3.76 (3H, singlet); 2.23 (3H, singlet).

EXAMPLE 78

N-[4-(5-Methoxycarbonylbenzoxazol-2-ylmethoxy)-2-methylphenyl]acetamide (Compound No. G1.117)

Melting Point: 175° to 183° C. Nuclear Magnetic Resonance Spectrum (200 MHz, CDCl$_3$), δ ppm: 8.37 (1H, doublet, J=1.5 Hz); 8.06 (1H, doublet of doublets, J=1.5 & 8.7 Hz); 7.55 (1H, doublet, J=8.7 Hz); 7.31 (1H, doublet, J=8.5 Hz); 6.78–6.92 (2H, multiplet); 5.25 (2H, singlet); 3.90 (3H, singlet); 2.16(3H, singlet); 2.09 (3H, singlet).

EXAMPLE 79

Methyl N-[4-(5-methoxycarbonylbenzoxazol-2-ylmethoxy)-2-methylphenyl]carbamate (Compound No. G1.118)

Melting Point: 132° to 135° C. Nuclear Magnetic Resonance Spectrum (200 MHz, CDCl$_3$), δ ppm: 8.45 (1H, doublet, J=1.2 Hz); 8.13(1H, doublet of doublets, J=1.2 & 8.6 Hz); 7.59(1H, doublet, J=8.6 Hz); 7.55(1H, broad singlet); 6.85–6.94 (2H, multiplet); 6.21 (1H, broad singlet); 5.31 (2H, singlet); 3.96 (3H, singlet); 3.76 (3H, singlet); 2.24 (3H, singlet).

EXAMPLE 80

N-[4-(6-Methoxycarbonylbenzoxazol-2-ylmethoxy)-2-methylphenyl]acetamide (Compound No. G 1.121)

Melting Point: 148° to 153° C. Nuclear Magnetic Resonance Spectrum (200 MHz, CDCl$_3$), δ ppm: 8.25 (1H, doublet, J=1.4 Hz); 8.09 (1H, doublet of doublets, J=1.4 & 8.4 Hz); 7.53 (1H, doublet, J=8.5 Hz); 6.83–6.94 (2H, multiplet); 5.31 (2H, singlet); 3.96 (3H, singlet); 2.23 (3H, singlet); 2.18 (3H, singlet).

EXAMPLE 81

Methyl N-[4-(6-methoxycarbonylbenzoxazol-2-ylmethoxy)-2-methylphenyl]carbamate (Compound No. G1.122)

Melting Point: approximately 190° C. Nuclear Magnetic Resonance Spectrum (200 MHz, CDCl$_3$), δ ppm: 8.25 (1H, doublet, J=0.8 Hz); 8.11 (1H, doublet of doublets, J=0.8 & 8.4 Hz); 7.79 (1H, doublet, J=8.4 Hz); 7.54 (1H, broad singlet); 6.84–6.93 (2H, multiplet); 6.21 (1H, broad singlet); 5.32 (2H, singlet); 3.97 (3H, singlet); 3.76 (3H, singlet); 2.24 (3H, singlet).

EXAMPLE 82

N-[4-(7-Methoxycarbonylbenzoxazol-2-ylmethoxy)-2-methylphenyl]acetamide (Compound No. G1.127)

Melting Point: 150° to 160° C. Nuclear Magnetic Resonance Spectrum (270 MHz, CDCl$_3$), δ ppm: 8.03 (1H, doublet, J=7.0 Hz); 7.95 (1H, doublet, J=7.6 Hz); 7.57–7.40 (2H, multiplet); 6.96–6.89 (3H, multiplet) 5.34 (2H, singlet); 4.01 (3H, singlet); 2.23 (3H, singlet). 2.18 (3H, singlet).

EXAMPLE 83

Methyl N-[4-(7-Methoxycarbonylbenzoxazol-2-ylmethoxy)-2-methylphenyl]carbamate (Compound No. G1.128)

Melting Point: 139° to 141° C. Nuclear Magnetic Resonance Spectrum (200 MHz, CDCl$_3$), δ ppm: 8.02 (1H, doublet, J=7.9 Hz); 7.95 (1H, doublet, J=8.0 & 1.3 Hz ); 7.46–7.33 (2H, multiplet); 6.94–6.88 (2H, multiplet) 6.26 (1H, broad singlet); 5.34 (2H, singlet); 4.01 (3H, singlet), 3.75 (3H, singlet), 2.23 (3H, singlet).

EXAMPLE 84

N-[4-(5,7-Dimethylbenzoxazol-2-ylmethoxy)-2-methylphenyl]acetamide (Compound No. G2.13)

Melting Point: 207° to 210° C. Nuclear Magnetic Resonance Spectrum (200 MHz, CDCl$_3$), δ ppm: 7.54–7.49 (1H, multiplet); 7.35–7.34 (1H, multiplet); 6.98–6.83 (4H, multiplet); 5.26 (2H, singlet); 2.48 (3H, singlet); 2.42 (3H, singlet); 2.23 (3H, singlet); 2.18 (3H, singlet).

EXAMPLE 85

N-[4-(6,7-Difluorobenzoxazol-2-ylmethoxy)-2-methylphenyl]acetamide (Compound No. G2.49)

Melting Point: 164° to 165° C. Nuclear Magnetic Resonance Spectrum (200 MHz, CDCl$_3$), δ ppm: 7.54–7.50 (1H, multiplet); 7.51–7.42 (1H, multiplet); 7.28–7.15 (1H, multiplet); 6.91–6.80 (3H, multiplet); 5.29 (2H, singlet); 2.24 (3H, singlet); 2.19 (3H, singlet).

EXAMPLE 86

N-[4-(5,7-Dichlorobenzoxazol-2-ylmethoxy)-2-methylphenyl]acetamide (Compound No. G2.61)

Melting Point: 190° to 193° C. Nuclear Magnetic Resonance Spectrum (200 MHz, CDCl$_3$), δ ppm: 7.64 (1H, doublet, J=1.9 Hz); 7.58–7.40 (1H, multiplet); 6.93–6.81 (3H, multiplet); 5.29 (2H, singlet); 2.24 (3H, singlet); 2.19 (3H, singlet).

EXAMPLE 87

N-[4-(Benzothiazol-2-ylmethoxy)phenyl]-2,2-dimethylpropionamide (Compound No. A1.32)

Melting Point: 156° to 158° C. Nuclear Magnetic Resonance Spectrum (200 MHz, CDCl$_3$), δ ppm: 8.03 (1H, doublet, J=7.2 Hz); 7.90 (1H, doublet of doublets, J=8.1 & 1.4 Hz); 7.56–7.35 (2H, multiplet); 7.46 (2H, doublet, J=9.0 Hz); 7.23 (1H, broad singlet); 7.00 (2H, doublet, J=9.0 Hz); 5.40 (2H, singlet); 1.30 (9H, singlet)

EXAMPLE 88

N-[4-(Benzothiazol-2-ylmethoxy)-2-methylphenyl]-2-ethoxyacetamide (Compound No. C1.36)

Melting Point: 94° to 95° C. Nuclear Magnetic Resonance Spectrum (200 MHz, CDCl$_3$), δ ppm: 8.17 (broad singlet), 8.03 (1H, doublet of doublets, J=8.0 & 1.3 Hz); 7.95 (1H, doublet of doublets, J=8.0 & 1.3 Hz); 7.83–7.78 (1H, multiplet); 7.50 (1H, triplet of doublets, J=8.0 & 1.3 Hz); 7.39 (1H, triplet of doublets, J=8.0 & 1.3 Hz); 6.92–6.88 (2H, multiplet); 5.46 (2H, singlet); 4.08 (2H, singlet); 3.67 (2H, quartet; J=7.9 Hz); 2.25 (3H, singlet); 1.30 (3H, triplet, J=7.0 Hz).

EXAMPLE 89

N-[4-(Benzothiazol-2-ylmethoxy)-2-methoxycarbonylphenyl]acetamide (Compound No. C10.78)

Melting Point: 192° to 193° C. Nuclear Magnetic Resonance Spectrum (200 MHz, DMSO-d6), δ ppm: 10.22 (1 H, broad singlet); 8.14 (1H, doublet, J=7.5 Hz); 8.03 (2H, broad doublet, J=7.9 Hz); 7.61–7.34 (4H, multiplet); 5.65 (2H, singlet); 3.84 (3H, singlet); 2.08 (3H, singlet).

EXAMPLE 90

N-[4-(Benzothiazol-2-ylmethoxy)-2,3,6-trichlorophenyl]acetamide (Compound No. C14.74)

Melting Point: 194° to 197° C. Nuclear Magnetic Resonance Spectrum (200 MHz, CDCl$_3$), δ ppm: 7.95 (1H, doublet, J=7.7 Hz); 7.86 (1H, doublet of doublets, J=1.2 & 7.7 Hz); 7.32–7.50 (2H, multiplet); 7.09 (1H, singlet); 5.47 (2H, singlet); 2.13 (3H, singlet).

EXAMPLE 91

N-[4-(Benzothiazol-2-ylmethoxy)phenyl]-4-bromobutyramide (Compound No. A1.58)

Melting Point: 163° to 165° C.

Nuclear Magnetic Resonance Spectrum (200 MHz, CDCl$_3$), δ ppm: 8.05–8.01 (1H, multiplet); 7.93–7.88 (1H, multiplet); 7.51–7.28 (4H, multiplet); 7.11 (1H, broad singlet); 7.03–6.99 (2H, multiplet); 5.47 (2H, singlet); 3.54 (2H, triplet, J=6.2 Hz); 2.55 (2H, triplet, J=6.9 Hz); 2.28 (2H, triplet, J=6.3 Hz).

EXAMPLE 92

N-[4-(Benzothiazol-2-ylmethoxy)phenyl]-5-bromopentanamide (Compound No. A1.60)

Melting Point: 151° to 153° C.

Nuclear Magnetic Resonance Spectrum (200 MHz, CDCl$_3$), δ ppm: 8.05–8.01 (1H, multiplet); 7.92–7.87 (1H, multiplet); 7.51–7.40 (4H, multiplet); 7.05–6.98 (3H, multiplet); 5.47 (2H, singlet); 3.48–3.42 (2H, multiplet); 2.38–2.35 (2H, multiplet); 1.95–1.90 (4H, broad multiplet).

EXAMPLE 93

N-[4-(Benzothiazol-2-ylmethoxy)phenyl]-2-methoxyacetamide (Compound No. A1.62)

Melting Point: 140° to 143° C.

Nuclear Magnetic Resonance Spectrum (200 MHz, CDCl$_3$), δ ppm: 8.16 (1H, broad singlet); 8.03 (1H, doublet, J=7.4 Hz); 7.90 (1H, doublet, J=8.8 Hz); 7.51 (2H, doublet, J=9.1 Hz); 7.10 (2H, doublet, J=9.1 Hz); 5.47 (2H, singlet); 4.00 (2H, singlet); 3.50 (3H, singlet).

EXAMPLE 94

N-[4-(Benzothiazol-2-ylmethoxy)phenyl]-2-ethoxyacetamide (Compound No. A1.65)

Melting Point: 118° to 120° C.

Nuclear Magnetic Resonance Spectrum (200 MHz, CDCl$_3$), δ ppm: 8.22 (1H, broad singlet); 8.03 (1H, doublet, J=7.7 Hz); 7.90 (1H, doublet of doublets, J=6.8 & 0.7 Hz); 7.54–7.35 (2H, multiplet); 7.51 (2H, doublet, J=9.0 Hz); 7.02 (2H, doublet, J=9.0 Hz); 5.47 (2H, singlet); 4.03 (2H, singlet); 3.65 (2H, quartet, J=7.0 Hz); 1.29 (3H, triplet, J=7.0 Hz).

EXAMPLE 95

N-[4-(Benzothiazol-2-ylmethoxy)phenyl]-3-methoxypropionamide (Compound No. A1.70)

Melting Point: 156° to 158° C.

Nuclear Magnetic Resonance Spectrum (200 MHz, CDCl$_3$), δ ppm: 8.12 (1H, broad singlet), 8.03 (1H, doublet, J=8.0 Hz); 7.90 (1H, doublet, J=7.7 Hz); 7.54–7.36 (2H, multiplet); 7.45 (2H, doublet, J=8.9 Hz); 6.99 (2H, doublet, J=8.9 Hz); 5.47 (2H, singlet); 3.71 (2H, triplet, J=5.5 Hz); 3.43 (3H, singlet); 2.61 (2H, triplet, J=5.5 Hz).

EXAMPLE 96

N-[4-(Benzothiazol-2-ylmethoxy)-2-methylphenyl]-3-methoxypropionamide (Compound No. C1.42)

Melting Point: 135° to 137° C.

Nuclear Magnetic Resonance Spectrum (200 MHz, CDCl$_3$), δ ppm: 8.14 (1H, broad singlet); 8.03 (1H, doublet, J=7.9 Hz); 7.89 (1H, doublet, J=7.9 Hz); 7.81–7.77 (1H, multiplet); 7.50–7.40 (2H, multiplet); 6.89–6.86 (2H, multiplet); 5.46 (2H, singlet); 3.73 (2H, triplet, J=5.9 Hz); 3.46 (3H, singlet); 2.66 (2H, triplet, J=5.9 Hz); 2.23 (3H, singlet).

EXAMPLE 97

N-[4-(Benzothiazol-2-ylmethoxy)-2-methoxymethylphenyl]acetamide (Compound No. C6.1)

Melting Point: 157° to 160° C.

Nuclear Magnetic Resonance Spectrum (200 MHz, CDCl$_3$), δ ppm: 8.33–8.30 (1H, multiplet); 8.06–8.01 (2H, multiplet); 7.92–7.88 (1H, multiplet); 7.51–7.40 (2H, multiplet); 7.04–6.98 (1H, multiplet); 6.89–6.88 (1H, multiplet); 5.47 (2H, singlet); 4.48 (2H, singlet); 3.37 (3H, singlet); 2.16 (3H, singlet).

EXAMPLE 98

N-[4-(Benzothiazol-2-ylmethoxy)-2-ethoxymethylphenyl]acetamide (Compound No. C6.29)

Melting Point: 154° to 156° C.

Nuclear Magnetic Resonance Spectrum (200 MHz, CDCl$_3$), δ ppm: 8.52–8.50 (1H, multiplet); 8.08–8.01 (2H, multiplet); 7.93–7.88 (1H, multiplet); 7.54–7.40 (2H, multiplet); 7.03–6.97 (1H, multiplet); 6.88–6.87 (1H, multiplet); 5.46 (2H, singlet); 4.53 (2H, singlet); 3.53 (2H, quartet, J=7.1 Hz); 2.16 (3H, singlet); 1.25 (3H, triplet, J=7.0 Hz).

EXAMPLE 99

N-[4-(Benzothiazol-2-ylmethoxy)-2-methoxyphenyl]acetamide (Compound No. C8.1)

Melting Point: 163° to 165° C.

Nuclear Magnetic Resonance Spectrum (200 MHz, CDCl$_3$), δ ppm: 8.24 (1H, doublet, J=8.8 Hz); 8.06 (1H, doublet of doublets, J=1.2 & 7.7 Hz); 7.90 (1H, doublet of doublets, J=1.2 & 8.1 Hz); 7.55–7.40 (3H, multiplet); 6.65–6.58 (2H, multiplet); 5.47 (2H, singlet); 3.87 (3H, singlet); 2.18 (3H, singlet).

EXAMPLE 100

N-[4-(Benzoxazol-2-ylmethoxy)-2-methoxyphenyl]acetamide (Compound No. C8.2)

Melting Point: 118° to 119° C.

Nuclear Magnetic Resonance Spectrum (200 MHz, CDCl$_3$), δ ppm: 8.24 (1H, doublet, J=8.8 Hz); 7.79–7.74

(1H, multiplet); 7.59–7.54 (2H, multiplet); 7.39–7.35 (2H, multiplet); 6.67–6.59 (2H, multiplet); 5.31 (2H, singlet); 3.85 (3H, singlet); 2.18 (3H, singlet).

EXAMPLE 101

N-[4-(Benzoxazol-2-ylmethoxy)-3-methoxyphenyl] acetamide (Compound No. C8.22)

Melting Point: 98° to 100° C.

Nuclear Magnetic Resonance Spectrum (200 MHz, CDCl$_3$), δ ppm: 7.76–7.71 (1H, multiplet); 7.58–7.53 (1H, multiplet); 7.42–7.33 (3H, multiplet); 7.23 (1H, broad singlet); 6.98 (1H, doublet, J=8.6 Hz); 6.75 (1H, doublet of doublets, J=8.6 & 2.2 Hz); 5.33 (2H, singlet); 3.86 (3H, singlet); 2.14 (3H, singlet).

EXAMPLE 102

N-[4-(Benzoxazol-2-ylmethoxy)-3-fluorophenyl] acetamide (Compound No. C9.22)

Melting Point: 140° to 142° C.

Nuclear Magnetic Resonance Spectrum (200 MHz, CDCl$_3$), δ ppm: 7.78–7.74 (1H, multiplet); 7.59–7.55 (1H, multiplet); 7.49–7.35 (3H, multiplet); 7.10–7.06 (3H, multiplet); 5.36 (2H, singlet); 2.16 (3H, singlet).

EXAMPLE 103

N-[4-(Benzoxazol-2-ylmethoxy)-2-trifluoromethylphenyl]acetamide (Compound No. C10.3)

Melting Point: 145° to 147° C.

Nuclear Magnetic Resonance Spectrum (200 MHz, CDCl$_3$), δ ppm: 7.99 (1H, doublet of doublets, J=9.7 & 1.0 Hz); 7.80–7.75 (1H, multiplet); 7.59–7.55 (1H, multiplet); 7.43–7.24 (4H, multiplet); 5.35 (2H, singlet); 2.20 (3H, singlet).

EXAMPLE 104

N-[4-(Benzothiazol-2-ylmethoxy)-3-trifluoromethylphenyl]acetamide (Compound No. C 10.17)

Melting Point: 174° to 175° C.

Nuclear Magnetic Resonance Spectrum (200 MHz, CDCl$_3$), δ ppm: 7.94 (1H, doublet, J=7.4 Hz); 7.85 (1H, doublet, J=7.4 Hz); 7.61–7.74 (2H, multiplet); 7.31–7.49 (2H, multiplet); 7.01 (1H, doublet, J=8.8 Hz); 5.46 (2H, singlet); 2.06 (3H, singlet).

EXAMPLE 105

N-[2-Acetyl-4-(benzothiazol-2-ylmethoxy)phenyl] acetamide (Compound No. C 10.42)

Melting Point: 134° to 137° C.

Nuclear Magnetic Resonance Spectrum (200 MHz, acetone-d6), δ ppm: 1.30 (1H, broad singlet); 8.65 (1H, doublet, J=9.2 Hz); 8.12–8.00 (2H, multiplet); 7.79 (1H, doublet, J=3.0 Hz); 7.60–7.35 (3H, multiplet); 5.65 (2H, singlet); 2.71 (3H, singlet); 2.12 (3H, singlet).

EXAMPLE 106

N-[4-(Benzoxazol-2-ylmethoxy)-2-nitrophenyl] acetamide (Compound No. C 10.49)

Melting Point: 162° to 165° C.

Nuclear Magnetic Resonance Spectrum (200 MHz, CDCl$_3$), δ ppm: 0.11 (1H, broad singlet); 8.71 (1H, doublet, J=9.3 Hz); 7.89 (1H, doublet, J=3.1 Hz); 7.79–7.75 (1H, multiplet); 7.60–7.55 (1H, multiplet); 7.44–7.36 (3H, multiplet); 5.38 (2H, singlet); 2.27 (3H, singlet).

EXAMPLE 107

N-[4-(5-Fluorobenzothiazol-2-ylmethoxy)phenyl] pentanamide (Compound No. F4.20)

Melting Point: 189° to 191° C.

Nuclear Magnetic Resonance Spectrum (200 MHz, CDCl$_3$), δ ppm: 7.82 (1H, doublet of doublets, J=8.9 & 5.1 Hz); 7.70 (1H, doublet of doublets, J=9.4 & 2.4 Hz); 7.45 (2H, doublet, J=8.9 Hz); 7.18 (1H, triplet of doublets, J$_f$=8.8 Hz & J$_d$=2.6 Hz); 7.05 (1H broad singlet); 6.99 (2H, doublet, J=9.1 Hz); 5.45 (2H, singlet); 2.34 (2H, triplet, J=7.6 Hz); 1.71 (2H, sextet, J=7.5 Hz); 1.40 (2H, quintet, J=7.5 Hz); 0.95 (3H, triplet, J=7.2 Hz).

EXAMPLE 108

N-[4-(5-Fluorobenzothiazol-2-ylmethoxy)phenyl] cyclohexanecarboxamide (Compound No. F4.22)

Melting Point: 211° to 212° C.

Nuclear Magnetic Resonance Spectrum (200 MHz, CDCl$_3$), δ ppm: 7.82 (1H, doublet of doublets, J=9.0 & 5.1 Hz); 7.70 (1H, doublet of doublets, J=9.2 & 2.5 Hz); 7.46 (2H, doublet, J=9.1 Hz); 7.18 (1H, triplet of doublets, J=8.8 & 2.5 Hz); 7.05 (1H, broad singlet); 6.99 (2H, doublet, J=9.1 Hz); 5.45 (2H, singlet); 2.30–2.10 (1H, multiplet); 2.03–1.18 (10H, multiplet).

EXAMPLE 109

N-[4-(5-Fluorobenzothiazol-2-ylmethoxy)phenyl]-2-fluoroacetamide (Compound No. F4.23)

Melting Point: 192° to 193° C.

Nuclear Magnetic Resonance Spectrum (200 MHz, CDCl$_3$), δ ppm: 7.84 (1H, broad singlet); 7.83 (1H, doublet of doublets, J=8.8 & 5.1 Hz); 7.71 (1H, doublet of doublets, J=7.4 & 2.5 Hz); 7.51 (2H, doublet, J=9.1 Hz); 7.19 (1H, triplet of doublets, J=8.8 & 2.4 Hz); 7.03 (2H, doublet, J=9.0 Hz); 5.47 (2H, singlet); 4.92 (2H, doublet, J=47.5 Hz).

EXAMPLE 110

N-[4-(5-Fluorobenzothiazol-2-ylmethoxy)phenyl]-2-chloroacetamide (Compound No. F4.25)

Melting Point: 198° to 200° C.

Nuclear Magnetic Resonance Spectrum (200 MHz, CDCl$_3$), δ ppm: 8.18 (1H, broad singlet); 7.83 (1H, doublet of doublets, J=8.8 & 5.1 Hz); 7.71 (1H, doublet of doublets, J=9.6 & 2.6 Hz); 7.49 (2H, doublet, J=9.0 Hz); 7.19 (1H, triplet of doublets, J=8.8 & 2.4 Hz); 7.03 (2H, doublet, J=9.1 Hz); 5.47 (2H, singlet); 4.19 (2H, singlet).

EXAMPLE 111

N-[4-(5-Fluorobenzothiazol-2-ylmethoxy)phenyl]2,2-dichloroacetamide (Compound No. F4.27)

Melting Point: 208° to 209° C.

Nuclear Magnetic Resonance Spectrum (200 MHz, CDCl$_3$), δ ppm: 8.05 (1H, broad singlet); 7.83 (1H, doublet of doublets, J=8.9 & 5.1 Hz); 7.71 (1H, doublet of doublets, J=9.3 & 2.0 Hz); 7.50 (2H, doublet, J=9.1 Hz); 7.19 (1H, triplet, doublet, J=8.8, 2.5 Hz); 7.05 (2H, doublet, J=9.1 Hz); 6.03 (1H, singlet); 5.48 (2H, singlet).

EXAMPLE 112

N-[4-(5-Fluorobenzothiazol-2-ylmethoxy)phenyl]-2,2,2-trifluoroacetamide (Compound No. F4.28)

Melting Point: 204° to 206° C.

Nuclear Magnetic Resonance Spectrum (200 MHz, CDCl$_3$) δ ppm: 7.88–7.68 (3H, multiplet); 7.52 (2H, doublet, J=9.0 Hz); 7.20–7.14 (1H, multiplet); 7.06 (2H, doublet, J=9.1 Hz); 5.48 (2H, singlet).

EXAMPLE 113

S-Methyl N-[4-(benzothiazol-2-ylmethoxy)phenyl] dithiocarbamate (Compound No. A1.16)

Melting Point: 136° to 138° C.

Nuclear Magnetic Resonance Spectrum (200 MHz, CDCl$_3$), δ ppm: 8.70–8.65 (1H, broad multiplet); 8.07–8.03 (1H, multiplet); 7.94–7.89 (1H, multiplet); 7.55–7.33 (3H, multiplet); 7.09–7.04 (2H, multiplet); 5.51 (2H, singlet); 2.64 (3H, singlet).

EXAMPLE 114

N-[4-(Benzothiazol-2-ylmethylthio)-2-methylphenyl]acetamide (Compound No. C1.3)

Melting Point: 116° to 117° C.

Nuclear Magnetic Resonance Spectrum (200 MHz, CDCl$_3$), δ ppm: 7.98–7.72 (3H, multiplet); 7.50–7.20 (4H, multiplet); 6.87 (1H, broad singlet); 4.48 (2H, singlet); 2.19 (3H, singlet).

EXAMPLE 115

N-[4-(Benzothiazol-2-ylmethoxy)-3-methylphenyl]acetamide (Compound No. C1.52)

Melting Point: 157° to 159° C.

Nuclear Magnetic Resonance Spectrum (200 MHz, CDCl$_3$), δ ppm: 8.05–7.89 (2H, multiplet); 7.51–7.22 (2H, multiplet); 7.05 (1H, broad singlet); 6.86 (1H, doublet, J=8.8 Hz); 5.46 (2H, singlet); 2.35 (3H, singlet); 2.15 (3H, singlet).

EXAMPLE 116

N-[4-(Benzothiazol-2-ylmethoxy)-2-ethylphenyl]acetamide (Compound No. C2.1)

Melting Point: 165° to 168° C.

Nuclear Magnetic Resonance Spectrum (200 MHz, CDCl$_3$), δ ppm: 8.03 (1H, doublet, J=9.2 Hz); 7.90 (1H, doublet of doublets, J=7.7 & 1.0 Hz); 7.52 (1H, doublet, J=8.5 Hz); 7.46–7.40 (2H, multiplet); 6.93–6.82 (3H, multiplet); 5.46 (2H, singlet); 2.58 (2H, quartet, J=7.7 Hz); 2.18 (3H, singlet); 1.22 (3H, triplet, J=7.7 Hz).

EXAMPLE 117

N-[4-(Benzothiazol-2-ylmethoxy)-3-ethylphenyl]acetamide (Compound No. C2.19)

Melting Point: 135° to 137° C.

Nuclear Magnetic Resonance Spectrum (200 MHz, CDCl$_3$), δ ppm: 8.03 (1H, doublet, J=8.2 Hz); 7.91 (1H, doublet of doublets, J=6.8 & 0.8 Hz); 7.51–7.40 (2H, multiplet); 7.31–7.28 (2H, multiplet); 7.03 (1H, broad singlet); 6.88 (1H, doublet, J=9.4 Hz); 5.47 (2H, singlet); 2.77 (2H, quartet, J=7.5 Hz); 2.15 (3H, singlet); 1.27 (3H, triplet, J=7.5 Hz).

EXAMPLE 118

N-[4-(Benzothiazol-2-ylmethoxy)-2-isopropylphenyl]acetamide (Compound No. C3.30)

Melting Point: 165° to 170° C.

Nuclear Magnetic Resonance Spectrum (270 MHz, CDCl$_3$), δ ppm: 8.03 (1H, doublet, J=8.7 Hz); 7.91 (1H, doublet, J=8.7 Hz); 7.57–7.36 (3H, multiplet); 7.15–6.78 (2H, multiplet); 5.46 (2H, singlet); 3.10–2.87 (1H, multiplet); 2.18 (3H, singlet); 1.21 (6H, doublet, J=6.8 Hz).

EXAMPLE 119

N-[4-(Benzothiazol-2-ylmethoxy)-2-t-butylphenyl]acetamide (Compound No. C4.27)

Melting Point: 158° to 165° C.

Nuclear Magnetic Resonance Spectrum (270 MHz, CDCl$_3$), δ ppm: 8.04 (1H, doublet, J=8.8 Hz); 7.91 (1H, doublet, J=8.8 Hz); 7.55–7.30 (2H, multiplet); 7.18–6.81 (3H, multiplet); 5.46 (2H, singlet); 2.19 (3H, singlet); 1.38 (9H, singlet).

EXAMPLE 120

N-[4-(Benzothiazol-2-ylmethoxy)-2-difluoromethylphenyl]acetamide (Compound No. C7.55)

Melting Point: 195° to 198° C.

Nuclear Magnetic Resonance Spectrum (200 MHz, CDCl$_3$), δ ppm: 8.04 (1H, doublet, J=7.7 Hz); 7.91 (1H, doublet of doublets, J=6.6 & 0.8 Hz); 7.81–7.77 (1H, multiplet); 7.56–7.42 (2H, multiplet); 7.32 (1H, broad singlet); 7.17–7.13 (2H, multiplet); 6.65 (1H, triplet, J=55.3 Hz); 5.50 (2H, singlet); 2.19 (3H, singlet).

EXAMPLE 121

N-[4-(Benzothiazol-2-ylmethoxy)-2-ethoxyphenyl]acetamide (Compound No. C8.39)

Melting Point: 131° to 133° C.

Nuclear Magnetic Resonance Spectrum (200 MHz, CDCl$_3$), δ ppm: 8.25 (1H, doublet, J=8.5 Hz); 8.03 (1H, doublet of doublets, J=8.5 & 1.2 Hz); 7.90 (1H, doublet of doublets, J=7.6 & 1.6 Hz); 7.56 (1H, singlet); 7.51 (1H, triplet of doublets, J=7.6 & 1.5 Hz); 7.40 (1H, triplet of doublets, J=7.8 & 1.4 Hz); 6.63–6.56 (1H, multiplet); 6.61 (1H, singlet); 5.46 (2H, singlet); 4.09 (2H, quartet, J=7.0 Hz); 2.18 (3H, singlet); 1.46 (3H, triplet, J=7.0 Hz).

EXAMPLE 122

N-[4-(Benzothiazol-2-ylmethoxy)-2-difluoromethoxyphenyl]acetamide (Compound No. C8.72)

Melting Point: 120° to 121° C.

Nuclear Magnetic Resonance Spectrum (200 MHz, CDCl$_3$), δ ppm: 8.23 (1H, doublet, J=9.4 Hz); 8.04 (1H, doublet of doublets, J=7.1 & 1.4 Hz); 7.91 (1H, doublet of doublets, J=7.1 & 1.4 Hz); 7.56–7.28 (3H, multiplet); 6.92–6.87 (2H, multiplet); 6.52(1H, triplet, J=73.2 Hz); 5.47 (2H, singlet); 2.20 (3H, singlet).

EXAMPLE 123

N-[4-(Benzothiazol-2-ylmethoxy)-2-(2,2,2-trifluoroethoxy)phenyl]acetamide (Compound No. C8.76)

Melting Point: 136° to 138° C.

Nuclear Magnetic Resonance Spectrum (200 MHz, CDCl$_3$), δ ppm: 8.24 (1H, doublet, J=9.0 Hz); 8.04 (1H, doublet, J=7.6 Hz); 7.90 (1H, doublet of doublets, J=7.9 & 1.8 Hz); 7.56–7.37 (3H, multiplet); 6.72 (1H, doublet of doublets, J=9.0 & 2.6 Hz); 6.64 (1H, doublet, J=2.6 Hz); 5.47 (2H, singlet); 4.40 (2H, quartet, J=8.0 Hz); 2.19 (3H, singlet).

EXAMPLE 124

N-[4-(Benzoxazol-2-ylmethoxy)-2-fluorophenyl]acetamide (Compound No. C9.3)

Melting Point: 135° to 136° C.

Nuclear Magnetic Resonance Spectrum (200 MHz, CDCl$_3$), δ ppm: 8.15 (1H, doublet, J=8.8 Hz); 7.79–7.74 (1H, multiplet); 7.59–7.54 (1H, multiplet); 7.43–7.36 (2H, multiplet); 7.18 (1H, broad singlet); 6.90–6.83 (2H, multiplet); 5.30 (2H, singlet); 2.20 (3H, singlet).

EXAMPLE 125

N-[4-(Benzothiazol-2-ylmethoxy)-3-fluorophenyl]acetamide (Compound No. C9.20)

Melting Point: 150° to 151° C.

Nuclear Magnetic Resonance Spectrum (200 MHz, CDCl$_3$), δ ppm: 8.05–7.89 (2H, multiplet); 7.51–7.28 (3H, multiplet); 7.04–7.02 (3H, multiplet); 5.53 (2H, singlet); 2.16 (3H, singlet).

EXAMPLE 126

N-[4-(Benzothiazol-2-ylmethoxy)-2-chlorophenyl]acetamide (Compound No. C9.36)

Melting Point: 159° to 161° C.

Nuclear Magnetic Resonance Spectrum (200 MHz, CDCl$_3$), δ ppm: 8.23 (1H, doublet, J=9.2 Hz); 8.04 (1H, doublet, J=8.1 Hz); 7.90 (1H, doublet of doublets, J=7.0 & 0.8 Hz); 7.56–7.37 (3H, multiplet); 7.10 (1H, doublet, J=2.8 Hz); 6.97 (1H, doublet of doublets, J=9.2 & 2.8 Hz); 5.45 (2H, singlet); 2.22 (3H, singlet).

EXAMPLE 127

N-[4-(Benzoxazol-2-ylmethoxy)-2-chlorophenyl]acetamide (Compound No. C9.38)

Melting Point: 130° to 131° C.

Nuclear Magnetic Resonance Spectrum (200 MHz, CDCl$_3$), δ ppm: 8.23 (1H, doublet, J=9.0 Hz); 7.79–7.75 (1H, multiplet); 7.59–7.55 (1H, multiplet); 7.45–7.29 (3H, multiplet); 7.12 (1H, doublet, J=2.8 Hz); 6.99 (1H, doublet of doublets, J=9.0 & 2.8 Hz); 5.29 (2H, singlet); 2.22 (3H, singlet); 1.57 (3H, singlet).

EXAMPLE 128

N-[4-(Benzothiazol-2-ylmethoxy)-3-chlorophenyl]acetamide (Compound No. C9.52)

Melting Point: 168° to 169° C.

Nuclear Magnetic Resonance Spectrum (200 MHz, CDCl$_3$), δ ppm: 8.03 (1H, doublet, J=8.1 Hz); 7.92 (1H, doublet of doublets, J=6.7 & 1.0 Hz); 7.67 (1H, doublet, J=2.5 Hz); 7.67–7.27 (2H, multiplet); 7.08 (1H, broad singlet); 7.00 (1H, doublet, J=8.9 Hz); 5.53 (2H, singlet); 2.16 (3H, singlet).

EXAMPLE 129

N-[4-(Benzoxazol-2-ylmethoxy)-3-chlorophenyl]acetamide (Compound No. C9.54)

Melting Point: 161° to 165° C.

Nuclear Magnetic Resonance Spectrum (200 MHz, CDCl$_3$), δ ppm: 7.78–7.73 (1H, multiplet); 7.63–7.55 (2H, multiplet); 7.43–7.29 (3H, multiplet); 7.09 (1 H, broad singlet); 7.09 (1H, doublet, J=8.7 Hz); 5.36 (2H, singlet); 2.16 (3H, singlet).

EXAMPLE 130

N-[3-Acetyl-4-(benzothiazol-2-ylmethoxy)phenyl]acetamide (Compound No. C10.44)

Melting Point: 233° to 238° C.

Nuclear Magnetic Resonance Spectrum (200 MHz, DMSO-d6), δ ppm: 10.00 (1H, broad singlet); 8.17 (1H, doublet, J=8.3 Hz); 8.05 (1H, doublet, J=7.8 Hz); 7.85 (1H, doublet, J=2.9 Hz); 7.77 (1H, doublet of doublets, J=8.8 & 2.9 Hz); 7.62–7.45 (2H, multiplet); 7.31 (1H, doublet, J=8.8 Hz); 5.72 (2H, singlet); 2.67 (3H, singlet); 2.03 (3H, singlet).

EXAMPLE 131

N-[4-(Benzoxazol-2-ylmethoxy)-3-nitrophenyl]acetamide (Compound No. C10.65)

Melting Point: 148° to 150° C.

Nuclear Magnetic Resonance Spectrum (200 MHz, CDCl$_3$), δ ppm: 8.03 (1H, doublet, J=2.9 Hz); 7.78–7.72 (2H, multiplet); 7.60–7.56 (1H, multiplet); 7.42–7.30 (4H, multiplet); 5.45 (2H, singlet); 2.19 (3H, singlet).

EXAMPLE 132

N-[4-(Benzothiazol-2-ylmethoxy)-2,3-dimethylphenyl]acetamide (Compound No. C11.1)

Melting Point: 207° to 209° C.

Nuclear Magnetic Resonance Spectrum (200 MHz, CDCl$_3$), δ ppm: 8.03 (1H, doublet, J=8.0 Hz); 7.91 (1H, doublet, J=7.6 Hz); 7.51–7.40 (2H, multiplet); 7.03 (2H, AB quartet, J=8.9 Hz, Δν=85.6); 6.89 (1H, broad singlet); 5.46 (2H, singlet); 2.31 (3H, singlet); 2.19 (6H, singlet).

EXAMPLE 133

N-[4-(Benzothiazol-2-ylmethoxy)-2,5-dimethylphenyl]acetamide (Compound No. C11.17)

Melting Point: 90° to 94° C.

Nuclear Magnetic Resonance Spectrum (200 MHz, CDCl$_3$), δ ppm: 8.03 (1H, doublet, J=7.5 Hz); 7.92 (1H, doublet, J=7.7 Hz); 7.51–7.44 (2H, multiplet); 7.40 (1H, singlet); 6.80 (1H, singlet); 6.75 (1H, singlet); 5.45 (2H, singlet); 2.31 (3H, singlet); 2.20 (3H, singlet); 2.18 (3H, singlet).

EXAMPLE 134

N-[4-(Benzothiazol-2-ylmethoxy)-2,6-dimethylphenyl]acetamide (Compound No. C11.33)

Melting Point: 198° to 204° C.

Nuclear Magnetic Resonance Spectrum (200 MHz, CDCl$_3$), δ ppm: 8.03 (1H, doublet, J=8.8 Hz); 7.91 (1H, doublet of doublets, J=7.7 & 0.8 Hz); 7.51–7.41 (2H, multiplet); 6.77 (2H, singlet); 6.59 (1H, singlet); 5.44 (2H, singlet); 2.22 (6H, singlet); 2.20 (3H, singlet).

EXAMPLE 135

N-[4-(Benzothiazol-2-ylmethoxy)-3,5-dimethylphenyl]acetamide (Compound No. C11.48)

Melting Point: 151° C.

Nuclear Magnetic Resonance Spectrum (200 MHz, CDCl$_3$), δ ppm: 8.23 (1H, broad singlet); 8.00 (1H, doublet, J=7.6 Hz); 7.90 (1H, doublet, J=8.1 Hz); 7.52–7.35 (2H, multiplet); 7.19 (2H, singlet); 5.14 (2H, singlet); 2.26 (6H, singlet); 2.13 (3H, singlet).

EXAMPLE 136

N-[4-(Benzothiazol-2-ylmethoxy)-2,3,5-trimethylphenyl]acetamide (Compound No. C11.63)

Melting Point: 215° to 220° C.

Nuclear Magnetic Resonance Spectrum (270 MHz, CDCl$_3$+CD$_3$OD), δ ppm: 7.94 (1H, doublet, J=9.0 Hz); 7.90 (1H, doublet, J=9.0 Hz); 7.50–7.31 (2H, multiplet); 7.02 (1H, singlet); 5.08 (2H, singlet); 2.24 (3H, singlet); 2.20 (3H, singlet); 2.10 (3H, singlet); 2.05 (3H, singlet).

EXAMPLE 137

N-[4-(Benzothiazol-2-ylmethoxy)-2,3,6-trimethylphenyl]acetamide (Compound No. C11.78)

Melting Point: 217° to 225° C.

Nuclear Magnetic Resonance Spectrum (270 MHz, CDCl$_3$), δ ppm: 8.03 (1H, doublet, J=8.1 Hz); 7.92 (1H, doublet, J=8.1 Hz); 7.56–7.36 (2H, multiplet); 6.69 (1H, singlet); 5.43 (2H, singlet); 2.32–2.16 (12H, multiplet).

EXAMPLE 138

N-[4-(Benzothiazol-2-ylmethoxy)-3,5-dimethoxyphenyl]acetamide (Compound No. C 12.45)

Amorphous solid

Nuclear Magnetic Resonance Spectrum (200 MHz, CDCl$_3$), δ ppm: 8.00 (1H, doublet of doublets, J=8.8 & 1.2 Hz); 7.93 (1H, doublet of doublets, J=6.7 & 1.1 Hz); 7.51–7.35 (2H, multiplet); 7.17 (1H, broad singlet); 6.82 (2H, singlet); 5.38 (2H, singlet); 3.82 (6H, singlet); 2.17 (3H, singlet).

EXAMPLE 139

N-[4-(Benzothiazol-2-ylmethoxy)-2,5-dichlorophenyl]acetamide (Compound No. C 14.15)

Melting Point: 188° C.

Nuclear Magnetic Resonance Spectrum (200 MHz, CDCl$_3$), δ ppm: 8.49 (1H, singlet); 8.04 (1H, doublet, J=8.3 Hz); 7.93 (1H, doublet, J=9.2 Hz); 7.38 (3H, multiplet); 7.10 (1H, singlet); 5.51 (2H, singlet); 2.23 (3H, singlet).

EXAMPLE 140

N-[4-(Benzothiazol-2-ylmethoxy)-2,6-dichlorophenyl]acetamide (Compound No. C14.31)

Melting Point: 169° to 172° C.

Nuclear Magnetic Resonance Spectrum (200 MHz, CDCl$_3$), δ ppm: 8.03 (1H, doublet, J=7.6 Hz); 7.89 (1H, doublet, J=8.1 Hz); 7.56–7.42 (2H, multiplet); 7.13 (1H, doublet, J=1.8 Hz); 6.97 (1H, doublet, J=1.8 Hz); 5.47 (2H, singlet); 2.26 (3H, broad singlet).

EXAMPLE 141

N-[4-(Benzothiazol-2-ylmethoxy)-3,5-dichlorophenyl]acetamide (Compound No. C14.45)

Melting Point: 173.5° to 175° C.

Nuclear Magnetic Resonance Spectrum (200 MHz, CDCl$_3$+CD$_3$OD), δ ppm: 7.96 (1H, doublet of doublets, J=8.7 & 1.5 Hz); 7.89 (1H, doublet of doublets, J=7.9 & 1.4 Hz); 7.57 (2H, singlet); 7.49–7.37 (2H, multiplet); 5.34 (2H, singlet); 2.08 (3H, singlet).

EXAMPLE 142

N-[4-(Benzothiazol-2-ylmethoxy)-3,5-dibromophenyl]acetamide (Compound No. C15.37)

Decomposed at 198° C.

Nuclear Magnetic Resonance Spectrum (270 MHz, CDCl$_3$+CD$_3$OD), δ ppm: 7.90–7.80 (2H, multiplet); 7.70 (2H, singlet); 7.41–7.25 (2H, multiplet); 5.24 (2H, singlet); 1.98 (3H, singlet).

EXAMPLE 143

Methyl N-[4-(benzothiazol-2-ylmethoxy)-2-chloro-6-methylphenyl]carbamate (Compound No. C16.113)

Melting Point: 184° to 187° C.

Nuclear Magnetic Resonance Spectrum (200 MHz, CDCl$_3$), δ ppm: 8.03 (1H, doublet, J=7.3 Hz); 7.90 (1H, doublet, J=7.7 Hz); 7.55–7.37 (2H, multiplet); 6.97 (1H, doublet, J=2.6 Hz); 6.83 (1H, doublet, J=2.6 Hz); 6.18 (1H, broad singlet); 5.43 (2H, singlet); 3.75 (3H, broad singlet); 2.28 (3H, singlet).

EXAMPLE 144

N-[4-(Benzothiazol-2-ylmethoxy)-5-isopropyl-2-methylphenyl]acetamide (Compound No. C 18.118)

Melting Point: 153° to 156° C.

Nuclear Magnetic Resonance Spectrum (200 MHz, CDCl$_3$), δ ppm: 8.04 (1H, doublet, J=8.6 Hz); 7.92 (1H, doublet, J=8.3 Hz); 7.51–7.41 (3H, multiplet); 6.84 (1H, doublet, J=8.3 Hz); 6.76 (2H, singlet); 5.46 (2H, singlet); 3.42 (1H, quartet, J=6.7 Hz); 2.21 (3H, singlet); 2.19 (3H, singlet); 1.28 (6H, doublet, J=6.8 Hz).

EXAMPLE 145

N-[4-(Benzothiazol-2-ylmethoxy)-2-chloro-6-methoxycarbonylphenyl]acetamide (Compound No. C18.130)

Melting Point: 141° to 143° C.

Nuclear Magnetic Resonance Spectrum (200 MHz, CDCl$_3$), δ ppm: 8.07 (1H, broad singlet); 8.04 (1H, doublet, J=8.5 Hz); 7.91 (1H, doublet, J=8.5 Hz); 7.37–7.57 (3H, multiplet); 7.31 (1H, singlet); 5.49 (2H, singlet); 3.89 (3H, singlet); 2.20 (3H, singlet).

EXAMPLE 146

N-[4-(5-Methoxybenzoxazol-2-ylmethoxy)-2-methylphenyl]acetamide (Compound No. G1.35)

Melting Point: 173° to 177° C.

Nuclear Magnetic Resonance Spectrum (200 MHz, CDCl$_3$) δ ppm: 7.56–7.51 (1H, multiplet); 7.43 (1H, doublet, J=9.0 Hz); 7.22 (1H, doublet, J=2.6 Hz); 6.99–6.82 (4H, multiplet); 5.26 (2H, singlet); 3.86 (3H, singlet); 2.24 (3H, singlet); 2.19 (3H, singlet).

EXAMPLE 147

Methyl N-[4-(5-methoxybenzoxazol-2-ylmethoxy)-2-methylphenyl]carbamate (Compound No. G1.36)

Melting Point: 160° to 162° C.

Nuclear Magnetic Resonance Spectrum (200 MHz, CDCl$_3$) δ ppm: 7.55–7.49 (1H, broad multiplet); 7.43 (1H, doublet, J=8.7 Hz); 7.22 (1H, doublet, J=2.4 Hz); 6.99–6.88 (3H, multiplet); 6.19 (1H, broad singlet); 5.26 (2H, singlet); 3.86 (3H, singlet); 3.76 (3H, singlet); 2.23 (3H, singlet).

EXAMPLE 148

N-[4-(5-Methylbenzothiazol-2-ylmethoxy)phenyl] acetamide (Compound No. F1.11)

Melting Point: 211° to 213° C.

Nuclear Magnetic Resonance Spectrum (200 MHz, CDCl$_3$). δ ppm: 7.82 (1H, singlet); 7.76 (1H, doublet, J=8.3 Hz); 7.44–7.38 (2H, multiplet); 7.26–7.21 (1H, multiplet); 7.09–7.03 (1H, multiplet); 7.01–6.95 (2H, multiplet); 5.45 (2H, singlet); 2.51 (3H, singlet); 2.15 (3H, singlet).

EXAMPLE 149

N-[4-(7-Methylbenzothiazol-2-ylmethoxy)phenyl] acetamide (Compound No. F1.31)

Melting Point: 164° to 166° C.

Nuclear Magnetic Resonance Spectrum (200 MHz, CDCl$_3$). δ ppm: 7.87 (1H, doublet, J=7.9 Hz); 7.45–7.38 (3H, multiplet); 7.20 (1H, doublet, J=7.0 Hz); 7.07–6.98 (3H, multiplet); 5.47 (2H, singlet); 2.57 (3H, singlet); 2.16 (3H, singlet).

EXAMPLE 150

N-[4-(7-Methoxybenzothiazol-2-ylmethoxy)phenyl] acetamide (Compound No. F3.29)

Melting Point: 163° to 164° C.

Nuclear Magnetic Resonance Spectrum (200 MHz, CDCl$_3$), δ ppm: 7.65 (1H, doublet, J=8.4 Hz); 7.48–7.39 (3H, multiplet); 7.02–6.82 (4H, multiplet); 5.45 (2H, singlet); 3.98 (3H, singlet); 2.16 (3H, singlet).

EXAMPLE 151

N-[4-(4-Fluorobenzothiazol-2-ylmethoxy)phenyl] acetamide (Compound No. F4.1)

Melting Point: 156° to 158° C.

Nuclear Magnetic Resonance Spectrum (200 MHz, CDCl$_3$), δ ppm: 7.66 (1H, doublet, J=8.0 Hz); 7.45–7.32 (3H, multiplet); 7.25–7.16 (1H, multiplet); 7.08–7.01 (1H, multiplet); 6.98–6.97 (2H, multiplet); 5.49 (2H, singlet); 2.16 (3H, singlet).

EXAMPLE 152

N-[4-(5-Chlorobenzothiazol-2-ylmethoxy)phenyl] acetamide (Compound No. F4.59)

Melting Point: 230° to 232° C.

Nuclear Magnetic Resonance Spectrum (200 MHz, CDCl$_3$), δ ppm: 8.01 (1H, doublet, J=2.0 Hz); 7.81 (1H, doublet, J=8.8 Hz); 7.45–7.36 (3H, multiplet); 7.09–7.08 (1H, multiplet); 7.01–6.95 (2H, multiplet); 5.45 (2H, singlet); 2.16 (3H, singlet).

EXAMPLE 153

N-[4-(6-Chlorobenzothiazol-2-ylmethoxy)phenyl] acetamide (Compound No. F4.69)

Melting Point: 218° C.

Nuclear Magnetic Resonance Spectrum (200 MHz, CDCl$_3$), δ ppm: 7.93 (1H, doublet, J=8.6 Hz); 7.88 (1H, doublet, J=2.1 Hz); 7.49–7.41 (3H, multiplet); 7.01–6.97 (3H, multiplet); 5.44 (2H, singlet); 2.16 (3H, singlet).

EXAMPLE 154

N-[4-(7-Chlorobenzothiazol-2-ylmethoxy)phenyl] acetamide (Compound No. F4.79)

Melting Point: 172° to 175° C.

Nuclear Magnetic Resonance Spectrum (200 MHz, CDCl$_3$). δ ppm: 7.94–7.90 (1H, multiplet); 7.50–7.41 (4H, multiplet); 7.08–6.98 (3H, multiplet); 5.45 (2H, singlet); 2.16 (3H, singlet).

EXAMPLE 155

N-[4-(6-Bromobenzothiazol-2-ylmethoxy)phenyl] acetamide (Compound No. F4.103)

Melting Point: 218° to 221° C.

Nuclear Magnetic Resonance Spectrum (200 MHz, CDCl$_3$). δ ppm: 8.04–8.03 (1H, multiplet); 7.78 (1H, doublet, J=8.8 Hz); 7.62–7.61 (1H, multiplet); 7.45–7.41 (2H, multiplet); 7.01–6.97 (3H, multiplet); 5.43 (2H, singlet); 2.16 (3H, singlet).

EXAMPLE 156

N-[4-(4,5-Difluorobenzothiazol-2-ylmethoxy) phenyl]acetamide (Compound No. F7.34)

Melting Point: 178° to 180° C.

Nuclear Magnetic Resonance Spectrum (200 MHz, CDCl$_3$), δ ppm: 7.62–7.54 (1 H, multiplet); 7.46–7.41 (2H, multiplet); 7.35–7.22 (1H, multiplet); 7.08–6.97 (3H, multiplet); 5.48 (2H, singlet); 2.16 (3H, singlet).

EXAMPLE 157

N-[4-(4,6-Difluorobenzothiazol-2-ylmethoxy) phenyl]acetamide (Compound No. F7.39)

Melting Point: 198° to 200° C.

Nuclear Magnetic Resonance Spectrum (200 MHz, CDCl$_3$), δ ppm: 7.45–7.36 (3H, multiplet); 7.07–6.96 (4H, multiplet); 5.45 (2H, singlet); 2.16 (3H, singlet).

EXAMPLE 158

N-[4-(5,6-Difluorobenzothiazol-2-ylmethoxy) phenyl]acetamide (Compound No. F7.45)

Melting Point: 212° to 214° C.

Nuclear Magnetic Resonance Spectrum (200 MHz, CDCl$_3$), δ ppm: 7.85–7.76 (1H, multiplet); 7.71–7.62 (1H, multiplet); 7.45–7.41 (2H, multiplet); 7.01–6.96 (3H, multiplet); 5.43 (2H, singlet); 2.16 (3H, singlet).

EXAMPLE 159

N-[4-(5-Fluoro-6-methylbenzothiazol-2-ylmethoxy)phenyl]acetamide (Compound No. F7.92)

Melting Point: 231° to 234° C.

Nuclear Magnetic Resonance Spectrum (200 MHz, $CDCl_3$), δ ppm: 7.67 (1H, singlet); 7.63 (1H, doublet, J=4.7 Hz); 7.57 (1H, doublet, J=8.9 Hz); 7.42 (1H, doublet, J=5.1 Hz); 7.06 (1H, broad singlet); 6.98 (1H, doublet, J=9.1 Hz); 6.99 (1H, doublet, J=4.3 Hz); 5.43 (2H, singlet); 2.41 (3H, doublet, J=2.2 Hz); 2.16 (3H, singlet).

EXAMPLE 160

N-[4-6-Fluoro-5-methylbenzothiazol-2-ylmethoxy)phenyl]acetamide (Compound No. F7.99)

Melting Point: 231° to 234° C.

Nuclear Magnetic Resonance Spectrum (200 MHz, $CDCl_3$), δ ppm: 7.81 (1H, doublet, J=6.8 Hz); 7.53–7.34 (3H, multiplet); 7.01–6.96 (3H, multiplet); 5.42 (2H, singlet); 2.42 (3H, doublet, J=2.2 Hz); 2.16 (3H, singlet).

EXAMPLE 161

N-[4-5-Chloro-6-methylbenzothiazol-2-ylmethox)phenyl]acetamide (Compound No. F7.120)

Melting Point: 236° to 239° C.

Nuclear Magnetic Resonance Spectrum (200 MHz, $CDCl_3$), δ ppm: 8.01 (1H, singlet); 7.73 (1H, singlet); 7.42 (2H, doublet, J=8.9 Hz); 7.05–6.96 (3H, multiplet); 5.43 (2H, singlet); 2.50 (3H, singlet); 2.16 (3H, singlet).

EXAMPLE 162

N-[4-5-Chloro-6-methoxybenzothiazol-2-ylmethoxy)phenyl]acetamide (Compound No. F7.147)

Melting Point: 222° to 225° C.

Nuclear Magnetic Resonance Spectrum (200 MHz, $CDCl_3$), δ ppm: 8.01 (1H, singlet); 7.43–7.35 (2H, multiplet); 7.06–6.96 (3H, multiplet); 5.41 (2H, singlet); 3.96 (3H, singlet); 2.15 (3H, singlet).

EXAMPLE 163

N-[4-(5-Chloro-6-fluorobenzothiazol-2-ylmethoxy)phenyl]acetamide (Compound No. F7.169)

Melting Point: 227° to 229° C.

Nuclear Magnetic Resonance Spectrum (200 MHz, $CDCl_3$), δ ppm: 8.05 (1H, doublet, J=6.7 Hz); 7.66 (1H, doublet, J=8.3 Hz); 7.45–7.41 (2H, multiplet); 7.06–6.96 (3H, multiplet); 5.43 (2H, singlet); 2.16 (3H, singlet).

EXAMPLE 164

N-[4-(7-Chloro-6-fluorobenzothiazol-2-ylmethoxy)phenyl]acetamide (Compound No. F7.173)

Melting Point: 182° to 185° C.

Nuclear Magnetic Resonance Spectrum (200 MHz, $CDCl_3$), δ ppm: 7.87 (1H, multiplet); 7.46–7.42 (2H, multiplet); 7.35 (1H, doublet, J=9.1 Hz); 7.09–6.97 (3H, multiplet); 5.43 (2H, singlet); 2.16 (3H, singlet).

EXAMPLE 165

N-[2-Methyl-4-(5-methylbenzothiazol-2-ylmethoxy)phenyl]acetamide (Compound No. G1.6)

Melting Point: 206° to 208° C.

Nuclear Magnetic Resonance Spectrum (200 MHz, $CDCl_3$), δ ppm: 7.83 (1H, singlet); 7.76 (1H, doublet, J=8.7 Hz); 7.53 (1H, doublet, J=8.9 Hz); 7.27–7.21 (1H, multiplet); 6.91–6.84 (3H, multiplet); 5.44 (2H, singlet); 2.52 (3H, singlet); 2.24 (3H, singlet); 2.19 (3H, singlet).

EXAMPLE 166

N-[2-Methyl-4-(6-methylbenzothiazol-2-ylmethoxy)phenyl]acetamide (Compound No. G1.11)

Melting Point: 192° to 193° C.

Nuclear Magnetic Resonance Spectrum (200 MHz, $CDCl_3$), δ ppm: 7.90 (1H, doublet, J=8.4 Hz); 7.68 (1H, singlet); 7.53 (1H, doublet, J=9.1 Hz); 7.30 (1H, doublet, J=8.8 Hz); 6.89–6.81 (3H, multiplet); 5.43 (2H, singlet); 2.49 (3H, singlet); 2.23 (3H, singlet); 2.18 (3H, singlet).

EXAMPLE 167

N-[4-(5-Methoxybenzothiazol-2-ylmethoxy)-2-methylphenyl]acetamide (Compound No. G1.32)

Melting Point: 203° to 204° C.

Nuclear Magnetic Resonance Spectrum (200 MHz, $CDCl_3$), δ ppm: 9.23 (1H, singlet); 7.99 (1H, doublet, J=8.8 Hz); 7.58 (1H, doublet, J=2.4 Hz); 7.26 (1H, doublet, J=8.8 Hz); 7.12 (1H, doublet of doublets, J=8.8 & 2.5 Hz); 7.10 (1H, doublet, J=2.5 Hz); 6.92 (1H, broad doublet, J=8.8 Hz); 5.56 (1H, singlet); 3.87 (3H, singlet); 2.18 (3H, singlet); 2.03 (3H, singlet).

EXAMPLE 168

N-[4-(6-Methoxybenzothiazol-2-ylmethoxy)-2-methylphenyl]acetamide (Compound No. G1.37)

Melting Point: 159° to 162° C.

Nuclear Magnetic Resonance Spectrum (200 MHz, $CDCl_3$), δ ppm: 7.90 (1H, doublet, J=9.1 Hz); 7.55–7.51 (1H, multiplet); 7.34 (1H, doublet, J=2.6 Hz); 7.12–7.06 (1H, multiplet); 6.89–6.86 (3H, multiplet); 5.41 (2H, singlet); 3.88 (3H, singlet); 2.24 (3H, singlet); 2.19 (3H, singlet).

EXAMPLE 169

N-[4-(4-Fluorobenzothiazol-2-ylmethoxy)-2-methylphenyl]acetamide (Compound No. G1.50)

Melting Point: 174° to 176° C.

Nuclear Magnetic Resonance Spectrum (200 MHz, $CDCl_3$), δ ppm: 7.65–7.64 (2H, multiplet); 7.29–7.24 (2H, multiplet); 6.89–6.86 (3H, multiplet); 5.48 (2H, singlet); 2.25 (3H, singlet); 2.19 (3H, singlet).

EXAMPLE 170

N-[4-(6-Fluorobenzothiazol-2-ylmethoxy)-2-methylphenyl]acetamide (Compound No. G1.60)

Melting Point: 204° to 205° C.

Nuclear Magnetic Resonance Spectrum (200 MHz, DMSO-d6), δ ppm: 9.22 (1H, singlet); 8.09–8.02 (2H, multiplet); 7.42 (1H, triplet of doublets, J=9.2 & 2.8 Hz); 7.25 (1H, doublet, J=8.6 Hz); 6.99–6.86 (2H, multiplet); 5.56 (2H, singlet); 2.17 (3H, singlet); 2.02 (3H, singlet).

EXAMPLE 171

N-[4-(5-Chlorobenzothiazol-2-ylmethoxy)-2-methylphenyl]acetamide (Compound No. G1.72)

Melting Point: 213° to 214° C.

Nuclear Magnetic Resonance Spectrum (200 MHz, CDCl$_3$), δ ppm: 8.08 (1H, doublet, J=1.8 Hz); 7.81 (1H, doublet, J=8.6 Hz); 7.55 (1H, doublet, J=8.6 Hz); 7.38 (1H, doublet of doublets, J=8.7 & 2.1 Hz); 6.89 (1H, singlet); 6.87 (1H, doublet, J=7.7 Hz); 6.84 (1H, broad singlet); 5.44 (2H, singlet); 2.24 (3H, singlet); 2.19 (3H, singlet).

EXAMPLE 172

N-[2-Methyl-4-(4-trifluoromethylbenzothiazol-2-ylmethoxy)phenyl]acetamide (Compound No G1.87)

Melting Point: 185° to 186° C.

Nuclear Magnetic Resonance Spectrum (200 MHz, CDCl$_3$), δ ppm: 8.10 (1H, doublet, J=8.0 Hz); 7.80 (1H, doublet, J=8.0 Hz); 7.55 (1H, doublet, J=8.8 Hz); 7.48 (1H, triplet, J=8.0 Hz); 6.96–6.84 (3H, multiplet); 5.52 (2H, singlet); 2.24 (3H, singlet); 2.19 (3H, singlet).

EXAMPLE 173

N-[2-Methyl-4-(6-trifluoromethylbenzothiazol-2-ylmethoxy)phenyl]acetamide Compound No. G1.97)

Melting Point: 203° to 205° C.

Nuclear Magnetic Resonance Spectrum (200 MHz, CDCl$_3$), δ ppm: 8.20–8.09 (2H, multiplet); 7.77–7.72 (1H, multiplet); 7.55–7.52 (1H, multiplet); 6.90–6.80 (3H, multiplet); 5.48 (2H, singlet); 2.25 (3H, singlet), 2.19 (3H, multiplet singlet).

EXAMPLE 174

N-[4-(5,6-Difluorobenzothiazol-2-ylmethoxy)-2-methylphenyl]acetamide (Compound No. G2.42)

Melting Point: 219° to 222° C.

Nuclear Magnetic Resonance Spectrum (200 MHz, CDCl$_3$), δ ppm: 7.84–7.53 (3H, multiplet); 6.88–6.83 (3H, multiplet); 5.42 (2H, singlet); 2.24 (3H, singlet); 2.19 (3H, singlet).

EXAMPLE 175

N-[4-(5-Fluoro-6-methylbenzothiazol-2-ylmethoxy)-2-methylphenyl]acetamide (Compound No. G2.86)

Melting Point: 222° to 225° C.

Nuclear Magnetic Resonance Spectrum (200 MHz, CDCl$_3$), δ ppm: 7.67 (1H, singlet); 7.64 (1H, doublet, J=4.8 Hz); 7.54 (1H, doublet, J=8.8 Hz); 6.88 (2H, singlet); 6.85–6.82 (1H, multiplet); 5.42 (2H, singlet); 2.41 (2H, doublet, J=1.8 Hz); 2.24 (3H, singlet); 2.19 (3H, singlet).

EXAMPLE 176

N-[4-(6-Fluoro-7-methylbenzothiazol-2-ylmethoxy)-2-methylphenyl]acetamide (Compound No. G2.97)

Melting Point: 191° to 195° C.

Nuclear Magnetic Resonance Spectrum (200 MHz, CDCl$_3$), δ ppm: 7.80 (1H, multiplet); 7.54 (1H, doublet, J=8.5 Hz); 7.19 (1H, doublet, J=8.9 Hz); 6.89 (2H, singlet); 6.86–6.81 (1H, multiplet); 5.42 (2H, singlet); 2.47 (3H, doublet, J=1.6 Hz); 2.24 (3H, singlet); 2.19 (3H, singlet).

EXAMPLE 177

N-[4-(5-Chloro-6-methylbenzothiazol-2-ylmethoxy)-2-methylphenyl]acetamide (Compound No. G2.115)

Melting Point: 249° to 251° C.

Nuclear Magnetic Resonance Spectrum (200 MHz, CDCl$_3$), δ ppm: 8.01 (1H, singlet); 7.73 (1H, singlet); 7.54 (1H, doublet, J=9.1 Hz); 6.88–6.81 (3H, multiplet); 5.42 (2H, singlet); 2.50 (3H, singlet); 2.24 (3H, singlet); 2.19 (3H, singlet).

EXAMPLE 178

N-[4-(5-Chloro-6-methoxybenzothiazol-2-ylmethoxy)-2-methylphenyl]acetamide (Compound No. G2.137)

Melting Point: 228° to 230° C.

Nuclear Magnetic Resonance Spectrum (200 MHz, CDCl$_3$), δ ppm: 8.02 (1H, singlet); 7.54 (1H, doublet, J=8.9 Hz); 7.36 (1H, singlet); 6.88 (2H, singlet); 6.85–6.81 (1H, multiplet); 5.40 (2H, singlet); 3.97 (3H, singlet); 2.24 (3H, singlet); 2.19 (3H, singlet).

EXAMPLE 179

N-[4-(5-Chloro-6-fluorobenzothiazol-2-ylmethoxy)-2-methylphenyl]acetamide (Compound No. G2.148)

Melting Point: 242° to 245° C.

Nuclear Magnetic Resonance Spectrum (200 MHz, CDCl$_3$), δ ppm: 8.05 (1H, doublet, J=6.6 Hz); 7.66 (1H, doublet, J=8.1 Hz); 7.55 (1H, doublet, J=8.6 Hz); 6.88 (2H, singlet); 6.84–6.83 (1H, multiplet); 5.42 (2H, singlet); 2.25 (3H, singlet); 2.19 (3H, singlet).

EXAMPLE 180

N-[4-(7-Chloro-6-fluorobenzothiazol-2-ylmethoxy)-2-methylphenyl]acetamide (Compound No. G2.166)

Melting Point: 218° to 220° C.

Nuclear Magnetic Resonance Spectrum (200 MHz, CDCl$_3$), δ ppm: 7.87 (1H, multiplet); 7.59–7.54 (1H, multiplet); 7.35 (1H, doublet, J=9.1 Hz); 6.89 (2H, singlet); 6.88–6.82 (1H, multiplet); 5.42 (2H, singlet); 2.25 (3H, singlet); 2.19 (3H, singlet).

EXAMPLE 181

N-[2-Ethyl-4-(5-methylbenzothiazol-2-ylmethoxy)phenyl]acetamide (Compound No. G5.3)

Melting Point: 218° to 221° C.

Nuclear Magnetic Resonance Spectrum (200 MHz, CDCl$_3$), δ ppm: 7.83–7.75 (3H, multiplet); 7.53–7.50 (1H, multiplet); 6.92–6.90 (3H, multiplet); 5.45 (2H, singlet); 2.60–2.52 (2H, multiplet); 2.59 (3H, singlet); 2.19 (3H, singlet); 1.22 (3H, triplet, J=7.2 Hz).

EXAMPLE 182

N-[2-Ethyl-4-(6-methylbenzothiazol-2-ylmethoxy)phenyl]acetamide (Compound No. G5.6)

Melting Point: 198° to 200° C.

Nuclear Magnetic Resonance Spectrum (200 MHz, CDCl$_3$), δ ppm: 7.90 (1H, doublet, J=9.2 Hz); 7.69 (1H, singlet); 7.52 (1H, doublet, J=8.6 Hz); 7.33–7.28 (1H, multiplet); 6.93–6.82 (3H, multiplet); 5.44 (2H, singlet); 2.57 (2H, quartet, J=7.8 Hz); 2.50 (3H, singlet); 1.22 (3H, triplet, J=7.6 Hz).

EXAMPLE 183

N-[2-Ethyl-4-(5-methoxybenzothiazol-2-ylmethoxy)phenyl]acetamide (Compound No. G5.17)

Melting Point: 169° to 172° C.

Nuclear Magnetic Resonance Spectrum (200 MHz, CDCl$_3$), δ ppm: 7.74 (1H, doublet, J=8.6 Hz); 7.50–7.51 (2H, multiplet); 7.05 (1H, doublet of doublets, J=4.3 & 2.6 Hz); 6.93–6.82 (3H, multiplet); 5.44 (2H, singlet); 3.90 (3H, singlet); 2.58 (2H, quartet, J=7.4 Hz); 2.19 (3H, singlet); 1.22 (3H, triplet, J=7.6 Hz).

EXAMPLE 184

N-[2-Ethyl-4-(6-fluorobenzothiazol-2-ylmethoxy)phenyl]acetamide (Compound No. G5.38)

Melting Point: 198° to 200° C.

Nuclear Magnetic Resonance Spectrum (200 MHz, CDCl$_3$), δ ppm: 8.00–7.93 (1H, multiplet); 7.60–7.51 (2H, multiplet); 7.26–7.23 (1H, multiplet); 6.93–6.81 (3H, multiplet); 5.44 (2H, singlet); 2.58 (2H, quartet, J=7.6 Hz); 2.19 (3H, singlet); 1.22 (3H, triplet, J=7.6 Hz).

EXAMPLE 185

N-[4-(5-Chlorobenzothiazol-2-ylmethoxy)-2-ethylphenyl]acetamide (Compound No. G5.45)

Melting Point: 210° to 213° C.

Nuclear Magnetic Resonance Spectrum (200 MHz, CDCl$_3$+CD$_3$OD), δ ppm: 8.00 (1H, doublet, J=2.0 Hz); 7.85 (1H, doublet, J=8.6 Hz); 7.39 (1H, doublet of doublets, J=2.0 & 8.6 Hz); 7.30–6.60 (3H, multiplet); 5.46 (2H, singlet); 2.59 (2H, quartet, J=7.6 Hz); 2.16 (3H, singlet); 1.21 (3H, triplet, J=7.6 Hz).

EXAMPLE 186

N-[4-(5,6-Difluorobenzothiazol-2-ylmethoxy)-2-ethylphenyl]acetamide (Compound No. G6.31)

Melting Point: 213° to 214° C.

Nuclear Magnetic Resonance Spectrum (200 MHz, CDCl$_3$), δ ppm: 8.24 (1H, doublet, J=9.8 Hz); 7.86–7.63 (2H, multiplet); 7.45–7.39 (1H, multiplet); 7.0 (1H, doublet, J=2.4 Hz); 6.98–6.92 (1H, multiplet); 5.42 (2H, singlet); 2.22 (3H, singlet).

EXAMPLE 187

N-[2-Chloro-4-(5-methylbenzothiazol-2-ylmethoxy)phenyl]acetamide (Compound No. H4.3)

Melting Point: 176° to 179° C.

Nuclear Magnetic Resonance Spectrum (200 MHz, CDCl$_3$), δ ppm: 8.22 (1H, doublet, J=8.9 Hz); 7.83 (1H, singlet); 7.81 (1H, doublet, J=7.5 Hz); 7.35–7.26 (2H, multiplet); 7.09 (1H, doublet, J=2.7 Hz); 6.99–6.95 (1H, multiplet); 5.44 (2H, singlet); 2.52 (3H, singlet); 2.22 (3H, singlet).

EXAMPLE 188

N-[2-Chloro-4-(6-methylbenzothiazol-2-ylmethoxy)phenyl]acetamide (Compound No. H4.8)

Melting Point: 151° to 153° C.

Nuclear Magnetic Resonance Spectrum (200 MHz, CDCl$_3$), δ ppm: 8.22 (1H, doublet, J=8.8 Hz); 7.91 (1H, doublet, J=8.4 Hz); 7.68 (1H, singlet); 7.41 (1H, singlet); 7.30 (1H, doublet of doublets, J=8.2 & 3.0 Hz); 7.09 (1H, doublet, J=3.0 Hz); 6.96 (1H, doublet of doublets, J=9.2 & 3.2 Hz); 5.43 (2H, singlet); 2.50 (3H, singlet); 2.22 (3H, singlet).

EXAMPLE 189

N-[2-Chloro-4-(5-methoxybenzothiazol-2-ylmethoxy)phenyl]acetamide (Compound No. H4.19)

Melting Point: 160° to 163° C.

Nuclear Magnetic Resonance Spectrum (200 MHz, CDCl$_3$), δ ppm: 8.23 (1H, doublet, J=9.0 Hz); 7.74 (1H, doublet, J=8.8 Hz); 7.52 (1H, doublet, J=2.4 Hz); 7.41 (1H, singlet); 7.10–6.94 (3H, multiplet); 5.43 (2H, singlet); 3.90 (3H, singlet); 2.22 (3H, singlet).

EXAMPLE 190

N-[2-Chloro-4-(6-fluorobenzothiazol-2-ylmethoxy)phenyl]acetamide (Compound No. H4.38)

Melting Point: 174° to 176° C.

Nuclear Magnetic Resonance Spectrum (200 MHz, CDCl$_3$), δ ppm: 8.24 (1H, doublet, J=9.2 Hz); 8.03 –7.94 (1H, multiplet); 7.58 (1H, doublet of doublets, J=8.0 & 2.6 Hz); 7.41 (1H, singlet); 7.30–7.19 (1H, multiplet); 7.09 (1H, doublet, J=2.8 Hz); 6.96 (1H, doublet of doublets, J=9.2 & 2.6 Hz); 5.42 (2H, singlet); 2.22 (3H, singlet).

EXAMPLE 191

N-[2-Chloro-4-(5-chlorobenzothiazol-2-ylmethoxy)phenyl]acetamide (Compound No. H4.43)

Melting Point: 192° to 193° C.

Nuclear Magnetic Resonance Spectrum (200 MHz, CDCl$_3$), δ ppm: 8.24 (1H, doublet, J=8.9 Hz); 8.20 (1H, doublet, J=2.0 Hz); 7.82 (1H, doublet, J=8.6 Hz); 7.42–7.37 (2H, multiplet); 7.09 (1H, doublet, J=2.9 Hz); 6.99–6.93 (1H, multiplet); 5.44 (2H, singlet); 2.22 (3H, singlet).

EXAMPLE 192

N-[2-Chloro-4-(5,6-difluorobenzothiazol-2-ylmethoxy)phenyl]acetamide (Compound No. H4.91)

Melting Point: 170° to 172° C.

Nuclear Magnetic Resonance Spectrum (200 MHz, CDCl$_3$), δ ppm: 8.24 (1H, doublet, J=9.8 Hz); 7.86–7.63 (2H, multiplet); 7.45–7.39 (1H, multiplet); 7.08 (1H, doublet, J=2.4 Hz); 6.98–6.92 (1H, multiplet); 5.42 (2H, singlet); 2.22 (3H, singlet).

EXAMPLE 193

N-[2,3-Dimethyl-4-(5-methylbenzothiazol-2-ylmethoxy)phenyl]acetamide (Compound No. H7.4)

Melting Point: 260° to 261° C.

Nuclear Magnetic Resonance Spectrum (200 MHz, CDCl$_3$), δ ppm: 7.83–7.75 (3H, multiplet); 7.29–7.26 (2H, multiplet); 6.83–6.79 (2H, multiplet); 5.44 (2H, singlet); 2.52 (3H, singlet); 2.31 (3H, singlet); 2.19 (3H, singlet).

EXAMPLE 194

N-[2,3-Dimethyl-4-(6-methylbenzothiazol-2-ylmethoxy)phenyl]acetamide (Compound No. H7.9)

Melting Point: 224° to 226° C.

Nuclear Magnetic Resonance Spectrum (200 MHz, DMSO-d6), δ ppm: 9.30 (1H, singlet); 7.93 (1H, singlet);

7.91 (1H, doublet, J=8.4 Hz); 7.37 (1H, doublet of doublets, J=7.8 & 1.4 Hz); 7.05 (1H, doublet, J=8.8 Hz); 6.93 (1H, doublet, J=9.0 Hz); 5.54 (2H, singlet); 2.46 (3H, singlet); 2.24 (3H, singlet); 2.09 (3H, singlet); 2.02 (3H, singlet).

EXAMPLE 195

N-[4-(6-Methoxybenzothiazol-2-ylmethoxy)-2,3-dimethylphenyl]acetamide (Compound No. H7.21)

Melting Point: 229° to 232° C.

Nuclear Magnetic Resonance Spectrum (200 MHz, $CDCl_3$), δ ppm: 7.90 (1H, doublet, J=8.9 Hz); 7.35 (1H, doublet, J=2.2 Hz); 7.23–7.08 (1H, multiplet); 6.84–6.79 (3H, multiplet); 5.41 (2H, singlet); 3.88 (3H, singlet); 2.30 (3H, singlet); 2.19 (6H, singlet).

EXAMPLE 196

N-[4-(6-Fluorobenzothiazol-2-ylmethoxy)-2,3-dimethylphenyl]acetamide (Compound No. H7.41)

Melting Point: 245° to 247° C.

Nuclear Magnetic Resonance Spectrum (200 MHz, DMSO-d6), δ ppm: 9.30 (1H, singlet); 8.09–8.02 (2H, multiplet); 7.42 (1H, triplet of doublets, J=8.6 & 2.6 Hz); 7.05 (2H, quartet, J=9.0 Hz); 6.94 (2H, doublet, J=8.6 Hz); 5.56 (2H, singlet); 2.25 (3H, singlet); 2.09 (3H, singlet); 2.02 (3H, singlet).

EXAMPLE 197

N-[4-(5-Chlorobenzothiazol-2-ylmethoxy)-2,3-dimethylphenyl]acetamide (Compound No. H7.49)

Melting Point: 246° to 250° C.

Nuclear Magnetic Resonance Spectrum (200 MHz, DMSO-d6), δ ppm: 9.29–9.27 (1H, broad singlet); 8.27–8.06 (2H, multiplet); 7.49 (1H, doublet of doublets, J=2.2 & 8.5 Hz); 7.04 (1H, doublet, J=8.4 Hz); 6.91 (1H, doublet, J=8.4 Hz); 5.55 (2H, singlet); 2.25 (3H, singlet); 2.10 (3H, singlet); 2.02 (3H, singlet).

EXAMPLE 198

N-[4-(5,6-Difluorobenzothiazol-2-ylmethoxy)-2,3-dimethylphenyl]acetamide (Compound No. H7.106)

Melting Point: 248° to 249° C.

Nuclear Magnetic Resonance Spectrum (200 MHz, $CDCl_3$), δ ppm: 7.80 (1H, doublet of doublets, J=10.5 & 7.3 Hz); 7.67 (1H, doublet of doublets, J=9.5 & 7.7 Hz); 7.29–7.25 (1H, multiplet); 6.87 (1H, broad singlet); 6.80 (1H, doublet, J=8.8 Hz); 5.42 (2H, singlet); 2.30 (3H, singlet); 2.20 (6H, singlet).

EXAMPLE 199

N-[4-(6-Methoxybenzothiazol-2-ylmethylthio)phenyl]acetamide (Compound No. F3.21)

Melting Point: 124° to 125° C.

Nuclear Magnetic Resonance Spectrum (200 MHz, $CDCl_3$), δ ppm: 7.80 (1H, doublet, J=8.8 Hz); 7.45–7.10 (6H, multiplet); 7.04 (1H, doublet of doublets, J=8.9 & 2.7 Hz); 4.42 (2H, singlet); 3.86 (3H, singlet); 2.15 (3H, singlet).

EXAMPLE 200

N-[4-(6-Ethoxybenzothiazol-2-ylmethoxy)phenyl]acetamide (Compound No. F3.56)

Melting Point: 139° to 141° C.

Nuclear Magnetic Resonance Spectrum (200 MHz, $CDCl_3$), δ ppm: 7.89 (1H, doublet, J=9.1 Hz); 7.43–7.31 (3H, multiplet); 7.11–6.97 (4H, multiplet); 5.41 (2H, singlet); 4.09 (2H, quartet, J=7.1 Hz); 2.13 (3H, singlet); 1.45 (3H, triplet, J=7.0 Hz).

EXAMPLE 201

N-[4-(5-Fluorobenzothiazol-2-ylmethoxy)phenyl]acetamide (Compound No. F4.11)

Melting Point: 201° C.

Nuclear Magnetic Resonance Spectrum (200 MHz, $CDCl_3$), δ ppm: 7.86–7.79 (1H, multiplet); 7.70 (1H, doublet of doublets, J=9.3 & 2.5 Hz); 7.43 (2H, doublet, J=9.0 Hz); 7.30–7.10 (2H, multiplet); 7.05 (1H, broad singlet); 7.00 (2H, doublet, J=8.9 Hz); 5.45 (2H, singlet); 2.16 (3H, singlet).

EXAMPLE 202

N-[4-(5-Fluorobenzothiazol-2-ylmethylthio)phenyl]acetamide (Compound No. F4.16)

Melting Point: 108° to 109° C.

Nuclear Magnetic Resonance Spectrum (200 MHz, $CDCl_3$), δ ppm: 7.74 (1H, doublet of doublets, J=8.8 & 5.1 Hz); 7.61 (1H, doublet of doublets, J=9.5 & 2.5 Hz); 7.45–7.33 (4H, multiplet); 7.13 (1H, triplet of doublets, J=8.8 & 2.5 Hz); 4.44 (2H, singlet); 2.14 (3H, singlet).

EXAMPLE 203

N-[4-(5-Trifluoromethylbenzothiazol-2-ylmethoxy)phenyl]acetamide (Compound No. F5.9)

Melting Point: 208° to 210° C.

Nuclear Magnetic Resonance Spectrum (200 MHz, $CDCl_3$) δ ppm: 8.29 (1H, singlet); 8.02 (1H, doublet, J=8.4 Hz); 7.67–7.66 (1H, multiplet); 7.46–7.41 (2H, multiplet); 7.09–7.02 (1H, broad multiplet); 7.01–6.97 (2H, multiplet); 5.48 (2H, singlet); 2.16 (3H, singlet).

EXAMPLE 204

N-[4-(4-Chloro-5-methoxybenzothiazol-2-ylmethoxy)phenyl]acetamide (Compound No. F7.136)

Melting Point: 193° to 195° C.

Nuclear Magnetic Resonance Spectrum (200 MHz, $CDCl_3$) δ ppm: 7.73 (1H, doublet, J=8.7 Hz); 7.43 (2H, doublet, J=9.2 Hz); 7.15–6.97 (4H, multiplet); 5.50 (2H, singlet); 4.01 (3H, singlet); 2.16 (3H, singlet).

EXAMPLE 205

N-[4-(5-Fluorobenzothiazol-2-ylmethoxy)-2-methylphenyl]acetamide (Compound No. G1.55)

Melting Point: 205° to 207° C.

Nuclear Magnetic Resonance Spectrum (200 MHz, $CDCl_3$) δ ppm: 7.86–7.79 (1H, multiplet); 7.74–7.68 (1H, multiplet); 7.69–7.53 (1H, multiplet); 7.19–7.18 (1H, multiplet); 6.89–6.85 (3H, multiplet); 5.44 (2H, singlet); 2.25 (3H, singlet); 2.19 (3H, singlet).

EXAMPLE 206

N-[2-Methyl-4-(5-trifluoromethylbenzothiazol-2-ylmethoxy)phenyl]acetamide (Compound No. G1.92)

Melting Point: 209° to 210° C.

Nuclear Magnetic Resonance Spectrum (200 MHz, CDCl$_3$) δ ppm: 8.29 (1H, singlet); 8.02 (1H, doublet, J=8.7 Hz); 7.67–7.53 (2H, multiplet); 6.89 (1H, singlet); 6.85–6.82 (2H, multiplet); 5.48 (2H, singlet); 2.25 (3H, singlet); 2.19 (3H, singlet).

EXAMPLE 207

N-[2-Ethyl-4-(6-methoxybenzothiazol-2-ylmethoxy)phenyl]acetamide (Compound No. G5.20)

Melting Point: 157° to 160° C.

Nuclear Magnetic Resonance Spectrum (200 MHz, CDCl$_3$) δ ppm: 7.90 (1H, doublet, J=8.9 Hz); 7.51 (1H, doublet, J=8.6 Hz); 7.34 (1H, doublet, J=2.3 Hz); 7.09 (1H, doublet of doublets, J=9.0 & 2.6 Hz); 6.91–5.82 (3H, multiplet); 5.41 (2H, singlet); 3.88 (3H, singlet); 2.57 (2H, quartet, J=7.4 Hz); 2.18 (3H, singlet); 1.21 (3H, triplet, J=7.4 Hz).

EXAMPLE 208

N-[2-Ethyl-4-(5-fluorobenzothiazol-2-ylmethoxy)phenyl]acetamide (Compound No. G5.33)

Melting Point: 197° to 198° C.

Nuclear Magnetic Resonance Spectrum (200 MHz, CDCl$_3$) δ ppm: 7.86–7.79 (1H, multiplet); 7.74–7.68 (1H, multiplet); 7.53 (1H, doublet, J=8.4 Hz); 7.26–7.18 (1H, multiplet); 6.92–6.84 (3H, multiplet); 5.45 (2H, singlet); 2.58 (2H, quartet, J=7.2 Hz); 2.19 (3H, singlet); 1.23 (3H, triplet, J=7.5 Hz).

EXAMPLE 209

N-[2-Ethyl-4-(5-trifluoromethylbenzothiazol-2-ylmethoxy)phenyl]acetamide (Compound No. G5.52)

Melting Point: 210° to 212° C.

Nuclear Magnetic Resonance Spectrum (200 MHz, CDCl$_3$) δ ppm: 8.29 (1H, singlet); 8.02 (1H, doublet, J=8.4 Hz); 7.64 (1H, doublet of doublets, J=9.0 & 1.8 Hz); 7.54 (1H, doublet, J=8.8 Hz); 6.93 (1H, singlet); 6.88 (4H, doublet of doublets, J=11.8 & 3.1 Hz); 5.49 (2H, singlet); 2.59 (2H, quartet, J=7.6 Hz); 2.19 (3H, singlet); 1.23 (3H, triplet, J=7.5 Hz).

EXAMPLE 210

N-[4-(5-Fluorobenzothiazol-2-ylmethoxy)-2-methoxyphenyl]acetamide (Compound No. G8.31)

Melting Point: 170° to 172° C.

Nuclear Magnetic Resonance Spectrum (200 MHz, CDCl$_3$) δ ppm: 8.24 (1H, doublet, J=8.8 Hz); 7.82 (1H, doublet of doublets, J=8.8 & 5.1 Hz); 7.71 (1H, doublet of doublets, J=9.3 & 2.4 Hz); 7.55 (1H, broad singlet); 7.19 (1H, triplet of doublets, J=8.8 & 2.4 Hz); 6.63–6.55 (2H, multiplet); 5.45 (2H, singlet); 3.87 (3H, singlet); 2.18 (3H, singlet).

EXAMPLE 211

N-[4-(6-Fluorobenzothiazol-2-ylmethoxy)-2-methoxyphenyl]acetamide (Compound No. G8.38)

Melting Point: 155° to 159° C.

Nuclear Magnetic Resonance Spectrum (200 MHz, CDCl$_3$) δ ppm: 8.24 (1H, doublet, J=8.8 Hz); 7.97 (1H, doublet of doublets, J=8.8 & 4.8 Hz); 7.57 (1H, doublet of doublets, J=8.1 & 2.5 Hz); 7.24 (1H, triplet of doublets, J=8.8 & 2.5 Hz); 6.63–6.55 (2H, multiplet); 5.54 (2H, singlet); 3.87 (3H, singlet); 2.17 (3H, singlet).

EXAMPLE 212

N-[2-Ethoxy-4-(5-fluorobenzothiazol-2-ylmethoxy)phenyl]acetamide (Compound No. G10.51)

Melting Point: 177.5° to 179° C.

Nuclear Magnetic Resonance Spectrum (200 MHz, CDCl$_3$) δ ppm: 8.25 (1H, doublet, J=8.7 Hz); 7.82 (1H, doublet of doublets, J=8.8 & 5.0 Hz); 7.71 (1H, doublet of doublets, J=9.4 & 2.5 Hz); 7.57 (1H, broad singlet); 7.18 (1H, triplet of doublets, J=8.8 & 2.5 Hz); 6.62–6.54 (2H, multiplet); 5.44 (2H, singlet); 4.10 (2H, quartet, J=7.0 Hz); 2.18 (3H, singlet); 1.46 (3H, triplet, J=7.0 HZ).

EXAMPLE 213

N-[2-Difluoromethyl-4-(5-fluorobenzothiazol-2-ylmethoxy)phenyl]acetamide (Compound No. G10.57)

Melting Point: 180° to 185° C.

Nuclear Magnetic Resonance Spectrum (200 MHz, CDCl$_3$) δ ppm: 7.87–7.69 (3H, multiplet); 7.31–7.12 (4H, multiplet); 6.66 (1H, triplet, J=54.7 Hz); 5.48 (2H, singlet); 2.20 (3H, singlet).

EXAMPLE 214

N-[2-Difluoromethoxy-4-(5-fluorobenzothiazol-2-ylmethoxy)phenyl]acetamide (Compound No. G10.61)

Melting Point: 137° to 138° C.

Nuclear Magnetic Resonance Spectrum (200 MHz, CDCl$_3$) δ ppm: 8.24 (1H, doublet, J=9.8 Hz); 7.83 (1H, doublet of doublets, J=8.8 & 4.8 Hz); 7.71 (1H, doublet of doublets, J=9.3 & 2.4 Hz); 7.34–7.30 (1H, multiplet); 7.20 (1H, triplet of doublets, J=8.8 & 2.5 Hz); 6.91–6.86 (2H, multiplet); 6.52(1H, triplet, J=73.1 Hz); 5.45(2H, singlet); 2.20(3H, singlet).

EXAMPLE 215

N-[4-(5-Fluorobenzothiazol-2-ylmethoxy)-2-(2,2,2-trifluoroethoxy)phenyl]acetamide (Compound No. G10.63)

Melting Point: 167° to 168° C.

Nuclear Magnetic Resonance Spectrum (200 MHz, CDCl$_3$) δ ppm: 8.25 (1H, doublet, J=9.0 Hz); 7.83(1H, doublet of doublets, J=8.8 & 5.1 Hz); 7.71 (1H, doublet of doublets, J=9.3 & 2.4 Hz); 7.42 (1H, broad singlet); 7.20 (1H, triplet of doublets, J=8.8 & 2.5 Hz); 6.70 (1H, doublet of doublets, J=8.9 & 2.7 Hz); 6.63 (1H, doublet, J=2.6 Hz); 5.45 (2H, singlet); 4.39 (2H, quartet, J=8.0 Hz); 2.19 (3H, singlet).

EXAMPLE 216

N-[2-Chloro-4-(6-methoxybenzothiazol-2-ylmethoxy)phenyl]acetamide (Compound No. H4.22)

Melting Point: 148° to 150° C.

Nuclear Magnetic Resonance Spectrum (200 MHz, CDCl$_3$) δ ppm: 8.21 (1H, doublet, J=9.0 Hz); 7.91 (1H, doublet, J=8.8 Hz); 7.42 (1H, singlet); 7.34 (1H, doublet, J=2.5 Hz); 7.13–7.07 (2H, multiplet); 6.96 (1H, doublet of doublets, J=9.0 & 2.9 Hz); 5.40 (2H, singlet); 3.88 (3H, singlet); 2.22 (3H, singlet).

EXAMPLE 217

N-[2-Chloro-4-(5-fluorobenzothiazol-2-ylmethoxy) phenyl]acetamide (Compound No. H4.35)

Melting Point: 160° to 167° C.

Nuclear Magnetic Resonance Spectrum (200 MHz, $CDCl_3$) δ ppm: 8.23 (1H, doublet, J=8.9 Hz); 7.83 (1H, doublet of doublets, J=8.8 & 5.1 Hz); 7.71 (1H, doublet of doublets, J=9.4 & 2.5 Hz); 7.42 (1H, broad singlet); 7.19 (1H, triplet of doublets, J=8.8 & 2.5 Hz); 7.09 (1H, doublet, J=2.9 Hz); 6.96 (1H, doublet of doublets, J=9.1 & 2.9 Hz); 5.44 (2H, singlet); 2.22 (3H, singlet).

EXAMPLE 218

N-[2-Chloro-4-(5-trifluoromethylbenzothiazol-2-ylmethoxy)phenyl]acetamide (Compound No. H4.50)

Melting Point: 183° to 184° C.

Nuclear Magnetic Resonance Spectrum (200 MHz, $CDCl_3$) δ ppm: 8.29 (1H, singlet); 8.25 (1H, doublet, J=9.0 Hz); 8.03 (1H, doublet, J=8.4 Hz); 7.66 (1H, doublet of doublets, J=8.4 & 1.6 Hz); 7.42 (1H, singlet); 7.10 (1H, doublet, J=2.9 Hz); 6.97 (1H, doublet of doublets, J=9.0 & 2.9 Hz); 5.48 (2H, singlet); 2.22 (3H, singlet).

EXAMPLE 219

N-[4-(5-Methoxybenzothiazol-2-ylmethoxy)-2,3-dimethylphenyl]acetamide (Compound No. H7.18)

Melting Point: 224° to 225° C.

Nuclear Magnetic Resonance Spectrum (200 MHz, $CDCl_3$) δ ppm: 9.30 (1H, singlet); 8.01 (1H, doublet, J=8.9 Hz); 7.57 (1H, doublet, J=2.4 Hz); 7.15–6.92 (3H, multiplet); 5.55 (2H, singlet); 3.87 (3H, singlet); 2.25 (3H, singlet); 2.10 (3H, singlet); 2.03 (3H, singlet).

EXAMPLE 220

N-[4-(5-Fluorobenzothiazol-2-ylmethoxy)-2,3-dimethylphenyl]acetamide (Compound No. H7.36)

Melting Point: 245° to 246° C.

Nuclear Magnetic Resonance Spectrum (200 MHz, $CDCl_3$) δ ppm: 7.84–7.79 (1H, multiplet); 7.73–7.69 (1H, multiplet); 7.28–7.18 (2H, multiplet); 6.83–6.78 (2H, multiplet); 5.44 (2H, singlet); 2.32 (3H, singlet); 2.20 (6H, singlet).

EXAMPLE 221

N-[2,3-Dimethyl-4-(5-trifluoromethylbenzothiazol-2-ylmethoxy)phenyl]acetamide (Compound No. H7.63)

Melting Point: 262° to 263° C.

Nuclear Magnetic Resonance Spectrum (200 MHz, $CDCl_3$) δ ppm: 8.29 (1H, singlet); 8.03 (1H, doublet, J=8.7Hz); 7.65 (1H, doublet, J=8.3 Hz); 6.90 (1H, singlet); 6.81 (2H, doublet, J=8.5 Hz); 5.47 (2H, singlet); 2.32 (3H, singlet); 2.20 (6H, singlet).

EXAMPLE 222

N-[4-(Benzothiazol-2-ylmethoxy)-2-methylphenyl]-N-methylacetamide (Compound No. D1.1)

Melting Point: 108° to 109° C.

Nuclear Magnetic Resonance Spectrum (200 MHz, $CDCl_3$), δ ppm: 8.05 (1H, doublet of doublets, J=7.2 & 1.3 Hz); 7.92 (1H, doublet of doublets, J=7.2 & 1.3 Hz); 7.52 (1H, triplet of doublets, J=7.2 & 1.3 Hz); 7.42 (1H, triplet of doublets, J=7.2 & 1.3 Hz); 7.06 (1H, doublet, J=8.4 Hz); 6.96 (1H, doublet, J=2.5 Hz); 6.89 (1H, doublet of doublets, J=8.4 & 2.5 Hz); 5.49 (2H, singlet); 3.15 (3H, singlet); 2.21 (3H, singlet); 1.76 (3H, singlet).

EXAMPLE 223

N-[4-(Benzothiazol-2-ylmethoxy)-2-methylphenyl]-N-ethylacetamide (Compound No. D1.5)

Amorphous

Nuclear Magnetic Resonance Spectrum (200 Mz, $CDCl_3$), δ ppm: 8.04 (1H, doublet of doublets, J=7.3 & 1.3 Hz); 7.92 (1H, doublet of doublets, J=7.3 & 1.3 Hz); 7.52(1H, triplet of doublets, J=7.3 & 1.3 Hz); 7.42 (1H, triplet of doublets, J=7.3 & 1.3 Hz); 7.02 (1H, doublet, J=8.6 Hz); 6.98 (1H, doublet, J=2.4 Hz); 6.89 (1H, doublet of doublets, J=8.6 & 2.4 Hz); 5.49 (2H, singlet); 4.04 (1H, sextet, J=7.3 Hz); 3.22 (1H, sextet, J=7.3 Hz); 2.21 (3H, singlet); 1.74 (3H, singlet); 1.10 (3H, triplet, J=7.0 Hz).

EXAMPLE 224

N-Allyl-N-[4-(benzothiazol-2-ylmethoxy)-2-methylphenyl]acetamide (Compound No. D1.13)

Oil

Nuclear Magnetic Resonance Spectrum (200Mz, $CDCl_3$), δ ppm: 8.05 (1H, doublet of doublets, J=7.5 & 1.3 Hz); 7.92 (1H, doublet of doublets, J=7.5 & 1.3 Hz); 7.52 (1H, triplet of doublets, J=7.5 & 1.3 Hz); 7.42 (1H, triplet of doublets, J=7.5 & 1.3 Hz); 7.00 (1H, doublet, J=8.6 Hz); 6.96 (1H, doublet, J=3.1 Hz); 6.86 (1H, doublet of doublets, J=8.6 & 3.1 Hz); 5.97–5.77 (1H, multiplet); 5.48 (2H, singlet); 5.11–4.99 (2H, multiplet); 4.68–4.57 (1H, multiplet); 3.73 (1H, doublet of doublets, J=14.4 & 7.2 Hz); 2.21 (3H, singlet); 1.76 (3H, singlet).

EXAMPLE 225

N-[4-(Benzothiazol-2-ylmethoxy)-2-methylphenyl]-N-methoxymethylacetamide (Compound No. D 1.50)

Oil

Nuclear Magnetic Resonance Spectrum (200 MHz, $CDCl_3$), δ ppm: 8.06–8.03 (1H, multiplet); 7.94–7.90 (1H, multiplet); 7.56–7.42 (2H, multiplet); 7.08 (1H, doublet, J=8.4 Hz); 6.97 (1H, doublet, J=3.0 Hz); 6.90 (1H, doublet of doublets, J=8.4 & 3.0 Hz); 5.49 (2H, singlet); 4.94 (2H, AB quartet, J=9.8Hz, Δν=158.1); 3.43 (3H, singlet); 2.22 (3H, singlet); 1.80 (3H, singlet).

EXAMPLE 226

N-[4-(Benzothiazol-2-ylmethoxy)-2-methylphenyl]-N-(2-ethoxyethyl)acetamide (Compound No. D1.109)

Oil

Nuclear Magnetic Resonance Spectrum (200 Mz, $CDCl_3$), δ ppm: 8.05 (1H, doublet of doublets, J=7.2 & 1.3 Hz); 7.92 (1H, doublet of doublets, J=7.2 & 1.3 Hz); 7.52 (1H, triplet of doublets, J=7.2 & 1.3 Hz); 7.42 (1H, triplet of doublets, J=7.2 & 1.3 Hz); 7.11 doublet, J=8.4 Hz); 6.95 (1H, doublet, J=2.9 Hz); 6.88 (1H, doublet of doublets, J=8.4 & 2.9 Hz); 5.48 (2H, singlet); 4.26–4.07 (1H, multiplet); 3.61–3.26 (5H, multiplet); 2.21 (3H, singlet); 1.75 (3H, singlet); 1.13 (3H, triplet, J=7.0 Hz).

EXAMPLE 227

N-[4-(Benzothiazol-2-ylmethoxy)-2-methylphenyl]-N-[2-(tetrahydropyran-2-yloxy)ethyl]acetamide (Compound No. D1.118)

Oil

Nuclear Magnetic Resonance Spectrum (200 MHz, $CDCl_3$), δ ppm: 8.05 (1H, doublet, J=7.2 Hz); 7.92 (1H, doublet, J=5.9 Hz); 7.56–7.37 (2H, multiplet); 7.12 (1H, doublet of doublets, J=8.5 & 5.4 Hz); 6.96–6.83 (2H, multiplet); 5.49 (2H, singlet); 4.59–4.50 (1H, broad multiplet); 4.38–4.12 (1H, multiplet); 3.95–3.18 (7H, multiplet); 2.21 (3H, broad singlet); 1.75 (3H, singlet); 1.80–1.35 (4H, multiplet).

EXAMPLE 228

N-Acetyl-N-[4-(benzothiazol-2-ylmethoxy)-2-methylphenyl]acetamide (Compound No. D2.1)

Melting Point: 119° to 121° C.

Nuclear Magnetic Resonance Spectrum (200 MHz, $CDCl_3$), δ ppm: 8.04 (1H, doublet, J=8.2 Hz); 7.92 (1H, doublet of doublets, J=7.7 & 1.6 Hz); 7.53–7.42 (2H, multiplet); 6.99–6.96 (3H, multiplet); 5.49 (2H, singlet); 2.27 (6H, singlet); 2.13(3H, singlet).

EXAMPLE 229

N-Acetyl-N-[4-(benzothiazol-2-ylmethoxy)-2-methylphenyl]butyramide (Compound No. D2.6)

Oil

Nuclear Magnetic Resonance Spectrum (200 MHz, $CDCl_3$), δ ppm: 8.04 (1H, doublet, J=7.4 Hz); 7.91 (1H, doublet, J=7.7 Hz); 7.54–7.41 (2H, multiplet); 7.01–6.95 (3H, multiplet); 5.49 (3H, singlet); 2.53–2.36 (2H, multiplet); 2.32 (3H, singlet); 2.11 (3H, singlet); 1.63 (2H, quartet, J=7.2 Hz); 0.89 (3H, triplet, J=7.2 Hz).

EXAMPLE 230

N-[4-(Benzothiazol-2-ylmethoxy)-2-methylphenyl]-N-ethoxycarbonylpropionamide (Compound No. D2.19)

Oil

Nuclear Magnetic Resonance Spectrum (200 MHz, $CDCl_3$), δ ppm: 8.03 (1H, doublet, J=8.0 Hz); 7.9 (1H, doublet of doublets, J=8.4 & 1.5 Hz); 7.54–7.39 (2H, multiplet); 6.98–6.90 (3H, multiplet); 5.47 (2H, singlet); 4.21–4.13 (2H, multiplet); 3.03–2.91 (2H, multiplet); 2.09 (3H, singlet); 1.25–1.13 (6H, multiplet).

EXAMPLE 231

N-[4-(Benzothiazol-2-ylmethoxy)-2-methylphenyl]-N-methoxycarbonyl-2-ethoxyacetamide (Compound No. D2.20)

Amorphous

Nuclear Magnetic Resonance Spectrum (200 MHz, $CDCl_3$), δ ppm: 8.04 (1H, doublet of doublets, J=7.2 & 1.3 Hz); 7.91 (1H, doublet of doublets, J=7.2 & 1.3 Hz); 7.51 (1H, triplet of doublets, J=7.2 & 1.3 Hz); 7.41 (1H, triplet of doublets, J=7.2 & 1.3 Hz); 6.99–6.87 (3H, multiplet); 5.47 (2H, singlet); 4.75 (2H, singlet); 3.71 (3H, singlet); 3.62 (2H, quartet, J=7.0 Hz); 2.10 (3H, singlet); 1.26 (3H, triplet, J=7.0 Hz).

EXAMPLE 232

N-[4-(Benzothiazol-2-ylmethoxy)-2-methylphenyl]-N-methoxycarbonyl-2-butenamide (Compound No. D2.21)

Oil

Nuclear Magnetic Resonance Spectrum (200 MHz, $CDCl_3$), δ ppm: 8.03 (1H, doublet, J=7.2 Hz); 7.90 (1H, doublet, J=7.6 Hz); 7.53–7.40 (2H, multiplet); 7.14–6.75 (5H, multiplet); 5.47 (2H, singlet); 3.73 (3H, singlet); 2.11 (3H, singlet); 1.91 (3H, doublet of doublets, J=6.8 & 1.5 Hz).

EXAMPLE 233

N-[4-(Benzothiazol-2-ylmethoxy)-2-methylphenyl]-N-methoxycarbonyl-3-methyl-2-butenamide (Compound No. D2.22)

Oil

Nuclear Magnetic Resonance Spectrum (200 MHz, $CDCl_3$), δ ppm: 8.02 (1H, doublet, J=8.1 Hz); 7.88 (1H, doublet, J=8.0 Hz); 7.52–7.37 (2H, multiplet); 7.02–6.88 (3H, multiplet); 6.49 (1H, broad singlet); 5.45 (2H, singlet); 3.70 (3H, singlet); 2.12 (6H, singlet); 1.93 (3H, broad singlet).

EXAMPLE 234

N-[4-Benzothiazol-2-ylmethoxy)-2-methylphenyl]-N-ethoxycarbonyl-2-methoxyacetamide (Compound No. D2.23)

Oil

Nuclear Magnetic Resonance Spectrum (200 MHz, $CDCl_3$), δ ppm: 8.04 (1H, doublet, J=8.8 Hz); 7.92 (1H, doublet of doublets, J=7.3 & 1.5 Hz); 7.55–7.41 (2H, multiplet); 6.99–6.91 (3H, multiplet); 5.48 (2H, singlet); 4.70 (2H, singlet); 4.22–4.11 (2H, multiplet); 3.48 (3H, singlet); 2.10 (3H, singlet); 1.17 (3H, triplet, J=7.1 Hz).

EXAMPLE 235

N-Acetyl-N-[4-(benzothiazol-2-ylmethoxy)-2-methylphenyl]-2-methoxyacetamide (Compound No. D2.25)

Oil

Nuclear Magnetic Resonance Spectrum (200 MHz, $CDCl_3$), δ ppm: 8.05 (1H, doublet, J=7.2 Hz); 7.92 (1H, doublet of doublets, J=7.8 & 1.8 Hz); 7.55–7.42 (2H, multiplet); 7.04–6.96 (3H, multiplet); 5.50 (2H, singlet); 4.37 (2H, quartet, J=17.6 Hz); 3.44 (3H, singlet); 2.17 (2H, singlet); 2.13 (6H, singlet).

EXAMPLE 236

N-Acetyl-N-[4-(benzothiazol-2-ylmethoxy)-2-methylphenyl]-3-methoxypropionamide (Compound No. D2.29)

Oil

Nuclear Magnetic Resonance Spectrum (200 MHz, $CDCl_3$), δ ppm: 8.07–8.02 (1H, multiplet); 7.93–7.90 (1H, multiplet); 7.56–7.42 (2H, multiplet); 7.03–6.95 (3H, multiplet); 5.49 (2H, singlet); 3.64 (2H, triplet, J=5.9 Hz); 3.32 (3H, singlet); 2.76–2.63 (2H, multiplet); 2.35 (3H, singlet); 2.13 (3H, singlet).

EXAMPLE 237

N-[4-(Benzothiazol-2-ylmethoxy)-2-methylphenyl]-N-methoxycarbonyl-3-methoxypropionamide (Compound No. D2.30)

Oil

Nuclear Magnetic Resonance Spectrum (200 MHz, $CDCl_3$), δ ppm: 8.04 (1H, doublet, J=7.7 Hz); 7.91 (1H, doublet of doublets, J=6.8 & 0.9 Hz); 7.55–7.41 (2H, multiplet); 6.99–6.90 (3H, multiplet); 5.47 (2H, singlet); 3.74 (2H, triplet, J=6.2 Hz); 3.72 (3H, singlet); 3.35 (3H, singlet); 3.32–3.18 (2H, singlet); 2.10 (3H, singlet).

EXAMPLE 238

N-[4-(Benzothiazol-2-ylmethoxy)-2-methylphenyl]-N-methoxycarbonyl-3-ethoxypropionamide (Compound No. D2.32)

Oil

Nuclear Magnetic Resonance Spectrum (200 MHz, $CDCl_3$), δ ppm: 8.03 (1H, doublet, J=7.9 Hz); 7.91 (1H, doublet, J=7.9 Hz); 7.37–7.56 (2H, multiplet); 6.86–7.00 (3H, multiplet); 5.47 (2H, singlet); 3.77 (2H, triplet, J=6.2 Hz); 3.72 (3H, singlet); 3.51 (2H, quartet, J=7.0 Hz); 3.22 (2H, multiplet); 2.11 (3H, singlet); 1.18 (3H, triplet, J=7.0 Hz).

EXAMPLE 239

N-Acetyl-N-[4-(benzothiazol-2-ylmethoxy)-2-methylphenyl]benzamide (Compound No. D2.41)

Melting Point: 111° to 113° C.

Nuclear Magnetic Resonance Spectrum (200 MHz, $CDCl_3$), δ ppm: 8.03 (1H, doublet, J=7.7 Hz); 7.91 (1H, doublet, J=7.7 Hz); 7.58–7.28 (7H, multiplet); 7, 03 (1H, doublet, J=8.5 Hz); 6.93–6.84 (2H, multiplet); 5.44 (2H, singlet); 2.35 (3H, singlet); 2.24 (3H, singlet).

EXAMPLE 240

N-[4-(Benzothiazol-2-ylmethoxy)-2-methylphenyl]-N-methoxycarbonyl-4-t-butylbenzamide (Compound No. D2.45)

Melting Point: 130° to 131.5° C.

Nuclear Magnetic Resonance Spectrum (200 MHz, $CDCl_3$), δ ppm: 8.04 (1H, doublet, J=7.5 Hz); 7.92 (1H, doublet of doublets, J=8.0 & 1.1 Hz); 7.66 (2H, doublet, J=8.5 Hz); 7.54–7.37 (4H, multiplet); 7.12 (1H, doublet, J=8.5 Hz); 6.99–6.89 (2H, multiplet); 5.49 (2H, singlet); 3.67 (3H, singlet); 2.27 (3H, singlet); 1.34 (9H, singlet).

EXAMPLE 241

N-[4-(Benzothiazol-2-ylmethoxy)-2-methylphenyl]-N-methoxycarbonyl-2-chlorobenzamide (Compound No. D2.46)

Melting Point: 136° to 137° C.

Nuclear Magnetic Resonance Spectrum (200 MHz, $CDCl_3$), δ ppm: 8.05 (1H, doublet, J=8.1 Hz); 7.92 (1H, doublet, J=7.3 Hz); 7.56–7.35 (6H, multiplet); 7.20 (1H, doublet, J=8.5 Hz); 7.02–6.95 (2H, multiplet); 5.51 (2H, singlet); 3.64 (3H, singlet); 2.27 (3H, singlet).

EXAMPLE 242

N-[4-(Benzothiazol-2-ylmethoxy)-2-methylphenyl]-N-methoxycarbonyl-3-chlorobenzamide (Compound No. D2.47)

Melting Point: 108.5° to 110.5° C.

Nuclear Magnetic Resonance Spectrum (200 MHz, $CDCl_3$), δ ppm: 8.05 (1H, doublet, J=8.1 Hz); 7.92 (1H, doublet, J=8.0 Hz); 7.65–7.33 (6H, multiplet); 7.11 (1H, doublet, J=8.4 Hz); 6.98–6.90 (2H, multiplet); 5.49 (2H, singlet); 3.68 (3H, singlet); 2.26 (3H, singlet).

EXAMPLE 243

N-[4-(Benzothiazol-2-ylmethoxy)-2-methylphenyl]-N-methoxycarbonyl-4-chlorobenzamide (Compound No. D2.48)

Amorphous

Nuclear Magnetic Resonance Spectrum (200 MHz, $CDCl_3$), δ ppm: 8.04 (1H, doublet of doublets, J=8.0 & 0.8 Hz); 7.90 (1H, doublet of doublets, J=8.3 & 1.5 Hz); 7.63 (2H, doublet, J=8.5 Hz); 7.54–7.36 (4H, multiplet); 7.10 (1H, doublet, J=8.6 Hz); 6.99–6.95 (2H, multiplet); 5.47 (2H, singlet); 3.67 (3H, singlet); 2.25 (3H, singlet).

EXAMPLE 244

N-[4-(Benzothiazol-2-ylmethoxy)-2-methylphenyl]-N-methoxycarbonyl-2,6-dichlorobenzamide (Compound No. D2.50)

Melting Point: 191° to 193° C.

Nuclear Magnetic Resonance Spectrum (200 MHz, $CDCl_3$), δ ppm: 8.05 (1H, doublet, J=7.7 Hz); 7.92 (1H, doublet of doublets, J=7.4 & 1.3 Hz); 7.56–7.19 (6H, multiplet); 7.04–6.95 (2H, multiplet); 5.51 (2H, singlet); 3.65 (3H, singlet); 2.30 (3H, singlet).

EXAMPLE 245

N-[4-(Benzothiazol-2-ylmethoxy)-2-methylphenyl]-N-methoxycarbonyl-3,4-dichlorobenzamide (Compound No. D2.51)

Amorphous

Nuclear Magnetic Resonance Spectrum (200 MHz, $CDCl_3$), δ ppm:
8.04 (1H, doublet, J=7.3 Hz);
7.90 (1H, doublet, J=8.1 Hz);

7.75 (1H, doublet, J=1.4 Hz);
7.54–7.36 (4H, multiplet);
7.09 (1H, doublet, J=8.4 Hz);
6.97–6.90 (2H, multiplet);
5.48 (2H, singlet);
3.68 (3H, singlet);
2.24 (3H, singlet).

EXAMPLE 246

N-[4-(Benzothiazol-2-ylmethoxy)-2-methylphenyl]-N-methoxycarbonyl-2,6-difluorobenzamide (Compound No. D2.53)

Melting Point: 151° to 152.5° C.

Nuclear Magnetic Resonance Spectrum (200 MHz, CDCl$_3$), δ ppm:
8.05 (1H, doublet, J=7.5 Hz);
7.92 (1H, doublet, J=7.3 Hz);
7.56–7.31 (3H, multiplet);
7.14 (1H, doublet, J=8.6 Hz);
7.02–6.92 (4H, multiplet);
5.50 (2H, singlet);
3.67 (3H, singlet);
2.25 (3H, singlet).

EXAMPLE 247

N-[4-(Benzothiazol-2-ylmethoxy)-2-methylphenyl]-N-methoxycarbonyl-3-methoxybenzamide (Compound No. D2.56)

Amorphous

Nuclear Magnetic Resonance Spectrum (200 MHz, CDCl$_3$), δ ppm:
8.04 (1H, doublet, J=7.6 Hz);
7.90 (1H, doublet, J=7.7 Hz);
7.55–7.22 (5H, multiplet);
7.13–6.89 (4H, multiplet);
5.48 (2H, singlet);
3.82 (3H, singlet);
3.65 (3H, singlet);
2.27 (3H, singlet).

EXAMPLE 248

N-[4-(Benzothiazol-2-ylmethoxy)-2-methylphenyl]-N-methoxycarbonyl-4-methoxybenzamide (Compound No. D2.57)

Melting Point: 126° to 128° C.

Nuclear Magnetic Resonance Spectrum (200 MHz, CDCl$_3$), δ ppm:
8.03 (1H, doublet, J=8.6 Hz);
7.90 (1H, doublet, J=8.6 Hz);
7.71 (2H, doublet, J=8.6 Hz);
7.53–7.39 (2H, multiplet);
7.11 (1H, doublet, J=8.4 Hz);
6.96–6.89 (4H, multiplet);
5.46 (2H, singlet);
3.84 (3H, singlet);
3.68 (3H, singlet);
2.26 (3H, singlet).

EXAMPLE 249

N-[4-(Benzothiazol-2-ylmethoxy)-2-methylphenyl]-N-methoxycarbonyl-2-methylbenzamide (Compound No. D2.60)

Oil

Nuclear Magnetic Resonance Spectrum (200 MHz, CDCl$_3$), δ ppm:
8.04 (1H, doublet, J=7.7 Hz);
7.90 (1H, doublet, J=7.4 Hz);
7.54–7.18 (6H, multiplet);
7.13 (1H, doublet, J=8.6 Hz);
7.01–6.92 (2H, multiplet);
5.49 (2H, singlet);
3.58 (3H, singlet);
2.45 (3H, singlet);
2.27 (3H, singlet).

EXAMPLE 250

N-[4-(Benzothiazol-2-ylmethoxy)-2-methylphenyl]-N-(2-furoyl)acetamide (Compound No. D2.63)

Oil

Nuclear Magnetic Resonance Spectrum (200 Mz, CDCl$_3$), δ ppm:
8.07–8.02 (1H, multiplet);
7.95–7.90 (1H, multiplet);
7.53–7.42 (3H, multiplet);
7.08–6.95 (3H, multiplet);
6.32–6.29 (1H, multiplet);
6.13–6.11 (1H, multiplet);
5.49 (2H, singlet);
2.56 (3H, singlet);
2.17 (3H, singlet)..

EXAMPLE 251

N-[4-(Benzoxazol-2-ylmethoxy)-2-methylphenyl]-N-methoxycarbonylfuran-2-carboxamide (Compound No. D2.65)

Oil

Nuclear Magnetic Resonance Spectrum (200 MHz, CDCl$_3$), δ ppm:
7.79–7.75 (1H, multiplet);
7.60–7.55 (1H, multiplet);
7.51 (1H, doublet, J=0.7 Hz);
7.40–7.36 (2H, multiplet);
7.13 (1H, doublet, J=8.5 Hz);
6.99–6.94 (2H, multiplet)
6.91 (2H, doublet, J=3.6 Hz);
6.47 (1H, doublet of doublets, J=3.6 & 1.7 Hz);
5.33 (2H, singlet);
3.77 (3H, singlet);
2.23 (3H, singlet).

EXAMPLE 252

N-[4-(Benzothiazol-2-ylmethoxy)-2-methylphenyl]-N-methoxycarbonylthiophen-2-carboxamide (Compound No. D2.66)

Gum

Nuclear Magnetic Resonance Spectrum (200 MHz, CDCl$_3$), δ ppm:
8.04 (1H, doublet, J=7.2 Hz);
7.92 (1H, doublet of doublets, J=1.6 & 7.2 Hz);

7.38–7.55 (4H, multiplet);
7.14 (1H, doublet, J=8.6 Hz);
6.87–7.01 (3H, multiplet);
5.49 (2H, singlet);
3.80 (3H, singlet);
2.25(3H, singlet).

EXAMPLE 253

N-[4-(Benzothiazol-2-ylmethoxy)-2-methylphenyl]-N-(2-thenoyl)acetamide (Compound No. D2.67)

Oil

Nuclear Magnetic Resonance Spectrum (200 Mz, CDCl$_3$), δ ppm:
8.07–8.02 (1H, multiplet);
7.95–7.91 (1H, multiplet);
7.53–7.42 (3H, multiplet);
7.19–6.87 (5H, multiplet);
5.50 (2H, singlet);
2.63 (3H, singlet);
2.17 (3H, singlet).

EXAMPLE 254

N-[4-(Benzothiazol-2-ylmethoxy)-2-methylphenyl]-N-methoxycarbonylnicotinamide (Compound No. D2.68)

Melting Point: 104° C.

Nuclear Magnetic Resonance Spectrum (200 MHz, CDCl$_3$), δ ppm:
8.89 (1H, multiplet);
8.72 (1H, doublet of doublets, J=1.4 & 4.9 Hz);
7.87–8.06 (3H, multiplet);
7.34–7.56 (3H, multiplet);
7.11 (1H, doublet, J=8.4 Hz);
6.89–6.99 (2H, multiplet);
5.49 (2H, singlet);
3.68 (3H, multiplet);
2.26 (3H, singlet).

EXAMPLE 255

N-{4-[1-(Benzothiazol-2-yl)propoxy]-2-methylphenyl}-N-ethylacetamide (Compound No. E7.10)

Oil

Nuclear Magnetic Resonance Spectrum (200 Mz, CDCl$_3$), δ ppm:
8.03 (1H, doublet of doublets, J=7.4 & 1.4 Hz);
7.87 (1H, doublet of doublets, J=7.4 & 1.4 Hz);
7.50 (1H, triplet of doublets, J=7.4 & 1.4 Hz);
7.39 (1H, triplet of doublets, J=7.4 & 1.4 Hz);
6.93 (1H, doublet, J=2.4 Hz);
6.92 (1H, doublet, J=8.6 Hz);
6.83 (1H, doublet of doublets, J=8.6 & 2.4 Hz);
5.50 (1H, doublet of doublets, J=7.0 & 5.6 Hz);
4.10–3.93 (1H, multiplet);
3.25–3.08 (1H, multiplet);
2.26–2.09 (2H, multiplet);
2.14 (3H, singlet);
1.70 (3H, doublet, J=1.3 Hz);
1.13 (3H, triplet, J=7.3 Hz);
1.07 (3H, triplet of doublets, J=7.2 & 2.2 Hz).

EXAMPLE 256

Propyl N-[4-(benzothiazol-2-ylmethoxy)phenyl]carbamate (Compound No. A1.25)

Melting Point: 159° to 163° C.

Nuclear Magnetic Resonance Spectrum (200 MHz, CDCl$_3$), δ ppm:
8.03 (1H, doublet of doublets, J=8.3 & 0.9 Hz);
7.90 (1H, doublet of doublets, J=7.1 & 1.1 Hz);
7.53–7.40 (2H, multiplet);
7.15 (4H, multiplet);
6.46 (1H, broad singlet);
5.46 (2H, singlet);
4.11 (2H, triplet, J=6.7 Hz);
1.69 (2H, sextet, J=6.7 Hz);
0.96 (3H, triplet, J=6.7 Hz).

EXAMPLE 257

Isopropyl N-[4-(benzothiazol-2-ylmethoxy)phenyl]carbamate (Compound No. A1.28)

Melting Point: 176° to 178° C.

Nuclear Magnetic Resonance Spectrum (200 MHz, CDCl$_3$), δ ppm:
8.03 (1H, doublet, J=8.2 Hz);
7.90 (1H, doublet of doublets, J=8.0 & 0.9 Hz);
7.54–7.36 (2H, multiplet);
7.20 (4H, multiplet);
6.41 (1H, broad singlet);
5.46(2H, singlet);
5.00 (1H, heptet, J=6.3 Hz);
1.29 (6H, doublet, J=6.3 Hz).

EXAMPLE 258

Butyl N-[4-(benzothiazol-2-ylmethoxy)phenyl]carbamate (Compound No. A1.31)

Melting Point: 149° to 152° C.

Nuclear Magnetic Resonance Spectrum (200 MHz, CDCl$_3$), δ ppm:
8.03 (1H, doublet, J=7.5 Hz);
7.90 (1H, doublet of doublets, J=7.9 & 1.5 Hz);
7.54–7.36 (2H, multiplet);
7.15 (4H, multiplet);
6.45 (1H, broad singlet);
5.46 (2H, singlet);
4.15 (2H, triplet, J=6.6 Hz);
1.61 (2H, quintet, J=4.5 Hz);
1.41 (2H, sextet, J=7.0 Hz);
0.94 (3H, triplet, J=7.3 Hz).

EXAMPLE 259

2,2,2-Trichloroethyl N-[4-(benzothiazol-2-ylmethoxy)phenyl]carbamate (Compound No. A1.56)

Melting Point: 153° to 154° C.

Nuclear Magnetic Resonance Spectrum (200 MHz, CDCl$_3$), δ ppm:
8.03 (1H, doublet, J=8.1 Hz);
7.90 (1H, doublet of doublets, J=6.7 & 0.7 Hz);
7.51–7.32 (4H, multiplet);
7.03 (2H, doublet, J=9.1 Hz);
6.78 (1H, broad singlet);
5.48 (2H, singlet);
4.81 (2H, singlet).

EXAMPLE 260

S-Methyl N-[4-(benzothiazol-2-ylmethoxy)-2-methylphenyl]thiocarbamate (Compound No. C1.11)

Melting Point: 145° to 147° C.

Nuclear Magnetic Resonance Spectrum (200 MHz, CDCl₃), δ ppm:
8.06–8.01 (1H, multiplet);
7.92–7.88 (1H, multiplet);
7.51–7.37 (3H, multiplet);
6.92–6.86 (2H, multiplet);
6.73 (1H, broad singlet);
5.47 (2H, singlet);
2.36 (3H, singlet);
2.26 (3H, singlet).

EXAMPLE 261

Ethyl N-[4-(benzothiazol-2-ylmethoxy)-2-methylphenyl]carbamate (Compound No. C1.17)

Melting Point: 124° to 127° C.

Nuclear Magnetic Resonance Spectrum (200 MHz, CDCl₃), δ ppm:
8.03 (1H, doublet, J=7.2 Hz);
7.90 (1H, doublet, J=6.9 Hz);
7.55–7.36 (3H, multiplet);
6.91–6.84 (2H, multiplet);
6.19 (1H, broad singlet);
5.46 (2H, singlet);
4.21 (2H, quartet, J=7.1 Hz);
2.24 (3H, singlet);
1.30 (3H, triplet, J=7.1 Hz).

EXAMPLE 262

2,2,2-Trichloroethyl N-[4-(benzothiazol-2-ylmethoxy)-2-methylphenyl]carbamate (Compound No. C 1.19)

Melting Point: 166° to 168° C.

Nuclear Magnetic Resonance Spectrum (200 MHz, CDCl₃), δ ppm:
8.03 (1H, doublet, J=7.3 Hz);
7.90 (1H, doublet of doublets, J=6.9 & 0.8 Hz);
7.54–7.36 (3H, multiplet);
6.91–6.87 (2H, multiplet);
6.49 (1H, broad singlet);
5.47 (2H, singlet);
4.81 (2H, singlet);
2.28 (3H, singlet).

EXAMPLE 263

Isopropyl N-[4-(benzothiazol-2-ylmethoxy)-2-methylphenyl]carbamate (Compound No. C1.23)

Melting Point: 118° to 120° C.

Nuclear Magnetic Resonance Spectrum (200 MHz, CDCl₃), δ ppm:
8.03 (1H, doublet of doublets, J=8.9 & 1.6 Hz);
7.90 (1H, doublet of doublets, J=7.1 & 1.5 Hz);
7.62–7.36 (3H, multiplet);
6.89–6.86 (2H, multiplet);
6.14 (1H, broad singlet);
5.46 (2H, singlet);
4.99 (1H, heptet, J=6.2 Hz);
2.24 (3H, singlet);
1.29 (6H, doublet, J=6.2 Hz).

EXAMPLE 264

Propyl N-[4-(benzothiazol-2-ylmethoxy)-2-methylphenyl]carbamate (Compound No. C 1.24)

Melting Point: 121° to 124° C.

Nuclear Magnetic Resonance Spectrum (200 MHz, CDCl₃), δ ppm:
8.03 (1H, doublet, J=8.3 Hz);
7.90 (1H, doublet, J=6.9 Hz);
7.62–7.36 (3H, multiplet);
6.91–6.84 (2H, multiplet);
6.19 (1H, broad singlet);
5.45 (2H, singlet);
4.11 (2H, doublet, J=6.8 Hz);
2.24 (3H, singlet);
1.69 (2H, sextet, J=6.8 Hz);
0.97 (3H, triplet, J=6.8 Hz).

EXAMPLE 265

N-[4-(Benzothiazol-2-ylmethoxy)-2-methylphenyl]-2,2-dimethylpropionamide (Compound No. C1.27)

Melting Point: 140° to 142° C.

Nuclear Magnetic Resonance Spectrum (200 MHz, CDCl₃), δ ppm:
8.03 (1H, doublet, J=8.0 Hz);
7.89 (1H, doublet, J=7.2 Hz);
7.63 (1H, doublet, J=9.4 Hz);
7.35–7.53 (2H, multiplet);
7.09 (1H, broad singlet);
6.84–6.91 (2H, multiplet);
5.46 (2H, singlet);
2.22 (3H, singlet);
1.33 (9H, singlet).

EXAMPLE 266

Butyl N-[4-(benzothiazol-2-ylmethoxy)-2-methylphenyl]carbamate (Compound No. C1.28)

Melting Point: 127° to 128° C.

Nuclear Magnetic Resonance Spectrum (200 MHz, CDCl₃), δ ppm:
8.03 (1H, doublet, J=8.2 Hz);
7.90 (1H, doublet of doublets, J=7.4 & 1.5 Hz);
7.55–7.36 (3H, multiplet);
6.91–6.84 (2H, multiplet);
6.18 (1H, broad singlet);
5.46 (2H, singlet);
4.15 (2H, triplet, J=7.2 Hz);
2.24 (3H, singlet);
1.66 (2H, heptet, J=7.2 Hz);
1.40 (2H, sextet, J=7.2 Hz);
0.94 (3H, triplet, J=7.2 Hz).

EXAMPLE 267

N-[4-(Benzothiazol-2-ylmethoxy)-2-methylphenyl]-3-ethoxypropionamide (Compound No. C1.44)

Melting Point: 135° to 137° C.

Nuclear Magnetic Resonance Spectrum (200 MHz, CDCl₃), δ ppm:
8.19 (1H, broad singlet);
8.03 (1H, doublet, J=7.9 Hz);
7.89 (1H, doublet, J=7.4 Hz);
7.79 (1H, doublet, J=9.6 Hz);
7.35–7.54 (2H, multiplet);
6.86–6.91 (2H, multiplet);
5.46 (2H, singlet);
3.77 (2H, triplet, J=5.6 Hz);
3.60 (2H, quartet, J=7.0 Hz);
2.66 (2H, triplet, J=5.6 Hz);

2.24 (3H, singlet);
1.56 (3H, triplet, J=7.0 Hz).

EXAMPLE 268

Methyl N-[4-(benzothiazol-2-ylmethoxy)-2-methoxyphenyl]carbamate (Compound No. C8.3)

Melting Point: 112° to 114° C.

Nuclear Magnetic Resonance Spectrum (200 MHz, $CDCl_3$), δ ppm:
8.06–8.01 (1H, multiplet);
7.92–7.88 (1H, multiplet);
7.55–7.36 (3H, multiplet);
7.01 (1H, broad singlet);
6.64–6.57 (2H, multiplet);
5.46 (2H, singlet);
3.85 (3H, singlet);
3.76 (3H, singlet).

EXAMPLE 269

Methyl N-[4-(benzoxazol-2-ylmethoxy)-2-methoxyphenyl]carbamate (Compound No. C8.6)

Melting Point: 91° to 93° C.

Nuclear Magnetic Resonance Spectrum (200 MHz, $CDCl_3$), δ ppm:
7.94–7.91 (1H, multiplet);
7.79–7.74 (1H, multiplet);
7.59–7.54 (1H, multiplet);
7.42–7.35 (2H, multiplet);
7.00 (1H, broad singlet);
6.67–6.59 (2H, multiplet);
5.03 (2H, singlet);
3.84 (3H, singlet);
3.76 (3H, singlet).

EXAMPLE 270

Methyl N-[4-(benzothiazol-2-ylmethoxy)-3-methoxyphenyl]carbamate (Compound No. C8.20)

Melting Point: 93° to 96° C.

Nuclear Magnetic Resonance Spectrum (200 MHz, $CDCl_3$), δ ppm:
8.02 (1H, doublet, J=7.2 Hz);
7.89(1H, doublet of doublets, J=6.8 & 1.0 Hz);
7.53–7.35 (2H, multiplet);
7.28 (1H, broad singlet);
6.94 (1H, doublet, J=8.6 Hz);
6.65 (1H, doublet of doublets, J=8.6 & 2.5 Hz);
6.53 (1H, broad singlet);
5.50 (2H, singlet);
3.92 (3H, singlet);
3.76 (3H, singlet).

EXAMPLE 271

Methyl N-[4-(benzoxazol-2-ylmethoxy)-3-methoxyphenyl]carbamate (Compound No. C8.23)

Melting Point: 97° to 99° C.

Nuclear Magnetic Resonance Spectrum (200 MHz, $CDCl_3$), δ ppm:
7.76–7.72 (2H, multiplet);
7.58–7.54 (1H, multiplet);
7.38–7.33 (2H, multiplet);
6.99 (1H, doublet, J=8.7 Hz);
6.67 (1H, doublet of doublets, J=8.7 & 1.9 Hz);
6.52 (1H, broad singlet);
5.33 (2H, singlet);
3.87 (3H, singlet);
3.76 (3H, singlet).

EXAMPLE 272

Methyl N-[4-(benzoxazol-2-ylmethoxy)-2-fluorophenyl]carbamate (Compound No. C9.6)

Melting Point: 110° to 115° C.

Nuclear Magnetic Resonance Spectrum (200 MHz, $CDCl_3$), δ ppm:
8.00–7.89 (1H, multiplet);
7.79–7.74 (1H, multiplet);
7.59–7.54 (1H, multiplet);
7.42–7.36 (2H, multiplet);
6.89–6.81 (2H, multiplet);
6.63 (1H, broad singlet);
5.29 (2H, singlet);
3.78 (3H, singlet).

EXAMPLE 273

Methyl N-[4-(benzoxazol-2-ylmethoxy)-3-fluorophenyl]carbamate (Compound No. C9.24)

Melting Point: 135° to 138° C.

Nuclear Magnetic Resonance Spectrum (200 MHz, $CDCl_3$), δ ppm:
7.78–7.73 (1H, multiplet);
7.60–7.55 (1H, multiplet);
7.41–7.32 (3H, multiplet);
7.09 (1H, triplet, J=8.8 Hz);
6.96–6.90 (1H, multiplet);
6.52 (1H, broad singlet);
5.35 (2H, singlet);
3.77 (3H, singlet).

EXAMPLE 274

Methyl N-[4-(benzoxazol-2-ylmethoxy)-3-chlorophenyl]carbamate (Compound No. C9.56)

Melting Point: 164° to 166° C.

Nuclear Magnetic Resonance Spectrum (200 MHz, $CDCl_3$), δ ppm:
7.77–7.73 (1H, multiplet);
7.59–7.50 (2H, multiplet);
7.42–7.35 (2H, multiplet);
7.19(1H, doublet of doublets, J=8.8 & 2.2 Hz);
7.06(1H, doublet, J=8.8 Hz);
6.63 (1H, broad singlet);
5.35 (2H, singlet);
3.76 (3H, singlet).

EXAMPLE 275

Methyl N-[4-(benzoxazol-2-ylmethoxy)-2-trifluoromethylphenyl]carbamate (Compound No. C 10.5)

Melting Point: 69° to 71° C.

Nuclear Magnetic Resonance Spectrum (200 MHz, $CDCl_3$), δ ppm:
7.93 (1H, doublet, J=9.2 Hz);
7.79–7.75 (1H, multiplet);
7.60–7.53 (1H, multiplet);

7.43–7.21 (4H, multiplet);
6.71 (1H, broad singlet);
5.34 (2H, singlet);
3.78 (3H, singlet).

EXAMPLE 276

Methyl N-[4-(benzothiazol-2-ylmethoxy)-3-trifluoromethylphenyl]carbamate (Compound No. C10.20)

Melting Point: 142° to 146° C.
Nuclear Magnetic Resonance Spectrum (200 MHz, CDCl$_3$), δ ppm:
8.03 (1H, doublet, J=7.3 Hz);
7.91 (1H, doublet of doublets, J=8.1 & 1.3 Hz);
7.73–7.56 (3H, multiplet);
7.65 (1H, doublet, J=1.3 Hz);
7.07 (1H, doublet, J=8.8 Hz);
6.59 (1H, broad singlet);
5.55 (2H, singlet);
3.78 (3H, singlet).

EXAMPLE 277

Methyl N-[4-(benzoxazol-2-ylmethoxy)-2-nitrophenyl]carbamate (Compound No. C10.50)

Melting Point: 130° to 132° C.
Nuclear Magnetic Resonance Spectrum (200 MHz, CDCl$_3$), δ ppm:
9.66 (1H, broad singlet);
8.51 (1H, doublet, J=9.4 Hz);
7.89 (1H, doublet, J=3.0 Hz);
7.79–7.75 (1H, multiplet);
7.44–7.37 (3H, multiplet);
5.37 (2H, singlet);
3.82 (3H, singlet).

EXAMPLE 278

Methyl N-[4-(benzothiazol-2-ylmethoxy)-2,3,5-trimethylphenyl]carbamate Compound No. C11.64

Melting Point: 158° to 160° C.
Nuclear Magnetic Resonance Spectrum (200 MHz, CDCl$_3$), δ ppm:
8.06–7.94 (2H, multiplet);
7.55–7.23 (3H, multiplet);
6.26 (1H, broad singlet);
5.16 (2H, singlet).
3.78 (3H, singlet);
2.34 (3H, singlet);
2.29 (3H, singlet);
2.16 (3H, singlet).

EXAMPLE 279

Methyl N-[4-(benzothiazol-2-ylmethoxy)-2,5-dichlorophenyl]carbamate (Compound No. C14.18)

Melting Point: 131° to 133° C.
Nuclear Magnetic Resonance Spectrum (200 MHz, CDCl$_3$) δ ppm:
8.28 (1H, singlet);
8.04 (1H, doublet, J=7.9 Hz);
7.92 (1H, doublet of doublets, J=7.8 & 1.9 Hz);
7.53–7.39 (2H, multiplet);
7.09 (1H, singlet);
6.86 (1H, broad singlet);
5.50 (2H, singlet);
3.81 (3H, singlet).

EXAMPLE 280

Methyl N-[4-(benzoxazol-2-ylmethoxy)phenyl]-N-methylcarbamate (Compound No. B1.5)

Melting Point: 76° to 78° C.
Nuclear Magnetic Resonance Spectrum (200 MHz, CDCl$_3$), δ ppm:
7.79–7.44 (1H, multiplet);
7.59–7.55 (1H, multiplet);
7.40–7.35 (2H, multiplet);
7.19–7.14 (2H, multiplet);
7.08–7.02 (2H, multiplet);
5.32 (2H, singlet);
3.68 (3H, singlet);
3.25 (3H, singlet).

EXAMPLE 281

Methyl N-[4-(benzoxazol-2-ylmethoxy)phenyl]-N-ethylcarbamate (Compound No. B1.10)

Oil
Nuclear Magnetic Resonance Spectrum (200 MHz, CDCl$_3$), δ ppm:
7.79–7.75 (1H, multiplet);
7.60–7.55 (1H, multiplet);
7.43–7.02 (4H, multiplet);
5.32 (2H, singlet);
3.66 (3H, singlet);
3.65 (2H, quartet, J=7.1 Hz);
1.12 (3H, triplet, J=7.1 Hz).

EXAMPLE 282

Methyl N-allyl-N-[4-(benzoxazol-2-ylmethoxy)phenyl]carbamate (Compound No. B2.37)

Oil
Nuclear Magnetic Resonance Spectrum (200 MHz, CDCl$_3$), δ ppm:
7.79–7.75 (1H, multiplet);
7.60–7.55 (1H, multiplet);
7.43–7.33 (2H, multiplet);
7.18–7.10 (2H, multiplet);
7.06–7.00 (2H, multiplet);
5.97–5.79 (1H, multiplet);
5.31 (2H, singlet);
5.17–5.15 (1H, multiplet);
5.11–5, 07 (1H, multiplet);
4.22–4.18 (2H, multiplet);
3.68 (3H, broad singlet).

EXAMPLE 283

Methyl N-[4-(benzothiazol-2-ylmethoxy)-2-methylphenyl]-N-methylcarbamate (Compound No. D1.2)

Melting Point: 88° to 91° C.
Nuclear Magnetic Resonance Spectrum (200 MHz, CDCl$_3$), δ ppm:
8.04 (1H, doublet, J=7.3 Hz);
7.91 (1H, doublet, J=7.3 Hz);
7.55–7.41 (2H, multiplet);

7.05 (2H, doublet, J=8.3 Hz);
6.93–6.83 (2H, multiplet);
5.46 (2H, singlet);
3.63 (3H, singlet);
3.16 (3H, singlet);
2.18 (3H, singlet).

EXAMPLE 284

Methyl N-[4-(benzoxazol-2-ylmethoxy)-2-methylphenyl]-N-methylcarbamate (Compound No. D1.4)

Oil

Nuclear Magnetic Resonance Spectrum (200 MHz, CDCl$_3$), δ ppm:
7.79–7.75 (1H, multiplet);
7.59–7.55 (1H, multiplet);
7.43–7.36 (2H, multiplet);
7.07–7.02 (1H, multiplet);
6.94–6.86 (2H, multiplet);
5.31 (2H, singlet);
3.63 (3H, singlet);
3.16 (3H, singlet);
2.17 (3H, singlet).

EXAMPLE 285

Methyl N-[4-(benzoxazol-2-ylmethoxy)-2-methylphenyl]-N-ethylcarbamate (Compound No. D1.8)

Oil

Nuclear Magnetic Resonance Spectrum (200 MHz, CDCl$_3$), δ ppm:
7.79–7.75 (1H, multiplet);
7.59–7.55 (1H, multiplet);
7.43–7.36 (2H, multiplet);
7.04–6.86 (3H, multiplet);
5.31 (2H, singlet);
3.78–3.37 (2H, broad multiplet);
3.62 (3H, singlet);
2.17 (3H, singlet);
1.12 (3H, triplet, J=7.4 Hz).

EXAMPLE 286

Methyl N-[4-(benzothiazol-2-ylmethoxy)-2-methylphenyl]-N-isopropylcarbamate (Compound No. D1.10)

Melting Point: 98° to 100° C.

Nuclear Magnetic Resonance Spectrum (200 MHz, CDCl$_3$), δ ppm:
8.07–7.89 (2H, multiplet);
7.52–7.41 (2H, multiplet);
7.00 (1H, doublet, J=8.8 Hz);
6.94 (1H, doublet, J=3.0 Hz);
6.87–6.82 (1H, multiplet);
5.47 (2H, singlet);
4.48 (1H, broad singlet);
3.62 (3H, broad singlet);
2.17 (3H, singlet).
1.27 (3H, doublet, J=6.8 Hz);
0.94 (3H, doublet, J=6.8 Hz).

EXAMPLE 287

Methyl N-allyl-N-[4-(benzothiazol-2-ylmethoxy)-2-methylphenyl]carbamate (Compound No. D1.14)

Oil

Nuclear Magnetic Resonance Spectrum (200 MHz, CDCl$_3$), δ ppm:
8.02 (1H, doublet of doublets, J=8.0 & 1.5 Hz);
7.89 (1H, doublet of doublets, J=8.0 & 1.5 Hz);
7.49 (1H, triplet of doublets, J=8.0 & 1.5 Hz);
7.39 (1H, triplet of doublets, J=8.0 & 1.5 Hz);
7.01 (1H, doublet, J=8.4 Hz);
6.91 (1H, doublet, J=2.6 Hz);
6.83 (1H, doublet of doublets, J=8.4 & 2.6 Hz);
5.98–5.79 (1H, multiplet);
5.44 (2H, singlet);
5.12–5.04 (2H, multiplet);
4.40–4.26 (1H, multiplet);
3.95–3.80 (1H, multiplet);
3.78–3.63 (3H, multiplet);
2.17 (3H, singlet).

EXAMPLE 288

Methyl N-allyl-N-[4-(benzoxazol-2-ylmethoxy)-2-methylphenyl]carbamate (Compound No. D1.16)

Oil

Nuclear Magnetic Resonance Spectrum (200 Mz, CDCl$_3$), δ ppm:
7.80–7.73 (1H, multiplet);
7.60–7.53 (1H, multiplet);
7.43–7.33 (2H, multiplet);
7.02 (1H, doublet, J=8.7 Hz);
6.94 (1H, doublet, J=2.9 Hz);
6.86 (1H, doublet of doublets, J=8.7 & 2.9 Hz);
6.00–5.80 (1H, multiplet);
5.30 (2H, singlet);
5.13–5.04 (2H, multiplet);
4.41–4.28 (1H, multiplet);
3.94–3.83 (1H, multiplet);
3.78–3.64 (3H, multiplet);
2.17 (3H, singlet).

EXAMPLE 289

Methyl N-[4-(benzothiazol-2-ylmethoxy)-2-methylphenyl]-N-(2-propynyl)carbamate (Compound No. D1.18).

Oil

Nuclear Magnetic Resonance Spectrum (200 MHz, CDCl$_3$), δ ppm:
8.04 (1H, doublet, J=7.2 Hz);
7.92 (1H, doublet, J=7.1 Hz);
7.57–7.35 (2H, multiplet);
7.19 (1H, doublet, J=8.5 Hz);
6.96–6.83 (2H, multiplet);
5.47 (2H, singlet);
4.57–4.10 (2H, multiplet);
3.82–3.66 (3H, multiplet);
2.22 (4H, broad singlet).

EXAMPLE 290

Methyl N-[4-benzothiazol-2-ylmethoxy)-2-methylphenyl]-N-(4-chlorophenacyl)carbamate
(Compound No. D1.40)

Oil

Nuclear Magnetic Resonance Spectrum (200 MHz, CDCl$_3$), δ ppm:
8.03 (2H, doublet, J=7.4 Hz);
7.88 (3H, doublet, J=8.6 Hz);
7.54–7.34 (4H, multiplet);
6.92–6.81 (2H, multiplet);
5.45 (2H, singlet);
4.88 (2H, AB quartet, J=16.9 Hz, Δv=183.3);
3.69 (3H, singlet);
2.28 (3H, singlet).

EXAMPLE 291

Methyl N-[4-(benzothiazol-2-ylmethoxy)-2-methylphenyl]-N-ethoxycarbonylcarbamate
(Compound No. D1.43).

Oil

Nuclear Magnetic Resonance Spectrum (200 MHz, CDCl$_3$), δ ppm:
8.04 (1H, doublet, J=8.0 Hz);
7.91 (1H, doublet, J=8.1 Hz);
7.55–7.31 (3H, multiplet);
6.92–6.82 (2H, multiplet);
5.46 (2H, singlet);
4.59 (1H, doublet, J=17.4 Hz);
4.21 (2H, quartet, J=7.2 Hz);
3.77 (1H, singlet);
3, 76 (3H, singlet);
2.22 (3H, singlet);
1.27 (3H, triplet, J=7.2 Hz).

EXAMPLE 292

Methyl N-[4-(benzothiazol-2-ylmethoxy)-2-methylphenyl]-N-methylthiomethylcarbamate
(Compound No. D1.62)

Melting Point: 87° to 88° C.

Nuclear Magnetic Resonance Spectrum (200 MHz, CDCl$_3$), δ ppm:
8.07–7.89 (2H, multiplet);
7.56–7.38 (2H, multiplet);
7.19–7.15 (1H, multiplet);
6.95–6.86 (2H, multiplet);
5.48 (2H, singlet);
4.73 (2H, AB quartet, J=13.8 Hz, Δv=111.3);
3.88 (3H, singlet);
3.81–3.61 (3H, multiplet);
2.23 (3H, singlet);
2.20 (3H, singlet).

EXAMPLE 293

Methyl N-[4-(benzothiazol-2-ylmethoxy)-2-methylphenyl]-N-benzyloxymethylcarbamate
(Compound No. D1.67)

Oil

Nuclear Magnetic Resonance Spectrum (200 MHz, CDCl$_3$), δ ppm:
8.05 (1H, doublet of doublets, J=8.0 & 0.7 Hz);
7.91 (1H, doublet of doublets, J=7.6 & 1.7 Hz);
7.52 (1H, triplet of doublets, J=7.6 & 1.4 Hz);
7.41 (1H, triplet of doublets, J=7.5 & 1.3 Hz);
7.33 (5H, multiplet);
7.12 (1H, doublet, J=8.6 Hz);
6.95–6.84 (2H, multiplet);
5.48 (2H, singlet);
5.31 (1H, doublet, J=10.0 Hz);
4.79 (1H, doublet, J=10.3 Hz);
4.69 (2H, broad singlet);
3.70 (3H, singlet);
2.21 (3H, singlet).

EXAMPLE 294

Methyl N-[4-(benzothiazol-2-ylmethoxy)-2-methylphenyl]-N-(2-ethoxyethyl)carbamate
(Compound No. D1.110)

Oil

Nuclear Magnetic Resonance Spectrum (200 MHz, CDCl$_3$), δ ppm:
8.04 (1H, doublet, J=7.9 Hz);
7.91 (1H, doublet of doublets, J=6.9 & 1.0 Hz);
7.51 triplet of doublets, J=7.6 & 1.4 Hz);
7.10 (1H, doublet, J=8.6 Hz);
6.92–6.83 (2H, multiplet);
5.47 (2H, singlet);
4.00–3.70 (2H, multiplet);
3.63 (3H, singlet);
3.60–3.48 (2H, multiplet);
3.44 (2H, quartet, J=7.0 Hz);
2.18 (3H, singlet);
1.14 (3H, triplet, J=7.0 Hz).

EXAMPLE 295

Methyl N-[4-(benzothiazol-2-ylmethoxy)-2-methylphenyl]-N-(2-vinyloxyethyl)carbamate
(Compound No. D1.112)

Oil

Nuclear Magnetic Resonance Spectrum (200 MHz, CDCl$_3$), δ ppm:
8.06–7.88 (2H, multiplet);
7.57–7.35 (2H, multiplet);
7.07 (1H, doublet, J=8.1 Hz);
6.95–6.82 (2H, multiplet);
6.50–6.37 (1H, multiplet);
5.47 (2H, singlet);
4.20–3.92 (2H, multiplet);
3.85–3.56 (4H, multiplet);
3.64 (3H, broad singlet);
2.17 (3H, singlet).

EXAMPLE 296

Methyl N-[4-(benzothiazol-2-ylmethoxy)-2-methylphenyl]-N-(2-propoxyethyl)carbamate
(Compound No. D1.113)

Oil

Nuclear Magnetic Resonance Spectrum (200 MHz, CDCl$_3$), δ ppm:
8.04 (1H, doublet, J=7.7 Hz);
7.91 (1H, doublet, J=8.1 Hz);
7.55–7.37 (1H, multiplet);
7.10 (1H, doublet, J=8.4 Hz);
6.88–6.82 (2H, multiplet);

5.46 (2H, singlet);
3.93–3.75 (2H, multiplet);
3.63–3.49 (5H, multiplet);
3.34 (2H, triplet, J=6.7 Hz);
2.18 (3H, singlet);
1.71–1.48 (2H, multiplet);
0.87 (3H, triplet, J=7.5 Hz).

EXAMPLE 297

Methyl N-[4-(benzothiazol-2-ylmethoxy)-2-methylphenyl]-N-(2-methylthioethyl)carbamate (Compound No. D1.114)

Melting Point: 119° to 120° C.
Nuclear Magnetic Resonance Spectrum (200 MHz, CDCl$_3$), δ ppm:
8.04 (1H, doublet, J=8.8 Hz);
7.92 (1H, doublet, J=7.6 Hz);
7.57–7.35 (2H, multiplet);
7.07 (1H, doublet, J=8.7 Hz);
6.96–6.82 (2H, multiplet);
5.47 (2H, singlet);
4.02–3.40 (2H, multiplet);
3.63 (3H, singlet);
2.65 (2H, triplet, J=7.7 Hz);
2.17 (3H, singlet);
2.13 (3H, singlet).

EXAMPLE 298

Methyl N-[4-(benzothiazol-2-ylmethoxy)-2-methylphenyl]-N-(2-ethylthioethyl)carbamate (Compound No. D1.116)

Oil
Nuclear Magnetic Resonance Spectrum (200 MHz, CDCl$_3$), δ ppm:
8.04 (1H, doublet, J=7.4 Hz);
7.92 (1H, doublet, J=7.6 Hz);
7.56–7.37 (2H, multiplet);
7.07 (1H, broad doublet, J=8.8 Hz);
6.95–6.82 (2H, multiplet);
5.47 (2H, singlet);
4.03–3.38 (2H, multiplet);
3.63 (3H, singlet);
2.80–2.45 (4H, multiplet);
2.19 (1H, singlet).
1.32–1.18 (3H, multiplet).

EXAMPLE 299

Methyl N-[4-(benzothiazol-2-ylmethoxy)-2-methylphenyl]-N-[2-(tetrahydropyran-2-yloxy)ethyl]carbamate (Compound No. D1.119)

Oil
Nuclear Magnetic Resonance Spectrum (200 MHz, CDCl$_3$), δ ppm:
8.04 (1H, doublet, J=7.9 Hz);
7.91 (1H, doublet, J=7.3 Hz);
7.55–7.37 (2H, multiplet);
7.19–6.80 (3H, multiplet);
5.47 (2H, singlet);
4.55 (1H, broad singlet);
4.10–3.39 (6H, multiplet);
3.63 (3H, singlet);
2.18 (3H, singlet);
1.90–1.35 (6H, multiplet).

EXAMPLE 300

N-[4-(Benzothiazol-2-ylmethoxy)-2-methylphenyl]-N-methoxycarbonylpropionamide (Compound No. D2.4)

Oil
Nuclear Magnetic Resonance Spectrum (200 MHz, CDCl$_3$), δ ppm:
8.06–7.89 (2H, multiplet);
7.56–7.38 (2H, multiplet);
6.99–6.91 (3H, multiplet);
5.48 (2H, singlet);
3.71 (3H, singlet);
3.02–2.91 (2H, multiplet);
2.09 (3H, singlet);
1.19 (3H, triplet, J=7.2 Hz).

EXAMPLE 301

N-[4-(Benzoxazol-2-ylmethoxy)-2-methylphenyl]-N-methoxycarbonylpropionamide (Compound No. D2.5)

Oil
Nuclear Magnetic Resonance Spectrum (200 MHz, CDCl$_3$), δ ppm:
7.79–7.75 (1H, multiplet);
7.60–7.55 (1H, multiplet);
7.40–7.36 (2H, multiplet);
6.97–6.93 (3H, multiplet);
5.32 (2H, singlet);
3.71 (3H, singlet);
2.96 (2H, quartet of doublets, J=7.4 & 2.9 Hz);
2.08 (3H, singlet);
1.18 (3H, triplet, J=7.4 Hz).

EXAMPLE 302

N-[4-(Benzothiazol-2-ylmethoxy)-2-methylphenyl]-N-methoxycarbonylbutyramide (Compound No. D2.7)

Oil
Nuclear Magnetic Resonance Spectrum (200 MHz, CDCl$_3$), δ ppm:
8.07–7.89 (2H, multiplet);
7.56–7.41 (2H, multiplet);
6.98–6.91 (3H, multiplet);
5.48 (2H, singlet);
3.71 (3H, singlet);
2.97–2.89 (2H, multiplet);
2.09 (3H, singlet);
1.71 (2H, quartet, J=7.6 Hz);
0.99 (3H, triplet, J=7.2 Hz).

EXAMPLE 303

N-[4-(Benzoxazol-2-ylmethoxy)-2-methylphenyl]-N-methoxycarbonylbutyramide (Compound No. D2.9)

Oil
Nuclear Magnetic Resonance Spectrum (200 MHz, CDCl$_3$), δ ppm:
7.79–7.75 (1H, multiplet);
7.60–7.55 (1H, multiplet);
7.43–7.36 (2H, multiplet);
6.99–6.94 (3H, multiplet);

5.32 (2H, singlet);
3.71 (3H, singlet);
2.93 (2H, triplet of doublets, J=7.3 & 2.0 Hz);
2.09 (3H, singlet);
1.80–1.62 (2H, multiplet);
0.98 (3H, triplet, J=7.3 Hz).

EXAMPLE 304

N-[4-(Benzothiazol-2-ylmethoxy)-2-methylphenyl]-N-methoxycarbonyl-2-methylpropionamide (Compound No. D2.10)

Melting Point: 90° to 92° C.

Nuclear Magnetic Resonance Spectrum (200 MHz, CDCl$_3$), δ ppm:
8.06–7.89 (2H, multiplet);
7.56–7.38 (2H, multiplet);
6.98–6.90 (3H, multiplet);
5.48 (2H, singlet);
3.71 (3H, singlet);
2.09 (3H, singlet);
1.25 (3H, doublet, J=2.0 Hz).

EXAMPLE 305

N-[4-(Benzothiazol-2-ylmethoxy)-2-methylphenyl]-N-methoxycarbonylpentanamide (Compound No. D2.11)

Oil

Nuclear Magnetic Resonance Spectrum (200 MHz, CDCl$_3$), δ ppm:
8.06–7.88 (2H, multiplet);
7.56–7.36 (2H, multiplet);
6.99–6.87 (3H, multiplet);
5.45 (2H, singlet);
3.71 (3H, singlet);
2.95 (2H, triplet of doublets, J=7.4 & 2.3 Hz);
2.09 (3H, singlet);
1.75–1.25 (4H, multiplet);
0.93 (3H, triplet, J=7.3 Hz).

EXAMPLE 306

N-[4-(Benzothiazol-2-ylmethoxy)-2-methylphenyl]-N-methoxycarbonyl-3-methylbutyramide (Compound No. D2.13)

Melting Point: 78° to 80° C.

Nuclear Magnetic Resonance Spectrum (200 MHz, CDCl$_3$), δ ppm:
8.06–7.90 (2H, multiplet);
7.56–7.38 (2H, multiplet);
6.98–6.91 (3H, multiplet);
5.48 (2H, singlet);
3.71 (3H, singlet);
2.84 (2H, doublet, J=6.8 Hz);
2.30–2.15 (1H, multiplet);
2.10 (3H, singlet);
0.99 (6H, doublet, J=6.6 Hz).

EXAMPLE 307

N-[4-(Benzothiazol-2-ylmethoxy)-2-methylphenyl]-N-methoxycarbonylcyclobutanecarboxamide (Compound No. D2.14)

Melting Point: 76° to 78° C.

Nuclear Magnetic Resonance Spectrum (200 MHz, CDCl$_3$), δ ppm:
8.06–7.89 (2H, multiplet);
7.55–7.38 (2H, multiplet);
6.98–6.91 (3H, multiplet);
5.48 (2H, singlet);
4.10–3.91 (1H, multiplet);
3.70 (3H, singlet);
2.46–2.20 (4H, multiplet);
2.08–1.80 (2H, multiplet).

EXAMPLE 308

N-[4-(Benzothiazol-2-ylmethoxy)-2-methylphenyl]-N-methoxycarbonylcyclopentanecarboxamide (Compound No. D2.15)

Oil

Nuclear Magnetic Resonance Spectrum (200 MHz, CDCl$_3$), δ ppm:
8.06–7.89 (2H, multiplet);
7.55–7.37 (2H, multiplet);
6.98–6.90 (3H, multiplet);
5.48 (2H, singlet);
3.85–3.68 (1H, multiplet);
3.71 (3H, singlet);
2.10 (3H, singlet);
1.97–1.53 (8H, multiplet).

EXAMPLE 309

N-[4-(Benzothiazol-2-ylmethoxy)-2-methylphenyl]-N-methoxycarbonylcyclohexanecarboxamide (Compound No. D2.17)

Oil

Nuclear Magnetic Resonance Spectrum (200 MHz, CDCl$_3$), δ ppm:
8.04 (1H, doublet, J=8.1 Hz);
7.91 (1H, doublet, J=8.4 Hz);
7.55–7.37 (2H, multiplet);
6.96–6.89 (3H, multiplet);
5.48 (2H, singlet);
3.71 (3H, singlet);
3.49–3.47 (1H, multiplet);
2.08 (3H, singlet);
2.04–1.23 (10H, multiplet).

EXAMPLE 310

N-[4-(Benzothiazol-2-ylmethoxy)-2-methylphenyl]-N-methoxycarbonyl-2-methoxyacetamide (Compound No. D2.26)

Melting Point: 70° to 73° C.

Nuclear Magnetic Resonance Spectrum (200 MHz, CDCl$_3$), cδ ppm:
8.07–7.90 (2H, multiplet);
7.56–7.38 (2H, multiplet);
7.08–6.89 (3H, multiplet);
5.48 (2H, singlet);
3.72 (3H, singlet);
3.49 (2H, singlet);
2.10 (3H, singlet).

EXAMPLE 311

N-[4-(Benzoxazol-2-ylmethoxy)-2-methylphenyl]-N-methoxycarbonyl-2-methoxyacetamide (Compound No. D2.28)

Oil

Nuclear Magnetic Resonance Spectrum (200 MHz, CDCl$_3$), δ ppm:
7.80–7.75 (1H, multiplet);
7.61–7.56 (1H, multiplet);
7.41–7.36 (2H, multiplet);
6.98–6.94 (3H, multiplet);
5.33 (2H, singlet);
4.71 (2H, singlet);
3.72 (3H, singlet)
3.48 (3H, singlet);
2.09 (3H, singlet).

EXAMPLE 312

N-[4-(Benzothiazol-2-ylmethoxy)-2-methylphenyl]-N-methoxycarbonylbenzamide (Compound No. D2.42)

Melting Point: 112° to 114° C.
Nuclear Magnetic Resonance Spectrum (200 MHz, CDCl$_3$), δ ppm:
8.07–7.90 (2H, multiplet);
7.72–7.40 (2H, multiplet);
7.12 (1H, doublet, J=8.6 Hz);
7.00–6.92 (2H, multiplet);
5.49 (2H, singlet);
3.66 (3H, singlet);
2.27 (3H, singlet).

EXAMPLE 313

N-[4-(Benzoxazol-2-ylmethoxy)-2-methylphenyl]-N-methoxycarbonylbenzamide (Compound No. D2.44)

Oil
Nuclear Magnetic Resonance Spectrum (200 MHz, CDCl$_3$), δ ppm:
8.09–7.67 (3H, multiplet);
7.60–7.36 (6H, multiplet);
7.12 (1H, doublet, J=8.3 Hz);
6.99–6.92 (2H, singlet);
5.33 (2H, singlet);
3.65 (3H, singlet);
2.27 (3H, singlet).

EXAMPLE 314

N-[4-(Benzothiazol-2-ylmethoxy)-2-methylphenyl]-N-methoxycarbonyl-2,4-difluorobenzamide (Compound No. D2.52)

Melting Point: 137° to 139° C.
Nuclear Magnetic Resonance Spectrum (200 MHz, CDCl$_3$), δ ppm:
8.07–7.90 (2H, multiplet);
7.70–7.38 (3H, multiplet);
7.11 (1H, doublet, J=8.4 Hz);
7.03–6.80 (4H, multiplet);
5.50 (2H, singlet);
3.69 (3H, singlet);
2.23 (3H, singlet).

EXAMPLE 315

N-[4-(Benzothiazol-2-ylmethoxy)-2-methylphenyl]-N-methoxycarbonyl-2-methoxybenzamide (Compound No. D2.54)

Melting Point: 126° to 128° C.

Nuclear Magnetic Resonance Spectrum (200 MHz, CDCl$_3$), δ ppm:
8.07–7.90 (2H, multiplet);
7.55–7.39 (3H, multiplet);
7.16–6.89 (5H, multiplet);
5.50 (2H, singlet);
3.88 (3H, singlet);
3.61 (3H, singlet);
2.27 (3H, singlet).

EXAMPLE 316

N-[4-(Benzoxazol-2-ylmethoxy)-2-methylphenyl]-N-methoxycarbonyl-2-methoxybenzamide (Compound No. D2.55)

Amorphous
Nuclear Magnetic Resonance Spectrum (200 MHz, CDCl$_3$), δ ppm:
7.80–7.75 (1H, multiplet);
7.58–7.36 (5H, multiplet);
7.15–6.89 (5H, multiplet);
5.34 (2H, singlet);
3.87 (3H, singlet);
3.60 (3H, singlet);
2.26 (3H, singlet);
3.66 (2H, singlet);
2.41 (3H, singlet);
2.26 (3H, singlet).

EXAMPLE 317

N-[4-(Benzothiazol-2-ylmethoxy)-2-methylphenyl]-N-methoxycarbonyl-4-methylbenzamide (Compound No. D2.61)

Melting Point: 132° to 133° C.
Nuclear Magnetic Resonance Spectrum (200 MHz, CDCl$_3$), δ ppm:
8.06–7.89 (2H, multiplet);
7.61 (2H, doublet of doublets, J=6.5 & 1.8 Hz);
7.55–7.41 (2H, multiplet);
7.27–7.21 (2H, multiplet);
7.11(1H, doublet, J=8.5 Hz);
6.98–6.90 (2H, multiplet);
5.48 (2H, singlet).

EXAMPLE 318

N-[4-(Benzothiazol-2-ylmethoxy)-2-methylphenyl]-N-methoxycarbonyl-3-chlorobenzothiophen-2-carboxamide (Compound No. D2.72)

Melting Point: 155° to 157° C.
Nuclear Magnetic Resonance Spectrum (200 MHz, CDCl$_3$), δ ppm:
8.04 (1H, doublet, J=7.3 Hz);
7.94–7.80 (3H, multiplet);
7.55–7.37 (4H, multiplet);
7.22 (1H, doublet, J=8.5 Hz);
7.01–6.91 (2H, multiplet);
5.49 (2H, singlet);
3.72 (3H, singlet);
2.30 (3H, singlet).

EXAMPLE 319

Methyl N-[4-(benzothiazol-2-ylmethoxy)-2-methylphenyl]-N-methoxycarbonylcarbamate (Compound No. D2.73)

Melting Point: 163° to 166° C.

Nuclear Magnetic Resonance Spectrum (200 MHz, CDCl$_3$), δ ppm:
8.07–7.90 (2H, multiplet);
7.52–7.41 (2H, multiplet);
7.05 (1H, doublet, J=8.6 Hz);
6.95–6.88 (2H, multiplet);
5.48 (2H, singlet);
3.76 (6H, singlet);
2.16 (3H, singlet).

EXAMPLE 320

Methyl N-[4-(benzoxazol-2-ylmethoxy)-2-methylphenyl]-N-methoxycarbonylcarbamate (Compound No. D2.74)

Melting Point: 141° to 144° C.
Nuclear Magnetic Resonance Spectrum (200 MHz, CDCl$_3$), δ ppm:
7.80–7.75 (1H, multiplet);
7.60–7.55 (1H, multiplet);
7.41–7.36 (2H, multiplet);
7.04 (1H, doublet, J=8.4 Hz);
6.95–6.90 (2H, multiplet);
5.32 (2H, singlet);
3.75 (3H, singlet);
2.15 (3H, singlet).

EXAMPLE 321

Methyl N-[4-(benzothiazol-2-ylmethoxy)-2-methylphenyl]-N-ethoxycarbonylcarbamate (Compound No. D2.75).

Melting Point: 84° to 86° C.
Nuclear Magnetic Resonance Spectrum (200 MHz, CDCl$_3$), δ ppm:
8.07–8.02 (1H, multiplet);
7.94–7.89 (1H, multiplet);
7.52–7.42 (2H, multiplet);
7.04 (1H, doublet, J=8.4 Hz);
6.95–6.87 (2H, multiplet);
5.48 (2H, multiplet);
4.24–4.20 (2H, multiplet);
3.76 (3H, singlet);
2.16 (3H, singlet);
1.21 (triplet, J=7.1 Hz).

EXAMPLE 322

Methyl N-[4-(benzoxazol-2-ylmethoxy)-2-methylphenyl]-N-ethoxycarbonylcarbamate (Compound No. D2.76).

Oil
Nuclear Magnetic Resonance Spectrum (200 MHz, CDCl$_3$), δ ppm:
7.79–7.75 (1H, multiplet);
7.59–7.55 (1H, multiplet);
7.40–7.35 (2H, multiplet);
7.04 (1H, doublet, J=8.5 Hz);
6.95–6.87 (2H, multiplet);
5.32 (2H, singlet);
4.21 (2H, quartet of doublets, J=7.1 & 2.2 Hz);
3.75 (3H, singlet);
2.15 (3H, singlet);
1.20 (3H, triplet, J=7.1 Hz).

EXAMPLE 323

Methyl N-[4-(benzothiazol-2-ylmethoxy)-2-methylphenyl]-N-propoxycarbonylcarbamate (Compound No. D2.77)

Oil
Nuclear Magnetic Resonance Spectrum (200 MHz, CDCl$_3$), δ ppm:
8.07–8.01 (1H, multiplet);
7.93–7.88 (1H, multiplet);
7.56–7.38 (2H, multiplet);
7.06–6.85 (3H, multiplet);
5.48 (2H, singlet);
4.10 (2H, triplet, J=6.6 Hz);
3.76 (3H, singlet);
2.16 (3H, singlet);
1.62–1.50 (2H, multiplet);
0.79 (3H, triplet, J=7.3 Hz).

EXAMPLE 324

Methyl N-[4-(benzoxazol-2-ylmethoxy)-2-methylphenyl]-N-propoxycarbonylcarbamate (Compound No. D2.78)

Oil
Nuclear Magnetic Resonance Spectrum (200 MHz, CDCl$_3$), δ ppm:
7.79–7.75 (1H, multiplet);
7.59–7.55 (1H, multiplet);
7.43–7.35 (2H, multiplet);
7.04 (1H, doublet, J=8.3 Hz);
6.95–6.87 (2H, multiplet);
5.32 (2H, singlet);
4.10 (2H, triplet, J=6.6 Hz);
3.75 (3H, singlet);
2.15 (3H, singlet);
1.59–1.51 (2H, multiplet);
0.78 (3H, triplet, J=7.4 Hz).

EXAMPLE 325

Methyl N-[4-(benzothiazol-2-ylmethoxy)-2-methylphenyl]-N-isopropoxycarbonylcarbamate (Compound No. D2.79)

Oil
Nuclear Magnetic Resonance Spectrum (200 MHz, CDCl$_3$), δ ppm:
8.04 (1H, doublet of doublets, J=8.1 & 0.7 Hz);
7.92 (1H, doublet, J=8.4 Hz);
7.55–7.41 (2H, multiplet);
7.03 (1H, doublet, J=8.6 Hz);
6.93–6.85 (2H, multiplet);
5, 48 (2H, singlet);
5.00 (1H, quintet, J=6.4 Hz);
3.75 (3H, singlet);
2.16 (3H, singlet);
1.20 (3H, singlet);
1.17 (3H, singlet).

EXAMPLE 326

Methyl N-[4-(benzothiazol-2-ylmethoxy)-2-methylphenyl]-N-butoxycarbonylcarbamate (Compound No. D2.80)

Oil

Nuclear Magnetic Resonance Spectrum (200 MHz, CDCl$_3$), δ ppm:
8.04 (1H, doublet, J=8.0 Hz);
7.91 (1H, doublet of doublets, J=7.7 & 2.2 Hz);
7.56–7.42 (2H, multiplet);
7.05–6.85 (3H, multiplet);
5.48 (2H, singlet);
3.76 (3H, singlet);
2.15 (3H, singlet);
1.56–1.46 (2H, multiplet);
1.27–1.20 (2H, multiplet);
0.82 (3H, triplet, J=7.3 Hz).

EXAMPLE 327

Methyl N-[4-(benzoxazol-2-ylmethoxy)-2-methylphenyl]-N-butoxycarbonylcarbamate (Compound No. D2.81)

Oil

Nuclear Magnetic Resonance Spectrum (200 MHz, CDCl$_3$), δ ppm:
7.79–7.75 (1H, multiplet);
7.60–7.55 (1H, multiplet);
7.43–7.36 (2H, multiplet);
7.03 (1H, doublet, J=8.5 Hz);
6.96–6.87 (2H, multiplet);
5.32 (2H, multiplet);
4.14 (2H, triplet, J=6.6 Hz);
3.76 (3H, singlet);
2.15 (3H, singlet);
1.60–1.46 (2H, multiplet);
1.31–1.13 (2H, multiplet);
0.83 (3H, triplet, J=7.2 Hz).

EXAMPLE 328

Methyl N-[4-(benzothiazol-2-ylmethoxy)-2-methylphenyl]-N-isobutoxycarbonylcarbamate (Compound No. D2.82)

Oil

Nuclear Magnetic Resonance Spectrum (200 MHz, CDCl$_3$), δ ppm:
8.04 (1H, doublet of doublets, J=7.3 & 1.3 Hz);
7.93–7.89 (1H, multiplet);
7.52–7.41 (2H, multiplet);
7.07–6.89 (3H, multiplet);
5.48 (2H, singlet);
3.91 (2H, doublet, J=6.4 Hz);
3.78 (3H, singlet);
2.16 (3H, singlet);
1.80–1.70 (1H, multiplet);
0.73 (3H, singlet);
0.77 (3H, singlet).

EXAMPLE 329

Methyl N-[4-(benzothiazol-2-ylmethoxy)-2-methylphenyl]-N-(2,2,2-trichloroethoxycarbonyl)carbamate (Compound No. D2.83)

Oil

Nuclear Magnetic Resonance Spectrum (200 MHz, CDCl$_3$), δ ppm:
8.06–7.88 (2H, multiplet);
7.55–7.37 (2H, multiplet);
7.08 (1H, doublet, J=8.6 Hz);
6.95–6.86 (2H, multiplet);
5.49 (2H, singlet);
4.74 (2H, singlet);
3.80 (3H, singlet).
2.20 (3H, singlet).

EXAMPLE 330

Methyl N-[4-(benzoxazol-2-ylmethoxy)-2-methylphenyl]-N-(2,2,2-trichloroethoxycarbonyl)carbamate (Compound No. D.2.84)

Melting Point: 102° to 105° C.

Nuclear Magnetic Resonance Spectrum (200 MHz, CDCl$_3$), δ ppm:
7.79–7.75 (1H, multiplet);
7.59–7.55 (1H, multiplet);
7.41–7.36 (2H, multiplet);
7.09 (1H, doublet, J=8.4 Hz);
6.97–6.90 (2H, multiplet);
5.33 (2H, singlet);
4.74 (2H, singlet);
3.80 (3H, singlet);
2.20 (3H, singlet).

EXAMPLE 331

Methyl N-[4-(benzothiazol-2-ylmethoxy)-2-methylphenyl]-N-phenoxycarbonylcarbamate (Compound No. D2.85)

Oil

Nuclear Magnetic Resonance Spectrum (200 MHz, CDCl$_3$), δ ppm:
8.05 (1H, doublet of doublets, J=7.3 & 1.4 Hz);
7.93–7.89 (1H, multiplet),
7.55–7.29 (5H, multiplet);
7.25–6.96 (5H, multiplet);
5.30 (2H, singlet);
3.81 (3H, singlet);
2.29 (3H, singlet).

EXAMPLE 332

Methyl N-[4-(benzothiazol-2-ylmethoxy)-2-fluorophenyl]carbamate (Compound No. C9.4)

Melting Point: 124° to 127° C.

Nuclear Magnetic Resonance Spectrum (200 MHz, CDCl$_3$), δ ppm:
8.04 (1H, doublet, J=8.1 Hz);
7.96–7.81 (2H, multiplet);
7.55–7.38 (2H, multiplet);
6.85–6.79 (2H, multiplet);
6.64 (1H, broad singlet);
5.45 (2H, singlet);
3.78 (3H, singlet).

EXAMPLE 333

Methyl N-[4-(benzothiazol-2-ylmethoxy)-3-fluorophenyl]carbamate (Compound No. C9.23)

Melting Point: 112° to 115° C.

Nuclear Magnetic Resonance Spectrum (200 MHz, CDCl$_3$), δ ppm:
8.03 (1H, doublet, J=8.0 Hz);
7.91 (1H, doublet, J=8.0 Hz);
7.55–7.35 (3H, multiplet);
7.03 (1H, triplet, J=8.6 Hz);
6.92 (1H, doublet of doublets, J=8.6 & 2.3 Hz);
6.55 (1H, broad singlet);
5.51 (2H, singlet);
3.77 (3H, singlet).

EXAMPLE 334

Methyl N-[4-(benzothiazol-2-ylmethoxy)-3-nitrophenyl]carbamate (Compound No. C10.64)

Melting Point: 198° to 200° C.

Nuclear Magnetic Resonance Spectrum (200 MHz, DMSO-d6), δ ppm:
9.80 (1H, broad singlet);
8.16 (1H, doublet, J=2.6 Hz);
8.04–7.97 (2H, multiplet);
7.69 (1H, doublet of doublets, J=9.0 & 2.6 Hz);
7.55–7.40 (2H, multiplet);
7.35 (1H, doublet, J=9.0 Hz);
5.65 (2H, singlet);
3.73 (3H, singlet).

EXAMPLE 335

Methyl N-[4-(4-methylbenzothiazol-2-ylmethoxy)phenyl]carbamate (Compound No. F1.3)

Melting Point: 147° to 150° C.

Nuclear Magnetic Resonance Spectrum (200 MHz, CDCl$_3$), δ ppm:
7.75–7.70 (1H, multiplet);
7.35–7.26 (4H, multiplet);
7.00 (2H, doublet of doublets, J=6.8 & 2.3 Hz);
6.47–6.46 (1H, broad multiplet);
5.47 (2H, singlet);
3.76 (3H, singlet);
2.76 (3H, singlet).

EXAMPLE 336

Methyl N-[4-(4-methoxybenzothiazol-2-ylmethoxy)phenyl]carbamate (Compound No. F3.3)

Melting Point: 117° to 120° C.

Nuclear Magnetic Resonance Spectrum (200 MHz, CDCl$_3$), δ ppm:
7.50–7.20 (4H, multiplet);
7.01–6.90 (3H, multiplet);
6.46 (1H, broad singlet);
5.47 (2H, singlet);
4.07 (3H, singlet);
3.78 (3H, singlet).

EXAMPLE 337

Methyl N-[4-(6-methoxybenzothiazol-2-ylmethoxy)phenyl]carbamate (Compound No. F3.22)

Melting Point: 118° to 120° C.

Nuclear Magnetic Resonance Spectrum (200 MHz, CDCl$_3$), δ ppm:
7.90 (1H, doublet, J=8.9 Hz);
7.33 (1H, doublet, J=2.7 Hz);
7.28–7.26 (3H, multiplet);
7.12–7.06 (1H, multiplet);
6.99 (2H, doublet of doublets, J=6.8 & 2.3 Hz);
6.48–6.47 (1H, broad multiplet);
5.41 (2H, singlet);
3.88 (3H, singlet);
3.76 (3H, singlet).

EXAMPLE 338

Methyl N-[4-(7-methoxybenzothiazol-2-ylmethoxy)phenyl]carbamate (Compound No. F3.31)

Melting Point: 174° to 176° C.

Nuclear Magnetic Resonance Spectrum (200 MHz, CDCl$_3$), δ ppm:
7.67–7.63 (1H, multiplet);
7.44 (1H, triplet, J=8.1 Hz);
7.32–7.26 (3H, multiplet);
6.99 (2H, doublet of doublets, J=6.8 & 2.3 Hz);
6.84 (1H, doublet, J=7.3 Hz);
6.48–6.47 (1H, broad multiplet);
5.45 (2H, singlet);
3.98 (3H, singlet);
3.76 (3H, singlet).

EXAMPLE 339

Methyl N-[4-(5-fluorobenzothiazol-2-ylmethoxy)phenyl]carbamate (Compound No. F4.12)

Melting Point: 174° to 176° C.

Nuclear Magnetic Resonance Spectrum (200 MHz, CDCl$_3$), δ ppm:
7.82 (1H, doublet of doublets, J=8.8 & 5.0 Hz);
7.70 (1H, doublet of doublets, J=9.6 & 2.7 Hz);
7.15 (4H, multiplet);
7.18 (1H, triplet of doublets, J=8.8 & 2.7 Hz);
6.50 (1H, broad singlet);
5.45 (2H, singlet);
3.76 (3H, singlet).

EXAMPLE 340

Methyl N-[4-(5-fluorobenzoxazol-2-ylmethoxy)phenyl]carbamate (Compound No. F4.14)

Melting Point: 133° to 134° C.

Nuclear Magnetic Resonance Spectrum (200 MHz, CDCl$_3$), δ ppm:
7.53–7.41 (2H, multiplet);
7.34–7.25 (3H, multiplet);
7.16–7.05 (1H, multiplet);
7.00 (2H, doublet of doublets, J=6.8 & 2.3 Hz);
6.49–6.48 (1H, broad multiplet);
5.28 (2H, singlet);
3.76 (3H, singlet).

EXAMPLE 341

Methyl N-[4-(6-fluorobenzoxazol-2-ylmethoxy)phenyl]carbamate (Compound No. F4.33)

Melting Point: 120° to 122° C.

Nuclear Magnetic Resonance Spectrum (200 MHz, CDCl$_3$), δ ppm:

7.68 (1H, doublet of doublets, J=8.8 & 5.0 Hz);
7.34–7.26 (3H, multiplet);
7.16–7.06 (1H, multiplet);
7.01 (2H, doublet of doublets, J=6.8 & 2.3 Hz);
6.49–6.48 (1H, broad multiplet);
5.27 (2H, singlet);
3.76 (3H, singlet).

EXAMPLE 342

Methyl N-[4-(7-fluorobenzothiazol-2-ylmethoxy)phenyl]carbamate (Compound No. F4.41)

Melting Point: 136° to 139° C.

Nuclear Magnetic Resonance Spectrum (200 Mz, CDCl$_3$), δ ppm:
7.83 (1H, doublet, J=8.3 Hz);
7.51–7.41 (1 H, multiplet);
7.32 (2H, doublet, J=9.0 Hz);
7.12 (1H, triplet, J=8.3 Hz);
6.99 (2H, doublet, J=9.0 Hz);
6.54 (1H, broad singlet);
5.46 (2H, singlet);
3.76 (3H, singlet).

EXAMPLE 343

Methyl N-[4-(7-fluorobenzoxazol-2-ylmethoxy)phenyl]carbamate (Compound No. F4.43)

Melting Point: 120° to 123° C.

Nuclear Magnetic Resonance Spectrum (200 MHz, CDCl$_3$), δ ppm:
7.55 (1H, doublet of doublets, J=7.9 & 1.0 Hz);
7.35–7.25 (2H, multiplet);
7.18–7.05 (1H, multiplet);
7.02 (2H, doublet of doublets, J=6.8 & 2.3 Hz);
6.50 (1H, broad singlet);
5.31 (2H, singlet);
3.76 (3H, singlet).

EXAMPLE 344

Methyl N-[4-(5-chlorobenzothiazol-2-ylmethoxy)phenyl]carbamate (Compound No. F4.61)

Melting Point: 211° to 213° C.

Nuclear Magnetic Resonance Spectrum (200 MHz, CDCl$_3$), δ ppm:
8.01 (1H, doublet, J=2.2 Hz);
7.81 (1H, doublet, J=8.3 Hz);
7.41–7.26 (3H, multiplet);
6.98 (2H, doublet of doublets, J=6.8 & 2.3 Hz);
6.48–6.47 (1H, broad multiplet);
5.44 (2H, singlet);
3.76 (3H, singlet).

EXAMPLE 345

Methyl N-[4-(6-chlorobenzothiazol-2-ylmethoxy)phenyl]carbamate (Compound No. F4.71)

Melting Point 195° to 197° C.

Nuclear Magnetic Resonance Spectrum (200 MHz, CDCl$_3$), δ ppm:
7.93 (1H, doublet, J=4.5 Hz);
7.87 (1H, doublet, J=2.3 Hz);
7.59 (1H, doublet of doublets, J=8.8 & 2.2 Hz);
7.34–7.26 (2H, multiplet);
6.98 (2H, doublet of doublets, J=6.8 & 2.3 Hz);
6.49–6.45 (1H, broad multiplet);
5.44 (2H, singlet);
3.76 (3H, singlet).

EXAMPLE 346

Methyl N-[4-(7-chlorobenzothiazol-2-ylmethoxy)phenyl]carbamate (Compound No. F4.81)

Melting Point: 159° to 162° C.

Nuclear Magnetic Resonance Spectrum (200 MHz, CDCl$_3$), δ ppm:
7.92 (1H, doublet of doublets, J=7.4 & 1.8 Hz);
7.49–7.26 (4H, multiplet);
7.00 (2H, doublet of doublets, J=6.8 & 2.3 Hz);
6.49–6.45 (1H, broad multiplet);
5.45 (2H, singlet);
3.76 (3H, singlet).

EXAMPLE 347

Methyl N-[4-(4-trifluoromethylbenzothiazol-2-ylmethoxy)phenyl]carbamate (Compound No. F5.3)

Melting Point: 179° to 180° C.

Nuclear Magnetic Resonance Spectrum (200 MHz, CDCl$_3$), δ ppm:
8.10 (1H, doublet, J=8.0 Hz);
7.80 (1H, doublet, J=8.0 Hz);
7.48 (1H, triplet, J=8.0 Hz);
7.32 (2H, doublet, J=8.8 Hz);
6.99 (2H, doublet, J=8.8 Hz);
6.48 (1H, broad singlet);
5.53 (2H, singlet);
3.77 (3H, singlet).

EXAMPLE 348

Methyl N-[2-methyl-4-(4-methylbenzothiazol-2-ylmethoxy)phenyl]carbamate (Compound No. G1.3)

Melting Point: 153° to 155° C.

Nuclear Magnetic Resonance Spectrum (200 MHz, CDCl$_3$), δ ppm:
7.75–7.70 (1H, multiplet);
7.60–7.51 (1H, broad multiplet);
7.34–7.26 (2H, multiplet);
6.92–6.85 (2H, multiplet);
6.21–6.19 (1H, broad multiplet);
5.47 (2H, singlet);
3.76 (3H, singlet);
2.76 (3H, singlet);
2.24 (3H, singlet).

EXAMPLE 349

Methyl N-[2-methyl-4-(5-methylbenzothiazol-2-ylmethoxy)phenyl]carbamate (Compound No. G1.8)

Melting Point: 131° to 133° C.

Nuclear Magnetic Resonance Spectrum (200 MHz, CDCl$_3$), δ ppm:
7.82–7.74 (3H, multiplet);
7.55–7.50 (1H, broad multiplet);
6.89–6.87 (2H, multiplet);
6.20–6.18 (1H, broad singlet);
5.44 (2H, singlet);
3.76 (3H, singlet);

2.51 (3H, singlet);
2.23 (3H, singlet).

EXAMPLE 350

Methyl N-[2-methyl-4-(6-methylbenzothiazol-2-ylmethoxy)phenyl]carbamate (Compound No. G1.13)

Melting Point: 153° to 155° C.

Nuclear Magnetic Resonance Spectrum (200 MHz, $CDCl_3$), δ ppm:
7.90 (1H, doublet, J=8.3 Hz);
7.68 (1H, doublet, J=8.9 Hz);
7.55–7.49 (1H, broad multiplet);
7.33–7.26 (1H, multiplet);
6.90–6.87 (2H, multiplet);
6.19 (1H, broad singlet);
5.43 (2H, singlet);
3.76 (3H, singlet);
2.49 (3H, singlet);
2.23 (3H, singlet).

EXAMPLE 351

Methyl N-[4-(4-methoxybenzothiazol-2-ylmethoxy)-2-methylphenyl]carbamate (Compound No. G1.30)

Melting Point: 125° to 126° C.

Nuclear Magnetic Resonance Spectrum (200 MHz, $CDCl_3$), δ ppm:
7.50–7.24 (3H, multiplet);
6.96–6.82 (3H, multiplet);
6.28 (1H, broad singlet);
5.48 (2H, singlet);
4.07 (3H, singlet);
3.77 (3H, singlet);
2.23 (3H, singlet).

EXAMPLE 352

Methyl N-[4-(5-methoxybenzothiazol-2-ylmethoxy)-2-methylphenyl]carbamate (Compound No. G1.34)

Melting Point: 159° to 161° C.

Nuclear Magnetic Resonance Spectrum (200 MHz, $CDCl_3$), δ ppm:
7.73 (1H, doublet, J=8.8 Hz);
7.57–7.50 (1H, broad multiplet);
7.51 (1H, doublet, J=2.3 Hz);
7.05 (1H, doublet of doublets, J=8.8 & 2.5 Hz);
6.89–6.86 (2H, multiplet);
6.20 (1H, broad singlet);
5.43 (2H, singlet);
3.90 (3H, singlet);
3.76 (3H, singlet);
2.24 (3H, singlet).

EXAMPLE 353

Methyl N-[4-(7-methoxybenzothiazol-2-ylmethoxy)-2-methylphenyl]carbamate (Compound No. G1.44)

Melting Point: 150° to 151° C.

Nuclear Magnetic Resonance Spectrum (200 MHz, $CDCl_3$), δ ppm:
7.67–7.63 (1H, multiplet);
7.53–7.45 (1H, broad multiplet);
7.44 (1H, triplet, J=8.1 Hz);
6.90–6.82 (3H, multiplet);
6.19 (1H, broad singlet);
5.44 (2H, singlet);
3.98 (3H, singlet);
3.76 (3H, singlet);
2.23 (3H, singlet).

EXAMPLE 354

Methyl N-[4-(4-fluorobenzothiazol-2-ylmethoxy)-2-methylphenyl]carbamate (Compound No. G1.52)

Melting Point: 165° to 167° C.

Nuclear Magnetic Resonance Spectrum (200 MHz, $CDCl_3$), δ ppm:
7.67 (1H, doublet, J=7.9 Hz);
7.43–7.15 (3H, multiplet);
6.88–6.86 (2H, multiplet);
6.23–6.18 (1H, broad multiplet);
5.48 (2H, singlet);
3.76 (3H, singlet);
2.24 (3H, singlet).

EXAMPLE 355

Methyl N-[4-(7-fluorobenzothiazol-2-ylmethoxy)-2-methylphenyl]carbamate (Compound No. G1.67)

Melting Point: 121° to 122° C.

Nuclear Magnetic Resonance Spectrum (200 Mz, $CDCl_3$), δ ppm:
7.83 (1H, doublet, J=8.4 Hz);
7.56–7.40 (2H, multiplet);
7.12 (1H, triplet, J=8.4 Hz);
6.91–6.83 (2H, multiplet);
6.23 (1H, broad singlet);
5.45 (2H, singlet);
3.76 (3H, singlet);
2.24 (3H, singlet).

EXAMPLE 356

Methyl N-[4-(5-chlorobenzothiazol-2-ylmethoxy)-2-methylphenyl]carbamate (Compound No. G1.74)

Melting Point: 179° to 182° C.

Nuclear Magnetic Resonance Spectrum (200 MHz, $CDCl_3$), δ ppm:
8.01 (1H, doublet, J=1.9 Hz);
7.81 (1H, doublet, J=8.2 Hz);
7.59–7.50 (1H, broad multiplet);
7.41–7.36 (1H, multiplet);
6.88–6.85 (2H, multiplet);
6.21–6.15 (1H, broad multiplet);
5.44 (2H, singlet);
3.76 (3H, singlet);
2.24 (3H, singlet).

EXAMPLE 357

Methyl N-[4-(6-chlorobenzothiazol-2-ylmethoxy)-2-methylphenyl]carbamate (Compound No. G1.81)

Melting Point: 150° to 152° C.

Nuclear Magnetic Resonance Spectrum (200 MHz, $CDCl_3$), δ ppm:
7.95–7.87 (2H, multiplet);
7.60–7.50 (1H, broad multiplet);
7.46 (1H, doublet of doublets, J=8.6 & 2.0 Hz);

6.88–6.85 (2H, multiplet);
6.21–6.20 (1H, broad multiplet);
5.43 (2H, singlet);
3.76 (3H, singlet);
2.24 (3H, singlet).

EXAMPLE 358

Methyl N-[4-(7-chlorobenzothiazol-2-ylmethoxy)-2-methylphenyl]carbamate (Compound No. G1.85)

Melting Point: 135° to 137° C.

Nuclear Magnetic Resonance Spectrum (200 MHz, $CDCl_3$), δ ppm:
7.92 (1H, doublet of doublets, J=7.4 & 1.7 Hz);
7.60–7.49 (1H, broad multiplet);
7.49–7.38 (2H, multiplet);
6.89–6.86 (2H, multiplet);
6.22–6.18 (1H, broad multiplet);
5.44 (2H, singlet);
3.76 (3H, singlet);
2.24 (3H, singlet).

EXAMPLE 359

Methyl N-[2-methyl-4-(4-trifluoromethylbenzothiazol-2-ylmethoxy)phenyl]carbamate (Compound No. G1.89)

Melting Point: 180° to 181° C.

Nuclear Magnetic Resonance Spectrum (200 MHz, $CDCl_3$), δ ppm:
8.10 (1H, doublet, J=8.0 Hz);
7.80 (1H, doublet, J=8.0 Hz);
7.57–7.49 (1H, multiplet);
7.48 (1H, triplet, J=8.0 Hz);
6.91–6.86 (2H, multiplet);
6.21 (1H, broad singlet);
5.53 (2H, singlet);
3.76 (3H, singlet);
2.24 (3H, singlet).

EXAMPLE 360

Methyl N-[2-methyl-4-(5-trifluoromethylbenzothiazol-2-ylmethoxy)phenyl]carbamate (Compound No. G1.94)

Melting Point: 173° to 176° C.

Nuclear Magnetic Resonance Spectrum (200 MHz, $CDCl_3$), δ ppm:
8.29 (1H, singlet);
8.01 (1H, doublet, J=9.0 Hz);
7.66–7.47 (2H, multiplet);
6.86 (2H, multiplet);
6.25 (1H, broad singlet);
5.47 (2H, singlet);
2.25 (3H, singlet).

EXAMPLE 361

Methyl N-[2-methyl-4-(6-trifluoromethylbenzothiazol-2-ylmethoxy)phenyl]carbamate (Compound No. G1.99)

Melting Point: 165° to 168° C.

Nuclear Magnetic Resonance Spectrum (200 MHz, $CDCl_3$), δ ppm:
8.20–8.09 (2H, multiplet);
7.77–7.71 (1H, multiplet);
7.60–7.58 (1H, multiplet);
6.91–6.85 (2H, multiplet);
6.22–6.20 (1H, broad multiplet);
5.47 (2H, singlet);
3.76 (3H, singlet);
2.24 (3H, singlet).

EXAMPLE 362

Methyl N-[4-(5-fluorobenzothiazol-2-ylmethoxy)-2-methoxyphenyl]carbamate (Compound No. G8.33)

Melting Point: 159° to 162° C.

Nuclear Magnetic Resonance Spectrum (200 MHz, $CDCl_3$), δ ppm:
7.95 (1H, broad doublet);
7.82 (1H, doublet of doublets, J=8.8 & 5.1 Hz);
7.71 (1H, doublet of doublets, J=9.5 & 2.5 Hz);
7.18 (1H, triplet of doublets, J=8.8 & 2.5 Hz);
7.01 (1H, broad singlet);
6.61 (1H, singlet);
6.59(1H, doublet of doublets, J=9.5 & 5.1 Hz);
5.45 (2H, singlet);
3.76 (3H, singlet).

EXAMPLE 363

Ethyl N-[4-(5-fluorobenzothiazol-2-ylmethoxy)-2-methoxyphenyl]carbamate (Compound No. G8.36)

Melting Point: 157° to 159° C.

Nuclear Magnetic Resonance Spectrum (200 MHz, $CDCl_3$), δ ppm:
8.00 (1H, broad doublet, J=7.9 Hz);
7.82 (1H, doublet of doublets, J=8.8 & 5.1 Hz);
7.71 (1H, doublet of doublets, J=9.5 & 2.4 Hz);
7.18 (1H, triplet of doublets, J=8.8 & 2.5 Hz);
6.99 (1H, broad singlet);
6.62–6.56 (2H, multiplet);
5.45 (2H, singlet);
4.21 (2H, quartet, J=7.2 Hz);
3.86 (3H, singlet);
1.31 (3H, triplet, J=7.2 Hz).

EXAMPLE 364

Methyl N-[4-(benzothiazol-2-ylmethoxy)-2-trifluoromethylphenyl]carbamate (Compound No. C 10.4)

Melting Point: 133° to 135° C.

Nuclear Magnetic Resonance Spectrum (200 MHz, $CDCl_3$), δ ppm:
8.07–7.89 (3H, multiplet);
7.52–7.42 (2H, multiplet);
7.29–7.20 (2H, multiplet);
6.81 (1H, broad singlet);
5.50 (2H, singlet);
3.78 (3H, singlet).

EXAMPLE 365

Methyl N-[4-(benzothiazol-2-ylmethoxy)-2-nitrophenyl]carbamate (Compound No. C 10.48)

Melting Point: 184° to 186° C.

Nuclear Magnetic Resonance Spectrum (200 MHz, $CDCl_3$), δ ppm:

9.65 (1H, broad singlet);
8.51 (1H, doublet, J=9.2 Hz);
8.08–8.04 (1H, multiplet);
7.94–7.85 (2H, multiplet);
7.53–7.36 (3H, multiplet);
5.52 (2H, singlet);
3.82 (3H, singlet).

EXAMPLE 366

Methyl N-[4-(benzoxazol-2-ylmethoxy)phenyl]carbamate (Compound No. A1.6)

Melting Point: 115° to 118° C.

Nuclear Magnetic Resonance Spectrum (200 MHz, CDCl$_3$), δ ppm:
7.78–7.74 (1H, multiplet);
7.58–7.54 (1H, multiplet);
7.42–7.29 (4H, multiplet);
7.02 (2H, doublet, J=9.0 Hz);
6.54 (1H, broad singlet);
5.30 (2H, singlet);
3.75 (3H, singlet).

EXAMPLE 367

Methyl N-[4-(benzoxazol-2-ylmethylthio)phenyl]carbamate (Compound No. A1.8)

Melting Point: 94° to 95° C.

Nuclear Magnetic Resonance Spectrum (200 MHz, CDCl$_3$), δ ppm:
7.69–7.62 (1H, multiplet);
7.54–7.47 (1H, multiplet);
7.44–7.24 (6H, multiplet);
6.60 (1H, broad singlet);
4.23 (2H, singlet);
3.77 (3H, singlet).

EXAMPLE 368

Methyl N-[4-(benzothiazol-2-ylmethoxy)-3-methylphenyl]carbamate (Compound No. C1.55)

Melting Point: 125° to 126° C.

Nuclear Magnetic Resonance Spectrum (200 MHz, CDCl$_3$), δ ppm:
8.03 (1H, broad doublet, J=7.3 Hz);
7.91 (1H, broad doublet, J=7.4 Hz);
7.55–7.36 (2H, multiplet);
7.22 (1H, broad singlet);
7.17–7.11 (1H, multiplet);
6.86 (1H, doublet, J=8.8 Hz);
6.44 (1H, broad singlet);
5.46 (2H, singlet);
3.76 (3H, singlet);
2.35 (3H, singlet).

EXAMPLE 369

Methyl N-[4-(benzothiazol-2-ylmethoxy)-2-ethylphenyl]carbamate (Compound No. C2.4)

Melting Point: 140° to 141° C.

Nuclear Magnetic Resonance Spectrum (200 MHz, CDCl$_3$), δ ppm:
8.03 (1H, doublet of doublets, J=8.7 & 1.5 Hz);
7.90 (1H, doublet of doublets, J=8.2 & 2.1 Hz);
7.51–7.40 (3H, multiplet);
6.92–6.86 (2H, multiplet);
6.21 (1H, broad singlet);
5.47 (2H, singlet);
3.75 (3H, singlet);
2.58 (2H, quartet, J=7.4 Hz);
1.21 (3H, triplet, J=7.4 Hz).

EXAMPLE 370

Methyl N-[4-(benzothiazol-2-ylmethoxy)-2-isopropylphenyl]carbamate (Compound No. C3.32)

Melting Point: 113° to 114° C.

Nuclear Magnetic Resonance Spectrum (200 MHz, CDCl$_3$), δ ppm:
8.03 (1H, doublet, J=8.0 Hz);
7.91 (1H, doublet, J=8.0 Hz);
7.54–7.37 (3H, multiplet);
6.98 (1H, doublet, J=2.9 Hz);
6.86 (1H, doublet of doublets, J=8.6 & 2.8 Hz);
6.23 (1H, broad singlet);
5.47 (2H, singlet);
3.78 (3H, singlet);
3.05 (1H, heptet, J=6.9 Hz);
1.22 (6H, doublet, J=6.9 Hz).

EXAMPLE 371

Methyl N-[4-(benzothiazol-2-ylmethoxy)-2-t-butylphenyl]carbamate (Compound No. C4.29)

Melting Point: 162° to 164° C.

Nuclear Magnetic Resonance Spectrum (200 MHz, CDCl$_3$), δ ppm:
8.04 (1H, doublet, J=7.7 Hz);
7.91 (1H, doublet, J=8.1 Hz);
7.54–7.34 (3H, multiplet);
7.10–7.09 (1H, multiplet);
6.89–6.84 (1H, multiplet);
6.29 (1H, broad singlet);
5.46 (2H, singlet);
3.75 (3H, singlet);
1.38 (9H, singlet).

EXAMPLE 372

Methyl N-[4-(benzothiazol-2-ylmethoxy)-2-chlorophenyl]carbamate (Compound No. C9.39)

Melting Point: 173.5° to 174.5° C.

Nuclear Magnetic Resonance Spectrum (200 MHz, CDCl$_3$), δ ppm:
8.04 (1H, broad doublet, J=7.8 Hz);
7.91 (1H, doublet, J=7.7 Hz);
7.66–7.31 (3H, multiplet);
7.09 (1H, doublet, J=2.9 Hz);
6.98 (1H, doublet of doublets, J=9.1 & 2.9 Hz);
6.92 (1H, broad singlet);
5.45 (2H, singlet);
3.79 (3H, singlet).

EXAMPLE 373

Methyl N-[4-(benzoxazol-2-ylmethoxy)-2-chlorophenyl]carbamate (Compound No. C9.40)

Melting Point: 120° to 122° C.

Nuclear Magnetic Resonance Spectrum (200 MHz, CDCl$_3$), δ ppm:

8.05–7.99 (1H, multiplet);
7.79–7.74 (1H, multiplet);
7.59–7.55 (1H, multiplet);
7.40–7.36 (2H, multiplet);
7.11 (1H, doublet, J=2.9 Hz);
7.00 (1H, doublet of doublets, J=8.9 & 2.8 Hz);
6.92 (1H, broad singlet);
5.29 (2H, singlet);
3.79 (3H, singlet).

EXAMPLE 374

Methyl N-[4-(benzoxazol-2-ylmethoxy)-3-nitrophenyl]carbamate (Compound No. C 10.66)

Melting Point: 113° to 115° C.

Nuclear Magnetic Resonance Spectrum (200 MHz, CDCl$_3$), δ ppm:
7.96 (1H, doublet, J=2.7 Hz);
7.79–7.72 (1H, multiplet);
7.59–7.55 (2H, multiplet);
7.43–7.33 (2H, multiplet);
7.28–7.24 (1H, multiplet);
6.80 (1H, broad singlet);
5.43 (2H, singlet);
3.78 (3H, singlet).

EXAMPLE 375

Methyl N-[4-(benzothiazol-2-ylmethoxy)-2,3-dimethylphenyl]carbamate (Compound No. C11.4)

Melting Point: 178° to 180° C.

Nuclear Magnetic Resonance Spectrum (200 MHz, CDCl$_3$), δ ppm:
8.03 (1H, doublet of doublets, J=8.1 & 1.4 Hz);
7.91 (1H, doublet of doublets, J=7.4 & 1.4 Hz);
7.55–7.36 (2H, multiplet);
7.29–7.26 (1H, broad multiplet);
6.82 (1H, doublet, J=8.8 Hz);
6.21 (1H, broad singlet);
5.46 (2H, singlet);
3.76 (3H, singlet);
2.37 (3H, singlet);
2.20 (3H, singlet).

EXAMPLE 376

Methyl N-[4-(benzothiazol-2-ylmethoxy)-2,5-dimethylphenyl]carbamate (Compound No. C11.20)

Melting Point: 127° to 128° C.

Nuclear Magnetic Resonance Spectrum (200 MHz, CDCl$_3$), δ ppm:
8.03 (1H, doublet of doublets, J=8.7 & 1.6 Hz);
7.91 (1H, doublet of doublets, J=7.3 & 1.4 Hz);
7.55–7.37 (3H, multiplet);
6.73 (1H, singlet);
6.17 (1H, broad singlet);
5.45 (2H, singlet);
3.76 (3H, singlet);
2.33 (3H, singlet);
2.20 (3H, singlet).

EXAMPLE 377

Methyl N-[4-(benzothiazol-2-ylmethoxy)-2,3,6-trimethylphenyl]carbamate (Compound No. C 11.79)

Melting Point: 177° to 179° C.

Nuclear Magnetic Resonance Spectrum (200 MHz, CDCl$_3$), δ ppm:
8.03 (1H, doublet, J=7.2 Hz);
7.91 (1H, doublet, J=8.1 Hz);
7.51–7.41 (2H, multiplet);
6.69 (1H, singlet);
5.95 (1H, broad singlet);
5.45 (2H, singlet);
3.76 (3H, singlet);
2.28 (3H, singlet);
2.23 (3H, singlet);
2.21 (3H, singlet).

EXAMPLE 378

Methyl N-[4-(benzothiazol-2-ylmethoxy)-3,5-dimethoxyphenyl]carbamate (Compound No. C 12.47)

Melting Point: 110° to 113° C.

Nuclear Magnetic Resonance Spectrum (200 MHz, CDCl$_3$), δ ppm:
8.02–7.90 (2H, multiplet);
7.52–7.38 (2H, multiplet);
6.70 (2H, singlet);
6.60 (1H, broad singlet);
5.37 (2H, singlet);
3.82 (6H, singlet);
3.77 (3H, singlet).

EXAMPLE 379

Methyl N-[4-(benzothiazol-2-ylmethoxy)-5-chloro-2-methylphenyl]carbamate (Compound No. C16.126)

Melting Point: 138° to 141° C.

Nuclear Magnetic Resonance Spectrum (200 MHz, CDCl$_3$), δ ppm:
8.03 (1H, doublet, J=6.9 Hz);
7.92 (1H, doublet of doublets, J=8.1 & 2.2 Hz);
7.81 (1H, broad singlet);
7.55–7.37 (2H, multiplet);
6.86 (1H, singlet);
6.22 (1H, broad singlet);
5.5 (2H, singlet);
3.78 (3H, singlet);
2.20 (3H, singlet).

EXAMPLE 380

Methyl N-[4-(benzothiazol-2-ylmethoxy)-5-isopropyl-2-methylphenyl]carbamate (Compound No. C 18.119)

Melting Point: 115° to 117° C.

Nuclear Magnetic Resonance Spectrum (200 MHz, CDCl$_3$), δ ppm:
8.03 (1H, doublet, J=8.7 Hz);
7.92 (1H, doublet of doublets, J=8.4 & 2.1 Hz);
7.55–7.37 (3H, multiplet);
6.75 (1H, singlet);
6.22 (1H, broad singlet);
5.46 (2H, singlet);
3.77 (3H, singlet);
3.43 (1H, quintet, J=7.0 Hz);
2.21 (3H, singlet);
1.29 (6H, doublet, J=6.9 Hz).

EXAMPLE 381

Methyl N-{4-[1-(benzothiazol-2-yl)ethoxy]phenyl}carbamate (Compound No. E1.3)

Amorphous

Nuclear Magnetic Resonance Spectrum (200 MHz, CDCl$_3$), δ ppm:
8.00 (1H, doublet, J=6.7 Hz);
7.86 (1H, doublet, J=7.7 Hz);
7.53–7.20 (4H, multiplet);
6.98–6.90 (2H, multiplet);
6.42 (1H, broad singlet);
5.69 (1H, quartet, J=6.6 Hz);
3.74 (3H, singlet);
1.83 (3H, doublet, J=6.5 Hz).

EXAMPLE 382

Methyl N-{4-[1-(benzothiazol-2-yl)ethoxy]-2-methylphenyl}carbamate (Compound No. E1.17)

Amorphous

Nuclear Magnetic Resonance Spectrum (200 MHz, CDCl$_3$), δ ppm:
8.04–7.89 (2H, multiplet);
7.52–7.32 (3H, multiplet);
6.87–6.79 (2H, multiplet);
6.16 (1H, broad singlet);
5.70 (1H, quartet, J=6.6 Hz);
3.74 (3H, singlet);
2.19 (3H, singlet);
1.82 (3H, doublet, J=6.5 Hz).

EXAMPLE 383

Methyl N-[4-(4-methylbenzoxazol-2-ylmethoxy)phenyl]carbamate (Compound No. F1.5)

Melting Point: 95° to 96° C.

Nuclear Magnetic Resonance Spectrum (200 MHz, CDCl$_3$), δ ppm:
7.40–7.13 (5H, multiplet);
7.05–6.99 (2H, multiplet);
6.50–6.49 (1H, broad multiplet);
5.29 (2H, singlet);
3.75 (3H, singlet);
2.63 (3H, singlet).

EXAMPLE 384

Methyl N-[4-(5-methylbenzoxazol-2-ylmethoxy)phenyl]carbamate (Compound No. F1.15)

Melting Point: 105° to 108° C.

Nuclear Magnetic Resonance Spectrum (200 MHz, CDCl$_3$), δ ppm:
7.53–7.52 (1H, multiplet);
7.42 (1H, doublet, J=8.4 Hz);
7.32–7.26 (2H, multiplet);
7.20–7.15 (1H, multiplet);
7.03–6.99 (2H, multiplet);
6.50–6.45 (1H, broad multiplet);
5.30 (2H, singlet);
3.76 (3H, singlet);
2.47 (3H, singlet).

EXAMPLE 385

Methyl N-[4-(6-methylbenzoxazol-2-ylmethoxy)phenyl]carbamate (Compound No. F1.25)

Melting Point: 102° to 104° C.

Nuclear Magnetic Resonance Spectrum (200 MHz, CDCl$_3$), δ ppm:
7.61 (1H, doublet, J=8.4 Hz);
7.35–7.26 (3H, multiplet);
7.19–7.15 (1H, multiplet);
7.01 (2H, doublet of doublets, J=6.8 & 2.2 Hz);
6.48–6.47 (1H, broad multiplet);
5.27 (2H, singlet);
3.76 (3H, singlet);
2.49 (3H, singlet).

EXAMPLE 386

Methyl N-[4-(7-methylbenzothiazol-2-ylmethoxy)phenyl]carbamate (Compound No. F1.33)

Melting Point: 150° to 151° C.

Nuclear Magnetic Resonance Spectrum (200 MHz, CDCl$_3$), δ ppm:
7.57 (1H, doublet, J=7.7 Hz);
7.33–7.14 (4H, multiplet);
7.03 (2H, doublet of doublets, J=6.8 & 2.3 Hz);
6.50 (1H, broad singlet);
5.29 (2H, singlet);
3.76 (3H singlet);
2.54 (3H, singlet).

EXAMPLE 387

Methyl N-[4-(5-nitrobenzoxazol-2-ylmethoxy)phenyl]carbamate (Compound No. F 1.69)

Melting Point: 184° to 187° C.

Nuclear Magnetic Resonance Spectrum (200 MHz, CDCl$_3$), δ ppm:
8.66 (1H, doublet, J=2.2 Hz);
8.36 (1H, doublet of doublets, J=9.0 & 2.3 Hz);
7.68 (1H, doublet, J=9.3 Hz);
7.35–7.26 (2H, multiplet);
7.03–6.99 (2H, multiplet);
6.51–5.48 (1H, broad multiplet);
5.34 (2H, singlet);
3.76 (3H, singlet).

EXAMPLE 388

Methyl N-[4-(5-methoxybenzoxazol-2-ylmethoxy)phenyl]carbamate (Compound No. F3.14)

Melting Point: 134° to 137° C.

Nuclear Magnetic Resonance Spectrum (200 MHz, CDCl$_3$), δ ppm:
7.43 (1H, doublet, J=8.7 Hz);
7.32–7.22 (3H, multiplet);
7.03–6.94 (1H, broad multiplet);
6.49–6.30 (1H, broad multiplet);
5.27 (2H, singlet);
3.86 (3H, singlet);
3.76 (3H, singlet).

EXAMPLE 389

Methyl N-[4-(5-chlorobenzothiazol-2-ylmethoxy)phenyl]carbamate (Compound No. F4.63)

Melting Point: 157° to 160° C.

Nuclear Magnetic Resonance Spectrum (200 MHz, CDCl$_3$), δ ppm:
7.74 (1H, doublet, J=2.3 Hz);
7.48 (1H, doublet, J=8.8 Hz);
7.38–7.26 (3H, multiplet);

7.00 (2H, doublet of doublets, J=6.9 & 0.2 Hz);
6.48 (1H, broad singlet);
5.29 (2H, singlet);
3.76 (3H, singlet).

EXAMPLE 390

Methyl N-[4-(5-trifluoromethylbenzoxazol-2-ylmethoxy)phenyl]carbamate (Compound No. F5.13)

Melting Point: 145° to 148° C.

Nuclear Magnetic Resonance Spectrum (200 MHz, $CDCl_3$) δ ppm:
8.05 (1H, singlet);
7.67 (2H, doublet, J=1.2 Hz);
7.34–7.28 (2H, multiplet);
7.01 (2H, doublet of doublets, J=6.9 & 1.3 Hz);
6.47 (1H, broad singlet);
5.33 (2H, singlet);
3.76 (3H, singlet).

EXAMPLE 391

Methyl N-[4-(5,7-dimethylbenzoxazol-2-ylmethoxy)phenyl]carbamate (Compound No. F7.17)

Melting Point: 157° to 159° C.

Nuclear Magnetic Resonance Spectrum (200 MHz, $CDCl_3$) δ ppm:
7.34–7.26 (3H, multiplet);
7.04–6.98 (3H, multiplet);
6.49 (1H, broad singlet);
5.26 (2H, singlet);
3.76 (3H, singlet);
2.48 (3H, singlet);
2.43 (3H, singlet).

EXAMPLE 392

Methyl N-[4-(6,7-difluorobenzoxazol-2-ylmethoxy)phenyl]carbamate (Compound No. F7.56)

Melting Point: 145° to 148° C.

Nuclear Magnetic Resonance Spectrum (200 MHz, $CDCl_3$) δ ppm:
7.51–7.42 (1H, multiplet);
7.34–7.28 (2H, multiplet);
7.24–7.14 (1H, multiplet);
7.01 (2H, doublet of doublets, J=6.8 & 2.3 Hz);
6.49–6.48 (1H, broad multiplet);
5.29 (2H, singlet);
3.78 (3H, singlet).

EXAMPLE 393

Methyl N-[4-(5,7-dichlorobenzoxazol-2-ylmethoxy)phenyl]carbamate (Compound No. F7.69)

Melting Point: 135° to 136° C.

Nuclear Magnetic Resonance Spectrum (200 MHz, $CDCl_3$), δ ppm:
7.65 (1H, doublet, J=1.8 Hz);
7.40 (1H, doublet, J=1.9 Hz);
7.34–7.26 (2H, multiplet);
7.10 (2H, doublet of doublets, J=6.8 & 2.3 Hz);
6.50–6.49 (1H, broad multiplet);
5.30 (2H, singlet);
3.76 (3H, singlet).

EXAMPLE 394

Methyl N-[2-methyl-4-(4-methylbenzoxazol-2-ylmethoxy)phenyl]carbamate (Compound No. G1.5)

Melting Point: 149° to 151° C.

Nuclear Magnetic Resonance Spectrum (200 MHz, $CDCl_3$), δ ppm:
7.60–7.45 (1H, broad multiplet);
7.40–7.36 (1H, multiplet);
7.29–7.22 (1H, multiplet);
7.17–7.14 (1H, multiplet);
6.93–6.89 (2H, multiplet);
6.21–6.18 (1H, broad multiplet);
5.29 (2H, singlet);
3.76 (3H, singlet);
2.63 (3H, singlet);
2.23 (3H, singlet).

EXAMPLE 395

Methyl N-[2-methyl-4-(5-methylbenzoxazol-2-ylmethoxy)phenyl]carbamate (Compound No. G1.10)

Melting Point: 164° to 166° C.

Nuclear Magnetic Resonance Spectrum (200 MHz, $CDCl_3$), δ ppm: 7.56–7.49 (1H, broad multiplet); 7.53 (1H, doublet, J=0.8 Hz); 7.42 (1H, doublet, J=8.4 Hz); 7.19–7.15 (1H, multiplet); 6.92–6.87 (2H, multiplet); 6.20–6.18 (1H, broad multiplet); 5.26 (2H, singlet); 3.76 (3H, singlet); 2.47 (3H, singlet); 2.23 (3H, singlet).

EXAMPLE 396

Methyl N-[2-methyl-4-(6-methylbenzoxazol-2-ylmethoxy)phenyl]carbamate (Compound No. G1.15)

Melting Point: 139° to 142° C.

Nuclear Magnetic Resonance Spectrum (200 MHz, $CDCl_3$), δ ppm: 7.61 (1H, doublet, J=8.2 Hz); 7.54–7.51 (1H, broad multiplet); 7.35 (1H, doublet, J=0.7 Hz); 7.17 (1H, doublet of doublets, J=8.0 & 1.3 Hz); 6.92–6.86 (3H, multiplet); 6.21–6.18 (1H, broad multiplet); 5.26 (2H, singlet); 3.76 (3H, singlet); 2.49 (3H, singlet); 2.23 (3H, singlet).

EXAMPLE 397

Methyl N-[2-methyl-4-(7-methylbenzoxazol-2-ylmethoxy)phenyl]carbamate (Compound No. G1.20)

Melting Point: 157° to 159° C.

Nuclear Magnetic Resonance Spectrum (200 MHz, $CDCl_3$), δ ppm: 7.59–7.53 (2H, multiplet); 7.29–7.14 (2H, multiplet); 6.94–6.89 (2H, multiplet); 6.19 (1H, broad singlet); 5.29 (2H, singlet); 3.76 (3H, singlet); 2.54 (3H, singlet); 2.24 (3H, singlet).

EXAMPLE 398

Methyl N-[4-(5-fluorobenzoxazol-2-ylmethoxy)-2-methylphenyl]carbamate (Compound No. G1.59)

Melting Point: 182° to 184° C.

Nuclear Magnetic Resonance Spectrum (200 MHz, $CDCl_3$), δ ppm: 7.59–7.49 (1H, broad multiplet); 7.53–7.41

(2H, multiplet); 7.11 (1H, triplet of doublets, J=9.1 & 2.6 Hz); 6.89–6.87 (2H, multiplet); 6.21 (1H, broad singlet); 5.28 (2H, singlet); 3.76(3H, singlet); 2.24(3H, singlet).

EXAMPLE 399

Methyl N-[4-(6-fluorobenzoxazol-2-ylmethoxy)-2-methylphenyl]carbamate (Compound No. G1.64)

Melting Point: 138° to 140° C.

Nuclear Magnetic Resonance Spectrum (200 MHz, CDCl$_3$), δ ppm: 7.68 (1H, doublet of doublets, J=8.8 & 5.0 Hz); 7.59–7.50 (1H, broad multiplet); 7.31–7.26 ( 1H, multiplet); 7.11 (1H, triplet of doublets, J=9.2 & 2.5 Hz); 6.91–6.87 (2H, multiplet); 6.23–6.19 (1H, broad multiplet); 5.27 (2H, singlet); 3.76 (3H, singlet); 2.23 (3H, singlet).

EXAMPLE 400

Methyl N-[4-(7-fluorobenzoxazol-2-ylmethoxy)-2-methylphenyl]carbamate (Compound No. G1.69)

Melting Point: 138° to 141° C.

Nuclear Magnetic Resonance Spectrum (200 MHz, CDCl$_3$), δ ppm: 7.58–7.53 (2H, multiplet); 7.35–7.25 (1H, multiplet); 6.93–6.88 (2H, multiplet); 6.21–6.20 (1H, broad multiplet); 5.31 (2H, singlet); 3.76 (3H, singlet); 2.24 (3H, singlet).

EXAMPLE 401

Methyl N-[4-(5-chlorobenzoxazol-2-ylmethoxy)-2-methylphenyl]carbamate (Compound No. G1.77)

Melting Point: 156° to 158° C.

Nuclear Magnetic Resonance Spectrum (200 MHz, CDCl$_3$), δ ppm: 7.74 (1H, doublet, J=2.1 Hz); 7.58–7.50 ( 1H, broad multiplet); 7.48 (1H, doublet, J=8.8 Hz); 7.35 (1H, doublet of doublets, J=8.7 & 2.0 Hz); 6.89–6.87 (2H, multiplet); 6.21 (1H, broad singlet); 5.28 (2H, singlet); 3.76 (3H, singlet); 2.23 (3H, singlet).

EXAMPLE 402

Methyl N-[2-methyl-4-(5-trifluoromethylbenzoxazol-2-ylmethoxy)phenyl]carbamate (Compound No. G1.96)

Melting Point: 141° to 143° C.

Nuclear Magnetic Resonance Spectrum (200 MHz, CDCl$_3$), δ ppm: 8.05 (1H, singlet); 7.67 (2H, doublet, J=1, 1 Hz); 7.60–7.50 (2H, broad multiplet); 6.91–6.87 (2H, multiplet); 6.20–6.19 (1H, broad multiplet); 5.32 (2H, singlet); 3.76 (3H, singlet); 2.24 (3H, singlet).

EXAMPLE 403

Methyl N-[4-(5,7-dimethylbenzoxazol-2-ylmethoxy)-2-methylphenyl]carbamate (Compound No. G2.14)

Melting Point: 154° to 155° C.

Nuclear Magnetic Resonance Spectrum (200 MHz, CDCl$_3$), δ ppm: 7.58–7.50 ( 1H, broad multiplet); 7.35 (1H, singlet); 6.98 (1H, singlet); 6.91–6.89 (2H, multiplet); 6.20 (1H, broad singlet); 5.26 (2H, singlet); 3.76 (3H, singlet); 2.48 (3H, singlet); 2.43 (3H, singlet); 2.23 (3H, singlet).

EXAMPLE 404

Methyl N-[4-(6,7-difluorobenzoxazol-2-ylmethoxy)-2-methylphenyl]carbamate (Compound No. G2.50)

Melting Point: 124° to 125° C.

Nuclear Magnetic Resonance Spectrum (200 MHz, CDCl$_3$) δ ppm: 7.59–7.43 (2H, multiplet); 7.24–7.14 (1H, multiplet); 6.92–6.87 (2H, multiplet); 6.20–6.19 ( 1 H, broad multiplet); 5.29 (2H, singlet); 3.76 (3H, singlet); 2.24 (3H, singlet).

EXAMPLE 405

Methyl N-[4-(5,7-dichlorobenzoxazol-2-ylmethoxy) -2-methylphenyl]carbamate (Compound No. G2.62)

Melting Point: 130° to 132° C.

Nuclear Magnetic Resonance Spectrum (200 MHz, CDCl$_3$), δ ppm: 7.65 (1H, doublet, J=1.9 Hz); 7.59–7.50 (1H, broad multiplet); 7.40 (1H, doublet, J=1.9 Hz); 6.91–6.90 (1H, broad multiplet); 5.29 (2H, singlet); 3.76 (3H, singlet); 2.24 (3H, singlet).

EXAMPLE 406

N-[4-(Benzothiazol-2-ylmethoxy)-2-methylphenyl]-N-(2-hydroxyethyl)acetamide (Compound No. D1.105)

Melting Point: 97° to 99° C.

Nuclear Magnetic Resonance Spectrum (200 MHz, CDCl$_3$), δ ppm: 8.07–8.03 ( 1H, multiplet); 7.93–7.89 (1H, multiplet); 7.56–7.38 (2H, multiplet); 7.11 (1H, doublet, J=8.6 Hz); 6.98 (1H, doublet, J=2.6 Hz); 6.91 (1H, doublet of doublets, J=8.6 & 2.8 Hz); 5.49 (2H, singlet); 4.28–4.10 (1H, multiplet); 3.82–3.74 (2H, multiplet); 3.38–3.27 (2H, multiplet); 2.24 (3H, singlet); 1.79 (3H, singlet).

EXAMPLE 407

Methyl N-[4-(benzoxazol-2-ylmethoxy)-2-methylphenyl]-N-hydroxymethylcarbamate (Compound No. D 1.49)

Melting Point: 132° to 133° C.

Nuclear Magnetic Resonance Spectrum (200 MHz, CDCl$_3$), δ ppm: 7.79–7.74 (1H, multiplet); 7.59–7.54 (1H, multiplet); 7.43–7.32 (2H, multiplet); 7.14(1H, doublet, J=8.3 Hz); 6.96–6.86 (2H, multiplet); 5.31 (2H, singlet); 5.15(1H, doublet of doublets, J=10.5 & 7.4 Hz); 4.78 (1H, doublet of doublets, J=10.4 & 8.5 Hz); 3.67 (3H, broad singlet); 3.42 (1H, triplet, J=7.9 Hz). 2.21 (3H, singlet).

EXAMPLE 408

Methyl N-[4-(benzothiazol-2-ylmethoxy)-2-methylphenyl]-N-methoxymethylcarbamate (Compound No. D 1.51)

Melting Point: 76° to 78° C.

Nuclear Magnetic Resonance Spectrum (200 MHz, CDCl$_3$), δ ppm: 8.06–7.88 (2H, multiplet); 7.55–7.37 (2H, multiplet); 7.10 (1H, doublet, J=9.0 Hz); 6.93 (1H, doublet, J=2.6 Hz); 6.87 (1H, doublet of doublets, J=8.6 & 3.0 Hz); 5.47 (2H, singlet); 5.20–5.15 ( 1H, multiplet); 4.64 (1H, doublet, J=10.0 Hz); 2.20 (3H, singlet); 3.81–3.65 (3H, multiplet); 3.44 (3H, singlet); 2.19 (3H, singlet).

EXAMPLE 409

Methyl N-[4-(benzothiazol-2-ylmethoxy)-2-methylphenyl]-N-ethoxymethylcarbamate (Compound No. D1.55)

Amorphous

Nuclear Magnetic Resonance Spectrum (200 MHz, CDCl$_3$), δ ppm: 8.04 (1H, doublet, J=8.8 Hz); 7.92 (1H, doublet, J=7.6Hz); 7.56–7.35 (2H, multiplet); 7.09 (1H, broad doublet, J=8.4 Hz); 6.95–6.82 (2H, multiplet); 5.47 (2H, singlet); 5.22 (1H, broad doublet, J=9.9 Hz); 4.70 (1H, doublet, J=10.4 Hz); 3.88–3.50 (5H, broad singlet); 2.19 (3H, singlet); 1.21 (3H, triplet, J=7.0 Hz).

EXAMPLE 410

Methyl N-[4-(benzothiazol-2-ylmethoxy)-2-methylphenyl]-N-isobutyloxymethylcarbamate (Compound No. D 1.56)

Oil

Nuclear Magnetic Resonance Spectrum (200 MHz, CDCl$_3$), δ ppm: 8.06–7.89 (2H, multiplet); 7.55–7.37 (2H, multiplet); 7.10 (1H, doublet, J=8.6 Hz); 6.93 (1H, doublet, J=3.0 Hz); 6.86 (1H, doublet of doublets, J=8.4 & 3.0 Hz); 5.47 (2H, singlet); 4.96 (2H, AB quartet, J=10.2 Hz, Av=108.5); 3.85–3.65 (3H, multiplet); 3.41–3.30 (2H, multiplet); 2.05 (3H, singlet); 1.92–1.80 (1H, multiplet); 0.91 (6H, doublet, J=6.6 Hz).

EXAMPLE 411

Methyl N-[4-(benzothiazol-2-ylmethoxy)-2-methylphenyl]-N-(2-butenyloxymethyl)carbamate (Compound No. D1.60)

Oil

Nuclear Magnetic Resonance Spectrum (200 MHz, CDCl$_3$), δ ppm: 8.03 (1H, doublet, J=8.0 Hz); 7.91 (1H, doublet, J=7.2 Hz); 7.55–7.37 (2H, multiplet); 7.10 (1H, broad doublet, J=8.7 Hz); 6.95–6.82 (2H, multiplet); 5.85–5.42 (2H, multiplet); 5.47 (2H, singlet); 5.30–5.05 (1H, multiplet); 4.70 (1H, doublet, J=10.4 Hz); 4.15–3.95 (2H, multiplet); 3.82–3.66 (3H, multiplet); 2.18 (3H, singlet); 1.75–1.65 (3H, multiplet).

EXAMPLE 412

Methyl N-acetoxymethyl-N-[4-(benzothiazol-2-ylmethoxy)-2-methylphenyl]carbamate (Compound No. D 1.68)

Oil

Nuclear Magnetic Resonance Spectrum (200 Mz, CDCl$_3$), δ ppm: 8.04 (1H, doublet of doublets, J=7.2 & 1.3 Hz); 7.91 (1H, doublet of doublets, J=7.2 & 1.3 Hz); 7.51 (1H, triplet of doublets, J=7.2 & 1.3 Hz); 7.43 (1H, triplet of doublets, J=7.2 & 1.3 Hz); 7.09 (1H, doublet, J=8.7 Hz); 6.93 (1H, doublet, J=3.0 Hz); 6.86(1H, doublet of doublets, J=8.7 & 3.0 Hz); 5.71 doublet, J=10.0 Hz); 5.47 (2H, singlet); 5.38 doublet, J=10.3 Hz); 3.83–3.69 (3H, multiplet); 2.20 (3H, singlet); 2.06 (3H, singlet).

EXAMPLE 413

Methyl N-acetoxymethyl-N-[4-(benzoxazol-2-ylmethoxy)-2-methylphenyl]carbamate (Compound No. D 1.69)

Oil

Nuclear Magnetic Resonance Spectrum (200 MHz, CDCl$_3$), δ ppm: 7.80–7.75 (1H, multiplet); 7.60–7.55 (1H, multiplet); 7.43–7.36 (2H, multiplet); 7.12–7.07 (1H, multiplet); 6.96–6.87 (2H, multiplet); 5.71 (1H, doublet, J=10.9 Hz); 5.41–5.35 (1H, multiplet); 5.31 (2H, singlet); 3.69 (3H, singlet); 2.20 (3H, singlet); 2.06 (3H, singlet).

EXAMPLE 414

Methyl N-[4-(benzoxazol-2-ylmethoxy)-2-methylphenyl]-N-propionyloxymethylcarbamate (Compound No. D 1.71)

Oil

Nuclear Magnetic Resonance Spectrum (200 MHz, CDCl$_3$), δ ppm: 7.79–7.75 (1H, multiplet); 7.60–7.55 (1H, multiplet); 7.43–7.35 (2H, multiplet); 7.09 (1H, broad doublet, J=8.7 Hz); 6.95–6.86 (2H, multiplet); 5.71 (1H, doublet, J=10.3 Hz); 5.40 (1H, doublet, J=9.9 Hz); 5.31 (2H, singlet); 3.68 (3H, broad singlet); 2.34 (2H, quartet, J=7.5 Hz); 2.20 (3H, singlet); 1.10 (3H, triplet, J=7.5 Hz).

EXAMPLE 415

Methyl N-[4-(benzothiazol-2-ylmethoxy)-2-methylphenyl]-N-butyryloxymethylcarbamate (Compound No. D 1.72)

Oil

Nuclear Magnetic Resonance Spectrum (200Mz, CDCl$_3$), δ ppm: 8.04 (1H, doublet of doublets, J=7.9 & 1.0 Hz); 7.91 (1H, doublet of doublets, J=7.9 & 1.0 Hz); 7.51 (1H, triplet of doublets, J=7.9 & 1.0 Hz); 7.41 (1H, triplet of doublets, J=7.9 & 1.0 Hz); 7.09 (1H, doublet, J=8.3 Hz); 6.93 (1H, doublet, J=3.0 Hz); 6.86 (1H, doublet of doublets, J=8.3 & 3.0 Hz); 5.72 (1H, doublet, J=10.3 Hz); 5.47 (2H, singlet); 5.40 (1H, doublet, J=10.3 Hz); 3.78–3.69 (3H, multiplet); 2.28 (2H, triplet, J=7.3 Hz); 2.21 (3H, singlet); 1.73–1.54 (2H, multiplet); 0.91 (3H, triplet, J=7.3 Hz).

EXAMPLE 416

Methyl N-[4-(benzothiazol-2-ylmethoxy)-2-methylphenyl]-N-isobutyryloxymethylcarbamate (Compound No. D 1.74)

Oil

Nuclear Magnetic Resonance Spectrum (200 MHz, CDCl$_3$), δ ppm: 8.07–7.89 (2H, multiplet); 7.56–7.37 (2H, multiplet); 7.09 (1H, doublet, J=8.6 Hz); 6.93 (1H, doublet, J=2.8 Hz); 6.86(1H, doublet of doublets, J=8.8 & 3.2 Hz); 5.55 (2H, AB quartet, J=10.2 Hz, Av=63.0); 5.47 (2H, singlet); 3.90–3.65 (3H, multiplet); 2.61–2.49 (1H, multiplet); 2.21 (3H, singlet); 1.38 (3H, doublet, J=7.0 Hz).

EXAMPLE 417

Methyl N-[4-(benzothiazol-2-ylmethoxy)-2-methylphenyl]-N-pentanoyloxymethylcarbamate (Compound No. D 1.76)

Oil

Nuclear Magnetic Resonance Spectrum (200 MHz, CDCl$_3$), δ ppm: 8.04 (1H, J=8.1 Hz); 7.92 (1H, doublet, J=7.6 Hz); 7.55–7.41 (2H, multiplet); 7.09 (1H, doublet, J=8.5 Hz); 6.93–6.83 (2H, multiplet); 5.56 (2H, AB quartet, J=10.2Hz, Av=62.7); 5.47 (2H, singlet); 3.72–3.66 (3H, multiplet); 2.13 (2H, triplet, J=7.2 Hz); 2.21 (3H, singlet); 1.62–1.50 (2H, multiplet).

EXAMPLE 418

Methyl N-[4-(benzothiazol-2-ylmethoxy)-2-methylphenyl]-N-(pivaloyloxymethyl)carbamate (Compound No. D 1.78)

Oil

Nuclear Magnetic Resonance Spectrum (200 MHz, CDCl$_3$), δ ppm: 8.04 (1H, doublet, J=7.7 Hz); 7.92 (1H, doublet, J=7.0 Hz); 7.36–7.56 (2H, multiplet); 7.09 (1H, doublet, J=8.7 Hz); 6.81–6.95 (2H, multiplet); 5.71 (1H, doublet, J=10.6 Hz); 5.47 (2H, singlet); 5.38 (1H, doublet, J=10.6 Hz); 3.70 (3H, broad singlet); 2.21 (3H, singlet); 1.18 (9H, singlet).

EXAMPLE 419

Methyl N-[4-(benzothiazol-2-ylmethoxy)-2-methylphenyl]-N-cyclopentylcarbonyloxymethylcarbamate (Compound No. D 1.79)

Oil

Nuclear Magnetic Resonance Spectrum (200 MHz, CDCl$_3$), δ ppm: 8.04 (1H, doublet, J=8.0 Hz); 7.91 (1H, doublet, J=7.7 Hz); 7.55–7.37 (2H, multiplet); 7.09 (1H, broad doublet, J=8.5 Hz); 6.94–6.83 (2H, multiplet); 5.71 (1H, doublet, J=10.0 Hz); 5.47 (2H, singlet); 5.40 (1H, broad doublet, J=10.1 Hz); 3.69 (3H, broad singlet); 2.74 (1H, quintet, J=7.9 Hz); 2.21 (3H, singlet); 1.95–1.53 (8H, multiplet).

EXAMPLE 420

Methyl N-[4-(benzothiazol-2-ylmethoxy)-2-methylphenyl]-N-cyclopentylcarbonyloxymethylcarbamate (Compound No. D 1.80)

Oil

Nuclear Magnetic Resonance Spectrum (200 MHz, CDCl$_3$), δ ppm: 8.04 (1H, doublet, J=7.5 Hz); 7.92 (1H, doublet, J=7.6 Hz); 7.37–7.57 (2H, multiplet); 7.08(1H, doublet, J=8.5 Hz); 6.81–6.95 (2H, multiplet); 5.71 (1H, doublet, J=10.2 Hz); 5.47 (2H, singlet); 5.37 (1H, doublet, J=10.2 Hz); 3.31 (1H, multiplet); 2.21 (3H, singlet); 1.10–1.95 (10H, multiplet).

EXAMPLE 421

Methyl N-[4-(benzothiazol-2-ylmethoxy)-2-methylphenyl]-N-methoxyacetoxymethylcarbamate (Compound No. D 1.81)

Oil

Nuclear Magnetic Resonance Spectrum (200 MHz, CDCl$_3$), δ ppm: 8.04 (1H, doublet, J=7.3 Hz); 7.91 (1H, doublet of doublets, J=7.4 & 1.5 Hz); 7.55–7.41 (2H, multiplet); 7.08 (1H, doublet, J=8.5 Hz); 6.94–6.84 (2H, multiplet); 5.64 (2H, AB quartet, J=10.3 Hz, Av=64.5); 5.47 (2H, singlet); 4.04 (2H, singlet); 3.69 (3H, singlet); 3.41 (3H, singlet); 2.20 (3H, singlet).

EXAMPLE 422

Methyl N-[4-(benzoxazol-2-ylmethoxy)-2-methylphenyl]-N-methoxyacetoxymethylcarbamate (Compound No. D 1.82)

Oil

Nuclear Magnetic Resonance Spectrum (200MHz, CDCl$_3$), δ ppm: 7.79–7.75 (1H, multiplet); 7.60–7.55 (1H, multiplet); 7.43–7.35 (2H, multiplet); 7.11–7.06 (1H, multiplet); 6.94–6.86 (2H, multiplet); 5.80 (1H, doublet, J=10.5 Hz); 5.55–5.49 (1H, multiplet); 5.31 (2H, singlet); 4.06 (2H, singlet); 3.76 (3H, broad singlet); 3.41 (3H, singlet); 2.20 (3H, singlet).

EXAMPLE 423

Methyl N-[4-(benzothiazol-2-ylmethoxy)-2-methylphenyl]-N-(3-methoxypropionyloxymethyl) carbamate (Compound No. D 1.83)

Oil

Nuclear Magnetic Resonance Spectrum (200 MHz, CDCl$_3$), δ ppm: 8.04 (1H, doublet, J=7.9 Hz); 7.92 (1H, doublet of doublets, J=6.9 & 0.9 Hz); 7.55–7.37 (2H, multiplet); 7.10(1H, doublet, J=8.4 Hz); 6.93–6.83 (3H, multiplet); 5.58 (2H, AB quartet, J=10.5 Hz, Av=64.3); 3.69 (3H, broad singlet); 3.63 (2H, triplet, J=6.4 Hz); 3.31 (3H, singlet); 2.59 (2H, triplet, J=6.4 Hz); 2.20 (3H, singlet).

EXAMPLE 424

Methyl N-[4-(benzothiazol-2-ylmethoxy)-2-methylphenyl]-N-(3-ethoxypropionyloxymethyl) carbamate (Compound No. D 1.85)

Oil

Nuclear Magnetic Resonance Spectrum (200 MHz, CDCl$_3$), δ ppm: 8.04 (1H, doublet, J=7.7 Hz); 7.91 (1H, doublet, J=7.3 Hz); 7.35–7.55 (2H, multiplet); 7.10(1H, doublet, J=8.5 Hz); 6.80–6.94 (2H, multiplet); 5.74 (1H, doublet, J=10.3 Hz); 5.46 (2H, singlet); 5.44 (1H, doublet, J=10.3 Hz); 3.56–3.85 (5H, multiplet); 3.46 (2H, quartet, J=7.0 Hz); 2.59 (3H, triplet, J=7.0 Hz); 2.20 (3H, singlet).

EXAMPLE 425

Methyl N-[4-(benzothiazol-2-ylmethoxy)-2-methylphenyl]-N-(3-methyl-3-butenoyloxymethyl) carbamate (Compound No. D 1.87)

Oil

Nuclear Magnetic Resonance Spectrum (200 MHz, CDCl$_3$), δ ppm: 8.02 (1H, doublet, J=7.7 Hz); 7.88 (1H, doublet of doublets, J=7.5 & 1.0 Hz); 7.53–7.38 (2H, multiplet); 7.08 (1H, broad doublet, J=8.5 Hz); 6.92–6.82 (2H, multiplet); 5.72 (1H, doublet, J=10.3 Hz); 5.45 (2H, singlet); 5.41 (1H, broad doublet, J=10.3 Hz); 4.88 (1H, broad singlet); 4.82 (1H, broad singlet); 3.67 (3H, broad singlet); 3.03 (2H, singlet); 2.19 (3H, singlet); 1.74 (3H, singlet).

EXAMPLE 426

Methyl N-[4-(benzothiazol-2-ylmethoxy)-2-methylphenyl]-N-chloroacetyloxymethylcarbamate (Compound No. D 1.88)

Oil

Nuclear Magnetic Resonance Spectrum (200 MHz, CDCl$_3$), δ ppm: 8.04 (1H, doublet, J=7.9 Hz); 7.90 (1H, doublet, J=7.7 Hz); 7.55–7.37 (2H, multiplet); 7.10(1H, doublet, J=8.5 Hz); 6.94–6.84 (2H, multiplet); 5.82(1H, doublet, J=10.1 Hz); 5.48(1H, doublet, J=10.1 Hz); 5.47 (2H, singlet); 4.06 (2H, singlet); 3.70 (3H, broad singlet); 2.21 (3H, singlet).

EXAMPLE 427

Methyl N-[4-(benzothiazol-2-ylmethoxy)-2-methylphenyl]-N-benzoyloxymethylcarbamate (Compound No. D 1.90)

Amorphous

Nuclear Magnetic Resonance Spectrum (200 MHz, $CDCl_3$), δ ppm: 8.05–8.01 (3H, multiplet); 7.93–7.88 (1H, multiplet); 7.62–7.37 (5H, multiplet); 7.19–7.13 (1H, multiplet); 6.94 (2H, doublet, J=3.1 Hz); 6.87 (1H, doublet of doublets, J=8.6 & 3.1 Hz); 5.98 (1H, doublet, J=10.7 Hz); 5.70–5.63 (1H, multiplet); 5.47 (2H, singlet); 3.83–3.72 (3H, multiplet); 2.26 (3H, singlet).

EXAMPLE 428

Methyl N-[4.(benzoxazol-2-ylmethoxy)-2-methylphenyl]-N-benzoyloxymethylcarbamate (Compound No. D 1.91)

Amorphous

Nuclear Magnetic Resonance Spectrum (200 MHz, $CDCl_3$), δ ppm: 8.12–8.01 (2H, multiplet); 7.79–7.74 (1H, multiplet); 7.61–7.52 (2H, multiplet); 7.48–7.35 (4H, multiplet); 7.18–7.13 (1H, multiplet); 6.97–6.87 (2H, multiplet); 6.00–5.95 ( 1 H, multiplet); 5.18–5.63 (1H, multiplet); 5.31 (2H, singlet); 3.72 (3H, broad singlet); 2.25 (3H, singlet).

EXAMPLE 429

Methyl N-[4-(benzothiazol-2-ylmethoxy)-2-methylphenyl]-N-(4-chlorobenzoyloxymethyl) carbamate (Compound No. D 1.92)

Oil

Nuclear Magnetic Resonance Spectrum (200 MHz, $CDCl_3$), δ ppm: 7.86–8.08 (4H, multiplet); 7.34–7.56 (4H, multiplet); 7.13 (1H, doublet, J=8.7 Hz); 6.83–6.97 (2H, multiplet); 5.97(1H, doublet, J=10.3 Hz); 5.65 (1H, doublet, J=10.3 Hz); 5.47 (2H, singlet); 3.70 (3H, broad singlet); 2.24 (3H, singlet).

EXAMPLE 430

Methyl N-[4-(benzothiazol-2-ylmethoxy)-2-methylphenyl]-N-4-methylbenzoyloxymethyl) carbamate (Compound No. D 1.93)

Oil

Nuclear Magnetic Resonance Spectrum (200 MHz, $CDCl_3$), δ ppm: 8.05–7.88 (2H, multiplet); 6.94–6.83 (5H, multiplet); 5.81 (2H, AB quartet, J=10.6 Hz, Δv=60.7); 5.46 (2H, singlet); 3.88–3.70 (3H, multiplet); 2.41 (3H, singlet); 2.25 (3H, singlet).

EXAMPLE 431

Methyl N-[4-(benzothiazol-2-ylmethoxy)-2-methylphenyl]-N-(4-methoxybenzoyloxymethyl) carbamate (Compound No. D 1.94)

Amorphous

Nuclear Magnetic Resonance Spectrum (200 MHz, $CDCl_3$), δ ppm: 8.06–7.88 (4H, multiplet); 7.55–7.37 (2H, multiplet); 7.14(1H, doublet, J=8.9 Hz); 6.93–6.83 (4H, multiplet); 5.79 (2H, AB quartet, J=10.3 Hz, Δv=60.8), 5.46 (2H, singlet); 3.86 (3H, singlet); 3.72 (3H, broad singlet); 2.24 (3H, singlet).

EXAMPLE 432

Methyl N-[4-(benzothiazol-2-ylmethoxy)-2-methylphenyl]-N-(phenylacetoxymethyl)carbamate (Compound No. D 1.95)

Oil

Nuclear Magnetic Resonance Spectrum (200 MHz, $CDCl_3$), δ ppm: 8.05 (1H, doublet, J=7.3 Hz); 7.92 (1H, doublet, J=7.4 Hz); 7.35–7.55 (2H, multiplet); 7.18–7.33 (5H, multiplet); 6.70–6.91 (3H, multiplet); 5.76(1H, doublet, J=10.0 Hz); 5.45 (2H, singlet); 5.38(1H, doublet, J=10.0 Hz); 3.68 (3H, broad singlet); 3.63 (2H, singlet); 2.11 (3H, singlet).

EXAMPLE 433

Methyl N-[4-(benzothiazol-2-ylmethoxy)-2-methylphenyl]-N-(2-thenoyloxymethyl)carbamate (Compound No. D 1.97)

Gum

Nuclear Magnetic Resonance Spectrum (200 MHz, $CDCl_3$), δ ppm: 8.03 (1H, doublet, J=7.6 Hz); 7.91 (1H, doublet, J=7.0 Hz); 7.80 (1H, multiplet); 7.36–7.59 (3H, multiplet); 7.06–7.19 (2H, multiplet); 6.82–6.89 (2H, multiplet); 5.92 (1H, doublet, J=10.2 Hz); 5.65 doublet, J=10.2 Hz); 5.47 (2H, singlet); 3.71 (3H, broad singlet); 2.25(3H, singlet).

EXAMPLE 434

Methyl N-[4-(benzoxazol-2-ylmethoxy)-2-methylphenyl]-N-(2-thenoyloxymethyl)carbamate (Compound No. D 1.98)

Amorphous

Nuclear Magnetic Resonance Spectrum (200 MHz, $CDCl_3$), δ ppm: 7.82–7.75 (2H, multiplet); 7.59–7.54 (2H, multiplet); 7.40–7.35 (2H, multiplet); 7.17–7.08 (2H, multiplet); 6.96–6.87 (2H, multiplet); 5.94–5.89 (1H, multiplet); 5.67–5.62 (1H, multiplet); 5.31 (2H, singlet); 3.71 (3H, broad singlet); 2.25 (3H, singlet).

EXAMPLE 435

Methyl N-[4-(benzothiazol-2-ylmethoxy)-2-methylphenyl]-N-(2-furoyloxymethyl)carbamate (Compound No. D 1.99)

Gum

Nuclear Magnetic Resonance Spectrum (200 MHz, $CDCl_3$), δ ppm: 8.03 (1H, doublet, J=7.3 Hz); 7.90 (1H, doublet, J=7.3 Hz); 7.34–7.69 (3H, multiplet); 7.08–7.21 (2H, multiplet); 6.83–6.95 (2H, multiplet); 6.50 (1H, multiplet); 5.91 (1H, doublet, J=10.3 Hz); 5.66 (1H, doublet, J=10.3 Hz); 5.46 (2H, singlet); 3.71 (3H, broad singlet); 2.24 (3H, singlet).

EXAMPLE 436

Methyl N-[4-(benzothiazol-2-ylmethoxy)-2-methylphenyl]-N-(nicotinoyloxymethyl)carbamate (Compound No. D1.100)

Oil

Nuclear Magnetic Resonance Spectrum (200 MHz, CDCl$_3$), δ ppm: 9.21 (1H, multiplet); 8.79 (1H, doublet of doublets, J=2.0 & 4.7 Hz); 8.28 (doublet of triplets, $J_d$=8.1Hz, $J_t$=1.5 Hz); 8.03 (1H, doublet, J=8.0 Hz); 7.90 (1H, doublet, J=8.7 Hz); 7.37–7.56 (3H, multiplet); 7.15 (1 H, doublet, J=8.4 Hz); 6.81–6.96 (2H, multiplet); 6.02 (1H, doublet, J=10.3 Hz); 5.67 (1H, doublet, J=10.3 Hz); 5.47 (2H, singlet); 3.72 (3H, broad singlet); 2.25 (3H, singlet).

EXAMPLE 437

Methyl N-[4-(benzothiazol-2-ylmethoxy)-2-methylphenyl]-N-(2-chloronicotinoyloxymethyl)carbamate (Compound No. D 1.101)

Oil

Nuclear Magnetic Resonance Spectrum (200 MHz, CDCl$_3$), δ ppm: 8.53 (1H, doublet of doublets, J=1.9 & 4.8 Hz); 8.16(1H, doublet of doublets, J=1.9 & 7.8 Hz); 8.03 (1H, doublet, J=7.7 Hz); 7.90 (1H, doublet, J=7.0 Hz); 7.29–7.55 (3H, multiplet); 7.17(1H, doublet, J=8.8 Hz); 6.83–6.94 (2H, multiplet); 6.04 (1H, doublet, J=10.3 Hz); 5.60 (1H, doublet, J=10.3 Hz); 5.47 (2H, singlet); 3.72 (3H, broad singlet); 2.04 (3H, singlet).

EXAMPLE 438

Methyl N-[4-(benzothiazol-2-ylmethoxy)-2-methylphenyl]-N-(2-pyrazinecarbonyloxymethyl)carbamate (Compound No. D 1.102)

Oil

Nuclear Magnetic Resonance Spectrum (200 MHz, CDCl$_3$), δ ppm: 9.27 (1H, doublet, J=1.4 Hz); 8.72 (2H, multiplet); 8.02 (1H, doublet, J=7.3 Hz); 7.90 (1H, doublet, J=7.7 Hz); 7.35–7.54 (2H, multiplet); 7.19 (1H, doublet, J=8.5 Hz); 6.82–6.96 (2H, multiplet); 6.08 (1H, doublet, J=10.3 Hz); 5.74 (1H, doublet, J=10.3 Hz); 5.46(2H, singlet); 3.72 (3H, broad singlet); 2.26 (3H, singlet).

EXAMPLE 439

Methyl N-[4-(benzothiazol-2-ylmethoxy)-2-methylphenyl]-N-methoxycarbonyloxymethylcarbamate (Compound No. D 1.103)

Oil

Nuclear Magnetic Resonance Spectrum (200 MHz, CDCl$_3$), δ ppm: 8.03 (1H, doublet, J=8.0 Hz); 7.90 (1H, doublet, J=7.0 Hz); 7.54–7.37 (2H, multiplet); 7.14–7.08 (1H, multiplet); 6.94–6.84 (2H, multiplet); 5.79 (1H, broad doublet, J=9.8 Hz); 5.47 (2H, singlet); 5.38 (1H, doublet, J=9.8 Hz); 3.75 (3H, singlet); 3.67 (3H, broad singlet); 2.20 (3H, singlet).

EXAMPLE 440

Methyl N-[4-(benzoxazol-2-ylmethoxy)-2-methylphenyl]-N-methoxycarbonoyloxymethylcarbamate (Compound No. D 1.104)

Oil

Nuclear Magnetic Resonance Spectrum (200 MHz, CDCl$_3$), δ ppm: 7.79–7.75 (1H, multiplet); 7.60–7.54 (1 H, multiplet); 7.43–7.33 (2H, multiplet); 7.12–7.07 (1H, multiplet); 6.95–6.85 (2H, multiplet); 5.82–5.75 (1H, multiplet); 5.42–5.35 (1H, multiplet); 5.31 (2H, singlet); 3.75 (6H, broad singlet); 2.20 (3H, singlet).

EXAMPLE 441

Methyl N-[4-(benzothiazol-2-ylmethoxy)-2-methylphenyl]-N'-(2-phenoxyethyl)carbamate (Compound No. D1.117)

Oil

Nuclear Magnetic Resonance Spectrum (200 MHz, CDCl$_3$), δ ppm: 8.04 (1H, doublet, J=7.6 Hz); 7.91 (1H, doublet, J=7.5 Hz); 7.55–7.36 (2H, multiplet); 7.28–7.20 (2H, multiplet); 7.11 (1H, doublet, J=8.6 Hz); 6.96–6.80 (5H, multiplet); 5.47 (2H, singlet); 4.17–4.07 (3H, multiplet); 3.84–3.71 (1H, multiplet); 3.64 (3H, broad singlet); 2.18(3H, singlet).

EXAMPLE 442

N-(2-Acetyloxyethyl)-N-[4-(benzothiazol-2-ylmethoxy)-2-methylphenyl]acetamide (Compound No. D1.122)

Oil

Nuclear Magnetic Resonance Spectrum (200 MHz, CDCl$_3$), δ ppm: 8.07–8.03 (1H, multiplet); 7.94–7.90 ( 1 H, multiplet); 7.56–7.39 (2H, multiplet); 7.10 (1n, doublet, J=8.4 Hz); 6.97 (1H, doublet, J=3.2 Hz); 6.90 ( 1H, doublet of doublets, J=8.8 & 2.8 Hz); 5.49 (2H, singlet); 4.36–4.18 (3H, multiplet); 3.42–3.33 ( 1 H, multiplet); 2.20 (3H, singlet); 1.95 (3H, singlet); 1.76 (3H, singlet).

EXAMPLE 443

Methyl N-(2-acetoxyethyl)-N-[4-(benzothiazol-2-ylmethoxy)-2-methylphenyl]carbamate (Compound No. D 1.123)

Oil

Nuclear Magnetic Resonance Spectrum (200 MHz, CDCl$_3$), δ ppm: 8.04 (1H, doublet, J=7.5 Hz); 7.91 (1H, doublet, J=7.4 Hz); 7.58–7.37 (2H, multiplet); 7.12–6.80 (3H, multiplet); 5.47 (2H, singlet); 4.25–4.12 (2H, broad multiplet); 4.07–3.52 (2H, multiplet); 3.64 (3H, singlet); 2.18 (3H, broad singlet); 1.96 (3H, singlet).

EXAMPLE 444

N-[4-(Benzothiazol-2-ylmethoxy)-2-methylphenyl]-N-(2-propionyloxyethyl)acetamide (Compound No. D1.125)

Oil

Nuclear Magnetic Resonance Spectrum (200 MHz, CDCl$_3$), δ ppm: 8.07–8.03 (1H, multiplet); 7.94–7.89 (1H, multiplet); 7.56–7.38 (2H, multiplet); 7.10 (1H, doublet, J=8.6 Hz); 6.97 (1H, doublet, J=3.0 Hz); 6.89(1H, doublet of doublets, J=8.4 & 3.0 Hz); 5.49(2H, singlet); 4.37–4.20 (3H, multiplet); 3.42–3.33 (1H, multiplet); 2.28–2.17 (5H, multiplet); 1.76 (3H, singlet); 1.05 (3H, triplet, J=7.6 Hz).

EXAMPLE 445

Methyl N-[4-(benzothiazol-2-ylmethoxy)-2-methylphenyl]-N-(2-propionyloxyethyl)carbamate (Compound No. D 1.126)

Oil

Nuclear Magnetic Resonance Spectrum (200 MHz, CDCl$_3$), δ ppm: 8.04 (1H, doublet, J=7.2 Hz); 7.91 (1H, doublet, J=6.8 Hz); 7.55–7.38 (2H, multiplet); 7.07 (1H, doublet, J=8.8 Hz); 6.94–6.81 (2H, multiplet); 5.47 (2H, singlet); 4.26–4.12 (2H, multiplet); 4.10–3.88 (1H, multiplet); 3.80–3.50 (1H, multiplet); 3.63 (1H, singlet); 2.24 (2H, quartet, J=7.7 Hz); 2.18(3H, singlet); 1.06 (3H, triplet, J=7.5 Hz).

EXAMPLE 446

N-[4-(Benzothiazol-2-ylmethoxy)-2-methylphenyl]-N-(2-cyclobutylcarbonyloxyethyl)acetamide (Compound No. D 1.128)

Oil

Nuclear Magnetic Resonance Spectrum (200 MHz, CDCl$_3$), δ ppm: 8.07–7.89 (2H, multiplet); 7.53–7.42 (2H, multiplet); 7.10 (1H, doublet, J=8.6 Hz); 7.09 (1H, doublet, J=8.4 Hz); 6.97–6.87 (2H, multiplet); 5.49 (2H, singlet); 4.38–4.20 (3H, multiplet); 3.41–2.98 (2H, multiplet); 2.32–1.76 (12H, multiplet).

EXAMPLE 447

N-[4-(Benzothiazol-2-ylmethoxy)-2-methylphenyl]-N-(2-chloroacetoxyethyl)acetamide (Compound No. D1.129)

Oil

Nuclear Magnetic Resonance Spectrum (200 MHz, CDCl$_3$), δ ppm: 8.05 (1H, doublet, J=7.4 Hz); 7.91 (1H, doublet, J=7.7 Hz); 7.52–7.42 (2H, multiplet); 7.14–6.89 (3H, multiplet); 5.50 (2H, singlet); 4.38–4.31 (3H, multiplet); 3.96 (3H, singlet); 3.38–3.24 (1H, multiplet); 2.20 (3H, singlet); 1.76 (3H, singlet).

EXAMPLE 448

N-[4-(Benzothiazol-2-ylmethoxy)-2-methylphenyl]-N-[2-(2-methoxyacetoxy)ethyl]acetamide (Compound No. D 1.130)

Oil

Nuclear Magnetic Resonance Spectrum (200 MHz, CDCl$_3$), δ ppm: 8.05 (1H, doublet, J=8.0 Hz); 7.92 (1H, doublet, J=7.3 Hz); 7.56–7.38 (2H, multiplet); 7.12 (1H, doublet, J=8.6 Hz); 6.96–6.87 (2H, multiplet); 5.49 (2H, singlet); 4.40–4.30 (3H, multiplet); 3.94 (2H, singlet); 3.38 (3H, singlet); 3.44–3.31 (1H, multiplet); 2.20 (3H, singlet); 1.76 (3H, singlet).

EXAMPLE 449

N-[4-(Benzothiazol-2-ylmethoxy)-2-methylphenyl]-N-(2-benzoyloxyethyl)acetamide (Compound No. D1.131)

Oil

Nuclear Magnetic Resonance Spectrum (200 MHz, CDCl$_3$), δ ppm: 8.07–7.88 (4H, multiplet); 7.57–7.33 (5H, multiplet); 7.09 (1H, doublet, J=8.6 Hz); 6.95 (1H, doublet, J=3.0 Hz); 6.82 (1H, doublet of doublets, J=8.8 & 3.0 Hz); 5.45 (2H, singlet); 4.48–4.41 (3H, multiplet); 3.61–3.54 (1 H, multiplet); 2.22 (3H, singlet); 1.78 (3H, singlet).

EXAMPLE 450

Methyl N-[4-(benzothiazol-2-ylmethoxy)-2-methylphenyl]-N-(2-benzoyloxyethyl)carbamate (Compound No. D1.132)

Oil

Nuclear Magnetic Resonance Spectrum (200 1MHz, CDCl$_3$), δ ppm: 8.04 (1H, doublet, J=8.2 Hz); 7.93–7.90 (3H, multiplet); 7.55–7.34 (5H, multiplet); 7.08 (1H, doublet, J=8.8 Hz); 6.90 (1H, doublet, J=2.6 Hz); 6.81 (1H, doublet of doublets, J=8.8 & 2.6 Hz); 5.44 (2H, singlet); 4.48–4.43 (2H, multiplet); 4.21–4.05 (1H, multiplet); 3.84–3.76 (1H, multiplet); 3.65(3H, singlet); 2.18 (3H, singlet).

EXAMPLE 451

N-[4-(Benzothiazol-2-ylmethoxy)-2-methylphenyl]-N-[2-(2-furoyloxy)ethyl]acetamide (Compound No. D 1.135)

Oil

Nuclear Magnetic Resonance Spectrum (200 MHz, CDCl$_3$), δ ppm: 8.07–8.03 (1H, multiplet); 7.94–7.89 (1H, multiplet); 7.57–7.39 (1H, multiplet); 7.14 (1H, doublet, J=8.6 Hz); 7.06 (1H, doublet, J=3.0 Hz); 6.95 (1H, doublet, J=3.0 Hz); 6.84 (1H, doublet of doublets, J=8.4 & 2.6 Hz); 6.43 (1H, doublet of doublets, J=3.6 & 1.8 Hz); 5.47 (2H, singlet); 4.50–4.37 (3H, multiplet); 3.57–3.43 (1H, multiplet); 1.77 (3H, singlet); 2.21 (3H, singlet).

EXAMPLE 452

N-[4-(Benzothiazol-2-ylmethoxy)-2-methylphenyl]-N-(2-isonicotinoyloxyethyl)acetamide (Compound No. D 1.136

Oil

Nuclear Magnetic Resonance Spectrum (200 MHz, CDCl$_3$), δ ppm: 8.75 (2H, doublet of doublets, J=4.4 & 1.1 Hz); 8.05 (1H, doublet, J=8.1 Hz); 7.92 (1H, doublet, J=8.3 Hz); 7.74 (2H, doublet of doublets, J=4.4 & 1.1 Hz); 7.56–7.38 (2H, multiplet); 7.07 (1H, doublet, J=8.5 Hz); 6.97 (1H, doublet, J=2.9 Hz); 6.85(1H, doublet of doublets, J=8.5 & 2.9 Hz); 5.47 (2H, singlet); 4.52–4.43 (3H, multiplet); 3.59–3.49 (1 H, multiplet); 2.22 (3H, singlet); 1.78(3H, singlet).

EXAMPLE 453

Methyl N-[4-(benzothiazol-2-ylmethoxy)-2-methylphenyl]-N-phenacylcarbamate (Compound No. D1.37)

Amorphous

Nuclear Magnetic Resonance Spectrum (200 MHz, $CDCl_3$), δ ppm: 8.04–7.87 (4H, multiplet); 7.57–7.38 (6H, multiplet); 6.92–6.83 (2H, multiplet); 5.45 (2H, singlet); 4.93 (2H, AB quartet, J=17.8 Hz, Δv=184.1); 3.69 (3H, singlet); 2.29 (3H, singlet).

EXAMPLE 454

Methyl N-[4-(benzothiazol-2-ylmethoxy)-2-methylphenyl]-N-[1-(ethoxycarbonyl)ethyl]carbamate (Compound No. D1.46)

Oil

Nuclear Magnetic Resonance Spectrum (200 MHz, $CDCl_3$), δ ppm: 8.04 (1H, doublet, J=7.7 Hz); 7.91 (1H, doublet, J=8.0 Hz); 7.56–7.35 (2H, multiplet); 6.95–6.82 (2H, multiplet); 5.47 (2H, singlet); 4.31–4.15 (3H, multiplet); 3.75–3.64 (3H, multiplet); 2.19 (3H, broad singlet); 1.31 (3H, triplet, J=7.1 Hz); 1.14 (3H, doublet, J=7.6 Hz).

EXAMPLE 455

Methyl N-[4-(benzothiazol-2-ylmethoxy)-2-methylphenyl]-N-[4-chlorophenylthiomethyl)carbamate (Compound No. D 1.65)

Oil

Nuclear Magnetic Resonance Spectrum (200 MHz, $CDCl_3$), δ ppm: 8.03 (1H, doublet, J=7.4 Hz); 7.88 doublet, J=8.1 Hz); 7.52–7.38 (2H, multiplet); 7.22 (2H, doublet, J=8.6 Hz); 7.14 (2H, doublet, J=8.6 Hz); 7.02 (1H, broad doublet, J=8.4 Hz); 6.87–6.79 (2H, multiplet); 5.43 (2H, singlet); 5.28 (1H, doublet, J=15.3 Hz); 4.88(1H, broad doublet, J=15.3 Hz); 3.61 (3H, singlet); 2.13(3H, broad singlet).

FORMULATION EXAMPLES

FORMULATION EXAMPLE 1

Wettable Powder 25 parts by weight of the title compound of Example 1 above (Compound No. A1.1), 2.5 pans by weight of sodium dodecylbenzenesulfonate, 2.5 parts by weight of calcium ligninsulfonate and 70 parts by weight of diatomaceous earth were mixed and pulverized using an air mill to give a wettable powder of the present invention containing 25 wt. % of Compound No. A1.1.

FORMULATION EXAMPLE 2

Emulsion 30 parts by weight of the title compound of Example 11 above (Compound No. A1.5), 2.68 parts by weight of calcium dodecylbenzenesulfonate, 4.92 parts by weight of polyoxyethylene stearyl ether and 0.4 pans by weight of calcium polyoxyethylene nonylphenyl ether phosphate were added to 62 pans by weight of xylene and the resulting mixture was stirred to give an emulsion of the present invention.

FORMULATION EXAMPLE 3

Granules 5 parts by weight of the title compound of Example 21 (Compound No. C1.5), 1 part by weight of white carbon, 5 parts by weight of calcium ligninsulfonate, 20 parts by weight of bentonite and 69 pans by weight of calcium carbonate were mixed and pulverized by means of an air mill. A kneader was charged with the resulting mixture and then 18 parts by weight of water were added. The resulting mixture was thoroughly kneaded to give a kneaded mixture which was forced through a screen having a mesh size of 7 mm to give moist granules. These were dried at 70° C. in a fluidized bed drier. The resulting dried granules were passed through screens of 1.00 mm and 0.30 mm mesh to select granules of the present invention having a diameter of from 0.30 to 1.00 mm.

FORMULATION EXAMPLE 4

Wettable Granules 80 parts by weight of the title compound of Example 29 (Compound No. C1.1), 1.25 pans by weight of polyacrylic acid sodium salt, 3.75 parts by weight of water, 3 parts by weight of sodium dodecylbenzenesulfonate, 7 parts by weight of dextrin and 5 parts by weight of titanium oxide were mixed and pulverized by means of an air mill. A rotating mixer or a fluidized bed mixer was charged with the resulting pulverized mixture and then water was sprayed onto the mixture to effect granulation. When the majority of the granules had attained a particle size of from 1.0 to 0.15 mm, they were removed from the mixer and dried in a fluidized bed drier. The dried granules were passed consecutively through screens having mesh sizes of 1.00 and 0.15 mm to select wettable granules of the present invention having a diameter of from 0.15 mm to 1.00 mm. Those granules obtained after the screening process having a diameter of greater than 1.00 mm were pulverized by means of an jet mill and the resulting granules were passed consecutively through the screens having mesh sizes of 1.00 and 0.15 mm to give additional wettable granules of the present invention having a diameter of from 0.15 to 1.00 mm, which were combined with the granules of the present invention having a diameter of from 0.15 to 1.00 mm obtained after the first screening.

FORMULATION EXAMPLE 5

Aqueous Suspension 25 parts by weight of the title compound of Example 105 (Compound No. G1.55), 0.7 parts by weight of sodium dioctylsulfosuccinate, 10 parts by weight of calcium ligninsulfonate, 44.15 parts by weight of water and 10.15 parts by weight of propylene glycol were mixed together and pulverized in a ball mill, a sand mill or a roller mill until the diameter of the solid particles was reduced to 5 µm or less. 10 parts by weight of a 0.05% (w/w) aqueous solution of xanthane gum were then added to 90 parts by weight of the resulting pulverized slurry, and this was then thoroughly mixed to give an aqueous suspension of the present invention.

We claim:
1. A compound of formula (I):

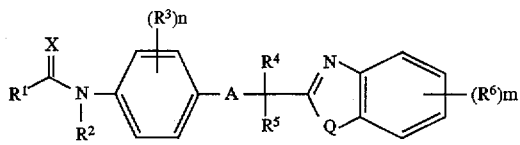

wherein:

$R^1$ represents:
- an alkyl group having from 1 to 6 carbon atoms, said alkyl group being unsubstituted or being substituted by an alkoxy group having from 1 to 6 carbon atoms or by from 1 to 4 halogen atoms;
- a cycloalkyl group having from 3 to 6 carbon atoms;
- an alkoxy group having from 1 to 6 carbon atoms, said alkoxy group being unsubstituted or being substituted by from 1 to 4 halogen atoms; or
- an alkylthio group having from 1 to 6 carbon atoms, said alkylthio group being unsubstituted or being substituted by from 1 to 4 halogen atoms;

$R^2$ represents:
- a hydrogen atom;
- an alkyl group having from 1 to 6 carbon atoms, said alkyl group being unsubstituted or being substituted by a hydroxy group or by from 1 to 4 halogen atoms;
- a cycloalkyl group having from 3 to 6 carbon atoms;
- an alkenyl group having from 2 to 6 carbon atoms, said alkenyl group being unsubstituted or being substituted by from 1 to 4 halogen atoms;
- an alkynyl group having from 2 to 6 carbon atoms, said alkynyl group being unsubstituted or being substituted by from 1 to 4 halogen atoms; or
- a group represented by the formula —$YR^7$;

$R^3$ represents:
- an alkyl group having from 1 to 6 carbon atoms, said alkyl group being unsubstituted or being substituted by an alkoxy group having from 1 to 6 carbon atoms or by from 1 to 4 halogen atoms;
- a cycloalkyl group having from 3 to 6 carbon atoms;
- an alkoxy group having from 1 to 6 carbon atoms, said alkoxy group being unsubstituted or being substituted by from 1 to 4 halogen atoms;
- an alkenyl group having from 2 to 6 carbon atoms, said alkenyl group being unsubstituted or being substituted by from 1 to 4 halogen atoms;
- an alkynyl group having from 2 to 6 carbon atoms, said alkynyl group being unsubstituted or being substituted by from 1 to 4 halogen atoms;
- a halogen atom;
- a nitro group; or
- a group of formula —$COR^8$, wherein $R^8$ represents a hydrogen atom, an alkyl group having from 1 to 6 carbon atoms, a cycloalkyl group having from 3 to 6 carbon atoms or an alkoxy group having from 1 to 6 carbon atoms;

$R^4$ and $R^5$ are the same or different and each represents a hydrogen atom or an alkyl group having from 1 to 6 carbon atoms;

$R^6$ represents:
- an alkyl group having from 1 to 6 carbon atoms, said alkyl group being unsubstituted or being substituted by an alkoxy group having from 1 to 6 carbon atoms or by from 1 to 4 halogen atoms;
- a cycloalkyl group having from 3 to 6 carbon atoms;
- an alkoxy group having from 1 to 6 carbon atoms, said alkoxy group being unsubstituted or being substituted by from 1 to 4 halogen atoms;
- an alkenyl group having from 2 to 6 carbon atoms, said alkenyl group being unsubstituted or being substituted by from 1 to 4 halogen atoms;
- an alkynyl group having from 2 to 6 carbon atoms, said alkynyl group being unsubstituted or being substituted by from 1 to 4 halogen atoms;
- a halogen atom;
- a nitro group; or
- a group of formula —$COR^8$, wherein $R^8$ represents a hydrogen atom, an alkyl group having from 1 to 6 carbon atoms, a cycloalkyl group having from 3 to 6 carbon atoms or an alkoxy group having from 1 to 6 carbon atoms;

A represents an oxygen atom or a sulfur atom;

X represents an oxygen atom or a sulfur atom;

Y represents a group selected from the group consisting of the groups of formulae —CO—, —COO—, —$CH_2O$—, —$CH_2S$—, —$CH_2CH_2O$—, —$CH_2CH_2S$—, —$CH_2CO$—, —$CH_2COO$—, —CH(Me)COO—, —$CH_2CH_2CO$—, —$CH_2OCO$—, $CH_2OCOO$— and —$CH_2CH_2OCO$—;

$R^7$ represents:
- an alkyl group having from 1 to 6 carbon atoms, said alkyl group being unsubstituted or being substituted by an alkoxy group having from 1 to 6 carbon atoms, an alkylthio group having from 1 to 6 carbon atoms or by from 1 to 4 halogen atoms;
- a cycloalkyl group having from 3 to 6 carbon atoms;
- an alkenyl group having from 2 to 6 carbon atoms, said alkenyl group being unsubstituted or being substituted by from 1 to 4 halogen atoms;
- an alkynyl group having from 2 to 6 carbon atoms, said alkynyl group being unsubstituted or being substituted by from 1 to 4 halogen atoms;
- a carbocyclic aryl group having from 6 to 14 ring carbon atoms, said aryl group being unsubstituted or being substituted by at least one substituent selected from the group consisting of alkyl groups having from 1 to 6 carbon atoms, alkoxy groups having from 1 to 6 carbon atoms and halogen atoms;
- an aralkyl group wherein the aryl moiety is a carbocyclic aryl group having from 6 to 10 ring carbon atoms which is unsubstituted or is substituted by from 1 to 4 halogen atoms, and the alkyl moiety has from 1 to 6 carbon atoms; or
- a heterocyclic group having from 4 to 10 ring atoms including at least one ring heteroatom selected from the group consisting of oxygen atoms, sulfur atoms and nitrogen atoms, said heterocyclic group being fully unsaturated, partly unsaturated or saturated and being either unsubstituted, substituted by at least one substituent selected from alkyl groups having from 1 to 6 carbon atoms, alkoxy groups having from 1 to 6 carbon atoms and halogen atoms, or fused with a carbocyclic aryl group having from 6 to 10 ring carbon atoms;

Q represents an oxygen atom or a sulfur atom;

m represents an integer from 0 to 4 and, where m is an integer from 2 to 4, each $R^6$ may be the same or different; and n represents an integer from 0 to 4 and, where n is an integer from 2 to 4, each $R^3$ may be the same or different;

and herbicidally acceptable addition salts thereof.

2. The compound according to claim 1, wherein:
$R^1$ represents:
an alkyl group having from 1 to 6 carbon atoms, said alkyl group being unsubstituted or being substituted by an alkoxy group having from 1 to 6 carbon atoms or by from 1 to 4 halogen atoms;
a cycloalkyl group having from 3 to 6 carbon atoms; or
an alkoxy group having from 1 to 6 carbon atoms, said alkoxy group being unsubstituted or being substituted by from 1 to 4 halogen atoms.

3. The compound according to claim 1, wherein:
$R^1$ represents:
an alkyl group having from 1 to 6 carbon atoms, said alkyl group being unsubstituted or being substituted by an alkoxy group having from 1 to 6 carbon atoms or by from 1 to 4 halogen atoms; or
an unsubstituted alkoxy group having from 1 to 6 carbon atoms.

4. The compound according to claim 1, wherein:
$R^1$ represents:
an alkyl group having from 1 to 3 carbon atoms, said alkyl group being unsubstituted or being substituted by an alkoxy group having from 1 to 3 carbon atoms; or
an unsubstituted alkoxy group having from 1 to 3 carbon atoms.

5. The compound according to claim 1, wherein $R^1$ represents a methyl group or a methoxy group.

6. The compound according to claim 1, wherein $R^1$ represents a methoxy group.

7. The compound according to claim 1, wherein:
$R^2$ represents:
a hydrogen atom;
an alkyl group having from 1 to 6 carbon atoms, said alkyl group being unsubstituted or being substituted by a hydroxy group or by from 1 to 4 halogen atoms;
a cycloalkyl group having from 3 to 6 carbon atoms; or
a group represented by the formula —$YR^7$, as defined in claim 1.

8. The compound according to claim 1, wherein:
$R^2$ represents:
a hydrogen atom;
an alkyl group having from 1 to 6 carbon atoms, said alkyl group being unsubstituted or being substituted by a hydroxy group; or
a group represented by the formula —$YR^7$, as defined in claim 1.

9. The compound according to claim 1, wherein:
$R^2$ represents:
a hydrogen atom;
an alkyl group having from 1 to 3 carbon atoms which is substituted by a hydroxy group; or
a group represented by the formula —$YR^7$, as defined in claim 1.

10. The compound according to claim 1, wherein $R^2$ represents a hydrogen atom, a hydroxymethyl group or a group represented by the formula —$YR^7$, as defined in claim 1.

11. The compound according to claim 1, wherein $R^2$ represents a hydrogen atom.

12. The compound according to claim 1, wherein Y represents a group selected from the group consisting of the groups of formulae —CO—, —COO—, —$CH_2O$—, —$CH_2CH_2O$—, —$CH_2CO$—, —$CH_2COO$—, —$CH_2CH_2CO$—, —$CH_2OCO$—, —$CH_2OCOO$— and —$CH_2CH_2OCO$—.

13. The compound according to claim 1, wherein Y represents a group selected from the group consisting of the groups of formulae —CO—, —COO—, —$CH_2O$—, —$CH_2CH_2O$—, —$CH_2OCO$— and —$CH_2OCOO$—.

14. The compound according to claim 1, wherein Y represents a group selected from the group consisting of the groups of formulae —CO—, —COO—, —$CH_2O$—, —$CH_2OCO$— and —$CH_2OCOO$—.

15. The compound according to claim 1, wherein Y represents a group selected from the group consisting of the groups of formulae —CO—, —COO— and —$CH_2OCO$—.

16. The compound according to claim 1, wherein:
$R^7$ represents:
an alkyl group having from 1 to 6 carbon atoms, said alkyl group being unsubstituted or being substituted by an alkoxy group having from 1 to 6 carbon atoms or by from 1 to 4 halogen atoms;
a cycloalkyl group having from 3 to 6 carbon atoms;
an alkenyl group having from 2 to 6 carbon atoms, said alkenyl group being unsubstituted or being substituted by from 1 to 4 halogen atoms;
an alkynyl group having from 2 to 6 carbon atoms, said alkynyl group being unsubstituted or being substituted by from 1 to 4 halogen atoms;
a carbocyclic aryl group having from 6 to 14 ring carbon atoms, said aryl group being unsubstituted or being substituted by from 1 to 3 alkyl groups having from 1 to 6 carbon atoms, 1 to 3 alkoxy groups having from 1 to 6 carbon atoms or by from 1 to 4 halogen atoms;
an aralkyl group wherein the aryl moiety is a carbocyclic aryl group having from 6 to 14 ring carbon atoms, said aryl group being unsubstituted or being substituted by from 1 to 4 halogen atoms, and the alkyl moiety has from 1 to 6 carbon atoms; or
a heterocyclic group having from 4 to 10 ring atoms including at least one ring heteroatom selected from the group consisting of oxygen atoms, sulfur atoms and nitrogen atoms, said heterocyclic group being fully unsaturated, partly unsaturated or saturated and being either unsubstituted, substituted by at least one substituent selected from alkyl groups having from 1 to 6 carbon atoms, alkoxy groups having from 1 to 6 carbon atoms and halogen atoms, or fused with a carbocyclic aryl group having from 6 to 10 ring carbon atoms.

17. The compound according to claim 1, wherein $R^7$ represents an alkyl group having from 1 to 6 carbon atoms, said alkyl group being unsubstituted or being substituted by an alkoxy group having from 1 to 6 carbon atoms or by from 1 to 4 halogen atoms.

18. The compound according to claim 1, wherein $R^7$ represents an alkyl group having from 1 to 3 carbon atoms, said alkyl group being unsubstituted or being substituted by from 1 to 4 halogen atoms.

19. The compound according to claim 1, wherein $R^7$ represents an ethyl group or a 2,2,2-trichloroethyl group.

20. The compound according to claim 1, wherein:
$R^3$ represents:
an alkyl group having from 1 to 6 carbon atoms, said alkyl group being unsubstituted or being substituted by a alkoxy group having from 1 to 6 carbon atoms or by from 1 to 4 halogen atoms;
a cycloalkyl group having from 3 to 6 carbon atoms;
an alkoxy group having from 1 to 6 carbon atoms, said alkoxy group being unsubstituted or being substituted by from 1 to 4 halogen atoms;

a halogen atom;

a nitro group; or a group represented by the formula —COR$^8$, as defined in claim 1.

21. The compound according to claim 1, wherein:
R$^3$ represents:
an alkyl group having from 1 to 6 carbon atoms, said alkyl group being unsubstituted or being substituted by an alkoxy group having from 1 to 6 carbon atoms or by from 1 to 4 halogen atoms;
an alkoxy group having from 1 to 6 carbon atoms, said alkoxy group being unsubstituted or being substituted by from 1 to 4 halogen atoms; or
a halogen atom.

22. The compound according to claim 1, wherein:
R$^3$ represents:
an unsubstituted alkyl group having from 1 to 3 carbon atoms;
an alkoxy group having from 1 to 3 carbon atoms; or
a halogen atom.

23. The compound according to claim 1, wherein R$^3$ represents a methyl group, an ethyl group, a methoxy group, an ethoxy group, a fluorine atom or a chlorine atom.

24. The compound according to claim 1, wherein R$^3$ represents a methyl group.

25. The compound according to claim 1, wherein R$^4$ and R$^5$ are the same or different and each represents a hydrogen atom or a methyl group.

26. The compound according to claim 1, wherein R$^4$ represents a hydrogen atom or a methyl group and R$^5$ represents a hydrogen atom.

27. The compound according to claim 1, wherein R$^4$ and R$^5$ each represent a hydrogen atom.

28. The compound according to claim 1, wherein:
R$^6$ represents:
an alkyl group having from 1 to 6 carbon atoms, said alkyl group being unsubstituted or being substituted by a alkoxy group having from 1 to 6 carbon atoms or by from 1 to 4 halogen atoms;
a cycloalkyl group having from 3 to 6 carbon atoms;
an alkoxy group having from 1 to 6 carbon atoms, said alkoxy group being unsubstituted or being substituted by from 1 to 4 halogen atoms;
a halogen atom; or
a group represented by the formula —COR$^8$, as defined in claim 1.

29. The compound according to claim 1, wherein:
R$^6$ represents:
an alkyl group having from 1 to 6 carbon atoms, said alkyl group being unsubstituted or being substituted by from 1 to 4 halogen atoms;
an alkoxy group having from 1 to 6 carbon atoms, said alkoxy group being unsubstituted or being substituted by from 1 to 4 halogen atoms; or
a halogen atom.

30. The compound according to claim 1, wherein:
R$^6$ represents:
an unsubstituted alkyl group having from 1 to 3 carbon atoms;
an unsubstituted alkoxy group having from 1 to 3 carbon atoms; or
a halogen atom.

31. The compound according to claim 1, wherein R$^6$ represents a methoxy group, a fluorine atom or a chlorine atom.

32. The compound according to claim 1, wherein R$^6$ represents a fluorine atom or a chlorine atom.

33. The compound according to claim 1, wherein R$^8$ represents an alkyl group having from 1 to 3 carbon atoms or an alkoxy group having from 1 to 3 carbon atoms.

34. The compound according to claim 1, wherein R$^8$ represents an alkoxy group having from 1 to 3 carbon atoms.

35. The compound according to claim 1, wherein R$^8$ represents a methoxy group.

36. The compound according to claim 1, wherein A represents an oxygen atom.

37. The compound according to claim 1, wherein X represents an oxygen atom.

38. The compound according to claim 1, wherein Q represents a sulfur atom.

39. The compound according to claim 1, wherein m represents an integer from 0 to 3.

40. The compound according to claim 1, wherein m represents an integer of 0 or 1.

41. The compound according to claim 1, wherein m represents an integer of 0.

42. The compound according to claim 1, wherein n represents an integer from 0 to 3.

43. The compound according to claim 1, wherein n represents an integer from 0 to 2.

44. The compound according to claim 1, wherein n represents an integer of 0 or 1.

45. The compound according to claim 1, wherein n represents an integer of 1.

46. The compound according to claim 1 wherein:
R$^1$ represents:
an alkyl group having from 1 to 6 carbon atoms, said alkyl group being unsubstituted or being substituted by an alkoxy group having from 1 to 6 carbon atoms or by from 1 to 4 halogen atoms;
a cycloalkyl group having from 3 to 6 carbon atoms; or
an alkoxy group having from 1 to 6 carbon atoms, said alkoxy group being unsubstituted or being substituted by from 1 to 4 halogen atoms;
R$^2$ represents:
a hydrogen atom;
an alkyl group having from 1 to 6 carbon atoms, said alkyl group being unsubstituted or being substituted by a hydroxy group or by from 1 to 4 halogen atoms;
a cycloalkyl group having from 3 to 6 carbon atoms; or
a group represented by the formula —YR$^7$, wherein:
Y represents a group selected from the group consisting of the the groups of formulae —CO—, —COO—, —CH$_2$O—, —CH$_2$CH$_2$O—, —CH$_2$CO—, —CH$_2$COO—, —CH$_2$CH$_2$CO—, —CH$_2$OCO—, —CH$_2$OCOO— and —CH$_2$CH$_2$OCO—, and
R$^7$ represents an alkyl group having from 1 to 6 carbon atoms, said alkyl group being unsubstituted or being substituted by an alkoxy group having from 1 to 6 carbon atoms or by from 1 to 4 halogen atoms,
a cycloalkyl group having from 3 to 6 carbon atoms,
an alkenyl group having from 2 to 6 carbon atoms, said alkenyl group being unsubstituted or being substituted by from 1 to 4 halogen atoms,
an alkynyl group having from 2 to 6 carbon atoms, said alkynyl group being unsubstituted or being substituted by from 1 to 4 halogen atoms,
a carbocyclic aryl group having from 6 to 14 ring carbon atoms, said aryl group being unsubstituted or being substituted by from 1 to 3 alkyl groups having from 1 to 6 carbon atoms, 1 to 3 alkoxy groups having from 1 to 6 carbon atoms or by from 1 to 4 halogen atoms, an aralkyl group wherein the aryl moiety is a carbocyclic aryl group having from 6 to 14 ring carbon atoms, said aryl group being unsubstituted or being substituted by from 1 to 4 halogen atoms, and the alkyl moiety has from 1 to 6 carbon atoms, or a heterocyclic group having from 4 to 10 ring atoms including at least one ring heteroatom selected from the group consisting of oxygen atoms, sulfur atoms and nitrogen atoms, said heterocyclic group being fully unsaturated, partly unsaturated or saturated and being either unsubstituted, substituted by at least one substituent selected from alkyl groups having from 1 to 6 carbon atoms, alkoxy groups having from 1 to 6 carbon atoms and halogen atoms, or fused with a carbocyclic aryl group having from 6 to 10 ring carbon atoms;

$R^3$ represents:

an alkyl group having from 1 to 6 carbon atoms, said alkyl group being unsubstituted or being substituted by a alkoxy group having from 1 to 6 carbon atoms or by from 1 to 4 halogen atoms;

a cycloalkyl group having from 3 to 6 carbon atoms;

an alkoxy group having from 1 to 6 carbon atoms, said alkoxy group being unsubstituted or being substituted by from 1 to 4 halogen atoms;

a halogen atom;

a nitro group; or a group represented by the formula —$COR^8$, wherein $R^8$ represents an alkyl group having from 1 to 3 carbon atoms or an alkoxy group having from 1 to 3 carbon atoms;

$R^4$ and $R^5$ are the same or different and each represents a hydrogen atom or a methyl group;

$R^6$ represents:

an alkyl group having from 1 to 6 carbon atoms, said alkyl group being unsubstituted or being substituted by a alkoxy group having from 1 to 6 carbon atoms or by from 1 to 4 halogen atoms;

a cycloalkyl group having from 3 to 6 carbon atoms;

an alkoxy group having from 1 to 6 carbon atoms, said alkoxy group being unsubstituted or being substituted by from 1 to 4 halogen atoms;

a halogen atom; or a group represented by the formula —$COR^8$, wherein $R^8$ represents an alkyl group having from 1 to 3 carbon atoms or an alkoxy group having from 1 to 3 carbon atoms; and m and n are the same or different and each represents an integer from 0 to 3.

47. The compound according to claim 1 wherein:

$R^1$ represents:

an alkyl group having from 1 to 6 carbon atoms, said alkyl group being unsubstituted or being substituted by an alkoxy group having from 1 to 6 carbon atoms or by from 1 to 4 halogen atoms; or an unsubstituted alkoxy group having from 1 to 6 carbon atoms;

$R^2$ represents:

a hydrogen atom;

an alkyl group having from 1 to 6 carbon atoms, said alkyl group being unsubstituted or being substituted by a hydroxy group; or a group represented by the formula —$YR^7$, wherein Y represents a group selected from the group consisting of the groups of formulae —CO—, —COO—, —$CH_2O$—, —$CH_2CH_2O$—, —$CH_2OCO$— and —$CH_2OCOO$— and $R^7$ represents an alkyl group having from 1 to 6 carbon atoms, said alkyl group being unsubstituted or being substituted by an alkoxy group having from 1 to 6 carbon atoms or by from 1 to 4 halogen atoms;

$R^3$ represents:

an alkyl group having from 1 to 6 carbon atoms, said alkyl group being unsubstituted or being substituted by an alkoxy group having from 1 to 6 carbon atoms or by from 1 to 4 halogen atoms;

an alkoxy group having from 1 to 6 carbon atoms, said alkoxy group being unsubstituted or being substituted by from 1 to 4 halogen atoms; or a halogen atom;

$R^4$ and $R^5$ are the same or different and each represents a hydrogen atom or a methyl group;

$R^6$ represents:

an alkyl group having from 1 to 6 carbon atoms, said alkyl group being unsubstituted or being substituted by from 1 to 4 halogen atoms;

an alkoxy group having from 1 to 6 carbon atoms, said alkoxy group being unsubstituted or being substituted by from 1 to 4 halogen atoms; or a halogen atom; and m represents an integer from 0 to 3 and n represents an integer from 0 to 2.

48. The compound according to claim 1 wherein:

$R^1$ represents:

an alkyl group having from 1 to 3 carbon atoms, said alkyl group being unsubstituted or being substituted by an alkoxy group having from 1 to 3 carbon atoms; or an unsubstituted alkoxy group having from 1 to 3 carbon atoms;

$R^2$ represents:

a hydrogen atom;

an alkyl group having from 1 to 3 carbon atoms which is substituted by a hydroxy group; or a group represented by the formula —$YR^7$, wherein Y represents a group selected from the group consisting of the groups of formulae —CO—, —COO—, —$CH_2O$—, —$CH_2OCO$— and —$CH_2OCOO$— and $R^7$ represents an alkyl group having from 1 to 3 carbon atoms, said alkyl group being unsubstituted or being substituted by from 1 to 4 halogen atoms;

$R^3$ represents:

an unsubstituted alkyl group having from 1 to 3 carbon atoms;

an alkoxy group having from 1 to 3 carbon atoms; or a halogen atom;

$R^4$ represents a hydrogen atom or a methyl group and $R^5$ represents a hydrogen atom;

$R^6$ represents:

an unsubstituted alkyl group having from 1 to 3 carbon atoms;

an unsubstituted alkoxy group having from 1 to 3 carbon atoms; or a halogen atom; and m and n are the same or different and each represents an integer of 0 or 1.

49. The compound according to claim 1 wherein:

$R^1$ represents a methyl group or a methoxy group;

$R^2$ represents a hydrogen atom, a hydroxymethyl group or a group represented by the formula —$YR^7$ wherein Y represents a group selected from the group consisting of the groups of formulae —CO—, —COO— or —CH$_2$OCO— and R$^7$ represents an ethyl group or a 2,2,2-trichloroethyl group;

R$^3$ represents a methyl group, an ethyl group, a methoxy group, an ethoxy group, a fluorine atom or a chlorine atom;

R$^4$ represents a hydrogen atom or a methyl group and R$^5$ represents a hydrogen atom;

R$^6$ represents a methoxy group, a fluorine atom or a chlorine atom;

m and n are the same or different and each represents an integer of 0 or 1;

A represents an oxygen atom;

X represents an oxygen atom; and

Q represents a sulfur atom.

50. The compound according to claim 1 wherein:

R$^1$ represents a methoxy group;

R$^2$ represents a hydrogen atom;

R$^3$ represents a methyl group;

R$^4$ and R$^5$ each represent a hydrogen atom;

m represents an integer of 0;

n represents an integer of 1;

A represents an oxygen atom;

X represents an oxygen atom; and

Q represents a sulfur atom.

51. The compound according to claim 1 wherein m represents an integer of 1 and R$^3$ is at the 2-position of the phenyl ring.

52. The compound according to claim 1, wherein:

R$^x$ represents an alkyl group having from 1 to 6 carbon atoms, said alkyl group being unsubstituted or being substituted by an alkoxy group having from 1 to 6 carbon atoms or by from 1 to 4 halogen atoms;

R$^2$ represents:
  a hydrogen atom;
  an alkyl group having from 1 to 6 carbon atoms, said alkyl group being unsubstituted or being substituted by from 1 to 4 halogen atoms;
  an alkenyl group having from 3 to 6 carbon atoms, said alkenyl group being unsubstituted;
  an alkynyl group having from 3 to 6 carbon atoms, said alkynyl group being unsubstituted; or
  an alkoxycarbonyl group wherein the alkoxy moiety has from 1 to 6 carbon atoms;

R$^3$ represents:
  an alkyl group having from 1 to 6 carbon atoms, said alkyl group being unsubstituted or being substituted by an alkoxy group having from 1 to 6 carbon atoms or by from 1 to 4 halogen atoms;
  an alkoxy group having from 1 to 6 carbon atoms, said alkoxy group being unsubstituted;
  an alkenyl group having from 3 to 6 carbon atoms, said alkenyl group being unsubstituted;
  an alkynyl group having from 3 to 6 carbon atoms, said alkynyl group being unsubstituted;
  a halogen atom;
  a nitro group; or
  a formyl group;

R$^4$ and R$^5$ are the same or different and each represents a hydrogen atom or an alkyl group having from 1 to 6 carbon atoms;

R$^6$ represents:
  an alkyl group having from 1 to 6 carbon atoms, said alkyl group being unsubstituted or being substituted by from 1 to 4 halogen atoms;
  an alkoxy group having from 1 to 6 carbon atoms, said alkoxy group being unsubstituted or being substituted by from 1 to 4 halogen atoms;
  an alkenyl group having from 3 to 6 carbon atoms, said alkenyl group being unsubstituted;
  an alkynyl group having from 3 to 6 carbon atoms, said alkynyl group being unsubstituted; or
  a halogen atom;

A represents an oxygen atom or a sulfur atom;

X represents an oxygen atom;

Q represents a sulfur atom;

m represents an integer from 0 to 4 and, where m is an integer from 2 to 4, each R$^6$ may be the same or different; and n represents an integer from 0 to 4 and, where n is an integer from 2 to 4, each R$^3$ may be the same or different;

and herbicidally acceptable addition salts thereof.

53. The compound according to claim 1, wherein:

R$^1$ represents:
  an alkoxy group having from 1 to 6 carbon atoms, said alkoxy group being unsubstituted or being substituted by from 1 to 4 halogen atoms; or
  an alkylthio group having from 1 to 6 carbon atoms, said alkylthio group being unsubstituted or being substituted by from 1 to 4 halogen atoms;

R$^2$ represents:
  a hydrogen atom; or
  an alkyl group having from 1 to 6 carbon atoms, said alkyl group being unsubstituted or being substituted by from 1 to 4 halogen atoms;

R$^3$ represents:
  an alkyl group having from 1 to 6 carbon atoms, said alkyl group being unsubstituted or being substituted by an alkoxy group having from 1 to 6 carbon atoms or by from 1 to 4 halogen atoms;
  an alkoxy group having from 1 to 6 carbon atoms, said alkoxy group being unsubstituted or being substituted by from 1 to 4 halogen atoms;
  a halogen atom;
  a nitro group; or
  a formyl group;

R$^4$ and R$^5$ are the same or different and each represents a hydrogen atom or an alkyl group having from 1 to 6 carbon atoms;

R$^6$ represents:
  an alkyl group having from 1 to 6 carbon atoms, said alkyl group being unsubstituted or being substituted by from 1 to 6 carbon atoms or by from 1 to 4 halogen atoms;
  an alkoxy group having from 1 to 6 carbon atoms, said alkoxy group being unsubstituted or being substituted by from 1 to 4 halogen atoms; or
  a halogen atom;

A represents an oxygen atom or a sulfur atom;

X represents an oxygen atom or a sulfur atom;

Q represents an oxygen atom or a sulfur atom;

m represents an integer from 0 to 4 and, where m is an integer from 2 to 4, each R$^6$ may be the same or different; and n represents an integer from 0 to 4 and, where n is an integer from 2 to 4, each R$^3$ may be the same or different;

and herbicidally acceptable addition salts thereof.

54. The compound according to claim 1, selected from the group consisting of:

N-[4-(benzothiazol-2-ylmethoxy)-2-methylphenyl]acetamide;

N-[4-(benzoxazol-2-ylmethoxy)-2-methylphenyl]acetamide;

methyl N-[4-(benzothiazol-2-ylmethoxy)-2-methylphenyl]carbamate;

methyl N-[4-(benzoxazol-2-ylmethoxy)-2-methylphenyl]carbamate;

methyl N-[4-(benzothiazol-2-ylmethoxy)-2-methylphenyl]-N-hydroxymethylcarbamate;

methyl N-[4-(benzothiazol-2-ylmethoxy)-2-methylphenyl]-N-propionyloxymethylcarbamate;

N-[4-(benzothiazol-2-ylmethoxy)-2-methylphenyl]-N-methoxycarbonylpropionamide;

methyl N-[4-(6-methoxybenzothiazol-2-ylmethoxy)-2-methylphenyl]carbamate;

methyl N-[4-(5-fluorobenzothiazol-2-ylmethoxy)-2-methylphenyl]carbamate; and methyl N-[4-(6-fluorobenzothiazol-2-ylmethoxy)-2-methylphenyl]carbamate.

55. A herbicidal composition comprising an effective amount of a herbicidal agent in admixture with an agriculturally or horticulturally acceptable carrier or diluent, wherein the herbicidal agent is a compound of formula (I):

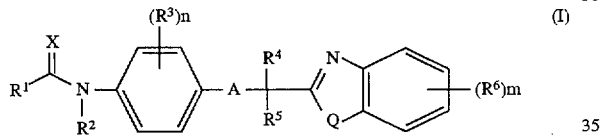

wherein:

$R^1$ represents:
   an alkyl group having from 1 to 6 carbon atoms, said alkyl group being up substituted or being substituted by an alkoxy group having from 1 to 6 carbon atoms or by from 1 to 4 halogen atoms;
   a cycloalkyl group having from 3 to 6 carbon atoms;
   an alkoxy group having from 1 to 6 carbon atoms, said alkoxy group being unsubstituted or being substituted by from 1 to 4 halogen atoms; or
   an alkylthio group having from 1 to 6 carbon atoms, said alkylthio group being unsubstituted or being substituted by from 1 to 4 halogen atoms;

$R^2$ represents:
   a hydrogen atom;
   an alkyl group having from 1 to 6 carbon atoms, said alkyl group being unsubstituted or being substituted by a hydroxy group or by from 1 to 4 halogen atoms;
   a cycloalkyl group having from 3 to 6 carbon atoms;
   an alkenyl group having from 2 to 6 carbon atoms, said alkenyl group being unsubstituted or being substituted by from 1 to 4 halogen atoms;
   an alkynyl group having from 2 to 6 carbon atoms, said alkynyl group being unsubstituted or being substituted by from 1 to 4 halogen atoms; or
   a group represented by the formula —$YR^7$;

$R^3$ represents:
   an alkyl group having from 1 to 6 carbon atoms, said alkyl group being unsubstituted or being substituted by an alkoxy group having from 1 to 6 carbon atoms or by from 1 to 4 halogen atoms;
   a cycloalkyl group having from 3 to 6 carbon atoms;
   an alkoxy group having from 1 to 6 carbon atoms, said alkoxy group being unsubstituted or being substituted by from 1 to 4 halogen atoms;
   an alkenyl group having from 2 to 6 carbon atoms, said alkenyl group being unsubstituted or being substituted by from 1 to 4 halogen atoms;
   an alkynyl group having from 2 to 6 carbon atoms, said alkynyl group being unsubstituted or being substituted by from 1 to 4 halogen atoms;
   a halogen atom;
   a nitro group; or
   a group of formula —$COR^8$, wherein $R^8$ represents a hydrogen atom, an alkyl group having from 1 to 6 carbon atoms, a cycloalkyl group having from 3 to 6 carbon atoms or an alkoxy group having from 1 to 6 carbon atoms;

$R^4$ and $R^5$ are the same or different and each represents a hydrogen atom or an alkyl group having from 1 to 6 carbon atoms;

$R^6$ represents:
   an alkyl group having from 1 to 6 carbon atoms, said alkyl group being unsubstituted or being substituted by an alkoxy group having from 1 to 6 carbon atoms or by from 1 to 4 halogen atoms;
   a cycloalkyl group having from 3 to 6 carbon atoms;
   an alkoxy group having from 1 to 6 carbon atoms, said alkoxy group being unsubstituted or being substituted by from 1 to 4 halogen atoms;
   an alkenyl group having from 2 to 6 carbon atoms, said alkenyl group being unsubstituted or being substituted by from 1 to 4 halogen atoms;
   an alkynyl group having from 2 to 6 carbon atoms, said alkynyl group being unsubstituted or being substituted by from 1 to 4 halogen atoms;
   a halogen atom;
   a nitro group; or
   a group of formula —$COR^8$, wherein $R^8$ represents a hydrogen atom, an alkyl group having from 1 to 6 carbon atoms, a cycloalkyl group having from 3 to 6 carbon atoms or an alkoxy group having from 1 to 6 carbon atoms;

A represents an oxygen atom or a sulfur atom;

X represents an oxygen atom or a sulfur atom;

Y represents a group selected from the group consisting of the groups of formulae —CO—, —COO—, —CH$_2$O—, —CH$_2$S—, —CH$_2$CH$_2$O—, —CH$_2$CH$_2$S—, —CH$_2$CO—, —CH$_2$COO—, —CH(Me)COO—, —CH$_2$CH$_2$CO—, —CH$_2$OCO—, CH$_2$OCOO— and —CH$_2$CH$_2$OCO—;

$R^7$ represents:
   an alkyl group having from 1 to 6 carbon atoms, said alkyl group being unsubstituted or being substituted by an alkoxy group having from 1 to 6 carbon atoms, an alkylthio group having from 1 to 6 carbon atoms or by from 1 to 4 halogen atoms;
   a cycloalkyl group having from 3 to 6 carbon atoms;
   an alkenyl group having from 2 to 6 carbon atoms, said alkenyl group being unsubstituted or being substituted by from 1 to 4 halogen atoms;
   an alkynyl group having from 2 to 6 carbon atoms, said alkynyl group being unsubstituted or being substituted by from 1 to 4 halogen atoms;
   a carbocyclic aryl group having from 6 to 14 ring carbon atoms, said aryl group being unsubstituted or being substituted by at least one substituent selected from the group consisting of alkyl groups having from 1 to 6 carbon atoms, alkoxy groups having from 1 to 6 carbon atoms and halogen atoms;

an aralkyl group wherein the aryl moiety is a carbocyclic aryl group having from 6 to 10 ring carbon atoms which is unsubstituted or is substituted by from 1 to 4 halogen atoms, and the alkyl moiety has from 1 to 6 carbon atoms; or a heterocyclic group having from 4 to 10 ring atoms including at least one ring heteroatom selected from the group consisting of oxygen atoms, sulfur atoms and nitrogen atoms, said heterocyclic group being fully unsaturated, partly unsaturated or saturated and being either unsubstituted, substituted by at least one substituent selected from alkyl groups having from 1 to 6 carbon atoms, alkoxy groups having from 1 to 6 carbon atoms and halogen atoms, or fused with a carbocyclic aryl group having from 6 to 10 ring carbon atoms;

Q represents an oxygen atom or a sulfur atom;

m represents an integer from 0 to 4 and, where m is an integer from 2 to 4, each $R^6$ may be the same or different; and n represents an integer from 0 to 4 and, where n is an integer from 2 to 4, each $R^3$ may be the same or different;

or a herbicidally acceptable addition salt thereof.

56. The composition according to claim 55, wherein:
$R^1$ represents:
an alkyl group having from 1 to 6 carbon atoms, said alkyl group being unsubstituted or being substituted by an alkoxy group having from 1 to 6 carbon atoms or by from 1 to 4 halogen atoms;
a cycloalkyl group having from 3 to 6 carbon atoms; or
an alkoxy group having from 1 to 6 carbon atoms, said alkoxy group being unsubstituted or being substituted by from 1 to 4 halogen atoms.

57. The composition according to claim 55, wherein:
$R^1$ represents:
an alkyl group having from 1 to 6 carbon atoms, said alkyl group being unsubstituted or being substituted by an alkoxy group having from 1 to 6 carbon atoms or by from 1 to 4 halogen atoms; or
an unsubstituted alkoxy group having from 1 to 6 carbon atoms.

58. The composition according to claim 55, wherein:
$R^1$ represents:
an alkyl group having from 1 to 3 carbon atoms, said alkyl group being unsubstituted or being substituted by an alkoxy group having from 1 to 3 carbon atoms; or
an unsubstituted alkoxy group having from 1 to 3 carbon atoms.

59. The composition according to claim 55, wherein $R^1$ represents a methyl group or a methoxy group.

60. The composition according to claim 55, wherein $R^1$ represents a methoxy group.

61. The composition according to claim 55, wherein:
$R^2$ represents:
a hydrogen atom;
an alkyl group having from 1 to 6 carbon atoms, said alkyl group being unsubstituted or being substituted by a hydroxy group or by from 1 to 4 halogen atoms;
a cycloalkyl group having from 3 to 6 carbon atoms; or
a group represented by the formula $-YR^7$, as defined in claim 55.

62. The composition according to claim 55, wherein:
$R^2$ represents:
a hydrogen atom;
an alkyl group having from 1 to 6 carbon atoms, said alkyl group being unsubstituted or being substituted by a hydroxy group; or
a group represented by the formula $-YR^7$, as defined in claim 55.

63. The composition according to claim 55, wherein:
$R^2$ represents:
a hydrogen atom;
an alkyl group having from 1 to 3 carbon atoms which is substituted by a hydroxy group; or
a group represented by the formula $-YR^7$, as defined in claim 55.

64. The composition according to claim 55, wherein $R^2$ represents a hydrogen atom, a hydroxymethyl group or a group represented by the formula $-YR^7$, as defined in claim 55.

65. The composition according to claim 55, wherein $R^2$ represents a hydrogen atom.

66. The composition according to claim 55, wherein Y represents a group selected from the group consisting of the groups of formulae $-CO-$, $-COO-$, $-CH_2O-$, $-CH_2CH_2O-$, $-CH_2CO-$, $-CH_2COO-$, $-CH_2CH_2CO-$, $-CH_2OCO-$, $-CH_2OCOO-$ and $-CH_2CH_2OCO-$.

67. The composition according to claim 55, wherein Y represents a group selected from the group consisting of the groups of formulae $-CO-$, $-COO-$, $-CH_2O-$, $-CH_2CH_2O-$, $-CH_2OCO-$ and $-CH_2OCOO-$.

68. The composition according to claim 55, wherein Y represents a group selected from the group consisting of the groups of formulae $-CO-$, $-COO-$, $-CH_2O-$, $-CH_2OCO-$, and $-CH_2OCOO-$.

69. The composition according to claim 55, wherein Y represents a group selected from the group consisting of the groups of formulae $-CO-$, $-COO-$ and $-CH_2OCO-$.

70. The composition according to claim 55, wherein:
$R^7$ represents:
an alkyl group having from 1 to 6 carbon atoms, said alkyl group being unsubstituted or being substituted by an alkoxy group having from 1 to 6 carbon atoms or by from 1 to 4 halogen atoms;
a cycloalkyl group having from 3 to 6 carbon atoms;
an alkenyl group having from 2 to 6 carbon atoms, said alkenyl group being unsubstituted or being substituted by from 1 to 4 halogen atoms;
an alkynyl group having from 2 to 6 carbon atoms, said alkynyl group being unsubstituted or being substituted by from 1 to 4 halogen atoms;
a carbocyclic aryl group having from 6 to 14 ring carbon atoms, said aryl group being unsubstituted or being substituted by from 1 to 3 alkyl groups having from 1 to 6 carbon atoms, 1 to 3 alkoxy groups having from 1 to 6 carbon atoms or by from 1 to 4 halogen atoms;
an aralkyl group wherein the aryl moiety is a carbocyclic aryl group having from 6 to 14 ring carbon atoms, said aryl group being unsubstituted or being substituted by from 1 to 4 halogen atoms, and the alkyl moiety has from 1 to 6 carbon atoms; or
a heterocyclic group having from 4 to 10 ring atoms including at least one ring heteroatom selected from the group consisting of oxygen atoms, sulfur atoms and nitrogen atoms, said heterocyclic group being fully unsaturated, partly unsaturated or saturated and being either unsubstituted, substituted by at least one substituent selected from alkyl groups having from 1 to 6 carbon atoms, alkoxy groups having from 1 to 6 carbon atoms and halogen atoms, or fused with a carbocyclic aryl group having from 6 to 10 ring carbon atoms.

71. The composition according to claim 55, wherein $R^7$ represents an alkyl group having from 1 to 6 carbon atoms, said alkyl group being unsubstituted or being substituted by an alkoxy group having from 1 to 6 carbon atoms or by from 1 to 4 halogen atoms.

72. The composition according to claim 55, wherein $R^7$ represents an alkyl group having from 1 to 3 carbon atoms, said alkyl group being unsubstituted or being substituted by from 1 to 4 halogen atoms.

73. The composition according to claim 55, wherein $R^7$ represents an ethyl group or a 2,2,2-trichloroethyl group.

74. The composition according to claim 55, wherein: $R^3$ represents:
an alkyl group having from 1 to 6 carbon atoms, said alkyl group being unsubstituted or being substituted by a alkoxy group having from 1 to 6 carbon atoms or by from 1 to 4 halogen atoms;
a cycloalkyl group having from 3 to 6 carbon atoms;
an alkoxy group having from 1 to 6 carbon atoms, said alkoxy group being unsubstituted or being substituted by from 1 to 4 halogen atoms;
a halogen atom;
a nitro group; or
a group represented by the formula —$COR^8$, as defined in claim 55.

75. The composition according to claim 55, wherein: $R^3$ represents:
an alkyl group having from 1 to 6 carbon atoms, said alkyl group being unsubstituted or being substituted by an alkoxy group having from 1 to 6 carbon atoms or by from 1 to 4 halogen atoms;
an alkoxy group having from 1 to 6 carbon atoms, said alkoxy group being;
unsubstituted or being substituted by from 1 to 4 halogen atoms; or
a halogen atom.

76. The composition according to claim 55, wherein: $R^3$ represents:
an unsubstituted alkyl group having from 1 to 3 carbon atoms;
an alkoxy group having from 1 to 3 carbon atoms; or
a halogen atom.

77. The composition according to claim 55, wherein $R^3$ represents a methyl group, an ethyl group, a methoxy group, an ethoxy group, a fluorine atom or a chlorine atom.

78. The composition according to claim 55, wherein $R^3$ represents a methyl group.

79. The composition according to claim 55, wherein $R^4$ and $R^5$ are the same or different and each represents a hydrogen atom or a methyl group.

80. The composition according to claim 55, wherein $R^4$ represents a hydrogen atom or a methyl group and $R^5$ represents a hydrogen atom.

81. The composition according to claim 55, wherein $R^4$ and $R^5$ each represent a hydrogen atom.

82. The composition according to claim 55, wherein: $R^6$ represents:
an alkyl group having from 1 to 6 carbon atoms, said alkyl group being unsubstituted or being substituted by a alkoxy group having from 1 to 6 carbon atoms or by from 1 to 4 halogen atoms;
a cycloalkyl group having from 3 to 6 carbon atoms;
an alkoxy group having from 1 to 6 carbon atoms, said alkoxy group being unsubstituted or being substituted by from 1 to 4 halogen atoms;
a halogen atom; or
a group represented by the formula —$COR^8$, as defined in claim 55.

83. The composition according to claim 55, wherein: $R^6$ represents:
an alkyl group having from 1 to 6 carbon atoms, said alkyl group being unsubstituted or being substituted by from 1 to 4 halogen atoms;
an alkoxy group having from 1 to 6 carbon atoms, said alkoxy group being unsubstituted or being substituted by from 1 to 4 halogen atoms; or
a halogen atom.

84. The composition according to claim 55, wherein: $R^6$ represents:
an unsubstituted alkyl group having from 1 to 3 carbon atoms;
an unsubstituted alkoxy group having from 1 to 3 carbon atoms; or
a halogen atom.

85. The composition according to claim 55, wherein $R^6$ represents a methoxy group, a fluorine atom or a chlorine atom.

86. The composition according to claim 55, wherein $R^6$ represents a fluorine atom or a chlorine atom.

87. The composition according to claim 55, wherein $R^8$ represents an alkyl group having from 1 to 3 carbon atoms or an alkoxy group having from 1 to 3 carbon atoms.

88. The composition according to claim 55, wherein $R^8$ represents an alkoxy group having from 1 to 3 carbon atoms.

89. The composition according to claim 55, wherein $R^8$ represents a methoxy group.

90. The composition according to claim 55, wherein A represents an oxygen atom.

91. The composition according to claim 55, wherein X represents an oxygen atom.

92. The composition according to claim 55, wherein Q represents a sulfur atom.

93. The composition according to claim 55, wherein m represents an integer from 0 to 3.

94. The composition according to claim 55, wherein m represents an integer of 0 or 1.

95. The composition according to claim 55, wherein m represents an integer of 0.

96. The composition according to claim 55, wherein n represents an integer from 0 to 3.

97. The composition according to claim 55, wherein n represents an integer from 0 to 2.

98. The composition according to claim 55, wherein n represents an integer of 0 or 1.

99. The composition according to claim 55, wherein n represents an integer of 1.

100. The composition according to claim 55 wherein: $R^1$ represents:
an alkyl group having from 1 to 6 carbon atoms, said alkyl group being unsubstituted or being substituted by an alkoxy group having from 1 to 6 carbon atoms or by from 1 to 4 halogen atoms;
a cycloalkyl group having from 3 to 6 carbon atoms; or
an alkoxy group having from 1 to 6 carbon atoms, said alkoxy group being; unsubstituted or being substituted by from 1 to 4 halogen atoms;
$R^2$ represents:
a hydrogen atom;

an alkyl group having from 1 to 6 carbon atoms, said
alkyl group being
unsubstituted or being substituted by a hydroxy group
or by from 1 to 4 halogen atoms;
a cycloalkyl group having from 3 to 6 carbon atoms; or
a group represented by the formula —$YR^7$, wherein:
Y represents a group selected from the group consisting of the the groups of formulae —CO—, —COO—, —$CH_2O$—, —$CH_2CH_2O$—, —$CH_2CO$—, —$CH_2COO$—, —$CH_2CH_2CO$—, —$CH_2OCO$—, —$CH_2OCOO$— and —$CH_2CH_2OCO$—, and $R^7$ represents an .alkyl group having from 1 to 6 carbon atoms, said alkyl group being unsubstituted or being substituted by an alkoxy group having from 1 to 6 carbon atoms or by from 1 to 4 halogen atoms, a cycloalkyl group having from 3 to 6 carbon atoms, an alkenyl group having from 2 to 6 carbon atoms, said alkenyl group being unsubstituted or being substituted by from 1 to 4 halogen atoms, an alkynyl group having from 2 to 6 carbon atoms, said alkynyl group being unsubstituted or being substituted by from 1 to 4 halogen atoms, a carbocyclic aryl group having from 6 to 14 ring carbon atoms, said aryl group being unsubstituted or being substituted by from 1 to 3 alkyl groups having from 1 to 6 carbon atoms, 1 to 3 alkoxy groups having from 1 to 6 carbon atoms or by from 1 to 4 halogen atoms, an aralkyl group wherein the aryl moiety is a carbocyclic aryl group having from 6 to 14 ring carbon atoms, said aryl group being unsubstituted or being substituted by from 1 to 4 halogen atoms, and the alkyl moiety has from 1 to 6 carbon atoms, or a heterocyclic group having from 4 to 10 ring atoms including at least one ring heteroatom selected from the group consisting of oxygen atoms, sulfur atoms and nitrogen atoms, said heterocyclic group being fully unsaturated, partly unsaturated or saturated and being either unsubstituted, substituted by at least one substituent selected from alkyl groups having from 1 to 6 carbon atoms, alkoxy groups having from 1 to 6 carbon atoms and halogen atoms, or fused with a carbocyclic aryl group having from 6 to 10 ring carbon atoms;

$R^3$ represents:
an alkyl group having from 1 to 6 carbon atoms, said alkyl group being unsubstituted or being substituted by a alkoxy group having from 1 to 6 carbon atoms or by from 1 to 4 halogen atoms;

a cycloalkyl group having from 3 to 6 carbon atoms;

an alkoxy group having from 1 to 6 carbon atoms, said alkoxy group being unsubstituted or being substituted by from 1 to 4 halogen atoms;

a halogen atom;

a nitro group; or a group represented by the formula —$COR^8$, wherein $R^8$ represents an alkyl group having from 1 to 3 carbon atoms or an alkoxy group having from 1 to 3 carbon atoms;

$R^4$ and $R^5$ are the same or different and each represents a hydrogen atom or a methyl group;

$R^6$ represents:
an alkyl group having from 1 to 6 carbon atoms, said alkyl group being unsubstituted or being substituted by a alkoxy group having from 1 to 6 carbon atoms or by from 1 to 4 halogen atoms;

a cycloalkyl group having from 3 to 6 carbon atoms;

an alkoxy group having from 1 to 6 carbon atoms, said alkoxy group being unsubstituted or being substituted by from 1 to 4 halogen atoms;

a halogen atom; or a group represented by the formula —$COR^8$, wherein $R^8$ represents an alkyl group having from 1 to 3 carbon atoms or an alkoxy group having from 1 to 3 carbon atoms; and m and n are the same or different and each represents an integer from 0 to 3.

101. The composition according to claim 55 wherein:

$R^1$ represents:
an alkyl group having from 1 to 6 carbon atoms; said alkyl group being unsubstituted or being substituted by an alkoxy group having from 1 to 6 carbon atoms or by from 1 to 4 halogen atoms; or an unsubstituted alkoxy group having from 1 to 6 carbon atoms;

$R^2$ represents:
a hydrogen atom;

an alkyl group having from 1 to 6 carbon atoms, said alkyl group being unsubstituted or being substituted by a hydroxy group; or a group represented by the formula —$YR^7$, wherein Y represents a group selected from the group consisting of the groups of formulae —CO—, —COO—, —$CH_2O$—, —$CH_2CH_2O$—, —$CH_2OCO$— and —$CH_2OCOO$— and $R^7$ represents an alkyl group having from 1 to 6 carbon atoms, said alkyl group being unsubstituted or being substituted by an alkoxy group having from 1 to 6 carbon atoms or by from 1 to 4 halogen atoms;

$R^3$ represents:
an alkyl group having from 1 to 6 carbon atoms, said alkyl group being unsubstituted or being substituted by an alkoxy group having from 1 to 6 carbon atoms or by from 1 to 4 halogen atoms;

an alkoxy group having from 1 to 6 carbon atoms, said alkoxy group being unsubstituted or being substituted by from 1 to 4 halogen atoms; or a halogen atom;

$R^4$ and $R^5$ are the same or different and each represents a hydrogen atom or a methyl group;

$R^6$ represents:
an alkyl group having from 1 to 6 carbon atoms, said alkyl group being unsubstituted or being substituted by from 1 to 4 halogen atoms;

an alkoxy group having from 1 to 6 carbon atoms, said alkoxy group being unsubstituted or being substituted by from 1 to 4 halogen atoms; or a halogen atom; and m represents an integer from 0 to 3 and n represents an integer from 0 to 2.

102. The composition according to claim 55 wherein:

$R^1$ represents:
an alkyl group having from 1 to 3 carbon atoms, said alkyl group being unsubstituted or being substituted by an alkoxy group having from 1 to 3 carbon atoms; or an unsubstituted alkoxy group having from 1 to 3 carbon atoms;

$R^2$ represents:
a hydrogen atom;

an alkyl group having from 1 to 3 carbon atoms which is substituted by a hydroxy group; or a group represented by the formula —YR$^7$, wherein Y represents a group selected from the group consisting of the groups of formulae —CO—, —COO—, —CH$_2$O—, —CH$_2$OCO— and —CH$_2$OCOO— and R$^7$ represents an alkyl group having from 1 to 3 carbon atoms, said alkyl group being unsubstituted or being substituted by from 1 to 4 halogen atoms;

R$^3$ represents:

an unsubstituted alkyl group having from 1 to 3 carbon atoms;

an alkoxy group having from 1 to 3 carbon atoms; or a halogen atom;

R$^4$ represents a hydrogen atom or a methyl group and R$^5$ represents a hydrogen atom;

R$^6$ represents:

an unsubstituted alkyl group having from 1 to 3 carbon atoms;

an unsubstituted alkoxy group having from 1 to 3 carbon atoms; or a halogen atom; and m and n are the same or different and each represents an integer of 0 or 1.

103. The composition according to claim 55 wherein:

R$^1$ represents a methyl group or a methoxy group;

R$^2$ represents a hydrogen atom, a hydroxymethyl group or a group represented by the formula —YR$^7$, wherein Y represents a group selected from the group consisting of the groups of formulae —CO—, —COO— or —CH$_2$OCO— and R$^7$ represents an ethyl group or a 2,2,2-trichloroethyl group;

R$^3$ represents a methyl group, an ethyl group, a methoxy group, an ethoxy group, a fluorine atom or a chlorine atom;

R$^4$ represents a hydrogen atom or a methyl group and R$^5$ represents a hydrogen atom;

R$^6$ represents a methoxy group, a fluorine atom or a chlorine atom;

m and n are the same or different and each represents an integer of 0 or 1;

A represents an oxygen atom;

X represents an oxygen atom; and

Q represents a sulfur atom.

104. The composition according to claim 55 wherein:

R$^1$ represents a methoxy group;

R$^2$ represents a hydrogen atom;

R$^3$ represents a methyl group;

R$^4$ and R$^5$ each represent a hydrogen atom;

m represents an integer of 0;

n represents an integer of 1;

A represents an oxygen atom;

X represents an oxygen atom; and

Q represents a sulfur atom.

105. The composition according to claim 55 wherein m represents an integer of 1 and R$^3$ is at the 2-position of the phenyl ring.

106. The composition according to claim 55, wherein:

R$^1$ represents an alkyl group having from 1 to 6 carbon atoms, said alkyl group being unsubstituted or being substituted by an alkoxy group having from 1 to 6 carbon atoms or by from 1 to 4 halogen atoms;

R$^2$ represents:

a hydrogen atom;

an alkyl group having from 1 to 6 carbon atoms, said alkyl group being unsubstituted or being substituted by from 1 to 4 halogen atoms;

an alkenyl group having from 3 to 6 carbon atoms, said alkenyl group being unsubstituted;

an alkynyl group having from 3 to 6 carbon atoms, said alkynyl group being unsubstituted; or an alkoxycarbonyl group wherein the alkoxy moiety has from 1 to 6 carbon atoms;

R$^3$ represents:

an alkyl group having from 1 to 6 carbon atoms, said alkyl group being unsubstituted or being substituted by an alkoxy group having from 1 to 6 carbon atoms or by from 1 to 4 halogen atoms;

an alkoxy group having from 1 to 6 carbon atoms, said alkoxy group being unsubstituted;

an alkenyl group having from 3 to 6 carbon atoms, said alkenyl group being unsubstituted;

an alkynyl group having from 3 to 6 carbon atoms, said alkynyl group being unsubstituted;

a halogen atom;

a nitro group; or a formyl group;

R$^4$ and R$^5$ are the same or different and each represents a hydrogen atom or an alkyl group having from 1 to 6 carbon atoms;

R$^6$ represents:

an alkyl group having from 1 to 6 carbon atoms, said alkyl group being unsubstituted or being substituted by from 1 to 4 halogen atoms;

an alkoxy group having from 1 to 6 carbon atoms, said alkoxy group being unsubstituted or being substituted by from 1 to 4 halogen atoms;

an alkenyl group having from 3 to 6 carbon atoms, said alkenyl group being unsubstituted;

an alkynyl group having from 3 to 6 carbon atoms, said alkynyl group being unsubstituted; or a halogen atom;

A represents an oxygen atom or a sulfur atom;

X represents an oxygen atom;

Q represents a sulfur atom;

m represents an integer from 0 to 4 and, where m is an integer from 2 to 4, each R$^6$ may be the same or different; and n represents an integer from 0 to 4 and, where n is an integer from 2 to 4, each R$^3$ may be the same or different;

and herbicidally acceptable addition salts thereof.

107. The composition according to claim 55, wherein:

R$^1$ represents:

an alkoxy group having from 1 to 6 carbon atoms, said alkoxy group being unsubstituted or being substituted by from 1 to 4 halogen atoms; or an alkylthio group having from 1 to 6 carbon atoms, said alkylthio group being unsubstituted or being substituted by from 1 to 4 halogen atoms;

R$^2$ represents:

a hydrogen atom; or an alkyl group having from 1 to 6 carbon atoms, said alkyl group being unsubstituted or being substituted by from 1 to 4 halogen atoms;

R$^3$ represents:

an alkyl group having from 1 to 6 carbon atoms, said alkyl group being unsubstituted or being substituted by an alkoxy group having from 1 to 6 carbon atoms or by from 1 to 4 halogen atoms;

an alkoxy group having from 1 to 6 carbon atoms, said alkoxy group being unsubstituted or being substituted by from 1 to 4 halogen atoms;

a halogen atom;

a nitro group; or a formyl group;

$R^4$ and $R^5$ are the same or different and each represents a hydrogen atom or an alkyl group having from 1 to 6 carbon atoms;

$R^6$ represents:

an alkyl group having from 1 to 6 carbon atoms, said alkyl group being unsubstituted or being substituted by from 1 to 6 carbon atoms or by from 1 to 4 halogen atoms;

an alkoxy group having from 1 to 6 carbon atoms, said alkoxy group being unsubstituted or being substituted by from 1 to 4 halogen atoms; or a halogen atom;

A represents an oxygen atom or a sulfur atom;

X represents an oxygen atom or a sulfur atom;

Q represents an oxygen atom or a sulfur atom;

m represents an integer from 0 to 4 and, where m is an integer from 2 to 4, each $R^6$ may be the same or different; and n represents an integer from 0 to 4 and, where n is an integer from 2 to 4, each $R^3$ may be the same or different;

and herbicidally acceptable addition salts thereof.

108. The composition according to claim 55, wherein the herbicidal agent is selected from the group consisting of:

N-[4-(benzothiazol-2-ylmethoxy)-2-methylphenyl] acetamide;

N-[4-(benzoxazol-2-ylmethoxy)-2-methylphenyl] acetamide;

methyl N-[4-(benzothiazol-2-ylmethoxy)-2-methylphenyl]carbamate;

methyl N-[4-(benzoxazol-2-ylmethoxy)-2-methylphenyl] carbamate;

methyl N-[4-(benzothiazol-2-ylmethoxy)-2-methylphenyl]-N-hydroxymethylcarbamate;

methyl N-[4-(benzothiazol-2-ylmethoxy)-2-methylphenyl]-N-propionyloxymethylcarbamate;

N-[4-(benzothiazol-2-ylmethoxy)-2-methylphenyl]-N-methoxycarbonylpropionamide;

methyl N-[4-(6-methoxybenzothiazol-2-ylmethoxy)-2-methylphenyl]carbamate;

methyl N-[4-(5-fluorobenzothiazol-2-ylmethoxy)-2-methylphenyl]carbamate; and methyl N-[4-(6-fluorobenzothiazol-2-ylmethoxy)-2-methylphenyl]carbamate.

109. A method of destroying weeds, either before or after germination of said weeds, by administering a herbicidal agent to a locus including said germinated or ungerminated weeds, wherein the herbicidal agent is a compound of formula (I):

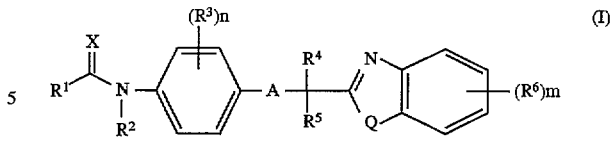

wherein:

$R^1$ represents:

an alkyl group having from 1 to 6 carbon atoms, said alkyl group being unsubstituted or being substituted by an alkoxy group having from 1 to 6 carbon atoms or by from 1 to 4 halogen atoms;

a cycloalkyl group having from 3 to 6 carbon atoms;

an alkoxy group having from 1 to 6 carbon atoms, said alkoxy group being unsubstituted or being substituted by from 1 to 4 halogen atoms; or an alkylthio group having from 1 to 6 carbon atoms, said alkylthio group being unsubstituted or being substituted by from 1 to 4 halogen atoms;

$R^2$ represents:

a hydrogen atom;

an alkyl group having from 1 to 6 carbon atoms, said alkyl group being unsubstituted or being substituted by a hydroxy group or by from 1 to 4 halogen atoms;

a cycloalkyl group having from 3 to 6 carbon atoms;

an alkenyl group having from 2 to 6 carbon atoms, said alkenyl group being unsubstituted or being substituted by from 1 to 4 halogen atoms;

an alkynyl group having from 2 to 6 carbon atoms, said alkynyl group being unsubstituted or being substituted by from 1 to 4 halogen atoms; or a group represented by the formula —$YR^7$;

$R^3$ represents:

an alkyl group having from 1 to 6 carbon atoms, said alkyl group being unsubstituted or being substituted by an alkoxy group having from 1 to 6 carbon atoms or by from 1 to 4 halogen atoms;

a cycloalkyl group having from 3 to 6 carbon atoms;

an alkoxy group having from 1 to 6 carbon atoms, said alkoxy group being unsubstituted or being substituted by from 1 to 4 halogen atoms;

an alkenyl group having from 2 to 6 carbon atoms, said alkenyl group being unsubstituted or being substituted by from 1 to 4 halogen atoms;

an alkynyl group having from 2 to 6 carbon atoms, said alkynyl group being unsubstituted or being substituted by from 1 to 4 halogen atoms;

a halogen atom;

a nitro group; or a group of formula —$COR^8$, wherein $R^8$ represents a hydrogen atom, an alkyl group having from 1 to 6 carbon atoms, a cycloalkyl group having from 3 to 6 carbon atoms or an alkoxy group having from 1 to 6 carbon atoms;

$R^4$ and $R^5$ are the same or different and each represents a hydrogen atom or an alkyl group having from 1 to 6 carbon atoms;

$R^6$ represents:

an alkyl group having from 1 to 6 carbon atoms, said alkyl group being unsubstituted or being substituted by an alkoxy group having from 1 to 6 carbon atoms or by from 1 to 4 halogen atoms;

a cycloalkyl group having from 3 to 6 carbon atoms;

an alkoxy group having from 1 to 6 carbon atoms, said alkoxy group being unsubstituted or being substituted by from 1 to 4 halogen atoms;

an alkenyl group having from 2 to 6 carbon atoms, said alkenyl group being unsubstituted or being substituted by from 1 to 4 halogen atoms;

an alkynyl group having from 2 to 6 carbon atoms, said alkynyl group being unsubstituted or being substituted by from 1 to 4 halogen atoms;

a halogen atom;

a nitro group; or a group of formula —$COR^8$, wherein $R^8$ represents a hydrogen atom, an alkyl group having from 1 to 6 carbon atoms, a cycloalkyl group having from 3 to 6 carbon atoms or an alkoxy group having from 1 to 6 carbon atoms;

A represents an oxygen atom or a sulfur atom;

X represents an oxygen atom or a sulfur atom;

Y represents a group selected from the group consisting of the groups of formulae —CO—, —COO—, —$CH_2O$—, —$CH_2S$—, —$CH_2CH_2O$—, —$CH_2CH_2S$—, —$CH_2CO$—, —$CH_2COO$—, —CH(Me)COO—, —$CH_2CH_2CO$—, —$CH_2OCO$—, $CH_2OCOO$— and —$CH_2CH_2OCO$—;

$R^7$ represents:

an alkyl group having from 1 to 6 carbon atoms, said alkyl group being unsubstituted or being substituted by an alkoxy group having from 1 to 6 carbon atoms, an alkylthio group having from 1 to 6 carbon atoms or by from 1 to 4 halogen atoms;

a cycloalkyl group having from 3 to 6 carbon atoms;

an alkenyl group having from 2 to 6 carbon atoms, said alkenyl group being unsubstituted or being substituted by from 1 to 4 halogen atoms;

an alkynyl group having from 2 to 6 carbon atoms, said alkynyl group being unsubstituted or being substituted by from 1 to 4 halogen atoms;

a carbocyclic aryl group having from 6 to 14 ring carbon atoms, said aryl group being unsubstituted or being substituted by at least one substituent selected from the group consisting of alkyl groups having from 1 to 6 carbon atoms, alkoxy groups having from 1 to 6 carbon atoms and halogen atoms;

an aralkyl group wherein the aryl moiety is a carbocyclic aryl group having from 6 to 10 ring carbon atoms which is unsubstituted or is substituted by from 1 to 4 halogen atoms, and the alkyl moiety has from 1 to 6 carbon atoms; or a heterocyclic group having from 4 to 10 ring atoms including at least one ring heteroatom selected from the group consisting of oxygen atoms, sulfur atoms and nitrogen atoms, said heterocyclic group being fully unsaturated, partly unsaturated or saturated and being either unsubstituted, substituted by at least one substituent selected from alkyl groups having from 1 to 6 carbon atoms, alkoxy groups having from 1 to 6 carbon atoms and halogen atoms, or fused with a carbocyclic aryl group having from 6 to 10 ring carbon atoms;

Q represents an oxygen atom or a sulfur atom;

m represents an integer from 0 to 4 and, where m is an integer from 2 to 4, each $R^6$ may be the same or different; and n represents an integer from 0 to 4 and, where n is an integer from 2 to 4, each $R^3$ may be the same or different;

or a herbicidally acceptable addition salt thereof.

110. The method according to claim 109, wherein:

$R^1$ represents:

an alkyl group having from 1 to 6 carbon atoms, said alkyl group being unsubstituted or being substituted by an alkoxy group having from 1 to 6 carbon atoms or by from 1 to 4 halogen atoms;

a cycloalkyl group having from 3 to 6 carbon atoms; or an alkoxy group having from 1 to 6 carbon atoms, said alkoxy group being unsubstituted or being substituted by from 1 to 4 halogen atoms.

111. The method according to claim 109, wherein:

$R^1$ represents:

an alkyl group having from 1 to 6 carbon atoms, said alkyl group being unsubstituted or being substituted by an alkoxy group having from 1 to 6 carbon atoms or by from 1 to 4 halogen atoms; or an unsubstituted alkoxy group having from 1 to 6 carbon atoms.

112. The method according to claim 109, wherein:

$R^1$ represents:

an alkyl group having from 1 to 3 carbon atoms, said alkyl group being unsubstituted or being substituted by an alkoxy group having from 1 to 3 carbon atoms; or an unsubstituted alkoxy group having from 1 to 3 carbon atoms.

113. The method according to claim 109, wherein $R^1$ represents a methyl group or a methoxy group.

114. The method according to claim 109, wherein $R^1$ represents a methoxy group.

115. The method according to claim 109, wherein:

$R^2$ represents:

a hydrogen atom;

an alkyl group having from 1 to 6 carbon atoms, said alkyl group being unsubstituted or being substituted by a hydroxy group or by from 1 to 4 halogen atoms;

a cycloalkyl group having from 3 to 6 carbon atoms; or a group represented by the formula —$YR^7$, as defined in claim 109.

116. The method according to claim 109, wherein:

$R^2$ represents:

a hydrogen atom;

an alkyl group having from 1 to 6 carbon atoms, said alkyl group being unsubstituted or being substituted by a hydroxy group; or a group represented by the formula —$YR^7$, as defined in claim 109.

117. The method according to claim 109, wherein:

$R^2$ represents:

a hydrogen atom;

an alkyl group having from 1 to 3 carbon atoms which is substituted by a hydroxy group; or a group represented by the formula —$YR^7$, as defined in claim 109.

118. The method according to claim 109, wherein $R^2$ represents a hydrogen atom, a hydroxymethyl group or a group represented by the formula —$YR^7$, as defined in claim 109.

119. The method according to claim 109, wherein $R^2$ represents a hydrogen atom.

120. The method according to claim 109, wherein Y represents a group selected from the group consisting of the groups of formulae —CO—, —COO—, —$CH_2O$—, —$CH_2CH_2O$, —$CH_2CO$—, —$CH_2COO$—, —$CH_2CH_2CO$—, —$CH_2OCO$—, —$CH_2OCOO$— and —$CH_2CH_2OCO$—.

121. The method according to claim 109, wherein Y represents a group selected from the group consisting of the groups of formulae —CO—, —COO—, —CH$_2$O—, —CH$_2$CH$_2$O—, —CH$_2$OCO— and —CH$_2$OCOO—.

122. The method according to claim 109, wherein Y represents a group selected from the group consisting of the groups of formulae —CO—, —COO—, —CH$_2$O—, —CH$_2$OCO— and —CH$_2$OCOO—.

123. The method according to claim 109, wherein Y represents a group selected from the group consisting of the groups of formulae —CO—, —COO— and —CH$_2$OCO—.

124. The method according to claim 109, wherein:
R$^7$ represents:
 an alkyl group having from 1 to 6 carbon atoms, said alkyl group being unsubstituted or being substituted by an alkoxy group having from 1 to 6 carbon atoms or by from 1 to 4 halogen atoms;
 a cycloalkyl group having from 3 to 6 carbon atoms;
 an alkenyl group having from 2 to 6 carbon atoms, said alkenyl group being unsubstituted or being substituted by from 1 to 4 halogen atoms;
 an alkynyl group having from 2 to 6 carbon atoms, said alkynyl group being unsubstituted or being substituted by from 1 to 4 halogen atoms;
 a carbocyclic aryl group having from 6 to 14 ring carbon atoms, said aryl group being unsubstituted or being substituted by from 1 to 3 alkyl groups having from 1 to 6 carbon atoms, 1 to 3 alkoxy groups having from 1 to 6 carbon atoms or by from 1 to 4 halogen atoms;
 an aralkyl group wherein the aryl moiety is a carbocyclic aryl group having from 6 to 14 ring carbon atoms, said aryl group being unsubstituted or being substituted by from 1 to 4 halogen atoms, and the alkyl moiety has from 1 to 6 carbon atoms; or
 a heterocyclic group having from 4 to 10 ring atoms including at least one ring heteroatom selected from the group consisting of oxygen atoms, sulfur atoms and nitrogen atoms, said heterocyclic group being fully unsaturated, partly unsaturated or saturated and being either unsubstituted, substituted by at least one substituent selected from alkyl groups having from 1 to 6 carbon atoms, alkoxy groups having from 1 to 6 carbon atoms and halogen atoms, or fused with a carbocyclic aryl group having from 6 to 10 ring carbon atoms.

125. The method according to claim 109, wherein R$^7$ represents an alkyl group having from 1 to 6 carbon atoms, said alkyl group being unsubstituted or being substituted by an alkoxy group having from 1 to 6 carbon atoms or by from 1 to 4 halogen atoms.

126. The method according to claim 109, wherein R$^7$ represents an alkyl group having from 1 to 3 carbon atoms, said alkyl group being unsubstituted or being substituted by from 1 to 4 halogen atoms.

127. The method according to claim 109, wherein R$^7$ represents an ethyl group or a 2,2,2-trichloroethyl group.

128. The method according to claim 109, wherein:
R$^3$ represents:
 an alkyl group having from 1 to 6 carbon atoms, said alkyl group being unsubstituted or being substituted by a alkoxy group having from 1 to 6 carbon atoms or by from 1 to 4 halogen atoms;
 a cycloalkyl group having from 3 to 6 carbon atoms;
 an alkoxy group having from 1 to 6 carbon atoms, said alkoxy group being unsubstituted or being substituted by from 1 to 4 halogen atoms;
 a halogen atom;
 a nitro group; or
 a group represented by the formula —COR$^8$, as defined in claim 109.

129. The method according to claim 109, wherein:
R$^3$ represents:
 an alkyl group having from 1 to 6 carbon atoms, said alkyl group being unsubstituted or being substituted by an alkoxy group having from 1 to 6 carbon atoms or by from 1 to 4 halogen atoms;
 an alkoxy group having from 1 to 6 carbon atoms, said alkoxy group being unsubstituted or being substituted by from 1 to 4 halogen atoms; or
 a halogen atom.

130. The method according to claim 109, wherein:
R$^3$ represents:
 an unsubstituted alkyl group having from 1 to 3 carbon atoms;
 an alkoxy group having from 1 to 3 carbon atoms; or
 a halogen atom.

131. The method according to claim 109, wherein R$^3$ represents a methyl group, an ethyl group, a methoxy group, an ethoxy group, a fluorine atom or a chlorine atom.

132. The method according to claim 109, wherein R$^3$ represents a methyl group.

133. The method according to claim 109, wherein R$^4$ and R$^5$ are the same or different and each represents a hydrogen atom or a methyl group.

134. The method according to claim 109, wherein R$^4$ represents a hydrogen atom or a methyl group and R$^5$ represents a hydrogen atom.

135. The method according to claim 109, wherein R$^4$ and R$^5$ each represent a hydrogen atom.

136. The method according to claim 109, wherein:
R$^6$ represents:
 an alkyl group having from 1 to 6 carbon atoms, said alkyl group being unsubstituted or being substituted by a alkoxy group having from 1 to 6 carbon atoms or by from 1 to 4 halogen atoms;
 a cycloalkyl group having from 3 to 6 carbon atoms;
 an alkoxy group having from 1 to 6 carbon atoms, said alkoxy group being unsubstituted or being substituted by from 1 to 4 halogen atoms;
 a halogen atom; or
 a group represented by the formula —COR$^8$, as defined in claim 109.

137. The method according to claim 109, wherein:
R$^6$ represents:
 an alkyl group having from 1 to 6 carbon atoms, said alkyl group being unsubstituted or being substituted by from 1 to 4 halogen atoms;
 an alkoxy group having from 1 to 6 carbon atoms, said alkoxy group being unsubstituted or being substituted by from 1 to 4 halogen atoms; or
 a halogen atom.

138. The method according to claim 109, wherein:
R$^6$ represents:
 an unsubstituted alkyl group having from 1 to 3 carbon atoms;
 an unsubstituted alkoxy group having from 1 to 3 carbon atoms; or
 a halogen atom.

139. The method according to claim 109, wherein R$^6$ represents a methoxy group, a fluorine atom or a chlorine atom.

140. The method according to claim 109, wherein R$^6$ represents a fluorine atom or a chlorine atom.

141. The method according to claim 109, wherein R$^8$ represents an alkyl group having from 1 to 3 carbon atoms or an alkoxy group having from 1 to 3 carbon atoms.

142. The method according to claim 109, wherein $R^8$ represents an alkoxy group having from 1 to 3 carbon atoms.

143. The method according to claim 109, wherein $R^8$ represents a methoxy group.

144. The method according to claim 109, wherein A represents an oxygen atom.

145. The method according to claim 109, wherein X represents an oxygen atom.

146. The method according to claim 109, wherein Q represents a sulfur atom.

147. The method according to claim 109, wherein m represents an integer from 0 to 3.

148. The method according to claim 109, wherein m represents an integer of 0 or 1.

149. The method according to claim 109, wherein m represents an integer of 0.

150. The method according to claim 109, wherein n represents an integer from 0 to 3.

151. The method according to claim 109, wherein n represents an integer from 0 to 2.

152. The method according to claim 109, wherein n represents an integer of 0 or 1.

153. The method according to claim 109, wherein n represents an integer of 1.

154. The method according to claim 109 wherein:

$R^1$ represents:
   an alkyl group having from 1 to 6 carbon atoms, said alkyl group being unsubstituted or being substituted by an alkoxy group having from 1 to 6 carbon atoms or by from 1 to 4 halogen atoms;
   a cycloalkyl group having from 3 to 6 carbon atoms; or
   an alkoxy group having from 1 to 6 carbon atoms, said alkoxy group being unsubstituted or being substituted by from 1 to 4 halogen atoms;

$R^2$ represents:
   a hydrogen atom;
   an alkyl group having from 1 to 6 carbon atoms, said alkyl group being unsubstituted or being substituted by a hydroxy group or by from 1 to 4 halogen atoms;
   a cycloalkyl group having from 3 to 6 carbon atoms; or
   a group represented by the formula —$YR^7$, wherein:
      Y represents a group selected from the group consisting of the the groups of formulae —CO—, —COO—, —$CH_2$—, —$CH_2CH_2O$—, —$CH_2CO$—, —$CH_2COO$—, —$CH_2CH_2CO$—, —$CH_2OCO$—, —$CH_2OCOO$— and —$CH_2CH_2OCO$—, and
      $R^7$ represents an alkyl group having from 1 to 6 carbon atoms, said alkyl group being unsubstituted or being substituted by an alkoxy group having from 1 to 6 carbon atoms or by from 1 to 4 halogen atoms,
   a cycloalkyl group having from 3 to 6 carbon atoms,
   an alkenyl group having from 2 to 6 carbon atoms, said alkenyl group being unsubstituted or being substituted by from 1 to 4 halogen atoms,
   an alkynyl group having from 2 to 6 carbon atoms, said alkynyl group being unsubstituted or being substituted by from 1 to 4 halogen atoms,
   a carbocyclic aryl group having from 6 to 14 ring carbon atoms, said aryl group being unsubstituted or being substituted by from 1 to 3 alkyl groups having from 1 to 6 carbon atoms, 1 to 3 alkoxy groups having from 1 to 6 carbon atoms or by from 1 to 4 halogen atoms,
   an aralkyl group wherein the aryl moiety is a carbocyclic aryl group having from 6 to 14 ring carbon atoms, said aryl group being unsubstituted or being substituted by from 1 to 4 halogen atoms, and the alkyl moiety has from 1 to 6 carbon atoms, or
   a heterocyclic group having from 4 to 10 ring atoms including at least one ring heteroatom selected from the group consisting of oxygen atoms, sulfur atoms and nitrogen atoms, said heterocyclic group being fully unsaturated, partly unsaturated or saturated and being either unsubstituted, substituted by at least one substituent selected from alkyl groups having from 1 to 6 carbon atoms, alkoxy groups having from 1 to 6 carbon atoms and halogen atoms, or fused with a carbocyclic aryl group having from 6 to 10 ring carbon atoms;

$R^3$ represents:
   an alkyl group having from 1 to 6 carbon atoms, said alkyl group being unsubstituted or being substituted by a alkoxy group having from 1 to 6 carbon atoms or by from 1 to 4 halogen atoms;
   a cycloalkyl group having from 3 to 6 carbon atoms;
   an alkoxy group having from 1 to 6 carbon atoms, said alkoxy group being unsubstituted or being substituted by from 1 to 4 halogen atoms;
   a halogen atom;
   a nitro group; or
   a group represented by the formula —$COR^8$, wherein $R^8$ represents an alkyl group having from 1 to 3 carbon atoms or an alkoxy group having from 1 to 3 carbon atoms;

$R^4$ and $R^5$ are the same or different and each represents a hydrogen atom or a methyl group;

$R^6$ represents:
   an alkyl group having from 1 to 6 carbon atoms, said alkyl group being unsubstituted or being substituted by a alkoxy group having from 1 to 6 carbon atoms or by from 1 to 4 halogen atoms;
   a cycloalkyl group having from 3 to 6 carbon atoms;
   an alkoxy group having from 1 to 6 carbon atoms, said alkoxy group being unsubstituted or being substituted by from 1 to 4 halogen atoms;
   a halogen atom; or
   a group represented by the formula —$COR^8$, wherein $R^8$ represents an alkyl group having from 1 to 3 carbon atoms or an alkoxy group having from 1 to 3 carbon atoms; and m and n are the same or different and each represents an integer from 0 to 3.

155. The method according to claim 109 wherein:

$R^1$ represents:
   an alkyl group having from 1 to 6 carbon atoms, said alkyl group being unsubstituted or being substituted by an alkoxy group having from 1 to 6 carbon atoms or by from 1 to 4 halogen atoms; or
   an unsubstituted alkoxy group having from 1 to 6 carbon atoms;

$R^2$ represents:
   a hydrogen atom;
   an alkyl group having from 1 to 6 carbon atoms, said alkyl group being unsubstituted or being substituted by a hydroxy group; or
   a group represented by the formula —$YR^7$, wherein Y represents a group selected from the group consisting of the groups of formulae —CO—, —COO—, —$CH_2O$—, —$CH_2CH_2O$—, —$CH_2OCO$— and —$CH_2OCOO$— and $R^7$ represents an alkyl group having from 1 to 6 carbon atoms, said alkyl group being unsubstituted or being substituted by an alkoxy group having from 1 to 6 carbon atoms or by from 1 to 4 halogen atoms;

$R^3$ represents:
an alkyl group having from 1 to 6 carbon atoms, said alkyl group being unsubstituted or being substituted by an alkoxy group having from 1 to 6 carbon atoms or by from 1 to 4 halogen atoms;
an alkoxy group having from 1 to 6 carbon atoms, said alkoxy group being unsubstituted or being substituted by from 1 to 4 halogen atoms; or
a halogen atom;

$R^4$ and $R^5$ are the same or different and each represents a hydrogen atom or a methyl group;

$R^6$ represents:
an alkyl group having from 1 to 6 carbon atoms, said alkyl group being unsubstituted or being substituted by from 1 to 4 halogen atoms;
an alkoxy group having from 1 to 6 carbon atoms, said alkoxy group being unsubstituted or being substituted by from 1 to 4 halogen atoms; or
a halogen atom; and m represents an integer from 0 to 3 and n represents an integer from 0 to 2.

156. The method according to claim 109 wherein:

$R^1$ represents:
an alkyl group having from 1 to 3 carbon atoms, said alkyl group being unsubstituted or being substituted by an alkoxy group having from 1 to 3 carbon atoms; or
an unsubstituted alkoxy group having from 1 to 3 carbon atoms;

$R^2$ represents:
a hydrogen atom;
an alkyl group having from 1 to 3 carbon atoms which is substituted by a hydroxy group; or
a group represented by the formula —$YR^7$, wherein Y represents a group selected from the group consisting of the groups of formulae —CO—, —COO—, —CH$_2$O—, —CH$_2$OCO— and —CH$_2$OCOO— and $R^7$ represents an alkyl group having from 1 to 3 carbon atoms, said alkyl group being unsubstituted or being substituted by from 1 to 4 halogen atoms;

$R^3$ represents:
an unsubstituted alkyl group having from 1 to 3 carbon atoms;
an alkoxy group having from 1 to 3 carbon atoms; or
a halogen atom;

$R^4$ represents a hydrogen atom or a methyl group and $R^5$ represents a hydrogen atom;

$R^6$ represents:
an unsubstituted alkyl group having from 1 to 3 carbon atoms;
an unsubstituted alkoxy group having from 1 to 3 carbon atoms; or
a halogen atom; and m and n are the same or different and each represents an integer of 0 or 1.

157. The method according to claim 109 wherein:

$R^1$ represents a methyl group or a methoxy group;

$R^2$ represents a hydrogen atom, a hydroxymethyl group or a group represented by the formula —$YR^7$, wherein Y represents a group selected from the group consisting of the groups of formulae —CO—, —COO— or —CH$_2$OCO— and $R^7$ represents an ethyl group or a 2,2,2-trichloroethyl group;

$R^3$ represents a methyl group, an ethyl group, a methoxy group, an ethoxy group, a fluorine atom or a chlorine atom;

$R^4$ represents a hydrogen atom or a methyl group and $R^5$ represents a hydrogen atom;

$R^6$ represents a methoxy group, a fluorine atom or a chlorine atom;

m and n are the same or different and each represents an integer of 0 or 1;

A represents an oxygen atom;

X represents an oxygen atom; and

Q represents a sulfur atom.

158. The method according to claim 109 wherein:

$R^1$ represents a methoxy group;

$R^2$ represents a hydrogen atom;

$R^3$ represents a methyl group;

$R^4$ and $R^5$ each represent a hydrogen atom;

m represents an integer of 0;

n represents an integer of 1;

A represents an oxygen atom;

X represents an oxygen atom; and

Q represents a sulfur atom.

159. The method according to claim 109 wherein m represents an integer of 1 and $R^3$ is at the 2-position of the phenyl ring.

160. The method according to claim 109, wherein:

$R^1$ represents an alkyl group having from 1 to 6 carbon atoms, said alkyl group being unsubstituted or being substituted by an alkoxy group having from 1 to 6 carbon atoms or by from 1 to 4 halogen atoms;

$R^2$ represents:
a hydrogen atom;
an alkyl group having from 1 to 6 carbon atoms, said alkyl group being unsubstituted or being substituted by from 1 to 4 halogen atoms;
an alkenyl group having from 3 to 6 carbon atoms, said alkenyl group being unsubstituted;
an alkynyl group having from 3 to 6 carbon atoms, said alkynyl group being unsubstituted; or
an alkoxycarbonyl group wherein the alkoxy moiety has from 1 to 6 carbon atoms;

$R^3$ represents:
an alkyl group having from 1 to 6 carbon atoms, said alkyl group being unsubstituted or being substituted by an alkoxy group having from 1 to 6 carbon atoms or by from 1 to 4 halogen atoms;
an alkoxy group having from 1 to 6 carbon atoms, said alkoxy group being unsubstituted;
an alkenyl group having from 3 to 6 carbon atoms, said alkenyl group being unsubstituted;
an alkynyl group having from 3 to 6 carbon atoms, said alkynyl group being unsubstituted;
a halogen atom;
a nitro group; or
a formyl group;

$R^4$ and $R^5$ are the same or different and each represents a hydrogen atom or an alkyl group having from 1 to 6 carbon atoms;

$R^6$ represents:
an alkyl group having from 1 to 6 carbon atoms, said alkyl group being unsubstituted or being substituted by from 1 to 4 halogen atoms;

an alkoxy group having from 1 to 6 carbon atoms, said alkoxy group being unsubstituted or being substituted by from 1 to 4 halogen atoms;

an alkenyl group having from 3 to 6 carbon atoms, said alkenyl group being unsubstituted;

an alkynyl group having from 3 to 6 carbon atoms, said alkynyl group being unsubstituted; or a halogen atom;

A represents an oxygen atom or a sulfur atom;

X represents an oxygen atom;

Q represents a sulfur atom;

m represents an integer from 0 to 4 and, where m is an integer from 2 to 4, each $R^6$ may be the same or different; and n represents an integer from 0 to 4 and, where n is an integer from 2 to 4, each $R^3$ may be the same or different;

and herbicidally acceptable addition salts thereof.

161. The method according to claim 109, wherein:

$R^1$ represents:
an alkoxy group having from 1 to 6 carbon atoms, said alkoxy group being unsubstituted or being substituted by from 1 to 4 halogen atoms; or
an alkylthio group having from 1 to 6 carbon atoms, said alkylthio group being unsubstituted or being substituted by from 1 to 4 halogen atoms;

$R^2$ represents:
a hydrogen atom; or
an alkyl group having from 1 to 6 carbon atoms, said alkyl group being unsubstituted or being substituted by from 1 to 4 halogen atoms;

$R^3$ represents:
an alkyl group having from 1 to 6 carbon atoms, said alkyl group being unsubstituted or being substituted by an alkoxy group having from 1 to 6 carbon atoms or by from 1 to 4 halogen atoms;
an alkoxy group having from 1 to 6 carbon atoms, said alkoxy group being unsubstituted or being substituted by from I to 4 halogen atoms;
a halogen atom;
a nitro group; or
a formyl group;

$R^4$ and $R^5$ are the same or different and each represents a hydrogen atom or an alkyl group having from 1 to 6 carbon atoms;

$R^6$ represents:
an alkyl group having from 1 to 6 carbon atoms, said alkyl group being unsubstituted or being substituted by from 1 to 6 carbon atoms or by from 1 to 4 halogen atoms;
an alkoxy group having from 1 to 6 carbon atoms, said alkoxy group being unsubstituted or being substituted by from 1 to 4 halogen atoms; or
a halogen atom;

A represents an oxygen atom or a sulfur atom;

X represents an oxygen atom or a sulfur atom;

Q represents an oxygen atom or a sulfur atom;

m represents an integer from 0 to 4 and, where m is an integer from 2 to 4, each $R^6$ may be the same or different; and n represents an integer from 0 to 4 and, where n is an integer from 2 to 4, each $R^3$ may be the same or different;

and herbicidally acceptable addition salts thereof.

162. The method according to claim 109, wherein the herbicidal agent is selected from the group consisting of:

N-[4-(benzothiazol-2-ylmethoxy)-2-methylphenyl] acetamide;

N-[4-(benzoxazol-2-ylmethoxy)-2-methylphenyl] acetamide;

methyl N-[4-(benzothiazol-2-ylmethoxy)-2-methylphenyl]carbamate;

methyl N-[4-(benzoxazol-2-ylmethoxy)-2-methylphenyl] carbamate;

methyl N-[4-(benzothiazol-2-ylmethoxy)-2-methylphenyl]-N-hydroxymethylcarbamate;

methyl N-[4-(benzothiazol-2-ylmethoxy)-2-methylphenyl]-N-propionyloxymethylcarbamate;

N-[4-(benzothiazol-2-ylmethoxy)-2-methylphenyl]-N-methoxycarbonylpropionamide;

methyl N-[4-(6-methoxybenzothiazol-2-ylmethoxy)-2-methylphenyl]carbamate;

methyl N-[4-(5-fluorobenzothiazol-2-ylmethoxy)-2-methylphenyl]carbamate; and methyl N-[4-(6-fluorobenzothiazol-2-ylmethoxy)-2-methylphenyl]carbamate.

163. A process for the preparation of a compound of formula (I):

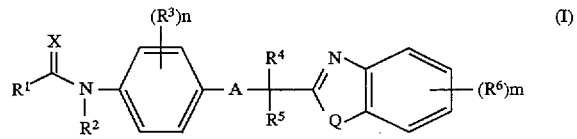

wherein:

$R^1$ represents:
an alkyl group having from 1 to 6 carbon atoms, said alkyl group being unsubstituted or being substituted by an alkoxy group having from 1 to 6 carbon atoms or by from 1 to 4 halogen atoms;
a cycloalkyl group having from 3 to 6 carbon atoms;
an alkoxy group having from 1 to 6 carbon atoms, said alkoxy group being unsubstituted or being substituted by from 1 to 4 halogen atoms; or
an alkylthio group having from 1 to 6 carbon atoms, said alkylthio group being unsubstituted or being substituted by from 1 to 4 halogen atoms;

$R^2$ represents:
a hydrogen atom;
an alkyl group having from 1 to 6 carbon atoms, said alkyl group being unsubstituted or being substituted by a hydroxy group or by from 1 to 4 halogen atoms;
a cycloalkyl group having from 3 to 6 carbon atoms;
an alkenyl group having from 2 to 6 carbon atoms, said alkenyl group being unsubstituted or being substituted by from 1 to 4 halogen atoms;
an alkynyl group having from 2 to 6 carbon atoms, said alkynyl group being unsubstituted or being substituted by from 1 to 4 halogen atoms; or
a group represented by the formula —$YR^7$;

$R^3$ represents:
an alkyl group having from 1 to 6 carbon atoms, said alkyl group being unsubstituted or being substituted by an alkoxy group having from 1 to 6 carbon atoms or by from 1 to 4 halogen atoms;
a cycloalkyl group having from 3 to 6 carbon atoms;
an alkoxy group having from 1 to 6 carbon atoms, said alkoxy group being unsubstituted or being substituted by from 1 to 4 halogen atoms;

an alkenyl group having from 2 to 6 carbon atoms, said alkenyl group being unsubstituted or being substituted by from 1 to 4 halogen atoms;

an alkynyl group having from 2 to 6 carbon atoms, said alkynyl group being unsubstituted or being substituted by from 1 to 4 halogen atoms;

a halogen atom;

a nitro group; or a group of formula —COR$^8$, wherein R$^8$ represents a hydrogen atom, an alkyl group having from 1 to 6 carbon atoms, a cycloalkyl group having from 3 to 6 carbon atoms or an alkoxy group having from 1 to 6 carbon atoms;

R$^4$ and R$^5$ are the same or different and each represents a hydrogen atom or an alkyl group having from 1 to 6 carbon atoms;

R$^6$ represents:

an alkyl group having from 1 to 6 carbon atoms, said alkyl group being unsubstituted or being substituted by an alkoxy group having from 1 to 6 carbon atoms or by from 1 to 4 halogen atoms;

a cycloalkyl group having from 3 to 6 carbon atoms;

an alkoxy group having from 1 to 6 carbon atoms, said alkoxy group being unsubstituted or being substituted by from 1 to 4 halogen atoms;

an alkenyl group having from 2 to 6 carbon atoms, said alkenyl group being unsubstituted or being substituted by from 1 to 4 halogen atoms;

an alkynyl group having from 2 to 6 carbon atoms, said alkynyl group being unsubstituted or being substituted by from 1 to 4 halogen atoms;

a halogen atom;

a nitro group; or a group of formula —COR$^8$, wherein R$^8$ represents a hydrogen atom, an alkyl group having from 1 to 6 carbon atoms, a cycloalkyl group having from 3 to 6 carbon atoms or an alkoxy group having from 1 to 6 carbon atoms;

A represents an oxygen atom or a sulfur atom;

X represents an oxygen atom or a sulfur atom;

Y represents a group selected from the group consisting of the groups of formulae —CO—, —COO—, —CH$_2$O—, —CH$_2$S—, —CH$_2$CH$_2$O—, —CH$_2$CH$_2$S—, —CH$_2$CO—, —CH$_2$COO—, —CH(Me)COO—, —CH$_2$CH$_2$CO—, —CH$_2$OCO—, CH$_2$OCOO— and —CH$_2$CH$_2$OCO—;

R$^7$ represents:

an alkyl group having from 1 to 6 carbon atoms, said alkyl group being unsubstituted or being substituted by an alkoxy group having from 1 to 6 carbon atoms, an alkylthio group having from 1 to 6 carbon atoms or by from 1 to 4 halogen atoms;

a cycloalkyl group having from 3 to 6 carbon atoms;

an alkenyl group having from 2 to 6 carbon atoms, said alkenyl group being unsubstituted or being substituted by from 1 to 4 halogen atoms;

an alkynyl group having from 2 to 6 carbon atoms, said alkynyl group being unsubstituted or being substituted by from 1 to 4 halogen atoms;

a carbocyclic aryl group having from 6 to 14 ring carbon atoms, said aryl group being unsubstituted or being substituted by at least one substituent selected from the group consisting of alkyl groups having from 1 to 6 carbon atoms, alkoxy groups having from 1 to 6 carbon atoms and halogen atoms;

an aralkyl group wherein the aryl moiety is a carbocyclic aryl group having from 6 to 10 ring carbon atoms which is unsubstituted or is substituted by from 1 to 4 halogen atoms, and the alkyl moiety has from 1 to 6 carbon atoms; or a heterocyclic group having from 4 to 10 ring atoms including at least one ring heteroatom selected from the group consisting of oxygen atoms, sulfur atoms and nitrogen atoms, said heterocyclic group being fully unsaturated, partly unsaturated or saturated and being either unsubstituted, substituted by at least one substituent selected from alkyl groups having from 1 to 6 carbon atoms, alkoxy groups having from 1 to 6 carbon atoms and halogen atoms, or fused with a carbocyclic aryl group having from 6 to 10 ring carbon atoms;

Q represents an oxygen atom or a sulfur atom;

m represents an integer from 0 to 4 and, where m is an integer from 2 to 4, each R$^6$ may be the same or different; and n represents an integer from 0 to 4 and, where n is an integer from 2 to 4, each R$^3$ may be the same or different;

and herbicidally acceptable addition salts thereof, comprising:

(i) reacting a compound of general formula (II):

$$K-\text{Ar}(R^3)_n-AH \quad (II)$$

wherein R$^3$, A and n are as defined above and K represents a group of formula N(R$^2$)C(=X)R$^1$ wherein R$^1$, X and R$^2$ are as defined above, a nitro group or an amino group, with a group of formula (III):

$$L-C(R^4)(R^5)-\text{(benzoxazole with (R^6)_m, Q, N)} \quad (III)$$

wherein R$^4$, R$^5$, R$^6$, Q and m are as defined above and L is a leaving group, to give a compound of formula (Ia), (VIa) or (VIIa):

$$K-\text{Ar}(R^3)_n-A-C(R^4)(R^5)-\text{(benzoxazole with (R^6)_m, Q, N)}$$

(Ia): K = N(R$^2$)C(=X)R$^1$
(VIa): K = NO$_2$
(VIIa): K = NH$_2$ wherein R$^3$, A, R$^4$, R$^5$, R$^6$, Q, m and n are as defined above and K is as shown;

(ii) where the compound produced in step (i) above is a compound of formula (VIa), wherein K represents a nitro group, reacting said compound with a reducing agent to give a compound of formula (VIIa) wherein K is an amino group;

(iii) where the compound is a compound of formula (VIIa), produced in steps (i) or (ii) above, reacting said compound with a group of formula R$^1$C(=X)L$^2$ wherein R$^1$ and X are as defined above and L$^2$ represents a leaving group, to give a compound of formula (Ia'):

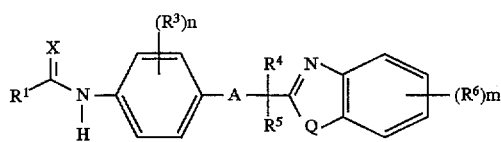

wherein $R^1$, X, $R^3$, A, $R^4$, $R^5$, $R^6$, Q, m and n are as defined above;

(iv) optionally, reacting said compound of formula (Ia) or (Ia') with a compound of formula $R^{2a}L^3$, wherein $R^{2a}$ represents any of the groups represented by $R^2$, as defined above, other than a hydrogen atom and $L^3$ represents a leaving group, to give a compound of formula (Ib'):

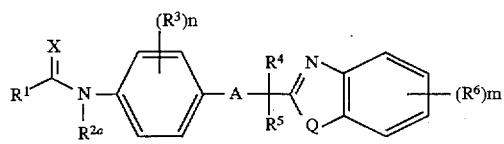

wherein $R^1$, $R^{2a}$, X, $R^3$, A, $R^4$, $R^5$, $R^6$, Q, m and n are as defined above;

(v) optionally reacting said compound of formula (Ib') with a suitable reagent to give a compound of formula (Ic'):

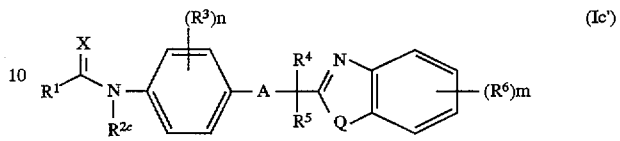

in which the group of formula $R^{2a}$ in the compound of formula (Ib') is converted to a group of formula $R^{2c}$, wherein $R^{2c}$ is a different group falling within the definition of the group $R^2$, and (vi) optionally, if desired, salifying the resulting compound of formula (I) to give the addition salt thereof.

* * * * *

UNITED STATES PATENT AND TRADEMARK OFFICE
CERTIFICATE OF CORRECTION

PATENT NO. : 5,736,487
DATED : April 7, 1998
INVENTOR(S) : SUGAI et al

It is certified that error appears in the above-identified patent and that said Letters Patent is hereby corrected as shown below:

Column 97, line 65: delete "G10.65" and insert
--G10.64--.

Column 102, line 53: delete "H2.66" and insert
--H2.67--.

Column 102, line 54: delete "H2.67" and insert
--H2.68--.

Column 102, line 55: delete "H2.68" and insert
--H2.69--.

Signed and Sealed this

Fifteenth Day of February, 2000

Attest:

Q. TODD DICKINSON

*Attesting Officer*   *Commissioner of Patents and Trademarks*